United States Patent
Kawanishi et al.

(10) Patent No.: US 7,015,345 B2
(45) Date of Patent: Mar. 21, 2006

(54) PROPIONIC ACID DERIVATIVES

(75) Inventors: Masashi Kawanishi, Shizuoka (JP); Hiroshi Umeno, Shizuoka (JP)

(73) Assignee: Asahi Kasei Pharma Corporation, Tokyo (JP)

( * ) Notice: Subject to any disclaimer, the term of this patent is extended or adjusted under 35 U.S.C. 154(b) by 0 days.

(21) Appl. No.: 10/367,857

(22) Filed: Feb. 19, 2003

(65) Prior Publication Data

US 2004/0072690 A1   Apr. 15, 2004

Related U.S. Application Data

(60) Provisional application No. 60/358,328, filed on Feb. 22, 2002.

(30) Foreign Application Priority Data

Feb. 21, 2002   (JP) .............. 2002/045287

(51) Int. Cl.
C07C 69/02    (2006.01)
C07C 69/025   (2006.01)
C07C 69/035   (2006.01)
C07C 69/03    (2006.01)
C07C 69/003   (2006.01)

(52) U.S. Cl. ................ 560/8; 560/19; 562/405; 562/433; 514/485

(58) Field of Classification Search .............. 560/8, 560/19; 562/405, 433; 514/485
See application file for complete search history.

(56) References Cited

U.S. PATENT DOCUMENTS

| | | | |
|---|---|---|---|
| 4,572,912 | A | 2/1986 | Yoshioka et al. |
| 4,687,777 | A | 8/1987 | Meguro et al. |
| 5,002,953 | A | 3/1991 | Hindley |
| 5,658,944 | A | 8/1997 | Chapman, Jr. et al. |
| 5,693,651 | A | 12/1997 | Nomura et al. |
| 6,300,339 | B1 | 10/2001 | Jeppesen et al. |
| 6,306,854 | B1 | 10/2001 | Brown et al. |
| 2003/0004341 | A1 | 1/2003 | Ebdrup et al. |

FOREIGN PATENT DOCUMENTS

| | | |
|---|---|---|
| EP | 1 026 149 A1 | 8/2000 |
| JP | 6-345714 A | 12/1994 |
| JP | 10-139768 A | 5/1998 |
| JP | 2000-344666 A | 12/2000 |
| JP | 2002-201171 A | 7/2002 |
| JP | 2002 2001171 * | 7/2002 |
| WO | WO 95/17394 A1 | 6/1995 |
| WO | WO 96/04260 A1 | 2/1996 |
| WO | WO 96/04261 A1 | 2/1996 |
| WO | WO 99/08501 A2 | 2/1999 |
| WO | WO 99/16758 A1 | 4/1999 |
| WO | WO 99/19313 A1 | 4/1999 |
| WO | WO 99/38850 A1 | 8/1999 |
| WO | WO 00/23415 A1 | 4/2000 |
| WO | WO 00/23416 A1 | 4/2000 |
| WO | WO 00/23417 A1 | 4/2000 |
| WO | WO 00/23425 A1 | 4/2000 |
| WO | WO 00/23451 A1 | 4/2000 |
| WO | WO 00/63153 A1 | 10/2000 |
| WO | WO 02/064130 A1 | 8/2002 |
| WO | WO 02/064549 A1 | 8/2002 |
| WO | WO 03/066581 A1 | 8/2003 |

* cited by examiner

*Primary Examiner*—Elvis O. Price
(74) *Attorney, Agent, or Firm*—Birch, Stewart, Kolasch & Birch, LLP

(57) ABSTRACT

A compound represented by the following formula (1) or a salt thereof:

(1)

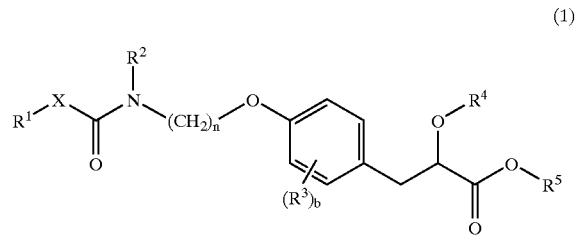

wherein $R^1$ represents a $C_{1-12}$ alkyl group, phenyl group, 1-naphthyl group and the like, $R^2$ represents a $C_{2-12}$ alkyl group, $(R^3)_b$ represents 0 to 4 substituents such as a halogen atom, $R^4$ represents a lower alkyl group, $R^5$ represents hydrogen atom or a lower alkyl group, n represents an integer from 2 to 4, and X represents —NH— or —O—, which has superior hypoglycemic action, hypolipidemic action and total cholesterol reducing action, and is useful as an active ingredient of a medicament for prophylactic and/or therapeutic treatment of diseases including diabetes mellitus, hyperlipidemia and the like.

25 Claims, No Drawings

PROPIONIC ACID DERIVATIVES

This application claims the benefit of 60/358,328 filed Feb. 22, 2002.

TECHNICAL FIELD

The present invention relates to novel propionic acid derivatives which improve diabetes mellitus and/or hyperlipidemia and the like and also to pharmaceutical compositions comprising the same.

BACKGROUND ART

For therapeutic treatment of diabetes mellitus, insulin preparations as injections or preparations of biguanide such as metformin hydrochloride or sulfonylurea such as tolbutamide as oral preparations have been conventionally used. However, the insulin preparations are inconvenient upon use as injections, whilst the biguanide preparations as oral preparations cause lactic acidosis and the sulfonylurea preparations have an adverse effect of severe hypoglycemia. Recently, thiazolidine-2,4-dione derivatives such as troglitazone (European Patent No. 139421), pioglitazone (European Patent No. 193256) and rosiglitazone (U.S. Pat. No. 5,002,953) have been focused, which are based on a novel mode of action of improvement of incompetence of insulin (insulin resistance) and free from the aforementioned adverse effects. However, troglitazone, pioglitazone and rosiglitazone have been reported to have side effects such as weight gain and edema, and troglitazone also has considerable problems, such as commercial distribution thereof has been discontinued due to high liver toxicity (J. Med. Chem., 35, 2617–2626, 1992). For these reasons, several thiazolidine-2,4-dione derivatives have been reported as described in Japanese Patent Unexamined Publication (Kokai) Nos. 10-139768 and 9-100280. However, no satisfactory therapeutic agent for insulin resistant diabetes mellitus is available at present.

Hyperlipidemia is a state of higher blood levels of triglyceride, cholesterol and the like than normal levels, and considered as an object of therapeutic treatment because the disease is a major risk factor of ischemic diseases. As hyperlipidemia is known to cause atherosclerosis, reduction of blood cholesterol level and/or blood triglyceride level is particularly effective for prophylaxis and treatment of atherosclerosis. Atherosclerosis is also known as a cause of myocardial infarction, cerebral thrombosis, peripheral artery obstruction, and atherosclerosis obliterans (Nippon Rinsho, Hyperlipidemia (First volume), 529–629, 2001).

As therapeutic agents for hyperlipidemia, fibrate-type drugs (for example, clofibrate, fenofibrate, bezafibrate) and statin-type drugs have been widely used. However, the fibrate-type drugs have insufficient cholesterol reducing effect, and the statin-type drugs have insufficient triglyceride decreasing effect. Moreover, the fibrate-type drugs are reported to have various side effects such as gastrointesitinal disorder, eruptions, headache, liver function failure, renal function failure, and biliary calculus. Furthermore, as the side effects of the statin-type drugs, rhabdomyolysis, myopathy, liver function failure, diarrhea, constipation and the like have been reported, and among them, rhabdomyolysis has been particularly problematic (Clin. Pharm. Ther., 69, 340–345, 2001; Nuc. Med. Commun., 22, 575–578, 2001; Ann. Pharmacoth., 35, 908–917, 2001). For these reasons, no satisfactory therapeutic agent for hyperlipidemia is available at present.

DISCLOSURE OF THE INVENTION

It is desired to provide novel and useful medicaments which can be used as therapeutic and prophylactic agents for diabetes mellitus and/or hyperlipidemia.

In order to achieve the aforementioned object, the inventors of the present invention synthesized variety of compounds and studied their activities. As a result, they found that compounds represented by the following formula (1) had extremely potent hypoglycemic action and reducing action on serum triglyceride at small doses in pathologic mice with obesity, diabetes mellitus, and hyperlipidemia, and they were useful as hypoglycemic agents and/or agents for reducing triglyceride and/or agents for reducing total cholesterol, in particular, as agents for therapeutic and/or prophylactic treatment of diabetes mellitus, hyperlipidemia and the like, and thus the present invention was achieved.

The present invention thus provides compounds represented by the following formula (1) or salts thereof:

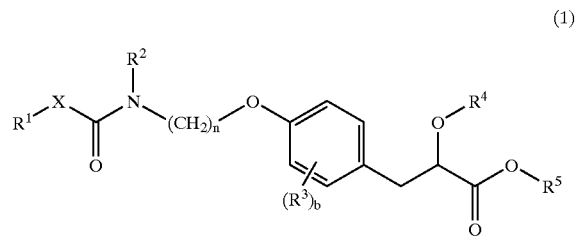

(1)

wherein $R^1$ represents a $C_{1-12}$ alkyl group which may be substituted with one or more substituents selected from the group consisting of a halogen atom, a lower alkoxyl group, and a phenyl group which may be substituted with one or more halogen atoms or a group represented by the following formula (1-1):

(1-1)

wherein $(R^6)_a$ represents "a" substituents ("a" is an integer from 0 to 5) selected from the group consisting of a halogen atom, a lower alkyl group, a lower alkoxyl group, a lower alkylthio group, nitro group, a lower alkoxycarbonyl group, cyano group, trifluoromethyl group, trifluoromethoxy group, and a phenyloxy group, which may be the same or different, or a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, $R^2$ represents a $C_{2-12}$ alkyl group which may be substituted with a substituent selected from the group consisting of a lower alkoxyl group, an aryloxy group, an aralkyloxy group, a lower alkylthio group, an arylthio group, an aralkylthio group, and a phenyl group, wherein $R^2$ may be further substituted with one or more halogen atoms provided that the methylene group in $R^2$, except that binds to the nitrogen atom, may be substituted with one or more halogen atoms, $(R^3)_b$ represents "b" substituents ("b" is an integer from 0 to 4) selected from the group consisting of a halogen atom, a lower alkyl group, and a lower alkoxyl group, which may be identical or different, $R^4$ represents a lower alkyl group, $R^5$ represents hydrogen atom or a lower alkyl group, "n" represents an integer from 2 to 4, and X represents —NH— or —O—, and From another aspect, there are provided medicaments comprising a compound of the aforementioned formula (1) or a pharmaceutically acceptable salt thereof as an active ingredient. These medicaments have, for example, hypoglycemic action, reducing action on triglyceride, and reducing action on total cholesterol, and are useful as medicaments for therapeutic and/or prophylactic treatment of diabetes mellitus, hyperlipidemia and the like. The present invention also provides use of the compounds represented by the aforementioned formula (1) or salts thereof for manufacture of the aforementioned medicaments.

From other aspects, the present invention provides methods for reducing blood glucose, which comprise the step of administering an effective amount of a compound represented by the aforementioned formula (1) or a pharmaceutically acceptable salt thereof to a mammal including human; methods for reducing triglyceride, which comprise the step of administering an effective amount of a compound represented by the aforementioned formula (1) or a pharmaceutically acceptable salt thereof to a mammal including human; and methods for reducing total cholesterol, which comprises the step of administering an effective amount of a compound represented by the aforementioned formula (1) or a pharmaceutically acceptable salt thereof to a mammal including human.

BEST MODE FOR CARRYING OUT THE INVENTION $R^1$ in the formula (1) represents a $C_{1-12}$ alkyl group, a group represented by the formula (1-1), or a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group. Among them, $R^1$ is preferably a $C_{1-12}$ alkyl group, a group represented by the formula (1-1), or 5-indanyl group.

Examples of $R^1$ include, for example, a $C_{1-12}$ alkyl group which may be substituted with one or more substituents selected from the group consisting of a halogen atom, a lower alkoxyl group, and a phenyl group which may be substituted with one or more halogen atoms.

Examples of the halogen atom substituting on the $C_{1-12}$ alkyl group include, for example, fluorine, chlorine, bromine, and iodine. Among them, fluorine and chlorine are preferred, and particularly preferred is fluorine.

The lower alkoxyl group consists of a lower alkyl group bonding to oxygen atom, and examples of the lower alkyl group include, for example, a group of a linear or branched saturated hydrocarbon having 1 to 5 carbon atoms. The lower alkoxyl group substituting on the $C_{1-12}$ alkyl group is preferably, for example, methoxy group, ethoxy group, or propoxy group, particularly preferably methoxy group.

Further, when the aforementioned $C_{1-12}$ alkyl group is substituted with a phenyl group which may be substituted with one or more halogen atoms, the phenyl group may be substituted with a halogen atom, or may be unsubstituted. Unsubstituted phenyl group is preferred, and a substituted phenyl group is also suitable. When the phenyl group is substituted with a halogen atom, a kind of the halogen atom is any one of fluorine, chlorine, bromine, and iodine. Preferred kinds of the halogen atom are fluorine and chlorine. More preferred is fluorine. The number of the halogen atom(s) is an integer from 1 to 5. The number may preferably be 1, 2, or 3, and more preferably be 1 or 2. As for the substitution position of the halogen atom, when the carbon atom of the phenyl group that forms a bonding to X is regarded as 1-position, the substitution position may be 2-, 3-, 4-, 5- or 6-position. When the number of the halogen atom is 1, the substitution position is, for example, preferably 2-, 3- or 4-position, more preferably 3- or 4-position. When the number of the halogen atoms is 2, one of the substitution positions is preferably 2-, 3- or 4-position, more preferably 3- or 4-position.

The $C_{1-12}$ alkyl group of the $C_{1-12}$ alkyl group which may be substituted with one or more of the substituents mentioned above include a saturated hydrocarbon having 1 to 12 carbon atoms, and the saturated hydrocarbon structure may contain a branched or cyclic structure. Preferred examples include, for example, methyl group, ethyl group, propyl group, butyl group, isopropyl group, isobutyl group, 1-methylpropyl group, t-butyl group, 3-methylbutyl group, 2,2-dimethylpropyl group, cyclopentyl group, cyclohexyl group, cycloheptyl group, cyclohexylmethyl group and the like. Among them, particularly preferred alkyl groups are methyl group, ethyl group, propyl group, butyl group, isopropyl group, isobutyl group, t-butyl group, 1-methylpropyl group, 2,2-dimethylpropyl group, cyclopentyl group, and cyclohexyl group. The $C_{1-12}$ alkyl group may be substituted, and an unsubstituted $C_{1-12}$ alkyl group is also suitable. When there are one or more substituents, types of the substituents may be those mentioned above, and the number of the substituent(s) is an integer from 1 to 20, preferably from 1 to 5, more preferably from 1 to 3. When the substituent is a lower alkoxyl group or a phenyl group which may be substituted with one or more halogen atoms, the number of the substituent is preferably 1. As for the substitution position of the substituent, when the carbon atoms of the alkyl group is defined 1-, 2-, 3-position and so on from the carbon atom that forms a bond, the substitution position is, for example, preferably 1-, 2- or 3-position, more preferably 2- or 3-position.

More specifically, preferred examples of the $C_{1-12}$ alkyl group which may be substituted with one or more substituents selected from the group consisting of a halogen atom, a lower alkoxyl group, and a phenyl group which may be substituted with one or more halogen atoms include methyl group, ethyl group, propyl group, butyl group, isopropyl group, isobutyl group, 1-methylpropyl group, t-butyl group, 3-methylbutyl group, 2,2-dimethylpropyl group, cyclopentyl group, cyclohexyl group, cycloheptyl group, cyclohexylmethyl group and the like. Further, 2,2,2-trifluoroethyl group, 2,2-difluoropropyl group, 2,2-difluorobutyl group, 2-methoxyethyl group, 2-ethoxyethyl group, 3-methoxypropyl group, 3-ethoxypropyl group, benzyl group, 2-phenylethyl group, 4-fluorobenzyl group, 4-chlorobenzyl group, 4-bromobenzyl group, 2,4-difluorobenzyl group, 3,5-difluorobenzyl group, 2-(4-fluorophenyl)ethyl group, 2-(4-chlorophenyl)ethyl group, 2-(4-bromophenyl)ethyl group, 2-(2,4-difluorophenyl)ethyl group and 2-(3,5-difluorophenyl)ethyl group are preferred. Furthermore, methyl group, ethyl group, propyl group, butyl group, isopropyl group, isobutyl group, t-butyl group, 1-methylpropyl group, 2,2-dimethylpropyl group, cyclopentyl group, and cyclohexyl group are particularly preferred, and 2-methoxyethyl group, benzyl group, 2-phenylethyl group and 2,2,2-trifluoroethyl group are also particularly preferred examples.

It is also preferred that $R^1$ is a group represented by the formula (1-1). In the formula (1-1), $(R^6)_a$ represents "a" ("a" is an integer from 0 to 5) of substituents selected from the group consisting of a halogen atom, a lower alkyl group, a lower alkoxyl group, a lower alkylthio group, nitro group, a lower alkoxycarbonyl group, cyano group, trifluoromethyl group, trifluoromethoxy group and phenyloxy group, which may be different from each other. Examples of the halogen atom include fluorine, chlorine, bromine, and iodine. Among them, fluorine, chlorine, and bromine are preferred, and fluorine and chlorine are particularly preferred examples. Examples of the lower alkyl group include a group of a linear or branched saturated hydrocarbon having 1 to 5 carbon atoms. Preferred are methyl group, ethyl group, propyl group, isopropyl group, butyl group, 2-methylpropyl group, and t-butyl group, and particularly preferred examples are methyl group and isopropyl group. The lower alkoxy group is a group consisting of a lower alkyl group bonding to oxygen atom, and examples of the lower alkyl group include a group of linear or branched saturated hydrocarbon having 1 to 5 carbon atoms. Thus, preferred examples of the lower alkoxyl group are, for example, methoxy group, ethoxy group, and propoxy group. A particularly preferred example is methoxy group. The lower alkylthio group is a group consisting of a lower alkyl group bonding to sulfur atom, and examples of the lower alkyl group include a group of linear or branched saturated hydrocarbon having 1 to 5 carbon atoms. Thus, preferred examples of lower alkylthio group include, for example, methylthio group, ethylthio group, and propylthio group. A particularly preferred example is methylthio group. The lower alkoxycarbonyl group is a group consisting of a lower alkyl group bonding to an ester bond (—O(C=O)—), and examples of the lower alkyl group include a group of linear or branched saturated hydrocarbon having 1 to 5 carbon atoms, provided that, in the lower alkoxycarbonyl group, the chemical bond deriving from the oxygen atom, among the two chemical bonds of the ester bond, binds to the lower alkyl group. Preferred examples of the lower alkoxycarbonyl group include, for example, methoxycarbonyl group, ethoxycarbonyl group, and propoxycarbonyl group. A particularly preferred example is methoxycarbonyl group. When $R^6$ is a group selected from a lower alkyl group, a lower alkoxyl group, a lower alkylthio group, and a lower alkoxycarbonyl group, and when two or more of $R^6$ are present, the lower alkyl moieties of two of the substituents may combine together to form a ring structure. Examples of the group represented by the formula (1-1) having such a structure include 3,4-(methylenedioxy)phenyl group and the like. Examples of the number of the substituents, "a", include an integer from 0 to 5. When "a" is 0, it is meant that there is no substitution with $R^6$, and consequently $R^1$ is phenyl group. When "a" is 1, it is meant that there is one substituent represented by $R^6$. When "a" is an integer from 2 to 5, it is meant that there are two or more substituents represented by $R^6$, and the substituents may be the same or different. Preferably, "a" is 0, 1, 2, or 3, most preferably 0, 1, or 2. As for the substitution position, when the carbon atom that forms a bonding to X is regarded as 1-position, the substitution position may be 2-, 3-, 4-, 5- or 6-position. When "a" is 1, a preferred substitution position is preferably 3- or 4-position, and when "a" is 2 or more, preferred substituting positions are a plurality of substitution positions including 3- and 4-positions, especially 4-position.

More specifically, preferred examples of the group represented by the formula (1-1) include phenyl group, 2,4-difluorophenyl group, 3,4-difluorophenyl group, 2-fluorophenyl group, 3-fluorophenyl group, 4-fluorophenyl group, 4-bromophenyl group, 2-chlorophenyl group, 4-chlorophenyl group, 2,4-dichlorophenyl group, 4-nitrophenyl group, 4-isopropylphenyl group, 4-phenyloxyphenyl group, 2-methylphenyl group, 3-methylphenyl group, 4-methylphenyl group, 2,4,5-trimethylphenyl group, 2,4,6-trimethylphenyl group, 2-trifluoromethylphenyl group, 3-trifluoromethylphenyl group, 4-trifluoromethylphenyl group, 2-trifluoromethoxyphenyl group, 4-trifluoromethoxyphenyl group, 3-cyanophenyl group, 4-cyanophenyl group, 2-methoxyphenyl group, 3-methoxyphenyl group, 4-methoxyphenyl group, 4-methyl-3-nitrophenyl group, 2-methoxy-5-methylphenyl group and 3,4-(methylenedioxy)phenyl group. Further, particularly preferred are phenyl group, 2,4-difluorophenyl group, 3,4-difluorophenyl group, 2-fluorophenyl group, 3-fluorophenyl group, 4-fluorophenyl group, 4-bromophenyl group, 2-chlorophenyl group, 4-chlorophenyl group, 2,4-dichlorophenyl group, 4-nitrophenyl group, 4-isopropylphenyl group, 4-phenyloxyphenyl group, 2-methylphenyl group, 3-methylphenyl group, 4-methylphenyl group, 2,4,5-trimethylphenyl group, 2,4,6-trimethylphenyl group, 2-trifluoromethylphenyl group, 3-trifluoromethylphenyl group, 4-trifluoromethylphenyl group, 2-trifluoromethoxyphenyl group, 4-trifluoromethoxyphenyl group, 2-methoxyphenyl group, 3-methoxyphenyl group, 4-methoxyphenyl group, 4-methyl-3-nitrophenyl group, 2-methoxy-5-methylphenyl group and 3,4-(methylenedioxy)phenyl group. Most preferred examples are phenyl group, 2,4-difluorophenyl group, 3,4-difluorophenyl group, 2-fluorophenyl group, 3-fluorophenyl group, 4-fluorophenyl group, 4-bromophenyl group, 2-chlorophenyl group, 4-chlorophenyl group, 2,4-dichlorophenyl group, 4-isopropylphenyl group and 3,4-(methylenedioxy)phenyl group.

Furthermore, $R^1$ is also preferably a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, and particularly preferred examples include 5-indanyl group, 3-butenyl group, and 2-propynyl group.

More specifically, preferred examples of $R^1$ include, for example, methyl group, ethyl group, propyl group, butyl group, isopropyl group, isobutyl group, 1-methylpropyl group, t-butyl group, 3-methylbutyl group, 2,2-dimethylpropyl group, cyclopentyl group, cyclohexyl group, cycloheptyl group, cyclohexylmethyl group, 2,2,2-trifluoroethyl group, 2,2-difluoropropyl group, 2,2-difluorobutyl group, 2-methoxyethyl group, 2-ethoxyethyl group, 3-methoxypropyl group, 3-ethoxypropyl group, benzyl group, 2-phenylethyl group, 4-fluorobenzyl group, 4-chlorobenzyl group, 4-bromobenzyl group, 2,4-difluorobenzyl group, 3,5-difluorobenzyl group, 2-(4-fluorophenyl)ethyl group, 2-(4-chlorophenyl)ethyl group, 2-(4-bromophenyl)ethyl group, 2-(2,4-difluorophenyl)ethyl group, 2-(3,5-difluorophenyl)ethyl group, phenyl group, 2,4-difluorophenyl group, 3,4-difluorophenyl group, 2-fluorophenyl group, 3-fluorophenyl group, 4-fluorophenyl group, 4-bromophenyl group, 2-chlorophenyl group, 4-chlorophenyl group, 2,4-dichlorophenyl group, 4-nitrophenyl group, 4-isopropylphenyl group, 4-phenyloxyphenyl group, 2-methylphenyl group, 3-methylphenyl group, 4-methylphenyl group, 2,4,5-trimethylphenyl group, 2,4,6-trimethylphenyl group, 2-trifluoromethylphenyl group, 3-trifluoromethylphenyl group, 4-trifluoromethylphenyl group, 2-trifluoromethoxyphenyl group, 4-trifluoromethoxyphenyl group, 3-cyanophenyl group, 4-cyanophenyl group, 2-methoxyphenyl group, 3-methoxyphenyl group, 4-methoxyphenyl group, 4-methyl-3-nitrophenyl group, 2-methoxy-5-methylphenyl group, 3,4-(methylenedioxy)phenyl group, 1-naphthyl group, 2-naphthyl group, 5-indanyl group, 5,6,7,8-tetrahydronaphthalen-2-yl group, allyl group, 3-butenyl group, and 2-propynyl group, and particularly preferred examples include methyl group, ethyl group, propyl group, butyl group, isopropyl group, isobutyl group, t-butyl group, 1-methylpropyl group, 2,2-dimethylpropyl group, cyclopentyl group, cyclohexyl group, 2-methoxyethyl group, benzyl group, 2-phenylethyl group, 2,2,2-trifluoroethyl group, phenyl group, 2,4-difluorophenyl group, 3,4-difluorophenyl group, 2-fluorophenyl group, 3-fluorophenyl group, 4-fluorophenyl group, 4-bromophenyl group, 2-chlorophenyl group, 4-chlorophenyl group, 2,4-dichlorophenyl group, 4-nitrophenyl group, 4-isopropylphenyl group, 4-phenyloxyphenyl group, 2-methylphenyl group, 3-methylphenyl group, 4-methylphenyl group, 2,4,5-trimethylphenyl group, 2,4,6-trimethylphenyl group, 2-trifluoromethylphenyl group, 3-trifluoromethylphenyl group, 4-trifluoromethylphenyl group, 2-trifluoromethoxyphenyl group, 4-trifluoromethoxyphenyl group, 2-methoxyphenyl group, 3-methoxyphenyl group, 4-methoxyphenyl group, 4-methyl-3-nitrophenyl group, 2-methoxy-5-methylphenyl group, 3,4-(methylenedioxy)phenyl group, 1-naphthyl group, 2-naphthyl group, 5-indanyl group, 5,6,7,8-tetrahydronaphthalen-2-yl group, allyl group, 3-butenyl group, and 2-propynyl group. Further, most preferred examples include methyl group, ethyl group, propyl group, butyl group, isopropyl group, isobutyl group, benzyl group, 2,2,2-trifluoroethyl group, phenyl group, 2,4-difluorophenyl group, 3,4-difluorophenyl group, 2-fluorophenyl group, 3-fluorophenyl group, 4-fluorophenyl group, 4-bromophenyl group, 2-chlorophenyl group, 4-chlorophenyl group, 2,4-dichlorophenyl group, 4-isopropylphenyl group, 3,4-(methylenedioxy)phenyl group, 5-indanyl group, 3-butenyl group, and 2-propynyl group.

Examples of $R^2$ include a $C_{2-12}$ alkyl group which may be substituted with a substituent selected from the group consisting of a lower alkoxyl group, an aryloxy group, an aralkyloxy group, a lower alkylthio group, an arylthio group, an aralkylthio group, and a phenyl group ($R^2$ may be substituted with one more or more halogen atoms, except for the methylene group in $R^2$ that binds to the nitrogen atom).

The $C_{2-12}$ alkyl group represented by $R^2$ may be, for example, a group of a linear or branched saturated hydrocarbon having 2 to 12 carbon atoms or saturated hydrocarbon having 2 to 12 carbon atoms and containing a cyclic structure. However, the carbon atom in the $C_{2-12}$ alkyl group adjacent to the nitrogen atom is not involved in any branched or cyclic structure, and constitutes methylene carbon (—$CH_2$—). Specifically, examples of the $C_{2-12}$ alkyl group include, for example, ethyl group, propyl group, butyl group, pentyl group, hexyl group, heptyl group, octyl group, nonyl group, decyl group, undecyl group, dodecyl group, 2-methylpropyl group, 3-methylbutyl group, 4-methylpropyl group, 2-ethylbutyl group, 2,2-dimethylbutyl group, 2-propylpentyl group, cyclopropylmethyl group, cyclobutylmethyl group, cyclopentylmethyl group, cyclohexylmethyl group, 2-cyclopentylethyl group, 3-cyclohexylpropyl group, and 4-cyclohexylbutyl group. Among them, preferred are ethyl group, propyl group, butyl group, pentyl group, hexyl group, heptyl group, octyl group, nonyl group, 3-methylbutyl group, 4-methylpentyl group, 2,2-dimethylbutyl group, 2-cyclopentylethyl group, 3-cyclohexylpropyl group, and 4-cyclohexylbutyl group. More preferred examples are ethyl group, propyl group, pentyl group, hexyl group, heptyl group, octyl group, 4-methylpentyl group, 2,2-dimethylbutyl group, 3-cyclohexylpropyl group, and 4-cyclohexylbutyl group.

When $R^2$ is substituted, preferred examples include ethyl group, propyl group, butyl group, pentyl group, and 2-methylpropyl group. Particularly preferred are ethyl group and propyl group. When $R^2$ is not substituted, preferred examples include butyl group, pentyl group, hexyl group, heptyl group, octyl group, nonyl group, 3-methylbutyl group, 4-methylpentyl group, 2,2-dimethylbutyl group, 2-cyclopentylethyl group, 3-cyclohexylpropyl group, and 4-cyclohexylbutyl group, and more preferred examples include pentyl group, hexyl group, heptyl group, octyl group, 4-methylpentyl group, 2,2-dimethylbutyl group, 3-cyclohexylpropyl group, and 4-cyclohexylbutyl group.

The $C_{2-12}$ alkyl group may be substituted with the aforementioned substituents. That is, the lower alkoxyl group among the aforementioned substituents has the same meaning as explained above, and preferred are, for example, methoxy group, ethoxy group, propoxy group, butoxy group, and pentyloxy group. Particularly preferred examples are ethoxy group, propoxy group, and butoxy group. Further, examples of the aryloxy group among the aforementioned substituents include a group consisting of an aromatic ring bonding to oxygen atom, and the group may contain nitrogen, sulfur or oxygen as a hetero element in addition to carbon and hydrogen as ring constituting elements. Example of the aryloxy group include, for example, phenoxy group, 3-pyridyloxy group, 4-pyridyloxy group, 2-thienyloxy group, 3-thienyloxy group, 2-furyloxy group and 3-furyloxy group. Preferred are phenoxy group, 2-thienyloxy group, 3-thienyloxy group, 2-furyloxy group, and 3-furyloxy group. A particularly preferred example is phenoxy group. The aralkyloxy group is a group consisting of, for example, aralkyl binding to oxygen atom, and the aralkyl has a structure consisting of an aromatic cyclic substituent binding to a lower alkyl group. Thus, examples of the aralkyloxy group include benzyloxy group, 2-phenylethyloxy group, 1-phenylethyloxy group, 3-phenylpropyloxy group, and 2-(4-pyridyl)ethyloxy group. Preferred are benzyloxy group, 2-phenylethyloxy group, and 3-phenylpropyloxy group. More preferred examples are benzyloxy group and 2-phenylethyloxy group. The lower alkylthio group has the same meaning as defined above. For example, methylthio group, ethylthio group, propylthio group, butylthio group, and pentylthio group are preferred, and particularly preferred examples are ethylthio group, propylthio group, and butylthio group. Examples of the arylthio group include, for example, a group consisting of an aromatic ring binding to sulfur atom, and the group may contain nitrogen, sulfur or oxygen as a hetero element in addition to carbon and hydrogen as ring constituting elements. Preferred examples of the arylthio group include phenylthio group and 4-pyridylthio group. A particularly preferred example is phenylthio group. The aralkylthio group is a group consisting of aralkyl binding to sulfur atom, and preferred examples of the aralkyl usually include those having a structure where a lower alkyl group is further substituted with an aromatic cyclic substituent. Examples of the aralkylthio group include benzylthio group, 2-phenylethylthio group, 1-phenylethylthio group, 3-phenylpropylthio group, and 2-(4-pyridyl) ethylthio group. Preferred examples are benzylthio group, 2-phenylethylthio group, and 3-phenylpropylthio group, and more preferred examples are benzylthio group and 2-phenylethylthio group.

When the $C_{2-12}$ alkyl group is substituted with the aforementioned substituents, the number of the substituents is not particularly limited so long as the number is not more than the substitutable number. The number is usually an integer from 1 to 4, preferably 1 or 2, particularly preferably 1. As for the substitution position, when the positions of the carbon atoms are defined 1-, 2-, . . . n-positions from the terminal carbon atom on the side of bonding to the nitrogen atom (the n-position is the position of the carbon atom most distal from the bonding, and therefore it means 2-position for ethyl group, or 3-position for propyl group), the substitution position is preferably between 2-position and n-position, particularly preferably n-position or (n−1)-position.

Further, $R^2$ may be substituted with one or more halogen atoms, except for the methylene group in $R^2$ that binds to the nitrogen atom. Examples of the halogen atom include fluorine, chlorine, bromine, and iodine. Fluorine, chlorine, and bromine are preferred, and fluorine and chlorine are more preferred. The number of the halogen atoms is not particularly limited so long as the number is substitutable. For example, the number is usually 1 to 15, preferably 1 to 10, more preferably 1 to 5. Substitution positions of the halogen atoms may be any positions in the alkyl moiety of $R^2$, or any positions in the moieties of substituents. Further, the substitution positions may include the both types.

More specifically, examples of $R^2$ include ethyl group, propyl group, butyl group, pentyl group, hexyl group, heptyl group, octyl group, nonyl group, decyl group, undecyl group, dodecyl group, 2-methylpropyl group, 3-methylbutyl group, 4-methylpropyl group, 2-ethylbutyl group, 2,2-dimethylbutyl group, 2-propylpentyl group, cyclopropylmethyl group, cyclobutylmethyl group, cyclopentylmethyl group, cyclohexylmethyl group, 2-cyclopentylethyl group, 3-cyclohexylpropyl group, 4-cyclohexylbutyl group and the like. Further, examples also include 2-methoxyethyl group, 2-ethoxyethyl group, 2-propoxyethyl group, 2-butoxyethyl group, 2-pentyloxyethyl group, 3-methoxypropyl group, 3-ethoxypropyl group, 3-propoxypropyl group, 3-butoxypropyl group, 3-pentyloxypropyl group, 2-methylthioethyl group, 2-ethylthioethyl group, 2-propylthioethyl group, 2-butylthioethyl group, 2-pentylthioethyl group, 3-methylthiopropyl group, 3-ethylthiopropyl group, 3-propylthiopropyl group, 3-butylthiopropyl group, 3-pentylthiopropyl group, 2-phenoxyethyl group, 3-phenoxypropyl group, 4-phenoxybutyl group, 5-phenoxypentyl group, 2-benzyloxyethyl group, 3-benzyloxypropyl group, 4-benzyloxybutyl group, 5-benzyloxypentyl group, 2-(2-phenylethoxy)ethyl group, 3-(2-phenylethoxy)propyl group, 4-(2-phenylethoxy)butyl group, 5-(2-phenylethoxy)pentyl group, 2-(3-phenylpropyloxy)ethyl group, 3-(3-phenylpropyloxy)propyl group, 4-(3-phenylpropyloxy)butyl group, 5-(3-phenylpropyloxy)pentyl group, 2-phenylthioethyl group, 3-phenylthiopropyl group, 4-phenylthiobutyl group, 5-phenylthiopentyl group, 2-benzylthioethyl group, 3-benzylthiopropyl group, 4-benzylthiobutyl group, 5-benzylthiopentyl group, 2-(2-phenylethylthio)ethyl group, 3-(2-phenylethylthio)propyl group, 4-(2-phenylethylthio)butyl group, 5-(2-phenylethylthio)pentyl group, 2-(3-phenylpropylthio)ethyl group, 3-(3-phenylpropylthio)propyl group, 4-(3-phenylpropylthio)butyl group, 5-(3-phenylpropylthio)pentyl group, 2-phenylethyl group, 3-phenylpropyl group, 4-phenylbutyl group, 5-phenylpentyl group and the like. Examples further include 7,7,7-trifluoroheptyl group, 6,6-difluoroheptyl group, 5,5-difluoroheptyl group, 4,4-difluoroheptyl group, 3,3-difluoroheptyl group, 6,6,6-trifluorohexyl group, 5,5-difluorohexyl group, 4,4-difluorohexyl group, 3,3-difluorohexyl group, 5,5,5-trifluoropentyl group, 4,4-difluoropentyl group, 3,3-difluoropentyl group, 6,6,7,7,7-pentafluoroheptyl group, 5,5,6,6-tetrafluoroheptyl group, 4,4,5,5-tetrafluoroheptyl group, 5,5,6,6,7,7,7-heptafluoroheptyl group, 4,4,5,5,6,6-hexafluoroheptyl group, 4,4,5,5,6,6,7,7,7-nonafluoroheptyl group, 3,3,4,4,5,5,6,6,7,7,7-undecafluoroheptyl group, 2,2,3,3,4,4,5,5,6,6,7,7,7-tridecafluoroheptyl group, 5,5,6,6,6-pentafluorohexyl group, 4,4,5,5-tetrafluorohexyl group, 3,3,4,4-tetrafluorohexyl group, 4,4,5,5,6,6,6-heptafluorohexyl group, 3,3,4,4,5,5-hexafluorohexyl group, 3,3,4,4,5,5,6,6,6-nonafluorohexyl group, 2,2,3,3,4,4,5,5,6,6,6-undecafluorohexyl group, 4,4,5,5,5-pentafluoropentyl group, 3,3,4,4-tetrafluoropentyl group, 3,3,4,4,5,5,5-heptafluoropentyl group, 2,2,3,3,4,4,5,5-nonafluoropentyl group, 2-(3,3,3-trifluoropropoxy)ethyl group, 2-(2,2-difluoropropoxy)ethyl group, 2-(1,1-difluoropropoxy)ethyl group, 2-(1,1,2,2,3,3,3-heptafluoropropoxy)ethyl group, 2-(4,4,4-trifluorobutoxy)ethyl group, 2-(3,3-difluorobutoxy)ethyl group, 2-(2,2-difluorobutoxy)ethyl group, 2-(1,1-difluorobutoxy)ethyl group, 2-(1,1,2,2,3,3,4,4,4-nonafluorobutoxy)ethyl group, 2-(5,5,5-trifluoropentyloxy)ethyl group, 2-(4,4-difluoropentyloxy)ethyl group, 2-(3,3-difluoropentyloxy)ethyl group, 2-(2,2-difluoropentyloxy)ethyl group, 2-(1,1-difluoropentyloxy)ethyl group, 2-(1,1,2,2,3,3,4,4,5,5-undecafluoropentyloxy)ethyl group, 3-(2,2,2-trifluoroethoxy)propyl group, 3-(1,1-difluoroethoxy)propyl group, 3-(1,1,2,2,2-pentafluoroethoxy)propyl group, 3-(3,3,3-trifluoropropoxy)propyl group, 3-(2,2-difluoropropoxy)propyl group, 3-(1,1-difluoropropoxy)propyl group, 3-(1,1,2,2,3,3,3-heptafluoropropoxy)propyl group, 2-(4-fluorophenoxy)ethyl group, 2-(3,5-difluorophenoxy)ethyl group, 2-(4-chlorophenoxy)ethyl group, 2-(3,5-dichlorophenoxy)ethyl group, 3-(4-fluorophenoxy)propyl group, 3-(3,5-difluorophenoxy)propyl group, 3-(4-chlorophenoxy)propyl group, 3-(3,5-dichlorophenoxy)propyl group, 4-(4-fluorophenoxy)butyl group, 4-(3,5-difluorophenoxy)butyl group, 4-(4-chlorophenoxy)butyl group, 4-(3,5-dichlorophenoxy)butyl group, 2-(4-fluorobenzyloxy)ethyl group, 2-(3,5-difluorobenzyloxy)ethyl group, 2-(4-chlorobenzyloxy)ethyl group, 2-(3,5-dichlorobenzyloxy)ethyl group, 3-(4-fluorobenzyloxy)propyl group, 3-(3,5-difluorobenzyloxy)propyl group, 3-(4-chlorobenzyloxy)propyl group, 3-(3,5-dichlorobenzyloxy)propyl group, 4-(4-fluorobenzyloxy)butyl group, 4-(3,5-difluorobenzyloxy)butyl group, 4-(4-chlorobenzyloxy)butyl group, 4-(3,5-dichlorobenzyloxy)butyl group, 2-[2-(4-fluorophenyl)ethoxy]ethyl group, 2-[2-(3,5-difluorophenyl)ethoxy]ethyl group, 2-[2-(4-chlorophenyl)ethoxy]ethyl group, 2-[2-(3,5-dichlorophenyl)ethoxy]ethyl group, 2-[2-(4-fluorophenyl)ethoxy]propyl group, 2-[2-(3,5-difluorophenyl)ethoxy]propyl group, 2-[2-(4-chlorophenyl)ethoxy]propyl group, 2-[2-(3,5-dichlorophenyl)ethoxy]propyl group, 2-(3,3,3-trifluoropropylthio)ethyl group, 2-(2,2-difluoropropylthio)ethyl group, 2-(1,1-difluoropropylthio)ethyl group, 2-(1,1,2,2,3,3,3-heptafluoropropylthio)ethyl group, 2-(4,4,4-trifluorobutylthio)ethyl group, 2-(3,3-difluorobutylthio)ethyl group, 2-(2,2-difluorobutylthio)ethyl group, 2-(1,1-difluorobutylthio)ethyl group, 2-(1,1,2,2,3,3,4,4,4-nonafluorobutylthio)ethyl group, 2-(5,5,5-trifluoropentylthio)ethyl group, 2-(4,4-difluoropentylthio)ethyl group, 2-(3,3-difluoropentylthio)ethyl group, 2-(2,2-difluoropentylthio)ethyl group, 2-(1,1-difluoropentylthio)ethyl group, 2-(1,1,2,2,3,3,4,4,5,5-undecafluoropentylthio)ethyl group, 3-(2,2,2-trifluoroethylthio)propyl group, 3-(1,1-difluoroethylthio)propyl group, 3-(1,1,2,2,2-pentafluoroethylthio)propyl group, 3-(3,3,3-trifluoropropylthio)propyl group, 3-(2,2-difluoropropylthio)propyl group, 3-(1,1-difluoropropylthio)

propyl group, 3-(1,1,2,2,3,3,3-heptafluoropropylthio)propyl group, 2-(4-fluorophenylthio)ethyl group, 2-(3,5-difluorophenylthio)ethyl group, 2-(4-chlorophenylthio)ethyl group, 2-(3,5-dichlorophenylthio)ethyl group, 3-(4-fluorophenylthio)propyl group, 3-(3,5-difluorophenylthio)propyl group, 3-(4-chlorophenylthio)propyl group, 3-(3,5-dichlorophenylthio)propyl group, 4-(4-fluorophenylthio)butyl group, 4-(3,5-difluorophenylthio)butyl group, 4-(4-chlorophenylthio)butyl group, 4-(3,5-dichlorophenylthio)butyl group, 2-(4-fluorobenzylthio)ethyl group, 2-(3,5-difluorobenzylthio)ethyl group, 2-(4-chlorobenzylthio)ethyl group, 2-(3,5-dichlorobenzylthio)ethyl group, 3-(4-fluorobenzylthio)propyl group, 3-(3,5-difluorobenzylthio)propyl group, 3-(4-chlorobenzylthio)propyl group, 3-(3,5-dichlorobenzylthio)propyl group, 4-(4-fluorobenzylthio)butyl group, 4-(3,5-difluorobenzylthio)butyl group, 4-(4-chlorobenzylthio)butyl group, 4-(3,5-dichlorobenzylthio)butyl group, 2-[2-(4-fluorophenyl)ethylthio]ethyl group, 2-[2-(3,5-difluorophenyl)ethylthio]ethyl group, 2-[2-(4-chlorophenyl)ethylthio]ethyl group, 2-[2-(3,5-dichlorophenyl)ethylthio]ethyl group, 2-[2-(4-fluorophenyl)ethylthio]propyl group, 2-[2-(3,5-difluorophenyl)ethylthio]propyl group, 2-[2-(4-chlorophenyl)ethylthio]propyl group, 2-[2-(3,5-dichlorophenyl)ethylthio]propyl group, 3-(4-fluorophenyl)propyl group, 3-(3,5-difluorophenyl)propyl group, 3-(4-chlorophenyl)propyl group, 3-(3,5-dichlorophenyl)propyl group, 4-(4-fluorophenyl)butyl group, 4-(3,5-difluorophenyl)butyl group, 4-(4-chlorophenyl)butyl group, 4-(3,5-dichlorophenyl)butyl group, 5-(4-fluorophenyl)pentyl group, 5-(3,5-difluorophenyl)pentyl group, 5-(4-chlorophenyl)pentyl group, 5-(3,5-dichlorophenyl)pentyl group and the like.

Among them, hexyl group, heptyl group, octyl group, nonyl group, 3-methylbutyl group, 4-methylpentyl group, 2,2-dimethylbutyl group, 2-cyclopentylethyl group, 3-cyclohexylpropyl group, 4-cyclohexylbutyl group, 2-propoxyethyl group, 2-pentyloxyethyl group, 2-benzyloxyethyl group, 3-benzyloxypropyl group, 2-phenylthioethyl group, 3-phenylthiopropyl group, 3-phenylpropyl group, 4-phenylbutyl group, 7,7,7-trifluoroheptyl group, 2-(4-chlorophenoxy)ethyl group, and 2-(3,5-dichlorophenoxy)ethyl group are preferred. Further, particularly preferred examples are hexyl group, heptyl group, octyl group, nonyl group, 3-methylbutyl group, 4-methylpentyl group, 2,2-dimethylbutyl group, 2-cyclopentylethyl group, 3-cyclohexylpropyl group, 4-cyclohexylbutyl group, 2-propoxyethyl group, 2-pentyloxyethyl group, 2-benzyloxyethyl group, 3-benzyloxypropyl group, 2-phenylthioethyl group, 3-phenylthiopropyl group, 3-phenylpropyl group, and 4-phenylbutyl group, and most preferred examples are hexyl group, heptyl group, octyl group, 2-butoxyethyl group, 2-propoxyethyl group, 2-butoxyethyl group, and 2-pentyloxyethyl group.

Example of $(R^3)_b$ include "b" substituents ("b" is an integer from 0 to 4) selected from a halogen atom, a lower alkyl group, and a lower alkoxyl group, which may be the same or different. The halogen atom is selected from fluorine, chlorine, bromine, and iodine. Among them, fluorine and chlorine are preferred, and fluorine is more preferred. Examples of the lower alkyl group include groups derived from linear or branched saturated hydrocarbons having 1 to 5 carbon atoms. Among them, methyl group and ethyl group are preferred, and methyl group is more preferred. Examples of the lower alkoxyl group include groups derived from linear or branched saturated hydrocarbons having 1 to 5 carbon atoms which bind to a moiety of a parent molecule by means of an oxygen atom. Among them, methoxy group and ethoxy group are preferred, and methoxy group is more preferred. As for the type of a substituent, a halogen atom and a lower alkoxyl group are preferred among a halogen atom, a lower alkyl group and a lower alkoxyl group, and a lower alkoxyl group is more preferred. The number of substituents (integer of "b") is 0, 1, 2, 3 or 4, preferably 0 or 1, particularly preferably 0. When "b" is 1 or more, and when positions of the carbon to which the methylene carbon binds and the carbon to which oxygen atom binds are defined as 1-position and 4-position, respectively, substitution position(s) of $R^3$ includes 2-, 3-, 5- and 6-position, and the position is preferably 2- or 3-position, more preferably 3-position.

More specifically, $(R^3)_b$ preferably consists of one methoxy group binding to the 3-position, and it is also preferred that "b" is 0 (i.e., no substituent is present).

$R^4$ represents a lower alkyl group. Examples of the lower alkyl group include groups derived from linear or branched saturated hydrocarbons having 1 to 5 carbon atoms. Among them, methyl group, ethyl group, and isopropyl group are preferred, and ethyl group and isopropyl group are more preferred.

$R^5$ represents hydrogen atom or a lower alkyl group. Examples of the lower alkyl group include groups derived from linear or branched saturated hydrocarbons having 1 to 5 carbon atoms. Among them, methyl group, ethyl group and isopropyl group are preferred, and ethyl group is more preferred. $R^5$ is most desirably ethyl group or hydrogen atom.

Symbol "n" is an integer from 2 to 4. "n" is most desirably 2 or 3.

X is —NH— or —O—. X may be —NH—. Most preferably X is —O—.

In the formula (1), the carbon to which —O—$R^4$ binds is an asymmetric carbon, and the carbon atom may have either the "S" or "R" configuration. The configuration of the asymmetric carbon is usually preferably "S" configuration. Further, the compounds represented by the formula (1) may further contain one or more asymmetric carbons' depending on types of substituents. Stereoisomers based on this or these asymmetric carbons such as optical isomers and diastereoisomers in pure forms, any mixtures of the stereoisomers, racemates and the like all fall within the scope of the present invention.

As the compounds having preferred combinations of $R^1$, $R^2$, $(R^3)_b$, $R^4$, $R^5$, n and X among the compounds represented by the formula (1), the following classes of compounds can be exemplified. Salts of these compounds are also preferred.

The compounds wherein $R^1$ is an unsubstituted alkyl group, $R^2$ is an unsubstituted $C_{1-12}$ alkyl group, b of $(R^3)_b$ is 0, $R^4$ is ethyl group, $R^5$ is hydrogen atom, n is 2, and X is —NH—, the compounds wherein $R^1$ is an alkyl group substituted with a substituent selected from the group consisting of a halogen atom, a lower alkoxyl group, and a phenyl group which may be substituted with one or more halogen atoms, $R^2$ is an unsubstituted $C_{1-12}$ alkyl group, b of $(R^3)_b$ is 0, $R^4$ is ethyl group, $R^5$ is hydrogen atom, n is 2, and X is —NH—, the compounds wherein $R^1$ is a substituent represented by the formula (1-1), $R^2$ is an unsubstituted $C_{1-12}$ alkyl group, b of $(R^3)_b$ is 0, $R^4$ is ethyl group, $R^5$ is hydrogen atom, n is 2, and X is —NH—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, $R^2$ is an unsubstituted $C_{1-12}$ alkyl group, b of $(R^3)_b$ is 0, $R^4$ is ethyl group, $R^5$ is hydrogen atom, n is 2, and X is —NH—, the compounds wherein $R^1$ is an unsubstituted alkyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is ethyl group, $R^5$ is hydrogen atom, n is 2, and X is —NH—, the compounds wherein $R^1$ is an alkyl group substituted with a substituent selected from the group consisting of a halogen atom, a lower alkoxyl group, and a phenyl group which may be substituted with one or more halogen atoms, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is ethyl group, $R^5$ is hydrogen atom, n is 2, and X is —NH—, the compounds wherein $R^1$ is a substituent represented by the formula (1-1), $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is ethyl group, $R^5$ is hydrogen atom, n is 2, and X is —NH—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is ethyl group, $R^5$ is hydrogen atom, n is 2, and X is —NH—, the compounds wherein $R^1$ is an unsubstituted alkyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is ethyl group, $R^5$ is hydrogen atom, n is 2, and X is —NH—, the compounds wherein $R^1$ is an alkyl group substituted with a halogen atom, a lower alkoxyl group, or a phenyl group which may be substituted with one or more halogen atoms, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is ethyl group, $R^5$ is hydrogen atom, n is 2, and X is —NH—, the compounds wherein $R^1$ is a substituent represented by the formula (1-1), $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is ethyl group, $R^5$ is hydrogen atom, n is 2, and X is —NH—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is ethyl group, $R^5$ is hydrogen atom, n is 2, and X is —NH—, the compounds wherein $R^1$ is an unsubstituted alkyl group, $R^2$ is an unsubstituted $C_{1-12}$ alkyl group, b of $(R^3)_b$ is 1, $R^4$ is ethyl group, $R^5$ is hydrogen atom, n is 2, and X is —NH—, the compounds wherein $R^1$ is an alkyl group substituted with a substituent selected from the group consisting of a halogen atom, a lower alkoxyl group, and a phenyl group which may be substituted with one or more halogen atoms, $R^2$ is an unsubstituted $C_{1-12}$ alkyl group, b of $(R^3)_b$ is 1, $R^4$ is ethyl group, $R^5$ is hydrogen atom, n is 2, and X is —NH—, the compounds wherein $R^1$ is a substituent represented by the formula (1-1), $R^2$ is an unsubstituted $C_{1-12}$ alkyl group, b of $(R^3)_b$ is 1, $R^4$ is ethyl group, $R^5$ is hydrogen atom, n is 2, and X is —NH—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, $R^2$ is an unsubstituted $C_{1-12}$ alkyl group, b of $(R^3)_b$ is 1, $R^4$ is ethyl group, $R^5$ is hydrogen atom, n is 2, and X is —NH—, the compounds wherein $R^1$ is an unsubstituted alkyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 1, $R^4$ is ethyl group, $R^5$ is hydrogen atom, n is 2, and X is —NH—, the compounds wherein $R^1$ is an alkyl group substituted with a substituent selected from the group consisting of a halogen atom, a lower alkoxyl group, and a phenyl group which may be substituted with one or more halogen atoms, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 1, $R^4$ is ethyl group, $R^5$ is hydrogen atom, n is 2, and X is —NH—, the compounds wherein $R^1$ is a substituent represented by the formula (1-1), $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 1, $R^4$ is ethyl group, $R^5$ is hydrogen atom, n is 2, and X is —NH—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group and 2-propynyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 1, $R^4$ is ethyl group, $R^5$ is hydrogen atom, n is 2, and X is —NH—, the compounds wherein $R^1$ is an unsubstituted alkyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is ethyl group, $R^5$ is hydrogen atom, n is 2, and X is —NH—, the compounds wherein $R^1$ is an alkyl group substituted with a halogen atom, a lower alkoxyl group, or a phenyl group which may be substituted with one or more halogen atoms, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is ethyl group, $R^5$ is hydrogen atom, n is 2, and X is —NH—, the compounds wherein $R^1$ is a substituent represented by the formula (1-1), $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is ethyl group, $R^5$ is hydrogen atom, n is 2, and X is —NH—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is ethyl group, $R^5$ is hydrogen atom, n is 2, and X is —NH—, the compounds wherein $R^1$ is an unsubstituted alkyl group, $R^2$ is an unsubstituted $C_{1-12}$ alkyl group, b of $(R^3)_b$ is 0, $R^4$ is isopropyl group, $R^5$ is hydrogen atom, n is 2, and X is —NH—, the compounds wherein $R^1$ is an alkyl group substituted with a halogen atom, a lower alkoxyl group, or a phenyl group which may be substituted with one or more halogen atoms, $R^2$ is an unsubstituted $C_{1-12}$ alkyl group, b of $(R^3)_b$ is 0, $R^4$ is isopropyl group, $R^5$ is hydrogen atom, n is 2, and X is —NH—, the compounds wherein $R^1$ is a substituent represented by the formula (1-1), $R^2$ is an unsubstituted $C_{1-12}$ alkyl group, b of $(R^3)_b$ is 0, $R^4$ is isopropyl group, $R^5$ is hydrogen atom, n is 2, and X is —NH—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group and 2-propynyl group, $R^2$ is an unsubstituted $C_{1-12}$ alkyl group, b of $(R^3)_b$ is 0, $R^4$ is isopropyl group, $R^5$ is hydrogen atom, n is 2, and X is —NH—, the compounds wherein $R^1$ is an unsubstituted alkyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is isopropyl group, $R^5$ is hydrogen atom, n is 2, and X is —NH—, the compounds wherein $R^1$ is an alkyl group substituted with a substituent selected from the group consisting of a halogen atom, a lower alkoxyl group, and a phenyl group which may be substituted with one or more halogen atoms, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is isopropyl group, $R^5$ is hydrogen atom, n is 2, and X is —NH—, the compounds wherein $R^1$ is a substituent represented by the formula (1-1), $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is isopropyl group, $R^5$ is hydrogen atom, n is 2, and X is —NH—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is isopropyl group, $R^5$ is hydrogen atom, n is 2, and X is —NH—, the compounds wherein $R^1$ is an unsubstituted alkyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is isopropyl group, $R^5$ is hydrogen atom, n is 2, and X is —NH—, the compounds wherein $R^1$ is an alkyl group substituted with a substituent selected from the group consisting of a halogen atom, a lower alkoxyl group, and a phenyl group which may be substituted with one or more halogen atoms, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is isopropyl group, $R^5$ is hydrogen atom, n is 2, and X is —NH—, the compounds wherein $R^1$ is a substituent represented by the formula (1-1), $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is isopropyl group, $R^5$ is hydrogen atom, n is 2, and X is —NH—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group and 2-propynyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is isopropyl group, $R^5$ is hydrogen atom, n is 2, and X is —NH—, the compounds wherein $R^1$ is an unsubstituted alkyl group, $R^2$ is an unsubstituted $C_{1-12}$ alkyl group, b of $(R^3)_b$ is 1, $R^4$ is isopropyl group, $R^5$ is hydrogen atom, n is 2, and X is —NH—, the compounds wherein $R^1$ is an alkyl group substituted with a substituent selected from the group consisting of a halogen atom, a lower alkoxyl group, and a phenyl group which may be substituted with one or more halogen atoms, $R^2$ is an unsubstituted $C_{1-12}$ alkyl group, b of $(R^3)_b$ is 1, $R^4$ is isopropyl group, $R^5$ is hydrogen atom, n is 2, and X is —NH—, the compounds wherein $R^1$ is a substituent represented by the formula (1-1), $R^2$ is an unsubstituted $C_{1-12}$ alkyl group, b of $(R^3)_b$ is 1, $R^4$ is isopropyl group, $R^5$ is hydrogen atom, n is 2, and X is —NH—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, $R^2$ is an unsubstituted $C_{1-12}$ alkyl group, b of $(R^3)_b$ is 1, $R^4$ is isopropyl group, $R^5$ is hydrogen atom, n is 2, and X is —NH—, the compounds wherein $R^1$ is an unsubstituted alkyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 1, $R^4$ is isopropyl group, $R^5$ is hydrogen atom, n is 2, and X is —NH—, the compounds wherein $R^1$ is an alkyl group substituted with a substituent selected from the group consisting of a halogen atom, a lower alkoxyl group, and a phenyl group which may be substituted with one or more halogen atoms, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 1, $R^4$ is isopropyl group, $R^5$ is hydrogen atom, n is 2, and X is —NH—, the compounds wherein $R^1$ is a substituent represented by the formula (1-1), $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 1, $R^4$ is isopropyl group, $R^5$ is hydrogen atom, n is 2, and X is —NH—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 1, $R^4$ is isopropyl group, $R^5$ is hydrogen atom, n is 2, and X is —NH—, the compounds wherein $R^1$ is an unsubstituted alkyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is isopropyl group, $R^5$ is hydrogen atom, n is 2, and X is —NH—, the compounds wherein $R^1$ is an alkyl group substituted with a substituent selected from the group consisting of a halogen atom, a lower alkoxyl group, and a phenyl group which may be substituted with one or more halogen atoms, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is isopropyl group, $R^5$ is hydrogen atom, n is 2, and X is —NH—, the compounds wherein $R^1$ is a substituent represented by the formula (1-1), $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is isopropyl group, $R^5$ is hydrogen atom, n is 2, and X is —NH—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group and 2-propynyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is isopropyl group, $R^5$ is hydrogen atom, n is 2, and X is —NH—, the compounds wherein $R^1$ is an unsubstituted alkyl group, $R^2$ is an unsubstituted $C_{1-12}$ alkyl group, b of $(R^3)_b$ is 0, $R^4$ is ethyl group, $R^5$ is ethyl group, n is 2, and X is —NH—, the compounds wherein $R^1$ is an alkyl group substituted with a substituent selected from the group consisting of a halogen atom, a lower alkoxyl group, and a phenyl group which may be substituted with one or more halogen atoms, $R^2$ is an unsubstituted $C_{1-12}$ alkyl group, b of $(R^3)_b$ is 0, $R^4$ is ethyl group, $R^5$ is ethyl group, n is 2, and X is —NH—, the compounds wherein $R^1$ is a substituent represented by the formula (1-1), $R^2$ is an unsubstituted $C_{1-12}$ alkyl group, b of $(R^3)_b$ is 0, $R^4$ is ethyl group, $R^5$ is ethyl group, n is 2, and X is —NH—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, $R^2$ is an unsubstituted $C_{1-12}$ alkyl group, b of $(R^3)_b$ is 0, $R^4$ is ethyl group, $R^5$ is ethyl group, n is 2, and X is —NH—, the compounds wherein $R^1$ is an unsubstituted alkyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is ethyl group, $R^5$ is ethyl group, n is 2, and X is —NH—, the compounds wherein $R^1$ is an alkyl group substituted with a substituent selected from the group consisting of a halogen atom, a lower alkoxyl group, and a phenyl group which may be substituted with one or more halogen atoms, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is ethyl group, $R^5$ is ethyl group, n is 2, and X is —NH—, the compounds wherein $R^1$ is a substituent represented by the formula (1-1), $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is ethyl group, $R^5$ is ethyl group, n is 2, and X is —NH—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is ethyl group, $R^5$ is ethyl group, n is 2, and X is —NH—, the compounds wherein $R^1$ is an unsubstituted alkyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is ethyl group, $R^5$ is ethyl group, n is 2, and X is —NH—, the compounds wherein $R^1$ is an alkyl group substituted with a substituent selected from the group consisting of a halogen atom, a lower alkoxyl group, and a phenyl group which may be substituted with one or more halogen atoms, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is ethyl group, $R^5$ is ethyl group, n is 2, and X is NH—, the compounds wherein $R^1$ is a substituent represented by the formula (1-1), $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is ethyl group, $R^5$ is ethyl group, n is 2, and X is —NH—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group and 2-propynyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is ethyl group, $R^5$ is ethyl group, n is 2, and X is —NH—, the compounds wherein $R^1$ is an unsubstituted alkyl group, $R^2$ is an unsubstituted $C_{1-12}$ alkyl group, b of $(R^3)_b$ is 1, $R^4$ is ethyl group, $R^5$ is ethyl group, n is 2, and X is —NH—, the compounds wherein $R^1$ is an alkyl group substituted with a substituent selected from the group consisting of a halogen atom, a lower alkoxyl group, and a phenyl group which may be substituted with one or more halogen atoms, $R^2$ is an unsubstituted $C_{1-12}$ alkyl group, b of $(R^3)_b$ is 1, $R^4$ is ethyl group, $R^5$ is ethyl group, n is 2, and X is —NH—, the compounds wherein $R^1$ is a substituent represented by the formula (1-1), $R^2$ is an unsubstituted $C_{1-12}$ alkyl group, b of $(R^3)_b$ is 1, $R^4$ is ethyl group, $R^5$ is ethyl group, n is 2, and X is —NH—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, $R^2$ is an unsubstituted $C_{1-12}$ alkyl group, b of $(R^3)_b$ is 1, $R^4$ is ethyl group, $R^5$ is ethyl group, n is 2, and X is —NH—, the compounds wherein $R^1$ is an unsubstituted alkyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 1, $R^4$ is ethyl group, $R^5$ is ethyl group, n is 2, and X is —NH—, the compounds wherein $R^1$ is an alkyl group substituted with a substituent selected from the group consisting of a halogen atom, a lower alkoxyl group, and a phenyl group which may be substituted with one or more halogen atoms, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 1, $R^4$ is ethyl group, $R^5$ is ethyl group, n is 2, and X is —NH—, the compounds wherein $R^1$ is a substituent represented by the formula (1-1), $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 1, $R^4$ is ethyl group, $R^5$ is ethyl group, n is 2, and X is —NH—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group and 2-propynyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 1, $R^4$ is ethyl group, $R^5$ is ethyl group, n is 2, and X is —NH—, the compounds wherein $R^1$ is an unsubstituted alkyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is ethyl group, $R^5$ is ethyl group, n is 2, and X is —NH—, the compounds wherein $R^1$ is an alkyl group substituted with a substituent selected from the group consisting of a halogen atom, a lower alkoxyl group, and a phenyl group which may be substituted with one or more halogen atoms, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is ethyl group, $R^5$ is ethyl group, n is 2, and X is —NH—, the compounds wherein $R^1$ is a substituent represented by the formula (1-1), $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is ethyl group, $R^5$ is ethyl group, n is 2, and X is —NH—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group and 2-propynyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is ethyl group, $R^5$ is ethyl group, n is 2, and X is —NH—, the compounds wherein $R^1$ is an unsubstituted alkyl group, $R^2$ is an unsubstituted $C_{1-12}$ alkyl group, b of $(R^3)_b$ is 0, $R^4$ is isopropyl group, $R^5$ is ethyl group, n is 2, and X is —NH—, the compounds wherein $R^1$ is an alkyl group substituted with a substituent selected from the group consisting of a halogen atom, a lower alkoxyl group, and a phenyl group which may be substituted with one or more halogen atoms, $R^2$ is an unsubstituted $C_{1-12}$ alkyl group, b of $(R^3)_b$ is 0, $R^4$ is isopropyl group, $R^5$ is ethyl group, n is 2, and X is —NH—, the compounds wherein $R^1$ is a substituent represented by the formula (1-1), $R^2$ is an unsubstituted $C_{1-12}$ alkyl group, b of $(R^3)_b$ is 0, $R^4$ is isopropyl group, $R^5$ is ethyl group, n is 2, and X is —NH—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, $R^2$ is an unsubstituted $C_{1-12}$ alkyl group, b of $(R^3)_b$ is 0, $R^4$ is isopropyl group, $R^5$ is ethyl group, n is 2, and X is —NH—, the compounds wherein $R^1$ is an unsubstituted alkyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is isopropyl group, $R^5$ is ethyl group, n is 2, and X is —NH—, the compounds wherein $R^1$ is an alkyl group substituted with a substituent selected from the group consisting of a halogen atom, a lower alkoxyl group, and a phenyl group which may be substituted with one or more halogen atoms, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is isopropyl group, $R^5$ is ethyl group, n is 2, and X is —NH—, the compounds wherein $R^1$ is a substituent represented by the formula (1-1), $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is isopropyl group, $R^5$ is ethyl group, n is 2, and X is —NH—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is isopropyl group, $R^5$ is ethyl group, n is 2, and X is —NH—, the compounds wherein $R^1$ is an unsubstituted alkyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is isopropyl group, $R^5$ is ethyl group, n is 2, and X is —NH—, the compounds wherein $R^1$ is an alkyl group substituted with a substituent selected from the group consisting of a halogen atom, a lower alkoxyl group, and a phenyl group which may be substituted with one or more halogen atoms, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is isopropyl group, $R^5$ is ethyl group, n is 2, and X is —NH—, the compounds wherein $R^1$ is a substituent represented by the formula (1-1), $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is isopropyl group, $R^5$ is ethyl group, n is 2, and X is —NH—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group and 2-propynyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is isopropyl group, $R^5$ is ethyl group, n is 2, and X is —NH—, the compounds wherein $R^1$ is an unsubstituted alkyl group, $R^2$ is an unsubstituted $C_{1-12}$ alkyl group, b of $(R^3)_b$ is 1, $R^4$ is isopropyl group, $R^5$ is ethyl group, n is 2, and X is —NH—, the compounds wherein $R^1$ is an alkyl group substituted with a substituent selected from the group consisting of a halogen atom, a lower alkoxyl group, and a phenyl group which may be substituted with one or more halogen atoms, $R^2$ is an unsubstituted $C_{1-12}$ alkyl group, b of $(R^3)_b$ is 1, $R^4$ is isopropyl group, $R^5$ is ethyl group, n is 2, and X is —NH—, the compounds wherein $R^1$ is a substituent represented by the formula (1-1), $R^2$ is an unsubstituted $C_{1-12}$ alkyl group, b of $(R^3)_b$ is 1, $R^4$ is isopropyl group, $R^5$ is ethyl group, n is 2, and X is —NH—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, $R^2$ is an unsubstituted $C_{1-12}$ alkyl group, b of $(R^3)_b$ is 1, $R^4$ is isopropyl group, $R^5$ is ethyl group, n is 2, and X is —NH—, the compounds wherein $R^1$ is an unsubstituted alkyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 1, $R^4$ is isopropyl group, $R^5$ is ethyl group, n is 2, and X is —NH—, the compounds wherein $R^1$ is an alkyl group substituted with a substituent selected from the group consisting of a halogen atom, a lower alkoxyl group, and a phenyl group which may be substituted with one or more halogen atoms, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 1, $R^4$ is isopropyl group, $R^5$ is ethyl group, n is 2, and X is —NH—, the compounds wherein $R^1$ is a substituent represented by the formula (1-1), $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 1, $R^4$ is isopropyl group, $R^5$ is ethyl group, n is 2, and X is —NH—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group and 2-propynyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 1, $R^4$ is isopropyl group, $R^5$ is ethyl group, n is 2, and X is NH—, the compounds wherein $R^1$ is an unsubstituted alkyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is isopropyl group, $R^5$ is ethyl group, n is 2, and X is —NH—, the compounds wherein $R^1$ is an alkyl group substituted with a substituent selected from the group consisting of a halogen atom, a lower alkoxyl group, and a phenyl group which may be substituted with one or more halogen atoms, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is isopropyl group, $R^5$ is ethyl group, n is 2, and X is —NH—, the compounds wherein $R^1$ is a substituent represented by the formula (1-1), $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is isopropyl group, $R^5$ is ethyl group, n is 2, and X is —NH—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is isopropyl group, $R^5$ is ethyl group, n is 2, and X is —NH—, the compounds wherein $R^1$ is an unsubstituted alkyl group, $R^2$ is an unsubstituted $C_{1-12}$ alkyl group, b of $(R^3)_b$ is 0, $R^4$ is ethyl group, $R^5$ is hydrogen atom, n is 2, and X is —O—, the compounds wherein $R^1$ is an alkyl group substituted with a substituent selected from the group consisting of a halogen atom, a lower alkoxyl group, and a phenyl group which may be substituted with one or more halogen atoms, $R^2$ is an unsubstituted $C_{1-12}$ alkyl group, b of $(R^3)_b$ is 0, $R^4$ is ethyl group, $R^5$ is hydrogen atom, n is 2, and X is —O—, the compounds wherein $R^1$ is a substituent represented by the formula (1-1), $R^2$ is an unsubstituted $C_{1-12}$ alkyl group, b of $(R^3)_b$ is 0, $R^4$ is ethyl group, $R^5$ is hydrogen atom, n is 2, and X is —O—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, $R^2$ is an unsubstituted $C_{1-12}$ alkyl group, b of $(R^3)_b$ is 0, $R^4$ is ethyl group, $R^5$ is hydrogen atom, n is 2, and X is —O—, the compounds wherein $R^1$ is an unsubstituted alkyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is ethyl group, $R^5$ is hydrogen atom, n is 2, and X is —O—, the compounds wherein $R^1$ is an alkyl group substituted with a substituent selected from the group consisting of a halogen atom, a lower alkoxyl group, and a phenyl group which may be substituted with one or more halogen atoms, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is ethyl group, $R^5$ is hydrogen atom, n is 2, and X is —O—, the compounds wherein $R^1$ is a substituent represented by the formula (1-1), $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is ethyl group, $R^5$ is hydrogen atom, n is 2, and X is —O—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is ethyl group, $R^5$ is hydrogen atom, n is 2, and X is —O—, the compounds wherein $R^1$ is an unsubstituted alkyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is ethyl group, $R^5$ is hydrogen atom, n is 2, and X is —O—, the compounds wherein $R^1$ is an alkyl group substituted with a substituent selected from the group consisting of a halogen atom, a lower alkoxyl group, and a phenyl group which may be substituted with one or more halogen atoms, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is ethyl group, $R^5$ is hydrogen atom, n is 2, and X is —O—, the compounds wherein $R^1$ is a substituent represented by the formula (1-1), $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is ethyl group, $R^5$ is hydrogen atom, n is 2, and X is —O—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is ethyl group, $R^5$ is hydrogen atom, n is 2, and X is —O—, the compounds wherein $R^1$ is an unsubstituted alkyl group, $R^2$ is an unsubstituted $C_{1-12}$ alkyl group, b of $(R^3)_b$ is 1, $R^4$ is ethyl group, $R^5$ is hydrogen atom, n is 2, and X is —O—, the compounds wherein $R^1$ is an alkyl group substituted with a substituent selected from the group consisting of a halogen atom, a lower alkoxyl group, and a phenyl group which may be substituted with one or more halogen atoms, $R^2$ is an unsubstituted $C_{1-12}$ alkyl group, b of $(R^3)_b$ is 1, $R^4$ is ethyl group, $R^5$ is hydrogen atom, n is 2, and X is —O—, the compounds wherein $R^1$ is a substituent represented by the formula (1-1), $R^2$ is an unsubstituted $C_{1-12}$ alkyl group, b of $(R^3)_b$ is 1, $R^4$ is ethyl group, $R^5$ is hydrogen atom, n is 2, and X is —O—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, $R^2$ is an unsubstituted $C_{1-12}$ alkyl group, b of $(R^3)_b$ is 1, $R^4$ is ethyl group, $R^5$ is hydrogen atom, n is 2, and X is —O—, the compounds wherein $R^1$ is an unsubstituted alkyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 1, $R^4$ is ethyl group, $R^5$ is hydrogen atom, n is 2, and X is —O—, the compounds wherein $R^1$ is an alkyl group substituted with a substituent selected from the group consisting of a halogen atom, a lower alkoxyl group, and a phenyl group which may be substituted with one or more halogen atoms, $R^2$ is an alkyl group substituted with a lower alkoxyl group, an aryloxy group, an aralkyloxy group, a lower alkylthio group, an arylthio group, an aralkylthio group, or a phenyl group, b Of $(R^3)_b$ is 1, $R^4$ is ethyl group, $R^5$ is hydrogen atom, n is 2, and X is —O—, the compounds wherein $R^1$ is a substituent represented by the formula (1-1), $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 1, $R^4$ is ethyl group, $R^5$ is hydrogen atom, n is 2, and X is —O—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group and 2-propynyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 1, $R^4$ is ethyl group, $R^5$ is hydrogen atom, n is 2, and X is —O—, the compounds wherein $R^1$ is an unsubstituted alkyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is ethyl group, $R^5$ is hydrogen atom, n is 2, and X is —O—, the compounds wherein $R^1$ is an alkyl group substituted with a substituent selected from the group consisting of a halogen atom, a lower alkoxyl group, and a phenyl group which may be substituted with one or more halogen atoms, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is ethyl group, $R^5$ is hydrogen atom, n is 2, and X is —O—, the compounds wherein $R^1$ is a substituent represented by the formula (1-1), $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is ethyl group, $R^5$ is hydrogen atom, n is 2, and X is —O—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group and 2-propynyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is ethyl group, $R^5$ is hydrogen atom, n is 2, and X is —O—, the compounds wherein $R^1$ is an unsubstituted alkyl group, $R^2$ is an unsubstituted $C_{1-12}$ alkyl group, b of $(R^3)_b$ is 0, $R^4$ is isopropyl group, $R^5$ is hydrogen atom, n is 2, and X is —O—, the compounds wherein $R^1$ is an alkyl group substituted with a substituent selected from the group consisting of a halogen atom, a lower alkoxyl group, and a phenyl group which may be substituted with one or more halogen atoms, $R^2$ is an unsubstituted $C_{1-12}$ alkyl group, b of $(R^3)_b$ is 0, $R^4$ is isopropyl group, $R^5$ is hydrogen atom, n is 2, and X is —O—, the compounds wherein $R^1$ is a substituent represented by the formula (1-1), $R^2$ is an unsubstituted $C_{1-12}$ alkyl group, b of $(R^3)_b$ is 0, $R^4$ is isopropyl group, $R^5$ is hydrogen atom, and n is 2, and X is —O—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, $R^2$ is an unsubstituted $C_{1-12}$ alkyl group, b of $(R^3)_b$ is 0, $R^4$ is isopropyl group, $R^5$ is hydrogen atom, n is 2, and X is —O—, the compounds wherein $R^1$ is an unsubstituted alkyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is isopropyl group, $R^5$ is hydrogen atom, n is 2, and X is —O—, the compounds wherein $R^1$ is an alkyl group substituted with a substituent selected from the group consisting of a halogen atom, a lower alkoxyl group, and a phenyl group which may be substituted with one or more halogen atoms, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is isopropyl group, $R^5$ is hydrogen atom, n is 2, and X is —O—, the compounds wherein $R^1$ is a substituent represented by the formula (1-1), $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is isopropyl group, $R^5$ is hydrogen atom, n is 2, and X is —O—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is isopropyl group, $R^5$ is hydrogen atom, n is 2, and X is —O—, the compounds wherein $R^1$ is an unsubstituted alkyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is isopropyl group, $R^5$ is hydrogen atom, n is 2, and X is —O—, the compounds wherein $R^1$ is an alkyl group substituted with a substituent selected from the group consisting of a halogen atom, a lower alkoxyl group, and a phenyl group which may be substituted with one or more halogen atoms, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is isopropyl group, $R^5$ is hydrogen atom, n is 2, and X is —O—, the compounds wherein $R^1$ is a substituent represented by the formula (1-1), $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is isopropyl group, $R^5$ is hydrogen atom, n is 2, and X is —O—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group and 2-propynyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is isopropyl group, $R^5$ is hydrogen atom, n is 2, and X is —O—, the compounds wherein $R^1$ is an unsubstituted alkyl group, $R^2$ is an unsubstituted $C_{1-12}$ alkyl group, b of $(R^3)_b$ is 1, $R^4$ is isopropyl group, $R^5$ is hydrogen atom, n is 2, and X is —O—, the compounds wherein $R^1$ is an alkyl group substituted with a substituent selected from the group a halogen atom, a lower alkoxyl group, and a phenyl group which may be substituted with one or more halogen atoms, $R^2$ is an unsubstituted $C_{1-12}$ alkyl group, b of $(R^3)_b$ is 1, $R^4$ is isopropyl group, $R^5$ is hydrogen atom, n is 2, and X is —O—, the compounds wherein $R^1$ is a substituent represented by the formula (1-1), $R^2$ is an unsubstituted $C_{1-12}$ alkyl group, b of $(R^3)_b$ is 1, $R^4$ is isopropyl group, $R^5$ is hydrogen atom, n is 2, and X is —O—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group and 2-propynyl group, $R^2$ is an unsubstituted $C_{1-12}$ alkyl group, b of $(R^3)_b$ is 1, $R^4$ is isopropyl group, $R^5$ is hydrogen atom, n is 2, and X is —O—, the compounds wherein $R^1$ is an unsubstituted alkyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 1, $R^4$ is isopropyl group, $R^5$ is hydrogen atom, n is 2, and X is —O—, the compounds wherein $R^1$ is an alkyl group substituted with a substituent selected from the group consisting of a halogen atom, a lower alkoxyl group, and a phenyl group which may be substituted with one or more halogen atoms, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 1, $R^4$ is isopropyl group, $R^5$ is hydrogen atom, n is 2, and X is —O—, the compounds wherein $R^1$ is a substituent represented by the formula (1-1), $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 1, $R^4$ is isopropyl group, $R^5$ is hydrogen atom, n is 2, and X is —O—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group and 2-propynyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 1, $R^4$ is isopropyl group, $R^5$ is hydrogen atom, n is 2, and X is —O—, the compounds wherein $R^1$ is an unsubstituted alkyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is isopropyl group, $R^5$ is hydrogen atom, n is 2, and X is —O—, the compounds wherein $R^1$ is an alkyl group substituted with a substituent selected from the group consisting of a halogen atom, a lower alkoxyl group, and a phenyl group which may be substituted with one or more halogen atoms, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is isopropyl group, $R^5$ is hydrogen atom, n is 2, and X is —O—, the compounds wherein $R^1$ is a substituent represented by the formula (1-1), $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is isopropyl group, $R^5$ is hydrogen atom, n is 2, and X is —O—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group and 2-propynyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is isopropyl group, $R^5$ is hydrogen atom, n is 2, and X is —O—, the compounds wherein $R^1$ is an unsubstituted alkyl group, $R^2$ is an unsubstituted $C_{1-12}$ alkyl group, b of $(R^3)_b$ is 0, $R^4$ is ethyl group, $R^5$ is ethyl group, n is 2, and X is —O—, the compounds wherein $R^1$ is an alkyl group substituted with a substituent selected from the group consisting of a halogen atom, a lower alkoxyl group, and a phenyl group which may be substituted with one or more halogen atoms, $R^2$ is an unsubstituted $C_{1-12}$ alkyl group, b of $(R^3)_b$ is 0, $R^4$ is ethyl group, $R^5$ is ethyl group, n is 2, and X is —O—, the compounds wherein $R^1$ is a substituent represented by the formula (1-1), $R^2$ is an unsubstituted $C_{1-12}$ alkyl group, b of $(R^3)_b$ is 0, $R^4$ is ethyl group, $R^5$ is ethyl group, n is 2, and X is —O—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group and 2-propynyl group, $R^2$ is an unsubstituted $C_{1-12}$ alkyl group, b of $(R^3)_b$ is 0, $R^4$ is ethyl group, $R^5$ is ethyl group, n is 2, and X is —O—, the compounds wherein $R^1$ is an unsubstituted alkyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is ethyl group, $R^5$ is ethyl group, n is 2, and X is —O—, the compounds wherein $R^1$ is an alkyl group substituted with a substituent selected from the group consisting of a halogen atom, a lower alkoxyl group, and a phenyl group which may be substituted with one or more halogen atoms, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is ethyl group, $R^5$ is ethyl group, n is 2, and X is —O—, the compounds wherein $R^1$ is a substituent represented by the formula (1-1), $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is ethyl group, $R^5$ is ethyl group, n is 2, and X is —O—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group and 2-propynyl group, $R^2$ is an alkyl group substituted with a lower-alkoxyl group, an aryloxy group, an aralkyloxy group, a lower alkylthio group, an arylthio group, an aralkylthio group, or a phenyl group, b of $(R^3)_b$ is 0, $R^4$ is ethyl group, $R^5$ is ethyl group, n is 2, and X is —O—, the compounds wherein $R^1$ is an unsubstituted alkyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is ethyl group, $R^5$ is ethyl group, n is 2, and X is —O—, the compounds wherein $R^1$ is an alkyl group substituted with a substituent selected from the group consisting of a halogen atom, a lower alkoxyl group, and a phenyl group which may be substituted with one or more halogen atoms, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is ethyl group, $R^5$ is ethyl group, n is 2, and X is —O—, the compounds wherein $R^1$ is a substituent represented by the formula (1-1), $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is ethyl group, $R^5$ is ethyl group, n is 2, and X is —O—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group and 2-propynyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is ethyl group, $R^5$ is ethyl group, n is 2, and X is —O—, the compounds wherein $R^1$ is an unsubstituted alkyl group, $R^2$ is an unsubstituted $C_{1-12}$ alkyl group, b of $(R^3)_b$ is 1, $R^4$ is ethyl group, $R^5$ is ethyl group, n is 2, and X is —O—, the compounds wherein $R^1$ is an alkyl group substituted with a substituent selected from the group consisting of a halogen atom, a lower alkoxyl group, and a phenyl group which may be substituted with one or more halogen atoms, $R^2$ is an unsubstituted $C_{1-12}$ alkyl group, b of $(R^3)_b$ is 1, $R^4$ is ethyl group, $R^5$ is ethyl group, n is 2, and X is —O—, the compounds wherein $R^1$ is a substituent represented by the formula (1-1), $R^2$ is an unsubstituted $C_{1-12}$ alkyl group, b of $(R^3)_b$ is 1, $R^4$ is ethyl group, $R^5$ is ethyl group, n is 2, and X is —O—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, $R^2$ is an unsubstituted $C_{1-12}$ alkyl group, b of $(R^3)_b$ is 1, $R^4$ is ethyl group, $R^5$ is ethyl group, n is 2, and X is —O—, the compounds wherein $R^1$ is an unsubstituted alkyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 1, $R^4$ is ethyl group, $R^5$ is ethyl group, n is 2, and X is —O—, the compounds wherein $R^1$ is an alkyl group substituted with a substituent selected from the group consisting of a halogen atom, a lower alkoxyl group, and a phenyl group which may be substituted with one or more halogen atoms, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 1, $R^4$ is ethyl group, $R^5$ is ethyl group, n is 2, and X is —O—, the compounds wherein $R^1$ is a substituent represented by the formula (1-1), $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 1, $R^4$ is ethyl group, $R^5$ is ethyl group, n is 2, and X is —O—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 1, $R^4$ is ethyl group, $R^5$ is ethyl group, n is 2, and X is —O—, the compounds wherein $R^1$ is an unsubstituted alkyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is ethyl group, $R^5$ is ethyl group, n is 2, and X is —O—, the compounds wherein $R^1$ is an alkyl group substituted with a substituent selected from the group consisting of a halogen atom, a lower alkoxyl group, and a phenyl group which may be substituted with one or more halogen atoms, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is ethyl group, $R^5$ is ethyl group, n is 2, and X is —O—, the compounds wherein $R^1$ is a substituent represented by the formula (1-1), $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is ethyl group, $R^5$ is ethyl group, n is 2, and X is —O—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is ethyl group, $R^5$ is ethyl group, n is 2, and X is —O—, the compounds wherein $R^1$ is an unsubstituted alkyl group, $R^2$ is an unsubstituted $C_{1-12}$ alkyl group, b of $(R^3)_b$ is 0, $R^4$ is isopropyl group, $R^5$ is ethyl group, n is 2, and X is —O—, the compounds wherein $R^1$ is an alkyl group substituted with a substituent selected from the group consisting of a halogen atom, a lower alkoxyl group, and a phenyl group which may be substituted with one or more halogen atoms, $R^2$ is an unsubstituted $C_{1-12}$ alkyl group, b of $(R^3)_b$ is 0, $R^4$ is isopropyl group, $R^5$ is ethyl group, n is 2, and X is —O—, the compounds wherein $R^1$ is a substituent represented by the formula (1-1), $R^2$ is an unsubstituted $C_{1-12}$ alkyl group, b of $(R^3)_b$ is 0, $R^4$ is isopropyl group, $R^5$ is ethyl group, n is 2, and X is —O—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, $R^2$ is an unsubstituted $C_{1-12}$ alkyl group, b of $(R^3)_b$ is 0, $R^4$ is isopropyl group, $R^5$ is ethyl group, n is 2, and X is —O—, the compounds wherein $R^1$ is an unsubstituted alkyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is isopropyl group, $R^5$ is ethyl group, n is 2, and X is —O—, the compounds wherein $R^1$ is an alkyl group substituted with a substituent selected from the group consisting of a halogen atom, a lower alkoxyl group, and a phenyl group which may be substituted with one or more halogen atoms, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is isopropyl group, $R^5$ is ethyl group, n is 2, and X is —O—, the compounds wherein $R^1$ is a substituent represented by the formula (1-1), $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is isopropyl group, $R^5$ is ethyl group, n is 2, and X is —O—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group and 2-propynyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is isopropyl group, $R^5$ is ethyl group, n is 2, and X is —O—, the compounds wherein $R^1$ is an unsubstituted alkyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is isopropyl group, $R^5$ is ethyl group, n is 2, and X is —O—, the compounds wherein $R^1$ is an alkyl group substituted with a substituent selected from the group consisting of a halogen atom, a lower alkoxyl group, and a phenyl group which may be substituted with one or more halogen atoms, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is isopropyl group, $R^5$ is ethyl group, n is 2, and X is —O—, the compounds wherein $R^1$ is a substituent represented by the formula (1-1), $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is isopropyl group, $R^5$ is ethyl group, n is 2, and X is —O—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group and 2-propynyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 0, $R^4$ is isopropyl group, $R^5$ is ethyl group, n is 2, and X is —O—, the compounds wherein $R^1$ is an unsubstituted alkyl group, $R^2$ is an unsubstituted $C_{1-12}$ alkyl group, b of $(R^3)_b$ is 1, $R^4$ is isopropyl group, $R^5$ is ethyl group, n is 2, and X is —O—, the compounds wherein $R^1$ is an alkyl group substituted with a substituent selected from the group consisting of a halogen atom, a lower alkoxyl group, and a phenyl group which may be substituted with one or more halogen atoms, $R^2$ is an unsubstituted $C_{1-12}$ alkyl group, b of $(R^3)_b$ is 1, $R^4$ is isopropyl group, $R^5$ is ethyl group, n is 2, and X is —O—, the compounds wherein $R^1$ is a substituent represented by the formula (1-1), $R^2$ is an unsubstituted $C_{1-12}$ alkyl group, b of $(R^3)_b$ is 1, $R^4$ is isopropyl group, $R^5$ is ethyl group, n is 2, and X is —O—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, $R^2$ is an unsubstituted $C_{1-12}$ alkyl group, b of $(R^3)_b$ is 1, $R^4$ is isopropyl group, $R^5$ is ethyl group, n is 2, and X is —O—, the compounds wherein $R^1$ is an unsubstituted alkyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 1, $R^4$ is isopropyl group, $R^5$ is ethyl group, n is 2, and X is —O—, the compounds wherein $R^1$ is an alkyl group substituted with a substituent selected from the group consisting of a halogen atom, a lower alkoxyl group, and a phenyl group which may be substituted with one or more halogen atoms, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 1, $R^4$ is isopropyl group, $R^5$ is ethyl group, n is 2, and X is —O—, the compounds wherein $R^1$ is a substituent represented by the formula (1-1), $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 1, $R^4$ is isopropyl group, $R^5$ is ethyl group, n is 2, and X is —O—, the compounds wherein $R^1$ is a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 1, $R^4$ is isopropyl group, $R^5$ is ethyl group, n is 2, and X is —O—, the compounds wherein $R^1$ is an unsubstituted alkyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is isopropyl group, $R^5$ is ethyl group, n is 2, and X is —O—, the compounds wherein $R^1$ is an alkyl group substituted with a substituent selected from the group consisting of a halogen atom, a lower alkoxyl group, and a phenyl group which may be substituted with one or more halogen atoms, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is isopropyl group, $R^5$ is ethyl group, n is 2, and X is —O—, the compounds wherein $R^1$ is a substituent represented by the formula (1-1), $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is isopropyl group, $R^5$ is ethyl group, n is 2, and X is —O—, and the compounds wherein $R^1$ is a substituent selected from the group consisting of 1-naphthyl group, 2-naphthyl group, 5-indanyl group, 5,6,7,8 -tetrahydronaphthalen-2-yl group, allyl group, 3-butenyl group, and 2-propynyl group, $R^2$ is an alkyl group which is substituted with a halogen atom and may have a substituent selected from the group consisting of a lower alkoxyl group, an aryloxy group, an aralkyloxy group, a lower alkylthio group, an arylthio group, an aralkylthio group, and a phenyl group, b of $(R^3)_b$ is 1, $R^4$ is isopropyl group, $R^5$ is ethyl group, n is 2, and X is —O—, the compounds wherein $R^1$ is an unsubstituted alkyl group, $R^2$ is an unsubstituted $C_{1-12}$ alkyl group, b of $(R^3)_b$ is 1, $R^4$ is ethyl group, $R^5$ is hydrogen atom, n is 3, and X is —O—, the compounds wherein $R^1$ is an alkyl group substituted with a halogen atom, a lower alkoxyl group, or a phenyl group (this phenyl group may be substituted with one or more halogen atoms), $R^2$ is an unsubstituted $C_{1-12}$ alkyl group, b of $(R^3)_b$ is 0, $R^4$ is ethyl group, $R^5$ is hydrogen atom, n is 3, and X is —O—, the compounds wherein $R^1$ is an unsubstituted alkyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is ethyl group, $R^5$ is hydrogen atom, n is 3, and X is —O—, the compounds wherein $R^1$ is an alkyl group substituted with a halogen atom, a lower alkoxyl group, or a phenyl group (this phenyl group may be substituted with one or more halogen atoms), $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is ethyl group, $R^5$ is hydrogen atom, n is 3, and X is —O—, the compounds wherein $R^1$ is an unsubstituted alkyl group, $R^2$ is an unsubstituted $C_{1-12}$ alkyl group, b of $(R^3)_b$ is 0, $R^4$ is isopropyl group, $R^5$ is hydrogen atom, n is 3, and X is —O—, the compounds wherein $R^1$ is an alkyl group substituted with a halogen atom, a lower alkoxyl group, or a phenyl group (this phenyl group may be substituted with one or more halogen atoms), $R^2$ is an unsubstituted $C_{1-12}$ alkyl group, b of $(R^3)_b$ is 0, $R^4$ is isopropyl group, $R^5$ is hydrogen atom, n is 3, and X is —O—, the compounds wherein $R^1$ is an unsubstituted alkyl group, $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is isopropyl group, $R^5$ is hydrogen atom, n is 3, and X is —O—, the compounds wherein $R^1$ is an alkyl group substituted with a halogen atom, a lower alkoxyl group, or a phenyl group (this phenyl group may be substituted with one or more halogen atoms), $R^2$ is an alkyl group substituted with a lower alkoxyl group, an aryloxy group, an aralkyloxy group, a lower alkylthio group, an arylthio group, an aralkylthio group, or a phenyl group, b of $(R^3)_b$ is 0, $R^4$ is isopropyl group, $R^5$ is hydrogen atom, n is 3, and X is —O—, the compounds wherein $R^1$ represents a $C_{1-12}$ alkyl group which may be substituted with one or more substituents selected from the group consisting of a halogen atom, a lower alkoxyl group, and a phenyl group which may be substituted with one or more halogen atoms, the compounds wherein $R^2$ represents a $C_{2-12}$ alkyl group which may be substituted with a substituent selected from a lower alkoxyl group, and a lower alkylthio group, the compounds wherein b of $(R^3)_b$ is 0, compounds or salts thereof wherein $R^4$ is methyl group, ethyl group, or isopropyl group, the compounds wherein $R^5$ is hydrogen atom or ethyl group, the compounds wherein n is 2 or 3, the compounds wherein X represents —O—, the compounds wherein $R^2$ represents a $C_{2-12}$ alkyl group which may be substituted with one or more substituents selected from the group consisting of a lower alkoxyl group, an aryloxy group, an aralkyloxy group, and a phenyl group ($R^2$ may be further substituted with one or more halogen atoms except for substitution on the methylene group in $R^2$ binding to the nitrogen atom), b of $(R^3)_b$ is 0, $R^4$ is ethyl group, $R^5$ is hydrogen atom or ethyl group, n is 2, and X is —O—, the compounds wherein $R^1$ is a substituent represented by the formula (1-1), $(R^6)_a$ represents "a" ("a" is an integer from 0 to 5) of fluorine atoms, $R^2$ represents an alkyl group selected from the group consisting of n-pentyl group, n-hexyl group, n-heptyl group, and n-octyl group, b of $(R^3)_b$ represents 0, $R^4$ represents ethyl group, $R^5$ represents hydrogen atom or ethyl group, n represents 2, and X represents —NH—, and the compounds wherein $R^1$ represents a substituent selected from the group consisting of methyl group, ethyl group, benzyl group, allyl group, propyl group, p-tolyl group, 4-bromophenyl group, 4-fluorophenyl group, 2-methoxyethyl group, isopropyl group, 2-propynyl group, 2-naphthyl group, isobutyl group, 2,2-dimethylpropyl group, and 3-butenyl group, $R^2$ represents heptyl group, b of $(R^3)_b$ represents 0, $R^4$ represents ethyl group, $R^5$ represents hydrogen atom or ethyl group, n represents 2, and X represents —O—.

Specific compounds of the compounds represented by the formula (1) according to the present invention include the following compounds and salts thereof.

Specific the compound wherein X is —NH— include the following compounds.

Examples of the the compounds wherein $R^1$ is an unsubstituted $C_{1-12}$ alkyl group include, for example, the following compounds.

2-Ethoxy-3-{4-[2-(3-ethyl-1-pentylureido)ethoxy] phenyl}propionic acid,
2-ethoxy-3-{4-[2-(3-ethyl-1-hexylureido)ethoxy] phenyl}propionic acid,
2-ethoxy-3-{4-[2-(3-ethyl-1-heptylureido)ethoxy] phenyl}propionic acid,
2-ethoxy-3-{4-[2-(3-ethyl-1-octylureido)ethoxy] phenyl}propionic acid,
2-ethoxy-3-{4-[2-(3-ethyl-1-isobutylureido)ethoxy] phenyl}propionic acid,
2-ethoxy-3-(4-{2-[3-ethyl-1-(3-methylbutyl)ureido] ethoxy}phenyl)propionic acid,
2-ethoxy-3-(4-{2-[3-ethyl-1-(4-methylpentyl)ureido] ethoxy}phenyl)propionic acid,
2-ethoxy-3-(4-{2-[3-ethyl-1-(2-propylpentyl)ureido] ethoxy}phenyl)propionic acid,
3-(4-{2-[1-(3,3-dimethylbutyl)-3-ethylureido] ethoxy}phenyl)-2-ethoxypropionic acid,
2-ethoxy-3-(4-{2-[3-ethyl-1-(2-ethylbutyl)ureido] ethoxy}phenyl)propionic acid,
3-{4-[2-(1-cyclohexylmethyl-3-ethylureido)ethoxy]phenyl}-2-ethoxypropionic acid,
3-(4-{2-[1-(4-cyclohexylbutyl)-3-ethylureido] ethoxy}phenyl)-2-ethoxypropionic acid,
3-{4-[2-(1-cyclopropylmethyl-3-ethylureido)ethoxy]phenyl}-2-ethoxypropionic acid,
3-{4-[2-(1-cyclobutylmethyl-3-ethylureido)ethoxy]phenyl}-2-ethoxypropionic acid,
3-{4-[2-(1-cyclopentylmethyl-3-ethylureido)ethoxy]phenyl}-2-ethoxypropionic acid,
3-(4-{2-[1-(2-cyclopentylethyl)-3-ethylureido] ethoxy}phenyl)-2-ethoxypropionic acid,
3-(4-{2-[1-(3-cyclohexylpropyl)-3-ethylureido] ethoxy}phenyl)-2-ethoxypropionic acid,
2-ethoxy-3-(4-{2-[3-ethyl-1-(3-phenylpropyl)ureido] ethoxy}phenyl)propionic acid,
2-ethoxy-3-(4-{2-[3-ethyl-1-(4-phenylbutyl)ureido] ethoxy}phenyl)propionic acid,
3-(4-{2-[1-(2-butoxyethyl)-3-ethylureido]ethoxy}phenyl)-2-ethoxypropionic acid,
2-ethoxy-3-(4-{2-[3-ethyl-1-(2-pentyloxyethyl)ureido] ethoxy}phenyl)propionic acid,
2-ethoxy-3-(4-{2-[3-ethyl-1-(3-propoxypropyl)ureido] ethoxy}phenyl)propionic acid,
3-(4-{2-[1-(2-butylthioethyl)-3-ethylureido] ethoxy}phenyl)-2-ethoxypropionic acid,
2-ethoxy-3-(4-{2-[3-ethyl-1-(2-pentylthioethyl)ureido] ethoxy}phenyl)propionic acid,
2-ethoxy-3-(4-{2-[3-ethyl-1-(3-propylthiopropyl)ureido] ethoxy}phenyl)propionic acid,
2-ethoxy-3-(4-{2-[3-ethyl-1-(3-phenoxypropyl)ureido] ethoxy}phenyl)propionic acid,
2-ethoxy-3-(4-{2-[3-ethyl-1-(4-phenoxybutyl)ureido] ethoxy}phenyl)propionic acid,
3-(4-{2-[1-(3-benzyloxypropyl)-3-ethylureido] ethoxy}phenyl)-2-ethoxypropionic acid,
2-ethoxy-3-(4-{2-[3-ethyl-1-(3-phenylthiopropyl)ureido] ethoxy}phenyl)propionic acid,
2-ethoxy-3-(4-{2-[3-ethyl-1-(4-phenylthiobutyl)ureido] ethoxy}phenyl)propionic acid,
3-(4-{2-[1-(3-benzylthiopropyl)-3-ethylureido] ethoxy}phenyl)-2-ethoxypropionic acid,
2-ethoxy-3-(4-{2-[3-ethyl-1-(7,7,7-trifluoroheptyl)ureido] ethoxy}phenyl)propionic acid,
3-(4-{2-[1-(6,6-difluoroheptyl)-3-ethylureido] ethoxy}phenyl)-2-ethoxypropionic acid,
2-ethoxy-3-(4-{2-[3-ethyl-1-(6,6,6-trifluorohexyl)ureido] ethoxy}phenyl)propionic acid,
3-(4-{2-[1-(5,5-difluorohexyl)-3-ethylureido] ethoxy}phenyl)-2-ethoxypropionic acid,
2-ethoxy-3-(4-{2-[3-ethyl-1-(5,5,6,6,7,7,7-heptafluoroheptyl)ureido]ethoxy}phenyl)propionic acid,
2-ethoxy-3-(4-{2-[3-ethyl-1-(2,2,3,3,4,4,5,5,6,6,7,7,7-tridecafluoroheptyl)ureido]ethoxy}phenyl)propionic acid,
2-ethoxy-3-(4-{2-[3-ethyl-1-(5,5,6,6,6-pentafluorohexyl) ureido]ethoxy}phenyl)propionic acid,
2-ethoxy-3-(4-{2-[3-ethyl-1-(2,2,3,3,4,4,5,5,6,6,6-undecafluorohexyl)ureido]ethoxy}phenyl)propionic acid,
3-[4-(2-{1-[2-(2,2-difluoropropoxy)ethyl]-3-ethylureido}ethoxy)phenyl]-2-ethoxypropionic acid,
2-ethoxy-3-[4-(2-{3-ethyl-1-[2-(1,1,2,2,3,3,3-heptafluoropropoxy)ethyl]ureido}ethoxy)phenyl]propionic acid,
2-ethoxy-3-[4-(2-{3-ethyl-1-[2-(4,4,4-trifluorobutoxy) ethyl]ureido}ethoxy)phenyl]propionic acid,
3-[4-(2-{1-[2-(3,3-difluorobutoxy)ethyl]-3-ethylureido}ethoxy)phenyl]-2-ethoxypropionic acid,
3-[4-(2-{1-[2-(2,2-difluorobutoxy)ethyl]-3-ethylureido}ethoxy)phenyl]-2-ethoxypropionic acid,
2-ethoxy-3-[4-(2-{3-ethyl-1-[2-(1,1,2,2,3,3,4,4,4-nonafluorobutoxy)ethyl]ureido}ethoxy)phenyl]propionic acid,
2-ethoxy-3-[4-(2-{3-ethyl-1-[3-(2,2,2-trifluoroethoxy)propyl]ureido}ethoxy)phenyl]propionic acid,
2-ethoxy-3-[4-(2-{3-ethyl-1-[3-(1,1,2,2,2-pentafluoroethoxy)propyl]ureido}ethoxy)phenyl]propionic acid,
2-ethoxy-3-[4-(2-{3-ethyl-1-[3-(4-fluorophenoxy)propyl] ureido}ethoxy)phenyl]propionic acid,
3-[4-(2-{1-[3-(3,5-dichlorophenoxy)propyl]-3-ethylureido}ethoxy)phenyl]-2-ethoxypropionic acid,
2-ethoxy-3-[4-(2-{3-ethyl-1-[4-(4-fluorophenoxy)butyl] ureido}ethoxy)phenyl]propionic acid,
3-[4-(2-{1-[4-(3,5-dichlorophenoxy)butyl]-3-ethylureido}ethoxy)phenyl]-2-ethoxypropionic acid,
2-ethoxy-3-[4-(2-{3-ethyl-1-[2-(4-fluorobenzyloxy)ethyl] ureido}ethoxy)phenyl]propionic acid,
3-[4-(2-{1-[2-(3,5-dichlorobenzyloxy)ethyl]-3-ethylureido}ethoxy)phenyl]-2-ethoxypropionic acid,
2-ethoxy-3-[4-(2-{3-ethyl-1-[3-(4-fluorobenzyloxy)propyl] ureido}ethoxy)phenyl]propionic acid,
3-[4-(2-{1-[3-(3,5-dichlorobenzyloxy)propyl]-3-ethylureido}ethoxy)phenyl]-2-ethoxypropionic acid,
2-ethoxy-3-[4-(2-{3-ethyl-1-[4-(4-fluorobenzyloxy)butyl] ureido}ethoxy)phenyl]propionic acid,
3-[4-(2-{1-[4-(3,5-dichlorobenzyloxy)butyl]-3-ethylureido}ethoxy)phenyl]-2-ethoxypropionic acid,
2-ethoxy-3-[4-(2-{3-ethyl-1-[3-(4-fluorophenyl)propyl] ureido}ethoxy)phenyl]propionic acid,
3-[4-(2-{1-[3-(3,5-dichlorophenyl)propyl]-3-ethylureido}ethoxy)phenyl]-2-ethoxypropionic acid, 2-ethoxy-3-{4-[2-(1-pentyl-3-propylureido)ethoxy]
  phenyl}propionic acid,
2-ethoxy-3-{4-[2-(1-hexyl-3-propylureido)ethoxy]
  phenyl}propionic acid,
2-ethoxy-3-{4-[2-(1-heptyl-3-propylureido)ethoxy]
  phenyl}propionic acid,
2-ethoxy-3-{4-[2-(1-octyl-3-propylureido)ethoxy]
  phenyl}propionic acid,
2-ethoxy-3-{4-[2-(1-isobutyl-3-propylureido)ethoxy]
  phenyl}propionic acid,
2-ethoxy-3-(4-{2-[1-(3-methylbutyl)-3-propylureido]
  ethoxy}phenyl)propionic acid,
2-ethoxy-3-(4-{2-[1-(4-methylpentyl)-3-propylureido]
  ethoxy}phenyl)propionic acid,
2-ethoxy-3-(4-{2-[3-propyl-1-(2-propylpentyl)ureido]
  ethoxy}phenyl)propionic acid,
3-(4-{2-[1-(3,3-dimethylbutyl)-3-propylureido]
  ethoxy}phenyl)-2-ethoxypropionic acid,
2-ethoxy-3-(4-{2-[1-(2-ethylbutyl)-3-propylureido]
  ethoxy}phenyl)propionic acid,
3-{4-[2-(1-cyclohexylmethyl-3-propylureido)ethoxy]phenyl}-2-ethoxypropionic acid,
3-(4-{2-[1-(4-cyclohexylbutyl)-3-propylureido]
  ethoxy}phenyl)-2-ethoxypropionic acid,
3-{4-[2-(1-cyclopropylmethyl-3-propylureido)ethoxy]phenyl}-2-ethoxypropionic acid,
3-{4-[2-(1-cyclobutylmethyl-3-propylureido)ethoxy]phenyl}-2-ethoxypropionic acid,
3-{4-[2-(1-cyclopentylmethyl-3-propylureido)ethoxy]phenyl}-2-ethoxypropionic acid,
3-(4-{2-[1-(2-cyclopentylethyl)-3-propylureido]
  ethoxy}phenyl)-2-ethoxypropionic acid,
3-(4-{2-[1-(3-cyclohexylpropyl)-3-propylureido]
  ethoxy}phenyl)-2-ethoxypropionic acid,
2-ethoxy-3-(4-{2-[1-(3-phenylpropyl)-3-propylureido]
  ethoxy}phenyl)propionic acid,
2-ethoxy-3-(4-{2-[1-(4-phenylbutyl)-3-propylureido]
  ethoxy}phenyl)propionic acid,
3-(4-{2-[1-(2-butoxyethyl)-3-propylureido]
  ethoxy}phenyl)-2-ethoxypropionic acid,
2-ethoxy-3-(4-{2-[1-(2-pentyloxyethyl)-3-propylureido]
  ethoxy}phenyl)propionic acid,
2-ethoxy-3-(4-{2-[3-propyl-1-(3-propoxypropyl)ureido]
  ethoxy}phenyl)propionic acid,
3-(4-{2-[1-(2-butylthioethyl)-3-propylureido]
  ethoxy}phenyl)-2-ethoxypropionic acid,
2-ethoxy-3-(4-{2-[1-(2-pentylthioethyl)-3-propylureido]
  ethoxy}phenyl)propionic acid,
2-ethoxy-3-(4-{2-[3-propyl-1-(3-propylthiopropyl)ureido]
  ethoxy}phenyl)propionic acid,
2-ethoxy-3-(4-{2-[1-(3-phenoxypropyl)-3-propylureido]
  ethoxy}phenyl)propionic acid,
2-ethoxy-3-(4-{2-[1-(4-phenoxybutyl)-3-propylureido]
  ethoxy}phenyl)propionic acid,
3-(4-{2-[1-(3-benzyloxypropyl)-3-propylureido]
  ethoxy}phenyl)-2-ethoxypropionic acid,
2-ethoxy-3-(4-{2-[1-(3-phenylthiopropyl)-3-propylureido]
  ethoxy}phenyl)propionic acid,
2-ethoxy-3-(4-{2-[1-(4-phenylthiobutyl)-3-propylureido]
  ethoxy}phenyl)propionic acid,
3-(4-{2-[1-(3-benzylthiopropyl)-3-propylureido]
  ethoxy}phenyl)-2-ethoxypropionic acid,
2-ethoxy-3-(4-{2-[3-propyl-1-(7,7,7-trifluoroheptyl)ureido]
  ethoxy}phenyl)propionic acid,
3-(4-{2-[1-(6,6-difluoroheptyl)-3-propylureido]
  ethoxy}phenyl)-2-ethoxypropionic acid,
2-ethoxy-3-(4-{2-[3-propyl-1-(6,6,6-trifluorohexyl)ureido]
  ethoxy}phenyl)propionic acid,
3-(4-{2-[1-(5,5-difluorohexyl)-3-propylureido]
  ethoxy}phenyl)-2-ethoxypropionic acid,
2-ethoxy-3-(4-{2-[1-(5,5,6,6,7,7,7-heptafluoroheptyl)-3-propylureido]ethoxy}phenyl)propionic acid,
2-ethoxy-3-(4-{2-[3-propyl-1-(2,2,3,3,4,4,5,5,6,6,7,7,7-tridecafluoroheptyl)ureido]ethoxy}phenyl)propionic acid,
2-ethoxy-3-(4-{2-[1-(5,5,6,6,6-pentafluorohexyl)-3-propylureido]ethoxy}phenyl)propionic acid,
2-ethoxy-3-(4-{2-[3-propyl-1-(2,2,3,3,4,4,5,5,6,6,6-undecafluorohexyl)ureido]ethoxy}phenyl)propionic acid,
3-[4-(2-{1-[2-(2,2-difluoropropoxy)ethyl]-3-propylureido}ethoxy)phenyl]-2-ethoxypropionic acid,
2-ethoxy-3-[4-(2-{1-[2-(1,1,2,2,3,3,3-heptafluoropropoxy)ethyl]-3-propylureido}ethoxy)phenyl]propionic acid,
2-ethoxy-3-[4-(2-{3-propyl-1-[2-(4,4,4-trifluorobutoxy)ethyl]ureido}ethoxy)phenyl]propionic acid,
3-[4-(2-{1-[2-(3,3-difluorobutoxy)ethyl]-3-propylureido}ethoxy)phenyl]-2-ethoxypropionic acid,
3-[4-(2-{1-[2-(2,2-difluorobutoxy)ethyl]-3-propylureido}ethoxy)phenyl]-2-ethoxypropionic acid,
2-ethoxy-3-[4-(2-{1-[2-(1,1,2,2,3,3,4,4,4-nonafluorobutoxy)ethyl]-3-propylureido}ethoxy)phenyl]propionic acid,
2-ethoxy-3-[4-(2-{3-propyl-1-[3-(2,2,2-trifluoroethoxy)propyl]ureido}ethoxy)phenyl]propionic acid,
2-ethoxy-3-[4-(2-{1-[3-(1,1,2,2,2-pentafluoroethoxy)propyl]-3-propylureido}ethoxy)phenyl]propionic acid,
2-ethoxy-3-[4-(2-{1-[3-(4-fluorophenoxy)propyl]-3-propylureido}ethoxy)phenyl]propionic acid,
3-[4-(2-{1-[3-(3,5-dichlorophenoxy)propyl]-3-propylureido}ethoxy)phenyl]-2-ethoxypropionic acid,
2-ethoxy-3-[4-(2-{1-[4-(4-fluorophenoxy)butyl]-3-propylureido}ethoxy)phenyl]propionic acid,
3-[4-(2-{1-[4-(3,5-dichlorophenoxy)butyl]-3-propylureido}ethoxy)phenyl]-2-ethoxypropionic acid,
2-ethoxy-3-[4-(2-{1-[2-(4-fluorobenzyloxy)ethyl]-3-propylureido}ethoxy)phenyl]propionic acid,
3-[4-(2-{1-[2-(3,5-dichlorobenzyloxy)ethyl]-3-propylureido}ethoxy)phenyl]-2-ethoxypropionic acid,
2-ethoxy-3-[4-(2-{1-[3-(4-fluorobenzyloxy)propyl]-3-propylureido}ethoxy)phenyl]propionic acid,
3-[4-(2-{1-[3-(3,5-dichlorobenzyloxy)propyl]-3-propylureido}ethoxy)phenyl]-2-ethoxypropionic acid,
2-ethoxy-3-[4-(2-{1-[4-(4-fluorobenzyloxy)butyl]-3-propylureido}ethoxy)phenyl]propionic acid,
3-[4-(2-{1-[4-(3,5-dichlorobenzyloxy)butyl]-3-propylureido}ethoxy)phenyl]-2-ethoxypropionic acid,
2-ethoxy-3-[4-(2-{1-[3-(4-fluorophenyl)propyl]-3-propylureido}ethoxy)phenyl]propionic acid,
3-[4-(2-{1-[3-(3,5-dichlorophenyl)propyl]-3-propylureido}ethoxy)phenyl]-2-ethoxypropionic acid,
3-{4-[2-(3-butyl-1-pentylureido)ethoxy]phenyl}-2-ethoxypropionic acid,
3-{4-[2-(3-butyl-1-hexylureido)ethoxy]phenyl}-2-ethoxypropionic acid,
3-{4-[2-(3-butyl-1-heptylureido)ethoxy]phenyl}-2-ethoxypropionic acid,
3-{4-[2-(3-butyl-1-octylureido)ethoxy]phenyl}-2-ethoxypropionic acid,
3-{4-[2-(3-butyl-1-isobutylureido)ethoxy]phenyl}-2-ethoxypropionic acid,
3-(4-{2-[3-butyl-1-(3-methylbutyl)ureido]ethoxy}phenyl)-2-ethoxypropionic acid, 3-(4-{2-[3-butyl-1-(4-methylpentyl)ureido]ethoxy}phenyl)-2-ethoxypropionic acid,
3-(4-{2-[3-butyl-1-(2-propylpentyl)ureido]ethoxy}phenyl)-2-ethoxypropionic acid,
3-(4-{2-[3-butyl-1-(3,3-dimethylbutyl)ureido]ethoxy}phenyl)-2-ethoxypropionic acid,
3-(4-{2-[3-butyl-1-(2-ethylbutyl)ureido]ethoxy}phenyl)-2-ethoxypropionic acid,
3-{4-[2-(3-butyl-1-cyclohexylmethylureido)ethoxy]phenyl}-2-ethoxypropionic acid,
3-(4-{2-[3-butyl-1-(4-cyclohexylbutyl)ureido]ethoxy}phenyl)-2-ethoxypropionic acid,
3-{4-[2-(3-butyl-1-cyclopropylmethylureido)ethoxy]phenyl}-2-ethoxypropionic acid,
3-{4-[2-(3-butyl-1-cyclobutylmethylureido)ethoxy]phenyl}-2-ethoxypropionic acid,
3-{4-[2-(3-butyl-1-cyclopentylmethylureido)ethoxy]phenyl}-2-ethoxypropionic acid,
3-(4-{2-[3-butyl-1-(2-cyclopentylethyl)ureido]ethoxy}phenyl)-2-ethoxypropionic acid,
3-(4-{2-[3-butyl-1-(3-cyclohexylpropyl)ureido]ethoxy}phenyl)-2-ethoxypropionic acid,
3-(4-{2-[3-butyl-1-(3-phenylpropyl)ureido]ethoxy}phenyl)-2-ethoxypropionic acid,
3-(4-{2-[3-butyl-1-(4-phenylbutyl)ureido]ethoxy}phenyl)-2-ethoxypropionic acid,
3-(4-{2-[1-(2-butoxyethyl)-3-butylureido]ethoxy}phenyl)-2-ethoxypropionic acid,
3-(4-{2-[3-butyl-1-(2-pentyloxyethyl)ureido]ethoxy}phenyl)-2-ethoxypropionic acid,
3-(4-{2-[3-butyl-1-(3-propoxypropyl)ureido]ethoxy}phenyl)-2-ethoxypropionic acid,
3-(4-{2-[3-butyl-1-(2-butylthioethyl)ureido]ethoxy}phenyl)-2-ethoxypropionic acid,
3-(4-{2-[3-butyl-1-(2-pentylthioethyl)ureido]ethoxy}phenyl)-2-ethoxypropionic acid,
3-(4-{2-[3-butyl-1-(3-propylthiopropyl)ureido]ethoxy}phenyl)-2-ethoxypropionic acid,
3-(4-{2-[3-butyl-1-(3-phenoxypropyl)ureido]ethoxy}phenyl)-2-ethoxypropionic acid,
3-(4-{2-[3-butyl-1-(4-phenoxybutyl)ureido]ethoxy}phenyl)-2-ethoxypropionic acid,
3-(4-{2-[1-(3-benzyloxypropyl)-3-butylureido]ethoxy}phenyl)-2-ethoxypropionic acid,
3-(4-{2-[3-butyl-1-(3-phenylthiopropyl)ureido]ethoxy}phenyl)-2-ethoxypropionic acid,
3-(4-{2-[3-butyl-1-(4-phenylthiobutyl)ureido]ethoxy}phenyl)-2-ethoxypropionic acid,
3-(4-{2-[1-(3-benzylthiopropyl)-3-butylureido]ethoxy}phenyl)-2-ethoxypropionic acid,
3-(4-{2-[3-butyl-1-(7,7,7-trifluoroheptyl)ureido]ethoxy}phenyl)-2-ethoxypropionic acid,
3-(4-{2-[3-butyl-1-(6,6-difluoroheptyl)ureido]ethoxy}phenyl)-2-ethoxypropionic acid,
3-(4-{2-[3-butyl-1-(6,6,6-trifluorohexyl)ureido]ethoxy}phenyl)-2-ethoxypropionic acid,
3-(4-{2-[3-butyl-1-(5,5-difluorohexyl)ureido]ethoxy}phenyl)-2-ethoxypropionic acid,
3-(4-{2-[3-butyl-1-(5,5,6,6,7,7,7-heptafluoroheptyl)ureido]ethoxy}phenyl)-2-ethoxypropionic acid,
3-(4-{2-[3-butyl-1-(2,2,3,3,4,4,5,5,6,6,7,7,7-tridecafluoroheptyl)ureido]ethoxy}phenyl)-2-ethoxypropionic acid,
3-(4-{2-[3-butyl-1-(5,5,6,6,6-pentafluorohexyl)ureido]ethoxy}phenyl)-2-ethoxypropionic acid,
3-(4-{2-[3-butyl-1-(2,2,3,3,4,4,5,5,6,6,6-undecafluorohexyl)ureido]ethoxy}phenyl)-2-ethoxypropionic acid,
3-[4-(2-{3-butyl-1-[2-(2,2-difluoropropoxy)ethyl]ureido}ethoxy)phenyl]-2-ethoxypropionic acid,
3-[4-(2-{3-butyl-1-[2-(1,1,2,2,3,3,3-heptafluoropropoxy)ethyl]ureido}ethoxy)phenyl]-2-ethoxypropionic acid,
3-[4-(2-{3-butyl-1-[2-(4,4,4-trifluorobutoxy)ethyl]ureido}ethoxy)phenyl]-2-ethoxypropionic acid,
3-[4-(2-{3-butyl-1-[2-(3,3-difluorobutoxy)ethyl]ureido}ethoxy)phenyl]-2-ethoxypropionic acid,
3-[4-(2-{3-butyl-1-[2-(2,2-difluorobutoxy)ethyl]ureido}ethoxy)phenyl]-2-ethoxypropionic acid,
3-[4-(2-{3-butyl-1-[2-(1,1,2,2,3,3,4,4,4-nonafluorobutoxy)ethyl]ureido}ethoxy)phenyl]-2-ethoxypropionic acid,
3-[4-(2-{3-butyl-1-[3-(2,2,2-trifluoroethoxy)propyl]ureido}ethoxy)phenyl]-2-ethoxypropionic acid,
3-[4-(2-{3-butyl-1-[3-(1,1,2,2,2-pentafluoroethoxy)propyl]ureido}ethoxy)phenyl]-2-ethoxypropionic acid,
3-[4-(2-{3-butyl-1-[3-(4-fluorophenoxy)propyl]ureido}ethoxy)phenyl]-2-ethoxypropionic acid,
3-[4-(2-{3-butyl-1-[3-(3,5-dichlorophenoxy)propyl]ureido}ethoxy)phenyl]-2-ethoxypropionic acid,
3-[4-(2-{3-butyl-1-[4-(4-fluorophenoxy)butyl]ureido}ethoxy)phenyl]-2-ethoxypropionic acid,
3-[4-(2-{3-butyl-1-[4-(3,5-dichlorophenoxy)butyl]ureido}ethoxy)phenyl]-2-ethoxypropionic acid,
3-[4-(2-{3-butyl-1-[2-(4-fluorobenzyloxy)ethyl]ureido}ethoxy)phenyl]-2-ethoxypropionic acid,
3-[4-(2-{3-butyl-1-[2-(3,5-dichlorobenzyloxy)ethyl]ureido}ethoxy)phenyl]-2-ethoxypropionic acid,
3-[4-(2-{3-butyl-1-[3-(4-fluorobenzyloxy)propyl]ureido}ethoxy)phenyl]-2-ethoxypropionic acid,
3-[4-(2-{3-butyl-1-[3-(3,5-dichlorobenzyloxy)propyl]ureido}ethoxy)phenyl]-2-ethoxypropionic acid,
3-[4-(2-{3-butyl-1-[4-(4-fluorobenzyloxy)butyl]ureido}ethoxy)phenyl]-2-ethoxypropionic acid,
3-[4-(2-{3-butyl-1-[4-(3,5-dichlorobenzyloxy)butyl]ureido}ethoxy)phenyl]-2-ethoxypropionic acid,
3-[4-(2-{3-butyl-1-[3-(4-fluorophenyl)propyl]ureido}ethoxy)phenyl]-2-ethoxypropionic acid,
3-[4-(2-{3-butyl-1-[3-(3,5-dichlorophenyl)propyl]ureido}ethoxy)phenyl]-2-ethoxypropionic acid,
2-ethoxy-3-{4-[2-(3-isopropyl-1-pentylureido)ethoxy]phenyl}propionic acid,
2-ethoxy-3-{4-[2-(1-hexyl-3-isopropylureido)ethoxy]phenyl}propionic acid,
2-ethoxy-3-{4-[2-(1-heptyl-3-isopropylureido)ethoxy]phenyl}propionic acid,
2-ethoxy-3-{4-[2-(3-isopropyl-1-octylureido)ethoxy]phenyl}propionic acid,
2-ethoxy-3-{4-[2-(1-isobutyl-3-isopropylureido)ethoxy]phenyl}propionic acid,
2-ethoxy-3-(4-{2-[3-isopropyl-1-(3-methylbutyl)ureido]ethoxy}phenyl)propionic acid,
2-ethoxy-3-(4-{2-[3-isopropyl-1-(4-methylpentyl)ureido]ethoxy}phenyl)propionic acid,
2-ethoxy-3-(4-{2-[3-isopropyl-1-(2-propylpentyl)ureido]ethoxy}phenyl)propionic acid,
3-(4-{2-[1-(3,3-dimethylbutyl)-3-isopropylureido]ethoxy}phenyl)-2-ethoxypropionic acid,
2-ethoxy-3-(4-{2-[1-(2-ethylbutyl)-3-isopropylureido]ethoxy}phenyl)propionic acid,
3-{4-[2-(1-cyclohexylmethyl-3-isopropylureido)ethoxy]phenyl}-2-ethoxypropionic acid,
3-(4-{2-[1-(4-cyclohexylbutyl)-3-isopropylureido]ethoxy}phenyl)-2-ethoxypropionic acid,
3-{4-[2-(1-cyclopropylmethyl-3-isopropylureido)ethoxy]phenyl}-2-ethoxypropionic acid, 3-{4-[2-(1-cyclobutylmethyl-3-isopropylureido)ethoxy]
  phenyl}-2-ethoxypropionic acid,
3-{4-[2-(1-cyclopentylmethyl-3-isopropylureido)ethoxy]
  phenyl}-2-ethoxypropionic acid,
3-(4-{2-[1-(2-cyclopentylethyl)-3-isopropylureido]
  ethoxy}phenyl)-2-ethoxypropionic acid,
3-(4-{2-[1-(3-cyclohexylpropyl)-3-isopropylureido]
  ethoxy}phenyl)-2-ethoxypropionic acid,
2-ethoxy-3-(4-{2-[3-isopropyl-1-(3-phenylpropyl)ureido]
  ethoxy}phenyl)propionic acid,
2-ethoxy-3-(4-{2-[3-isopropyl-1-(4-phenylbutyl)ureido]
  ethoxy}phenyl)propionic acid,
3-(4-{2-[1-(2-butoxyethyl)-3-isopropylureido]
  ethoxy}phenyl)-2-ethoxypropionic acid,
2-ethoxy-3-(4-{2-[3-isopropyl-1-(2-pentyloxyethyl)ureido]
  ethoxy}phenyl)propionic acid,
2-ethoxy-3-(4-{2-[3-isopropyl-1-(3-propoxypropyl)ureido]
  ethoxy}phenyl)propionic acid,
3-(4-{2-[1-(2-butylthioethyl)-3-isopropylureido]
  ethoxy}phenyl)-2-ethoxypropionic acid,
2-ethoxy-3-(4-{2-[3-isopropyl-1-(2-pentylthioethyl)ureido]
  ethoxy}phenyl)propionic acid,
2-ethoxy-3-(4-{2-[3-isopropyl-1-(3-propylthiopropyl)ureido]ethoxy}phenyl)propionic acid,
2-ethoxy-3-(4-{2-[3-isopropyl-1-(3-phenoxypropyl)ureido]
  ethoxy}phenyl)propionic acid,
2-ethoxy-3-(4-{2-[3-isopropyl-1-(4-phenoxybutyl)ureido]
  ethoxy}phenyl)propionic acid,
3-(4-{2-[1-(3-benzyloxypropyl)-3-isopropylureido]
  ethoxy}phenyl)-2-ethoxypropionic acid,
2-ethoxy-3-(4-{2-[3-isopropyl-1-(3-phenylthiopropyl)ureido]ethoxy}phenyl)propionic acid,
2-ethoxy-3-(4-{2-[3-isopropyl-1-(4-phenylthiobutyl)ureido]ethoxy}phenyl)propionic acid,
3-(4-{2-[1-(3-benzylthiopropyl)-3-isopropylureido]
  ethoxy}phenyl)-2-ethoxypropionic acid,
2-ethoxy-3-(4-{2-[3-isopropyl-1-(7,7,7-trifluoroheptyl)ureido]ethoxy}phenyl)propionic acid,
3-(4-{2-[1-(6,6-difluoroheptyl)-3-isopropylureido]
  ethoxy}phenyl)-2-ethoxypropionic acid,
2-ethoxy-3-(4-{2-[3-isopropyl-1-(6,6,6-trifluorohexyl)ureido]ethoxy}phenyl)propionic acid,
3-(4-{2-[1-(5,5-difluorohexyl)-3-isopropylureido]
  ethoxy}phenyl)-2-ethoxypropionic acid,
2-ethoxy-3-(4-{2-[1-(5,5,6,6,7,7,7-heptafluoroheptyl)-3-isopropylureido]ethoxy}phenyl)propionic acid,
2-ethoxy-3-(4-{2-[3-isopropyl-1-(2,2,3,3,4,4,5,5,6,6,7,7,7-tridecafluoroheptyl)ureido]ethoxy}phenyl)propionic
  acid,
2-ethoxy-3-(4-{2-[3-isopropyl-1-(5,5,6,6,6-pentafluorohexyl)ureido]ethoxy}phenyl)propionic acid,
2-ethoxy-3-(4-{2-[3-isopropyl-1-(2,2,3,3,4,4,5,5,6,6,6-undecafluorohexyl)ureido]ethoxy}phenyl)propionic acid,
3-[4-(2-{1-[2-(2,2-difluoropropoxy)ethyl]-3-isopropylureido}ethoxy)phenyl]-2-ethoxypropionic acid,
2-ethoxy-3-[4-(2-{1-[2-(1,1,2,2,3,3,3-heptafluoropropoxy)ethyl]-3-isopropylureido}ethoxy)phenyl]propionic acid,
2-ethoxy-3-[4-(2-{3-isopropyl-1-[2-(4,4,4-trifluorobutoxy)ethyl]ureido}ethoxy)phenyl]propionic acid,
3-[4-(2-{1-[2-(3,3-difluorobutoxy)ethyl]-3-isopropylureido}ethoxy)phenyl]-2-ethoxypropionic acid,
3-[4-(2-{1-[2-(2,2-difluorobutoxy)ethyl]-3-isopropylureido}ethoxy)phenyl]-2-ethoxypropionic acid,
2-ethoxy-3-[4-(2-{3-isopropyl-1-[2-(1,1,2,2,3,3,4,4,4-nonafluorobutoxy)ethyl]ureido}ethoxy)phenyl]propionic
  acid,
2-ethoxy-3-[4-(2-{3-isopropyl-1-[3-(2,2,2-trifluoroethoxy)propyl]ureido}ethoxy)phenyl]propionic acid,
2-ethoxy-3-[4-(2-{3-isopropyl-1-[3-(1,1,2,2,2-pentafluoroethoxy)propyl]ureido}ethoxy)phenyl]propionic acid,
2-ethoxy-3-[4-(2-{1-[3-(4-fluorophenoxy)propyl]-3-isopropylureido}ethoxy)phenyl]propionic acid,
3-[4-(2-{1-[3-(3,5-dichlorophenoxy)propyl]-3-isopropylureido}ethoxy)phenyl]-2-ethoxypropionic acid,
2-ethoxy-3-[4-(2-{1-[4-(4-fluorophenoxy)butyl]-3-isopropylureido}ethoxy)phenyl]propionic acid,
3-[4-(2-{1-[4-(3,5-dichlorophenoxy)butyl]-3-isopropylureido}ethoxy)phenyl]-2-ethoxypropionic acid,
2-ethoxy-3-[4-(2-{1-[2-(4-fluorobenzyloxy)ethyl]-3-isopropylureido}ethoxy)phenyl]propionic acid,
3-[4-(2-{1-[2-(3,5-dichlorobenzyloxy)ethyl]-3-isopropylureido}ethoxy)phenyl]-2-ethoxypropionic acid,
2-ethoxy-3-[4-(2-{1-[3-(4-fluorobenzyloxy)propyl]-3-isopropylureido}ethoxy)phenyl]propionic acid,
3-[4-(2-{1-[3-(3,5-dichlorobenzyloxy)propyl]-3-isopropylureido}ethoxy)phenyl]-2-ethoxypropionic acid,
2-ethoxy-3-[4-(2-{1-[4-(4-fluorobenzyloxy)butyl]-3-isopropylureido}ethoxy)phenyl]propionic acid,
3-[4-(2-{1-[4-(3,5-dichlorobenzyloxy)butyl]-3-isopropylureido}ethoxy)phenyl]-2-ethoxypropionic acid,
2-ethoxy-3-[4-(2-{1-[3-(4-fluorophenyl)propyl]-3-isopropylureido}ethoxy)phenyl]propionic acid,
3-[4-(2-{1-[3-(3,5-dichlorophenyl)propyl]-3-isopropylureido}ethoxy)phenyl]-2-ethoxypropionic acid,
2-ethoxy-3-{4-[2-(3-isobutyl-1-pentylureido)ethoxy]
  phenyl}propionic acid,
2-ethoxy-3-{4-[2-(1-hexyl-3-isobutylureido)ethoxy]
  phenyl}propionic acid,
2-ethoxy-3-{4-[2-(1-heptyl-3-isobutylureido)ethoxy]
  phenyl}propionic acid,
2-ethoxy-3-{4-[2-(3-isobutyl-1-octylureido)ethoxy]
  phenyl}propionic acid,
2-ethoxy-3-{4-[2-(1,3-diisobutylureido)ethoxy]
  phenyl}propionic acid,
2-ethoxy-3-(4-{2-[3-isobutyl-1-(3-methylbutyl)ureido]
  ethoxy}phenyl)propionic acid,
2-ethoxy-3-(4-{2-[3-isobutyl-1-(4-methylpentyl)ureido]
  ethoxy}phenyl)propionic acid,
2-ethoxy-3-(4-{2-[3-isobutyl-1-(2-propylpentyl)ureido]
  ethoxy}phenyl)propionic acid,
3-(4-{2-[1-(3,3-dimethylbutyl)-3-isobutylureido]
  ethoxy}phenyl)-2-ethoxypropionic acid,
2-ethoxy-3-(4-{2-[1-(2-ethylbutyl)-3-isobutylureido]
  ethoxy}phenyl)propionic acid,
3-{4-[2-(1-cyclohexylmethyl-3-isobutylureido)ethoxy]phenyl}-2-ethoxypropionic acid,
3-(4-{2-[1-(4-cyclohexylbutyl)-3-isobutylureido]
  ethoxy}phenyl)-2-ethoxypropionic acid,
3-{4-[2-(1-cyclopropylmethyl-3-isobutylureido)ethoxy]
  phenyl}-2-ethoxypropionic acid,
3-{4-[2-(1-cyclobutylmethyl-3-isobutylureido)ethoxy]phenyl}-2-ethoxypropionic acid,
3-{4-[2-(1-cyclopentylmethyl-3-isobutylureido)ethoxy]
  phenyl}-2-ethoxypropionic acid,
3-(4-{2-[1-(2-cyclopentylethyl)-3-isobutylureido]
  ethoxy}phenyl)-2-ethoxypropionic acid,
3-(4-{2-[1-(3-cyclohexylpropyl)-3-isobutylureido]
  ethoxy}phenyl)-2-ethoxypropionic acid,
2-ethoxy-3-(4-{2-[3-isobutyl-1-(3-phenylpropyl)ureido]
  ethoxy}phenyl)propionic acid,
2-ethoxy-3-(4-{2-[3-isobutyl-1-(4-phenylbutyl)ureido]
  ethoxy}phenyl)propionic acid, 3-(4-{2-[1-(2-butoxyethyl)-3-isobutylureido]
ethoxy}phenyl)-2-ethoxypropionic acid,
2-ethoxy-3-(4-{2-[3-isobutyl-1-(2-pentyloxyethyl)ureido]
ethoxy}phenyl)propionic acid,
2-ethoxy-3-(4-{2-[3-isobutyl-1-(3-propoxypropyl)ureido]
ethoxy}phenyl)propionic acid,
3-(4-{2-[1-(2-butylthioethyl)-3-isobutylureido]
ethoxy}phenyl)-2-ethoxypropionic acid,
2-ethoxy-3-(4-{2-[3-isobutyl-1-(2-pentylthioethyl)ureido]
ethoxy}phenyl)propionic acid,
2-ethoxy-3-(4-{2-[3-isobutyl-1-(3-propylthiopropyl)ureido]
ethoxy}phenyl)propionic acid,
2-ethoxy-3-(4-{2-[3-isobutyl-1-(3-phenoxypropyl)ureido]
ethoxy}phenyl)propionic acid,
2-ethoxy-3-(4-{2-[3-isobutyl-1-(4-phenoxybutyl)ureido]
ethoxy}phenyl)propionic acid,
3-(4-{2-[1-(3-benzyloxypropyl)-3-isobutylureido]
ethoxy}phenyl)-2-ethoxypropionic acid,
2-ethoxy-3-(4-{2-[3-isobutyl-1-(3-phenylthiopropyl)ureido]ethoxy}phenyl)propionic acid,
2-ethoxy-3-(4-{2-[3-isobutyl-1-(4-phenylthiobutyl)ureido]
ethoxy}phenyl)propionic acid,
3-(4-{2-[1-(3-benzylthiopropyl)-3-isobutylureido]
ethoxy}phenyl)-2-ethoxypropionic acid,
2-ethoxy-3-(4-{2-[3-isobutyl-1-(7,7,7-trifluoroheptyl)ureido]ethoxy}phenyl)propionic acid,
3-(4-{2-[1-(6,6-difluoroheptyl)-3-isobutylureido]
ethoxy}phenyl)-2-ethoxypropionic acid,
2-ethoxy-3-(4-{2-[3-isobutyl-1-(6,6,6-trifluorohexyl)ureido]ethoxy}phenyl)propionic acid,
3-(4-{2-[1-(5,5-difluorohexyl)-3-isobutylureido]
ethoxy}phenyl)-2-ethoxypropionic acid,
2-ethoxy-3-(4-{2-[1-(5,5,6,6,7,7,7-heptafluoroheptyl)-3-
isobutylureido]ethoxy}phenyl)propionic acid,
2-ethoxy-3-(4-{2-[3-isobutyl-1-(2,2,3,3,4,4,5,5,6,6,7,7,7-
tridecafluoroheptyl)ureido]ethoxy}phenyl)propionic
acid,
2-ethoxy-3-(4-{2-[3-isobutyl-1-(5,5,6,6,6 -pentafluoro-
hexyl)ureido]ethoxy}phenyl)propionic acid,
2-ethoxy-3-(4-{2-[3-isobutyl-1-(2,2,3,3,4,4,5,5,6,6,6-undecafluorohexyl)ureido]ethoxy}phenyl)propionic acid,
3-[4-(2-{1-[2-(2,2-difluoropropoxy)ethyl]-3-
isobutylureido}ethoxy)phenyl]-2-ethoxypropionic acid,
2-ethoxy-3-[4-(2-{1-[2-(1,1,2,2,3,3,3-heptafluoropropoxy)
ethyl]-3-isobutylureido}ethoxy)phenyl]propionic acid,
2-ethoxy-3-[4-(2-{3-isobutyl-1-[2-(4,4,4-trifluorobutoxy)
ethyl]ureido}ethoxy)phenyl]propionic acid,
3-[4-(2-{1-[2-(3,3-difluorobutoxy)ethyl]-3-
isobutylureido}ethoxy)phenyl]-2-ethoxypropionic acid,
3-[4-(2-{1-[2-(2,2-difluorobutoxy)ethyl]-3-
isobutylureido}ethoxy)phenyl]-2-ethoxypropionic acid,
2-ethoxy-3-[4-(2-{3-isobutyl-1-[2-(1,1,2,2,3,3,4,4,4-nonafluorobutoxy)ethyl]ureido}ethoxy)phenyl]propionic
acid,
2-ethoxy-3-[4-(2-{3-isobutyl-1-[3-(2,2,2-trifluoroethoxy)
propyl]ureido}ethoxy)phenyl]propionic acid,
2-ethoxy-3-[4-(2-{3-isobutyl-1-[3-(1,1,2,2,2-pentafluoroethoxy)propyl]ureido}ethoxy)phenyl]propionic acid,
2-ethoxy-3-[4-(2-{1-[3-(4-fluorophenoxy)propyl]-3-
isobutylureido}ethoxy)phenyl]propionic acid,
3-[4-(2-{1-[3-(3,5-dichlorophenoxy)propyl]-3-
isobutylureido}ethoxy)phenyl]-2-ethoxypropionic acid,
2-ethoxy-3-[4-(2-{1-[4-(4-fluorophenoxy)butyl]-3-
isobutylureido}ethoxy)phenyl]propionic acid,
3-[4-(2-{1-[4-(3,5-dichlorophenoxy)butyl]-3-
isobutylureido}ethoxy)phenyl]-2-ethoxypropionic acid, 2-ethoxy-3-[4-(2-{1-[2-(4-fluorobenzyloxy)ethyl]-3-
isobutylureido}ethoxy)phenyl]propionic acid,
3-[4-(2-{1-[2-(3,5-dichlorobenzyloxy)ethyl]-3-
isobutylureido}ethoxy)phenyl]-2-ethoxypropionic acid,
2-ethoxy-3-[4-(2-{1-[3-(4-fluorobenzyloxy)propyl]-3-
isobutylureido}ethoxy)phenyl]propionic acid,
3-[4-(2-{1-[3-(3,5-dichlorobenzyloxy)propyl]-3-
isobutylureido}ethoxy)phenyl]-2-ethoxypropionic acid,
2-ethoxy-3-[4-(2-{1-[4-(4-fluorobenzyloxy)butyl]-3-
isobutylureido}ethoxy)phenyl]propionic acid,
3-[4-(2-{1-[4-(3,5-dichlorobenzyloxy)butyl]-3-
isobutylureido}ethoxy)phenyl]-2-ethoxypropionic acid,
2-ethoxy-3-[4-(2-{1-[3-(4-fluorophenyl)propyl]-3-
isobutylureido}ethoxy)phenyl]propionic acid,
3-[4-(2-{1-[3-(3,5-dichlorophenyl)propyl]-3-
isobutylureido}ethoxy)phenyl]-2-ethoxypropionic acid,
2-ethoxy-3-(4-{2-[3-(1-methylpropyl)-1-pentylureido]
ethoxy}phenyl)propionic acid,
2-ethoxy-3-(4-{2-[1-hexyl-3-(1-methylpropyl)ureido]
ethoxy}phenyl)propionic acid,
2-ethoxy-3-(4-{2-[1-heptyl-3-(1-methylpropyl)ureido]
ethoxy}phenyl)propionic acid,
2-ethoxy-3-(4-{2-[3-(1-methylpropyl)-1-octylureido]
ethoxy}phenyl)propionic acid,
2-ethoxy-3-(4-{2-[1-isobutyl-3-(1-methylpropyl)ureido]
ethoxy}phenyl)propionic acid,
2-ethoxy-3-(4-{2-[3-(1-methylpropyl)-1-(3-methylbutyl)
ureido]ethoxy}phenyl)propionic acid,
2-ethoxy-3-(4-{2-[1-(4-methylpentyl)-3-(1-methylpropyl)
ureido]ethoxy}phenyl)propionic acid,
2-ethoxy-3-(4-{2-[3-(1-methylpropyl)-1-(2-propylpentyl)
ureido]ethoxy}phenyl)propionic acid,
3-(4-{2-[1-(3,3-dimethylbutyl)-3-(1-methylpropyl)ureido]
ethoxy}phenyl)-2-ethoxypropionic acid,
2-ethoxy-3-(4-{2-[1-(2-ethylbutyl)-3-(1-methylpropyl)ureido]ethoxy}phenyl)propionic acid,
3-(4-{2-[1-cyclohexylmethyl-3-(1-methylpropyl)ureido]
ethoxy}phenyl)-2-ethoxypropionic acid,
3-(4-{2-[1-(4-cyclohexylbutyl)-3-(1-methylpropyl)ureido]
ethoxy}phenyl)-2-ethoxypropionic acid,
3-(4-{2-[1-cyclopropylmethyl-3-(1-methylpropyl)ureido]
ethoxy}phenyl)-2-ethoxypropionic acid,
3-(4-{2-[1-cyclobutylmethyl-3-(1-methylpropyl)ureido]
ethoxy}phenyl)-2-ethoxypropionic acid,
3-(4-{2-[1-cyclopentylmethyl-3-(1-methylpropyl)ureido]
ethoxy}phenyl)-2-ethoxypropionic acid,
3-(4-{2-[1-(2-cyclopentylethyl)-3-(1-methylpropyl)ureido]
ethoxy}phenyl)-2-ethoxypropionic acid,
3-(4-{2-[1-(3-cyclohexylpropyl)-3-(1-methylpropyl)ureido]
ethoxy}phenyl)-2-ethoxypropionic acid,
2-ethoxy-3-(4-{2-[3-(1-methylpropyl)-1-(3-phenylpropyl)
ureido]ethoxy}phenyl)propionic acid,
2-ethoxy-3-(4-{2-[3-(1-methylpropyl)-1-(4-phenylbutyl)
ureido]ethoxy}phenyl)propionic acid,
3-(4-{2-[1-(2-butoxyethyl)-3-(1-methylpropyl)ureido]
ethoxy}phenyl)-2-ethoxypropionic acid,
2-ethoxy-3-(4-{2-[3-(1-methylpropyl)-1-(2-pentyloxyethyl)
ureido]ethoxy}phenyl)propionic acid,
2-ethoxy-3-(4-{2-[3-(1-methylpropyl)-1-(3-propoxypropyl)
ureido]ethoxy}phenyl)propionic acid,
3-(4-{2-[1-(2-butylthioethyl)-3-(1-methylpropyl)ureido]
ethoxy}phenyl)-2-ethoxypropionic acid,
2-ethoxy-3-(4-{2-[3-(1-methylpropyl)-1-(2-pentylthioethyl)
ureido]ethoxy}phenyl)propionic acid,
2-ethoxy-3-(4-{2-[3-(1-methylpropyl)-1-(3-propylthiopropyl)ureido]ethoxy}phenyl)propionic acid, 2-ethoxy-3-(4-{2-[3-(1-methylpropyl)-1-(3-phenoxypropyl) ureido]ethoxy}phenyl)propionic acid,
2-ethoxy-3-(4-{2-[3-(1-methylpropyl)-1-(4-phenoxybutyl) ureido]ethoxy}phenyl)propionic acid,
3-(4-{2-[1-(3-benzyloxypropyl)-3-(1-methylpropyl)ureido] ethoxy}phenyl)-2-ethoxypropionic acid,
2-ethoxy-3-(4-{2-[3-(1-methylpropyl)-1-(3-phenylthiopropyl)ureido]ethoxy}phenyl)propionic acid,
2-ethoxy-3-(4-{2-[3-(1-methylpropyl)-1-(4-phenylthiobutyl)ureido]ethoxy}phenyl)propionic acid,
3-(4-{2-[1-(3-benzylthiopropyl)-3-(1-methylpropyl)ureido] ethoxy}phenyl)-2 -ethoxypropionic acid,
2-ethoxy-3-(4-{2-[3-(1-methylpropyl)-1-(7,7,7-trifluoroheptyl)ureido]ethoxy}phenyl)propionic acid,
3-(4-{2-[1-(6,6-difluoroheptyl)-3-(1-methylpropyl)ureido] ethoxy}phenyl)-2-ethoxypropionic acid,
2-ethoxy-3-(4-{2-[3-(1-methylpropyl)-1-(6,6,6-trifluorohexyl)ureido]ethoxy}phenyl)propionic acid,
3-(4-{2-[1-(5,5-difluorohexyl)-3-(1-methylpropyl)ureido] ethoxy}phenyl)-2-ethoxypropionic acid,
2-ethoxy-3-(4-{2-[1-(5,5,6,6,7,7,7-heptafluoroheptyl)-3-(1-methylpropyl)ureido]ethoxy}phenyl)propionic acid,
2-ethoxy-3-(4-{2-[3-(1-methylpropyl)-1-(2,2,3,3,4,4,5,5,6,6,7,7,7-tridecafluoroheptyl)ureido]ethoxy}phenyl)propionic acid,
2-ethoxy-3-(4-{2-[3-(1-methylpropyl)-1-(5,5,6,6,6-pentafluorohexyl)ureido]ethoxy}phenyl)propionic acid,
2-ethoxy-3-(4-{2-[3-(1-methylpropyl)-1-(2,2,3,3,4,4,5,5,6,6-undecafluorohexyl)ureido]ethoxy}phenyl)propionic acid,
3-[4-(2-{1-[2-(2,2-difluoropropoxy)ethyl]-3-(1-methylpropyl)ureido}ethoxy)phenyl]-2-ethoxypropionic acid,
2-ethoxy-3-[4-(2-{1-[2-(1,1,2,2,3,3,3-heptafluoropropoxy) ethyl]-3-(1-methylpropyl)ureido}ethoxy)phenyl]propionic acid,
2-ethoxy-3-[4-(2-{3-(1-methylpropyl)-1-[2-(4,4,4-trifluorobutoxy)ethyl]ureido}ethoxy)phenyl]propionic acid,
3-[4-(2-{1-[2-(3,3-difluorobutoxy)ethyl]-3-(1-methylpropyl)ureido}ethoxy)phenyl]-2-ethoxypropionic acid,
3-[4-(2-{1-[2-(2,2-difluorobutoxy)ethyl]-3-(1-methylpropyl)ureido}ethoxy)phenyl]-2-ethoxypropionic acid,
2-ethoxy-3-[4-(2-{3-(1-methylpropyl)-1-[2-(1,1,2,2,3,3,4,4,4-nonafluorobutoxy)ethyl]ureido}ethoxy)phenyl]propionic acid,
2-ethoxy-3-[4-(2-{3-(1-methylpropyl)-1-[3-(2,2,2-trifluoroethoxy)propyl]ureido}ethoxy)phenyl]propionic acid,
2-ethoxy-3-[4-(2-{3-(1-methylpropyl)-1-[3-(1,1,2,2,2-pentafluoroethoxy)propyl]ureido}ethoxy)phenyl]propionic acid,
2-ethoxy-3-[4-(2-{1-[3-(4-fluorophenoxy)propyl]-3-(1-methylpropyl)ureido}ethoxy)phenyl]propionic acid,
3-[4-(2-{1-[3-(3,5-dichlorophenoxy)propyl]-3-(1-methylpropyl)ureido}ethoxy)phenyl]-2-ethoxypropionic acid,
2-ethoxy-3-[4-(2-{1-[4-(4-fluorophenoxy)butyl]-3-(1-methylpropyl)ureido}ethoxy)phenyl]propionic acid,
3-[4-(2-{1-[4-(3,5-dichlorophenoxy)butyl]-3-(1-methylpropyl)ureido}ethoxy)phenyl]-2-ethoxypropionic acid,
2-ethoxy-3-[4-(2-{1-[2-(4-fluorobenzyloxy)ethyl]-3-(1-methylpropyl)ureido}ethoxy)phenyl]propionic acid,
3-[4-(2-{1-[2-(3,5-dichlorobenzyloxy)ethyl]-3-(1-methylpropyl)ureido}ethoxy)phenyl]-2-ethoxypropionic acid,
2-ethoxy-3-[4-(2-{1-[3-(4-fluorobenzyloxy)propyl]-3-(1-methylpropyl)ureido}ethoxy)phenyl]propionic acid,
3-[4-(2-{1-[3-(3,5-dichlorobenzyloxy)propyl]-3-(1-methylpropyl)ureido}ethoxy)phenyl]-2-ethoxypropionic acid,
2-ethoxy-3-[4-(2-{1-[4-(4-fluorobenzyloxy)butyl]-3-(1-methylpropyl)ureido}ethoxy)phenyl]propionic acid,
3-[4-(2-{1-[4-(3,5-dichlorobenzyloxy)butyl]-3-(1-methylpropyl)ureido}ethoxy)phenyl]-2-ethoxypropionic acid,
2-ethoxy-3-[4-(2-{1-[3-(4-fluorophenyl)propyl]-3-(1-methylpropyl)ureido}ethoxy)phenyl]propionic acid,
3-[4-(2-{1-[3-(3,5-dichlorophenyl)propyl]-3-(1-methylpropyl)ureido}ethoxy)phenyl]-2-ethoxypropionic acid,
3-(4-{2-[3-(2,2-dimethylpropyl)-1-pentylureido] ethoxy}phenyl)-2-ethoxypropionic acid,
3-(4-{2-[3-(2,2-dimethylpropyl)-1-hexylureido] ethoxy}phenyl)-2-ethoxypropionic acid,
3-(4-{2-[3-(2,2-dimethylpropyl)-1-heptylureido] ethoxy}phenyl)-2-ethoxypropionic acid,
3-(4-{2-[3-(2,2-dimethylpropyl)-1-octylureido] ethoxy}phenyl)-2-ethoxypropionic acid,
3-(4-{2-[3-(2,2-dimethylpropyl)-1-isobutylureido] ethoxy}phenyl)-2-ethoxypropionic acid,
3-(4-{2-[3-(2,2-dimethylpropyl)-1-(3-methylbutyl)ureido] ethoxy}phenyl)-2-ethoxypropionic acid,
3-(4-{2-[3-(2,2-dimethylpropyl)-1-(4-methylpentyl)ureido] ethoxy}phenyl)-2 -ethoxypropionic acid,
3-(4-{2-[3-(2,2-dimethylpropyl)-1-(2-propylpentyl)ureido] ethoxy}phenyl)-2-ethoxypropionic acid,
3-(4-{2-[1-(3,3-dimethylbutyl)-3-(2,2-dimethylpropyl)ureido]ethoxy}phenyl)-2-ethoxypropionic acid,
3-(4-{2-[3-(2,2-dimethylpropyl)-1-(2-ethylbutyl)ureido] ethoxy}phenyl)-2-ethoxypropionic acid,
3-(4-{2-[1-cyclohexylmethyl-3-(2,2-dimethylpropyl)ureido]ethoxy}phenyl)-2-ethoxypropionic acid,
3-(4-{2-[1-(4-cyclohexylbutyl)-3-(2,2-dimethylpropyl)ureido]ethoxy}phenyl)-2-ethoxypropionic acid,
3-(4-{2-[1-cyclopropylmethyl-3-(2,2-dimethylpropyl)ureido]ethoxy}phenyl)-2-ethoxypropionic acid,
3-(4-{2-[1-cyclobutylmethyl-3-(2,2-dimethylpropyl)ureido] ethoxy}phenyl)-2-ethoxypropionic acid,
3-(4-{2-[1-cyclopentylmethyl-3-(2,2-dimethylpropyl)ureido]ethoxy}phenyl)-2-ethoxypropionic acid,
3-(4-{2-[1-(2-cyclopentylethyl)-3-(2,2-dimethylpropyl)ureido]ethoxy}phenyl)-2-ethoxypropionic acid,
3-(4-{2-[1-(3-cyclohexylpropyl)-3-(2,2-dimethylpropyl) ureido]ethoxy}phenyl)-2-ethoxypropionic acid,
3-(4-{2-[3-(2,2-dimethylpropyl)-1-(3-phenylpropyl)ureido] ethoxy}phenyl)-2-ethoxypropionic acid,
3-(4-{2-[3-(2,2-dimethylpropyl)-1-(4-phenylbutyl)ureido] ethoxy}phenyl)-2-ethoxypropionic acid,
3-(4-{2-[1-(2-butoxyethyl)-3-(2,2-dimethylpropyl)ureido] ethoxy}phenyl)-2-ethoxypropionic acid,
3-(4-{2-[3-(2,2-dimethylpropyl)-1-(2-pentyloxyethyl)ureido]ethoxy}phenyl)-2-ethoxypropionic acid,
3-(4-{2-[3-(2,2-dimethylpropyl)-1-(3-propoxypropyl)ureido]ethoxy}phenyl)-2-ethoxypropionic acid,
3-(4-{2-[1-(2-butylthioethyl)-3-(2,2-dimethylpropyl)ureido]ethoxy}phenyl)-2-ethoxypropionic acid,
3-(4-{2-[3-(2,2-dimethylpropyl)-1-(2-pentylthioethyl)ureido]ethoxy}phenyl)-2-ethoxypropionic acid,
3-(4-{2-[3-(2,2-dimethylpropyl)-1-(3-propylthiopropyl)ureido]ethoxy}phenyl)-2-ethoxypropionic acid,
3-(4-{2-[3-(2,2-dimethylpropyl)-1-(3-phenoxypropyl)ureido]ethoxy}phenyl)-2-ethoxypropionic acid,
3-(4-{2-[3-(2,2-dimethylpropyl)-1-(4-phenoxybutyl)ureido] ethoxy}phenyl)-2-ethoxypropionic acid,
3-(4-{2-[1-(3-benzyloxypropyl)-3-(2,2-dimethylpropyl)ureido]ethoxy}phenyl)-2-ethoxypropionic acid,
3-(4-{2-[3-(2,2-dimethylpropyl)-1-(3-phenylthiopropyl) ureido]ethoxy}phenyl)-2-ethoxypropionic acid,
3-(4-{2-[3-(2,2-dimethylpropyl)-1-(4-phenylthiobutyl)ureido]ethoxy}phenyl)-2-ethoxypropionic acid, 3-(4-{2-[1-(3-benzylthiopropyl)-3-(2,2-dimethylpropyl)ureido]ethoxy}phenyl)-2-ethoxypropionic acid,
3-(4-{2-[3-(2,2-dimethylpropyl)-1-(7,7,7-trifluoroheptyl)ureido]ethoxy}phenyl)-2-ethoxypropionic acid,
3-(4-{2-[1-(6,6-difluoroheptyl)-3-(2,2-dimethylpropyl)ureido]ethoxy}phenyl)-2-ethoxypropionic acid,
3-(4-{2-[3-(2,2-dimethylpropyl)-1-(6,6,6-trifluorohexyl)ureido]ethoxy}phenyl)-2-ethoxypropionic acid,
3-(4-{2-[1-(5,5-difluorohexyl)-3-(2,2-dimethylpropyl)ureido]ethoxy}phenyl)-2-ethoxypropionic acid,
3-(4-{2-[3-(2,2-dimethylpropyl)-1-(5,5,6,6,7,7,7-heptafluoroheptyl)ureido]ethoxy}phenyl)-2-ethoxypropionic acid,
3-(4-{2-[3-(2,2-dimethylpropyl)-1-(2,2,3,3,4,4,5,5,6,6,7,7,7-tridecafluoroheptyl)ureido]ethoxy}phenyl)-2-ethoxypropionic acid,
3-(4-{2-[3-(2,2-dimethylpropyl)-1-(5,5,6,6,6-pentafluorohexyl)ureido]ethoxy}phenyl)-2-ethoxypropionic acid,
3-(4-{2-[3-(2,2-dimethylpropyl)-1-(2,2,3,3,4,4,5,5,6,6,6-undecafluorohexyl)ureido]ethoxy}phenyl)-2-ethoxypropionic acid,
3-[4-(2-{1-[2-(2,2-difluoropropoxy)ethyl]-3-(2,2-dimethylpropyl)ureido}ethoxy)phenyl]-2-ethoxypropionic acid,
3-[4-(2-{3-(2,2-dimethylpropyl)-1-[2-(1,1,2,2,3,3,3-heptafluoropropoxy)ethyl]ureido}ethoxy)phenyl]-2-ethoxypropionic acid,
3-[4-(2-{3-(2,2-dimethylpropyl)-1-[2-(4,4,4-trifluorobutoxy)ethyl]ureido}ethoxy)phenyl]-2-ethoxypropionic acid,
3-[4-(2-{1-[2-(3,3-difluorobutoxy)ethyl]-3-(2,2-dimethylpropyl)ureido}ethoxy)phenyl]-2-ethoxypropionic acid,
3-[4-(2-{1-[2-(2,2-difluorobutoxy)ethyl]-3-(2,2-dimethylpropyl)ureido}ethoxy)phenyl]-2-ethoxypropionic acid,
3-[4-(2-{3-(2,2-dimethylpropyl)-1-[2-(1,1,2,2,3,3,4,4,4-nonafluorobutoxy)ethyl]ureido}ethoxy)phenyl]-2-ethoxypropionic acid,
3-[4-(2-{3-(2,2-dimethylpropyl)-1-[3-(2,2,2-trifluoroethoxy)propyl]ureido}ethoxy)phenyl]-2-ethoxypropionic acid,
3-[4-(2-{3-(2,2-dimethylpropyl)-1-[3-(1,1,2,2,2-pentafluoroethoxy)propyl]ureido}ethoxy)phenyl]-2-ethoxypropionic acid,
3-[4-(2-{3-(2,2-dimethylpropyl)-1-[3-(4-fluorophenoxy)propyl]ureido}ethoxy)phenyl]-2-ethoxypropionic acid,
3-[4-(2-{1-[3-(3,5-dichlorophenoxy)propyl]-3-(2,2-dimethylpropyl)ureido}ethoxy)phenyl]-2-ethoxypropionic acid,
3-[4-(2-{3-(2,2-dimethylpropyl)-1-[4-(4-fluorophenoxy)butyl]ureido}ethoxy)phenyl]-2-ethoxypropionic acid,
3-[4-(2-{1-[4-(3,5-dichlorophenoxy)butyl]-3-(2,2-dimethylpropyl)ureido}ethoxy)phenyl]-2-ethoxypropionic acid,
3-[4-(2-{3-(2,2-dimethylpropyl)-1-[2-(4-fluorobenzyloxy)ethyl]ureido}ethoxy)phenyl]-2-ethoxypropionic acid,
3-[4-(2-{1-[2-(3,5-dichlorobenzyloxy)ethyl]-3-(2,2-dimethylpropyl)ureido}ethoxy)phenyl]-2-ethoxypropionic acid,
3-[4-(2-{3-(2,2-dimethylpropyl)-1-[3-(4-fluorobenzyloxy)propyl]ureido}ethoxy)phenyl]-2-ethoxypropionic acid,
3-[4-(2-{1-[3-(3,5-dichlorobenzyloxy)propyl]-3-(2,2-dimethylpropyl)ureido}ethoxy)phenyl]-2-ethoxypropionic acid,
3-[4-(2-{3-(2,2-dimethylpropyl)-1-[4-(4-fluorobenzyloxy)butyl]ureido}ethoxy)phenyl]-2-ethoxypropionic acid,
3-[4-(2-{1-[4-(3,5-dichlorobenzyloxy)butyl]-3-(2,2-dimethylpropyl)ureido}ethoxy)phenyl]-2-ethoxypropionic acid,
3-[4-(2-{3-(2,2-dimethylpropyl)-1-[3-(4-fluorophenyl)propyl]ureido}ethoxy)phenyl]-2-ethoxypropionic acid,
3-[4-(2-{1-[3-(3,5-dichlorophenyl)propyl]-3-(2,2-dimethylpropyl)ureido}ethoxy)phenyl]-2-ethoxypropionic acid,
3-{4-[2-(3-cyclopentyl-1-pentylureido)ethoxy]phenyl}-2-ethoxypropionic acid,
3-{4-[2-(3-cyclopentyl-1-hexylureido)ethoxy]phenyl}-2-ethoxypropionic acid,
3-{4-[2-(3-cyclopentyl-1-heptylureido)ethoxy]phenyl}-2-ethoxypropionic acid,
3-{4-[2-(3-cyclopentyl-1-octylureido)ethoxy]phenyl}-2-ethoxypropionic acid,
3-{4-[2-(3-cyclopentyl-1-isobutylureido)ethoxy]phenyl}-2-ethoxypropionic acid,
3-(4-{2-[3-cyclopentyl-1-(3-methylbutyl)ureido]ethoxy}phenyl)-2-ethoxypropionic acid,
3-(4-{2-[3-cyclopentyl-1-(4-methylpentyl)ureido]ethoxy}phenyl)-2-ethoxypropionic acid,
3-(4-{2-[3-cyclopentyl-1-(2-propylpentyl)ureido]ethoxy}phenyl)-2-ethoxypropionic acid,
3-(4-{2-[3-cyclopentyl-1-(3,3-dimethylbutyl)ureido]ethoxy}phenyl)-2-ethoxypropionic acid,
3-(4-{2-[3-cyclopentyl-1-(2-ethylbutyl)ureido]ethoxy}phenyl)-2-ethoxypropionic acid,
3-{4-[2-(1-cyclohexylmethyl-3-cyclopentylureido)ethoxy]phenyl}-2-ethoxypropionic acid,
3-(4-{2-[1-(4-cyclohexylbutyl)-3-cyclopentylureido]ethoxy}phenyl)-2-ethoxypropionic acid,
3-{4-[2-(3-cyclopentyl-1-cyclopropylmethylureido)ethoxy]phenyl}-2-ethoxypropionic acid,
3-{4-[2-(1-cyclobutylmethyl-3-cyclopentylureido)ethoxy]phenyl}-2-ethoxypropionic acid,
3-{4-[2-(3-cyclopentyl-1-cyclopentylmethylureido)ethoxy]phenyl}-2-ethoxypropionic acid,
3-(4-{2-[3-cyclopentyl-1-(2-cyclopentylethyl)ureido]ethoxy}phenyl)-2-ethoxypropionic acid,
-3-(4-{2-[1-(3-cyclohexylpropyl)-3-cyclopentylureido]ethoxy}phenyl)-2-ethoxypropionic acid,
3-(4-{2-[3-cyclopentyl-1-(3-phenylpropyl)ureido]ethoxy}phenyl)-2-ethoxypropionic acid,
3-(4-{2-[3-cyclopentyl-1-(4-phenylbutyl)ureido]ethoxy}phenyl)-2-ethoxypropionic acid,
3-(4-{2-[1-(2-butoxyethyl)-3-cyclopentylureido]ethoxy}phenyl)-2-ethoxypropionic acid,
3-(4-{2-[3-cyclopentyl-1-(2-pentyloxyethyl)ureido]ethoxy}phenyl)-2-ethoxypropionic acid,
3-(4-{2-[3-cyclopentyl-1-(3-propoxypropyl)ureido]ethoxy}phenyl)-2-ethoxypropionic acid,
3-(4-{2-[1-(2-butylthioethyl)-3-cyclopentylureido]ethoxy}phenyl)-2-ethoxypropionic acid,
3-(4-{2-[3-cyclopentyl-1-(2-pentylthioethyl)ureido]ethoxy}phenyl)-2-ethoxypropionic acid,
3-(4-{2-[3-cyclopentyl-1-(3-propylthiopropyl)ureido]ethoxy}phenyl)-2-ethoxypropionic acid,
3-(4-{2-[3-cyclopentyl-1-(3-phenoxypropyl)ureido]ethoxy}phenyl)-2-ethoxypropionic acid,
3-(4-{2-[3-cyclopentyl-1-(4-phenoxybutyl)ureido]ethoxy}phenyl)-2-ethoxypropionic acid,
3-(4-{2-[1-(3-benzyloxypropyl)-3-cyclopentylureido]ethoxy}phenyl)-2-ethoxypropionic acid,
3-(4-{2-[3-cyclopentyl-1-(3-phenylthiopropyl)ureido]ethoxy}phenyl)-2-ethoxypropionic acid,
3-(4-{2-[3-cyclopentyl-1-(4-phenylthiobutyl)ureido]ethoxy}phenyl)-2-ethoxypropionic acid,
3-(4-{2-[1-(3-benzylthiopropyl)-3-cyclopentylureido]ethoxy}phenyl)-2-ethoxypropionic acid,
3-(4-{2-[3-cyclopentyl-1-(7,7,7-trifluoroheptyl)ureido]ethoxy}phenyl)-2-ethoxypropionic acid,
3-(4-{2-[3-cyclopentyl-1-(6,6-difluoroheptyl)ureido]ethoxy}phenyl)-2-ethoxypropionic acid, 3-(4-{2-[3-cyclopentyl-1-(6,6,6-trifluorohexyl)ureido]
ethoxy}phenyl)-2-ethoxypropionic acid,
3-(4-{2-[3-cyclopentyl-1-(5,5-difluorohexyl)ureido]
ethoxy}phenyl)-2-ethoxypropionic acid,
3-(4-{2-[3-cyclopentyl-1-(5,5,6,6,7,7,7-heptafluoroheptyl)
ureido]ethoxy}phenyl)-2-ethoxypropionic acid,
3-(4-{2-[3-cyclopentyl-1-(2,2,3,3,4,4,5,5,6,6,7,7,7-tridecafluoroheptyl)ureido]ethoxy}phenyl)-2-ethoxypropionic
acid,
3-(4-{2-[3-cyclopentyl-1-(5,5,6,6,6-pentafluorohexyl)ureido]ethoxy}phenyl)-2 -ethoxypropionic acid,
3-(4-{2-[3-cyclopentyl-1-(2,2,3,3,4,4,5,5,6,6,6-undecafluorohexyl)ureido]ethoxy}phenyl)-2-ethoxypropionic acid,
3-[4-(2-{3-cyclopentyl-1-[2-(2,2-difluoropropoxy)ethyl]
ureido}ethoxy)phenyl]-2-ethoxypropionic acid,
3-[4-(2-{3-cyclopentyl-1-[2-(1,1,2,2,3,3,3-heptafluoropropoxy)ethyl]ureido}ethoxy)phenyl]-2-ethoxypropionic
acid,
3-[4-(2-{3-cyclopentyl-1-[2-(4,4,4-trifluorobutoxy)ethyl]
ureido}ethoxy)phenyl]-2-ethoxypropionic acid,
3-[4-(2-{3-cyclopentyl-1-[2-(3,3-difluorobutoxy)ethyl]
ureido}ethoxy)phenyl]-2-ethoxypropionic acid,
3-[4-(2-{3-cyclopentyl-1-[2-(2,2-difluorobutoxy)ethyl]
ureido}ethoxy)phenyl]-2-ethoxypropionic acid,
3-[4-(2-{3-cyclopentyl-1-[2-(1,1,2,2,3,3,4,4,4-nonafluorobutoxy)ethyl]ureido}ethoxy)phenyl]-2-ethoxypropionic acid,
3-[4-(2-{3-cyclopentyl-1-[3-(2,2,2-trifluoroethoxy)propyl]
ureido}ethoxy)phenyl]-2-ethoxypropionic acid,
3-[4-(2-{3-cyclopentyl-1-[3-(1,1,2,2,2-pentafluoroethoxy)
propyl]ureido}ethoxy)phenyl]-2-ethoxypropionic acid,
3-[4-(2-{3-cyclopentyl-1-[3-(4-fluorophenoxy)propyl]
ureido}ethoxy)phenyl]-2-ethoxypropionic acid,
3-[4-(2-{3-cyclopentyl-1-[3-(3,5-dichlorophenoxy)propyl]
ureido}ethoxy)phenyl]-2-ethoxypropionic acid,
3-[4-(2-{3-cyclopentyl-1-[4-(4-fluorophenoxy)butyl]
ureido}ethoxy)phenyl]-2-ethoxypropionic acid,
3-[4-(2-{3-cyclopentyl-1-[4-(3,5-dichlorophenoxy)butyl]
ureido}ethoxy)phenyl]-2-ethoxypropionic acid,
3-[4-(2-{3-cyclopentyl-1-[2-(4-fluorobenzyloxy)ethyl]
ureido}ethoxy)phenyl]-2-ethoxypropionic acid,
3-[4-(2-{3-cyclopentyl-1-[2-(3,5-dichlorobenzyloxy)ethyl]
ureido}ethoxy)phenyl]-2-ethoxypropionic acid,
3-[4-(2-{3-cyclopentyl-1-[3-(4-fluorobenzyloxy)propyl]
ureido}ethoxy)phenyl]-2-ethoxypropionic acid,
3-[4-(2-{3-cyclopentyl-1-[3-(3,5-dichlorobenzyloxy)propyl]ureido}ethoxy)phenyl]-2-ethoxypropionic acid,
3-[4-(2-{3-cyclopentyl-1-[4-(4-fluorobenzyloxy)butyl]
ureido}ethoxy)phenyl]-2-ethoxypropionic acid,
3-[4-(2-{3-cyclopentyl-1-[4-(3,5-dichlorobenzyloxy)butyl]
ureido}ethoxy)phenyl]-2-ethoxypropionic acid,
3-[4-(2-{3-cyclopentyl-1-[3-(4-fluorophenyl)propyl]
ureido}ethoxy)phenyl]-2-ethoxypropionic acid,
3-[4-(2-{3-cyclopentyl-1-[3-(3,5-dichlorophenyl)propyl]
ureido}ethoxy)phenyl]-2-ethoxypropionic acid,
3-{4-[2-(3-cyclohexyl-1-pentylureido)ethoxy]phenyl}-2-
ethoxypropionic acid,
3-{4-[2-(3-cyclohexyl-1-hexylureido)ethoxy]phenyl}-2-
ethoxypropionic acid,
3-{4-[2-(3-cyclohexyl-1-heptylureido)ethoxy]phenyl}-2-
ethoxypropionic acid,
3-{4-[2-(3-cyclohexyl-1-octylureido)ethoxy]phenyl}-2-
ethoxypropionic acid,
3-{4-[2-(3-cyclohexyl-1-isobutylureido)ethoxy]phenyl}-2-
ethoxypropionic acid,
3-(4-{2-[3-cyclohexyl-1-(3-methylbutyl)ureido]
ethoxy}phenyl)-2-ethoxypropionic acid,
3-(4-{2-[3-cyclohexyl-1-(4-methylpentyl)ureido]
ethoxy}phenyl)-2-ethoxypropionic acid,
3-(4-{2-[3-cyclohexyl-1-(2-propylpentyl)ureido]
ethoxy}phenyl)-2-ethoxypropionic acid,
3-(4-{2-[3-cyclohexyl-1-(3,3-dimethylbutyl)ureido]
ethoxy}phenyl)-2-ethoxypropionic acid,
3-(4-{2-[3-cyclohexyl-1-(2-ethylbutyl)ureido]
ethoxy}phenyl)-2-ethoxypropionic acid,
3-{4-[2-(3-cyclohexyl-1-cyclohexylmethylureido)ethoxy]
phenyl}-2-ethoxypropionic acid,
3-(4-{2-[3-cyclohexyl-1-(4-cyclohexylbutyl)ureido]
ethoxy}phenyl)-2-ethoxypropionic acid,
3-{4-[2-(3-cyclohexyl-1-cyclopropylmethylureido)ethoxy]
phenyl}-2-ethoxypropionic acid,
3-{4-[2-(1-cyclobutylmethyl-3-cyclohexylureido)ethoxy]
phenyl}-2-ethoxypropionic acid,
3-{4-[2-(3-cyclohexyl-1-cyclopentylmethylureido)ethoxy]
phenyl}-2-ethoxypropionic acid,
3-{4-(2-[3-cyclohexyl-1-(2-cyclopentylethyl)ureido]
ethoxy}phenyl)-2-ethoxypropionic acid,
3-(4-{2-[3-cyclohexyl-1-(3-cyclohexylpropyl)ureido]
ethoxy}phenyl)-2-ethoxypropionic acid,
3-(4-{2-[3-cyclohexyl-1-(3-phenylpropyl)ureido]
ethoxy}phenyl)-2-ethoxypropionic acid,
3-(4-{2-[3-cyclohexyl-1-(4-phenylbutyl)ureido]
ethoxy}phenyl)-2-ethoxypropionic acid,
3-(4-{2-[1-(2-butoxyethyl)-3-cyclohexylureido]
ethoxy}phenyl)-2-ethoxypropionic acid,
3-(4-{2-[3-cyclohexyl-1-(2-pentyloxyethyl)ureido]
ethoxy}phenyl)-2-ethoxypropionic acid,
3-(4-{2-[3-cyclohexyl-1-(3-propoxypropyl)ureido]
ethoxy}phenyl)-2-ethoxypropionic acid,
3-(4-{2-[1-(2-butylthioethyl)-3-cyclohexylureido]
ethoxy}phenyl)-2-ethoxypropionic acid,
3-(4-{2-[3-cyclohexyl-1-(2-pentylthioethyl)ureido]
ethoxy}phenyl)-2-ethoxypropionic acid,
3-(4-{2-[3-cyclohexyl-1-(3-propylthiopropyl)ureido]
ethoxy}phenyl)-2-ethoxypropionic acid,
3-(4-{2-[3-cyclohexyl-1-(3-phenoxypropyl)ureido]
ethoxy}phenyl)-2-ethoxypropionic acid,
3-(4-{2-[3-cyclohexyl-1-(4-phenoxybutyl)ureido]
ethoxy}phenyl)-2-ethoxypropionic acid,
3-(4-{2-[1-(3-benzyloxypropyl)-3-cyclohexylureido]
ethoxy}phenyl)-2-ethoxypropionic acid,
3-(4-{2-[3-cyclohexyl-1-(3-phenylthiopropyl)ureido]
ethoxy}phenyl)-2-ethoxypropionic acid,
3-(4-{2-[3-cyclohexyl-1-(4-phenylthiobutyl)ureido]
ethoxy}phenyl)-2-ethoxypropionic acid,
3-(4-{2-[1-(3-benzylthiopropyl)-3-cyclohexylureido]
ethoxy}phenyl)-2-ethoxypropionic acid,
3-(4-{2-[3-cyclohexyl-1-(7,7,7-trifluoroheptyl)ureido]
ethoxy}phenyl)-2-ethoxypropionic acid,
3-(4-{2-[3-cyclohexyl-1-(6,6-difluoroheptyl)ureido]
ethoxy}phenyl)-2-ethoxypropionic acid,
3-(4-{2-[3-cyclohexyl-1-(6,6,6-trifluorohexyl)ureido]
ethoxy}phenyl)-2-ethoxypropionic acid,
3-(4-{2-[3-cyclohexyl-1-(5,5-difluorohexyl)ureido]
ethoxy}phenyl)-2-ethoxypropionic acid,
3-(4-{2-[3-cyclohexyl-1-(5,5,6,6,7,7,7-heptafluoroheptyl)
ureido]ethoxy}phenyl)-2-ethoxypropionic acid,
3-(4-{2-[3-cyclohexyl-1-(2,2,3,3,4,4,5,5,6,6,7,7,7-tridecafluoroheptyl)ureido]ethoxy}phenyl)-2-ethoxypropionic
acid,
3-(4-{2-[3-cyclohexyl-1-(5,5,6,6,6-pentafluorohexyl)ureido]ethoxy}phenyl)-2 -ethoxypropionic acid,
3-(4-{2-[3-cyclohexyl-1-(2,2,3,3,4,4,5,5,6,6,6-undecafluorohexyl)ureido]ethoxy}phenyl)-2-ethoxypropionic acid, 3-[4-(2-{3-cyclohexyl-1-[2-(2,2-difluoropropoxy)ethyl]
ureido}ethoxy)phenyl]-2-ethoxypropionic acid,
3-[4-(2-{3-cyclohexyl-1-[2-(1,1,2,2,3,3,3-heptafluoropropoxy)ethyl]ureido}ethoxy)phenyl]-2-ethoxypropionic
acid,
3-[4-(2-{3-cyclohexyl-1-[2-(4,4,4-trifluorobutoxy)ethyl]
ureido}ethoxy)phenyl]-2-ethoxypropionic acid,
3-[4-(2-{3-cyclohexyl-1-[2-(3,3-difluorobutoxy)ethyl]
ureido}ethoxy)phenyl]-2-ethoxypropionic acid,
3-[4-(2-{3-cyclohexyl-1-[2-(2,2-difluorobutoxy)ethyl]
ureido}ethoxy)phenyl]-2-ethoxypropionic acid,
3-[4-(2-{3-cyclohexyl-1-[2-(1,1,2,2,3,3,4,4,4-nonafluorobutoxy)ethyl]ureido}ethoxy)phenyl]-2-ethoxypropionic acid,
3-[4-(2-{3-cyclohexyl-1-[3-(2,2,2-trifluoroethoxy)propyl]
ureido}ethoxy)phenyl]-2-ethoxypropionic acid,
3-[4-(2-{3-cyclohexyl-1-[3-(1,1,2,2,2-pentafluoroethoxy)
propyl]ureido}ethoxy)phenyl]-2-ethoxypropionic acid,
3-[4-(2-{3-cyclohexyl-1-[3-(4-fluorophenoxy)propyl]
ureido}ethoxy)phenyl]-2-ethoxypropionic acid,
3-[4-(2-{3-cyclohexyl-1-[3-(3,5-dichlorophenoxy)propyl]
ureido}ethoxy)phenyl]-2-ethoxypropionic acid,
3-[4-(2-{3-cyclohexyl-1-[4-(4-fluorophenoxy)butyl]
ureido}ethoxy)phenyl]-2-ethoxypropionic acid,
3-[4-(2-{3-cyclohexyl-1-[4-(3,5-dichlorophenoxy)butyl]
ureido}ethoxy)phenyl]-2-ethoxypropionic acid,
3-[4-(2-{3-cyclohexyl-1-[2-(4-fluorobenzyloxy)ethyl]
ureido}ethoxy)phenyl]-2-ethoxypropionic acid,
3-[4-(2-{3-cyclohexyl-1-[2-(3,5-dichlorobenzyloxy)ethyl]
ureido}ethoxy)phenyl]-2-ethoxypropionic acid,
3-[4-(2-{3-cyclohexyl-1-[3-(4-fluorobenzyloxy)propyl]
ureido}ethoxy)phenyl]-2-ethoxypropionic acid,
3-[4-(2-{3-cyclohexyl-1-[3-(3,5-dichlorobenzyloxy)propyl]
ureido}ethoxy)phenyl]-2-ethoxypropionic acid,
3-[4-(2-{3-cyclohexyl-1-[4-(4-fluorobenzyloxy)butyl]
ureido}ethoxy)phenyl]-2-ethoxypropionic acid,
3-[4-(2-{3-cyclohexyl-1-[4-(3,5-dichlorobenzyloxy)butyl]
ureido}ethoxy)phenyl]-2-ethoxypropionic acid,
3-[4-(2-{3-cyclohexyl-1-[3-(4-fluorophenyl)propyl]
ureido}ethoxy)phenyl]-2-ethoxypropionic acid, and
3-[4-(2-{3-cyclohexyl-1-[3-(3,5-dichlorophenyl)propyl]
ureido}ethoxy)phenyl]-2-ethoxypropionic acid.

Examples of the compounds wherein $R^1$ is a substituted $C_{1-12}$ alkyl group include the following compounds.

2-Ethoxy-3-(4-{2-[1-pentyl-3-(2,2,2-trifluoroethyl)ureido]
ethoxy}phenyl)propionic acid,
2-ethoxy-3-(4-{2-[1-hexyl-3-(2,2,2-trifluoroethyl)ureido]
ethoxy}phenyl)propionic acid,
2-ethoxy-3-(4-{2-[1-heptyl-3-(2,2,2-trifluoroethyl)ureido]
ethoxy}phenyl)propionic acid,
2-ethoxy-3-(4-{2-[1-octyl-3-(2,2,2-trifluoroethyl)ureido]
ethoxy}phenyl)propionic acid,
2-ethoxy-3-(4-{2-[1-isobutyl-3-(2,2,2-trifluoroethyl)ureido]
ethoxy}phenyl)propionic acid,
2-ethoxy-3-(4-{2-[1-(3-methylbutyl)-3-(2,2,2-trifluoroethyl)ureido]ethoxy}phenyl)propionic acid,
2-ethoxy-3-(4-{2-[1-(4-methylpentyl)-3-(2,2,2-trifluoroethyl)ureido]ethoxy}phenyl)propionic acid,
2-ethoxy-3-(4-{2-[1-(2-propylpentyl)-3-(2,2,2-trifluoroethyl)ureido]ethoxy}phenyl)propionic acid,
3-(4-{2-[1-(3,3-dimethylbutyl)-3-(2,2,2-trifluoroethyl)ureido]ethoxy}phenyl)-2-ethoxypropionic acid,
2-ethoxy-3-(4-{2-[1-(1-ethylbutyl)-3-(2,2,2-trifluoroethyl)
ureido]ethoxy}phenyl)propionic acid,
3-(4-{2-[1-cyclohexylmethyl-3-(2,2,2-trifluoroethyl)ureido]ethoxy}phenyl)-2-ethoxypropionic acid,
3-(4-{2-[1-(4-cyclohexylbutyl)-3-(2,2,2-trifluoroethyl)ureido]ethoxy}phenyl)-2-ethoxypropionic acid,
3-(4-{2-[1-cyclopropylmethyl-3-(2,2,2-trifluoroethyl)ureido]ethoxy}phenyl)-2 -ethoxypropionic acid,
3-(4-{2-[1-cyclobutylmethyl-3-(2,2,2-trifluoroethyl)ureido]
ethoxy}phenyl)-2-ethoxypropionic acid,
3-(4-{2-[1-cyclopentylmethyl-3-(2,2,2-trifluoroethyl)ureido]ethoxy}phenyl)-2-ethoxypropionic acid,
3-(4-{2-[1-(2-cyclopentylethyl)-3-(2,2,2-trifluoroethyl)ureido]ethoxy}phenyl)-2-ethoxypropionic acid,
3-(4-{2-[1-(3-cyclohexylpropyl)-3-(2,2,2-trifluoroethyl)
ureido]ethoxy}phenyl)-2-ethoxypropionic acid,
2-ethoxy-3-(4-{2-[1-(3-phenylpropyl)-3-(2,2,2-trifluoroethyl)ureido]ethoxy}phenyl)propionic acid,
2-ethoxy-3-(4-{2-[1-(4-phenylbutyl)-3-(2,2,2-trifluoroethyl)ureido]ethoxy}phenyl)propionic acid,
3-(4-{2-[1-(2-butoxyethyl)-3-(2,2,2-trifluoroethyl)ureido]
ethoxy}phenyl)-2-ethoxypropionic acid,
2-ethoxy-3-(4-{2-[1-(2-pentyloxyethyl)-3-(2,2,2-trifluoroethyl)ureido]ethoxy}phenyl)propionic acid,
2-ethoxy-3-(4-{2-[1-(3-propoxypropyl)-3-(2,2,2-trifluoroethyl)ureido]ethoxy}phenyl)propionic acid,
3-(4-{2-[1-(2-butylthioethyl)-3-(2,2,2-trifluoroethyl)ureido]
ethoxy}phenyl)-2-ethoxypropionic acid,
2-ethoxy-3-(4-{2-[1-(2-pentylthioethyl)-3-(2,2,2-trifluoroethyl)ureido]ethoxy}phenyl)propionic acid,
2-ethoxy-3-(4-{2-[1-(3-propylthiopropyl)-3-(2,2,2-trifluoroethyl)ureido]ethoxy}phenyl)propionic acid,
2-ethoxy-3-(4-{2-[1-(3-phenoxypropyl)-3-(2,2,2-trifluoroethyl)ureido]ethoxy}phenyl)propionic acid,
2-ethoxy-3-(4-{2-[1-(4-phenoxybutyl)-3-(2,2,2-trifluoroethyl)ureido]ethoxy}phenyl)propionic acid,
3-(4-{2-[1-(3-benzyloxypropyl)-3-(2,2,2-trifluoroethyl)ureido]ethoxy}phenyl)-2-ethoxypropionic acid,
2-ethoxy-3-(4-{2-[1-(3-phenylthiopropyl)-3-(2,2,2-trifluoroethyl)ureido]ethoxy}phenyl)propionic acid,
2-ethoxy-3-(4-{2-[1-(4-phenylthiobutyl)-3-(2,2,2-trifluoroethyl)ureido]ethoxy}phenyl)propionic acid,
3-(4-{2-[1-(3-benzylthiopropyl)-3-(2,2,2-trifluoroethyl)ureido]ethoxy}phenyl)-2-ethoxypropionic acid,
2-ethoxy-3-(4-{2-[3-(2,2,2-trifluoroethyl)-1-(7,7,7-trifluoroheptyl)ureido]ethoxy}phenyl)propionic acid,
2-ethoxy-3-(4-{2-[3-(2,2,2-trifluoroethyl)-1-(6,6-difluoroheptyl)ureido]ethoxy}phenyl)propionic acid,
2-ethoxy-3-(4-{2-[3-(2,2,2-trifluoroethyl)-1-(6,6,6-trifluorohexyl)ureido]ethoxy}phenyl)propionic acid,
3-(4-{2-[1-(5,5-difluorohexyl)-3-(2,2,2-trifluoroethyl)ureido]ethoxy}phenyl)-2-ethoxypropionic acid,
2-ethoxy-3-(4-{2-[1-(5,5,6,6,7,7,7-heptafluoroheptyl)-3-(2,2,2-trifluoroethyl)ureido]ethoxy}phenyl)propionic acid,
2-ethoxy-3-(4-{2-[1-(2,2,3,3,4,4,5,5,6,6,7,7,7-tridecafluoroheptyl)-3-(2,2,2-trifluoroethyl)ureido]ethoxy}phenyl)
propionic acid,
2-ethoxy-3-(4-{2-[1-(5,5,6,6,6-pentafluorohexyl)-3-(2,2,2-trifluoroethyl)ureido]ethoxy}phenyl)propionic acid,
2-ethoxy-3-(4-{2-[3-(2,2,2-trifluoroethyl)-1-(2,2,3,3,4,4,5,5,6,6,6-undecafluorohexyl)ureido]ethoxy}phenyl)propionic acid,
3-[4-(2-{1-[2-(2,2-difluoropropoxy)ethyl]-3-(2,2,2-trifluoroethyl)ureido}ethoxy)phenyl]-2-ethoxypropionic acid,
2-ethoxy-3-[4-(2-{1-[2-(1,1,2,2,3,3,3-heptafluoropropoxy)
ethyl]-3-(2,2,2-trifluoroethyl)ureido}ethoxy)phenyl]propionic acid,
2-ethoxy-3-[4-(2-{1-[2-(4,4,4-trifluorobutoxy)ethyl]-3-(2,2,2-trifluoroethyl)ureido}ethoxy)phenyl]]propionic acid,
3-[4-(2-{1-[2-(3,3-difluorobutoxy)ethyl]-3-(2,2,2-trifluoroethyl)ureido}ethoxy)phenyl]-2-ethoxypropionic acid, 3-[4-(2-{1-[2-(2,2-difluorobutoxy)ethyl]-3-(2,2,2-trifluoroethyl)ureido}ethoxy)phenyl]-2-ethoxypropionic acid,
2-ethoxy-3-[4-(2-{1-[2-(1,1,2,2,3,3,4,4,4-nonafluorobutoxy)ethyl]-3-(2,2,2-trifluoroethyl)ureido}ethoxy)phenyl]propionic acid,
2-ethoxy-3-[4-(2-{1-[3-(2,2,2-trifluoroethoxy)propyl]-3-(2,2,2-trifluoroethyl)ureido}ethoxy)phenyl]propionic acid,
2-ethoxy-3-[4-(2-{1-[3-(1,1,2,2,2-pentafluoroethoxy)propyl]-3-(2,2,2-trifluoroethyl)ureido}ethoxy)phenyl]propionic acid,
2-ethoxy-3-[4-(2-{1-[3-(4-fluorophenoxy)propyl]-3-(2,2,2-trifluoroethyl)ureido}ethoxy)phenyl]propionic acid,
3-[4-(2-{1-[3-(3,5-dichlorophenoxy)propyl]-3-(2,2,2-trifluoroethyl)ureido}ethoxy)phenyl]-2-ethoxypropionic acid,
2-ethoxy-3-[4-(2-{1-[4-(4-fluorophenoxy)butyl]-3-(2,2,2-trifluoroethyl)ureido}ethoxy)phenyl]propionic acid,
3-[4-(2-{1-[4-(3,5-dichlorophenoxy)butyl]-3-(2,2,2-trifluoroethyl)ureido}ethoxy)phenyl]-2-ethoxypropionic acid,
2-ethoxy-3-[4-(2-{1-[2-(4-fluorobenzyloxy)ethyl]-3-(2,2,2-trifluoroethyl)ureido}ethoxy)phenyl]propionic acid,
3-[4-(2-{1-[2-(3,5-dichlorobenzyloxy)ethyl]-3-(2,2,2-trifluoroethyl)ureido}ethoxy)phenyl]-2-ethoxypropionic acid,
2-ethoxy-3-[4-(2-{1-[3-(4-fluorobenzyloxy)propyl]-3-(2,2,2-trifluoroethyl)ureido}ethoxy)phenyl]propionic acid,
3-[4-(2-{1-[3-(3,5-dichlorobenzyloxy)propyl]-3-(2,2,2-trifluoroethyl)ureido}ethoxy)phenyl]-2-ethoxypropionic acid,
2-ethoxy-3-[4-(2-{1-[4-(4-fluorobenzyloxy)butyl]-3-(2,2,2-trifluoroethyl)ureido}ethoxy)phenyl]propionic acid,
3-[4-(2-{1-[4-(3,5-dichlorobenzyloxy)butyl]-3-(2,2,2-trifluoroethyl)ureido}ethoxy)phenyl]-2-ethoxypropionic acid,
2-ethoxy-3-[4-(2-{1-[3-(4-fluorophenyl)propyl]-3-(2,2,2-trifluoroethyl)ureido}ethoxy)phenyl]propionic acid,
3-[4-(2-{1-[3-(3,5-dichlorophenyl)propyl]-3-(2,2,2-trifluoroethyl)ureido}ethoxy)phenyl]-2-ethoxypropionic acid,
2-ethoxy-3-(4-{2-[3-(2-methoxyethyl)-1-pentylureido]ethoxy}phenyl)propionic acid,
2-ethoxy-3-(4-{2-[1-hexyl-3-(2-methoxyethyl)ureido]ethoxy}phenyl)propionic acid,
2-ethoxy-3-(4-{2-[1-heptyl-3-(2-methoxyethyl)ureido]ethoxy}phenyl)propionic acid,
2-ethoxy-3-(4-{2-[3-(2-methoxyethyl)-1-octylureido]ethoxy}phenyl)propionic acid,
2-ethoxy-3-(4-{2-[1-isobutyl-3-(2-methoxyethyl)ureido]ethoxy}phenyl)propionic acid,
2-ethoxy-3-(4-{2-[1-(3-methylbutyl)-3-(2-methoxyethyl)ureido]ethoxy}phenyl)propionic acid,
2-ethoxy-3-(4-{2-[3-(2-methoxyethyl)-1-(4-methylpentyl)ureido]ethoxy}phenyl)propionic acid,
2-ethoxy-3-(4-{2-[3-(2-methoxyethyl)-1-(2-propylpentyl)ureido]ethoxy}phenyl)propionic acid,
3-(4-{2-[1-(3,3-dimethylbutyl)-3-(2-methoxyethyl)ureido]ethoxy}phenyl)-2-ethoxypropionic acid,
2-ethoxy-3-(4-{2-[1-(2-ethylbutyl)-3-(2-methoxyethyl)ureido]ethoxy}phenyl)propionic acid,
3-(4-{2-[1-cyclohexylmethyl-3-(2-methoxyethyl)ureido]ethoxy}phenyl)-2-ethoxypropionic acid,
3-(4-{2-[1-(4-cyclohexylbutyl)-3-(2-methoxyethyl)ureido]ethoxy}phenyl)-2-ethoxypropionic acid,
3-(4-{2-[1-cyclopropylmethyl-3-(2-methoxyethyl)ureido]ethoxy}phenyl)-2-ethoxypropionic acid,
3-(4-{2-[1-cyclobutylmethyl-3-(2-methoxyethyl)ureido]ethoxy}phenyl)-2-ethoxypropionic acid,
3-(4-{2-[1-cyclopentylmethyl-3-(2-methoxyethyl)ureido]ethoxy}phenyl)-2-ethoxypropionic acid,
3-(4-{2-[1-(2-cyclopentylethyl)-3-(2-methoxyethyl)ureido]ethoxy}phenyl)-2-ethoxypropionic acid,
3-(4-{2-[1-(3-cyclohexylpropyl)-3-(2-methoxyethyl)ureido]ethoxy}phenyl)-2-ethoxypropionic acid,
2-ethoxy-3-(4-{2-[3-(2-methoxyethyl)-1-(3-phenylpropyl)ureido]ethoxy}phenyl)propionic acid,
2-ethoxy-3-(4-{2-[3-(2-methoxyethyl)-1-(4-phenylbutyl)ureido]ethoxy}phenyl)propionic acid,
3-(4-{2-[1-(2-butoxyethyl)-3-(2-methoxyethyl)ureido]ethoxy}phenyl)-2-ethoxypropionic acid,
2-ethoxy-3-(4-{2-[3-(2-methoxyethyl)-1-(2-pentyloxyethyl)ureido]ethoxy}phenyl)propionic acid,
2-ethoxy-3-(4-{2-[3-(2-methoxyethyl)-1-(3-propoxypropyl)ureido]ethoxy}phenyl)propionic acid,
3-(4-{2-[1-(2-butylthioethyl)-3-(2-methoxyethyl)ureido]ethoxy}phenyl)-2-ethoxypropionic acid,
2-ethoxy-3-(4-{2-[3-(2-methoxyethyl)-1-(2-pentylthioethyl)ureido]ethoxy}phenyl)propionic acid,
2-ethoxy-3-(4-{2-[3-(2-methoxyethyl)-1-(3-propylthiopropyl)ureido]ethoxy}phenyl)propionic acid,
2-ethoxy-3-(4-{2-[3-(2-methoxyethyl)-1-(3-phenoxypropyl)ureido]ethoxy}phenyl)propionic acid,
2-ethoxy-3-(4-{2-[3-(2-methoxyethyl)-1-(4-phenoxybutyl)ureido]ethoxy}phenyl)propionic acid,
3-(4-{2-[1-(3-benzyloxypropyl)-3-(2-methoxyethyl)ureido]ethoxy}phenyl)-2-ethoxypropionic acid,
2-ethoxy-3-(4-{2-[3-(2-methoxyethyl)-1-(3-phenylthiopropyl)ureido]ethoxy}phenyl)propionic acid,
2-ethoxy-3-(4-{2-[3-(2-methoxyethyl)-1-(4-phenylthiobutyl)ureido]ethoxy}phenyl)propionic acid,
3-(4-{2-[1-(3-benzylthiopropyl)-3-(2-methoxyethyl)ureido]ethoxy}phenyl)-2-ethoxypropionic acid,
2-ethoxy-3-(4-{2-[3-(2-methoxyethyl)-1-(7,7,7-trifluoroheptyl)ureido]ethoxy}phenyl)propionic acid,
3-(4-{2-[1-(6,6-difluoroheptyl)-3-(2-methoxyethyl)ureido]ethoxy}phenyl)-2-ethoxypropionic acid,
2-ethoxy-3-(4-{2-[3-(2-methoxyethyl)-1-(6,6,6-trifluorohexyl)ureido]ethoxy}phenyl)propionic acid,
3-(4-{2-[1-(5,5-difluorohexyl)-3-(2-methoxyethyl)ureido]ethoxy}phenyl)-2-ethoxypropionic acid,
2-ethoxy-3-(4-{2-[1-(5,5,6,6,7,7,7-heptafluoroheptyl)-3-(2-methoxyethyl)ureido]ethoxy}phenyl)propionic acid,
2-ethoxy-3-(4-{2-[3-(2-methoxyethyl)-1-(2,2,3,3,4,4,5,5,6,6,7,7,7-tridecafluoroheptyl)ureido]ethoxy}phenyl)propionic acid,
2-ethoxy-3-(4-{2-[3-(2-methoxyethyl)-1-(5,5,6,6,6-pentafluorohexyl)ureido]ethoxy}phenyl)propionic acid,
2-ethoxy-3-(4-{2-[3-(2-methoxyethyl)-1-(2,2,3,3,4,4,5,5,6,6,6-undecafluorohexyl)ureido]ethoxy}phenyl)propionic acid,
3-[4-(2-{1-[2-(2,2-difluoropropoxy)ethyl]-3-(2-methoxyethyl)ureido}ethoxy)phenyl]-2-ethoxypropionic acid,
2-ethoxy-3-[4-(2-{1-[2-(1,1,2,2,3,3,3-heptafluoropropoxy)ethyl]-3-(2-methoxyethyl)ureido}ethoxy)phenyl]propionic acid,
2-ethoxy-3-[4-(2-{3-(2-methoxyethyl)-1-[2-(4,4,4-trifluorobutoxy)ethyl]ureido}ethoxy)phenyl]propionic acid,
3-[4-(2-{1-[2-(3,3-difluorobutoxy)ethyl]-3-(2-methoxyethyl)ureido}ethoxy)phenyl]-2-ethoxypropionic acid,
3-[4-(2-{1-[2-(2,2-difluorobutoxy)ethyl]-3-(2-methoxyethyl)ureido}ethoxy)phenyl]-2-ethoxypropionic acid,
2-ethoxy-3-[4-(2-{3-(2-methoxyethyl)-1-[2-(1,1,2,2,3,3,4,4,4-nonafluorobutoxy)ethyl]ureido}ethoxy)phenyl]propionic acid, 2-ethoxy-3-[4-(2-{3-(2-methoxyethyl)-1-[3-(2,2,2-trifluoroethoxy)propyl]ureido}ethoxy)phenyl]propionic acid,
2-ethoxy-3-[4-(2-{3-(2-methoxyethyl)-1-[3-(1,1,2,2,2-pentafluoroethoxy)propyl]ureido}ethoxy)phenyl]propionic acid,
2-ethoxy-3-[4-(2-{1-[3-(4-fluorophenoxy)propyl]-3-(2-methoxyethyl)ureido}ethoxy)phenyl]propionic acid,
3-[4-(2-{1-[3-(3,5-dichlorophenoxy)propyl]-3-(2-methoxyethyl)ureido}ethoxy)phenyl]-2-ethoxypropionic acid,
2-ethoxy-3-[4-(2-{1-[4-(4-fluorophenoxy)butyl]-3-(2-methoxyethyl)ureido}ethoxy)phenyl]propionic acid,
3-[4-(2-{1-[4-(3,5-dichlorophenoxy)butyl]-3-(2-methoxyethyl)ureido}ethoxy)phenyl]-2-ethoxypropionic acid,
2-ethoxy-3-[4-(2-{1-[2-(4-fluorobenzyloxy)ethyl]-3-(2-methoxyethyl)ureido}ethoxy)phenyl]propionic acid,
3-[4-(2-{1-[2-(3,5-dichlorobenzyloxy)ethyl]-3-(2-methoxyethyl)ureido}ethoxy)phenyl]-2-ethoxypropionic acid,
2-ethoxy-3-[4-(2-{1-[3-(4-fluorobenzyloxy)propyl]-3-(2-methoxyethyl)ureido}ethoxy)phenyl]propionic acid,
3-[4-(2-{1-[3-(3,5-dichlorobenzyloxy)propyl]-3-(2-methoxyethyl)ureido}ethoxy)phenyl]-2-ethoxypropionic acid,
2-ethoxy-3-[4-(2-{1-[4-(4-fluorobenzyloxy)butyl]-3-(2-methoxyethyl)ureido}ethoxy)phenyl]propionic acid,
3-[4-(2-{1-[4-(3,5-dichlorobenzyloxy)butyl]-3-(2-methoxyethyl)ureido}ethoxy)phenyl]-2-ethoxypropionic acid,
2-ethoxy-3-[4-(2-{1-[3-(4-fluorophenyl)propyl]-3-(2-methoxyethyl)ureido}ethoxy)phenyl]propionic acid,
3-[4-(2-{1-[3-(3,5-dichlorophenyl)propyl]-3-(2-methoxyethyl)ureido}ethoxy)phenyl]-2-ethoxypropionic acid,
3-{4-[2-(3-benzyl-1-pentylureido)ethoxy]phenyl}-2-ethoxypropionic acid,
3-{4-[2-(3-benzyl-1-hexylureido)ethoxy]phenyl}-2-ethoxypropionic acid,
3-{4-[2-(3-benzyl-1-heptylureido)ethoxy]phenyl}-2-ethoxypropionic acid,
3-{4-[2-(3-benzyl-1-octylureido)ethoxy]phenyl}-2-ethoxypropionic acid,
3-{4-[2-(3-benzyl-1-isobutylureido)ethoxy]phenyl}-2-ethoxypropionic acid,
3-(4-{2-[3-benzyl-1-(3-methylbutyl)ureido]ethoxy}phenyl)-2-ethoxypropionic acid,
3-(4-{2-[3-benzyl-1-(4-methylpentyl)ureido]ethoxy}phenyl)-2-ethoxypropionic acid,
3-(4-{2-[3-benzyl-1-(2-propylpentyl)ureido]ethoxy}phenyl)-2-ethoxypropionic acid,
3-(4-{2-[3-benzyl-1-(3,3-dimethylbutyl)ureido]ethoxy}phenyl)-2-ethoxypropionic acid,
3-(4-{2-[3-benzyl-1-(2-ethylbutyl)ureido]ethoxy}phenyl)-2-ethoxypropionic acid,
3-{4-[2-(3-benzyl-1-cyclohexylmethylureido)ethoxy]phenyl}-2-ethoxypropionic acid,
3-(4-{2-[3-benzyl-1-(4-cyclohexylbutyl)ureido]ethoxy}phenyl)-2-ethoxypropionic acid,
3-{4-[2-(3-benzyl-1-cyclopropylmethylureido)ethoxy]phenyl}-2-ethoxypropionic acid,
3-{4-[2-(3-benzyl-1-cyclobutylmethylureido)ethoxy]phenyl}-2-ethoxypropionic acid,
3-{4-[2-(3-benzyl-1-cyclopentylmethylureido)ethoxy]phenyl}-2-ethoxypropionic acid,
3-(4-{2-[3-benzyl-1-(2-cyclopentylethyl)ureido]ethoxy}phenyl)-2-ethoxypropionic acid,
3-(4-{2-[3-benzyl-1-(3-cyclohexylpropyl)ureido]ethoxy}phenyl)-2-ethoxypropionic acid,
3-(4-{2-[3-benzyl-1-(3-phenylpropyl)ureido]ethoxy}phenyl)-2-ethoxypropionic acid,
3-(4-{2-[3-benzyl-1-(4-phenylbutyl)ureido]ethoxy}phenyl)-2-ethoxypropionic acid,
3-(4-{2-[3-benzyl-1-(2-butoxyethyl)ureido]ethoxy}phenyl)-2-ethoxypropionic acid,
3-(4-{2-[3-benzyl-1-(2-pentyloxyethyl)ureido]ethoxy}phenyl)-2-ethoxypropionic acid,
3-(4-{2-[3-benzyl-1-(3-propoxypropyl)ureido]ethoxy}phenyl)-2-ethoxypropionic acid,
3-(4-{2-[3-benzyl-1-(2-butylthioethyl)ureido]ethoxy}phenyl)-2-ethoxypropionic acid,
3-(4-{2-[3-benzyl-1-(2-pentylthioethyl)ureido]ethoxy}phenyl)-2-ethoxypropionic acid,
3-(4-{2-[3-benzyl-1-(3-propylthiopropyl)ureido]ethoxy}phenyl)-2-ethoxypropionic acid,
3-(4-{2-[3-benzyl-1-(3-phenoxypropyl)ureido]ethoxy}phenyl)-2-ethoxypropionic acid,
3-(4-{2-[3-benzyl-1-(4-phenoxybutyl)ureido]ethoxy}phenyl)-2-ethoxypropionic acid,
3-(4-{2-[3-benzyl-1-(3-benzyloxypropyl)ureido]ethoxy}phenyl)-2-ethoxypropionic acid,
3-(4-{2-[3-benzyl-1-(3-phenylthiopropyl)ureido]ethoxy}phenyl)-2-ethoxypropionic acid,
3-(4-{2-[3-benzyl-1-(4-phenylthiobutyl)ureido]ethoxy}phenyl)-2-ethoxypropionic acid,
3-(4-{2-[3-benzyl-1-(3-benzylthiopropyl)ureido]ethoxy}phenyl)-2-ethoxypropionic acid,
3-(4-{2-[3-benzyl-1-(7,7,7-trifluoroheptyl)ureido]ethoxy}phenyl)-2-ethoxypropionic acid,
3-(4-{2-[3-benzyl-1-(6,6-difluoroheptyl)ureido]ethoxy}phenyl)-2-ethoxypropionic acid,
3-(4-{2-[3-benzyl-1-(6,6,6-trifluorohexyl)ureido]ethoxy}phenyl)-2-ethoxypropionic acid,
3-(4-{2-[3-benzyl-1-(5,5-difluorohexyl)ureido]ethoxy}phenyl)-2-ethoxypropionic acid,
3-(4-{2-[3-benzyl-1-(5,5,6,6,7,7,7-heptafluoroheptyl)ureido]ethoxy}phenyl)-2-ethoxypropionic acid,
3-(4-{2-[3-benzyl-1-(2,2,3,3,4,4,5,5,6,6,7,7,7-tridecafluoroheptyl)ureido]ethoxy}phenyl)-2-ethoxypropionic acid,
3-(4-{2-[3-benzyl-1-(5,5,6,6,6-pentafluorohexyl)ureido]ethoxy}phenyl)-2-ethoxypropionic acid,
3-(4-{2-[3-benzyl-1-(2,2,3,3,4,4,5,5,6,6,6-undecafluorohexyl)ureido]ethoxy}phenyl)-2-ethoxypropionic acid,
3-[4-(2-{3-benzyl-1-[2-(2,2-difluoropropoxy)ethyl]ureido}ethoxy)phenyl]-2-ethoxypropionic acid,
3-[4-(2-{3-benzyl-1-[2-(1,1,2,2,3,3,3-heptafluoropropoxy)ethyl]ureido}ethoxy)phenyl]-2-ethoxypropionic acid,
3-[4-(2-{3-benzyl-1-[2-(4,4,4-trifluorobutoxy)ethyl]ureido}ethoxy)phenyl]-2-ethoxypropionic acid,
3-[4-(2-{3-benzyl-1-[2-(3,3-difluorobutoxy)ethyl]ureido}ethoxy)phenyl]-2-ethoxypropionic acid,
3-[4-(2-{3-benzyl-1-[2-(2,2-difluorobutoxy)ethyl]ureido}ethoxy)phenyl]-2-ethoxypropionic acid,
3-[4-(2-{3-benzyl-1-[2-(1,1,2,2,3,3,4,4,4-nonafluorobutoxy)ethyl]ureido}ethoxy)phenyl]-2-ethoxypropionic acid,
3-[4-(2-{3-benzyl-1-[3-(2,2,2-trifluoroethoxy)propyl]ureido}ethoxy)phenyl]-2-ethoxypropionic acid,
3-[4-(2-{3-benzyl-1-[3-(1,1,2,2,2-pentafluoroethoxy)propyl]ureido}ethoxy)phenyl]-2 -ethoxypropionic acid,
3-[4-(2-{3-benzyl-1-[3-(4-fluorophenoxy)propyl]ureido}ethoxy)phenyl]-2-ethoxypropionic acid,
3-[4-(2-{3-benzyl-1-[3-(3,5-dichlorophenoxy)propyl]ureido}ethoxy)phenyl]-2-ethoxypropionic acid,
3-[4-(2-{3-benzyl-1-[4-(4-fluorophenoxy)butyl]ureido}ethoxy)phenyl]-2-ethoxypropionic acid,
3-[4-(2-{3-benzyl-1-[4-(3,5-dichlorophenoxy)butyl]ureido}ethoxy)phenyl]-2-ethoxypropionic acid,
3-[4-(2-{3-benzyl-1-[2-(4-fluorobenzyloxy)ethyl]ureido}ethoxy)phenyl]-2-ethoxypropionic acid, 3-[4-(2-{3-benzyl-1-[2-(3,5-dichlorobenzyloxy)ethyl]ureido}ethoxy)phenyl]-2-ethoxypropionic acid,
3-[4-(2-{3-benzyl-1-[3-(4-fluorobenzyloxy)propyl]ureido}ethoxy)phenyl]-2-ethoxypropionic acid,
3-[4-(2-{3-benzyl-1-[3-(3,5-dichlorobenzyloxy)propyl]ureido}ethoxy)phenyl]-2-ethoxypropionic acid,
3-[4-(2-{3-benzyl-1-[4-(4-fluorobenzyloxy)butyl]ureido}ethoxy)phenyl]-2-ethoxypropionic acid,
3-[4-(2-{3-benzyl-1-[4-(3,5-dichlorobenzyloxy)butyl]ureido}ethoxy)phenyl]-2-ethoxypropionic acid,
3-[4-(2-{3-benzyl-1-[3-(4-fluorophenyl)propyl]ureido}ethoxy)phenyl]-2-ethoxypropionic acid,
3-[4-(2-{3-benzyl-1-[3-(3,5-dichlorophenyl)propyl]ureido}ethoxy)phenyl]-2-ethoxypropionic acid,
2-ethoxy-3-{4-[2-(1-pentyl-3-phenethylureido)ethoxy]phenyl}propionic acid,
2-ethoxy-3-{4-[2-(1-hexyl-3-phenethylureido)ethoxy]phenyl}propionic acid,
2-ethoxy-3-{4-[2-(1-heptyl-3-phenethylureido)ethoxy]phenyl}propionic acid,
2-ethoxy-3-{4-[2-(1-octyl-3-phenethylureido)ethoxy]phenyl}propionic acid,
2-ethoxy-3-{4-[2-(1-isobutyl-3-phenethylureido)ethoxy]phenyl}propionic acid,
2-ethoxy-3-(4-{2-[1-(3-methylbutyl)-3-phenethylureido]ethoxy}phenyl)propionic acid,
2-ethoxy-3-(4-{2-[1-(4-methylpentyl)-3-phenethylureido]ethoxy}phenyl)propionic acid,
2-ethoxy-3-(4-{2-[3-phenethyl-1-(2-propylpentyl)ureido]ethoxy}phenyl)propionic acid,
3-(4-{2-[1-(3,3-dimethylbutyl)-3-phenethylureido]ethoxy}phenyl)-2-ethoxypropionic acid,
2-ethoxy-3-(4-{2-[1-(2-ethylbutyl)-3-phenethylureido]ethoxy}phenyl)propionic acid,
3-{4-[2-(1-cyclohexylmethyl-3-phenethylureido)ethoxy]phenyl}-2-ethoxypropionic acid,
3-(4-{2-[1-(4-cyclohexylbutyl)-3-phenethylureido]ethoxy}phenyl)-2-ethoxypropionic acid,
3-{4-[2-(1-cyclopropylmethyl-3-phenethylureido)ethoxy]phenyl}-2-ethoxypropionic acid,
3-{4-[2-(1-cyclobutylmethyl-3-phenethylureido)ethoxy]phenyl}-2-ethoxypropionic acid,
3-{4-[2-(1-cyclopentylmethyl-3-phenethylureido)ethoxy]phenyl}-2-ethoxypropionic acid,
3-(4-{2-[1-(2-cyclopentylethyl)-3-phenethylureido]ethoxy}phenyl)-2-ethoxypropionic acid,
3-(4-{2-[1-(3-cyclohexylpropyl)-3-phenethylureido]ethoxy}phenyl)-2-ethoxypropionic acid,
2-ethoxy-3-(4-{2-[3-phenethyl-1-(3-phenylpropyl)ureido]ethoxy}phenyl)propionic acid,
2-ethoxy-3-(4-{2-[3-phenethyl-1-(4-phenylbutyl)ureido]ethoxy}phenyl)propionic acid,
2-ethoxy-3-(4-{2-[3-phenethyl-1-(2-butoxyethyl)ureido]ethoxy}phenyl)propionic acid,
2-ethoxy-3-(4-{2-[1-(2-pentyloxyethyl)-3-phenethylureido]ethoxy}phenyl)propionic acid,
2-ethoxy-3-(4-{2-[3-phenethyl-1-(3-propoxypropyl)ureido]ethoxy}phenyl)propionic acid,
3-(4-{2-[1-(2-butylthioethyl)-3-phenethylureido]ethoxy}phenyl)-2-ethoxypropionic acid,
2-ethoxy-3-(4-{2-[1-(2-pentylthioethyl)-3-phenethylureido]ethoxy}phenyl)propionic acid,
2-ethoxy-3-(4-{2-[3-phenethyl-1-(3-propylthiopropyl)ureido]ethoxy)phenyl)propionic acid,
2-ethoxy-3-(4-{2-[3-phenethyl-1-(3-phenoxypropyl)ureido]ethoxy}phenyl)propionic acid,
2-ethoxy-3-(4-{2-[3-phenethyl-1-(4-phenoxybutyl)ureido]ethoxy}phenyl)propionic acid,
3-(4-{2-[1-(3-benzyloxypropyl)-3-phenethylureido]ethoxy}phenyl)-2-ethoxypropionic acid,
2-ethoxy-3-(4-{2-[3-phenethyl-1-(3-phenylthiopropyl)ureido]ethoxy}phenyl)propionic acid,
2-ethoxy-3-(4-{2-[3-phenethyl-1-(4-phenylthiobutyl)ureido]ethoxy}phenyl)propionic acid,
2-ethoxy-3-(4-{2-[3-phenethyl-1-(3-benzylthiopropyl)ureido]ethoxy}phenyl)propionic acid,
2-ethoxy-3-(4-{2-[3-phenethyl-1-(7,7,7-trifluoroheptyl)ureido]ethoxy}phenyl)propionic acid,
3-(4-{2-[1-(6,6-difluoroheptyl)-3-phenethylureido]ethoxy}phenyl)-2-ethoxypropionic acid,
2-ethoxy-3-(4-{2-[3-phenethyl-1-(6,6,6-trifluorohexyl)ureido]ethoxy}phenyl)propionic acid,
3-(4-{2-[1-(5,5-difluorohexyl)-3-phenylureido]ethoxy}phenyl)-2-ethoxypropionic acid,
2-ethoxy-3-(4-{2-[1-(5,5,6,6,7,7,7-heptafluoroheptyl)-3-phenethylureido]ethoxy}phenyl)propionic acid,
2-ethoxy-3-(4-{2-[3-phenethyl-1-(2,2,3,3,4,4,5,5,6,6,7,7,7-tridecafluoroheptyl)ureido]ethoxy}phenyl)propionic acid,
2-ethoxy-3-(4-{2-[1-(5,5,6,6,6-pentafluorohexyl)-3-phenethylureido]ethoxyphenyl)propionic acid,
2-ethoxy-3-(4-{2-[3-phenethyl-1-(2,2,3,3,4,4,5,5,6,6,6-undecafluorohexyl)ureido]ethoxy}phenyl)propionic acid,
3-[4-(2-{1-[2-(2,2-difluoropropoxy)ethyl]-3-phenethylureido}ethoxy)phenyl]-2-ethoxypropionic acid,
2-ethoxy-3-[4-(2-{1-[2-(1,1,2,2,3,3,3-heptafluoropropoxy)ethyl]-3-phenethylureido}ethoxy)phenyl]propionic acid,
2-ethoxy-3-[4-(2-{(3-phenethyl-1-[2-(4,4,4-trifluorobutoxy)ethyl]ureido}ethoxy)phenyl]propionic acid,
3-[4-(2-{1-[2-(3,3-difluorobutoxy)ethyl]-3-phenethylureido}ethoxy)phenyl]-2-ethoxypropionic acid,
3-[4-(2-{1-[2-(2,2-difluorobutoxy)ethyl]-3-phenethylureido}ethoxy)phenyl]-2-ethoxypropionic acid,
2-ethoxy-3-[4-(2-{1-[2-(1,1,2,2,3,3,4,4,4-nonafluorobutoxy)ethyl]-3-phenethylureido}ethoxy)phenyl]propionic acid,
2-ethoxy-3-[4-(2-{3-phenethyl-1-[3-(2,2,2-trifluoroethoxy)propyl]ureido}ethoxy)phenyl]propionic acid,
2-ethoxy-3-[4-(2-{1-[3-(1,1,2,2,2-pentafluoroethoxy)propyl]-3-phenethylureido}ethoxy)phenyl]propionic acid,
2-ethoxy-3-[4-(2-{1-[3-(4-fluorophenoxy)propyl]-3-phenethylureido}ethoxy)phenyl]propionic acid,
3-[4-(2-{1-[3-(3,5-dichlorophenoxy)propyl]-3-phenethylureido}ethoxy)phenyl]-2-ethoxypropionic acid,
2-ethoxy-3-[4-(2-{1-[4-(4-fluorophenoxy)butyl]-3-phenethylureido}ethoxy)phenyl]propionic acid,
3-[4-(2-{1-[4-(3,5-dichlorophenoxy)butyl]-3-phenethylureido}ethoxy)phenyl]-2-ethoxypropionic acid,
2-ethoxy-3-[4-(2-{1-[2-(4-fluorobenzyloxy)ethyl]-3-phenethylureido}ethoxy)phenyl]propionic acid,
3-[4-(2-{1-[2-(3,5-dichlorobenzyloxy)ethyl]-3-phenethylureido}ethoxy)phenyl]-2-ethoxypropionic acid,
2-ethoxy-3-[4-(2-{1-[3-(4-fluorobenzyloxy)propyl]-3-phenethylureido}ethoxy)phenyl]propionic acid,
3-[4-(2-{1-[3-(3,5-dichlorobenzyloxy)propyl]-3-phenethylureido}ethoxy)phenyl]-2-ethoxypropionic acid,
2-ethoxy-3-[4-(2-{1-[4-(4-fluorobenzyloxy)butyl]-3-phenethylureido}ethoxy)phenyl]propionic acid,
3-[4-(2-{1-[4-(3,5-dichlorobenzyloxy)butyl]-3-phenethylureido}ethoxy)phenyl]-2-ethoxypropionic acid,
2-ethoxy-3-[4-(2-{1-[3-(4-fluorophenyl)propyl]-3-phenethylureido}ethoxy)phenyl]propionic acid, 3-[4-(2-{1-[3-(3,5-dichlorophenyl)propyl]-3-phenethylureido}ethoxy)phenyl]-2-ethoxypropionic acid,
3-(4-{2-[3-(2,4-difluorobenzyl)-1-pentylureido]ethoxy}phenyl)-2-ethoxypropionic acid,
3-(4-{2-[3-(2,4-difluorobenzyl)-1-hexylureido]ethoxy}phenyl)-2-ethoxypropionic acid,
3-(4-{2-[3-(2,4-difluorobenzyl)-1-heptylureido]ethoxy}phenyl)-2-ethoxypropionic acid,
3-(4-{2-[3-(2,4-difluorobenzyl)-1-octylureido]ethoxy}phenyl)-2-ethoxypropionic acid,
3-(4-{2-[3-(2,4-difluorobenzyl)-1-isobutylureido]ethoxy}phenyl)-2-ethoxypropionic acid,
3-(4-{2-[3-(2,4-difluorobenzyl)-1-(3-methylbutyl)ureido]ethoxy}phenyl)-2-ethoxypropionic acid,
3-(4-{2-[3-(2,4-difluorobenzyl)-1-(4-methylpentyl)ureido]ethoxy}phenyl)-2-ethoxypropionic acid,
3-(4-{2-[3-(2,4-difluorobenzyl)-1-(2-propylpentyl)ureido]ethoxy}phenyl)-2-ethoxypropionic acid,
3-(4-{2-[1-(3,3-dimethylbutyl)-3-(2,4-difluorobenzyl)ureido]ethoxy}phenyl)-2-ethoxypropionic acid,
3-(4-{2-[3-(2,4-difluorobenzyl)-1-(2-ethylbutyl)ureido]ethoxy}phenyl)-2-ethoxypropionic acid,
3-(4-{2-[1-cyclohexylmethyl-3-(2,4-difluorobenzyl)ureido]ethoxy}phenyl)-2-ethoxypropionic acid,
3-(4-{2-[1-(4-cyclohexylbutyl)-3-(2,4-difluorobenzyl)ureido]ethoxy}phenyl)-2-ethoxypropionic acid,
3-(4-{2-[1-cyclopropylmethyl-3-(2,4-difluorobenzyl)ureido]ethoxy}phenyl)-2-ethoxypropionic acid,
3-(4-{2-[1-cyclobutylmethyl-3-(2,4-difluorobenzyl)ureido]ethoxy}phenyl)-2-ethoxypropionic acid,
3-(4-{2-[1-cyclopentylmethyl-3-(2,4-difluorobenzyl)ureido]ethoxy}phenyl)-2-ethoxypropionic acid,
3-(4-{2-[1-(2-cyclopentylethyl)-3-(2,4-difluorobenzyl)ureido]ethoxy}phenyl)-2-ethoxypropionic acid,
3-(4-{2-[1-(3-cyclohexylpropyl)-3-(2,4-difluorobenzyl)ureido]ethoxy}phenyl)-2-ethoxypropionic acid,
3-(4-{2-[3-(2,4-difluorobenzyl)-1-(3-phenylpropyl)ureido]ethoxy}phenyl)-2-ethoxypropionic acid,
3-(4-{2-[3-(2,4-difluorobenzyl)-1-(4-phenylbutyl)ureido]ethoxy}phenyl)-2-ethoxypropionic acid,
3-(4-{2-[1-(2-butoxyethyl)-3-(2,4-difluorobenzyl)ureido]ethoxy}phenyl)-2-ethoxypropionic acid,
3-(4-{2-[3-(2,4-difluorobenzyl)-1-(2-pentyloxyethyl)ureido]ethoxy}phenyl)-2-ethoxypropionic acid,
3-(4-{2-[3-(2,4-difluorobenzyl)-1-(3-propoxypropyl)ureido]ethoxy}phenyl)-2-ethoxypropionic acid,
3-(4-{2-[1-(2-butylthioethyl)-3-(2,4-difluorobenzyl)ureido]ethoxy}phenyl)-2-ethoxypropionic acid,
3-(4-{2-[3-(2,4-difluorobenzyl)-1-(2-pentylthioethyl)ureido]ethoxy}phenyl)-2-ethoxypropionic acid,
3-(4-{2-[3-(2,4-difluorobenzyl)-1-(3-propylthiopropyl)ureido]ethoxy}phenyl)-2-ethoxypropionic acid,
3-(4-{2-[3-(2,4-difluorobenzyl)-1-(3-phenoxypropyl)ureido]ethoxy}phenyl)-2-ethoxypropionic acid,
3-(4-{2-[3-(2,4-difluorobenzyl)-1-(4-phenoxybutyl)ureido]ethoxy}phenyl)-2-ethoxypropionic acid,
3-(4-{2-[3-(2,4-difluorobenzyl)-1-(3-benzyloxypropyl)ureido]ethoxy}phenyl)-2-ethoxypropionic acid,
3-(4-{2-[3-(2,4-difluorobenzyl)-1-(3-phenylthiopropyl)ureido]ethoxy}phenyl)-2-ethoxypropionic acid,
3-(4-{2-[3-(2,4-difluorobenzyl)-1-(4-phenylthiobutyl)ureido]ethoxy}phenyl)-2-ethoxypropionic acid,
3-(4-{2-[3-(2,4-difluorobenzyl)-1-(3-benzylthiopropyl)ureido]ethoxy}phenyl)-2-ethoxypropionic acid,
3-(4-{2-[3-(2,4-difluorobenzyl)-1-(7,7,7-trifluoroheptyl)ureido]ethoxy}phenyl)-2-ethoxypropionic acid,
3-(4-{2-[3-(2,4-difluorobenzyl)-1-(6,6-difluoroheptyl)ureido]ethoxy}phenyl)-2-ethoxypropionic acid,
3-(4-{2-[3-(2,4-difluorobenzyl)-1-(6,6,6-trifluorohexyl)ureido]ethoxy}phenyl)-2-ethoxypropionic acid,
3-(4-{2-[3-(2,4-difluorobenzyl)-1-(5,5-difluorohexyl)ureido]ethoxy}phenyl)-2-ethoxypropionic acid,
3-(4-{2-[3-(2,4-difluorobenzyl)-1-(5,5,6,6,7,7,7-heptafluoroheptyl)ureido]ethoxy}phenyl)-2-ethoxypropionic acid,
3-(4-{2-[3-(2,4-difluorobenzyl)-1-(2,2,3,3,4,4,5,5,6,6,7,7,7-tridecafluoroheptyl)ureido]ethoxy}phenyl)-2-ethoxypropionic acid,
3-(4-{2-[3-(2,4-difluorobenzyl)-1-(5,5,6,6,6-pentafluorohexyl)ureido]ethoxy}phenyl)-2-ethoxypropionic acid,
3-(4-{2-[3-(2,4-difluorobenzyl)-1-(2,2,3,3,4,4,5,5,6,6,6-undecafluorohexyl)ureido]ethoxy}phenyl)-2-ethoxypropionic acid,
3-[4-(2-{3-(2,4-difluorobenzyl)-1-[2-(2,2-difluoropropoxy)ethyl]ureido}ethoxy)phenyl]-2-ethoxypropionic acid,
3-[4-(2-{3-(2,4-difluorobenzyl)-1-[2-(1,1,2,2,3,3,3-heptafluoropropoxy)ethyl]ureido}ethoxy)phenyl]-2-ethoxypropionic acid,
3-[4-(2-{3-(2,4-difluorobenzyl)-1-[2-(4,4,4-trifluorobutoxy)ethyl]ureido}ethoxy)phenyl]-2-ethoxypropionic acid,
3-[4-(2-{3-(2,4-difluorobenzyl)-1-[2-(3,3-difluorobutoxy)ethyl]ureido}ethoxy)phenyl]-2-ethoxypropionic acid,
3-[4-(2-{3-(2,4-difluorobenzyl)-{[2-(2,2-difluorobutoxy)ethyl]ureido}ethoxy)phenyl]-2-ethoxypropionic acid,
3-[4-(2-{3-(2,4-difluorobenzyl)-1-[2-(1,1,2,2,3,3,4,4,4-nonafluorobutoxy)ethyl]ureido}ethoxy)phenyl]-2-ethoxypropionic acid,
3-[4-(2-{3-(2,4-difluorobenzyl)-1-[3-(2,2,2-trifluoroethoxy)propyl]ureido}ethoxy)phenyl]-2-ethoxypropionic acid,
3-[4-(2-{3-(2,4-difluorobenzyl)-1-[3-(1,1,2,2,2-pentafluoroethoxy)propyl]ureido}ethoxy)phenyl]-2-ethoxypropionic acid,
3-[4-(2-{3-(2,4-difluorobenzyl)-1-[3-(4-fluorophenoxy)propyl]ureido}ethoxy)phenyl]-2-ethoxypropionic acid,
3-[4-(2-{1-[3-(3,5-dichlorophenoxy)propyl]-3-(2,4-difluorobenzyl)ureido}ethoxy)phenyl]-2-ethoxypropionic acid,
3-[4-(2-{3-(2,4-difluorobenzyl)-1-[4-(4-fluorophenoxy)butyl]ureido}ethoxy)phenyl]-2-ethoxypropionic acid,
3-[4-(2-{1-[4-(3,5-dichlorophenoxy)butyl]-3-(2,4-difluorobenzyl)ureido}ethoxy)phenyl]-2-ethoxypropionic acid,
3-[4-(2-{3-(2,4-difluorobenzyl)-1-[2-(4-fluorobenzyloxy)ethyl]ureido}ethoxy)phenyl]-2-ethoxypropionic acid,
3-[4-(2-{1-[2-(3,5-dichlorobenzyloxy)ethyl]-3-(2,4-difluorobenzyl)ureido}ethoxy)phenyl]-2-ethoxypropionic acid,
3-[4-(2-{3-(2,4-difluorobenzyl)--[3-(4-fluorobenzyloxy)propyl]ureido}ethoxy)phenyl]-2-ethoxypropionic acid,
3-[4-(2-{1-[3-(3,5-dichlorobenzyloxy)propyl]-3-(2,4-difluorobenzyl)ureido}ethoxy)phenyl]-2-ethoxypropionic acid,
3-[4-(2-(3-(2,4-difluorobenzyl)-1-[4-(4-fluorobenzyloxy)butyl]ureido}ethoxy)phenyl]-2-ethoxypropionic acid,
3-[4-(2-{1-[4-(3,5-dichlorobenzyloxy)butyl]-3-(2,4-difluorobenzyl)ureido}ethoxy)phenyl]-2-ethoxypropionic acid,
3-[4-(2-{3-(2,4-difluorobenzyl)-1-[3-(4-fluorophenyl)propyl]ureido}ethoxy)phenyl]-2-ethoxypropionic acid,
3-[4-(2-{1-[3-(3,5-dichlorophenyl)propyl]-3-(2,4-difluorobenzyl)ureido}ethoxy)phenyl]-2-ethoxypropionic acid,
2-ethoxy-3-(4-{2-[3-(4-fluorobenzyl)-1-pentylureido]ethoxy}phenyl)propionic acid,
2-ethoxy-3-(4-{2-[3-(4-fluorobenzyl)-1-hexylureido]ethoxy}phenyl)propionic acid,
2-ethoxy-3-(4-{2-[3-(4-fluorobenzyl)-1-heptylureido]ethoxy}phenyl)propionic acid, 2-ethoxy-3-(4-{2-[3-(4-fluorobenzyl)-1-octylureido]ethoxy}phenyl)propionic acid,
2-ethoxy-3-(4-{2-[3-(4-fluorobenzyl)-1-isobutylureido]ethoxy}phenyl)propionic acid,
2-ethoxy-3-(4-{2-[3-(4-fluorobenzyl)-1-(3-methylbutyl)ureido]ethoxy}phenyl)propionic acid,
2-ethoxy-3-(4-{2-[3-(4-fluorobenzyl)-1-(4-methylpentyl)ureido]ethoxy}phenyl)propionic acid,
2-ethoxy-3-(4-{2-[3-(4-fluorobenzyl)-1-(2-propylpentyl)ureido]ethoxy}phenyl)propionic acid,
3-(4-{2-[1-(3,3-dimethylbutyl)-3-(4-fluorobenzyl)ureido]ethoxy}phenyl)-2-ethoxypropionic acid,
2-ethoxy-3-(4-{2-[1-(2-ethylbutyl)-3-(4-fluorobenzyl)ureido]ethoxy}phenyl)propionic acid,
3-(4-{2-[1-cyclohexylmethyl-3-(4-fluorobenzyl)ureido]ethoxy}phenyl)-2-ethoxypropionic acid,
3-(4-{2-[1-(4-cyclohexylbutyl)-3-(4-fluorobenzyl)ureido]ethoxy}phenyl)-2-ethoxypropionic acid,
3-(4-{2-[1-cyclopropylmethyl-3-(4-fluorobenzyl)ureido]ethoxy}phenyl)-2-ethoxypropionic acid,
3-(4-{2-[1-cyclobutylmethyl-3-(4-fluorobenzyl)ureido]ethoxy}phenyl)-2-ethoxypropionic acid,
3-(4-{2-[1-cyclopentylmethyl-3-(4-fluorobenzyl)ureido]ethoxy}phenyl)-2-ethoxypropionic acid,
3-(4-[({2-[1-(2-cyclopentylethyl)-3-(4-fluorobenzyl)ureido]ethoxy}phenyl)-2-ethoxypropionic acid,
3-(4-{2-[1-(3-cyclohexylpropyl)-3-(4-fluorobenzyl)ureido]ethoxy}phenyl)-2-ethoxypropionic acid,
2-ethoxy-3-(4-{2-[3-(4-fluorobenzyl)-1-(3-phenylpropyl)ureido]ethoxy}phenyl)propionic acid,
2-ethoxy-3-(4-{2-[3-(4-fluorobenzyl)-1-(4-phenylbutyl)ureido]ethoxy}phenyl)propionic acid,
3-(4-{2-[1-(2-butoxyethyl)-3-(4-fluorobenzyl)ureido]ethoxy}phenyl)-2-ethoxypropionic acid,
2-ethoxy-3-(4-{2-[3-(4-fluorobenzyl)-1-(2-pentyloxyethyl)ureido]ethoxy}phenyl)propionic acid,
2-ethoxy-3-(4-{2-[3-(4-fluorobenzyl)-1-(3-propoxypropyl)ureido]ethoxy}phenyl)propionic acid,
3-(4-{2-[1-(2-butylthioethyl)-3-(4-fluorobenzyl)ureido]ethoxy}phenyl)-2-ethoxypropionic acid,
2-ethoxy-3-(4-{2-[3-(4-fluorobenzyl)-1-(2-pentylthioethyl)ureido]ethoxy}phenyl)propionic acid,
2-ethoxy-3-(4-{2-[3-(4-fluorobenzyl)-1-(3-propylthiopropyl)ureido]ethoxy}phenyl)propionic acid,
2-ethoxy-3-(4-{2-[3-(4-fluorobenzyl)-1-(3-phenoxypropyl)ureido]ethoxy}phenyl)propionic acid,
2-ethoxy-3-(4-{2-[3-(4-fluorobenzyl)-1-(4-phenoxybutyl)ureido]ethoxy}phenyl)propionic acid,
3-(4-{2-[1-(3-benzyloxypropyl)-3-(4-fluorobenzyl)ureido]ethoxy}phenyl)-2-ethoxypropionic acid,
2-ethoxy-3-(4-{2-[3-(4-fluorobenzyl)-1-(3-phenylthiopropyl)ureido]ethoxy}phenyl)propionic acid,
2-ethoxy-3-(4-{2-[3-(4-fluorobenzyl)-1-(4-phenylthiobutyl)ureido]ethoxy}phenyl)propionic acid,
3-(4-{2-[1-(3-benzylthiopropyl)-3-(4-fluorobenzyl)ureido]ethoxy}phenyl)-2-ethoxypropionic acid,
2-ethoxy-3-(4-{2-[3-(4-fluorobenzyl)-1-(7,7,7-trifluoroheptyl)ureido]ethoxy}phenyl)propionic acid,
3-(4-{2-[1-(6,6-difluoroheptyl)-3-(4-fluorobenzyl)ureido]ethoxy}phenyl)-2-ethoxypropionic acid,
2-ethoxy-3-(4-{2-[3-(4-fluorobenzyl)-1-(6,6,6-trifluorohexyl)ureido]ethoxy}phenyl)propionic acid,
3-(4-{2-[1-(5,5-difluorohexyl)-3-(4-fluorobenzyl)ureido]ethoxy}phenyl)-2-ethoxypropionic acid,
2-ethoxy-3-(4-{2-[3-(4-fluorobenzyl)-1-(5,5,6,6,7,7,7-heptafluoroheptyl)ureido]ethoxy}phenyl)propionic acid,
2-ethoxy-3-(4-{2-[3-(4-fluorobenzyl)-1-(2,2,3,3,4,4,5,5,6,6,7,7,7-tridecafluoroheptyl)ureido]ethoxy}phenyl)propionic acid,
2-ethoxy-3-(4-{2-[3-(4-fluorobenzyl)-1-(5,5,6,6,6-pentafluorohexyl)ureido]ethoxy}phenyl)propionic acid,
2-ethoxy-3-(4-{2-[3-(4-fluorobenzyl)-1-(2,2,3,3,4,4,5,5,6,6-undecafluorohexyl)ureido]ethoxy}phenyl)propionic acid,
3-[4-(2-{1-[2-(2,2-difluoropropoxy)ethyl]-3-(4-fluorobenzyl)ureido}ethoxy)phenyl]-2-ethoxypropionic acid,
2-ethoxy-3-[4-(2-{3-(4-fluorobenzyl)-1-[2-(1,1,2,2,3,3,3-heptafluoropropoxy)ethyl]ureido}ethoxy)phenyl]propionic acid,
2-ethoxy-3-[4-(2-{3-(4-fluorobenzyl)-1-[2-(4,4,4-trifluorobutoxy)ethyl]ureido}ethoxy)phenyl]propionic acid,
3-[4-(2-{1-[2-(3,3-difluorobutoxy)ethyl]-3-(4-fluorobenzyl)ureido}ethoxy)phenyl]-2-ethoxypropionic acid,
3-[4-(2-{1-[2-(2,2-difluorobutoxy)ethyl]-3-(4-fluorobenzyl)ureido}ethoxy)phenyl]-2-ethoxypropionic acid,
2-ethoxy-3-[4-(2-{3-(4-fluorobenzyl)-1-[2-(1,1,2,2,3,3,4,4,4-nonafluorobutoxy)ethyl]ureido}ethoxy)phenyl]propionic acid,
2-ethoxy-3-[4-(2-{3-(4-fluorobenzyl)-1-[3-(2,2,2-trifluoroethoxy)propyl]ureido}ethoxy)phenyl]propionic acid,
2-ethoxy-3-[4-(2-{3-(4-fluorobenzyl)-1-[3-(1,1,2,2,2-pentafluoroethoxy)propyl]ureido}ethoxy)phenyl]propionic acid,
2-ethoxy-3-[4-(2-{3-(4-fluorobenzyl)-1-[3-(4-fluorophenoxy)propyl]ureido}ethoxy)phenyl]propionic acid,
3-[4-(2-{1-[3-(3,5-dichlorophenoxy)propyl]-3-(4-fluorobenzyl)ureido}ethoxy)phenyl]-2-ethoxypropionic acid,
2-ethoxy-3-[4-(2-{3-(4-fluorobenzyl)-1-[4-(4-fluorophenoxy)butyl]ureido}ethoxy)phenyl]propionic acid,
3-[4-(2-{1-[4-(3,5-dichlorophenoxy)butyl]-3-(4-fluorobenzyl)ureido}ethoxy)phenyl]-2-ethoxypropionic acid,
2-ethoxy-3-[4-(2-{3-(4-fluorobenzyl)-1-[2-(4-fluorobenzyloxy)ethyl]ureido}ethoxy)phenyl]propionic acid,
3-[4-(2-{1-[2-(3,5-dichlorobenzyloxy)ethyl]-3-(4-fluorobenzyl)ureido}ethoxy)phenyl]-2-ethoxypropionic acid,
2-ethoxy-3-[4-(2-{3-(4-fluorobenzyl)-1-[3-(4-fluorobenzyloxy)propyl]ureido}ethoxy)phenyl]propionic acid,
3-[4-(2-{1-[3-(3,5-dichlorobenzyloxy)propyl]-3-(4-fluorobenzyl)ureido}ethoxy)phenyl]-2-ethoxypropionic acid,
2-ethoxy-3-[4-(2-{3-(4-fluorobenzyl)-1-[4-(4-fluorobenzyloxy)butyl]ureido}ethoxy)phenyl]propionic acid,
3-[4-(2-{1-[4-(3,5-dichlorobenzyloxy)butyl]-3-(4-fluorobenzyl)ureido}ethoxy)phenyl]-2-ethoxypropionic acid,
2-ethoxy-3-[4-(2-{3-(4-fluorobenzyl)-1-[3-(4-fluorophenyl)propyl]ureido}ethoxy)phenyl]propionic acid, and
3-[4-(2-{1-[3-(3,5-dichlorophenyl)propyl]-3-(4-fluorobenzyl)ureido}ethoxy)phenyl]-2-ethoxypropionic acid, Examples of the compounds wherein R$^1$ is indan-5-yl group include the following compounds.

2-Ethoxy-3-{4-[2-(3-indan-5-yl-1-pentylureido)ethoxy]phenyl}propionic acid,
2-ethoxy-3-{4-[2-(1-hexyl-3-indan-5-ylureido)ethoxy]phenyl}propionic acid,
2-ethoxy-3-{4-[2-(1-heptyl-3-indan-5-ylureido)ethoxy]phenyl}propionic acid,
2-ethoxy-3-{4-[2-(3-indan-5-yl-1-octylureido)ethoxy]phenyl}propionic acid,
2-ethoxy-3-{4-[2-(3-indan-5-yl-1-isobutylureido)ethoxy]phenyl}propionic acid,
2-ethoxy-3-(4-{2-[3-indan-5-yl-1-(3-methylbutyl)ureido]ethoxy}phenyl)propionic acid,
2-ethoxy-3-(4-{2-[3-indan-5-yl-1-(4-methylpentyl)ureido]ethoxy}phenyl)propionic acid, 2-ethoxy-3-(4-{2-[3-indan-5-yl-1-(2-propylpentyl)ureido]ethoxy}phenyl)propionic acid,
3-(4-{2-[1-(3,3-dimethylbutyl)-3-indan-5-ylureido]ethoxy}phenyl)-2-ethoxypropionic acid,
2-ethoxy-3-(4-{2-[1-(2-ethylbutyl)-3-indan-5-ylureido]ethoxy}phenyl)propionic acid,
3-{4-[2-(1-cyclohexylmethyl-3-indan-5-ylureido)ethoxy]phenyl}-2-ethoxypropionic acid,
3-(4-{2-[1-(4-cyclohexylbutyl)-3-indan-5-ylureido]ethoxy}phenyl)-2-ethoxypropionic acid,
3-{4-[2-(1-cyclopropylmethyl-3-indan-5-ylureido)ethoxy]phenyl}-2-ethoxypropionic acid,
3-{4-[2-(1-cyclobutylmethyl-3-indan-5-ylureido)ethoxy]phenyl}-2-ethoxypropionic acid,
3-{4-[2-(1-cyclopentylmethyl-3-indan-5-ylureido)ethoxy]phenyl}-2-ethoxypropionic acid,
3-(4-{2-[1-(2-cyclopentylethyl)-3-indan-5-ylureido]ethoxy}phenyl)-2-ethoxypropionic acid,
3-(4-{2-[1-(3-cyclohexylpropyl)-3-indan-5-ylureido]ethoxy}phenyl)-2-ethoxypropionic acid,
2-ethoxy-3-(4-{2-[3-indan-5-yl-1-(3-phenylpropyl)ureido]ethoxy}phenyl)propionic acid,
2-ethoxy-3-(4-{2-[3-indan-5-yl-1-(4-phenylbutyl)ureido]ethoxy}phenyl)propionic acid,
3-(4-{2-[1-(2-butoxyethyl)-3-indan-5-ylureido]ethoxy}phenyl)-2-ethoxypropionic acid,
2-ethoxy-3-(4-{2-[3-indan-5-yl-1-(2-pentyloxyethyl)ureido]ethoxy}phenyl)propionic acid,
2-ethoxy-3-(4-{2-[3-indan-5-yl-1-(3-propoxypropyl)ureido]ethoxy}phenyl)propionic acid,
3-(4-{2-[1-(2-butylthioethyl)-3-indan-5-ylureido]ethoxy}phenyl)-2-ethoxypropionic acid,
2-ethoxy-3-(4-{2-[3-indan-5-yl-1-(2-pentylthioethyl)ureido]ethoxy}phenyl)propionic acid,
2-ethoxy-3-(4-{2-[3-indan-5-yl-1-(3-propylthiopropyl)ureido]ethoxy}phenyl)propionic acid,
2-ethoxy-3-(4-{2-[3-indan-5-yl-1-(3-phenoxypropyl)ureido]ethoxy}phenyl)propionic acid,
2-ethoxy-3-(4-{2-[3-indan-5-yl-1-(4-phenoxybutyl)ureido]ethoxy}phenyl)propionic acid,
3-(4-{2-[1-(3-benzyloxypropyl)-3-indan-5-ylureido]ethoxy}phenyl)-2-ethoxypropionic acid,
2-ethoxy-3-(4-{2-[3-indan-5-yl-1-(3-phenylthiopropyl)ureido]ethoxy}phenyl)propionic acid,
2-ethoxy-3-(4-{2-[3-indan-5-yl-1-(4-phenylthiobutyl)ureido]ethoxy}phenyl)propionic acid,
3-(4-{2-[1-(3-benzylthiopropyl)-3-indan-5-ylureido]ethoxy}phenyl)-2-ethoxypropionic acid,
2-ethoxy-3-(4-{2-[3-indan-5-yl-1-(7,7,7-trifluoroheptyl)ureido]ethoxy}phenyl)propionic acid,
3-(4-{2-[1-(6,6-difluoroheptyl)-3-indan-5-ylureido]ethoxy}phenyl)-2-ethoxypropionic acid,
2-ethoxy-3-(4-{2-[3-indan-5-yl-1-(6,6,6-trifluorohexyl)ureido]ethoxy}phenyl)propionic acid,
3-(4-{2-[1-(5,5-difluorohexyl)-3-indan-5-ylureido]ethoxy}phenyl)-2-ethoxypropionic acid,
2-ethoxy-3-(4-{2-[1-(5,5,6,6,7,7,7-heptafluoroheptyl)-3-indan-5-ylureido]ethoxy}phenyl)propionic acid,
2-ethoxy-3-(4-{2-[3-indan-5-yl-1-(2,2,3,3,4,4,5,5,6,6,7,7,7-tridecafluoroheptyl)ureido]ethoxy}phenyl)propionic acid,
2-ethoxy-3-(4-{2-[3-indan-5-yl-1-(5,5,6,6,6-pentafluorohexyl)ureido]ethoxy}phenyl)propionic acid,
2-ethoxy-3-(4-{2-[3-indan-5-yl-1-(2,2,3,3,4,4,5,5,6,6,6-undecafluorohexyl)ureido]ethoxy}phenyl)propionic acid,
3-[4-(2-{1-[2-(2,2-difluoropropoxy)ethyl]-3-indan-5-ylureido}ethoxy)phenyl]-2-ethoxypropionic acid,
2-ethoxy-3-[4-(2-{1-[2-(1,1,2,2,3,3,3-heptafluoropropoxy)ethyl]-3-indan-5-ylureido}ethoxy)phenyl]propionic acid,
2-ethoxy-3-[4-(2-{3-indan-5-yl-1-[2-(4,4,4-trifluorobutoxy)ethyl]ureido}ethoxy)phenyl]propionic acid,
3-[4-(2-{1-[2-(3,3-difluorobutoxy)ethyl]-3-indan-5-ylureido}ethoxy)phenyl]-2-ethoxypropionic acid,
3-[4-(2-{1-[2-(2,2-difluorobutoxy)ethyl]-3-indan-5-ylureido}ethoxy)phenyl]-2-ethoxypropionic acid,
2-ethoxy-3-[4-(2-{3-indan-5-yl-1-[2-(1,1,2,2,3,3,4,4,4-nonafluorobutoxy)ethyl]ureido}ethoxy)phenyl]propionic acid,
2-ethoxy-3-[4-(2-{3-indan-5-yl]-[3-(2,2,2-trifluoroethoxy)propyl]ureido}ethoxy)phenyl]propionic acid,
2-ethoxy-3-[4-(2-{3-indan-5-yl-1-[3-(1,1,2,2,2-pentafluoroethoxy)propyl]ureido}ethoxy)phenyl]propionic acid,
2-ethoxy-3-[4-(2-{1-[3-(4-fluorophenoxy)propyl]-3-indan-5-ylureido}ethoxy)phenyl]propionic acid,
3-[4-(2-{1-[3-(3,5-dichlorophenoxy)propyl]-3-indan-5-ylureido}ethoxy)phenyl]-2-ethoxypropionic acid,
2-ethoxy-3-[4-(2-{1-[4-(4-fluorophenoxy)butyl]-3-indan-5-ylureido}ethoxy)phenyl]propionic acid,
3-[4-(2-{1-[4-(3,5-dichlorophenoxy)butyl]-3-indan-5-ylureido}ethoxy)phenyl]-2-ethoxypropionic acid,
2-ethoxy-3-[4-(2-{1-[2-(4-fluorobenzyloxy)ethyl]-3-indan-5-ylureido}ethoxy)phenyl]propionic acid,
3-[4-(2-{1-[2-(3,5-dichlorobenzyloxy)ethyl]-3-indan-5-ylureido}ethoxy)phenyl]-2-ethoxypropionic acid,
2-ethoxy-3-[4-(2-{1-[3-(4-fluorobenzyloxy)propyl]-3-indan-5-ylureido}ethoxy)phenyl]propionic acid,
3-[4-(2-{1-[3-(3,5-dichlorobenzyloxy)propyl]-3-indan-5-ylureido}ethoxy)phenyl]-2-ethoxypropionic acid,
2-ethoxy-3-[4-(2-{1-[4-(4-fluorobenzyloxy)butyl]-3-indan-5-ylureido}ethoxy)phenyl]propionic acid,
3-[4-(2-{1-[4-(3,5-dichlorobenzyloxy)butyl]-3-indan-5-ylureido}ethoxy)phenyl]-2-ethoxypropionic acid,
2-ethoxy-3-[4-(2-{1-[3-(4-fluorophenyl)propyl]-3-indan-5-ylureido}ethoxy)phenyl]propionic acid, and
3-[4-(2-{1-[3-(3,5-dichlorophenyl)propyl]-3-indan-5-ylureido}ethoxy)phenyl]-2-ethoxypropionic acid.

Examples of the compounds wherein $R^1$ is a group represented by the formula (1-1) include the following compounds.

2-Ethoxy-3-{4-[2-(1-pentyl-3-phenylureido)ethoxy]phenyl}propionic acid,
2-ethoxy-3-{4-[2-(1-hexyl-3-phenylureido)ethoxy]phenyl}propionic acid,
2-ethoxy-3-{4-[2-(1-heptyl-3-phenylureido)ethoxy]phenyl}propionic acid,
2-ethoxy-3-{4-[2-(1-octyl-3-phenylureido)ethoxy]phenyl}propionic acid,
2-ethoxy-3-{4-[2-(1-isobutyl-3-phenylureido)ethoxy]phenyl}propionic acid,
2-ethoxy-3-(4-{2-[1-(3-methylbutyl)-3-phenylureido]ethoxy}phenyl)propionic acid,
2-ethoxy-3-(4-{2-[1-(4-methylpentyl)-3-phenylureido]ethoxy}phenyl)propionic acid,
2-ethoxy-3-(4-{2-[3-phenyl-1-(2-propylpentyl)ureido]ethoxy}phenyl)propionic acid,
3-(4-{2-[1-(3,3-dimethylbutyl)-3-phenylureido]ethoxy}phenyl)-2-ethoxypropionic acid,
2-ethoxy-3-(4-{2-[1-(2-ethylbutyl)-3-phenylureido]ethoxy}phenyl)propionic acid,
3-{4-[2-(1-cyclohexylmethyl-3-phenylureido)ethoxy]phenyl}-2-ethoxypropionic acid,
3-(4-{2-[1-(4-cyclohexylbutyl)-3-phenylureido]ethoxy}phenyl)-2-ethoxypropionic acid, 3-{4-[2-(1-cyclopropylmethyl-3-phenylureido)ethoxy]phenyl}-2-ethoxypropionic acid,
3-{4-[2-(1-cyclobutylmethyl-3-phenylureido)ethoxy]phenyl}-2-ethoxypropionic acid,
3-{4-[2-(1-cyclopentylmethyl-3-phenylureido)ethoxy]phenyl}-2-ethoxypropionic acid,
3-(4-{2-[1-(2-cyclopentylethyl)-3-phenylureido]ethoxy}phenyl)-2-ethoxypropionic acid,
3-(4-{2-[1-(3-cyclohexylpropyl)-3-phenylureido]ethoxy}phenyl)-2-ethoxypropionic acid,
2-ethoxy-3-(4-{2-[3-phenyl-1-(3-phenylpropyl)ureido]ethoxy}phenyl)propionic acid,
2-ethoxy-3-(4-{2-[3-phenyl-1-(4-phenylbutyl)ureido]ethoxy}phenyl)propionic acid,
3-(4-{2-[1-(2-butoxyethyl)-3-phenylureido]ethoxy}phenyl)-2-ethoxypropionic acid,
2-ethoxy-3-(4-{2-[1-(2-pentyloxyethyl)-3-phenylureido]ethoxy}phenyl)propionic acid,
2-ethoxy-3-(4-{2-[3-phenyl-1-(3-propoxypropyl)ureido]ethoxy}phenyl)propionic acid,
3-(4-{2-[1-(2-butylthioethyl)-3-phenylureido]ethoxy}phenyl)-2-ethoxypropionic acid,
2-ethoxy-3-(4-{2-[1-(2-pentylthioethyl)-3-phenylureido]ethoxy}phenyl)propionic acid,
2-ethoxy-3-(4-{2-[3-phenyl-1-(3-propylthiopropyl)ureido]ethoxy}phenyl)propionic acid,
2-ethoxy-3-(4-{2-[1-(3-phenoxypropyl)-3-phenylureido]ethoxy}phenyl)propionic acid,
2-ethoxy-3-(4-{2-[1-(4-phenoxybutyl)-3-phenylureido]ethoxy}phenyl)propionic acid,
3-(4-{2-[1-(3-benzyloxypropyl)-3-phenylureido]ethoxy}phenyl)-2-ethoxypropionic acid,
2-ethoxy-3-(4-{2-[3-phenyl-1-(3-phenylthiopropyl)ureido]ethoxy}phenyl)propionic acid,
2-ethoxy-3-(4-{2-[3-phenyl-1-(4-phenylthiobutyl)ureido]ethoxy}phenyl)propionic acid,
3-(4-{2-[1-(3-benzylthiopropyl)-3-phenylureido]ethoxy}phenyl)-2-ethoxypropionic acid,
2-ethoxy-3-(4-{2-[3-phenyl-1-(7,7,7-trifluoroheptyl)ureido]ethoxy}phenyl)propionic acid,
3-(4-{2-[1-(6,6-difluoroheptyl)-3-phenylureido]ethoxy}phenyl)-2-ethoxypropionic acid,
2-ethoxy-3-(4-{2-[3-phenyl-1-(6,6,6-trifluorohexyl)ureido]ethoxy}phenyl)propionic acid,
3-(4-{2-[1-(5,5-difluorohexyl)-3-phenylureido]ethoxy}phenyl)-2-ethoxypropionic acid,
2-ethoxy-3-(4-{2-[1-(5,5,6,6,7,7,7-heptafluoroheptyl)-3-phenylureido]ethoxy}phenyl)propionic acid,
2-ethoxy-3-(4-{2-[3-phenyl-1-(2,2,3,3,4,4,5,5,6,6,7,7,7-tridecafluoroheptyl)ureido]ethoxy}phenyl)propionic acid,
2-ethoxy-3-(4-{2-[1-(5,5,6,6,6-pentafluorohexyl)-3-phenylureido]ethoxy}phenyl)propionic acid,
2-ethoxy-3-(4-{2-[3-phenyl-1-(2,2,3,3,4,4,5,5,6,6,6-undecafluorohexyl)ureido]ethoxy}phenyl)propionic acid,
3-[4-(2-{1-[2-(2,2-difluoropropoxy)ethyl]-3-phenylureido}ethoxy)phenyl]-2-ethoxypropionic acid,
2-ethoxy-3-[4-(2-{1-[2-(1,1,2,2,3,3,3-heptafluoropropoxy)ethyl]-3-phenylureido}ethoxy)phenyl]propionic acid,
2-ethoxy-3-(4-{2-[3-phenyl-1-[2-(4,4,4-trifluorobutoxy)ethyl]ureido}ethoxy)phenyl]propionic acid,
3-[4-(2-{1-[2-(3,3-difluorobutoxy)ethyl]-3-phenylureido}ethoxy)phenyl]-2-ethoxypropionic acid,
3-[4-(2-{1-[2-(2,2-difluorobutoxy)ethyl]-3-phenylureido}ethoxy)phenyl]-2-ethoxypropionic acid,
2-ethoxy-3-[4-(2-{1-[2-(1,1,2,2,3,3,4,4,4-nonafluorobutoxy)ethyl]-3-phenylureido}ethoxy)phenyl]propionic acid,
2-ethoxy-3-[4-(2-{3-phenyl-1-[3-(2,2,2-trifluoroethoxy)propyl]ureido}ethoxy)phenyl]propionic acid,
2-ethoxy-3-[4-(2-{1-[3-(1,1,2,2,2-pentafluoroethoxy)propyl]-3-phenylureido}ethoxy)phenyl]propionic acid,
2-ethoxy-3-[4-(2-{1-[3-(4-fluorophenoxy)propyl]-3-phenylureido}ethoxy)phenyl]propionic acid,
3-[4-(2-{1-[3-(3,5-dichlorophenoxy)propyl]-3-phenylureido}ethoxy)phenyl]-2-ethoxypropionic acid,
2-ethoxy-3-[4-(2-{1-[4-(4-fluorophenoxy)butyl]-3-phenylureido}ethoxy)phenyl]propionic acid,
3-[4-(2-{1-[4-(3,5-dichlorophenoxy)butyl]-3-phenylureido}ethoxy)phenyl]-2-ethoxypropionic acid,
2-ethoxy-3-[4-(2-{1-[2-(4-fluorobenzyloxy)ethyl]-3-phenylureido}ethoxy)phenyl]propionic acid,
3-[4-(2-{1-[2-(3,5-dichlorobenzyloxy)ethyl]-3-phenylureido}ethoxy)phenyl]-2-ethoxypropionic acid,
2-ethoxy-3-[4-(2-{1-[3-(4-fluorobenzyloxy)propyl]-3-phenylureido}ethoxy)phenyl]propionic acid,
3-[4-(2-{1-[3-(3,5-dichlorobenzyloxy)propyl]-3-phenylureido}ethoxy)phenyl]-2-ethoxypropionic acid,
2-ethoxy-3-[4-(2-{1-[4-(4-fluorobenzyloxy)butyl]-3-phenylureido}ethoxy)phenyl]propionic acid,
3-[4-(2-{1-[4-(3,5-dichlorobenzyloxy)butyl]-3-phenylureido}ethoxy)phenyl]-2-ethoxypropionic acid,
2-ethoxy-3-[4-(2-{1-[3-(4-fluorophenyl)propyl]-3-phenylureido}ethoxy)phenyl]propionic acid,
3-[4-(2-{1-[3-(3,5-dichlorophenyl)propyl]-3-phenylureido}ethoxy)phenyl]-2-ethoxypropionic acid,
3-(4-{2-[3-(2,4-difluorophenyl)-1-pentylureido]ethoxy}phenyl)-2-ethoxypropionic acid,
3-(4-{2-[3-(2,4-difluorophenyl)-1-hexylureido]ethoxy}phenyl)-2-ethoxypropionic acid,
3-(4-{2-[3-(2,4-difluorophenyl)-1-heptylureido]ethoxy}phenyl)-2-ethoxypropionic acid,
3-(4-{2-[3-(2,4-difluorophenyl)-1-octylureido]ethoxy}phenyl)-2-ethoxypropionic acid,
3-(4-{2-[3-(2,4-difluorophenyl)-1-isobutylureido]ethoxy}phenyl)-2-ethoxypropionic acid,
3-(4-{2-[3-(2,4-difluorophenyl)-1-(3-methylbutyl)ureido]ethoxy}phenyl)-2-ethoxypropionic acid,
3-(4-{2-[3-(2,4-difluorophenyl)-1-(4-methylpentyl)ureido]ethoxy}phenyl)-2-ethoxypropionic acid,
3-(4-{2-[3-(2,4-difluorophenyl)-1-(2-propylpentyl)ureido]ethoxy}phenyl)-2-ethoxypropionic acid,
3-(4-{2-[3-(2,4-difluorophenyl)-1-(3,3-dimethylbutyl)ureido]ethoxy}phenyl)-2-ethoxypropionic acid,
3-(4-{2-[3-(2,4-difluorophenyl)-1-(2-ethylbutyl)ureido]ethoxy}phenyl)-2-ethoxypropionic acid,
3-(4-{2-[1-cyclohexylmethyl-3-(2,4-difluorophenyl)ureido]ethoxy}phenyl)-2-ethoxypropionic acid,
3-(4-{2-[1-(4-cyclohexylbutyl)-3-(2,4-difluorophenyl)ureido]ethoxy}phenyl)-2-ethoxypropionic acid,
3-(4-{2-[1-cyclopropylmethyl-3-(2,4-difluorophenyl)ureido]ethoxy}phenyl)-2-ethoxypropionic acid,
3-(4-{2-[1-cyclobutylmethyl-3-(2,4-difluorophenyl)ureido]ethoxy}phenyl)-2-ethoxypropionic acid,
3-(4-{2-[1-cyclopentylmethyl-3-(2,4-difluorophenyl)ureido]ethoxy}phenyl)-2-ethoxypropionic acid,
3-(4-{2-[1-(2-cyclopentylethyl)-3-(2,4-difluorophenyl)ureido]ethoxy}phenyl)-2 -ethoxypropionic acid,
3-(4-{2-[1-(3-cyclohexylpropyl)-3-(2,4-difluorophenyl)ureido]ethoxy}phenyl)-2-ethoxypropionic acid,
3-(4-{2-[3-(2,4-difluorophenyl)-1-(3-phenylpropyl)ureido]ethoxy}phenyl)-2-ethoxypropionic acid, 3-(4-{2-[3-(2,4-difluorophenyl)-1-(4-phenylbutyl)ureido]ethoxy}phenyl)-2-ethoxypropionic acid,
3-(4-{2-[1-(2-butoxyethyl)-3-(2,4-difluorophenyl)ureido]ethoxy}phenyl)-2-ethoxypropionic acid,
3-(4-{2-[3-(2,4-difluorophenyl)-1-(2-pentyloxyethyl)ureido]ethoxy}phenyl)-2-ethoxypropionic acid,
3-(4-{2-[3-(2,4-difluorophenyl)-1-(3-propoxypropyl)ureido]ethoxy}phenyl)-2-ethoxypropionic acid,
3-(4-{2-[1-(2-butylthioethyl)-3-(2,4-difluorophenyl)ureido]ethoxy}phenyl)-2-ethoxypropionic acid,
3-(4-{2-[3-(2,4-difluorophenyl)-1-(2-pentylthioethyl)ureido]ethoxy}phenyl)-2-ethoxypropionic acid,
3-(4-{2-[3-(2,4-difluorophenyl)-1-(3-propylthiopropyl)ureido]ethoxy}phenyl)-2-ethoxypropionic acid,
3-(4-{2-[3-(2,4-difluorophenyl)-1-(3-phenoxypropyl)ureido]ethoxy}phenyl)-2-ethoxypropionic acid,
3-(4-{2-[3-(2,4-difluorophenyl)-1-(4-phenoxybutyl)ureido]ethoxy}phenyl)-2-ethoxypropionic acid,
3-(4-{2-[1-(3-benzyloxypropyl)-3-(2,4-difluorophenyl)ureido]ethoxy}phenyl)-2-ethoxypropionic acid,
3-(4-{2-[3-(2,4-difluorophenyl)-1-(3-phenylthiopropyl)ureido]ethoxy}phenyl)-2-ethoxypropionic acid,
3-(4-{2-[3-(2,4-difluorophenyl)-1-(4-phenylthiobutyl)ureido]ethoxy}phenyl)-2-ethoxypropionic acid,
3-(4-{2-[1-(3-benzylthiopropyl)-3-(2,4-difluorophenyl)ureido]ethoxy}phenyl)-2-ethoxypropionic acid,
3-(4-{2-[3-(2,4-difluorophenyl)-1-(7,7,7-trifluoroheptyl)ureido]ethoxy}phenyl)-2-ethoxypropionic acid,
3-(4-{2-[1-(6,6-difluoroheptyl)-3-(2,4-difluorophenyl)ureido]ethoxy}phenyl)-2-ethoxypropionic acid,
3-(4-{2-[3-(2,4-difluorophenyl)-1-(6,6,6-trifluorohexyl)ureido]ethoxy}phenyl)-2-ethoxypropionic acid,
3-(4-{2-[1-(5,5-difluorohexyl)-3-(2,4-difluorophenyl)ureido]ethoxy}phenyl)-2-ethoxypropionic acid,
3-(4-{2-[3-(2,4-difluorophenyl)-1-(5,5,6,6,7,7,7-heptafluoroheptyl)ureido]ethoxy}phenyl)-2-ethoxypropionic acid,
3-(4-{2-[3-(2,4-difluorophenyl)-1-(2,2,3,3,4,4,5,5,6,6,7,7,7-tridecafluoroheptyl)ureido]ethoxy}phenyl)-2-ethoxypropionic acid,
3-(4-{2-[3-(2,4-difluorophenyl)-1-(5,5,6,6,6-pentafluorohexyl)ureido]ethoxy}phenyl)-2-ethoxypropionic acid,
3-(4-{2-[3-(2,4-difluorophenyl)-1-(2,2,3,3,4,4,5,5,6,6,6-undecafluorohexyl)ureido]ethoxy}phenyl)-2-ethoxypropionic acid,
3-[4-(2-{3-(2,4-difluorophenyl)-1-[2-(2,2-difluoropropoxy)ethyl]ureido}ethoxy)phenyl]-2-ethoxypropionic acid,
3-[4-(2-{3-(2,4-difluorophenyl)-1-[2-(1,1,2,2,3,3,3-heptafluoropropoxy)ethyl]ureido}ethoxy)phenyl]-2-ethoxypropionic acid,
3-[4-(2-{3-(2,4-difluorophenyl)-1-[2-(4,4,4-trifluorobutoxy)ethyl]ureido}ethoxy)phenyl]-2-ethoxypropionic acid,
3-[4-(2-{1-[2-(3,3-difluorobutoxy)ethyl]-3-(2,4-difluorophenyl)ureido}ethoxy)phenyl]-2-ethoxypropionic acid,
3-[4-(2-{1-[2-(2,2-difluorobutoxy)ethyl]-3-(2,4-difluorophenyl)ureido}ethoxy)phenyl]-2-ethoxypropionic acid,
3-[4-(2-{3-(2,4-difluorophenyl)-1-[2-(1,1,2,2,3,3,4,4,4-nonafluorobutoxy)ethyl]ureido}ethoxy)phenyl]-2-ethoxypropionic acid,
3-[4-(2-{3-(2,4-difluorophenyl)-1-[3-(2,2,2-trifluoroethoxy)propyl]ureido}ethoxy)phenyl]-2-ethoxypropionic acid,
3-[4-(2-{3-(2,4-difluorophenyl)-1-[3-(1,1,2,2,2-pentafluoroethoxy)propyl]ureido}ethoxy)phenyl]-2-ethoxypropionic acid,
3-[4-(2-{3-(2,4-difluorophenyl)-1-[3-(4-fluorophenoxy)propyl]ureido}ethoxy)phenyl]-2-ethoxypropionic acid,
3-[4-(2-{1-[3-(3,5-dichlorophenoxy)propyl]-3-(2,4-difluorophenyl)ureido}ethoxy)phenyl]-2-ethoxypropionic acid,
3-[4-(2-{3-(2,4-difluorophenyl)-1-[4-(4-fluorophenoxy)butyl]ureido}ethoxy)phenyl]-2-ethoxypropionic acid,
3-[4-(2-{1-[4-(3,5-dichlorophenoxy)butyl]-3-(2,4-difluorophenyl)ureido}ethoxy)phenyl]-2-ethoxypropionic acid,
3-[4-(2-{3-(2,4-difluorophenyl)-1-[2-(4-fluorobenzyloxy)ethyl]ureido}ethoxy)phenyl]-2-ethoxypropionic acid,
3-[4-(2-{1-[2-(3,5-dichlorobenzyloxy)ethyl]-3-(2,4-difluorophenyl)ureido}ethoxy)phenyl]-2-ethoxypropionic acid,
3-[4-(2-{3-(2,4-difluorophenyl)-1-[3-(4-fluorobenzyloxy)propyl]ureido}ethoxy)phenyl]-2-ethoxypropionic acid,
3-[4-(2-{1-[3-(3,5-dichlorobenzyloxy)propyl]-3-(2,4-difluorophenyl)ureido}ethoxy)phenyl]-2-ethoxypropionic acid,
3-[4-(2-{3-(2,4-difluorophenyl)-1-[4-(4-fluorobenzyloxy)butyl]ureido}ethoxy)phenyl]-2-ethoxypropionic acid,
3-[4-(2-{1-[4-(3,5-dichlorobenzyloxy)butyl]-3-(2,4-difluorophenyl)ureido}ethoxy)phenyl]-2-ethoxypropionic acid,
3-[4-(2-{3-(2,4-difluorophenyl)-1-[3-(4-fluorophenyl)propyl]ureido}ethoxy)phenyl]-2-ethoxypropionic acid,
3-[4-(2-{1-[3-(3,5-dichlorophenyl)propyl]-3-(2,4-difluorophenyl)ureido}ethoxy)phenyl]-2-ethoxypropionic acid,
3-(4-{2-[3-(3,4-difluorophenyl)-1-pentylureido]ethoxy}phenyl)-2-ethoxypropionic acid,
3-(4-{2-[3-(3,4-difluorophenyl)-1-hexylureido]ethoxy}phenyl)-2-ethoxypropionic acid,
3-(4-{2-[3-(3,4-difluorophenyl)-1-heptylureido]ethoxy}phenyl)-2-ethoxypropionic acid,
3-(4-{2-[3-(3,4-difluorophenyl)-1-octylureido]ethoxy}phenyl)-2-ethoxypropionic acid,
3-(4-{2-[3-(3,4-difluorophenyl)-1-isobutylureido]ethoxy}phenyl)-2-ethoxypropionic acid,
3-(4-{2-[3-(3,4-difluorophenyl)-1-(3-methylbutyl)ureido]ethoxy}phenyl)-2-ethoxypropionic acid,
3-(4-{2-[3-(3,4-difluorophenyl)-1-(4-methylpentyl)ureido]ethoxy}phenyl)-2-ethoxypropionic acid,
3-(4-{2-[3-(3,4-difluorophenyl)-1-(2-propylpentyl)ureido]ethoxy}phenyl)-2-ethoxypropionic acid,
3-(4-{2-[3-(3,4-difluorophenyl)-1-(3,3-dimethylbutyl)ureido]ethoxy}phenyl)-2-ethoxypropionic acid,
3-(4-{2-[3-(3,4-difluorophenyl)-1-(2-ethylbutyl)ureido]ethoxy}phenyl)-2-ethoxypropionic acid,
3-(4-{2-[1-cyclohexylmethyl-3-(3,4-difluorophenyl)ureido]ethoxy}phenyl)-2-ethoxypropionic acid,
3-(4-{2-[1-(4-cyclohexylbutyl)-3-(3,4-difluorophenyl)ureido]ethoxy}phenyl)-2-ethoxypropionic acid,
3-(4-{2-[1-cyclopropylmethyl-3-(3,4-difluorophenyl)ureido]ethoxy}phenyl)-2-ethoxypropionic acid,
3-(4-{2-[1-cyclobutylmethyl-3-(3,4-difluorophenyl)ureido]ethoxy}phenyl)-2-ethoxypropionic acid,
3-(4-{2-[1-cyclopentylmethyl-3-(3,4-difluorophenyl)ureido]ethoxy}phenyl)-2-ethoxypropionic acid,
3-(4-{2-[1-(2-cyclopentylethyl)-3-(3,4-difluorophenyl)ureido]ethoxy}phenyl)-2-ethoxypropionic acid,
3-(4-{2-[1-(3-cyclohexylpropyl)-3-(3,4-difluorophenyl)ureido]ethoxy}phenyl)-2-ethoxypropionic acid,
3-(4-{2-[3-(3,4-difluorophenyl)-1-(3-phenylpropyl)ureido]ethoxy}phenyl)-2-ethoxypropionic acid,
3-(4-{2-[3-(3,4-difluorophenyl)-1-(4-phenylbutyl)ureido]ethoxy}phenyl)-2-ethoxypropionic acid,
3-(4-{2-[1-(2-butoxyethyl)-3-(3,4-difluorophenyl)ureido]ethoxy}phenyl)-2-ethoxypropionic acid,
3-(4-{2-[3-(3,4-difluorophenyl)-1-(2-pentyloxyethyl)ureido]ethoxy}phenyl)-2-ethoxypropionic acid,
3-(4-{2-[3-(3,4-difluorophenyl)-1-(3-propoxypropyl)ureido]ethoxy}phenyl)-2-ethoxypropionic acid, 3-(4-{2-[1-(2-butylthioethyl)-3-(3,4-difluorophenyl)ureido]ethoxy}phenyl)-2-ethoxypropionic acid,
3-(4-{2-[3-(3,4-difluorophenyl)-1-(2-pentylthioethyl)ureido]ethoxy}phenyl)-2-ethoxypropionic acid,
3-(4-{2-[3-(3,4-difluorophenyl)-1-(3-propylthiopropyl)ureido]ethoxy}phenyl)-2-ethoxypropionic acid,
3-(4-{2-[3-(3,4-difluorophenyl)-1-(3-phenoxypropyl)ureido]ethoxy}phenyl)-2-ethoxypropionic acid,
3-(4-{2-[3-(3,4-difluorophenyl)-1-(4-phenoxybutyl)ureido]ethoxy}phenyl)-2-ethoxypropionic acid,
3-(4-{2-[1-(3-benzyloxypropyl)-3-(3,4-difluorophenyl)ureido]ethoxy}phenyl)-2-ethoxypropionic acid,
3-(4-{2-[3-(3,4-difluorophenyl)-1-(3-phenylthiopropyl)ureido]ethoxy}phenyl)-2-ethoxypropionic acid,
3-(4-{2-[3-(3,4-difluorophenyl)-1-(4-phenylthiobutyl)ureido]ethoxy}phenyl)-2-ethoxypropionic acid,
3-(4-{2-[1-(3-benzylthiopropyl)-3-(3,4-difluorophenyl)ureido]ethoxy}phenyl)-2-ethoxypropionic acid,
3-(4-{2-[3-(3,4-difluorophenyl)-1-(7,7,7-trifluoroheptyl)ureido]ethoxy}phenyl)-2-ethoxypropionic acid,
3-(4-{2-[1-(6,6-difluoroheptyl)-3-(3,4-difluorophenyl)ureido]ethoxy}phenyl)-2-ethoxypropionic acid,
3-(4-{2-[3-(3,4-difluorophenyl)-1-(6,6,6-trifluorohexyl)ureido]ethoxy}phenyl)-2-ethoxypropionic acid,
3-(4-{2-[1-(5,5-difluorohexyl)-3-(3,4-difluorophenyl)ureido]ethoxy}phenyl)-2-ethoxypropionic acid,
3-(4-{2-[3-(3,4-difluorophenyl)-1-(5,5,6,6,7,7,7-heptafluoroheptyl)ureido]ethoxy}phenyl)-2-ethoxypropionic acid,
3-(4-{2-[3-(3,4-difluorophenyl)-1-(2,2,3,3,4,4,5,5,6,6,7,7,7-tridecafluoroheptyl)ureido]ethoxy}phenyl)-2-ethoxypropionic acid,
3-(4-{2-[3-(3,4-difluorophenyl)-1-(5,5,6,6,6-pentafluorohexyl)ureido]ethoxy}phenyl)-2-ethoxypropionic acid,
3-(4-{2-[3-(3,4-difluorophenyl)-1-(2,2,3,3,4,4,5,5,6,6,6-undecafluorohexyl)ureido]ethoxy}phenyl)-2-ethoxypropionic acid,
3-[4-(2-{3-(3,4-difluorophenyl)-1-[2-(2,2-difluoropropoxy)ethyl]ureido}ethoxy)phenyl]-2-ethoxypropionic acid,
3-[4-(2-{3-(3,4-difluorophenyl)-1-[2-(1,1,2,2,3,3,3-heptafluoropropoxy)ethyl]ureido}ethoxy)phenyl]-2-ethoxypropionic acid,
3-[4-(2-{3-(3,4-difluorophenyl)-1-[2-(4,4,4-trifluorobutoxy)ethyl]ureido}ethoxy)phenyl] -2-ethoxypropionic acid,
3-[4-(2-{1-[2-(3,3-difluorobutoxy)ethyl]-3-(3,4-difluorophenyl)ureido}ethoxy)phenyl]-2-ethoxypropionic acid,
3-[4-(2-{1-[2-(2,2-difluorobutoxy)ethyl]-3-(3,4-difluorophenyl)ureido}ethoxy)phenyl]-2-ethoxypropionic acid,
3-[4-(2-{3-(3,4-difluorophenyl)-1-[2-(1,1,2,2,3,3,4,4,4-nonafluorobutoxy)ethyl]ureido}ethoxy)phenyl]-2-ethoxypropionic acid,
3-[4-(2-{3-(3,4-difluorophenyl)-1-[3-(2,2,2-trifluoroethoxy)propyl]ureido}ethoxy)phenyl]-2-ethoxypropionic acid,
3-[4-(2-{3-(3,4-difluorophenyl)-1-[3-(1,1,2,2,2-pentafluoroethoxy)propyl]ureido}ethoxy)phenyl]-2-ethoxypropionic acid,
3-[4-(2-{3-(3,4-difluorophenyl)-1-[3-(4-fluorophenoxy)propyl]ureido}ethoxy)phenyl]-2-ethoxypropionic acid,
3-[4-(2-{1-[3-(3,5-dichlorophenoxy)propyl]-3-(3,4-difluorophenyl)ureido}ethoxy)phenyl]-2-ethoxypropionic acid,
3-[4-(2-{3-(3,4-difluorophenyl)-1-[4-(4-fluorophenoxy)butyl]ureido}ethoxy)phenyl]-2-ethoxypropionic acid,
3-[4-(2-{1-[4-(3,5-dichlorophenoxy)butyl]-3-(3,4-difluorophenyl)ureido}ethoxy)phenyl]-2-ethoxypropionic acid,
3-[4-(2-{3-(3,4-difluorophenyl)-1-[2-(4-fluorobenzyloxy)ethyl]ureido}ethoxy)phenyl]-2-ethoxypropionic acid,
3-[4-(2-{1-[2-(3,5-dichlorobenzyloxy)ethyl]-3-(3,4-difluorophenyl)ureido}ethoxy)phenyl]-2-ethoxypropionic acid,
3-[4-(2-{3-(3,4-difluorophenyl)-1-[3-(4-fluorobenzyloxy)propyl]ureido}ethoxy)phenyl]-2-ethoxypropionic acid,
3-[4-(2-{1-[3-(3,5-dichlorobenzyloxy)propyl]-3-(3,4-difluorophenyl)ureido}ethoxy)phenyl]-2-ethoxypropionic acid,
3-[4-(2-{3-(3,4-difluorophenyl)-1-[4-(4-fluorobenzyloxy)butyl]ureido}ethoxy)phenyl]-2-ethoxypropionic acid,
3-[4-(2-{1-[4-(3,5-dichlorobenzyloxy)butyl]-3-(3,4-difluorophenyl)ureido}ethoxy)phenyl]-2-ethoxypropionic acid,
3-[4-(2-{3-(3,4-difluorophenyl)-1-[3-(4-fluorophenyl)propyl]ureido}ethoxy)phenyl]-2-ethoxypropionic acid,
3-[4-(2-{1-[3-(3,5-dichlorophenyl)propyl]-3-(3,4-difluorophenyl)ureido}ethoxy)phenyl]-2-ethoxypropionic acid,
2-ethoxy-3-(4-{2-[3-(2-fluorophenyl)-1-pentylureido]ethoxy}phenyl)propionic acid,
2-ethoxy-3-(4-{2-[3-(2-fluorophenyl)-1-hexylureido]ethoxy}phenyl)propionic acid,
2-ethoxy-3-(4-{2-[3-(2-fluorophenyl)-1-heptylureido]ethoxy}phenyl)propionic acid,
2-ethoxy-3-(4-{2-[3-(2-fluorophenyl)-1-octylureido]ethoxy}phenyl)propionic acid,
2-ethoxy-3-(4-{2-[3-(2-fluorophenyl)-1-isobutylureido]ethoxy}phenyl)propionic acid,
2-ethoxy-3-(4-{2-[3-(2-fluorophenyl)-1-(3-methylbutyl)ureido]ethoxy}phenyl)propionic acid,
2-ethoxy-3-(4-{2-[3-(2-fluorophenyl)-1-(4-methylpentyl)ureido]ethoxy}phenyl)propionic acid,
2-ethoxy-3-(4-{2-[3-(2-fluorophenyl)-1-(2-propylpentyl)ureido]ethoxy}phenyl)propionic acid,
3-(4-{2-[1-(3,3-dimethylbutyl)-3-(2-fluorophenyl)ureido]ethoxy}phenyl)-2-ethoxypropionic acid,
2-ethoxy-3-(4-{2-[1-(2-ethylbutyl)-3-(2-fluorophenyl)ureido]ethoxy}phenyl)propionic acid,
3-(4-{2-[1-cyclohexylmethyl-3-(2-fluorophenyl)ureido]ethoxy}phenyl)-2-ethoxypropionic acid,
3-(4-{2-[1-(4-cyclohexylbutyl)-3-(2-fluorophenyl)ureido]ethoxy}phenyl)-2-ethoxypropionic acid,
3-(4-{2-[1-cyclopropylmethyl-3-(2-fluorophenyl)ureido]ethoxy}phenyl)-2-ethoxypropionic acid,
3-(4-{2-[1-cyclobutylmethyl-3-(2-fluorophenyl)ureido]ethoxy}phenyl)-2-ethoxypropionic acid,
3-(4-{2-[1-cyclopentylmethyl-3-(2-fluorophenyl)ureido]ethoxy}phenyl)-2-ethoxypropionic acid,
3-(4-{2-[1-(2-cyclopentylethyl)-3-(2-fluorophenyl)ureido]ethoxy}phenyl)-2-ethoxypropionic acid,
3-(4-{2-[1-(3-cyclohexylpropyl)-3-(2-fluorophenyl)ureido]ethoxy}phenyl)-2-ethoxypropionic acid,
2-ethoxy-3-(4-{2-[3-(2-fluorophenyl)-1-(3-phenylpropyl)ureido]ethoxy}phenyl)propionic acid,
2-ethoxy-3-(4-{2-[3-(2-fluorophenyl)-1-(4-phenylbutyl)ureido]ethoxy}phenyl)propionic acid,
3-(4-{2-[1-(2-butoxyethyl)-3-(2-fluorophenyl)ureido]ethoxy}phenyl)-2-ethoxypropionic acid,
2-ethoxy-3-(4-{2-[3-(2-fluorophenyl)-1-(2-pentyloxyethyl)ureido]ethoxy}phenyl)propionic acid,
2-ethoxy-3-(4-{2-[3-(2-fluorophenyl)-1-(3-propoxypropyl)ureido]ethoxy}phenyl)propionic acid,
3-(4-{2-[1-(2-butylthioethyl)-3-(2-fluorophenyl)ureido]ethoxy}phenyl)-2-ethoxypropionic acid,
2-ethoxy-3-(4-{2-[3-(2-fluorophenyl)-1-(2-pentylthioethyl)ureido]ethoxy}phenyl)propionic acid,
2-ethoxy-3-(4-{2-[3-(2-fluorophenyl)-1-(3-propylthiopropyl)ureido]ethoxy}phenyl)propionic acid,
2-ethoxy-3-(4-{2-[3-(2-fluorophenyl)-1-(3-phenoxypropyl)ureido]ethoxy}phenyl)propionic acid, 2-ethoxy-3-(4-{2-[3-(2-fluorophenyl)-1-(4-phenoxybutyl) ureido]ethoxy}phenyl)propionic acid,
3-(4-{2-[1-(3-benzyloxypropyl)-3-(2-fluorophenyl)ureido] ethoxy}phenyl)-2-ethoxypropionic acid,
2-ethoxy-3-(4-{2-[3-(2-fluorophenyl)-1-(3-phenylthiopropyl)ureido]ethoxy}phenyl)propionic acid,
2-ethoxy-3-(4-{2-[3-(2-fluorophenyl)-1-(4-phenylthiobutyl)ureido]ethoxy}phenyl)propionic acid,
3-(4-{2-[1-(3-benzylthiopropyl)-3-(2-fluorophenyl)ureido] ethoxy}phenyl)-2-ethoxypropionic acid,
2-ethoxy-3-(4-{2-[3-(2-fluorophenyl)-1-(7,7,7-trifluoroheptyl)ureido]ethoxy}phenyl)propionic acid,
3-(4-{2-[1-(6,6-difluoroheptyl)-3-(2-fluorophenyl)ureido] ethoxy}phenyl)-2-ethoxypropionic acid,
2-ethoxy-3-(4-{2-[3-(2-fluorophenyl)-1-(6,6,6-trifluorohexyl)ureido]ethoxy}phenyl)propionic acid,
3-(4-{2-[1-(5,5-difluorohexyl)-3-(2-fluorophenyl)ureido] ethoxy}phenyl)-2 -ethoxypropionic acid,
2-ethoxy-3-(4-{2-[3-(2-fluorophenyl)-1-(5,5,6,6,7,7,7-heptafluoroheptyl)ureido]ethoxy}phenyl)propionic acid,
2-ethoxy-3-(4-{2-[3-(2-fluorophenyl)-1-(2,2,3,3,4,4,5,5,6, 6,7,7,7-tridecafluoroheptyl)ureido]ethoxy}phenyl)propionic acid,
2-ethoxy-3-(4-{2-[3-(2-fluorophenyl)-1-(5,5,6,6,6-pentafluorohexyl)ureido]ethoxy}phenyl)propionic acid,
2-ethoxy-3-(4-{2-[3-(2-fluorophenyl)-1-(2,2,3,3,4,4,5,5,6, 6,6-undecafluorohexyl)ureido]ethoxy}phenyl)propionic acid,
3-[4-(2-{1-[2-(2,2-difluoropropoxy)ethyl]-3-(2-fluorophenyl)ureido}ethoxy)phenyl]-2-ethoxypropionic acid,
2-ethoxy-3-[4-(2-{3-(2-fluorophenyl)-1-[2-(1,1,2,2,3,3,3-heptafluoropropoxy)ethyl]ureido}ethoxy)phenyl]propionic acid,
2-ethoxy-3-[4-(2-{3-(2-fluorophenyl)-1-[2-(4,4,4-trifluorobutoxy)ethyl]ureido}ethoxy)phenyl]propionic acid,
3-[4-(2-{1-[2-(3,3-difluorobutoxy)ethyl]-3-(2-fluorophenyl)ureido}ethoxy)phenyl]-2-ethoxypropionic acid,
3-[4-(2-{1-[2-(2,2-difluorobutoxy)ethyl]-3-(2-fluorophenyl)ureido}ethoxy)phenyl]-2-ethoxypropionic acid,
2-ethoxy-3-[4-(2-{3-(2-fluorophenyl)-1-[2-(1,1,2,2,3,3,4,4, 4-nonafluorobutoxy)ethyl]ureido}ethoxy)phenyl]propionic acid,
2-ethoxy-3-[4-(2-{3-(2-fluorophenyl)-1-[3-(2,2,2-trifluoroethoxy)propyl]ureido}ethoxy)phenyl]propionic acid,
2-ethoxy-3-[4-(2-{3-(2-fluorophenyl)-1-[3-(1,1,2,2,2-pentafluoroethoxy)propyl]ureido}ethoxy)phenyl]propionic acid,
2-ethoxy-3-[4-(2-{1-[3-(4-fluorophenoxy)propyl]-3-(2-fluorophenyl)ureido}ethoxy)phenyl]propionic acid,
3-[4-(2-{1-[3-(3,5-dichlorophenoxy)propyl]-3-(2-fluorophenyl)ureido}ethoxy)phenyl]-2-ethoxypropionic acid,
2-ethoxy-3-[4-(2-{1-[4-(4-fluorophenoxy)butyl]-3-(2-fluorophenyl)ureido}ethoxy)phenyl]propionic acid,
3-[4-(2-{1-[4-(3,5-dichlorophenoxy)butyl]-3-(2-fluorophenyl)ureido}ethoxy)phenyl]-2-ethoxypropionic acid,
2-ethoxy-3-[4-(2-(1-[2-(4-fluorobenzyloxy)ethyl]-3-(2-fluorophenyl)ureido}ethoxy)phenyl]propionic acid,
3-[4-(2-1'-[2-(3,5-dichlorobenzyloxy)ethyl]-3-(2-fluorophenyl)ureido}ethoxy)phenyl]-2-ethoxypropionic acid,
2-ethoxy-3-[4-(2-{1-[3-(4-fluorobenzyloxy)propyl]-3-(2-fluorophenyl)ureido}ethoxy)phenyl]propionic acid,
3-[4-(2-{1-[3-(3,5-dichlorobenzyloxy)propyl]-3-(2-fluorophenyl)ureido}ethoxy)phenyl]-2-ethoxypropionic acid,
2-ethoxy-3-[4-(2-{1-[4-(4-fluorobenzyloxy)butyl]-3-(2-fluorophenyl)ureido}ethoxy)phenyl]propionic acid,
3-[4-(2-{1-[4-(3,5-dichlorobenzyloxy)butyl]-3-(2-fluorophenyl)ureido}ethoxy)phenyl]-2-ethoxypropionic acid, 2-ethoxy-3-[4-(2-{3-(2-fluorophenyl)-1-[3-(4-fluorophenyl)propyl]ureido}ethoxy)phenyl]propionic acid,
3-[4-(2-{1-[3-(3,5-dichlorophenyl)propyl]-3-(2-fluorophenyl)ureido}ethoxy)phenyl]-2-ethoxypropionic acid,
2-ethoxy-3-(4-{2-[3-(3-fluorophenyl)-1-pentylureido] ethoxy}phenyl)propionic acid,
2-ethoxy-3-(4-{2-[3-(3-fluorophenyl)-1-hexylureido] ethoxy}phenyl)propionic acid,
2-ethoxy-3-(4-{2-[3-(3-fluorophenyl)-1-heptylureido] ethoxy}phenyl)propionic acid,
2-ethoxy-3-(4-{2-[3-(3-fluorophenyl)-1-octylureido] ethoxy}phenyl)propionic acid,
2-ethoxy-3-(4-{2-[3-(3-fluorophenyl)-1-isobutylureido] ethoxy}phenyl)propionic acid,
2-ethoxy-3-(4-{2-[3-(3-fluorophenyl)-1-(3-methylbutyl) ureido]ethoxy}phenyl)propionic acid,
2-ethoxy-3-(4-{2-[3-(3-fluorophenyl)-1-(4-methylpentyl) ureido]ethoxy}phenyl)propionic acid,
2-ethoxy-3-(4-{2-[3-(3-fluorophenyl)-1-(2-propylpentyl) ureido]ethoxy}phenyl)propionic acid,
3-(4-{2-[1-(3,3-dimethylbutyl)-3-(3-fluorophenyl)ureido] ethoxy}phenyl)-2-ethoxypropionic acid,
2-ethoxy-3-(4-{2-[1-(2-ethylbutyl)-3-(3-fluorophenyl)ureido]ethoxy}phenyl)propionic acid,
3-(4-{2-[1-cyclohexylmethyl-3-(3-fluorophenyl)ureido] ethoxy}phenyl)-2-ethoxypropionic acid,
3-(4-{2-[1-(4-cyclohexylbutyl)-3-(3-fluorophenyl)ureido] ethoxy}phenyl)-2-ethoxypropionic acid,
3-(4-{2-[1-cyclopropylmethyl-3-(3-fluorophenyl)ureido] ethoxy}phenyl)-2-ethoxypropionic acid,
3-(4-{2-[1-cyclobutylmethyl-3-(3-fluorophenyl)ureido] ethoxy}phenyl)-2-ethoxypropionic acid,
3-(4-{2-[1-cyclopentylmethyl-3-(3-fluorophenyl)ureido] ethoxy}phenyl)-2-ethoxypropionic acid,
3-(4-{2-[1-(2-cyclopentylethyl)-3-(3-fluorophenyl)ureido] ethoxy}phenyl)-2-ethoxypropionic acid,
3-(4-{2-[1-(3-cyclohexylpropyl)-3-(3-fluorophenyl)ureido] ethoxy}phenyl)-2-ethoxypropionic acid,
2-ethoxy-3-(4-{2-[3-(3-fluorophenyl)-1-(3-phenylpropyl) ureido]ethoxy}phenyl)propionic acid,
2-ethoxy-3-(4-{2-[3-(3-fluorophenyl)-1-(4-phenylbutyl) ureido]ethoxy}phenyl)propionic acid,
3-(4-{2-[1-(2-butoxyethyl)-3-(3-fluorophenyl)ureido] ethoxy}phenyl)-2-ethoxypropionic acid,
2-ethoxy-3-(4-{2-[3-(3-fluorophenyl)-1-(2-pentyloxyethyl) ureido]ethoxy}phenyl)propionic acid,
2-ethoxy-3-(4-{2-[3-(3-fluorophenyl)-1-(3-propoxypropyl) ureido]ethoxy}phenyl)propionic acid,
3-(4-{2-[1-(2-butylthioethyl)-3-(3-fluorophenyl)ureido] ethoxy}phenyl)-2-ethoxypropionic acid,
2-ethoxy-3-(4-{2-[3-(3-fluorophenyl)-1-(2-pentylthioethyl) ureido]ethoxy}phenyl)propionic acid,
2-ethoxy-3-(4-{2-[3-(3-fluorophenyl)-1-(3-propylthiopropyl)ureido]ethoxy}phenyl)propionic acid,
2-ethoxy-3-(4-{2-[3-(3-fluorophenyl)-1-(3-phenoxypropyl) ureido]ethoxy}phenyl)propionic acid,
2-ethoxy-3-(4-{2-[3-(3-fluorophenyl)-1-(4-phenoxybutyl) ureido]ethoxy}phenyl)propionic acid,
3-(4-{2-[1-(3-benzyloxypropyl)-3-(3-fluorophenyl)ureido] ethoxy}phenyl)-2 -ethoxypropionic acid,
2-ethoxy-3-(4-{2-[3-(3-fluorophenyl)-1-(3-phenylthiopropyl)ureido]ethoxy}phenyl)propionic acid,
2-ethoxy-3-(4-{2-[3-(3-fluorophenyl)-1-(4-phenylthiobutyl)ureido]ethoxy}phenyl)propionic acid,
3-(4-{2-[1-(3-benzylthiopropyl)-3-(3-fluorophenyl)ureido] ethoxy}phenyl)-2-ethoxypropionic acid, 2-ethoxy-3-(4-{2-[3-(3-fluorophenyl)-1-(7,7,7-trifluoroheptyl)ureido]ethoxy}phenyl)propionic acid,
3-(4-{2-[1-(6,6-difluoroheptyl)-3-(3-fluorophenyl)ureido]ethoxy}phenyl)-2-ethoxypropionic acid,
2-ethoxy-3-(4-{2-[3-(3-fluorophenyl)-1-(6,6,6-trifluorohexyl)ureido]ethoxy}phenyl)propionic acid,
3-(4-{2-[1-(5,5-difluorohexyl)-3-(3-fluorophenyl)ureido]ethoxy}phenyl)-2-ethoxypropionic acid,
2-ethoxy-3-(4-{2-[3-(3-fluorophenyl)-1-(5,5,6,6,7,7,7-heptafluoroheptyl)ureido]ethoxy}phenyl)propionic acid,
2-ethoxy-3-(4-{2-[3-(3-fluorophenyl)-1-(2,2,3,3,4,4,5,5,6,6,7,7,7-tridecafluoroheptyl)ureido]ethoxy}phenyl)propionic acid,
2-ethoxy-3-(4-{2-[3-(3-fluorophenyl)-1-(5,5,6,6,6-pentafluorohexyl)ureido]ethoxy}phenyl)propionic acid,
2-ethoxy-3-(4-{2-[3-(3-fluorophenyl)-1-(2,2,3,3,4,4,5,5,6,6-undecafluorohexyl)ureido]ethoxy}phenyl)propionic acid,
3-[4-(2-{1-[2-(2,2-difluoropropoxy)ethyl]-3-(3-fluorophenyl)ureido}ethoxy)phenyl]-2-ethoxypropionic acid,
2-ethoxy-3-[4-(2-{3-(3-fluorophenyl)-1-[2-(1,1,2,2,3,3,3-heptafluoropropoxy)ethyl]ureido}ethoxy)phenyl]propionic acid,
2-ethoxy-3-[4-(2-{3-(3-fluorophenyl)-1-[2-(4,4,4-trifluorobutoxy)ethyl]ureido}ethoxy)phenyl]propionic acid,
3-[4-(2-{1-[2-(3,3-difluorobutoxy)ethyl]-3-(3-fluorophenyl)ureido}ethoxy)phenyl]-2-ethoxypropionic acid,
3-[4-(2-{1-[2-(2,2-difluorobutoxy)ethyl]-3-(3-fluorophenyl)ureido}ethoxy)phenyl]-2-ethoxypropionic acid,
2-ethoxy-3-[4-(2-{3-(3-fluorophenyl)-1-[2-(1,1,2,2,3,3,4,4-nonafluorobutoxy)ethyl]ureido}ethoxy)phenyl]propionic acid,
2-ethoxy-3-[4-(2-{3-(3-fluorophenyl)-1-[3-(2,2,2-trifluoroethoxy)propyl]ureido}ethoxy)phenyl]propionic acid,
2-ethoxy-3-[4-(2-{3-(3-fluorophenyl)-1-[3-(1,1,2,2,2-pentafluoroethoxy)propyl]ureido}ethoxy)phenyl]propionic acid,
2-ethoxy-3-[4-(2-{1-[3-(4-fluorophenoxy)propyl]-3-(3-fluorophenyl)ureido}ethoxy)phenyl]propionic acid,
3-[4-(2-{1-[3-(3,5-dichlorophenoxy)propyl]-3-(3-fluorophenyl)ureido}ethoxy)phenyl]-2-ethoxypropionic acid,
2-ethoxy-3-[4-(2-{1-[4-(4-fluorophenoxy)butyl]-3-(3-fluorophenyl)ureido}ethoxy)phenyl]propionic acid,
3-[4-(2-{1-[4-(3,5-dichlorophenoxy)butyl]-3-(3-fluorophenyl)ureido}ethoxy)phenyl]-2-ethoxypropionic acid,
2-ethoxy-3-[4-(2-{1-[2-(4-fluorobenzyloxy)ethyl]-3-(3-fluorophenyl)ureido}ethoxy)phenyl]propionic acid,
3-[4-(2-{1-[2-(3,5-dichlorobenzyloxy)ethyl]-3-(3-fluorophenyl)ureido}ethoxy)phenyl]-2-ethoxypropionic acid,
2-ethoxy-3-[4-(2-{1-[3-(4-fluorobenzyloxy)propyl]-3-(3-fluorophenyl)ureido}ethoxy)phenyl]propionic acid,
3-[4-(2-{1-[3-(3,5-dichlorobenzyloxy)propyl]-3-(3-fluorophenyl)ureido}ethoxy)phenyl]-2-ethoxypropionic acid,
2-ethoxy-3-[4-(2-{1-[4-(4-fluorobenzyloxy)butyl]-3-(3-fluorophenyl)ureido}ethoxy)phenyl]propionic acid,
3-[4-(2-{1-[4-(3,5-dichlorobenzyloxy)butyl]-3-(3-fluorophenyl)ureido}ethoxy)phenyl]-2-ethoxypropionic acid,
2-ethoxy-3-[4-(2-{3-(3-fluorophenyl)-1-[3-(4-fluorophenyl)propyl]ureido}ethoxy)phenyl]propionic acid,
3-[4-(2-{1-[3-(3,5-dichlorophenyl)propyl]-3-(3-fluorophenyl)ureido}ethoxy)phenyl]-2-ethoxypropionic acid,
2-ethoxy-3-(4-{2-[3-(4-fluorophenyl)-1-pentylureido]ethoxy}phenyl)propionic acid,
2-ethoxy-3-(4-{2-[3-(4-fluorophenyl)-1-hexylureido]ethoxy}phenyl)propionic acid,
2-ethoxy-3-(4-{2-[3-(4-fluorophenyl)-1-heptylureido]ethoxy}phenyl)propionic acid,
2-ethoxy-3-(4-{2-[3-(4-fluorophenyl)-1-octylureido]ethoxy}phenyl)propionic acid,
2-ethoxy-3-(4-{2-[3-(4-fluorophenyl)-1-isobutylureido]ethoxy}phenyl)propionic acid,
2-ethoxy-3-(4-{2-[3-(4-fluorophenyl)-1-(3-methylbutyl)ureido]ethoxy}phenyl)propionic acid,
2-ethoxy-3-(4-{2-[3-(4-fluorophenyl)-1-(4-methylpentyl)ureido]ethoxy}phenyl)propionic acid,
2-ethoxy-3-(4-{2-[3-(4-fluorophenyl)-1-(2-propylpentyl)ureido]ethoxy}phenyl)propionic acid,
3-(4-{2-[1-(3,3-dimethylbutyl)-3-(4-fluorophenyl)ureido]ethoxy}phenyl)-2-ethoxypropionic acid,
2-ethoxy-3-(4-{2-[1-(2-ethylbutyl)-3-(4-fluorophenyl)ureido]ethoxy}phenyl)propionic acid,
3-(4-{2-[1-cyclohexylmethyl-3-(4-fluorophenyl)ureido]ethoxy}phenyl)-2-ethoxypropionic acid,
3-(4-{2-[1-(4-cyclohexylbutyl)-3-(4-fluorophenyl)ureido]ethoxy}phenyl)-2-ethoxypropionic acid,
3-(4-{2-[1-cyclopropylmethyl-3-(4-fluorophenyl)ureido]ethoxy}phenyl)-2-ethoxypropionic acid,
3-(4-{2-[1-cyclobutylmethyl-3-(4-fluorophenyl)ureido]ethoxy}phenyl)-2-ethoxypropionic acid,
3-(4-{2-[1-cyclopentylmethyl-3-(4-fluorophenyl)ureido]ethoxy}phenyl)-2-ethoxypropionic acid,
3-(4-{2-[1-(2-cyclopentylethyl)-3-(4-fluorophenyl)ureido]ethoxy}phenyl)-2-ethoxypropionic acid,
3-(4-{2-[1-(3-cyclohexylpropyl)-3-(4-fluorophenyl)ureido]ethoxy}phenyl)-2-ethoxypropionic acid,
2-ethoxy-3-(4-{2-[3-(4-fluorophenyl)-1-(3-phenylpropyl)ureido]ethoxy}phenyl)propionic acid,
2-ethoxy-3-(4-{2-[3-(4-fluorophenyl)-1-(4-phenylbutyl)ureido]ethoxy}phenyl)propionic acid,
3-(4-{2-[1-(2-butoxyethyl)-3-(4-fluorophenyl)ureido]ethoxy}phenyl)-2-ethoxypropionic acid,
2-ethoxy-3-(4-{2-[3-(4-fluorophenyl)-1-(2 -pentyloxyethyl)ureido]ethoxy}phenyl)propionic acid,
2-ethoxy-3-(4-{2-[3-(4-fluorophenyl)-1-(3-propoxypropyl)ureido]ethoxy}phenyl)propionic acid,
3-(4-{2-[1-(2-butylthioethyl)-3-(4-fluorophenyl)ureido]ethoxy}phenyl)-2-ethoxypropionic acid,
2-ethoxy-3-(4-{2-[3-(4-fluorophenyl)-1-(2-pentylthioethyl)ureido]ethoxy}phenyl)propionic acid,
2-ethoxy-3-(4-{2-[3-(4-fluorophenyl)-1-(3-propylthiopropyl)ureido]ethoxy}phenyl)propionic acid,
2-ethoxy-3-(4-{2-[3-(4-fluorophenyl)-1-(3-phenoxypropyl)ureido]ethoxy}phenyl)propionic acid,
2-ethoxy-3-(4-{2-[3-(4-fluorophenyl)-1-(4-phenoxybutyl)ureido]ethoxy}phenyl)propionic acid,
3-(4-{2-[1-(3-benzyloxypropyl)-3-(4-fluorophenyl)ureido]ethoxy}phenyl)-2-ethoxypropionic acid,
2-ethoxy-3-(4-{2-[3-(4-fluorophenyl)-1-(3-phenylthiopropyl)ureido]ethoxy}phenyl)propionic acid,
2-ethoxy-3-(4-{2-[3-(4-fluorophenyl)-1-(4-phenylthiobutyl)ureido]ethoxy}phenyl)propionic acid,
3-(4-{2-[1-(3-benzylthiopropyl)-3-(4-fluorophenyl)ureido]ethoxy}phenyl)-2-ethoxypropionic acid,
2-ethoxy-3-(4-{2-[3-(4-fluorophenyl)-1-(7,7,7-trifluoroheptyl)ureido]ethoxy}phenyl)propionic acid,
3-(4-{2-[1-(6,6-difluoroheptyl)-3-(4-fluorophenyl)ureido]ethoxy}phenyl)-2-ethoxypropionic acid,
2-ethoxy-3-(4-{2-[3-(4-fluorophenyl)-1-(6,6,6-trifluorohexyl)ureido]ethoxy}phenyl)propionic acid,
3-(4-{2-[1-(5,5-difluorohexyl)-3-(4-fluorophenyl)ureido]ethoxy}phenyl)-2-ethoxypropionic acid,
2-ethoxy-3-(4-{2-[3-(4-fluorophenyl)-1-(5,5,6,6,7,7,7-heptafluoroheptyl)ureido]ethoxy}phenyl)propionic acid, 2-ethoxy-3-(4-{2-[3-(4-fluorophenyl)-1-(2,2,3,3,4,4,5,5,6,6,7,7,7-tridecafluoroheptyl)ureido]ethoxy}phenyl)propionic acid,
2-ethoxy-3-(4-{2-[3-(4-fluorophenyl)-1-(5,5,6,6,6-pentafluorohexyl)ureido]ethoxy}phenyl)propionic acid,
2-ethoxy-3-(4-{2-[3-(4-fluorophenyl)-1-(2,2,3,3,4,4,5,5,6,6-undecafluorohexyl)ureido]ethoxy}phenyl)propionic acid,
3-[4-(2-{1-[2-(2,2-difluoropropoxy)ethyl]-3-(4-fluorophenyl)ureido}ethoxy)phenyl]-2-ethoxypropionic acid,
2-ethoxy-3-[4-(2-{3-(4-fluorophenyl)-1-[2-(1,1,2,2,3,3,3-heptafluoropropoxy)ethyl]ureido}ethoxy)phenyl]propionic acid,
2-ethoxy-3-[4-(2-{3-(4-fluorophenyl)-1-[2-(4,4,4-trifluorobutoxy)ethyl]ureido}ethoxy)phenyl]propionic acid,
3-[4-(2-{1-[2-(3,3-difluorobutoxy)ethyl]-3-(4-fluorophenyl)ureido}ethoxy)phenyl]-2-ethoxypropionic acid,
3-[4-(2-{1-[2-(2,2-difluorobutoxy)ethyl]-3-(4-fluorophenyl)ureido}ethoxy)phenyl]-2-ethoxypropionic acid,
2-ethoxy-3-[4-(2-{3-(4-fluorophenyl)-1-[2-(1,1,2,2,3,3,4,4,4-nonafluorobutoxy)ethyl]ureido}ethoxy)phenyl]propionic acid,
2-ethoxy-3-[4-(2-{3-(4-fluorophenyl)-1-[3-(2,2,2-trifluoroethoxy)propyl]ureido}ethoxy)phenyl]propionic acid,
2-ethoxy-3-[4-(2-{3-(4-fluorophenyl)-1-[3-(1,1,2,2,2-pentafluoroethoxy)propyl]ureido}ethoxy)phenyl]propionic acid,
2-ethoxy-3-[4-(2-{1-[3-(4-fluorophenoxy)propyl]-3-(4-fluorophenyl)ureido}ethoxy)phenyl]propionic acid,
3-[4-(2-{1-[3-(3,5-dichlorophenoxy)propyl]-3-(4-fluorophenyl)ureido}ethoxy)phenyl]-2-ethoxypropionic acid,
2-ethoxy-3-[4-(2-{1-[4-(4-fluorophenoxy)butyl]-3-(4-fluorophenyl)ureido}ethoxy)phenyl]propionic acid,
3-[4-(2-{1-[4-(3,5-dichlorophenoxy)butyl]-3-(4-fluorophenyl)ureido}ethoxy)phenyl]-2-ethoxypropionic acid,
2-ethoxy-3-[4-(2-{1-[2-(4-fluorobenzyloxy)ethyl]-3-(4-fluorophenyl)ureido}ethoxy)phenyl]propionic acid,
3-[4-(2-{1-[2-(3,5-dichlorobenzyloxy)ethyl]-3-(4-fluorophenyl)ureido}ethoxy)phenyl]-2-ethoxypropionic acid,
2-ethoxy-3-[4-(2-{1-[3-(4-fluorobenzyloxy)propyl]-3-(4-fluorophenyl)ureido}ethoxy)phenyl]propionic acid,
3-[4-(2-{1-[3-(3,5-dichlorobenzyloxy)propyl]-3-(4-fluorophenyl)ureido}ethoxy)phenyl]-2-ethoxypropionic acid,
2-ethoxy-3-[4-(2-{1 -[4-(4-fluorobenzyloxy)butyl]-3-(4-fluorophenyl)ureido}ethoxy)phenyl]propionic acid,
3-[4-(2-{1-[4-(3,5-dichlorobenzyloxy)butyl]-3-(4-fluorophenyl)ureido}ethoxy)phenyl]-2-ethoxypropionic acid,
2-ethoxy-3-[4-(2-{3-(4-fluorophenyl)-1-[3-(4-fluorophenyl)propyl]ureido}ethoxy)phenyl]propionic acid,
3-[4-(2-{1-[3-(3,5-dichlorophenyl)propyl]-3-(4-fluorophenyl)ureido}ethoxy)phenyl]-2-ethoxypropionic acid,
3-(4-{2-[3-(4-bromophenyl)-1-pentylureido]ethoxy}phenyl)-2-ethoxypropionic acid,
3-(4-{2-[3-(4-bromophenyl)-1-hexylureido]ethoxy}phenyl)-2-ethoxypropionic acid,
3-(4-{2-[3-(4-bromophenyl)-1-heptylureido]ethoxy}phenyl)-2-ethoxypropionic acid,
3-(4-{2-[3-(4-bromophenyl)-1-octylureido]ethoxy}phenyl)-2-ethoxypropionic acid,
3-(4-{2-[3-(4-bromophenyl)-1-isobutylureido]ethoxy}phenyl)-2-ethoxypropionic acid,
3-(4-{2-[3-(4-bromophenyl)-1-(3-methylbutyl)ureido]ethoxy}phenyl)-2-ethoxypropionic acid,
3-(4-{2-[3-(4-bromophenyl)-1-(4-methylpentyl)ureido]ethoxy}phenyl)-2-ethoxypropionic acid,
3-(4-{2-[3-(4-bromophenyl)-1-(2-propylpentyl)ureido]ethoxy}phenyl)-2-ethoxypropionic acid,
3-(4-{2-[3-(4-bromophenyl)-1-(3,3-dimethylbutyl)ureido]ethoxy}phenyl)-2-ethoxypropionic acid,
3-(4-{2-[3-(4-bromophenyl)-1-(2-ethylbutyl)ureido]ethoxy}phenyl)-2-ethoxypropionic acid,
3-(4-{2-[3-(4-bromophenyl)-1-cyclohexylmethylureido]ethoxy}phenyl)-2-ethoxypropionic acid,
3-(4-{2-[3-(4-bromophenyl)-1-(4-cyclohexylbutyl)ureido]ethoxy}phenyl)-2-ethoxypropionic acid,
3-(4-{2-[3-(4-bromophenyl)-1-cyclopropylmethylureido]ethoxy}phenyl)-2-ethoxypropionic acid,
3-(4-{2-[3-(4-bromophenyl)-1-cyclobutylmethylureido]ethoxy}phenyl)-2 -ethoxypropionic acid,
3-(4-{2-[3-(4-bromophenyl)-1-cyclopentylmethylureido]ethoxy}phenyl)-2-ethoxypropionic acid,
3-(4-{2-[3-(4-bromophenyl)-1-(2-cyclopentylethyl)ureido]ethoxy}phenyl)-2-ethoxypropionic acid,
3-(4-{2-[3-(4-bromophenyl)-1-(3-cyclohexylpropyl)ureido]ethoxy}phenyl)-2-ethoxypropionic acid,
3-(4-{2-[3-(4-bromophenyl)-1-(3-phenylpropyl)ureido]ethoxy}phenyl)-2-ethoxypropionic acid,
3-(4-{2-[3-(4-bromophenyl)-1-(4-phenylbutyl)ureido]ethoxy}phenyl)-2-ethoxypropionic acid,
3-(4-{2-[3-(4-bromophenyl)-1-(2-butoxyethyl)ureido]ethoxy}phenyl)-2-ethoxypropionic acid,
3-(4-{2-[3-(4-bromophenyl)-1-(2-pentyloxyethyl)ureido]ethoxy}phenyl)-2-ethoxypropionic acid,
3-(4-{2-[3-(4-bromophenyl)-1-(3-propoxypropyl)ureido]ethoxy}phenyl)-2-ethoxypropionic acid,
3-(4-{2-[3-(4-bromophenyl)-1-(2-butylthioethyl)ureido]ethoxy}phenyl)-2-ethoxypropionic acid,
3-(4-{2-[3-(4-bromophenyl)-1-(2-pentylthioethyl)ureido]ethoxy}phenyl)-2-ethoxypropionic acid,
3-(4-{2-[3-(4-bromophenyl)-1-(3-propylthiopropyl)ureido]ethoxy}phenyl)-2-ethoxypropionic acid,
3-(4-{2-[3-(4-bromophenyl)-1-(3-phenoxypropyl)ureido]ethoxy}phenyl)-2-ethoxypropionic acid,
3-(4-{2-[3-(4-bromophenyl)-1-(4-phenoxybutyl)ureido]ethoxy}phenyl)-2-ethoxypropionic acid,
3-(4-{2-[1-(3-benzyloxypropyl)-3-(4-bromophenyl)ureido]ethoxy}phenyl)-2-ethoxypropionic acid,
3-(4-{2-[3-(4-bromophenyl)-1-(3-phenylthiopropyl)ureido]ethoxy}phenyl)-2-ethoxypropionic acid,
3-(4-{2-[3-(4-bromophenyl)-1-(4-phenylthiobutyl)ureido]ethoxy}phenyl)-2-ethoxypropionic acid,
3-(4-{2-[1-(3-benzylthiopropyl)-3-(4-bromophenyl)ureido]ethoxy}phenyl)-2-ethoxypropionic acid,
3-(4-{2-[3-(4-bromophenyl)-1-(7,7,7-trifluoroheptyl)ureido]ethoxy}phenyl)-2-ethoxypropionic acid,
3-(4-{2-[3-(4-bromophenyl)-1-(6,6-difluoroheptyl)ureido]ethoxy}phenyl)-2-ethoxypropionic acid,
3-(4-{2-[3-(4-bromophenyl)-1-(6,6,6-trifluorohexyl)ureido]ethoxy}phenyl)-2-ethoxypropionic acid,
3-(4-{2-[3-(4-bromophenyl)-1-(5,5-difluorohexyl)ureido]ethoxy}phenyl)-2-ethoxypropionic acid,
3-(4-{2-[3-(4-bromophenyl)-1-(5,5,6,6,7,7,7-heptafluoroheptyl)ureido]ethoxy}phenyl)-2-ethoxypropionic acid,
3-(4-{2-[3-(4-bromophenyl)-1-(2,2,3,3,4,4,5,5,6,6,7,7,7-tridecafluoroheptyl)ureido]ethoxy}phenyl)-2-ethoxypropionic acid,
3-(4-{2-[3-(4-bromophenyl)-1-(5,5,6,6,6-pentafluorohexyl)ureido]ethoxy}phenyl)-2-ethoxypropionic acid,
3-(4-{2-[3-(4-bromophenyl)-1-(2,2,3,3,4,4,5,5,6,6-undecafluorohexyl)ureido]ethoxy}phenyl)-2-ethoxypropionic acid,
3-[4-(2-{3-(4-bromophenyl)-1-[2-(2,2-difluoropropoxy)ethyl]ureido}ethoxy)phenyl]-2-ethoxypropionic acid, 3-[4-(2-{3-(4-bromophenyl)-1-[2-(1,1,2,2,3,3,3-heptafluoropropoxy)ethyl]ureido}ethoxy)phenyl]-2-ethoxypropionic acid,
3-[4-(2-{3-(4-bromophenyl)-1-[2-(4,4,4-trifluorobutoxy)ethyl]ureido}ethoxy)phenyl]-2-ethoxypropionic acid,
3-[4-(2-{3-(4-bromophenyl)-1-[2-(3,3-difluorobutoxy)ethyl]ureido}ethoxy)phenyl]-2-ethoxypropionic acid,
3-[4-(2-{3-(4-bromophenyl)-1-[2-(2,2-difluorobutoxy)ethyl]ureido}ethoxy)phenyl]-2-ethoxypropionic acid,
3-[4-(2-{3-(4-bromophenyl)-1-[2-(1,1,2,2,3,3,4,4,4-nonafluorobutoxy)ethyl]ureido}ethoxy)phenyl]-2-ethoxypropionic acid,
3-[4-(2-{3-(4-bromophenyl)-1-[3-(2,2,2-trifluoroethoxy)propyl]ureido}ethoxy)phenyl]-2-ethoxypropionic acid,
3-[4-(2-{3-(4-bromophenyl)-1-[3-(1,1,2,2,2-pentafluoroethoxy)propyl]ureido}ethoxy)phenyl]-2-ethoxypropionic acid,
3-[4-(2-{3-(4-bromophenyl)-1-[3-(4-fluorophenoxy)propyl]ureido}ethoxy)phenyl]-2-ethoxypropionic acid,
3-[4-(2-{3-(4-bromophenyl)-1-[3-(3,5-dichlorophenoxy)propyl]ureido}ethoxy)phenyl]-2-ethoxypropionic acid,
3-[4-(2-{3-(4-bromophenyl)-1-[4-(4-fluorophenoxy)butyl]ureido}ethoxy)phenyl]-2-ethoxypropionic acid,
3-[4-(2-{3-(4-bromophenyl)-1-[4-(3,5-dichlorophenoxy)butyl]ureido}ethoxy)phenyl]-2-ethoxypropionic acid,
3-[4-(2-{3-(4-bromophenyl)-1-[2-(4-fluorobenzyloxy)ethyl]ureido}ethoxy)phenyl]-2-ethoxypropionic acid,
3-[4-(2-{3-(4-bromophenyl)-1-[2-(3,5-dichlorobenzyloxy)ethyl]ureido}ethoxy)phenyl]-2-ethoxypropionic acid,
3-[4-(2-{3-(4-bromophenyl)-1-[3-(4-fluorobenzyloxy)propyl]ureido}ethoxy)phenyl]-2-ethoxypropionic acid,
3-[4-(2-{3-(4-bromophenyl)-1-[3-(3,5-dichlorobenzyloxy)propyl]ureido}ethoxy)phenyl]-2-ethoxypropionic acid,
3-[4-(2-{3-(4-bromophenyl)-1-[4-(4-fluorobenzyloxy)butyl]ureido}ethoxy)phenyl]-2-ethoxypropionic acid,
3-[4-(2-{3-(4-bromophenyl)-1-[4-(3,5-dichlorobenzyloxy)butyl]ureido}ethoxy)phenyl]-2-ethoxypropionic acid,
3-[4-(2-{3-(4-bromophenyl)-1-[3-(4-fluorophenyl)propyl]ureido}ethoxy)phenyl]-2-ethoxypropionic acid,
3-[4-(2-{3-(4-bromophenyl)-1-[3-(3,5-dichlorophenyl)propyl]ureido}ethoxy)phenyl]-2-ethoxypropionic acid,
3-(4-{2-[3-(2-chlorophenyl)-1-pentylureido]ethoxy}phenyl)-2-ethoxypropionic acid,
3-(4-{2-[3-(2-chlorophenyl)-1-hexylureido]ethoxy}phenyl)-2-ethoxypropionic acid,
3-(4-{2-[3-(2-chlorophenyl)-1-heptylureido]ethoxy}phenyl)-2-ethoxypropionic acid,
3-(4-{2-[3-(2-chlorophenyl)-1-octylureido]ethoxy}phenyl)-2-ethoxypropionic acid,
3-(4-{2-[3-(2-chlorophenyl)-1-isobutylureido]ethoxy}phenyl)-2-ethoxypropionic acid,
3-(4-{2-[3-(2-chlorophenyl)-1-(3-methylbutyl)ureido]ethoxy}phenyl)-2-ethoxypropionic acid,
3-(4-{2-[3-(2-chlorophenyl)-1-(4-methylpentyl)ureido]ethoxy}phenyl)-2-ethoxypropionic acid,
3-(4-{2-[3-(2-chlorophenyl)-1-(2-propylpentyl)ureido]ethoxy}phenyl)-2-ethoxypropionic acid,
3-(4-{2-[3-(2-chlorophenyl)-1-(3,3-dimethylbutyl)ureido]ethoxy}phenyl)-2-ethoxypropionic acid,
3-(4-{2-[3-(2-chlorophenyl)-1-(2-ethylbutyl)ureido]ethoxy}phenyl)-2-ethoxypropionic acid,
3-(4-{2-[3-(2-chlorophenyl)-1-cyclohexylmethylureido]ethoxy}phenyl)-2-ethoxypropionic acid,
3-(4-{2-[3-(2-chlorophenyl)-1-(4-cyclohexylbutyl)ureido]ethoxy}phenyl)-2-ethoxypropionic acid,
3-(4-{2-[3-(2-chlorophenyl)-1-cyclopropylmethylureido]ethoxy}phenyl)-2-ethoxypropionic acid,
3-(4-{2-[3-(2-chlorophenyl)-1-cyclobutylmethylureido]ethoxy}phenyl)-2-ethoxypropionic acid,
3-(4-{2-[3-(2-chlorophenyl)-1-cyclopentylmethylureido]ethoxy}phenyl)-2-ethoxypropionic acid,
3-(4-{2-[3-(2-chlorophenyl)-1-(2-cyclopentylethyl)ureido]ethoxy}phenyl)-2-ethoxypropionic acid,
3-(4-{2-[3-(2-chlorophenyl)-1-(3-cyclohexylpropyl)ureido]ethoxy}phenyl)-2-ethoxypropionic acid,
3-(4-{2-[3-(2-chlorophenyl)-1-(3-phenylpropyl)ureido]ethoxy}phenyl)-2-ethoxypropionic acid,
3-(4-{2-[3-(2-chlorophenyl)-1-(4-phenylbutyl)ureido]ethoxy}phenyl)-2-ethoxypropionic acid,
3-(4-{2-[1-(2-butoxyethyl)-3-(2-chlorophenyl)ureido]ethoxy}phenyl)-2-ethoxypropionic acid,
3-(4-{2-[3-(2-chlorophenyl)-1-(2-pentyloxyethyl)ureido]ethoxy}phenyl)-2-ethoxypropionic acid,
3-(4-{2-[3-(2-chlorophenyl)-1-(3-propoxypropyl)ureido]ethoxy}phenyl)-2-ethoxypropionic acid,
3-(4-{2-[1-(2-butylthioethyl)-3-(2-chlorophenyl)ureido]ethoxy}phenyl)-2-ethoxypropionic acid,
3-(4-{2-[3-(2-chlorophenyl)-1-(2-pentylthioethyl)ureido]ethoxy}phenyl)-2-ethoxypropionic acid,
3-(4-{2-[3-(2-chlorophenyl)-1-(3-propylthiopropyl)ureido]ethoxy}phenyl)-2-ethoxypropionic acid,
3-(4-{2-[3-(2-chlorophenyl)-1-(3-phenoxypropyl)ureido]ethoxy}phenyl)-2-ethoxypropionic acid,
3-(4-{2-[3-(2-chlorophenyl)-1-(4-phenoxybutyl)ureido]ethoxy}phenyl)-2-ethoxypropionic acid,
3-(4-{2-[1-(3-benzyloxypropyl)-3-(2-chlorophenyl)ureido]ethoxy}phenyl)-2-ethoxypropionic acid,
3-(4-{2-[3-(2-chlorophenyl)-1-(3-phenylthiopropyl)ureido]ethoxy}phenyl)-2-ethoxypropionic acid,
3-(4-{2-[3-(2-chlorophenyl)-1-(4-phenylthiobutyl)ureido]ethoxy}phenyl)-2-ethoxypropionic acid,
3-(4-{2-[1-(3-benzylthiopropyl)-3-(2-chlorophenyl)ureido]ethoxy}phenyl)-2-ethoxypropionic acid,
3-(4-{2-[3-(2-chlorophenyl)-1-(7,7,7-trifluoroheptyl)ureido]ethoxy}phenyl)-2-ethoxypropionic acid,
3-(4-{2-[3-(2-chlorophenyl)-1-(6,6-difluoroheptyl)ureido]ethoxy}phenyl)-2-ethoxypropionic acid,
3-(4-{2-[3-(2-chlorophenyl)-1-(6,6,6-trifluorohexyl)ureido]ethoxy}phenyl)-2-ethoxypropionic acid,
3-(4-{2-[3-(2-chlorophenyl)-1-(5,5-difluorohexyl)ureido]ethoxy}phenyl)-2-ethoxypropionic acid,
3-(4-{2-[3-(2-chlorophenyl)-1-(5,5,6,6,7,7,7-heptafluoroheptyl)ureido]ethoxy}phenyl)-2-ethoxypropionic acid,
3-(4-{2-[3-(2-chlorophenyl)-1-(2,2,3,3,4,4,5,5,6,6,7,7,7-tridecafluoroheptyl)ureido]ethoxy}phenyl)-2-ethoxypropionic acid,
3-(4-{2-[3-(2-chlorophenyl)-1-(5,5,6,6,6-pentafluorohexyl)ureido]ethoxy}phenyl)-2-ethoxypropionic acid,
3-(4-{2-[3-(2-chlorophenyl)-1-(2,2,3,3,4,4,5,5,6,6,6-undecafluorohexyl)ureido]ethoxy}phenyl)-2-ethoxypropionic acid,
3-[4-(2-{3-(2-chlorophenyl)-1-[2-(2,2-difluoropropoxy)ethyl]ureido}ethoxy)phenyl]-2-ethoxypropionic acid,
3-[4-(2-{3-(2-chlorophenyl)-1-[2-(1,1,2,2,3,3,3-heptafluoropropoxy)ethyl]ureido}ethoxy)phenyl]-2-ethoxypropionic acid,
3-[4-(2-{3-(2-chlorophenyl)-1-[2-(4,4,4-trifluorobutoxy)ethyl]ureido}ethoxy)phenyl]-2-ethoxypropionic acid,
3-[4-(2-{3-(2-chlorophenyl)-1-[2-(3,3-difluorobutoxy)ethyl]ureido}ethoxy)phenyl]-2-ethoxypropionic acid,
3-[4-(2-{3-(2-chlorophenyl)-1-[2-(2,2-difluorobutoxy)ethyl]ureido}ethoxy)phenyl]-2-ethoxypropionic acid, 3-[4-(2-{3-(2-chlorophenyl)-1-[2-(1,1,2,2,3,3,4,4,4-nonafluorobutoxy)ethyl]ureido}ethoxy)phenyl]-2-ethoxypropionic acid,
3-[4-(2-{3-(2-chlorophenyl)-1-[3-(2,2,2-trifluoroethoxy)propyl]ureido}ethoxy)phenyl]-2-ethoxypropionic acid,
3-[4-(2-{3-(2-chlorophenyl)-1-[3-(1,1,2,2,2-pentafluoroethoxy)propyl]ureido}ethoxy)phenyl]-2-ethoxypropionic acid,
3-[4-(2-{3-(2-chlorophenyl)-1-[3-(4-fluorophenoxy)propyl]ureido}ethoxy)phenyl]-2-ethoxypropionic acid,
3-[4-(2-{3-(2-chlorophenyl)-1-[3-(3,5-dichlorophenoxy)propyl]ureido}ethoxy)phenyl]-2-ethoxypropionic acid,
3-[4-(2-{3-(2-chlorophenyl)-1-[4-(4-fluorophenoxy)butyl]ureido}ethoxy)phenyl]-2-ethoxypropionic acid,
3-[4-(2-{3-(2-chlorophenyl)-1-[4-(3,5-dichlorophenoxy)butyl]ureido}ethoxy)phenyl]-2-ethoxypropionic acid,
3-[4-(2-{3-(2-chlorophenyl)-1-[2-(4-fluorobenzyloxy)ethyl]ureido}ethoxy)phenyl]-2-ethoxypropionic acid,
3-[4-(2-{3-(2-chlorophenyl)-1-[2-(3,5-dichlorobenzyloxy)ethyl]ureido}ethoxy)phenyl]-2-ethoxypropionic acid,
3-[4-(2-{3-(2-chlorophenyl)-1-[3-(4-fluorobenzyloxy)propyl]ureido}ethoxy)phenyl]-2-ethoxypropionic acid,
3-[4-(2-{3-(2-chlorophenyl)-1-[3-(3,5-dichlorobenzyloxy)propyl]ureido}ethoxy)phenyl]-2-ethoxypropionic acid,
3-[4-(2-{3-(2-chlorophenyl)-1-[4-(4-fluorobenzyloxy)butyl]ureido}ethoxy)phenyl]-2-ethoxypropionic acid,
3-[4-(2-{3-(2-chlorophenyl)-1-[4-(3,5-dichlorobenzyloxy)butyl]ureido}ethoxy)phenyl]-2-ethoxypropionic acid,
3-[4-(2-{3-(2-chlorophenyl)-1-[3-(4-fluorophenyl)propyl]ureido}ethoxy)phenyl]-2-ethoxypropionic acid,
3-[4-(2-{3-(2-chlorophenyl)-1-[3-(3,5-dichlorophenyl)propyl]ureido}ethoxy)phenyl]-2-ethoxypropionic acid,
3-(4-{2-[3-(4-chlorophenyl)-1-pentylureido]ethoxy}phenyl)-2-ethoxypropionic acid,
3-(4-{2-[3-(4-chlorophenyl)-1-hexylureido]ethoxy}phenyl)-2-ethoxypropionic acid,
3-(4-{2-[3-(4-chlorophenyl)-1-heptylureido]ethoxy}phenyl)-2-ethoxypropionic acid,
3-(4-{2-[3-(4-chlorophenyl)-1-octylureido]ethoxy}phenyl)-2-ethoxypropionic acid,
3-(4-{2-[3-(4-chlorophenyl)-1-isobutylureido]ethoxy}phenyl)-2-ethoxypropionic acid,
3-(4-{2-[3-(4-chlorophenyl)-1-(3-methylbutyl)ureido]ethoxy}phenyl)-2-ethoxypropionic acid,
3-(4-{2-[3-(4-chlorophenyl)-1-(4-methylpentyl)ureido]ethoxy}phenyl)-2-ethoxypropionic acid,
3-(4-{2-[3-(4-chlorophenyl)-1-(2-propylpentyl)ureido]ethoxy}phenyl)-2-ethoxypropionic acid,
3-(4-{2-[3-(4-chlorophenyl)-1-(3,3-dimethylbutyl)ureido]ethoxy}phenyl)-2-ethoxypropionic acid,
3-(4-{2-[3-(4-chlorophenyl)-1-(2-ethylbutyl)ureido]ethoxy}phenyl)-2-ethoxypropionic acid,
3-(4-{2-[3-(4-chlorophenyl)-1-cyclohexylmethylureido]ethoxy}phenyl)-2-ethoxypropionic acid,
3-(4-{2-[3-(4-chlorophenyl)-1-(4-cyclohexylbutyl)ureido]ethoxy}phenyl)-2-ethoxypropionic acid,
3-(4-{2-[3-(4-chlorophenyl)-1-cyclopropylmethylureido]ethoxy}phenyl)-2-ethoxypropionic acid,
3-(4-{2-[3-(4-chlorophenyl)-1-cyclobutylmethylureido]ethoxy}phenyl)-2-ethoxypropionic acid,
3-(4-{2-[3-(4-chlorophenyl)-1-cyclopentylmethylureido]ethoxy}phenyl)-2-ethoxypropionic acid,
3-(4-{2-[3-(4-chlorophenyl)-1-(2-cyclopentylethyl)ureido]ethoxy}phenyl)-2-ethoxypropionic acid,
3-(4-{2-[3-(4-chlorophenyl)-1-(3-cyclohexylpropyl)ureido]ethoxy}phenyl)-2-ethoxypropionic acid,
3-(4-{2-[3-(4-chlorophenyl)-1-(3-phenylpropyl)ureido]ethoxy}phenyl)-2-ethoxypropionic acid,
3-(4-{2-[3-(4-chlorophenyl)-1-(4-phenylbutyl)ureido]ethoxy}phenyl)-2-ethoxypropionic acid,
3-(4-{2-[1-(2-butoxyethyl)-3-(4-chlorophenyl)ureido]ethoxy}phenyl)-2-ethoxypropionic acid,
3-(4-{2-[3-(4-chlorophenyl)-1-(2-pentyloxyethyl)ureido]ethoxy}phenyl)-2-ethoxypropionic acid,
3-(4-{2-[3-(4-chlorophenyl)-(3-propoxypropyl)ureido]ethoxy}phenyl)-2-ethoxypropionic acid,
3-(4-{2-[1-(2-butylthioethyl)-3-(4-chlorophenyl)ureido]ethoxy}phenyl)-2-ethoxypropionic acid,
3-(4-{2-[3-(4-chlorophenyl)-1-(2-pentylthioethyl)ureido]ethoxy}phenyl)-2-ethoxypropionic acid,
3-(4-{2-[3-(4-chlorophenyl)-1-(3-propylthiopropyl)ureido]ethoxy}phenyl)-2-ethoxypropionic acid,
3-4-{2-[3-(4-chlorophenyl)-1-(3-phenoxypropyl)ureido]ethoxy}phenyl)-2-ethoxypropionic acid,
3-(4-{2-[3-(4-chlorophenyl)-1-(4-phenoxybutyl)ureido]ethoxy}phenyl)-2-ethoxypropionic acid,
3-(4-{2-[1-(3-benzyloxypropyl)-3-(4-chlorophenyl)ureido]ethoxy}phenyl)-2-ethoxypropionic acid,
3-(4-{2-[3-(4-chlorophenyl)-1-(3-phenylthiopropyl)ureido]ethoxy}phenyl)-2-ethoxypropionic acid,
3-(4-{2-[3-(4-chlorophenyl)-1-(4-phenylthiobutyl)ureido]ethoxy}phenyl)-2-ethoxypropionic acid,
3-(4-{2-[1-(3-benzylthiopropyl)-3-(4-chlorophenyl)ureido]ethoxy}phenyl)-2-ethoxypropionic acid,
3-(4-{2-[3-(4-chlorophenyl)-1-(7,7,7-trifluoroheptyl)ureido]ethoxy}phenyl)-2-ethoxypropionic acid,
3-(4-{2-[3-(4-chlorophenyl)-1-(6,6-difluoroheptyl)ureido]ethoxy}phenyl)-2 -ethoxypropionic acid,
3-(4-{2-[3-(4-chlorophenyl)-1-(6,6,6-trifluorohexyl)ureido]ethoxy}phenyl)-2-ethoxypropionic acid,
3-(4-{2-[3-(4-chlorophenyl)-1-(5,5-difluorohexyl)ureido]ethoxy}phenyl)-2-ethoxypropionic acid,
3-(4-{2-[3-(4-chlorophenyl)-1-(5,5,6,6,7,7,7-heptafluoroheptyl)ureido]ethoxy}phenyl)-2-ethoxypropionic acid,
3-(4-{2-[3-(4-chlorophenyl)-1-(2,2,3,3,4,4,5,5,6,6,7,7,7-tridecafluoroheptyl)ureido]ethoxy}phenyl)-2-ethoxypropionic acid,
3-(4-{2-[3-(4-chlorophenyl)-1-(5,5,6,6,6-pentafluorohexyl)ureido]ethoxy}phenyl)-2-ethoxypropionic acid,
3-(4-{2-[3-(4-chlorophenyl)-1-(2,2,3,3,4,4,5,5,6,6,6-undecafluorohexyl)ureido]ethoxy}phenyl)-2-ethoxypropionic acid,
3-[4-(2-{3-(4-chlorophenyl)-1-[2-(2,2-difluoropropoxy)ethyl]ureido}ethoxy)phenyl]-2-ethoxypropionic acid,
3-[4-(2-{3-(4-chlorophenyl)-1-[2-(1,1,2,2,3,3,3-heptafluoropropoxy)ethyl]ureido}ethoxy)phenyl]-2-ethoxypropionic acid,
3-[4-(2-{3-(4-chlorophenyl)-1-[2-(4,4,4-trifluorobutoxy)ethyl]ureido}ethoxy)phenyl]-2-ethoxypropionic acid,
3-[4-(2-{3-(4-chlorophenyl)-1-[2-(3,3-difluorobutoxy)ethyl]ureido}ethoxy)phenyl]-2-ethoxypropionic acid,
3-[4-(2-{3-(4-chlorophenyl)-1-[2-(2,2-difluorobutoxy)ethyl]ureido}ethoxy)phenyl]-2-ethoxypropionic acid,
3-[4-(2-{3-(4-chlorophenyl)-1-[2-(1,1,2,2,3,3,4,4,4-nonafluorobutoxy)ethyl]ureido}ethoxy)phenyl]-2-ethoxypropionic acid,
3-[4-(2-{3-(4-chlorophenyl)-1-[3-(2,2,2-trifluoroethoxy)propyl]ureido}ethoxy)phenyl]-2-ethoxypropionic acid,
3-[4-(2-{3-(4-chlorophenyl)-1-[3-(1,1,2,2,2-pentafluoroethoxy)propyl]ureido}ethoxy)phenyl]-2-ethoxypropionic acid,
3-[4-(2-{3-(4-chlorophenyl)-1-[3-(4-fluorophenoxy)propyl]ureido}ethoxy)phenyl]-2-ethoxypropionic acid, 3-[4-(2-{3-(4-chlorophenyl)-1-[3-(3,5-dichlorophenoxy)propyl]ureido}ethoxy)phenyl]-2-ethoxypropionic acid,
3-[4-(2-{3-(4-chlorophenyl)-1-[4-(4-fluorophenoxy)butyl]ureido}ethoxy)phenyl]-2-ethoxypropionic acid,
3-[4-(2-{3-(4-chlorophenyl)-1-[4-(3,5-dichlorophenoxy)butyl]ureido}ethoxy)phenyl]-2-ethoxypropionic acid,
3-[4-(2-{3-(4-chlorophenyl)-1-[2-(4-fluorobenzyloxy)ethyl]ureido}ethoxy)phenyl]-2-ethoxypropionic acid,
3-[4-(2-{3-(4-chlorophenyl)-1-[2-(3,5-dichlorobenzyloxy)ethyl]ureido}ethoxy)phenyl]-2-ethoxypropionic acid,
3-[4-(2-{3-(4-chlorophenyl)-1-[3-(4-fluorobenzyloxy)propyl]ureido}ethoxy)phenyl]-2-ethoxypropionic acid,
3-[4-(2-{3-(4-chlorophenyl)-1-[3-(3,5-dichlorobenzyloxy)propyl]ureido}ethoxy)phenyl]-2-ethoxypropionic acid,
3-[4-(2-{3-(4-chlorophenyl)-1-[4-(4-fluorobenzyloxy)butyl]ureido}ethoxy)phenyl]-2-ethoxypropionic acid,
3-[4-(2-{3-(4-chlorophenyl)-1-[4-(3,5-dichlorobenzyloxy)butyl]ureido}ethoxy)phenyl]-2-ethoxypropionic acid,
3-[4-(2-{3-(4-chlorophenyl)-1-[3-(4-fluorophenyl)propyl]ureido}ethoxy)phenyl]-2-ethoxypropionic acid,
3-[4-(2-{3-(4-chlorophenyl)-1-[3-(3,5-dichlorophenyl)propyl]ureido}ethoxy)phenyl]-2-ethoxypropionic acid,
3-(4-{2-[3-(2,4-dichlorophenyl)-1-pentylureido]ethoxy}phenyl)-2-ethoxypropionic acid,
3-(4-{2-[3-(2,4-dichlorophenyl)-1-hexylureido]ethoxy}phenyl)-2-ethoxypropionic acid,
3-(4-{2-[3-(2,4-dichlorophenyl)-1-heptylureido]ethoxy}phenyl)-2-ethoxypropionic acid,
3-(4-{2-[3-(2,4-dichlorophenyl)-1-octylureido]ethoxy}phenyl)-2-ethoxypropionic acid,
3-(4-{2-[3-(2,4-dichlorophenyl)-1-isobutylureido]ethoxy}phenyl)-2-ethoxypropionic acid,
3-(4-{2-[3-(2,4-dichlorophenyl)-1-(3-methylbutyl)ureido]ethoxy}phenyl)-2-ethoxypropionic acid,
3-(4-{2-[3-(2,4-dichlorophenyl)-1-(4-methylpentyl)ureido]ethoxy}phenyl)-2-ethoxypropionic acid,
3-(4-{2-[3-(2,4-dichlorophenyl)-1-(2-propylpentyl)ureido]ethoxy}phenyl)-2-ethoxypropionic acid,
3-(4-{2-[3-(2,4-dichlorophenyl)-1-(3,3-dimethylbutyl)ureido]ethoxy}phenyl)-2-ethoxypropionic acid,
3-(4-{2-[3-(2,4-dichlorophenyl)-1-(2-ethylbutyl)ureido]ethoxy}phenyl)-2-ethoxypropionic acid,
3-(4-{2-[1-cyclohexylmethyl-3-(2,4-dichlorophenyl)ureido]ethoxy}phenyl)-2-ethoxypropionic acid,
3-(4-{2-[1-(4-cyclohexylbutyl)-3-(2,4-dichlorophenyl)ureido]ethoxy}phenyl)-2-ethoxypropionic acid,
3-(4-{2-[1-cyclopropylmethyl-3-(2,4-dichlorophenyl)ureido]ethoxy}phenyl)-2-ethoxypropionic acid,
3-(4-{2-[1-cyclobutylmethyl-3-(2,4-dichlorophenyl)ureido]ethoxy}phenyl)-2-ethoxypropionic acid,
3-(4-{2-[1-cyclopentylmethyl-3-(2,4-dichlorophenyl)ureido]ethoxy}phenyl)-2-ethoxypropionic acid,
3-(4-{2-[1-(2-cyclopentylethyl)-3-(2,4-dichlorophenyl)ureido]ethoxy}phenyl)-2-ethoxypropionic acid,
3-(4-{2-[1-(3-cyclohexylpropyl)-3-(2,4-dichlorophenyl)ureido]ethoxy}phenyl)-2-ethoxypropionic acid,
3-(4-{2-[3-(2,4-dichlorophenyl)-1-(3-phenylpropyl)ureido]ethoxy}phenyl)-2-ethoxypropionic acid,
3-(4-{2-[3-(2,4-dichlorophenyl)-1-(4-phenylbutyl)ureido]ethoxy}phenyl)-2-ethoxypropionic acid,
3-(4-{2-[1-(2-butoxyethyl)-3-(2,4-dichlorophenyl)ureido]ethoxy}phenyl)-2-ethoxypropionic acid,
3-(4-{2-[3-(2,4-dichlorophenyl)-1-(2-pentyloxyethyl)ureido]ethoxy}phenyl)-2-ethoxypropionic acid,
3-(4-{2-[3-(2,4-dichlorophenyl)-1-(3-propoxypropyl)ureido]ethoxy}phenyl)-2-ethoxypropionic acid,
3-(4-{2-[1-(2-butylthioethyl)-3-(2,4-dichlorophenyl)ureido]ethoxy}phenyl)-2-ethoxypropionic acid,
3-(4-{2-[3-(2,4-dichlorophenyl)-1-(2-pentylthioethyl)ureido]ethoxy}phenyl)-2-ethoxypropionic acid,
3-(4-{2-[3-(2,4-dichlorophenyl)-1-(3-propylthiopropyl)ureido]ethoxy}phenyl)-2-ethoxypropionic acid,
3-(4-{2-[3-(2,4-dichlorophenyl)-1-(3-phenoxypropyl)ureido]ethoxy}phenyl)-2-ethoxypropionic acid,
3-(4-{2-[3-(2,4-dichlorophenyl)-1-(4-phenoxybutyl)ureido]ethoxy}phenyl)-2-ethoxypropionic acid,
3-(4-{2-[1-(3-benzyloxypropyl)-3-(2,4-dichlorophenyl)ureido]ethoxy}phenyl)-2-ethoxypropionic acid,
3-(4-{2-[3-(2,4-dichlorophenyl)-1-(3-phenylthiopropyl)ureido]ethoxy}phenyl)-2-ethoxypropionic acid,
3-(4-{2-[3-(2,4-dichlorophenyl)-1-(4-phenylthiobutyl)ureido]ethoxy}phenyl)-2-ethoxypropionic acid,
3-(4-{2-[1-(3-benzylthiopropyl)-3-(2,4-dichlorophenyl)ureido]ethoxy}phenyl)-2-ethoxypropionic acid,
3-(4-{2-[3-(2,4-dichlorophenyl)-1-(7,7,7-trifluoroheptyl)ureido]ethoxy}phenyl)-2-ethoxypropionic acid,
3-(4-{2-[3-(2,4-dichlorophenyl)-1-(6,6-difluoroheptyl)ureido]ethoxy}phenyl)-2-ethoxypropionic acid,
3-(4-{2-[3-(2,4-dichlorophenyl)-1-(6,6,6-trifluorohexyl)ureido]ethoxy}phenyl)-2-ethoxypropionic acid,
3-(4-{2-[3-(2,4-dichlorophenyl)-1-(5,5-difluorohexyl)ureido]ethoxy}phenyl)-2-ethoxypropionic acid,
3-(4-{2-[3-(2,4-dichlorophenyl)-1-(5,5,6,6,7,7,7-heptafluoroheptyl)ureido]ethoxy}phenyl)-2-ethoxypropionic acid,
3-(4-{2-[3-(2,4-dichlorophenyl)-1-(2,2,3,3,4,4,5,5,6,6,7,7,7-tridecafluoroheptyl)ureido]ethoxy}phenyl)-2-ethoxypropionic acid,
3-(4-{2-[3-(2,4-dichlorophenyl)-1-(5,5,6,6,6-pentafluorohexyl)ureido]ethoxy}phenyl)-2-ethoxypropionic acid,
3-(4-{2-[3-(2,4-dichlorophenyl)-1-(2,2,3,3,4,4,5,5,6,6,6-undecafluorohexyl)ureido]ethoxy}phenyl)-2-ethoxypropionic acid,
3-[4-(2-{3-(2,4-dichlorophenyl)-1-[2-(2,2-difluoropropoxy)ethyl]ureido}ethoxy)phenyl]-2-ethoxypropionic acid,
3-[4-(2-{3-(2,4-dichlorophenyl)-1-[2-(1,1,2,2,3,3,3-heptafluoropropoxy)ethyl]ureido}ethoxy)phenyl]-2-ethoxypropionic acid,
3-[4-(2-{3-(2,4-dichlorophenyl)-1-[2-(4,4,4-trifluorobutoxy)ethyl]ureido}ethoxy)phenyl]-2-ethoxypropionic acid,
3-[4-(2-{3-(2,4-dichlorophenyl)-1-[2-(3,3-difluorobutoxy)ethyl]ureido}ethoxy)phenyl]-2-ethoxypropionic acid,
3-[4-(2-{3-(2,4-dichlorophenyl)-1-[2-(2,2-difluorobutoxy)ethyl]ureido}ethoxy)phenyl]-2-ethoxypropionic acid,
3-[4-(2-{3-(2,4-dichlorophenyl)-1-[2-(1,1,2,2,3,3,4,4,4-nonafluorobutoxy)ethyl]ureido}ethoxy)phenyl]-2-ethoxypropionic acid,
3-[4-(2-{3-(2,4-dichlorophenyl)-1-[3-(2,2,2-trifluoroethoxy)propyl]ureido}ethoxy)phenyl]-2-ethoxypropionic acid,
3-[4-(2-{3-(2,4-dichlorophenyl)-1-[3-(1,1,2,2,2-pentafluoroethoxy)propyl]ureido}ethoxy)phenyl]-2-ethoxypropionic acid,
3-[4-(2-{3-(2,4-dichlorophenyl)-1-[3-(4-fluorophenoxy)propyl]ureido}ethoxy)phenyl]-2-ethoxypropionic acid,
3-[4-(2-{1-[3-(3,5-dichlorophenoxy)propyl]-3-(2,4-dichlorophenyl)ureido}ethoxy)phenyl]-2-ethoxypropionic acid,
3-[4-(2-{3-(2,4-dichlorophenyl)-1-[4-(4-fluorophenoxy)butyl]ureido}ethoxy)phenyl]-2-ethoxypropionic acid,
3-[4-(2-{1-[4-(3,5-dichlorophenoxy)butyl]-3-(2,4-dichlorophenyl)ureido}ethoxy)phenyl]-2-ethoxypropionic acid,
3-[4-(2-{3-(2,4-dichlorophenyl)-1-[2-(4-fluorobenzyloxy)ethyl]ureido}ethoxy)phenyl]-2-ethoxypropionic acid, 3-[4-(2-{1-[2-(3,5-dichlorobenzyloxy)ethyl]-3-(2,4-dichlorophenyl)ureido}ethoxy)phenyl]-2-ethoxypropionic acid,
3-[4-(2-{3-(2,4-dichlorophenyl)-1-[3-(4-fluorobenzyloxy)propyl]ureido}ethoxy)phenyl]-2-ethoxypropionic acid,
3-[4-(2-{1-[3-(3,5-dichlorobenzyloxy)propyl]-3-(2,4-dichlorophenyl)ureido}ethoxy)phenyl]-2-ethoxypropionic acid,
3-[4-(2-{3-(2,4-dichlorophenyl)-1-[4-(4-fluorobenzyloxy)butyl]ureido}ethoxy)phenyl]-2-ethoxypropionic acid,
3-[4-(2-{1-[4-(3,5-dichlorobenzyloxy)butyl]-3-(2,4-dichlorophenyl)ureido}ethoxy)phenyl]-2-ethoxypropionic acid,
3-[4-(2-{3-(2,4-dichlorophenyl)-1-[3-(4-fluorophenyl)propyl]ureido}ethoxy)phenyl]-2-ethoxypropionic acid,
3-[4-(2-{3-(2,4-dichlorophenyl)-1-[3-(3,5-dichlorophenyl)propyl]ureido}ethoxy)phenyl] -2-ethoxypropionic acid,
2-ethoxy-3-(4-{2-[3-(4-nitrophenyl)-1-pentylureido]ethoxy}phenyl)propionic acid,
2-ethoxy-3-(4-{2-[1-hexyl-3-(4-nitrophenyl)ureido]ethoxy}phenyl)propionic acid,
2-ethoxy-3-(4-{2-[1-heptyl-3-(4-nitrophenyl)ureido]ethoxy}phenyl)propionic acid,
2-ethoxy-3-(4-{2-[3-(4-nitrophenyl)-1-octylureido]ethoxy}phenyl)propionic acid,
2-ethoxy-3-(4-{2-[1-isobutyl-3-(4-nitrophenyl)ureido]ethoxy}phenyl)propionic acid,
2-ethoxy-3-(4-{2-[1-(3-methylbutyl)-3-(4-nitrophenyl)ureido]ethoxy}phenyl)propionic acid,
2-ethoxy-3-(4-{2-[1-(4-methylpentyl)-3-(4-nitrophenyl)ureido]ethoxy}phenyl)propionic acid,
2-ethoxy-3-(4-{2-[3-(4-nitrophenyl)-1-(2-propylpentyl)ureido]ethoxy}phenyl)propionic acid,
3-(4-{2-[1-(3,3-dimethylbutyl)-3-(4-nitrophenyl)ureido]ethoxy}phenyl)-2-ethoxypropionic acid,
2-ethoxy-3-(4-{2-[1-(2-ethylbutyl)-3-(4-nitrophenyl)ureido]ethoxy}phenyl)propionic acid,
3-(4-{2-[1-cyclohexylmethyl-3-(4-nitrophenyl)ureido]ethoxy}phenyl)-2-ethoxypropionic acid,
3-(4-{2-[1-(4-cyclohexylbutyl)-3-(4-nitrophenyl)ureido]ethoxy}phenyl)-2-ethoxypropionic acid,
3-(4-{2-[1-cyclopropylmethyl-3-(4-nitrophenyl)ureido]ethoxy}phenyl)-2-ethoxypropionic acid,
3-(4-{2-[1-cyclobutylmethyl-3-(4-nitrophenyl)ureido]ethoxy}phenyl)-2-ethoxypropionic acid,
3-(4-{2-[1-cyclopentylmethyl-3-(4-nitrophenyl)ureido]ethoxy}phenyl)-2-ethoxypropionic acid,
3-(4-{2-[1-(2-cyclopentylethyl)-3-(4-nitrophenyl)ureido]ethoxy}phenyl)-2-ethoxypropionic acid,
3-(4-{2-[1-(3-cyclohexylpropyl)-3-(4-nitrophenyl)ureido]ethoxy}phenyl)-2-ethoxypropionic acid,
2-ethoxy-3-(4-{2-[3-(4-nitrophenyl)-1-(3-phenylpropyl)ureido]ethoxy}phenyl)propionic acid,
2-ethoxy-3-(4-{2-[3-(4-nitrophenyl)-1-(4-phenylbutyl)ureido]ethoxy}phenyl)propionic acid,
3-(4-{2-[1-(2-butoxyethyl)-3-(4-nitrophenyl)ureido]ethoxy}phenyl)-2-ethoxypropionic acid,
2-ethoxy-3-(4-{2-[3-(4-nitrophenyl)-1-(2-pentyloxyethyl)ureido]ethoxy}phenyl)propionic acid,
2-ethoxy-3-(4-{2-[3-(4-nitrophenyl)-1-(3-propoxypropyl)ureido]ethoxy}phenyl)propionic acid,
3-(4-{2-[1-(2-butylthioethyl)-3-(4-nitrophenyl)ureido]ethoxy}phenyl)-2-ethoxypropionic acid,
2-ethoxy-3-(4-{2-[3-(4-nitrophenyl)-1-(2-pentylthioethyl)ureido]ethoxy}phenyl)propionic acid,
2-ethoxy-3-(4-{2-[3-(4-nitrophenyl)-1-(3-propylthiopropyl)ureido]ethoxy}phenyl)propionic acid,
2-ethoxy-3-(4-{2-[3-(4-nitrophenyl)-1-(3-phenoxypropyl)ureido]ethoxy}phenyl)propionic acid,
2-ethoxy-3-(4-{2-[3-(4-nitrophenyl)-1-(4-phenoxybutyl)ureido]ethoxy}phenyl)propionic acid,
3-(4-{2-[1-(3-benzyloxypropyl)-3-(4-nitrophenyl)ureido]ethoxy}phenyl)-2-ethoxypropionic acid,
2-ethoxy-3-(4-{2-[3-(4-nitrophenyl)-1-(3-phenylthiopropyl)ureido]ethoxy}phenyl)propionic acid,
2-ethoxy-3-(4-{2-[3-(4-nitrophenyl)-1-(4-phenylthiobutyl)ureido]ethoxy}phenyl)propionic acid,
3-(4-{2-[1-(3-benzylthiopropyl)-3-(4-nitrophenyl)ureido]ethoxy}phenyl)-2-ethoxypropionic acid,
2-ethoxy-3-(4-{2-[3-(4-nitrophenyl)-1-(7,7,7-trifluoroheptyl)ureido]ethoxy}phenyl)propionic acid,
3-(4-{2-[1-(6,6-difluoroheptyl)-3-(4-nitrophenyl)ureido]ethoxy}phenyl)-2-ethoxypropionic acid,
2-ethoxy-3-(4-{2-[3-(4-nitrophenyl)-1-(6,6,6-trifluorohexyl)ureido]ethoxy}phenyl)propionic acid,
3-(4-{2-[1-(5,5-difluorohexyl)-3-(4-nitrophenyl)ureido]ethoxy}phenyl)-2-ethoxypropionic acid,
2-ethoxy-3-(4-{2-[1-(5,5,6,6,7,7,7-heptafluoroheptyl)-3-(4-nitrophenyl)ureido]ethoxy}phenyl)propionic acid,
2-ethoxy-3-(4-{2-[3-(4-nitrophenyl)-1-(2,2,3,3,4,4,5,5,6,6,7,7,7-tridecafluoroheptyl)ureido]ethoxy}phenyl)propionic acid,
2-ethoxy-3-(4-{2-[3-(4-nitrophenyl)-1-(5,5,6,6,6-pentafluorohexyl)ureido]ethoxy}phenyl)propionic acid,
2-ethoxy-3-(4-{2-[3-(4-nitrophenyl)-1-(2,2,3,3,4,4,5,5,6,6,6-undecafluorohexyl)ureido]ethoxy}phenyl)propionic acid,
3-[4-(2-{1-[2-(2,2-difluoropropoxy)ethyl]-3-(4-nitrophenyl)ureido}ethoxy)phenyl]-2-ethoxypropionic acid,
2-ethoxy-3-[4-(2-{1-[2-(1,1,2,2,3,3,3-heptafluoropropoxy)ethyl]-3-(4-nitrophenyl)ureido}ethoxy)phenyl]propionic acid,
2-ethoxy-3-[4-(2-{3-(4-nitrophenyl)-1-[2-(4,4,4-trifluorobutoxy)ethyl]ureido}ethoxy)phenyl]propionic acid,
3-[4-(2-{1-[2-(3,3-difluorobutoxy)ethyl]-3-(4-nitrophenyl)ureido}ethoxy)phenyl]-2-ethoxypropionic acid,
3-[4-(2-{1-[2-(2,2-difluorobutoxy)ethyl]-3-(4-nitrophenyl)ureido}ethoxy)phenyl]-2-ethoxypropionic acid,
2-ethoxy-3-[4-(2-{3-(4-nitrophenyl)-1-[2-(1,1,2,2,3,3,4,4,4-nonafluorobutoxy)ethyl]ureido}ethoxy)phenyl]propionic acid,
2-ethoxy-3-[4-(2-{3-(4-nitrophenyl)-1-[3-(2,2,2-trifluoroethoxy)propyl]ureido}ethoxy)phenyl]propionic acid,
2-ethoxy-3-[4-(2-{3-(4-nitrophenyl)-1-[3-(1,1,2,2,2-pentafluoroethoxy)propyl]ureido}ethoxy)phenyl]propionic acid,
2-ethoxy-3-[4-(2-{1-[3-(4-fluorophenoxy)propyl]-3-(4-nitrophenyl)ureido}ethoxy)phenyl]propionic acid,
3-[4-(2-{1-[3-(3,5-dichlorophenoxy)propyl]-3-(4-nitrophenyl)ureido}ethoxy)phenyl]-2-ethoxypropionic acid,
2-ethoxy-3-[4-(2-{1-[4-(4-fluorophenoxy)butyl]-3-(4-nitrophenyl)ureido}ethoxy)phenyl]propionic acid,
3-[4-{1-(2-[4-(3,5-dichlorophenoxy)butyl]-3-(4-nitrophenyl)ureido}ethoxy)phenyl]-2-ethoxypropionic acid,
2-ethoxy-3-[4-(2-{1-[2-(4-fluorobenzyloxy)ethyl]-3-(4 -nitrophenyl)ureido}ethoxy)phenyl]propionic acid,
3-[4-(2-{1-[2-(3,5-dichlorobenzyloxy)ethyl]-3-(4-nitrophenyl)ureido}ethoxy)phenyl]-2-ethoxypropionic acid,
2-ethoxy-3-[4-(2-{1-[3-(4-fluorobenzyloxy)propyl]-3-(4-nitrophenyl)ureido}ethoxy)phenyl]propionic acid,
3-[4-(2-{1-[3-(3,5-dichlorobenzyloxy)propyl]-3-(4-nitrophenyl)ureido}ethoxy)phenyl]-2-ethoxypropionic acid,
2-ethoxy-3-[4-(2-{1-[4-(4-fluorobenzyloxy)butyl]-3-(4-nitrophenyl)ureido}ethoxy)phenyl]propionic acid,
3-[4-(2-{1-[4-(3,5-dichlorobenzyloxy)butyl]-3-(4-nitrophenyl)ureido}ethoxy)phenyl]-2-ethoxypropionic acid, 2-ethoxy-3-[4-(2-{1-[3-(4-fluorophenyl)propyl]-3-(4-nitrophenyl)ureido}ethoxy)phenyl]propionic acid,
3-[4-(2-{1-[3-(3,5-dichlorophenyl)propyl]-3-(4-nitrophenyl)ureido}ethoxy)phenyl]-2-ethoxypropionic acid,
2-ethoxy-3-(4-{2-[3-(4-isopropylphenyl)-1-pentylureido]ethoxy}phenyl)propionic acid,
2-ethoxy-3-(4-{2-[1-hexyl-3-(4-isopropylphenyl)ureido]ethoxy}phenyl)propionic acid,
2-ethoxy-3-(4-{2-[1-heptyl-3-(4-isopropylphenyl)ureido]ethoxy}phenyl)propionic acid,
2-ethoxy-3-(4-{2-[3-(4-isopropylphenyl)-1-octylureido]ethoxy}phenyl)propionic acid,
2-ethoxy-3-(4-{2-[1-isobutyl-3-(4-isopropylphenyl)ureido]ethoxy}phenyl)propionic acid,
2-ethoxy-3-(4-{2-[3-(4-isopropylphenyl)-1-(3-methylbutyl)ureido]ethoxy}phenyl)propionic acid,
2-ethoxy-3-(4-{2-[3-(4-isopropylphenyl)-1-(4-methylpentyl)ureido]ethoxy}phenyl)propionic acid,
2-ethoxy-3-(4-{2-[3-(4-isopropylphenyl)-1-(2-propylpentyl)ureido]ethoxy}phenyl)propionic acid,
3-(4-{2-[1-(3,3-dimethylbutyl)-3-(4-isopropylphenyl)ureido]ethoxy}phenyl)-2-ethoxypropionic acid,
2-ethoxy-3-(4-{2-[1-(2-ethylbutyl)-3-(4-isopropylphenyl)ureido]ethoxy}phenyl)propionic acid,
3-(4-{2-[1-cyclohexylmethyl-3-(4-isopropylphenyl)ureido]ethoxy}phenyl)-2-ethoxypropionic acid,
3-(4-{2-[1-(4-cyclohexylbutyl)-3-(4-isopropylphenyl)ureido]ethoxy}phenyl)-2 -ethoxypropionic acid,
3-(4-{2-[1-cyclopropylmethyl-3-(4-isopropylphenyl)ureido]ethoxy}phenyl)-2-ethoxypropionic acid,
3-(4-{2-[1-cyclobutylmethyl-3-(4-isopropylphenyl)ureido]ethoxy}phenyl)-2-ethoxypropionic acid,
3-(4-{2-[1-cyclopentylmethyl-3-(4-isopropylphenyl)ureido]ethoxy}phenyl)-2-ethoxypropionic acid,
3-(4-{2-[1-(2-cyclopentylethyl)-3-(4-isopropylphenyl)ureido]ethoxy}phenyl)-2-ethoxypropionic acid,
3-(4-{2-[1-(3-cyclohexylpropyl)-3-(4-isopropylphenyl)ureido]ethoxy}phenyl)-2-ethoxypropionic acid,
2-ethoxy-3-(4-{2-[3-(4-isopropylphenyl)-1-(3-phenylpropyl)ureido]ethoxy}phenyl)propionic acid,
2-ethoxy-3-(4-{2-[3-(4-isopropylphenyl)-1-(4-phenylbutyl)ureido]ethoxy}phenyl)propionic acid,
3-(4-{2-[1-(2-butoxyethyl)-3-(4-isopropylphenyl)ureido]ethoxy}phenyl)-2-ethoxypropionic acid,
2-ethoxy-3-(4-{2-[3-(4-isopropylphenyl)-1-(2-pentyloxyethyl)ureido]ethoxy}phenyl)propionic acid,
2-ethoxy-3-(4-{2-[3-(4-isopropylphenyl)-1-(3-propoxypropyl)ureido]ethoxy}phenyl)propionic acid,
3-(4-{2-[1-(2-butylthioethyl)-3-(4-isopropylphenyl)ureido]ethoxy}phenyl)-2-ethoxypropionic acid,
2-ethoxy-3-(4-{2-[3-(4-isopropylphenyl)-1-(2-pentylthioethyl)ureido]ethoxy}phenyl)propionic acid,
2-ethoxy-3-(4-{2-[3-(4-isopropylphenyl)-1-(3-propylthiopropyl)ureido]ethoxy}phenyl)propionic acid,
2-ethoxy-3-(4-{2-[3-(4-isopropylphenyl)-1-(3-phenoxypropyl)ureido]ethoxy}phenyl)propionic acid,
2-ethoxy-3-(4-{2-[3-(4-isopropylphenyl)-1-(4-phenoxybutyl)ureido]ethoxy}phenyl)propionic acid,
3-(4-{2-[1-(3-benzyloxypropyl)-3-(4-isopropylphenyl)ureido]ethoxy}phenyl)-2-ethoxypropionic acid,
2-ethoxy-3-(4-{2-[3-(4-isopropylphenyl)-1-(3-phenylthiopropyl)ureido]ethoxy}phenyl)propionic acid,
2-ethoxy-3-(4-{2-[3-(4-isopropylphenyl)-1-(4-phenylthiobutyl)ureido]ethoxy}phenyl)propionic acid,
3-(4-{2-[1-(3-benzylthiopropyl)-3-(4-isopropylphenyl)ureido]ethoxy}phenyl)-2-ethoxypropionic acid,
2-ethoxy-3-(4-{2-[3-(4-isopropylphenyl)-1-(7,7,7-trifluoroheptyl)ureido]ethoxy}phenyl)propionic acid,
3-(4-{2-[1-(6,6-difluoroheptyl)-3-(4-isopropylphenyl)ureido]ethoxy}phenyl)-2-ethoxypropionic acid,
2-ethoxy-3-(4-{2-[3-(4-isopropylphenyl)-1-(6,6,6-trifluorohexyl)ureido]ethoxy}phenyl)propionic acid,
3-(4-{2-[1-(5,5-difluorohexyl)-3-(4-isopropylphenyl)ureido]ethoxy}phenyl)-2-ethoxypropionic acid,
2-ethoxy-3-(4-{2-[1-(5,5,6,6,7,7,7-heptafluoroheptyl)-3-(4-isopropylphenyl)ureido]ethoxy}phenyl)propionic acid,
2-ethoxy-3-(4-{2-[3-(4-isopropylphenyl)-1-(2,2,3,3,4,4,5,5,6,6,7,7,7-tridecafluoroheptyl)ureido]ethoxy}phenyl)propionic acid,
2-ethoxy-3-(4-{2-[3-(4-isopropylphenyl)-1-(5,5,6,6,6-pentafluorohexyl)ureido]ethoxy}phenyl)propionic acid,
2-ethoxy-3-(4-{2-[3-(4-isopropylphenyl)-1-(2,2,3,3,4,4,5,5,6,6,6-undecafluorohexyl)ureido]ethoxy}phenyl)propionic acid,
3-[4-(2-{1-[2-(2,2-difluoropropoxy)ethyl]-3-(4-isopropylphenyl)ureido}ethoxy)phenyl]-2-ethoxypropionic acid,
2-ethoxy-3-[4-(2-{1-[2-(1,1,2,2,3,3,3-heptafluoropropoxy)ethyl]-3-(4-isopropylphenyl)ureido}ethoxy)phenyl]propionic acid,
2-ethoxy-3-[4-(2-{3-(4-isopropylphenyl)-1-[2-(4,4,4-trifluorobutoxy)ethyl]ureido}ethoxy)phenyl]propionic acid,
3-[4-(2-{1-[2-(3,3-difluorobutoxy)ethyl]-3-(4-isopropylphenyl)ureido}ethoxy)phenyl]-2-ethoxypropionic acid,
3-[4-(2-{1-[2-(2,2-difluorobutoxy)ethyl]-3-(4-isopropylphenyl)ureido}ethoxy)phenyl]-2-ethoxypropionic acid,
2-ethoxy-3-[4-(2-{3-(4-isopropylphenyl)-1-[2-(1,1,2,2,3,3,4,4,4 -nonafluorobutoxy)ethyl]ureido}ethoxy)phenyl]propionic acid,
2-ethoxy-3-[4-(2-{3-(4-isopropylphenyl)-1-[3-(2,2,2-trifluoroethoxy)propyl]ureido}ethoxy)phenyl]propionic acid,
2-ethoxy-3-[4-(2-{3-(4-isopropylphenyl)-1-[3-(1,1,2,2,2-pentafluoroethoxy)propyl]ureido}ethoxy)phenyl]propionic acid,
2-ethoxy-3-[4-(2-{1-[3-(4-fluorophenoxy)propyl]-3-(4-isopropylphenyl)ureido}ethoxy)phenyl]propionic acid,
3-[4-(2-{1-[3-(3,5-dichlorophenoxy)propyl]-3-(4-isopropylphenyl)ureido}ethoxy)phenyl]-2-ethoxypropionic acid,
2-ethoxy-3-[4-(2-{1-[4-(4-fluorophenoxy)butyl]-3-(4-isopropylphenyl)ureido}ethoxy)phenyl]propionic acid,
3-[4-(2-{1-[4-(3,5-dichlorophenoxy)butyl]-3-(4-isopropylphenyl)ureido}ethoxy)phenyl]-2-ethoxypropionic acid,
2-ethoxy-3-[4-(2-{1-[2-(4-fluorobenzyloxy)ethyl]-3-(4-isopropylphenyl)ureido}ethoxy)phenyl]propionic acid,
3-[4-(2-{1-[2-(3,5-dichlorobenzyloxy)ethyl]-3-(4-isopropylphenyl)ureido}ethoxy)phenyl]-2-ethoxypropionic acid,
2-ethoxy-3-[4-(2-{1-[3-(4-fluorobenzyloxy)propyl]-3-(4-isopropylphenyl)ureido}ethoxy)phenyl]propionic acid,
3-[4-(2-{1-[3-(3,5-dichlorobenzyloxy)propyl]-3-(4-isopropylphenyl)ureido}ethoxy)phenyl]-2-ethoxypropionic acid,
2-ethoxy-3-[4-(2-{1-[4-(4-fluorobenzyloxy)butyl]-3-(4-isopropylphenyl)ureido}ethoxy)phenyl]propionic acid,
3-[4-(2-{1-[4-(3,5-dichlorobenzyloxy)butyl]-3-(4-isopropylphenyl)ureido}ethoxy)phenyl]-2-ethoxypropionic acid,
2-ethoxy-3-[4-(2-{1-[3-(4-fluorophenyl)propyl]-3-(4-isopropylphenyl)ureido}ethoxy)phenyl]propionic acid,
3-[4-(2-{1-[3-(3,5-dichlorophenyl)propyl]-3-(4-isopropylphenyl)ureido}ethoxy)phenyl]-2-ethoxypropionic acid,
2-ethoxy-3-(4-{2-[1-pentyl-3-(4-phenoxyphenyl)ureido]ethoxy}phenyl)propionic acid,
2-ethoxy-3-(4-{2-[1-hexyl-3-(4-phenoxyphenyl)ureido]ethoxy}phenyl)propionic acid, 2-ethoxy-3-(4-{2-[1-heptyl-3-(4-phenoxyphenyl)ureido]ethoxy}phenyl)propionic acid,
2-ethoxy-3-(4-{2-[1-octyl-3-(4-phenoxyphenyl)ureido]ethoxy}phenyl)propionic acid,
2-ethoxy-3-(4-{2-[1-isobutyl-3-(4-phenoxyphenyl)ureido]ethoxy}phenyl)propionic acid,
2-ethoxy-3-(4-{2-[1-(3-methylbutyl)-3-(4-phenoxyphenyl)ureido]ethoxy}phenyl)propionic acid,
2-ethoxy-3-(4-{2-[1-(4-methylpentyl)-3-(4-phenoxyphenyl)ureido]ethoxy}phenyl)propionic acid,
2-ethoxy-3-(4-{2-[3-(4-phenoxyphenyl)-1-(2-propylpentyl)ureido]ethoxy}phenyl)propionic acid,
3-(4-{2-[1-(3,3-dimethylbutyl)-3-(4-phenoxyphenyl)ureido]ethoxy}phenyl)-2-ethoxypropionic acid,
2-ethoxy-3-(4-{2-[1-(2-ethylbutyl)-3-(4-phenoxyphenyl)ureido]ethoxy}phenyl)propionic acid,
3-(4-{2-[1-cyclohexylmethyl-3-(4-phenoxyphenyl)ureido]ethoxy}phenyl)-2-ethoxypropionic acid,
3-(4-{2-[1-(4-cyclohexylbutyl)-3-(4-phenoxyphenyl)ureido]ethoxy}phenyl)-2-ethoxypropionic acid,
3-(4-{2-[1-cyclopropylmethyl-3-(4-phenoxyphenyl)ureido]ethoxy}phenyl)-2-ethoxypropionic acid,
3-(4-{2-[1-cyclobutylmethyl-3-(4-phenoxyphenyl)ureido]ethoxy}phenyl)-2-ethoxypropionic acid,
3-(4-{2-[1-cyclopentylmethyl-3-(4-phenoxyphenyl)ureido]ethoxy}phenyl)-2-ethoxypropionic acid,
3-(4-{2-[1-(2-cyclopentylethyl)-3-(4-phenoxyphenyl)ureido]ethoxy}phenyl)-2-ethoxypropionic acid,
3-(4-{2-[1-(3-cyclohexylpropyl)-3-(4-phenoxyphenyl)ureido]ethoxy}phenyl)-2-ethoxypropionic acid,
2-ethoxy-3-(4-{2-[3-(4-phenoxyphenyl)-1-(3-phenylpropyl)ureido]ethoxy}phenyl)propionic acid,
2-ethoxy-3-(4-{2-[3-(4-phenoxyphenyl)-1-(4-phenylbutyl)ureido]ethoxy}phenyl)propionic acid,
3-(4-{2-[1-(2-butoxyethyl)-3-(4-phenoxyphenyl)ureido]ethoxy}phenyl)-2-ethoxypropionic acid,
2-ethoxy-3-(4-{2-[1-(2-pentyloxyethyl)-3-(4-phenoxyphenyl)ureido]ethoxy}phenyl)propionic acid,
2-ethoxy-3-(4-{2-[3-(4-phenoxyphenyl)-1-(3-propoxypropyl)ureido]ethoxy}phenyl)propionic acid,
3-(4-{2-[1-(2-butylthioethyl)-3-(4-phenoxyphenyl)ureido]ethoxy}phenyl)-2-ethoxypropionic acid,
2-ethoxy-3-(4-{2-[1-(2-pentylthioethyl)-3-(4-phenoxyphenyl)ureido]ethoxy}phenyl)propionic acid,
2-ethoxy-3-(4-{2-[3-(4-phenoxyphenyl)-1-(3-propylthiopropyl)ureido]ethoxy}phenyl)propionic acid,
2-ethoxy-3-(4-{2-[3-(4-phenoxyphenyl)-1-(3-phenoxypropyl)ureido]ethoxy}phenyl)propionic acid,
2-ethoxy-3-(4-{2-[1-(4-phenoxybutyl)-3-(4-phenoxyphenyl)ureido]ethoxy}phenyl)propionic acid,
3-(4-{2-[1-(3-benzyloxypropyl)-3-(4-phenoxyphenyl)ureido]ethoxy}phenyl)-2-ethoxypropionic acid,
2-ethoxy-3-(4-{1-[3-(4-phenoxyphenyl)-1-(3-phenylthiopropyl)ureido]ethoxy}phenyl)propionic acid,
2-ethoxy-3-(4-{2-[3-(4-phenoxyphenyl)-1-(4-phenylthiobutyl)ureido]ethoxy}phenyl)propionic acid,
3-(4-{2-[1-(3-benzylthiopropyl)-3-(4-phenoxyphenyl)ureido]ethoxy}phenyl)-2-ethoxypropionic acid,
2-ethoxy-3-(4-{2-[3-(4-phenoxyphenyl)-1-(7,7,7-trifluoroheptyl)ureido]ethoxy}phenyl)propionic acid,
3-(4-{2-[1-(6,6-difluoroheptyl)-3-(4-phenoxyphenyl)ureido]ethoxy}phenyl)-2-ethoxypropionic acid,
2-ethoxy-3-(4-{2-[3-(4-phenoxyphenyl)-1-(6,6,6-trifluorohexyl)ureido]ethoxy}phenyl)propionic acid,
3-(4-{2-[1-(5,5-difluorohexyl)-3-(4-phenoxyphenyl)ureido]ethoxy}phenyl)-2-ethoxypropionic acid,
2-ethoxy-3-(4-{2-[1-(5,5,6,6,7,7,7-heptafluoroheptyl)-3-(4-phenoxyphenyl)ureido]ethoxy}phenyl)propionic acid,
2-ethoxy-3-(4-{2-[3-(4-phenoxyphenyl)-1-(2,2,3,3,4,4,5,5,6,6,7,7,7-tridecafluoroheptyl)ureido]ethoxy}phenyl)propionic acid,
2-ethoxy-3-(4-{2-[1-(5,5,6,6,6-pentafluorohexyl)-3-(4-phenoxyphenyl)ureido]ethoxy}phenyl)propionic acid,
2-ethoxy-3-(4-{2-[3-(4-phenoxyphenyl)-1-(2,2,3,3,4,4,5,5,6,6,6-undecafluorohexyl)ureido]ethoxy}phenyl)propionic acid,
3-[4-(2-{1-[2-(2,2-difluoropropoxy)ethyl]-3-(4-phenoxyphenyl)ureido}ethoxy)phenyl]-2-ethoxypropionic acid,
2-ethoxy-3-[4-(2-{1-[2-(1,1,2,2,3,3,3-heptafluoropropoxy)ethyl]-3-(4-phenoxyphenyl)ureido}ethoxy)phenyl]propionic acid,
2-ethoxy-3-[4-(2-{3-(4-phenoxyphenyl)-1-[2-(4,4,4-trifluorobutoxy)ethyl]ureido}ethoxy)phenyl]propionic acid,
3-[4-(2-{1-[2-(3,3-difluorobutoxy)ethyl]-3-(4-phenoxyphenyl)ureido}ethoxy)phenyl]-2-ethoxypropionic acid,
3-[4-(2-{1-[2-(2,2-difluorobutoxy)ethyl]-3-(4-phenoxyphenyl)ureido}ethoxy)phenyl]-2-ethoxypropionic acid,
2-ethoxy-3-[4-(2-{1-[2-(1,1,2,2,3,3,4,4,4-nonafluorobutoxy)ethyl]-3-(4-phenoxyphenyl)ureido}ethoxy)phenyl]propionic acid,
2-ethoxy-3-[4-(2-{3-(4-phenoxyphenyl)-1-[3-(2,2,2-trifluoroethoxy)propyl]ureido}ethoxy)phenyl]propionic acid,
2-ethoxy-3-[4-(2-{1-[3-(1,1,2,2,2-pentafluoroethoxy)propyl]-3-(4-phenoxyphenyl)ureido}ethoxy)phenyl]propionic acid,
2-ethoxy-3-[4-(2-{1-[3-(4-fluorophenoxy)propyl]-3-(4-phenoxyphenyl)ureido}ethoxy)phenyl]propionic acid,
3-[4-(2-{1-[3-(3,5-dichlorophenoxy)propyl]-3-(4-phenoxyphenyl)ureido}ethoxy)phenyl]-2-ethoxypropionic acid,
2-ethoxy-3-[4-(2-{1-[4-(4-fluorophenoxy)butyl]-3-(4-phenoxyphenyl)ureido}ethoxy)phenyl]propionic acid,
3-[4-(2-{1-[4-(3,5-dichlorophenoxy)butyl]-3-(4-phenoxyphenyl)ureido}ethoxy)phenyl]-2-ethoxypropionic acid,
2-ethoxy-3-[4-(2-{1-[2-(4-fluorobenzyloxy)ethyl]-3-(4-phenoxyphenyl)ureido}ethoxy)phenyl]propionic acid,
3-[4-(2-{1-[2-(3,5-dichlorobenzyloxy)ethyl]-3-(4-phenoxyphenyl)ureido}ethoxy)phenyl]-2-ethoxypropionic acid,
2-ethoxy-3-[4-(2-{1-[3-(4-fluorobenzyloxy)propyl]-3-(4-phenoxyphenyl)ureido}ethoxy)phenyl]propionic acid,
3-[4-(2-{1-[3-(3,5-dichlorobenzyloxy)propyl]-3-(4-phenoxyphenyl)ureido}ethoxy)phenyl]-2-ethoxypropionic acid,
2-ethoxy-3-[4-(2-{1-[4-(4-fluorobenzyloxy)butyl]-3-(4-phenoxyphenyl)ureido}ethoxy)phenyl]propionic acid,
3-[4-(2-{1-[4-(3,5-dichlorobenzyloxy)butyl]-3-(4-phenoxyphenyl)ureido}ethoxy)phenyl]-2-ethoxypropionic acid,
2-ethoxy-3-[4-(2-{1-[3-(4-fluorophenyl)propyl]-3-(4-phenoxyphenyl)ureido}ethoxy)phenyl]propionic acid,
3-[4-(2-{1-[3-(3,5-dichlorophenyl)propyl]-3-(4-phenoxyphenyl)ureido}ethoxy)phenyl]-2-ethoxypropionic acid,
2-ethoxy-3-(4-{2-[3-(2-methylphenyl)-1-pentylureido]ethoxy}phenyl)propionic acid,
2-ethoxy-3-(4-{2-[1-hexyl-3-(2-methylphenyl)ureido]ethoxy}phenyl)propionic acid,
2-ethoxy-3-(4-{2-[1-heptyl-3-(2-methylphenyl)ureido]ethoxy}phenyl)propionic acid,
2-ethoxy-3-(4-{2-[3-(2-methylphenyl)-1-octylureido]ethoxy}phenyl)propionic acid,
2-ethoxy-3-(4-{2-[1-isobutyl-3-(2-methylphenyl)ureido]ethoxy}phenyl)propionic acid,
2-ethoxy-3-(4-{2-[1-(3-methylbutyl)-3-(2-methylphenyl)ureido]ethoxy}phenyl)propionic acid,
2-ethoxy-3-(4-{2-[1-(4-methylpentyl)-3-(2-methylphenyl)ureido]ethoxy}phenyl)propionic acid, 2-ethoxy-3-(4-{2-[3-(2-methylphenyl)-1-(2-propylpentyl) ureido]ethoxy}phenyl)propionic acid,
3-(4-{2-[1-(3,3-dimethylbutyl)-3-(2-methylphenyl)ureido] ethoxy}phenyl)-2-ethoxypropionic acid,
2-ethoxy-3-(4-{2-[1-(2-ethylbutyl)-3-(2-methylphenyl)ureido]ethoxy}phenyl)propionic acid,
3-(4-{2-[1-cyclohexylmethyl-3-(2-methylphenyl)ureido] ethoxy}phenyl)-2-ethoxypropionic acid,
3-(4-{2-[1-(4-cyclohexylbutyl)-3-(2-methylphenyl)ureido] ethoxy}phenyl)-2-ethoxypropionic acid,
3-(4-{2-[1-cyclopropylmethyl-3-(2-methylphenyl)ureido] ethoxy}phenyl)-2-ethoxypropionic acid,
3-(4-{2-[1-cyclobutylmethyl-3-(2-methylphenyl)ureido] ethoxy}phenyl)-2-ethoxypropionic acid,
3-(4-{2-[1-cyclopentylmethyl-3-(2-methylphenyl)ureido] ethoxy}phenyl)-2-ethoxypropionic acid,
3-(4-{2-[1-(2-cyclopentylethyl)-3-(2-methylphenyl)ureido] ethoxy}phenyl)-2-ethoxypropionic acid,
3-(4-{2-[1-(3-cyclohexylpropyl)-3-(2-methylphenyl)ureido]ethoxy}phenyl)-2-ethoxypropionic acid,
2-ethoxy-3-(4-{2-[3-(2-methylphenyl)-1-(3-phenylpropyl) ureido]ethoxy}phenyl)propionic acid,
2-ethoxy-3-(4-{2-[3-(2-methylphenyl)-1-(4-phenylbutyl) ureido]ethoxy}phenyl)propionic acid,
3-(4-{2-[1-(2-butoxyethyl)-3-(2-methylphenyl)ureido] ethoxy}phenyl)-2-ethoxypropionic acid,
2-ethoxy-3-(4-{2-[3-(2-methylphenyl)-1-(2-pentyloxyethyl)ureido]ethoxy}phenyl)propionic acid,
2-ethoxy-3-(4-{2-[3-(2-methylphenyl)-1-(3-propoxypropyl) ureido]ethoxy}phenyl)propionic acid,
3-(4-{2-[1-(2-butylthioethyl)-3-(2-methylphenyl)ureido] ethoxy}phenyl)-2-ethoxypropionic acid,
2-ethoxy-3-(4-{2-[3-(2-methylphenyl)-1-(2-pentylthioethyl)ureido]ethoxy}phenyl)propionic acid,
2-ethoxy-3-(4-{2-[3-(2-methylphenyl)-1-(3-propylthiopropyl)ureido]ethoxy}phenyl)propionic acid,
2-ethoxy-3-(4-{2-[3-(2-methylphenyl)-1-(3-phenoxypropyl)ureido]ethoxy}phenyl)propionic acid,
2-ethoxy-3-(4-{2-[3-(2-methylphenyl)-1-(4-phenoxybutyl) ureido]ethoxy}phenyl)propionic acid,
3-(4-{2-[1-(3-benzyloxypropyl)-3-(2-methylphenyl)ureido] ethoxy}phenyl)-2-ethoxypropionic acid,
2-ethoxy-3-(4-{2-[3-(2-methylphenyl)-1-(3-phenylthiopropyl)ureido]ethoxy}phenyl)propionic acid,
2-ethoxy-3-(4-{2-[3-(2-methylphenyl)-1-(4-phenylthiobutyl)ureido]ethoxy}phenyl)propionic acid,
3-(4-{2-[1-(3-benzylthiopropyl)-3-2-methylphenyl)ureido] ethoxy}phenyl)-2 -ethoxypropionic acid,
2-ethoxy-3-(4-{2-[3-(2-methylphenyl)-1-(7,7,7-trifluoroheptyl)ureido]ethoxy}phenyl)propionic acid,
3-(4-{2-[1-(6,6-difluoroheptyl)-3-(2-methylphenyl)ureido] ethoxy}phenyl)-2-ethoxypropionic acid,
2-ethoxy-3-(4-{2-[3-(2-methylphenyl)-1-(6,6,6-trifluorohexyl)ureido]ethoxy}phenyl)propionic acid,
3-(4-{2-[1-(5,5-difluorohexyl)-3-(2-methylphenyl)ureido] ethoxy}phenyl)-2-ethoxypropionic acid,
2-ethoxy-3-(4-{2-[1-(5,5,6,6,7,7,7-heptafluoroheptyl)-3-(2-methylphenyl)ureido]ethoxy}phenyl)propionic acid,
2-ethoxy-3-(4-{2-[3-(2-methylphenyl)-1-(2,2,3,3,4,4,5,5,6,6,7,7,7-tridecafluoroheptyl)ureido]ethoxy}phenyl)propionic acid,
2-ethoxy-3-(4-{2-[3-(2-methylphenyl)-1-(5,5,6,6,6-pentafluorohexyl)ureido]ethoxy}phenyl)propionic acid,
2-ethoxy-3-(4-{2-[3-(2-methylphenyl)-1-(2,2,3,3,4,4,5,5,6,6-undecafluorohexyl)ureido]ethoxy}phenyl)propionic acid,
3-[4-(2-{1-[2-(2,2-difluoropropoxy)ethyl]-3-(2-methylphenyl)ureido}ethoxy)phenyl]-2-ethoxypropionic acid,
2-ethoxy-3-[4-(2-{1-[2-(1,1,2,2,3,3,3-heptafluoropropoxy)ethyl]-3-(2-methylphenyl)ureido}ethoxy)phenyl]propionic acid,
2-ethoxy-3-[4-(2-{3-(2-methylphenyl)-1-[2-(4,4,4-trifluorobutoxy)ethyl]ureido}ethoxy)phenyl]propionic acid,
3-[4-(2-{1-[2-(3,3-difluorobutoxy)ethyl]-3-(2-methylphenyl)ureido}ethoxy)phenyl]-2-ethoxypropionic acid,
3-[4-(2-{1-[2-(2,2-difluorobutoxy)ethyl]-3-(2-methylphenyl)ureido}ethoxy)phenyl]-2-ethoxypropionic acid,
2-ethoxy-3-[4-(2-{3-(2-methylphenyl)-1-[2-(1,1,2,2,3,3,4,4,4-nonafluorobutoxy)ethyl]ureido}ethoxy)phenyl]propionic acid,
2-ethoxy-3-[4-(2-{3-(2-methylphenyl)-1-[3-(2,2,2-trifluoroethoxy)propyl]ureido}ethoxy)phenyl]propionic acid,
2-ethoxy-3-[4-(2-{3-(2-methylphenyl)-1-[3-(1,1,2,2,2-pentafluoroethoxy)propyl]ureido}ethoxy)phenyl]propionic acid,
2-ethoxy-3-[4-(2-{1-[3-(4-fluorophenoxy)propyl]-3-(2-methylphenyl)ureido}ethoxy)phenyl]propionic acid,
3-[4-(2-{1-[3-(3,5-dichlorophenoxy)propyl]-3-(2-methylphenyl)ureido}ethoxy)phenyl]-2-ethoxypropionic acid,
2-ethoxy-3-[4-(2-{1-[4-(4-fluorophenoxy)butyl]-3-(2-methylphenyl)ureido}ethoxy)phenyl]propionic acid,
3-[4-(2-{1-[4-(3,5-dichlorophenoxy)butyl]-3-(2-methylphenyl)ureido}ethoxy)phenyl]-2-ethoxypropionic acid,
2-ethoxy-3-[4-(2-{1-[2-(4-fluorobenzyloxy)ethyl]-3-(2-methylphenyl)ureido}ethoxy)phenyl]propionic acid,
3-[4-(2-{1-[2-(3,5-dichlorobenzyloxy)ethyl]-3-(2-methylphenyl)ureido}ethoxy)phenyl]-2-ethoxypropionic acid,
2-ethoxy-3-[4-(2-{1-[3-(4-fluorobenzyloxy)propyl]-3-(2-methylphenyl)ureido}ethoxy)phenyl]propionic acid,
3-[4-(2-{1-[3-(3,5-dichlorobenzyloxy)propyl]-3-(2-methylphenyl)ureido}ethoxy)phenyl]-2-ethoxypropionic acid,
2-ethoxy-3-[4-(2-{1-[4-(4-fluorobenzyloxy)butyl]-3-(2-methylphenyl)ureido}ethoxy)phenyl]propionic acid,
3-[4-(2-{1-[4-(3,5-dichlorobenzyloxy)butyl]-3-(2-methylphenyl)ureido}ethoxy)phenyl]-2-ethoxypropionic acid,
2-ethoxy-3-[4-(2-{1-[3-(4-fluorophenyl)propyl]-3-(2-methylphenyl)ureido}ethoxy)phenyl]propionic acid,
3-[4-(2-{1-[3-(3,5-dichlorophenyl)propyl] 3-(2-methylphenyl)ureido}ethoxy)phenyl]-2-ethoxypropionic acid,
2-ethoxy-3-(4-{2-[3-(3-methylphenyl)-1-pentylureido] ethoxy}phenyl)propionic acid,
2-ethoxy-3-(4-{2-[1-hexyl-3-(3-methylphenyl)ureido] ethoxy}phenyl)propionic acid,
2-ethoxy-3-(4-{2-[1-heptyl-3-(3-methylphenyl)ureido] ethoxy}phenyl)propionic acid,
2-ethoxy-3-(4-{2-[3-(3-methylphenyl)-1-octylureido] ethoxy}phenyl)propionic acid,
2-ethoxy-3-(4-{2-[1-isobutyl-3-(3-methylphenyl)ureido] ethoxy}phenyl)propionic acid,
2-ethoxy-3-(4-{2-[1-(3-methylbutyl)-3-(3-methylphenyl) ureido]ethoxy}phenyl)propionic acid,
2-ethoxy-3-(4-{2-[1-(4-methylpentyl)-3-(3-methylphenyl) ureido]ethoxy}phenyl)propionic acid,
2-ethoxy-3-(4-{2-[3-(3-methylphenyl)-1-(2-propylpentyl) ureido]ethoxy}phenyl)propionic acid,
3-(4-{2-[1-(3,3-dimethylbutyl)-3-(3-methylphenyl)ureido] ethoxy}phenyl)-2-ethoxypropionic acid,
2-ethoxy-3-(4-{2-[1-(2-ethylbutyl)-3-(3-methylphenyl)ureido]ethoxy}phenyl)propionic acid,
3-(4-{2-[1-cyclohexylmethyl-3-(3-methylphenyl)ureido] ethoxy}phenyl)-2-ethoxypropionic acid,
3-(4-{2-[1-(4-cyclohexylbutyl)-3-(3-methylphenyl)ureido] ethoxy}phenyl)-2-ethoxypropionic acid, 3-(4-{2-[1-cyclopropylmethyl-3-(3-methylphenyl)ureido]ethoxy}phenyl)-2-ethoxypropionic acid,
3-(4-{2-[1-cyclobutylmethyl-3-(3-methylphenyl)ureido]ethoxy}phenyl)-2-ethoxypropionic acid,
3-(4-{2-[1-cyclopentylmethyl-3-(3-methylphenyl)ureido]ethoxy}phenyl)-2-ethoxypropionic acid,
3-(4-{2-[1-(2-cyclopentylethyl)-3-(3-methylphenyl)ureido]ethoxy}phenyl)-2-ethoxypropionic acid,
3-(4-{2-[1-(3-cyclohexylpropyl)-3-(3-methylphenyl)ureido]ethoxy}phenyl)-2-ethoxypropionic acid,
2-ethoxy-3-(4-{2-[3-(3-methylphenyl)-1-(3-phenylpropyl)ureido]ethoxy}phenyl)propionic acid,
2-ethoxy-3-(4-{2-[3-(3-methylphenyl)-1-(4-phenylbutyl)ureido]ethoxy}phenyl)propionic acid,
3-(4-{2-[1-(2-butoxyethyl)-3-(3-methylphenyl)ureido]ethoxy}phenyl)-2-ethoxypropionic acid,
2-ethoxy-3-(4-{2-[3-(3-methylphenyl)-1-(2-pentyloxyethyl)ureido]ethoxy}phenyl)propionic acid,
2-ethoxy-3-(4-{2-[3-(3-methylphenyl)-1-(3-propoxypropyl)ureido]ethoxy}phenyl)propionic acid,
3-(4-{2-[1-(2-butylthioethyl)-3-(3-methylphenyl)ureido]ethoxy}phenyl)-2-ethoxypropionic acid,
2-ethoxy-3-(4-{2-[3-(3-methylphenyl)-1-(2-pentylthioethyl)ureido]ethoxy}phenyl)propionic acid,
2-ethoxy-3-(4-{2-[3-(3-methylphenyl)-1-(3-propylthiopropyl)ureido]ethoxy}phenyl)propionic acid,
2-ethoxy-3-(4-{2-[3-(3-methylphenyl)-1-(3-phenoxypropyl)ureido]ethoxy}phenyl)propionic acid,
2-ethoxy-3-(4-{2-[3-(3-methylphenyl)-1-(4-phenoxybutyl)ureido]ethoxy}phenyl)propionic acid,
3-(4-{2-[1-(3-benzyloxypropyl)-3-(3-methylphenyl)ureido]ethoxy}phenyl)-2-ethoxypropionic acid,
2-ethoxy-3-(4-{2-[3-(3-methylphenyl)-1-(3-phenylthiopropyl)ureido]ethoxy}phenyl)propionic acid,
2-ethoxy-3-(4-{2-[3-(3-methylphenyl)-1-(4-phenylthiobutyl)ureido]ethoxy}phenyl)propionic acid,
3-(4-{2-[1-(3-benzylthiopropyl)-3-(3-methylphenyl)ureido]ethoxy}phenyl)-2-ethoxypropionic acid,
2-ethoxy-3-(4-{2-[3-(3-methylphenyl)-1-(7,7,7-trifluoroheptyl)ureido]ethoxy}phenyl)propionic acid,
3-(4-{2-[1-(6,6-difluoroheptyl)-3-(3-methylphenyl)ureido]ethoxy}phenyl)-2-ethoxypropionic acid,
2-ethoxy-3-(4-{2-[3-(3-methylphenyl)-1-(6,6,6-trifluorohexyl)ureido]ethoxy}phenyl)propionic acid,
3-(4-{2-[1-(5,5-difluorohexyl)-3-(3-methylphenyl)ureido]ethoxy}phenyl)-2-ethoxypropionic acid,
2-ethoxy-3-(4-{2-[1-(5,5,6,6,7,7,7-heptafluoroheptyl)-3-(3-methylphenyl)ureido]ethoxy}phenyl)propionic acid,
2-ethoxy-3-(4-{2-[3-(3-methylphenyl)-1-(2,2,3,3,4,4,5,5,6,6,7,7,7-tridecafluoroheptyl)ureido]ethoxy}phenyl)propionic acid,
2-ethoxy-3-(4-{2-[3-(3-methylphenyl)-1-(5,5,6,6,6-pentafluorohexyl)ureido]ethoxy}phenyl)propionic acid,
2-ethoxy-3-(4-{2-[3-(3-methylphenyl)-1-(2,2,3,3,4,4,5,5,6,6-undecafluorohexyl)ureido]ethoxy}phenyl)propionic acid,
3-[4-(2-{1-[2-(2,2-difluoropropoxy)ethyl]-3-(3-methylphenyl)ureido}ethoxy)phenyl]-2-ethoxypropionic acid,
2-ethoxy-3-[4-(2-{1-[2-(1,1,2,2,3,3,3-heptafluoropropoxy)ethyl]-3-(3-methylphenyl)ureido}ethoxy)phenyl]propionic acid,
2-ethoxy-3-[4-(2-{3-(3-methylphenyl)-1-[2-(4,4,4-trifluorobutoxy)ethyl]ureido}ethoxy)phenyl]propionic acid,
3-[4-(2-{1-[2-(3,3-difluorobutoxy)ethyl]-3-(3-methylphenyl)ureido}ethoxy)phenyl]-2-ethoxypropionic acid,
3-[4-(2-{1-[2-(2,2-difluorobutoxy)ethyl]-3-(3-methylphenyl)ureido}ethoxy)phenyl]-2-ethoxypropionic acid,
2-ethoxy-3-[4-(2-{3-(3-methylphenyl)-1-[2-(1,1,2,2,3,3,4,4,4-nonafluorobutoxy)ethyl]ureido}ethoxy)phenyl]propionic acid,
2-ethoxy-3-[4-(2-{3-(3-methylphenyl)-1-[3-(2,2,2-trifluoroethoxy)propyl]ureido}ethoxy)phenyl]propionic acid,
2-ethoxy-3-[4-(2-{3-(3-methylphenyl)-1-[3-(1,1,2,2,2-pentafluoroethoxy)propyl]ureido}ethoxy)phenyl]propionic acid,
2-ethoxy-3-[4-(2-{1-[3-(4-fluorophenoxy)propyl]-3-(3-methylphenyl)ureido}ethoxy)phenyl]propionic acid,
3-[4-(2-{1-[3-(3,5-dichlorophenoxy)propyl]-3-(3-methylphenyl)ureido}ethoxy)phenyl]-2-ethoxypropionic acid,
2-ethoxy-3-[4-(2-{1-[4-(4-fluorophenoxy)butyl]-3-(3-methylphenyl)ureido}ethoxy)phenyl]propionic acid,
3-[4-(2-{1-[4-(3,5-dichlorophenoxy)butyl]-3-(3-methylphenyl)ureido}ethoxy)phenyl]-2-ethoxypropionic acid,
2-ethoxy-3-[4-(2-{1-[2-(4-fluorobenzyloxy)ethyl]-3-(3-methylphenyl)ureido}ethoxy)phenyl]propionic acid,
3-[4-(2-{1-[2-(3,5-dichlorobenzyloxy)ethyl]-3-(3-methylphenyl)ureido}ethoxy)phenyl]-2-ethoxypropionic acid,
2-ethoxy-3-[4-(2-{1-[3-(4-fluorobenzyloxy)propyl]-3-(3-methylphenyl)ureido}ethoxy)phenyl]propionic acid,
3-[4-(2-{1-[3-(3,5-dichlorobenzyloxy)propyl]-3-(3-methylphenyl)ureido}ethoxy)phenyl]-2-ethoxypropionic acid,
2-ethoxy-3-[4-(2-{1-[4-(4-fluorobenzyloxy)butyl]-3-(3-methylphenyl)ureido}ethoxy)phenyl]propionic acid,
3-[4-(2-{1-[4-(3,5-dichlorobenzyloxy)butyl]-3-(3-methylphenyl)ureido}ethoxy)phenyl]-2-ethoxypropionic acid,
2-ethoxy-3-[4-(2-{1-[3-(4-fluorophenyl)propyl]-3-(3-methylphenyl)ureido}ethoxy)phenyl]propionic acid,
3-[4-(2-{1-[3-(3,5-dichlorophenyl)propyl]-3-(3-methylphenyl)ureido}ethoxy)phenyl]-2-ethoxypropionic acid,
2-ethoxy-3-(4-{2-[3-(4-methylphenyl)-1-pentylureido]ethoxy}phenyl)propionic acid,
2-ethoxy-3-(4-{2-[1-hexyl-3-(4-methylphenyl)ureido]ethoxy}phenyl)propionic acid,
2-ethoxy-3-(4-{2-[1-heptyl-3-(4-methylphenyl)ureido]ethoxy}phenyl)propionic acid,
2-ethoxy-3-(4-{2-[3-(4-methylphenyl)-1-octylureido]ethoxy}phenyl)propionic acid,
2-ethoxy-3-(4-{2-[1-isobutyl-3-(4-methylphenyl)ureido]ethoxy}phenyl)propionic acid,
2-ethoxy-3-(4-{2-[1-(3-methylbutyl)-3-(4-methylphenyl)ureido]ethoxy}phenyl)propionic acid,
2-ethoxy-3-(4-{2-[1-(4-methylpentyl)-3-(4-methylphenyl)ureido]ethoxy}phenyl)propionic acid,
2-ethoxy-3-(4-{2-[3-(4-methylphenyl)-1-(2-propylpentyl)ureido]ethoxy}phenyl)propionic acid,
3-(4-{2-[1-(3,3-dimethylbutyl)-3-(4-methylphenyl)ureido]ethoxy}phenyl)-2-ethoxypropionic acid,
2-ethoxy-3-(4-{2-[1-(2-ethylbutyl)-3-(4-methylphenyl)ureido]ethoxy}phenyl)propionic acid,
3-(4-{2-[1-cyclohexylmethyl-3-(4-methylphenyl)ureido]ethoxy}phenyl)-2-ethoxypropionic acid,
3-(4-{2-[1-(4-cyclohexylbutyl)-3-(4-methylphenyl)ureido]ethoxy}phenyl)-2-ethoxypropionic acid,
3-(4-{2-[1-cyclopropylmethyl-3-(4-methylphenyl)ureido]ethoxy}phenyl)-2-ethoxypropionic acid,
3-(4-{2-[1-cyclobutylmethyl-3-(4-methylphenyl)ureido]ethoxy}phenyl)-2-ethoxypropionic acid,
3-(4-{2-[1-cyclopentylmethyl-3-(4-methylphenyl)ureido]ethoxy}phenyl)-2-ethoxypropionic acid,
3-(4-{2-[1-(2-cyclopentylethyl)-3-(4-methylphenyl)ureido]ethoxy}phenyl)-2-ethoxypropionic acid,
3-(4-{2-[1-(3-cyclohexylpropyl)-3-(4-methylphenyl)ureido]ethoxy}phenyl)-2-ethoxypropionic acid, 2-ethoxy-3-(4-{2-[3-(4-methylphenyl)-1-(3-phenylpropyl) ureido]ethoxy}phenyl)propionic acid,
2-ethoxy-3-(4-{2-[3-(4-methylphenyl)-1-(4-phenylbutyl) ureido]ethoxy}phenyl)propionic acid,
3-(4-{2-[1-(2-butoxyethyl)-3-(4-methylphenyl)ureido] ethoxy}phenyl)-2-ethoxypropionic acid,
2-ethoxy-3-(4-{2-[3-(4-methylphenyl)-1-(2-pentyloxyethyl)ureido]ethoxy}phenyl)propionic acid,
2-ethoxy-3-(4-{2-[3-(4-methylphenyl)-1-(3-propoxypropyl) ureido]ethoxy}phenyl)propionic acid,
3-(4-{2-[1-(2-butylthioethyl)-3-(4-methylphenyl)ureido] ethoxy}phenyl)-2-ethoxypropionic acid,
2-ethoxy-3-(4-{2-[3-(4-methylphenyl)-1-(2-pentylthioethyl)ureido]ethoxy}phenyl)propionic acid,
2-ethoxy-3-(4-{2-[3-(4-methylphenyl)-1-(3-propylthiopropyl)ureido]ethoxy}phenyl)propionic acid,
2-ethoxy-3-(4-{2-[3-(4-methylphenyl)-1-(3-phenoxypropyl)ureido]ethoxy}phenyl)propionic acid,
2-ethoxy-3-(4-{2-[3-(4-methylphenyl)-1-(4-phenoxybutyl) ureido]ethoxy}phenyl)propionic acid,
3-(4-{2-[1-(3-benzyloxypropyl)-3-(4-methylphenyl)ureido] ethoxy}phenyl)-2-ethoxypropionic acid,
2-ethoxy-3-(4-{2-[3-(4-methylphenyl)-1-(3-phenylthiopropyl)ureido]ethoxy}phenyl)propionic acid,
2-ethoxy-3-(4-{2-[3-(4-methylphenyl)-1-(4-phenylthiobutyl)ureido]ethoxy}phenyl)propionic acid,
3-(4-{2-[1-(3-benzylthiopropyl)-3-(4-methylphenyl)ureido] ethoxy}phenyl)-2-ethoxypropionic acid,
2-ethoxy-3-(4-{2-[3-(4-methylphenyl)-1-(7,7,7-trifluoroheptyl)ureido]ethoxy}phenyl)propionic acid,
3-(4-{2-[1-(6,6-difluoroheptyl)-3-(4-methylphenyl)ureido] ethoxy}phenyl)-2-ethoxypropionic acid,
2-ethoxy-3-(4-{2-[3-(4-methylphenyl)-1-(6,6,6-trifluorohexyl)ureido]ethoxy}phenyl)propionic acid,
3-(4-{2-[1-(5,5-difluorohexyl)-3-(4-methylphenyl)ureido] ethoxy}phenyl)-2-ethoxypropionic acid,
2-ethoxy-3-(4-{2-[1-(5,5,6,6,7,7,7-heptafluoroheptyl)-3-(4-methylphenyl)ureido]ethoxy}phenyl)propionic acid,
2-ethoxy-3-(4-{2-[3-(4-methylphenyl)-1-(2,2,3,3,4,4,5,5,6,6,7,7,7-tridecafluoroheptyl)ureido]ethoxy}phenyl)propionic acid,
2-ethoxy-3-(4-{2-[3-(4-methylphenyl)-1-(5,5,6,6,6-pentafluorohexyl)ureido]ethoxy}phenyl)propionic acid,
2-ethoxy-3-(4-{2-[3-(4-methylphenyl)-1-(2,2,3,3,4,4,5,5,6,6-undecafluorohexyl)ureido]ethoxy}phenyl)propionic acid,
3-[4-(2-{1-[2-(2,2-difluoropropoxy)ethyl]-3-(4-methylphenyl)ureido}ethoxy)phenyl]-2-ethoxypropionic acid,
2-ethoxy-3-[4-(2-{1-[2-(1,1,2,2,3,3,3-heptafluoropropoxy) ethyl]-3-(4-methylphenyl)ureido}ethoxy)phenyl]propionic acid,
2-ethoxy-3-[4-(2-{3-(4-methylphenyl)-1-[2-(4,4,4-trifluorobutoxy)ethyl]ureido}ethoxy)phenyl]propionic acid,
3-[4-(2-{1-[2-(3,3-difluorobutoxy)ethyl]-3-(4-methylphenyl)ureido}ethoxy)phenyl]-2-ethoxypropionic acid,
3-[4-(2-{1-[2-(2,2-difluorobutoxy)ethyl]-3-(4-methylphenyl)ureido}ethoxy)phenyl]-2-ethoxypropionic acid,
2-ethoxy-3-[4-(2-{3-(4-methylphenyl)-1-[2-(1,1,2,2,3,3,4,4,4-nonafluorobutoxy)ethyl]ureido}ethoxy)phenyl]propionic acid,
2-ethoxy-3-[4-(2-{3-(4-methylphenyl)-1-[3-(2,2,2-trifluoroethoxy)propyl]ureido}ethoxy)phenyl]propionic acid,
2-ethoxy-3-[4-(2-{3-(4-methylphenyl)-1-[3-(1,1,2,2,2-pentafluoroethoxy)propyl]ureido}ethoxy)phenyl]propionic acid,
2-ethoxy-3-[4-(2-{1-[3-(4-fluorophenoxy)propyl]-3-(4-methylphenyl)ureido}ethoxy)phenyl]propionic acid,
3-[4-(2-{1-[3-(3,5-dichlorophenoxy)propyl]-3-(4-methylphenyl)ureido}ethoxy)phenyl]-2-ethoxypropionic acid,
2-ethoxy-3-[4-(2-{1-[4-(4-fluorophenoxy)butyl]-3-(4-methylphenyl)ureido}ethoxy)phenyl]propionic acid,
3-[4-(2-{1-[4-(3,5-dichlorophenoxy)butyl]-3-(4-methylphenyl)ureido}ethoxy)phenyl]-2-ethoxypropionic acid,
2-ethoxy-3-[4-(2-{1-[2-(4-fluorobenzyloxy)ethyl]-3-(4-methylphenyl)ureido}ethoxy)phenyl]propionic acid,
3-[4-(2-{1-[2-(3,5-dichlorobenzyloxy)ethyl]-3-(4-methylphenyl)ureido}ethoxy)phenyl]-2-ethoxypropionic acid,
2-ethoxy-3-[4-(2-{1-[3-(4-fluorobenzyloxy)propyl]-3-(4-methylphenyl)ureido}ethoxy)phenyl]propionic acid,
3-[4-(2-{1-[3-(3,5-dichlorobenzyloxy)propyl]-3-(4-methylphenyl)ureido}ethoxy)phenyl]-2-ethoxypropionic acid,
2-ethoxy-3-[4-(2-{1-[4-(4-fluorobenzyloxy)butyl]-3-(4-methylphenyl)ureido}ethoxy)phenyl]propionic acid,
3-[4-(2-{1-[4-(3,5-dichlorobenzyloxy)butyl]-3-(4-methylphenyl)ureido}ethoxy)phenyl]-2-ethoxypropionic acid,
2-ethoxy-3-[4-(2-{1-[3-(4-fluorophenyl)propyl]-3-(4-methylphenyl)ureido}ethoxy)phenyl]propionic acid,
3-[4-(2-{1-[3-(3,5-dichlorophenyl)propyl]-3-(4-methylphenyl)ureido}ethoxy)phenyl]-2-ethoxypropionic acid,
2-ethoxy-3-(4-{2-[1-pentyl-3-(2,4,5-trimethylphenyl)ureido]ethoxy}phenyl)propionic acid,
2-ethoxy-3-(4-{2-[1-hexyl-3-(2,4,5-trimethylphenyl)ureido]ethoxy}phenyl)propionic acid,
2-ethoxy-3-(4-{2-[1-heptyl-3-(2,4,5-trimethylphenyl)ureido]ethoxy}phenyl)propionic acid,
2-ethoxy-3-(4-{2-[1-octyl-3-(2,4,5-trimethylphenyl)ureido] ethoxy}phenyl)propionic acid,
2-ethoxy-3-(4-{2-[1-isobutyl-3-(2,4,5-trimethylphenyl)ureido]ethoxy}phenyl)propionic acid,
2-ethoxy-3-(4-{2-[1-(3-methylbutyl)-3-(2,4,5-trimethylphenyl)ureido]ethoxy}phenyl)propionic acid,
2-ethoxy-3-(4-{2-[1-(4-methylpentyl)-3-(2,4,5-trimethylphenyl)ureido]ethoxy}phenyl)propionic acid,
2-ethoxy-3-(4-{2-[1-(2-propylpentyl)-3-(2,4,5-trimethylphenyl)ureido]ethoxy}phenyl)propionic acid,
3-(4-{2-[1-(3,3-dimethylbutyl)-3-(2,4,5-trimethylphenyl) ureido]ethoxy}phenyl)-2-ethoxypropionic acid,
2-ethoxy-3-(4-{2-[1-(2-ethylbutyl)-3-(2,4,5-trimethylphenyl)ureido]ethoxy}phenyl)propionic acid,
3-(4-{2-[1-cyclohexylmethyl-3-(2,4,5-trimethylphenyl)ureido]ethoxy}phenyl)-2-ethoxypropionic acid,
3-(4-{2-[1-(4-cyclohexylbutyl)-3-(2,4,5-trimethylphenyl) ureido]ethoxy}phenyl)-2-ethoxypropionic acid,
3-(4-{2-[1-cyclopropylmethyl-3-(2,4,5-trimethylphenyl) ureido]ethoxy}phenyl)-2-ethoxypropionic acid,
3-(4-{2-[1-cyclobutylmethyl-3-(2,4,5-trimethylphenyl)ureido]ethoxy}phenyl)-2-ethoxypropionic acid,
3-(4-{2-[1-cyclopentylmethyl-3-(2,4,5-trimethylphenyl) ureido]ethoxy}phenyl)-2-ethoxypropionic acid,
3-(4-{2-[1-(2-cyclopentylethyl)-3-(2,4,5-trimethylphenyl) ureido]ethoxy}phenyl)-2-ethoxypropionic acid,
3-(4-{2-[1-(3-cyclohexylpropyl)-3-(2,4,5-trimethylphenyl) ureido]ethoxy}phenyl)-2-ethoxypropionic acid,
2-ethoxy-3-(4-{2-[1-(3-phenylpropyl)-3-(2,4,5-trimethylphenyl)ureido]ethoxy}phenyl)propionic acid,
2-ethoxy-3-(4-{2-[1-(4-phenylbutyl)-3-(2,4,5-trimethylphenyl)ureido]ethoxy}phenyl)propionic acid,
3-(4-{2-[1-(2-butoxyethyl)-3-(2,4,5-trimethylphenyl)ureido]ethoxy}phenyl)-2-ethoxypropionic acid,
2-ethoxy-3-(4-{2-[1-(2-pentyloxyethyl)-3-(2,4,5-trimethylphenyl)ureido]ethoxy}phenyl)propionic acid,
2-ethoxy-3-(4-{2-[1-(3-propoxypropyl)-3-(2,4,5-trimethylphenyl)ureido]ethoxy}phenyl)propionic acid, 3-(4-{2-[1-(2-butylthioethyl)-3-(2,4,5-trimethylphenyl)ureido]ethoxy}phenyl)-2-ethoxypropionic acid,
2-ethoxy-3-(4-{2-[1-(2-pentylthioethyl)-3-(2,4,5-trimethylphenyl)ureido]ethoxy}phenyl)propionic acid,
2-ethoxy-3-(4-{2-[1-(3-propylthiopropyl)-3-(2,4,5-trimethylphenyl)ureido]ethoxy}phenyl)propionic acid,
2-ethoxy-3-(4-{2-[1-(3-phenoxypropyl)-3-(2,4,5-trimethylphenyl)ureido]ethoxy}phenyl)propionic acid,
2-ethoxy-3-(4-{2-[1-(4-phenoxybutyl)-3-(2,4,5-trimethylphenyl)ureido]ethoxy}phenyl)propionic acid,
3-(4-{2-[1-(3-benzyloxypropyl)-3-(2,4,5-trimethylphenyl)ureido]ethoxy}phenyl)-2-ethoxypropionic acid,
2-ethoxy-3-(4-{2-[1-(3-phenylthiopropyl)-3-(2,4,5-trimethylphenyl)ureido]ethoxy}phenyl)propionic acid,
2-ethoxy-3-(4-{2-[1-(4-phenylthiobutyl)-3-(2,4,5-trimethylphenyl)ureido]ethoxy}phenyl)propionic acid,
3-(4-{2-[1-(3-benzylthiopropyl)-3-(2,4,5-trimethylphenyl)ureido]ethoxy}phenyl)-2-ethoxypropionic acid,
2-ethoxy-3-(4-{2-[1-(7,7,7-trifluoroheptyl)-3-(2,4,5-trimethylphenyl)ureido]ethoxy}phenyl)propionic acid,
3-(4-{2-[1-(6,6-difluoroheptyl)-3-(2,4,5-trimethylphenyl)ureido]ethoxy}phenyl)-2-ethoxypropionic acid,
2-ethoxy-3-(4-{2-[1-(6,6,6-trifluorohexyl)-3-(2,4,5-trimethylphenyl)ureido]ethoxy}phenyl)propionic acid,
3-(4-{2-[1-(5,5-difluorohexyl)-3-(2,4,5-trimethylphenyl)ureido]ethoxy phenyl)-2-ethoxypropionic acid,
2-ethoxy-3-(4-{2-[1-(5,5,6,6,7,7,7-heptafluoroheptyl)-3-(2,4,5-trimethylphenyl)ureido]ethoxy}phenyl)propionic acid,
2-ethoxy-3-(4-{2-[1-(2,2,3,3,4,4,5,5,6,6,7,7,7-tridecafluoroheptyl)-3-(2,4,5-trimethylphenyl)ureido]ethoxy}phenyl)propionic acid,
2-ethoxy-3-(4-{2-[1-(5,5,6,6,6-pentafluorohexyl)-3-(2,4,5-trimethylphenyl)ureido]ethoxy}phenyl)propionic acid,
2-ethoxy-3-(4-{2-[3-(2,4,5-trimethylphenyl)-1-(2,2,3,3,4,4,5,5,6,6,6-undecafluorohexyl)ureido]ethoxy}phenyl)propionic acid,
3-[4-(2-{1-[2-(2,2-difluoropropoxy)ethyl]-3-(2,4,5-trimethylphenyl)ureido}ethoxy)phenyl]-2-ethoxypropionic acid,
2-ethoxy-3-[4-(2-{1-[2-(1,1,2,2,3,3,3-heptafluoropropoxy)ethyl]-3-(2,4,5 -trimethylphenyl)ureido}ethoxy)phenyl]propionic acid,
2-ethoxy-3-[4-(2-{1-[2-(4,4,4-trifluorobutoxy)ethyl]-3-(2,4,5-trimethylphenyl)ureido}ethoxy)phenyl]propionic acid,
3-[4-(2-{1-[2-(3,3-difluorobutoxy)ethyl]-3-(2,4,5-trimethylphenyl)ureido}ethoxy)phenyl]-2-ethoxypropionic acid,
3-[4-(2-{1-[2-(2,2-difluorobutoxy)ethyl]-3-(2,4,5-trimethylphenyl)ureido}ethoxy)phenyl]-2-ethoxypropionic acid,
2-ethoxy-3-[4-(2-{1-[2-(1,1,2,2,3,3,4,4,4-nonafluorobutoxy)ethyl]-3-(2,4,5-trimethylphenyl)ureido}ethoxy)phenyl]propionic acid,
2-ethoxy-3-[4-(2-{1-[3-(2,2,2-trifluoroethoxy)propyl]-3-(2,4,5-trimethylphenyl)ureido}ethoxy)phenyl]propionic acid,
2-ethoxy-3-[4-(2-{1-[3-(1,1,2,2,2-pentafluoroethoxy)propyl]-3-(2,4,5-trimethylphenyl)ureido}ethoxy)phenyl]propionic acid,
2-ethoxy-3-[4-(2-{1-[3-(4-fluorophenoxy)propyl]-3-(2,4,5-trimethylphenyl)ureido}ethoxy)phenyl]propionic acid,
3-[4-(2-{1-[3-(3,5-dichlorophenoxy)propyl]-3-(2,4,5-trimethylphenyl)ureido}ethoxy)phenyl]-2-ethoxypropionic acid,
2-ethoxy-3-[4-(2-{1-[4-(4-fluorophenoxy)butyl]-3-(2,4,5-trimethylphenyl)ureido}ethoxy)phenyl]propionic acid,
3-[4-(2-{1-[4-(3,5-dichlorophenoxy)butyl]-3-(2,4,5-trimethylphenyl)ureido}ethoxy)phenyl]-2-ethoxypropionic acid,
2-ethoxy-3-[4-(2-{1-[2-(4-fluorobenzyloxy)ethyl]-3-(2,4,5-trimethylphenyl)ureido}ethoxy)phenyl]propionic acid,
3-[4-(2-{1-[2-(3,5-dichlorobenzyloxy)ethyl]-3-(2,4,5-trimethylphenyl)ureido}ethoxy)phenyl]-2-ethoxypropionic acid,
2-ethoxy-3-[4-(2-{1-[3-(4-fluorobenzyloxy)propyl]-3-(2,4,5-trimethylphenyl)ureido}ethoxy)phenyl]propionic acid,
3-[4-(2-{1-[3-(3,5-dichlorobenzyloxy)propyl]-3-(2,4,5-trimethylphenyl)ureido}ethoxy)phenyl]-2-ethoxypropionic acid,
2-ethoxy-3-[4-(2-{1-[4-(4-fluorobenzyloxy)butyl]-3-(2,4,5-trimethylphenyl)ureido}ethoxy)phenyl]propionic acid,
3-[4-(2-{1-[4-(3,5-dichlorobenzyloxy)butyl]-3-(2,4,5-trimethylphenyl)ureido}ethoxy)phenyl]-2-ethoxypropionic acid,
2-ethoxy-3-[4-(2-{1-[3-(4-fluorophenyl)propyl]-3-(2,4,5-trimethylphenyl)ureido}ethoxy)phenyl]propionic acid,
3-[4-(2-{1-[3-(3,5-dichlorophenyl)propyl]-3-(2,4,5-trimethylphenyl)ureido}ethoxy)phenyl]-2-ethoxypropionic acid,
2-ethoxy-3-(4-{2-[1-pentyl-3-(2,4,6-trimethylphenyl)ureido]ethoxy}phenyl)propionic acid,
2-ethoxy-3-(4-{2-[1-hexyl-3-(2,4,6-trimethylphenyl)ureido]ethoxy}phenyl)propionic acid,
2-ethoxy-3-(4-{2-[1-heptyl-3-(2,4,6-trimethylphenyl)ureido]ethoxy}phenyl)propionic acid,
2-ethoxy-3-(4-{2-[1-octyl-3-(2,4,6-trimethylphenyl)ureido]ethoxy}phenyl)propionic acid,
2-ethoxy-3-(4-{2-[1-isobutyl-3-(2,4,6-trimethylphenyl)ureido]ethoxy}phenyl)propionic acid,
2-ethoxy-3-(4-{2-[1-(3-methylbutyl)-3-(2,4,6-trimethylphenyl)ureido]ethoxy}phenyl)propionic acid,
2-ethoxy-3-(4-{2-[1-(4-methylpentyl)-3-(2,4,6-trimethylphenyl)ureido]ethoxy}phenyl)propionic acid,
2-ethoxy-3-(4-{2-[1-(2-propylpentyl)-3-(2,4,6-trimethylphenyl)ureido]ethoxy}phenyl)propionic acid,
3-(4-{2-[1-(3,3-dimethylbutyl)-3-(2,4,6-trimethylphenyl)ureido]ethoxy}phenyl)-2-ethoxypropionic acid,
2-ethoxy-3-(4-{2-[1-(2-ethylbutyl)-3-(2,4,6-trimethylphenyl)ureido]ethoxy}phenyl)propionic acid,
3-(4-{2-[1-cyclohexylmethyl-3-(2,4,6-trimethylphenyl)ureido]ethoxy}phenyl)-2-ethoxypropionic acid,
3-(4-{2-[1-(4-cyclohexylbutyl)-3-(2,4,6-trimethylphenyl)ureido]ethoxy}phenyl)-2-ethoxypropionic acid,
3-(4-{2-[1-cyclopropylmethyl-3-(2,4,6-trimethylphenyl)ureido]ethoxy}phenyl)-2-ethoxypropionic acid,
3-(4-{2-[1-cyclobutylmethyl-3-(2,4,6-trimethylphenyl)ureido]ethoxy}phenyl)-2-ethoxypropionic acid,
3-(4-{2-[1-cyclopentylmethyl-3-(2,4,6-trimethylphenyl)ureido]ethoxy}phenyl)-2-ethoxypropionic acid,
3-(4-{2-[1-(2-cyclopentylethyl)-3-(2,4,6-trimethylphenyl)ureido]ethoxy}phenyl)-2-ethoxypropionic acid,
3-(4-{2-[1-(3-cyclohexylpropyl)-3-(2,4,6-trimethylphenyl)ureido]ethoxy}phenyl)-2-ethoxypropionic acid,
2-ethoxy-3-(4-{2-[1-(3-phenylpropyl)-3-(2,4,6-trimethylphenyl)ureido]ethoxy}phenyl)propionic acid,
2-ethoxy-3-(4-{2-[1-(4-phenylbutyl)-3-(2,4,6-trimethylphenyl)ureido]ethoxy}phenyl)propionic acid,
3-(4-{2-[1-(2-butoxyethyl)-3-(2,4,6-trimethylphenyl)ureido]ethoxy}phenyl)-2-ethoxypropionic acid,
2-ethoxy-3-(4-{2-[1-(2-pentyloxyethyl)-3-(2,4,6-trimethylphenyl)ureido]ethoxy}phenyl)propionic acid,
2-ethoxy-3-(4-{2-[1-(3-propoxypropyl)-3-(2,4,6-trimethylphenyl)ureido]ethoxy}phenyl)propionic acid,
3-(4-{2-[1-(2-butylthioethyl)-3-(2,4,6-trimethylphenyl)ureido]ethoxy}phenyl)-2-ethoxypropionic acid,
2-ethoxy-3-(4-{2-[1-(2-pentylthioethyl)-3-(2,4,6-trimethylphenyl)ureido]ethoxy}phenyl)propionic acid, 2-ethoxy-3-(4-{2-[1-(3-propylthiopropyl)-3-(2,4,6-trimethylphenyl)ureido]ethoxy}phenyl)propionic acid,
2-ethoxy-3-(4-{2-[1-(3-phenoxypropyl)-3-(2,4,6-trimethylphenyl)ureido]ethoxy}phenyl)propionic acid,
2-ethoxy-3-(4-{2-[1-(4-phenoxybutyl)-3-(2,4,6-trimethylphenyl)ureido]ethoxy}phenyl)propionic acid,
3-(4-{2-[1-(3-benzyloxypropyl)-3-(2,4,6-trimethylphenyl)ureido]ethoxy}phenyl)-2-ethoxypropionic acid,
2-ethoxy-3-(4-{2-[1-(3-phenylthiopropyl)-3-(2,4,6-trimethylphenyl)ureido]ethoxy}phenyl)propionic acid,
2-ethoxy-3-(4-{2-[1-(4-phenylthiobutyl)-3-(2,4,6-trimethylphenyl)ureido]ethoxy}phenyl)propionic acid,
3-(4-{2-[1-(3-benzylthiopropyl)-3-(2,4,6-trimethylphenyl)ureido]ethoxy}phenyl)-2-ethoxypropionic acid,
2-ethoxy-3-(4-{2-[1-(7,7,7-trifluoroheptyl)-3-(2,4,6-trimethylphenyl)ureido]ethoxy}phenyl)propionic acid,
3-(4-{2-[1-(6,6-difluoroheptyl)-3-(2,4,6-trimethylphenyl)ureido]ethoxy}phenyl)-2-ethoxypropionic acid,
2-ethoxy-3-(4-{2-[1-(6,6,6-trifluorohexyl)-3-(2,4,6-trimethylphenyl)ureido]ethoxy}phenyl)propionic acid,
3-(4-{2-[1-(5,5-difluorohexyl)-3-(2,4,6-trimethylphenyl)ureido]ethoxy}phenyl)-2-ethoxypropionic acid,
2-ethoxy-3-(4-{2-[1-(5,5,6,6,7,7,7-heptafluoroheptyl)-3-(2,4,6-trimethylphenyl)ureido]ethoxy}phenyl)propionic acid,
2-ethoxy-3-(4-{2-[1-(2,2,3,3,4,4,5,5,6,6,7,7,7-tridecafluoroheptyl)-3-(2,4,6-trimethylphenyl)ureido]ethoxy}phenyl)propionic acid,
2-ethoxy-3-(4-{2-[1-(5,5,6,6,6-pentafluorohexyl)-3-(2,4,6-trimethylphenyl)ureido]ethoxy}phenyl)propionic acid,
2-ethoxy-3-(4-{2-[3-(2,4,6-trimethylphenyl)-1-(2,2,3,3,4,4,5,5,6,6,6-undecafluorohexyl)ureido]ethoxy}phenyl)propionic acid,
3-[4-(2-{1-[2-(2,2-difluoropropoxy)ethyl]-3-(2,4,6-trimethylphenyl)ureido}ethoxy)phenyl]-2-ethoxypropionic acid,
2-ethoxy-3-[4-(2-{1-[2-(1,1,2,2,3,3,3-heptafluoropropoxy)ethyl]-3-(2,4,6-trimethylphenyl)ureido}ethoxy)phenyl]propionic acid,
2-ethoxy-3-[4-(2-{1-[2-(4,4,4-trifluorobutoxy)ethyl]-3-(2,4,6-trimethylphenyl)ureido}ethoxy)phenyl]propionic acid,
3-[4-(2-{1-[2-(3,3-difluorobutoxy)ethyl]-3-(2,4,6-trimethylphenyl)ureido}ethoxy)phenyl]-2-ethoxypropionic acid,
3-[4-(2-{1-[2-(2,2-difluorobutoxy)ethyl]-3-(2,4,6-trimethylphenyl)ureido}ethoxy)phenyl]-2-ethoxypropionic acid,
2-ethoxy-3-[4-(2-{1-[2-(1,1,2,2,3,3,4,4,4-nonafluorobutoxy)ethyl]-3-(2,4,6-trimethylphenyl)ureido}ethoxy)phenyl]propionic acid,
2-ethoxy-3-[4-(2-{1-[3-(2,2,2-trifluoroethoxy)propyl]-3-(2,4,6-trimethylphenyl)ureido}ethoxy)phenyl]propionic acid,
2-ethoxy-3-[4-(2-{1-[3-(1,1,2,2,2-pentafluoroethoxy)propyl]-3-(2,4,6-trimethylphenyl)ureido}ethoxy)phenyl]propionic acid,
2-ethoxy-3-[4-(2-{1-[3-(4-fluorophenoxy)propyl]-3-(2,4,6-trimethylphenyl)ureido}ethoxy)phenyl]propionic acid,
3-[4-(2-{1-[3-(3,5-dichlorophenoxy)propyl]-3-(2,4,6-trimethylphenyl)ureido}ethoxy)phenyl]-2-ethoxypropionic acid,
2-ethoxy-3-[4-(2-{1-[4-(4-fluorophenoxy)butyl]-3-(2,4,6-trimethylphenyl)ureido}ethoxy)phenyl]propionic acid,
3-[4-(2-{1-[4-(3,5-dichlorophenoxy)butyl]-3-(2,4,6-trimethylphenyl)ureido}ethoxy)phenyl]-2-ethoxypropionic acid,
2-ethoxy-3-[4-(2-{1-[2-(4-fluorobenzyloxy)ethyl]-3-(2,4,6-trimethylphenyl)ureido}ethoxy)phenyl]propionic acid,
3-[4-(2-{1-[2-(3,5-dichlorobenzyloxy)ethyl]-3-(2,4,6-trimethylphenyl)ureido}ethoxy)phenyl]-2-ethoxypropionic acid,
2-ethoxy-3-[4-(2-1-[3-(4-fluorobenzyloxy)propyl]-3-(2,4,6-trimethylphenyl)ureido}ethoxy)phenyl]propionic acid,
3-[4-(2-{1-[3-(3,5-dichlorobenzyloxy)propyl]-3-(2,4,6-trimethylphenyl)ureido}ethoxy)phenyl]-2-ethoxypropionic acid,
2-ethoxy-3-[4-(2-{1-[4-(4-fluorobenzyloxy)butyl]-3-(2,4,6-trimethylphenyl)ureido}ethoxy)phenyl]propionic acid,
3-[4-(2-{1-[4-(3,5-dichlorobenzyloxy)butyl]-3-(2,4,6-trimethylphenyl)ureido}ethoxy)phenyl]-2-ethoxypropionic acid,
2-ethoxy-3-[4-(2-{1-[3-(4-fluorophenyl)propyl]-3-(2,4,6-trimethylphenyl)ureido}ethoxy)phenyl]propionic acid,
3-[4-(2-{1-[3-(3,5-dichlorophenyl)propyl]-3-(2,4,6-trimethylphenyl)ureido}ethoxy)phenyl]-2-ethoxypropionic acid,
2-ethoxy-3-(4-{2-[1-pentyl-3-(2-trifluoromethylphenyl)ureido]ethoxy}phenyl)propionic acid,
2-ethoxy-3-(4-{2-[1-hexyl-3-(2-trifluoromethylphenyl)ureido]ethoxy}phenyl)propionic acid,
2-ethoxy-3-(4-{2-[1-heptyl-3-(2-trifluoromethylphenyl)ureido]ethoxy}phenyl)propionic acid,
2-ethoxy-3-(4-{2-[1-octyl-3-(2-trifluoromethylphenyl)ureido]ethoxy}phenyl)propionic acid,
2-ethoxy-3-(4-{2-[1-isobutyl-3-(2-trifluoromethylphenyl)ureido]ethoxy}phenyl)propionic acid,
2-ethoxy-3-(4-{2-[1-(3-methylbutyl)-3-(2-trifluoromethylphenyl)ureido]ethoxy}phenyl)propionic acid,
2-ethoxy-3-(4-{2-[1-(4-methylpentyl)-3-(2-trifluoromethylphenyl)ureido]ethoxy}phenyl)propionic acid,
2-ethoxy-3-(4-{2-[1-(2-propylpentyl)-3-(2-trifluoromethylphenyl)ureido]ethoxy}phenyl)propionic acid,
3-(4-{2-[1-(3,3-dimethylbutyl)-3-(2-trifluoromethylphenyl)ureido]ethoxy}phenyl)-2-ethoxypropionic acid,
2-ethoxy-3-(4-{2-[1-(2-ethylbutyl)-3-(2-trifluoromethylphenyl)ureido]ethoxy}phenyl)propionic acid,
3-(4-{2-[1-cyclohexylmethyl-3-(2-trifluoromethylphenyl)ureido]ethoxy}phenyl)-2-ethoxypropionic acid,
3-(4-{2-[1-(4-cyclohexylbutyl)-3-(2-trifluoromethylphenyl)ureido]ethoxy}phenyl)-2-ethoxypropionic acid,
3-(4-{2-[1-cyclopropylmethyl-3-(2-trifluoromethylphenyl)ureido]ethoxy}phenyl)-2-ethoxypropionic acid,
3-(4-{2-[1-cyclobutylmethyl-3-(2-trifluoromethylphenyl)ureido]ethoxy}phenyl)-2-ethoxypropionic acid,
3-(4-{2-[1-cyclopentylmethyl-3-(2-trifluoromethylphenyl)ureido]ethoxy}phenyl)-2-ethoxypropionic acid,
3-(4-{2-[1-(2-cyclopentylethyl)-3-(2-trifluoromethylphenyl)ureido]ethoxy}phenyl)-2-ethoxypropionic acid,
3-(4-{2-[1-(3-cyclohexylpropyl)-3-(2-trifluoromethylphenyl)ureido]ethoxy}phenyl)-2-ethoxypropionic acid,
2-ethoxy-3-(4-{2-[1-(3-phenylpropyl)-3-(2-trifluoromethylphenyl)ureido]ethoxy}phenyl)propionic acid,
2-ethoxy-3-(4-{2-[1-(4-phenylbutyl)-3-(2-trifluoromethylphenyl)ureido]ethoxy}phenyl)propionic acid,
3-(4-{2-[1-(2-butoxyethyl)-3-(2-trifluoromethylphenyl)ureido]ethoxy}phenyl)-2-ethoxypropionic acid,
2-ethoxy-3-(4-{2-[1-(2-pentyloxyethyl)-3-(2-trifluoromethylphenyl)ureido]ethoxy}phenyl)propionic acid,
2-ethoxy-3-(4-{2-[1-(3-propoxypropyl)-3-(2-trifluoromethylphenyl)ureido]ethoxy}phenyl)propionic acid,
3-(4-{2-[1-(2-butylthioethyl)-3-(2-trifluoromethylphenyl)ureido]ethoxy}phenyl)-2-ethoxypropionic acid,
2-ethoxy-3-(4-{2-[1-(2-pentylthioethyl)-3-(2-trifluoromethylphenyl)ureido]ethoxy}phenyl)propionic acid,
2-ethoxy-3-(4-{2-[1-(3-propylthiopropyl)-3-(2-trifluoromethylphenyl)ureido]ethoxy}phenyl)propionic acid, 2-ethoxy-3-(4-{2-[1-(3-phenoxypropyl)-3-(2-trifluoromethylphenyl)ureido]ethoxy}phenyl)propionic acid,
2-ethoxy-3-(4-{2-[1-(4-phenoxybutyl)-3-(2-trifluoromethylphenyl)ureido]ethoxy}phenyl)propionic acid,
3-(4-{2-[1-(3-benzyloxypropyl)-3-(2-trifluoromethylphenyl)ureido]ethoxy}phenyl)-2-ethoxypropionic acid,
2-ethoxy-3-(4-{2-[1-(3-phenylthiopropyl)-3-(2-trifluoromethylphenyl)ureido]ethoxy}phenyl)propionic acid,
2-ethoxy-3-(4-{2-[1-(4-phenylthiobutyl)-3-(2-trifluoromethylphenyl)ureido]ethoxy}phenyl)propionic acid,
3-(4-{2-[1-(3-benzylthiopropyl)-3-(2-trifluoromethylphenyl)ureido]ethoxy}phenyl)-2-ethoxypropionic acid,
2-ethoxy-3-(4-{2-[1-(7,7,7-trifluoroheptyl)-3-(2-trifluoromethylphenyl)ureido]ethoxy}phenyl)propionic acid,
3-(4-{2-[1-(6,6-difluoroheptyl)-3-(2-trifluoromethylphenyl)ureido]ethoxy}phenyl)-2-ethoxypropionic acid,
2-ethoxy-3-(4-{2-[1-(6,6,6-trifluorohexyl)-3-(2-trifluoromethylphenyl)ureido]ethoxy}phenyl)propionic acid,
3-(4-{2-[1-(5,5-difluorohexyl)-3-(2-trifluoromethylphenyl)ureido]ethoxy}phenyl)-2-ethoxypropionic acid,
2-ethoxy-3-(4-{2-[1-(5,5,6,6,7,7,7-heptafluoroheptyl)-3-(2-trifluoromethylphenyl)ureido]ethoxy}phenyl)propionic acid,
2-ethoxy-3-(4-{2-[1-(2,2,3,3,4,4,5,5,6,6,7,7,7-tridecafluoroheptyl)-3-(2-trifluoromethylphenyl)ureido]ethoxy}phenyl)propionic acid,
2-ethoxy-3-(4-{2-[1-(5,5,6,6,6-pentafluorohexyl)-3-(2-trifluoromethylphenyl)ureido]ethoxy}phenyl)propionic acid,
2-ethoxy-3-(4-{2-[3-(2-trifluoromethylphenyl)-1-(2,2,3,3,4,4,5,5,6,6 -undecafluorohexyl)ureido]ethoxy}phenyl)propionic acid,
3-[4-(2-{1-[2-(2,2-difluoropropoxy)ethyl]-3-(2-trifluoromethylphenyl)ureido}ethoxy)phenyl]-2-ethoxypropionic acid,
2-ethoxy-3-[4-(2-{1-[2-(1,1,2,2,3,3,3-heptafluoropropoxy)ethyl]-3-(2-trifluoromethylphenyl)ureido}ethoxy)phenyl]propionic acid,
2-ethoxy-3-[4-(2-{1-[2-(4,4,4-trifluorobutoxy)ethyl]-3-(2-trifluoromethylphenyl)ureido}ethoxy)phenyl]propionic acid,
3-[4-(2-{1-[2-(3,3-difluorobutoxy)ethyl]-3-(2-trifluoromethylphenyl)ureido}ethoxy)phenyl]-2-ethoxypropionic acid,
3-[4-(2-{1-[2-(2,2-difluorobutoxy)ethyl]-3-(2-trifluoromethylphenyl)ureido}ethoxy)phenyl]-2-ethoxypropionic acid,
2-ethoxy-3-[4-(2-{1-[2-(1,1,2,2,3,3,4,4,4-nonafluorobutoxy)ethyl]-3-(2-trifluoromethylphenyl)ureido}ethoxy)phenyl]propionic acid,
2-ethoxy-3-[4-(2-{1-[3-(2,2,2-trifluoroethoxy)propyl]-3-(2-trifluoromethylphenyl)ureido}ethoxy)phenyl]propionic acid,
2-ethoxy-3-[4-(2-{1-[3-(1,1,2,2,2-pentafluoroethoxy)propyl]-3-(2-trifluoromethylphenyl)ureido}ethoxy)phenyl]propionic acid,
2-ethoxy-3-[4-(2-{1-[3-(4-fluorophenoxy)propyl]-3-(2-trifluoromethylphenyl)ureido}ethoxy)phenyl]propionic acid,
3-[4-(2-{1-[3-(3,5-dichlorophenoxy)propyl]-3-(2-trifluoromethylphenyl)ureido}ethoxy)phenyl]-2-ethoxypropionic acid,
2-ethoxy-3-[4-(2-{1-[4-(4-fluorophenoxy)butyl]-3-(2-trifluoromethylphenyl)ureido}ethoxy)phenyl]propionic acid,
3-[4-(2-{1-[4-(3,5-dichlorophenoxy)butyl]-3-(2-trifluoromethylphenyl)ureido}ethoxy)phenyl]-2-ethoxypropionic acid,
2-ethoxy-3-[4-(2-{1-[2-(4-fluorobenzyloxy)ethyl]-3-(2-trifluoromethylphenyl)ureido}ethoxy)phenyl]propionic acid,
3-[4-(2-{1-[2-(3,5-dichlorobenzyloxy)ethyl]-3-(2-trifluoromethylphenyl)ureido}ethoxy)phenyl]-2-ethoxypropionic acid,
2-ethoxy-3-[4-(2-{1-[3-(4-fluorobenzyloxy)propyl]-3-(2-trifluoromethylphenyl)ureido}ethoxy)phenyl]propionic acid,
3-[4-(2-{1-[3-(3,5-dichlorobenzyloxy)propyl]-3-(2-trifluoromethylphenyl)ureido}ethoxy)phenyl]-2-ethoxypropionic acid,
2-ethoxy-3-[4-(2-{1-[4-(4-fluorobenzyloxy)butyl]-3-(2-trifluoromethylphenyl)ureido}ethoxy)phenyl]propionic acid,
3-[4-(2-{1-[4-(3,5-dichlorobenzyloxy)butyl]-3-(2-trifluoromethylphenyl)ureido}ethoxy)phenyl]-2-ethoxypropionic acid,
2-ethoxy-3-[4-(2-{1-[3-(4-fluorophenyl)propyl]-3-(2-trifluoromethylphenyl)ureido}ethoxy)phenyl]propionic acid,
3-[4-(2-{1-[3-(3,5-dichlorophenyl)propyl]-3-(2-trifluoromethylphenyl)ureido}ethoxy)phenyl]-2-ethoxypropionic acid,
2-ethoxy-3-(4-{2-[1-pentyl-3-(3-trifluoromethylphenyl)ureido]ethoxy}phenyl)propionic acid,
2-ethoxy-3-(4-{2-[1-hexyl-3-(3-trifluoromethylphenyl)ureido]ethoxy}phenyl)propionic acid,
2-ethoxy-3-(4-{2-[1-heptyl-3-(3-trifluoromethylphenyl)ureido]ethoxy}phenyl)propionic acid,
2-ethoxy-3-(4-{2-[1-octyl-3-(3-trifluoromethylphenyl)ureido]ethoxy}phenyl)propionic acid,
2-ethoxy-3-(4-{2-[1-isobutyl-3-(3-trifluoromethylphenyl)ureido]ethoxy}phenyl)propionic acid,
2-ethoxy-3-(4-{2-[1-(3-methylbutyl)-3-(3-trifluoromethylphenyl)ureido]ethoxy}phenyl)propionic acid,
2-ethoxy-3-(4-{2-[1-(4-methylpentyl)-3-(3-trifluoromethylphenyl)ureido]ethoxy}phenyl)propionic acid,
2-ethoxy-3-(4-{2-[1-(2-propylpentyl)-3-(3-trifluoromethylphenyl)ureido]ethoxy}phenyl)propionic acid,
3-(4-{2-[1-(3,3-dimethylbutyl)-3-(3-trifluoromethylphenyl)ureido]ethoxy}phenyl)-2-ethoxypropionic acid,
2-ethoxy-3-(4-{2-[1-(2-ethylbutyl)-3-(3-trifluoromethylphenyl)ureido]ethoxy}phenyl)propionic acid,
3-(4-{2-[1-cyclohexylmethyl-3-(3-trifluoromethylphenyl)ureido]ethoxy}phenyl)-2-ethoxypropionic acid,
3-(4-{2-[1-(4-cyclohexylbutyl)-3-(3-trifluoromethylphenyl)ureido]ethoxy}phenyl)-2-ethoxypropionic acid,
3-(4-{2-[1-cyclopropylmethyl-3-(3-trifluoromethylphenyl)ureido]ethoxy}phenyl)-2 -ethoxypropionic acid,
3-(4-{2-[1-cyclobutylmethyl-3-(3-trifluoromethylphenyl)ureido]ethoxy}phenyl)-2-ethoxypropionic acid,
3-(4-{2-[1-cyclopentylmethyl-3-(3-trifluoromethylphenyl)ureido]ethoxy}phenyl)-2-ethoxypropionic acid,
3-(4-{2-[1-(2-cyclopentylethyl)-3-(3-trifluoromethylphenyl)ureido]ethoxy}phenyl)-2-ethoxypropionic acid,
3-(4-{2-[1-(3-cyclohexylpropyl)-3-(3-trifluoromethylphenyl)ureido]ethoxy}phenyl)-2-ethoxypropionic acid,
2-ethoxy-3-(4-{2-[1-(3-phenylpropyl)-3-(3-trifluoromethylphenyl)ureido]ethoxy}phenyl)propionic acid,
2-ethoxy-3-(4-{2-[1-(4-phenylbutyl)-3-(3-trifluoromethylphenyl)ureido]ethoxy}phenyl)propionic acid,
3-(4-{2-[1-(2-butoxyethyl)-3-(3-trifluoromethylphenyl)ureido]ethoxy}phenyl)-2-ethoxypropionic acid, 2-ethoxy-3-(4-{2-[1-(2-pentyloxyethyl)-3-(3-trifluoromethylphenyl)ureido]ethoxy}phenyl)propionic acid,
2-ethoxy-3-(4-{2-[1-(3-propoxypropyl)-3-(3-trifluoromethylphenyl)ureido]ethoxy}phenyl)propionic acid,
3-(4-{2-[1-(2-butylthioethyl)-3-(3-trifluoromethylphenyl)ureido]ethoxy}phenyl)-2-ethoxypropionic acid,
2-ethoxy-3-(4-{2-[1-(2-pentylthioethyl)-3-(3-trifluoromethylphenyl)ureido]ethoxy}phenyl)propionic acid,
2-ethoxy-3-(4-{2-[1-(3-propylthiopropyl)-3-(3-trifluoromethylphenyl)ureido]ethoxy}phenyl)propionic acid,
2-ethoxy-3-(4-{2-[1-(3-phenoxypropyl)-3-(3-trifluoromethylphenyl)ureido]ethoxy}phenyl)propionic acid,
2-ethoxy-3-(4-{2-[1-(4-phenoxybutyl)-3-(3-trifluoromethylphenyl)ureido]ethoxy}phenyl)propionic acid,
3-(4-{2-[1-(3-benzyloxypropyl)-3-(3-trifluoromethylphenyl)ureido]ethoxy}phenyl)-2-ethoxypropionic acid,
2-ethoxy-3-(4-{2-[1-(3-phenylthiopropyl)-3-(3-trifluoromethylphenyl)ureido]ethoxy}phenyl)propionic acid,
2-ethoxy-3-(4-{2-[1-(4-phenylthiobutyl)-3-(3-trifluoromethylphenyl)ureido]ethoxy}phenyl)propionic acid,
3-(4-{2-[1-(3-benzylthiopropyl)-3-(3-trifluoromethylphenyl)ureido]ethoxy}phenyl)-2-ethoxypropionic acid,
2-ethoxy-3-(4-{2-[1-(7,7,7-trifluoroheptyl)-3-(3-trifluoromethylphenyl)ureido]ethoxy}phenyl)propionic acid,
3-(4-{2-[1-(6,6-difluoroheptyl)-3-(3-trifluoromethylphenyl)ureido]ethoxy}phenyl)-2-ethoxypropionic acid,
2-ethoxy-3-(4-{2-[1-(6,6,6-trifluorohexyl)-3-(3-trifluoromethylphenyl)ureido]ethoxy}phenyl)propionic acid,
3-(4-{2-[1-(5,5-difluorohexyl)-3-(3-trifluoromethylphenyl)ureido]ethoxy}phenyl)-2-ethoxypropionic acid,
2-ethoxy-3-(4-{2-[1-(5,5,6,6,7,7,7-heptafluoroheptyl)-3-(3-trifluoromethylphenyl)ureido]ethoxy}phenyl)propionic acid,
2-ethoxy-3-(4-{2-[1-(2,2,3,3,4,4,5,5,6,6,7,7,7-tridecafluoroheptyl)-3-(3-trifluoromethylphenyl)ureido]ethoxy}phenyl)propionic acid,
2-ethoxy-3-(4-{2-[1-(5,5,6,6,6-pentafluorohexyl)-3-(3-trifluoromethylphenyl)ureido]ethoxy}phenyl)propionic acid,
2-ethoxy-3-(4-{2-[3-(3-trifluoromethylphenyl)-1-(2,2,3,3,4,4,5,5,6,6-undecafluorohexyl)ureido]ethoxy}phenyl)propionic acid,
3-[4-(2-{1-[2-(2,2-difluoropropoxy)ethyl]-3-(3-trifluoromethylphenyl)ureido}ethoxy)phenyl]-2-ethoxypropionic acid,
2-ethoxy-3-[4-(2-{1-[2-(1,1,2,2,3,3,3-heptafluoropropoxy)ethyl]-3-(3-trifluoromethylphenyl)ureido}ethoxy)phenyl]propionic acid,
2-ethoxy-3-[4-(2-{1-[2-(4,4,4-trifluorobutoxy)ethyl]-3-(3-trifluoromethylphenyl)ureido}ethoxy)phenyl]propionic acid,
3-[4-(2-{1-[2-(3,3-difluorobutoxy)ethyl]-3-(3-trifluoromethylphenyl)ureido}ethoxy)phenyl]-2-ethoxypropionic acid,
3-[4-(2-{1-[2-(2,2-difluorobutoxy)ethyl]-3-(3-trifluoromethylphenyl)ureido}ethoxy)phenyl]-2-ethoxypropionic acid,
2-ethoxy-3-[4-(2-{1-[2-(1,1,2,2,3,3,4,4,4-nonafluorobutoxy)ethyl]-3-(3-trifluoromethylphenyl)ureido}ethoxy)phenyl]propionic acid,
2-ethoxy-3-[4-(2-{1-[3-(2,2,2-trifluoroethoxy)propyl]-3-(3-trifluoromethylphenyl)ureido}ethoxy)phenyl]propionic acid,
2-ethoxy-3-[4-(2-{1-[3-(1,1,2,2,2-pentafluoroethoxy)propyl]-3-(3-trifluoromethylphenyl)ureido}ethoxy)phenyl]propionic acid,
2-ethoxy-3-[4-(2-{1-[3-(4-fluorophenoxy)propyl]-3-(3-trifluoromethylphenyl)ureido}ethoxy)phenyl]propionic acid,
3-[4-(2-{1-[3-(3,5-dichlorophenoxy)propyl]-3-(3-trifluoromethylphenyl)ureido}ethoxy)phenyl]-2-ethoxypropionic acid,
2-ethoxy-3-[4-(2-{1-[4-(4-fluorophenoxy)butyl]-3-(3-trifluoromethylphenyl)ureido}ethoxy)phenyl]propionic acid,
3-[4-(2-{1-[4-(3,5-dichlorophenoxy)butyl]-3-(3-trifluoromethylphenyl)ureido}ethoxy)phenyl]-2-ethoxypropionic acid,
2-ethoxy-3-[4-(2-{1-[2-(4-fluorobenzyloxy)ethyl]-3-(3-trifluoromethylphenyl)ureido}ethoxy)phenyl]propionic acid,
3-[4-(2-{1-[2-(3,5-dichlorobenzyloxy)ethyl]-3-(3-trifluoromethylphenyl)ureido}ethoxy)phenyl]-2-ethoxypropionic acid,
2-ethoxy-3-[4-(2-{1-[3-(4-fluorobenzyloxy)propyl]-3-(3-trifluoromethylphenyl)ureido}ethoxy)phenyl]propionic acid,
3-[4-(2-{1-[3-(3,5-dichlorobenzyloxy)propyl]-3-(3-trifluoromethylphenyl)ureido}ethoxy)phenyl]-2-ethoxypropionic acid,
2-ethoxy-3-[4-(2-{1-[4-(4-fluorobenzyloxy)butyl]-3-(3-trifluoromethylphenyl)ureido}ethoxy)phenyl]propionic acid,
3-[4-(2-{1-[4-(3,5-dichlorobenzyloxy)butyl]-3-(3-trifluoromethylphenyl)ureido}ethoxy)phenyl]-2-ethoxypropionic acid,
2-ethoxy-3-[4-(2-{1-[3-(4-fluorophenyl)propyl]-3-(3-trifluoromethylphenyl)ureido}ethoxy)phenyl]propionic acid,
3-[4-(2-{1-[3-(3,5-dichlorophenyl)propyl]-3-(3-trifluoromethylphenyl)ureido}ethoxy)phenyl]-2-ethoxypropionic acid,
2-ethoxy-3-(4-{2-[1-pentyl-3-(4-trifluoromethylphenyl)ureido]ethoxy}phenyl)propionic acid,
2-ethoxy-3-(4-{2-[1-hexyl-3-(4-trifluoromethylphenyl)ureido]ethoxy}phenyl)propionic acid,
2-ethoxy-3-(4-{2-[1-heptyl-3-(4-trifluoromethylphenyl)ureido]ethoxy}phenyl)propionic acid,
2-ethoxy-3-(4-{2-[1-octyl-3-(4-trifluoromethylphenyl)ureido]ethoxy}phenyl)propionic acid,
2-ethoxy-3-(4-{2-[1-isobutyl-3-(4-trifluoromethylphenyl)ureido]ethoxy}phenyl)propionic acid,
2-ethoxy-3-(4-{2-[1-(3-methylbutyl)-3-(4-trifluoromethylphenyl)ureido]ethoxy}phenyl)propionic acid,
2-ethoxy-3-(4-{2-[1-(4-methylpentyl)-3-(4-trifluoromethylphenyl)ureido]ethoxy}phenyl)propionic acid,
2-ethoxy-3-(4-{2-[1-(2-propylpentyl)-3-(4-trifluoromethylphenyl)ureido]ethoxy}phenyl)propionic acid,
3-(4-{2-[1-(3,3-dimethylbutyl)-3-(4-trifluoromethylphenyl)ureido]ethoxy}phenyl)-2-ethoxypropionic acid,
2-ethoxy-3-(4-{2-[1-(2-ethylbutyl)-3-(4-trifluoromethylphenyl)ureido]ethoxy}phenyl)propionic acid,
3-(4-{2-[1-cyclohexylmethyl-3-(4-trifluoromethylphenyl)ureido]ethoxy}phenyl)-2-ethoxypropionic acid,
3-(4-{2-[1-(4-cyclohexylbutyl)-3-(4-trifluoromethylphenyl)ureido]ethoxy}phenyl)-2-ethoxypropionic acid,
3-(4-{2-[1-cyclopropylmethyl-3-(4-trifluoromethylphenyl)ureido]ethoxy}phenyl)-2-ethoxypropionic acid,
3-(4-{2-[1-cyclobutylmethyl-3-(4-trifluoromethylphenyl)ureido]ethoxy}phenyl)-2-ethoxypropionic acid,
3-(4-{2-[1-cyclopentylmethyl-3-(4-trifluoromethylphenyl)ureido]ethoxy}phenyl)-2-ethoxypropionic acid, 3-(4-{2-[1-(2-cyclopentylethyl)-3-(4-trifluoromethylphenyl)ureido]ethoxy}phenyl)-2-ethoxypropionic acid,
3-(4-{2-[1-(3-cyclohexylpropyl)-3-(4-trifluoromethylphenyl)ureido]ethoxy}phenyl)-2-ethoxypropionic acid,
2-ethoxy-3-(4-{2-[1-(3-phenylpropyl)-3-(4-trifluoromethylphenyl)ureido]ethoxy}phenyl)propionic acid,
2-ethoxy-3-(4-{2-[1-(4-phenylbutyl)-3-(4-trifluoromethylphenyl)ureido]ethoxy}phenyl)propionic acid,
3-(4-{2-[1-(2-butoxyethyl)-3-(4-trifluoromethylphenyl)ureido]ethoxy}phenyl)-2-ethoxypropionic acid,
2-ethoxy-3-(4-{2-[1-(2-pentyloxyethyl)-3-(4-trifluoromethylphenyl)ureido]ethoxy}phenyl)propionic acid,
2-ethoxy-3-(4-{2-[1-(3-propoxypropyl)-3-(4-trifluoromethylphenyl)ureido]ethoxy}phenyl)propionic acid,
3-(4-{2-[1-(2-butylthioethyl)-3-(4-trifluoromethylphenyl)ureido]ethoxy}phenyl)-2-ethoxypropionic acid,
2-ethoxy-3-(4-{2-[1-(2-pentylthioethyl)-3-(4-trifluoromethylphenyl)ureido]ethoxy}phenyl)propionic acid,
2-ethoxy-3-(4-{2-[1-(3-propylthiopropyl)-3-(4-trifluoromethylphenyl)ureido]ethoxy}phenyl)propionic acid,
2-ethoxy-3-(4-{2-[1-(3-phenoxypropyl)-3-(4-trifluoromethylphenyl)ureido]ethoxy}phenyl)propionic acid,
2-ethoxy-3-(4-{2-[1-(4-phenoxybutyl)-3-(4-trifluoromethylphenyl)ureido]ethoxy}phenyl)propionic acid,
3-(4-{2-[1-(3-benzyloxypropyl)-3-(4-trifluoromethylphenyl)ureido]ethoxy}phenyl)-2-ethoxypropionic acid,
2-ethoxy-3-(4-{2-[1-(3-phenylthiopropyl)-3-(4-trifluoromethylphenyl)ureido]ethoxy}phenyl)propionic acid,
2-ethoxy-3-(4-{2-[1-(4-phenylthiobutyl)-3-(4-trifluoromethylphenyl)ureido]ethoxy}phenyl)propionic acid,
3-(4-{2-[1-(3-benzylthiopropyl)-3-(4-trifluoromethylphenyl)ureido]ethoxy}phenyl)-2-ethoxypropionic acid,
2-ethoxy-3-(4-{2-[1-(7,7,7-trifluoroheptyl)-3-(4-trifluoromethylphenyl)ureido]ethoxy}phenyl)propionic acid,
3-(4-{2-[1-(6,6-difluoroheptyl)-3-(4-trifluoromethylphenyl)ureido]ethoxy}phenyl)-2-ethoxypropionic acid,
2-ethoxy-3-(4-{2-[1-(6,6,6-trifluorohexyl)-3-(4-trifluoromethylphenyl)ureido]ethoxy}phenyl)propionic acid,
3-(4-{2-[1-(5,5-difluorohexyl)-3-(4-trifluoromethylphenyl)ureido]ethoxy}phenyl)-2-ethoxypropionic acid,
2-ethoxy-3-(4-{2-[1-(5,5,6,6,7,7,7-heptafluoroheptyl)-3-(4-trifluoromethylphenyl)ureido]ethoxy}phenyl)propionic acid,
2-ethoxy-3-(4-{2-[1-(2,2,3,3,4,4,5,5,6,6,7,7,7-tridecafluoroheptyl)-3-(4-trifluoromethylphenyl)ureido]ethoxy}phenyl)propionic acid,
2-ethoxy-3-(4-{2-[1-(5,5,6,6,6-pentafluorohexyl)-3-(4-trifluoromethylphenyl)ureido]ethoxy}phenyl)propionic acid,
2-ethoxy-3-(4-{2-[3-(4-trifluoromethylphenyl)-1-(2,2,3,3,4,4,5,5,6,6-undecafluorohexyl)ureido]ethoxy}phenyl)propionic acid,
3-[4-(2-{1-[2-(2,2-difluoropropoxy)ethyl]-3-(4-trifluoromethylphenyl)ureido}ethoxy)phenyl]-2-ethoxypropionic acid,
2-ethoxy-3-[4-(2-{1-[2-(1,1,2,2,3,3,3-heptafluoropropoxy)ethyl]-3-(4-trifluoromethylphenyl)ureido}ethoxy)phenyl]propionic acid,
2-ethoxy-3-[4-(2-{1-[2-(4,4,4-trifluorobutoxy)ethyl]-3-(4-trifluoromethylphenyl)ureido}ethoxy)phenyl]propionic acid,
3-[4-(2-{1-[2-(3,3-difluorobutoxy)ethyl]-3-(4-trifluoromethylphenyl)ureido}ethoxy)phenyl]-2-ethoxypropionic acid,
3-[4-(2-{1-[2-(2,2-difluorobutoxy)ethyl]-3-(4-trifluoromethylphenyl)ureido}ethoxy)phenyl]-2-ethoxypropionic acid,
2-ethoxy-3-[4-(2-{1-[2-(1,1,2,2,3,3,4,4,4-nonafluorobutoxy)ethyl]-3-(4-trifluoromethylphenyl)ureido}ethoxy)phenyl]propionic acid,
2-ethoxy-3-[4-(2-{1-[3-(2,2,2-trifluoroethoxy)propyl]-3-(4-trifluoromethylphenyl)ureido}ethoxy)phenyl]propionic acid,
2-ethoxy-3-[4-(2-{1-[3-(1,2,2,2-pentafluoroethoxy)propyl]-3-(4-trifluoromethylphenyl)ureido}ethoxy)phenyl]propionic acid,
2-ethoxy-3-[4-(2-{1-[3-(4-fluorophenoxy)propyl]-3-(4-trifluoromethylphenyl)ureido}ethoxy)phenyl]propionic acid,
3-[4-(2-{1-[3-(3,5-dichlorophenoxy)propyl]-3-(4-trifluoromethylphenyl)ureido}ethoxy)phenyl]-2-ethoxypropionic acid,
2-ethoxy-3-[4-(2-{1-[4-(4-fluorophenoxy)butyl]-3-(4-trifluoromethylphenyl)ureido}ethoxy)phenyl]propionic acid,
3-[4-(2-{1-[4-(3,5-dichlorophenoxy)butyl]-3-(4-trifluoromethylphenyl)ureido}ethoxy)phenyl]-2-ethoxypropionic acid,
2-ethoxy-3-[4-(2-{1-[2-(4-fluorobenzyloxy)ethyl]-3-(4-trifluoromethylphenyl)ureido}ethoxy)phenyl]propionic acid,
3-[4-(2-{1-[2-(3,5-dichlorobenzyloxy)ethyl]-3-(4-trifluoromethylphenyl)ureido}ethoxy)phenyl]-2-ethoxypropionic acid,
2-ethoxy-3-[4-(2-{1-[3-(4-fluorobenzyloxy)propyl]-3-(4-trifluoromethylphenyl)ureido}ethoxy)phenyl]propionic acid,
3-[4-(2-{1-[3-(3,5-dichlorobenzyloxy)propyl]-3-(4-trifluoromethylphenyl)ureido}ethoxy)phenyl]-2-ethoxypropionic acid,
2-ethoxy-3-[4-(2-{1-[4-(4-fluorobenzyloxy)butyl]-3-(4-trifluoromethylphenyl)ureido}ethoxy)phenyl]propionic acid,
3-[4-(2-{1-[4-(3,5-dichlorobenzyloxy)butyl]-3-(4-trifluoromethylphenyl)ureido}ethoxy)phenyl]-2-ethoxypropionic acid,
2-ethoxy-3-[4-(2-{1-[3-(4-fluorophenyl)propyl]-3-(4-trifluoromethylphenyl)ureido}ethoxy)phenyl]propionic acid,
3-[4-(2-{1-[3-(3,5-dichlorophenyl)propyl]-3-(4-trifluoromethylphenyl)ureido}ethoxy)phenyl]-2-ethoxypropionic acid,
2-ethoxy-3-(4-{2-[1-pentyl-3-(2-trifluoromethoxyphenyl)ureido]ethoxy}phenyl)propionic acid,
2-ethoxy-3-(4-{2-[1-hexyl-3-(2-trifluoromethoxyphenyl)ureido]ethoxy}phenyl)propionic acid,
2-ethoxy-3-(4-{2-[1-heptyl-3-(2-trifluoromethoxyphenyl)ureido]ethoxy}phenyl)propionic acid,
2-ethoxy-3-(4-{2-[1-octyl-3-(2-trifluoromethoxyphenyl)ureido]ethoxy}phenyl)propionic acid,
2-ethoxy-3-(4-{2-[1-isobutyl-3-(2-trifluoromethoxyphenyl)ureido]ethoxy}phenyl)propionic acid,
2-ethoxy-3-(4-{2-[1-(3-methylbutyl)-3-(2-trifluoromethoxyphenyl)ureido]ethoxy}phenyl)propionic acid,
2-ethoxy-3-(4-{2-[1-(4-methylpentyl)-3-(2-trifluoromethoxyphenyl)ureido]ethoxy}phenyl)propionic acid,
2-ethoxy-3-(4-{2-[1-(2-propylpentyl)-3-(2-trifluoromethoxyphenyl)ureido]ethoxy}phenyl)propionic acid,
3-(4-{2-[1-(3,3-dimethylbutyl)-3-(2-trifluoromethoxyphenyl)ureido]ethoxy}phenyl)-2-ethoxypropionic acid,
2-ethoxy-3-(4-{2-[1-(2-ethylbutyl)-3-(2-trifluoromethoxyphenyl)ureido]ethoxy}phenyl)propionic acid,
3-(4-{2-[1-cyclohexylmethyl-3-(2-trifluoromethoxyphenyl)ureido]ethoxy}phenyl)-2-ethoxypropionic acid, 3-(4-{2-[1-(4-cyclohexylbutyl)-3-(2-trifluoromethoxyphenyl)ureido]ethoxy}phenyl)-2-ethoxypropionic acid,
3-(4-{2-[1-cyclopropylmethyl-3-(2-trifluoromethoxyphenyl)ureido]ethoxy}phenyl)-2-ethoxypropionic acid,
3-(4-{2-[1-cyclobutylmethyl-3-(2-trifluoromethoxyphenyl)ureido]ethoxy}phenyl)-2-ethoxypropionic acid,
3-(4-{2-[1-cyclopentylmethyl-3-(2-trifluoromethoxyphenyl)ureido]ethoxy}phenyl)-2-ethoxypropionic acid,
3-(4-{2-[1-(2-cyclopentylethyl)-3-(2-trifluoromethoxyphenyl)ureido]ethoxy}phenyl)-2-ethoxypropionic acid,
3-(4-{2-[1-(3-cyclohexylpropyl)-3-(2-trifluoromethoxyphenyl)ureido]ethoxy}phenyl)-2-ethoxypropionic acid,
2-ethoxy-3-(4-{2-[1-(3-phenylpropyl)-3-(2-trifluoromethoxyphenyl)ureido]ethoxy}phenyl)propionic acid,
2-ethoxy-3-(4-{2-[1-(4-phenylbutyl)-3-(2-trifluoromethoxyphenyl)ureido]ethoxy}phenyl)propionic acid,
3-(4-{2-[1-(2-butoxyethyl)-3-(2-trifluoromethoxyphenyl)ureido]ethoxy}phenyl)-2-ethoxypropionic acid,
2-ethoxy-3-(4-{2-[1-(2-pentyloxyethyl)-3-(2-trifluoromethoxyphenyl)ureido]ethoxy}phenyl)propionic acid,
2-ethoxy-3-(4-{2-[1-(3-propoxypropyl)-3-(2-trifluoromethoxyphenyl)ureido]ethoxy}phenyl)propionic acid,
3-(4-{2-[1-(2-butylthioethyl)-3-(2-trifluoromethoxyphenyl)ureido]ethoxy}phenyl)-2-ethoxypropionic acid,
2-ethoxy-3-(4-{2-[1-(2-pentylthioethyl)-3-(2-trifluoromethoxyphenyl)ureido]ethoxy}phenyl)propionic acid,
2-ethoxy-3-(4-{2-[1-(3-propylthiopropyl)-3-(2-trifluoromethoxyphenyl)ureido]ethoxy}phenyl)propionic acid,
2-ethoxy-3-(4-{2-[1-(3-phenoxypropyl)-3-(2-trifluoromethoxyphenyl)ureido]ethoxy}phenyl)propionic acid,
2-ethoxy-3-(4-{2-[1-(4-phenoxybutyl)-3-(2-trifluoromethoxyphenyl)ureido]ethoxy}phenyl)propionic acid,
3-(4-{2-[1-(3-benzyloxypropyl)-3-(2-trifluoromethoxyphenyl)ureido]ethoxy}phenyl)-2-ethoxypropionic acid,
2-ethoxy-3-(4-{2-[1-(3-phenylthiopropyl)-3-(2-trifluoromethoxyphenyl)ureido]ethoxy}phenyl)propionic acid,
2-ethoxy-3-(4-{2-[1-(4-phenylthiobutyl)-3-(2-trifluoromethoxyphenyl)ureido]ethoxy}phenyl)propionic acid,
3-(4-{2-[1-(3-benzylthiopropyl)-3-(2-trifluoromethoxyphenyl)ureido]ethoxy}phenyl)-2-ethoxypropionic acid,
2-ethoxy-3-(4-{2-[1-(7,7,7-trifluoroheptyl)-3-(2-trifluoromethoxyphenyl)ureido]ethoxy}phenyl)propionic acid,
3-(4-{2-[1-(6,6-difluoroheptyl)-3-(2-trifluoromethoxyphenyl)ureido]ethoxy}phenyl)-2-ethoxypropionic acid,
2-ethoxy-3-(4-{2-[1-(6,6,6-trifluorohexyl)-3-(2-trifluoromethoxyphenyl)ureido]ethoxy}phenyl)propionic acid,
3-(4-{2-[1-(5,5-difluorohexyl)-3-(2-trifluoromethoxyphenyl)ureido]ethoxy}phenyl)-2-ethoxypropionic acid,
2-ethoxy-3-(4-{2-[1-(5,5,6,6,7,7,7-heptafluoroheptyl)-3-(2-trifluoromethoxyphenyl)ureido]ethoxy}phenyl)propionic acid,
2-ethoxy-3-(4-{2-[1-(2,2,3,3,4,4,5,5,6,6,7,7,7-tridecafluoroheptyl)-3-(2-trifluoromethoxyphenyl)ureido]ethoxy}phenyl)propionic acid,
2-ethoxy-3-(4-{2-[1-(5,5,6,6,6-pentafluorohexyl)-3-(2-trifluoromethoxyphenyl)ureido]ethoxy}phenyl)propionic acid,
2-ethoxy-3-(4-{2-[3-(2-trifluoromethoxyphenyl)-1-(2,2,3,3,4,4,5,5,6,6,6-undecafluorohexyl)ureido]ethoxy}phenyl)propionic acid,
3-[4-(2-{1-[2-(2,2-difluoropropoxy)ethyl]-3-(2-trifluoromethoxyphenyl)ureido}ethoxy)phenyl]-2-ethoxypropionic acid,
2-ethoxy-3-[4-(2-{1-[2-(1,1,2,2,3,3,3-heptafluoropropoxy)ethyl]-3-(2-trifluoromethoxyphenyl)ureido}ethoxy)phenyl]propionic acid,
2-ethoxy-3-[4-(2-{1-[2-(4,4,4-trifluorobutoxy)ethyl]-3-(2-trifluoromethoxyphenyl)ureido}ethoxy)phenyl]propionic acid,
3-[4-(2-{1-[2-(3,3-difluorobutoxy)ethyl]-3-(2-trifluoromethoxyphenyl)ureido}ethoxy)phenyl]-2-ethoxypropionic acid,
3-[4-(2-{1-[2-(2,2-difluorobutoxy)ethyl]-3-(2-trifluoromethoxyphenyl)ureido}ethoxy)phenyl]-2-ethoxypropionic acid,
2-ethoxy-3-[4-(2-{1-[2-(1,1,2,2,3,3,4,4,4-nonafluorobutoxy)ethyl]-3-(2-trifluoromethoxyphenyl)ureido}ethoxy)phenyl]propionic acid,
2-ethoxy-3-3-[4-(2-{1-[3-(2,2,2-trifluoroethoxy)propyl]-3-(2-trifluoromethoxyphenyl)ureido}ethoxy)phenyl]propionic acid,
2-ethoxy-3-[4-(2-{1-[3-(1,1,2,2,2-pentafluoroethoxy)propyl]-3-(2-trifluoromethoxyphenyl)ureido}ethoxy)phenyl]propionic acid,
2-ethoxy-3-[4-(2-{1-[3-(4-fluorophenoxy)propyl]-3-(2-trifluoromethoxyphenyl)ureido}ethoxy)phenyl]propionic acid,
3-[4-(2-{1-[4-(3,5-dichlorophenoxy)propyl]-3-(2-trifluoromethoxyphenyl)ureido}ethoxy)phenyl]-2-ethoxypropionic acid,
2-ethoxy-3-[4-(2-{1-[4-(4-fluorophenoxy)butyl]-3-(2-trifluoromethoxyphenyl)ureido}ethoxy)phenyl]propionic acid,
3-[4-(2-{1-[4-(3,5-dichlorophenoxy)butyl]-3-(2-trifluoromethoxyphenyl)ureido}ethoxy)phenyl]-2-ethoxypropionic acid,
2-ethoxy-3-[4-(2-{1-[2-(4-fluorobenzyloxy)ethyl]-3-(2-trifluoromethoxyphenyl)ureido}ethoxy)phenyl]propionic acid,
3-[4-(2-{1-[3-(3,5-dichlorobenzyloxy)ethyl]-3-(2-trifluoromethoxyphenyl)ureido}ethoxy)phenyl]-2-ethoxypropionic acid,
2-ethoxy-3-[4-(2-{1-[3-(4-fluorobenzyloxy)propyl]-3-(2-trifluoromethoxyphenyl)ureido}ethoxy)phenyl]propionic acid,
3-[4-(2-{1-[3-(3,5-dichlorobenzyloxy)propyl]-3-(2-trifluoromethoxyphenyl)ureido}ethoxy)phenyl]-2-ethoxypropionic acid,
2-ethoxy-3-[4-(2-4-(4-fluorobenzyloxy)butyl]-3-(2-trifluoromethoxyphenyl)ureido}ethoxy)phenyl]propionic acid,
3-[4-(2-{1-[4-(3,5-dichlorobenzyloxy)butyl]-3-(2-trifluoromethoxyphenyl)ureido}ethoxy)phenyl]-2-ethoxypropionic acid,
2-ethoxy-3-[4-(2-{1-[3-(4-fluorophenyl)propyl]-3-(2-trifluoromethoxyphenyl)ureido}ethoxy)phenyl]propionic acid,
3-[4-(2-{1-[3-(3,5-dichlorophenyl)propyl]-3-(2-trifluoromethoxyphenyl)ureido}ethoxy)phenyl]-2-ethoxypropionic acid,
2-ethoxy-3-(4-{2-[1-pentyl-3-(4-trifluoromethoxyphenyl)ureido]ethoxy}phenyl)propionic acid,
2-ethoxy-3-(4-{2-[1-hexyl-3-(4-trifluoromethoxyphenyl)ureido]ethoxy}phenyl)propionic acid,
2-ethoxy-3-(4-{2-[1-heptyl-3-(4-trifluoromethoxyphenyl)ureido]ethoxy}phenyl)propionic acid,
2-ethoxy-3-(4-{2-[1-octyl-3-(4-trifluoromethoxyphenyl)ureido]ethoxy}phenyl)propionic acid,
2-ethoxy-3-(4-{2-[1-isobutyl-3-(4-trifluoromethoxyphenyl)ureido]ethoxy}phenyl)propionic acid,
2-ethoxy-3-(4-{2-[1-(3-methylbutyl)-3-(4-trifluoromethoxyphenyl)ureido]ethoxy}phenyl)propionic acid,
2-ethoxy-3-(4-{2-[1-(4-methylpentyl)-3-(4-trifluoromethoxyphenyl)ureido]ethoxy}phenyl)propionic acid, 2-ethoxy-3-(4-{2-[1-(2-propylpentyl)-3-(4-trifluoromethoxyphenyl)ureido]ethoxy}phenyl)propionic acid,
3-(4-{2-[1-(3,3-dimethylbutyl)-3-(4-trifluoromethoxyphenyl)ureido]ethoxy}phenyl)-2-ethoxypropionic acid,
2-ethoxy-3-(4-{2-[1-(2-ethylbutyl)-3-(4-trifluoromethoxyphenyl)ureido]ethoxy}phenyl)propionic acid,
3-(4-{2-[1-cyclohexylmethyl-3-(4-trifluoromethoxyphenyl)ureido]ethoxy}phenyl)-2-ethoxypropionic acid,
3-(4-{2-[1-(4-cyclohexylbutyl)-3-(4-trifluoromethoxyphenyl)ureido]ethoxy}phenyl)-2-ethoxypropionic acid,
3-(4-{2-[1-cyclopropylmethyl-3-(4-trifluoromethoxyphenyl)ureido]ethoxy}phenyl)-2-ethoxypropionic acid,
3-(4-{2-[1-cyclobutylmethyl-3-(4-trifluoromethoxyphenyl)ureido]ethoxy}phenyl)-2-ethoxypropionic acid,
3-(4-{2-[1-cyclopentylmethyl-3-(4-trifluoromethoxyphenyl)ureido]ethoxy}phenyl)-2-ethoxypropionic acid,
3-(4-{2-[1-(2-cyclopentylethyl)-3-(4-trifluoromethoxyphenyl)ureido]ethoxy}phenyl)-2-ethoxypropionic acid,
3-(4-{2-[1-(3-cyclohexylpropyl)-3-(4-trifluoromethoxyphenyl)ureido]ethoxy}phenyl)-2-ethoxypropionic acid,
2-ethoxy-3-(4-{2-[1-(3-phenylpropyl)-3-(4-trifluoromethoxyphenyl)ureido]ethoxy}phenyl)propionic acid,
2-ethoxy-3-(4-{2-[1-(4-phenylbutyl)-3-(4-trifluoromethoxyphenyl)ureido]ethoxy}phenyl)propionic acid,
3-(4-{2-[1-(2-butoxyethyl)-3-(4-trifluoromethoxyphenyl)ureido]ethoxy}phenyl)-2-ethoxypropionic acid,
2-ethoxy-3-(4-{2-[1-(2-pentyloxyethyl)-3-(4-trifluoromethoxyphenyl)ureido]ethoxy}phenyl)propionic acid,
2-ethoxy-3-(4-{2-[1-(3-propoxypropyl)-3-(4-trifluoromethoxyphenyl)ureido]ethoxy}phenyl)propionic acid,
3-(4-{2-[1-(2-butylthioethyl)-3-(4-trifluoromethoxyphenyl)ureido]ethoxy}phenyl)-2-ethoxypropionic acid,
2-ethoxy-3-(4-{2-[1-(2-pentylthioethyl)-3-(4-trifluoromethoxyphenyl)ureido]ethoxy}phenyl)propionic acid,
2-ethoxy-3-(4-{2-[1-(3-propylthiopropyl)-3-(4-trifluoromethoxyphenyl)ureido]ethoxy}phenyl)propionic acid,
2-ethoxy-3-(4-{2-[1-(3-phenoxypropyl)-3-(4-trifluoromethoxyphenyl)ureido]ethoxy}phenyl)propionic acid,
2-ethoxy-3-(4-{2-[1-(4-phenoxybutyl)-3-(4-trifluoromethoxyphenyl)ureido]ethoxy}phenyl)propionic acid,
3-(4-{2-[1-(3-benzyloxypropyl)-3-(4-trifluoromethoxyphenyl)ureido]ethoxy}phenyl)-2-ethoxypropionic acid,
2-ethoxy-3-(4-{2-[1-(3-phenylthiopropyl)-3-(4-trifluoromethoxyphenyl)ureido]ethoxy}phenyl)propionic acid,
2-ethoxy-3-(4-{2-[1-(4-phenylthiobutyl)-3-(4-trifluoromethoxyphenyl)ureido]ethoxy}phenyl)propionic acid,
3-(4-{2-[1-(3-benzylthiopropyl)-3-(4-trifluoromethoxyphenyl)ureido]ethoxy}phenyl)-2-ethoxypropionic acid,
2-ethoxy-3-(4-{2-[1-(7,7,7-trifluoroheptyl)-3-(4-trifluoromethoxyphenyl)ureido]ethoxy}phenyl)propionic acid,
3-(4-{2-[1-(6,6-difluoroheptyl)-3-(4-trifluoromethoxyphenyl)ureido]ethoxy}phenyl)-2-ethoxypropionic acid,
2-ethoxy-3-(4-{2-[1-(6,6,6-trifluorohexyl)-3-(4-trifluoromethoxyphenyl)ureido]ethoxy}phenyl)propionic acid,
3-(4-{2-[1-(5,5-difluorohexyl)-3-(4-trifluoromethoxyphenyl)ureido]ethoxy}phenyl)-2-ethoxypropionic acid,
2-ethoxy-3-(4-{2-[1-(5,5,6,6,7,7,7-heptafluoroheptyl)-3-(4-trifluoromethoxyphenyl)ureido]ethoxy}phenyl)propionic acid,
2-ethoxy-3-(4-{2-[1-(2,2,3,3,4,4,5,5,6,6,7,7,7-tridecafluoroheptyl)-3-(4-trifluoromethoxyphenyl)ureido]ethoxy}phenyl)propionic acid,
2-ethoxy-3-(4-{2-[1-(5,5,6,6,6-pentafluorohexyl)-3-(4-trifluoromethoxyphenyl)ureido]ethoxy}phenyl)propionic acid,
2-ethoxy-3-(4-{2-[3-(4-trifluoromethoxyphenyl)-1-(2,2,3,3,4,4,5,5,6,6,6-undecafluorohexyl)ureido]ethoxy}phenyl)propionic acid,
3-[4-(2-{1-[2-(2,2-difluoropropoxy)ethyl]-3-(4-trifluoromethoxyphenyl)ureido}ethoxy)phenyl]-2-ethoxypropionic acid,
2-ethoxy-3-[4-(2-{1-[2-(1,1,2,2,3,3,3-heptafluoropropoxy)ethyl]-3-(4-trifluoromethoxyphenyl)ureido}ethoxy)phenyl]propionic acid,
2-ethoxy-3-[4-(2-{1-[2-(4,4,4-trifluorobutoxy)ethyl]-3-(4-trifluoromethoxyphenyl)ureido}ethoxy)phenyl]propionic acid,
3-[4-(2-{1-[2-(3,3-difluorobutoxy)ethyl]-3-(4-trifluoromethoxyphenyl)ureido}ethoxy)phenyl]-2-ethoxypropionic acid,
3-[4-(2-{1-[2-(2,2-difluorobutoxy)ethyl]-3-(4-trifluoromethoxyphenyl)ureido}ethoxy)phenyl]-2-ethoxypropionic acid,
2-ethoxy-3-[4-(2-{1-[2-(1,1,2,2,3,3,4,4,4-nonafluorobutoxy)ethyl]-3-(4-trifluoromethoxyphenyl)ureido}ethoxy)phenyl]propionic acid,
2-ethoxy-3-[4-(2-{1-[3-(2,2,2-trifluoroethoxy)propyl]-3-(4-trifluoromethoxyphenyl)ureido}ethoxy)phenyl]propionic acid,
2-ethoxy-3-[4-(2-{1-[3-(1,1,2,2,2-pentafluoroethoxy)propyl]-3-(4-trifluoromethoxyphenyl)ureido}ethoxy)phenyl]propionic acid,
2-ethoxy-3-[4-(2-{1-[3-(4-fluorophenoxy)propyl]-3-(4-trifluoromethoxyphenyl)ureido}ethoxy)phenyl]propionic acid,
3-[4-(2-{1-[3-(3,5-dichlorophenoxy)propyl]-3-(4-trifluoromethoxyphenyl)ureido}ethoxy)phenyl]-2-ethoxypropionic acid,
2-ethoxy-3-[4-(2-{1-[4-(4-fluorophenoxy)butyl]-3-(4-trifluoromethoxyphenyl)ureido}ethoxy)phenyl]propionic acid,
3-[4-(2-{1-[4-(3,5-dichlorophenoxy)butyl]-3-(4-trifluoromethoxyphenyl)ureido}ethoxy)phenyl]-2-ethoxypropionic acid,
2-ethoxy-3-[4-(2-{1-[2-(4-fluorobenzyloxy)ethyl]-3-(4-trifluoromethoxyphenyl)ureido}ethoxy)phenyl]propionic acid,
3-[4-(2-{1-[2-(3,5-dichlorobenzyloxy)ethyl]-3-(4-trifluoromethoxyphenyl)ureido}ethoxy)phenyl]-2-ethoxypropionic acid,
2-ethoxy-3-[4-(2-{1-[3-(4-fluorobenzyloxy)propyl]-3-(4-trifluoromethoxyphenyl)ureido}ethoxy)phenyl]propionic acid,
3-[4-(2-{1-[3-(3,5-dichlorobenzyloxy)propyl]-3-(4-trifluoromethoxyphenyl)ureido}ethoxy)phenyl]-2-ethoxypropionic acid,
2-ethoxy-3-[4-(2-{1-[4-(4-fluorobenzyloxy)butyl]-3-(4-trifluoromethoxyphenyl)ureido}ethoxy)phenyl]propionic acid,
3-[4-(2-{1-[4-(3,5-dichlorobenzyloxy)butyl]-3-(4-trifluoromethoxyphenyl)ureido}ethoxy)phenyl]-2-ethoxypropionic acid,
2-ethoxy-3-[4-(2-{1-[3-(4-fluorophenyl)propyl]-3-(4-trifluoromethoxyphenyl)ureido}ethoxy)phenyl]propionic acid,
3-[4-(2-{1-[3-(3,5-dichlorophenyl)propyl]-3-(4-trifluoromethoxyphenyl)ureido}ethoxy)phenyl]-2-ethoxypropionic acid,
2-ethoxy-3-(4-{2-[3-(2-methoxyphenyl)-1-pentylureido]ethoxy}phenyl)propionic acid,
2-ethoxy-3-(4-{2-[1-hexyl-3-(2-methoxyphenyl)ureido]ethoxy}phenyl)propionic acid, 2-ethoxy-3-(4-{2-[1-heptyl-3-(2-methoxyphenyl)ureido]ethoxy}phenyl)propionic acid,
2-ethoxy-3-(4-{2-[3-(2-methoxyphenyl)-1-octylureido]ethoxy}phenyl)propionic acid,
2-ethoxy-3-(4-{2-[1-isobutyl-3-(2-methoxyphenyl)ureido]ethoxy}phenyl)propionic acid,
2-ethoxy-3-(4-{2-[1-(3-methylbutyl)-3-(2-methoxyphenyl)ureido]ethoxy}phenyl)propionic acid,
2-ethoxy-3-(4-{2-[1-(4-methylpentyl)-3-(2-methoxyphenyl)ureido]ethoxy}phenyl)propionic acid,
2-ethoxy-3-(4-{2-[3-(2-methoxyphenyl)-1-(2-propylpentyl)ureido]ethoxy}phenyl)propionic acid,
3-(4-{2-[1-(3,3-dimethylbutyl)-3-(2-methoxyphenyl)ureido]ethoxy}phenyl)-2-ethoxypropionic acid,
2-ethoxy-3-(4-{2-[1-(2-ethylbutyl)-3-(2-methoxyphenyl)ureido]ethoxy}phenyl)propionic acid,
3-(4-{2-[1-cyclohexylmethyl-3-(2-methoxyphenyl)ureido]ethoxy}phenyl)-2-ethoxypropionic acid,
3-(4-{2-[1-(4-cyclohexylbutyl)-3-(2-methoxyphenyl)ureido]ethoxy}phenyl)-2-ethoxypropionic acid,
3-(4-{2-[1-cyclopropylmethyl-3-(2-methoxyphenyl)ureido]ethoxy}phenyl)-2-ethoxypropionic acid,
3-(4-{2-[1-cyclobutylmethyl-3-(2-methoxyphenyl)ureido]ethoxy}phenyl)-2-ethoxypropionic acid,
3-(4-{2-[1-cyclopentylmethyl-3-(2-methoxyphenyl)ureido]ethoxy}phenyl)-2-ethoxypropionic acid,
3-(4-{2-[1-(2-cyclopentylethyl)-3-(2-methoxyphenyl)ureido]ethoxy}phenyl)-2-ethoxypropionic acid,
3-(4-{2-[1-(3-cyclohexylpropyl)-3-(2-methoxyphenyl)ureido]ethoxy}phenyl)-2-ethoxypropionic acid,
2-ethoxy-3-(4-{2-[3-(2-methoxyphenyl)-1-(3-phenylpropyl)ureido]ethoxy}phenyl)propionic acid,
2-ethoxy-3-(4-{2-[3-(2-methoxyphenyl)-1-(4-phenylbutyl)ureido]ethoxy}phenyl)propionic acid,
3-(4-{2-[1-(2-butoxyethyl)-3-(2-methoxyphenyl)ureido]ethoxy}phenyl)-2-ethoxypropionic acid,
2-ethoxy-3-(4-{2-[3-(2-methoxyphenyl)-1-(2-pentyloxyethyl)ureido]ethoxy}phenyl)propionic acid,
2-ethoxy-3-(4-{2-[3-(2-methoxyphenyl)-1-(3-propoxypropyl)ureido]ethoxy}phenyl)propionic acid,
3-(4-{2-[1-(2-butylthioethyl)-3-(2-methoxyphenyl)ureido]ethoxy}phenyl)-2-ethoxypropionic acid,
2-ethoxy-3-(4-{2-[3-(2-methoxyphenyl)-1-(2-pentylthioethyl)ureido]ethoxy}phenyl)propionic acid,
2-ethoxy-3-(4-{2-[3-(2-methoxyphenyl)-1-(3-propylthiopropyl)ureido]ethoxy}phenyl)propionic acid,
2-ethoxy-3-(4-{2-[3-(2-methoxyphenyl)-1-(3-phenoxypropyl)ureido]ethoxy}phenyl)propionic acid,
2-ethoxy-3-(4-{2-[3-(2-methoxyphenyl)-1-(4-phenoxybutyl)ureido]ethoxy}phenyl)propionic acid,
3-(4-{2-[1-(3-benzyloxypropyl)-3-(2-methoxyphenyl)ureido]ethoxy}phenyl)-2-ethoxypropionic acid,
2-ethoxy-3-(4-{2-[3-(2-methoxyphenyl)-1-(3-phenylthiopropyl)ureido]ethoxy}phenyl)propionic acid,
2-ethoxy-3-(4-{2-[3-(2-methoxyphenyl)-1-(4-phenylthiobutyl)ureido]ethoxy}phenyl)propionic acid,
3-(4-{2-[1-(3-benzylthiopropyl)-3-(2-methoxyphenyl)ureido]ethoxy}phenyl)-2-ethoxypropionic acid,
2-ethoxy-3-(4-{2-[3-(2-methoxyphenyl)-1-(7,7,7-trifluoroheptyl)ureido]ethoxy}phenyl)propionic acid,
3-(4-{2-[1-(6,6-difluoroheptyl)-3-(2-methoxyphenyl)ureido]ethoxy}phenyl)-2-ethoxypropionic acid,
2-ethoxy-3-(4-{2-[3-(2-methoxyphenyl)-1-(6,6,6-trifluorohexyl)ureido]ethoxy}phenyl)propionic acid,
3-(4-{2-[1-(5,5-difluorohexyl)-3-(2-methoxyphenyl)ureido]ethoxy}phenyl)-2-ethoxypropionic acid,
2-ethoxy-3-(4-{2-[1-(5,5,6,6,7,7,7-heptafluoroheptyl)-3-(2-methoxyphenyl)ureido]ethoxy}phenyl)propionic acid,
2-ethoxy-3-(4-{2-[3-(2-methoxyphenyl)-1-(2,2,3,3,4,4,5,5,6,6,7,7,7-tridecafluoroheptyl)ureido]ethoxy}phenyl)propionic acid,
2-ethoxy-3-(4-{2-[3-(2-methoxyphenyl)-1-(5,5,6,6,6-pentafluorohexyl)ureido]ethoxy}phenyl)propionic acid,
2-ethoxy-3-(4-{2-[3-(2-methoxyphenyl)-1-(2,2,3,3,4,4,5,5,6,6,6-undecafluorohexyl)ureido]ethoxy}phenyl)propionic acid,
3-[4-(2-{1-[2-(2,2-difluoropropoxy)ethyl]-3-(2-methoxyphenyl)ureido}ethoxy)phenyl]-2-ethoxypropionic acid,
2-ethoxy-3-[4-(2-{1-[2-(1,1,2,2,3,3,3-heptafluoropropoxy)ethyl]-3-(2-methoxyphenyl)ureido}ethoxy)phenyl]propionic acid,
2-ethoxy-3-[4-(2-{3-(2-methoxyphenyl)-1-[2-(4,4,4-trifluorobutoxy)ethyl]ureido}ethoxy)phenyl]propionic acid,
3-[4-(2-{1-[2-(3,3-difluorobutoxy)ethyl]-3-(2-methoxyphenyl)ureido}ethoxy)phenyl]-2-ethoxypropionic acid,
3-[4-(2-{1-[2-(2,2-difluorobutoxy)ethyl]-3-(2-methoxyphenyl)ureido}ethoxy)phenyl]-2-ethoxypropionic acid,
2-ethoxy-3-[4-(2-{3-(2-methoxyphenyl)-1-[2-(1,1,2,2,3,3,4,4,4-nonafluorobutoxy)ethyl]ureido}ethoxy)phenyl]propionic acid,
2-ethoxy-3-[4-(2-{3-(2-methoxyphenyl)-1-[3-(2,2,2-trifluoroethoxy)propyl]ureido}ethoxy)phenyl]propionic acid,
2-ethoxy-3-[4-(2-{3-(2-methoxyphenyl)-1-[3-(1,1,2,2,2-pentafluoroethoxy)propyl]ureido}ethoxy)phenyl]propionic acid,
2-ethoxy-3-[4-(2-{1-[3-(4-fluorophenoxy)propyl]-3-(2-methoxyphenyl)ureido}ethoxy)phenyl]propionic acid,
3-[4-(2-{1-[3-(3,5-dichlorophenoxy)propyl]-3-(2-methoxyphenyl)ureido}ethoxy)phenyl]-2-ethoxypropionic acid,
2-ethoxy-3-[4-(2-{1-[4-(4-fluorophenoxy)butyl]-3-(2-methoxyphenyl)ureido}ethoxy)phenyl]propionic acid,
3-[4-(2-{1-[4-(3,5-dichlorophenoxy)butyl]-3-(2-methoxyphenyl)ureido}ethoxy)phenyl]-2-ethoxypropionic acid,
2-ethoxy-3-[4-(2-{1-[2-(4-fluorobenzyloxy)ethyl]-3-(2-methoxyphenyl)ureido}ethoxy)phenyl]propionic acid,
3-[4-(2-{1-[2-(3,5-dichlorobenzyloxy)ethyl]-3-(2-methoxyphenyl)ureido}ethoxy)phenyl]-2-ethoxypropionic acid,
2-ethoxy-3-[4-(2-{1-[3-(4-fluorobenzyloxy)propyl]-3-(2-methoxyphenyl)ureido}ethoxy)phenyl]propionic acid,
3-[4-(2-{1-[3-(3,5-dichlorobenzyloxy)propyl]-3-(2-methoxyphenyl)ureido}ethoxy)phenyl]-2-ethoxypropionic acid,
2-ethoxy-3-[4-(2-{1-[4-(4-fluorobenzyloxy)butyl]-3-(2-methoxyphenyl)ureido}ethoxy)phenyl]propionic acid,
3-[4-(2-{1-[4-(3,5-dichlorobenzyloxy)butyl]-3-(2-methoxyphenyl)ureido}ethoxy)phenyl]-2-ethoxypropionic acid,
2-ethoxy-3-[4-(2-{1-[3-(4-fluorophenyl)propyl]-3-(2-methoxyphenyl)ureido}ethoxy)phenyl]propionic acid,
3-[4-(2-{1-[3-(3,5-dichlorophenyl)propyl]-3-(2-methoxyphenyl)ureido}ethoxy)phenyl]-2-ethoxypropionic acid,
2-ethoxy-3-(4-{2-[3-(3-methoxyphenyl)-1-pentylureido]ethoxy}phenyl)propionic acid,
2-ethoxy-3-(4-{2-[1-hexyl-3-(3-methoxyphenyl)ureido]ethoxy}phenyl)propionic acid,
2-ethoxy-3-(4-{2-[1-heptyl-3-(3-methoxyphenyl)ureido]ethoxy}phenyl)propionic acid,
2-ethoxy-3-(4-{2-[3-(3-methoxyphenyl)-1-octylureido]ethoxy}phenyl)propionic acid,
2-ethoxy-3-(4-{2-[1-isobutyl-3-(3-methoxyphenyl)ureido]ethoxy}phenyl)propionic acid,
2-ethoxy-3-(4-{2-[1-(3-methylbutyl)-3-(3-methoxyphenyl)ureido]ethoxy}phenyl)propionic acid,
2-ethoxy-3-(4-{2-[1-(4-methylpentyl)-3-(3-methoxyphenyl)ureido]ethoxy}phenyl)propionic acid, 2-ethoxy-3-(4-{2-[3-(3-methoxyphenyl)-1-(2-propylpentyl)ureido]ethoxy}phenyl)propionic acid,
3-(4-{2-[1-(3,3-dimethylbutyl)-3-(3-methoxyphenyl)ureido]ethoxy}phenyl)-2-ethoxypropionic acid,
2-ethoxy-3-(4-{2-[1-(2-ethylbutyl)-3-(3-methoxyphenyl)ureido]ethoxy}phenyl)propionic acid,
3-(4-{2-[1-cyclohexylmethyl-3-(3-methoxyphenyl)ureido]ethoxy}phenyl)-2-ethoxypropionic acid,
3-(4-{2-[1-(4-cyclohexylbutyl)-3-(3-methoxyphenyl)ureido]ethoxy}phenyl)-2-ethoxypropionic acid,
3-(4-{2-[1-cyclopropylmethyl-3-(3-methoxyphenyl)ureido]ethoxy}phenyl)-2-ethoxypropionic acid,
3-(4-{2-[1-cyclobutylmethyl-3-(3-methoxyphenyl)ureido]ethoxy}phenyl)-2-ethoxypropionic acid,
3-(4-{2-[1-cyclopentylmethyl-3-(3-methoxyphenyl)ureido]ethoxy}phenyl)-2-ethoxypropionic acid,
3-(4-{2-[1-(2-cyclopentylethyl)-3-(3-methoxyphenyl)ureido]ethoxy}phenyl)-2-ethoxypropionic acid,
3-(4-{2-[1-(3-cyclohexylpropyl)-3-(3-methoxyphenyl)ureido]ethoxy}phenyl)-2-ethoxypropionic acid,
2-ethoxy-3-(4-{2-[3-(3-methoxyphenyl)-1-(3-phenylpropyl)ureido]ethoxy}phenyl)propionic acid,
2-ethoxy-3-(4-{2-[3-(3-methoxyphenyl)-1-(4-phenylbutyl)ureido]ethoxy}phenyl)propionic acid,
3-(4-{2-[1-(2-butoxyethyl)-3-(3-methoxyphenyl)ureido]ethoxy}phenyl)-2-ethoxypropionic acid,
2-ethoxy-3-(4-{2-[3-(3-methoxyphenyl)-1-(2-pentyloxyethyl)ureido]ethoxy}phenyl)propionic acid,
2-ethoxy-3-(4-{2-[3-(3-methoxyphenyl)-1-(3-propoxypropyl)ureido]ethoxy}phenyl)propionic acid,
3-(4-{2-[1-(2-butylthioethyl)-3-(3-methoxyphenyl)ureido]ethoxy}phenyl)-2-ethoxypropionic acid,
2-ethoxy-3-(4-{2-[3-(3-methoxyphenyl)-1-(2-pentylthioethyl)ureido]ethoxy}phenyl)propionic acid,
2-ethoxy-3-(4-{2-[3-(3-methoxyphenyl)-1-(3-propylthiopropyl)ureido]ethoxy}phenyl)propionic acid,
2-ethoxy-3-(4-{2-[3-(3-methoxyphenyl)-1-(3-phenoxypropyl)ureido]ethoxy}phenyl)propionic acid,
2-ethoxy-3-(4-{2-[3-(3-methoxyphenyl)-1-(4-phenoxybutyl)ureido]ethoxy}phenyl)propionic acid,
3-(4-{2-[1-(3-benzyloxypropyl)-3-(3-methoxyphenyl)ureido]ethoxy}phenyl)-2-ethoxypropionic acid,
2-ethoxy-3-(4-{2-[3-(3-methoxyphenyl)-1-(3-phenylthiopropyl)ureido]ethoxy}phenyl)propionic acid,
2-ethoxy-3-(4-{2-[3-(3-methoxyphenyl)-1-(4-phenylthiobutyl)ureido]ethoxy}phenyl)propionic acid,
3-(4-{2-[1-(3-benzylthiopropyl)-3-(3-methoxyphenyl)ureido]ethoxy}phenyl)-2-ethoxypropionic acid,
2-ethoxy-3-(4-{2-[3-(3-methoxyphenyl)-1-(7,7,7-trifluoroheptyl)ureido]ethoxy}phenyl)propionic acid,
3-(4-{2-[1-(6,6-difluoroheptyl)-3-(3-methoxyphenyl)ureido]ethoxy}phenyl)-2-ethoxypropionic acid,
2-ethoxy-3-(4-{2-[3-(3-methoxyphenyl)-1-(6,6,6-trifluorohexyl)ureido]ethoxy}phenyl)propionic acid,
3-(4-{2-[1-(5,5-difluorohexyl)-3-(3-methoxyphenyl)ureido]ethoxy}phenyl)-2-ethoxypropionic acid,
2-ethoxy-3-(4-{2-[1-(5,5,6,6,7,7,7-heptafluoroheptyl)-3-(3-methoxyphenyl)ureido]ethoxy}phenyl)propionic acid,
2-ethoxy-3-(4-{2-[3-(3-methoxyphenyl)-1-(2,2,3,3,4,4,5,5,6,6,7,7,7-tridecafluoroheptyl)ureido]ethoxy}phenyl)propionic acid,
2-ethoxy-3-(4-{2-[3-(3-methoxyphenyl)-1-(5,5,6,6,6-pentafluorohexyl)ureido]ethoxy}phenyl)propionic acid,
2-ethoxy-3-(4-{2-[3-(3-methoxyphenyl)-1-(2,2,3,3,4,4,5,5,6,6,6-undecafluorohexyl)ureido]ethoxy}phenyl)propionic acid,
3-[4-(2-{1-[2-(2,2-difluoropropoxy)ethyl]-3-(3-methoxyphenyl)ureido}ethoxy)phenyl]-2-ethoxypropionic acid,
2-ethoxy-3-[4-(2-{1-[2-(1,1,2,2,3,3,3-heptafluoropropoxy)ethyl]-3-(3-methoxyphenyl)ureido}ethoxy)phenyl]propionic acid,
2-ethoxy-3-[4-(2-{3-(3-methoxyphenyl)-1-[2-(4,4,4-trifluorobutoxy)ethyl]ureido}ethoxy)phenyl]propionic acid,
3-[4-(2-{1-[2-(3,3-difluorobutoxy)ethyl]-3-(3-methoxyphenyl)ureido}ethoxy)phenyl]-2-ethoxypropionic acid,
3-[4-(2-{1-[2-(2,2-difluorobutoxy)ethyl]-3-(3-methoxyphenyl)ureido}ethoxy)phenyl]-2-ethoxypropionic acid,
2-ethoxy-3-[4-(2-{3-(3-methoxyphenyl)-1-[2-(1,1,2,2,3,3,4,4,4-nonafluorobutoxy)ethyl]ureido}ethoxy)phenyl]propionic acid,
2-ethoxy-3-[4-(2-{3-(3-methoxyphenyl)-1-[3-(2,2,2-trifluoroethoxy)propyl]ureido}ethoxy)phenyl]propionic acid,
2-ethoxy-3-[4-(2-{3-(3-methoxyphenyl)-1-[3-(1,1,2,2,2-pentafluoroethoxy)propyl]ureido}ethoxy)phenyl]propionic acid,
2-ethoxy-3-[4-(2-{1-[3-(4-fluorophenoxy)propyl]-3-(3-methoxyphenyl)ureido}ethoxy)phenyl]propionic acid,
3-[4-(2-{1-[3-(3,5-dichlorophenoxy)propyl]-3-(3-methoxyphenyl)ureido}ethoxy)phenyl]-2-ethoxypropionic acid,
2-ethoxy-3-[4-(2-{1-[4-(4-fluorophenoxy)butyl]-3-(3-methoxyphenyl)ureido}ethoxy)phenyl]propionic acid,
3-[4-(2-{1-[4-(3,5-dichlorophenoxy)butyl]-3-(3-methoxyphenyl)ureido}ethoxy)phenyl]-2-ethoxypropionic acid,
2-ethoxy-3-[4-(2-{1-[2-(4-fluorobenzyloxy)ethyl]-3-(3-methoxyphenyl)ureido}ethoxy)phenyl]propionic acid,
3-[4-(2-{1-[2-(3,5-dichlorobenzyloxy)ethyl]-3-(3-methoxyphenyl)ureido}ethoxy)phenyl]-2-ethoxypropionic acid,
2-ethoxy-3-[4-(2-{1-[3-(4-fluorobenzyloxy)propyl]-3-(3-methoxyphenyl)ureido}ethoxy)phenyl]propionic acid,
3-[4-(2-{1-[3-(3,5-dichlorobenzyloxy)propyl]-3-(3-methoxyphenyl)ureido}ethoxy)phenyl]-2-ethoxypropionic acid,
2-ethoxy-3-[4-(2-{1-[4-(4-fluorobenzyloxy)butyl]-3-(3-methoxyphenyl)ureido}ethoxy)phenyl]propionic acid,
3-[4-(2-{1-[4-(3,5-dichlorobenzyloxy)butyl]-3-(3-methoxyphenyl)ureido}ethoxy)phenyl]-2-ethoxypropionic acid,
2-ethoxy-3-[4-(2-{1-[3-(4-fluorophenyl)propyl]-3-(3-methoxyphenyl)ureido}ethoxy)phenyl]propionic acid,
3-[4-(2-{1-[3-(3,5-dichlorophenyl)propyl]-3-(3-methoxyphenyl)ureido}ethoxy)phenyl]-2-ethoxypropionic acid,
2-ethoxy-3-(4-{2-[3-(4-methoxyphenyl)-1-pentylureido]ethoxy}phenyl)propionic acid,
2-ethoxy-3-(4-{2-[1-hexyl-3-(4-methoxyphenyl)ureido]ethoxy}phenyl)propionic acid,
2-ethoxy-3-(4-{2-[1-heptyl-3-(4-methoxyphenyl)ureido]ethoxy}phenyl)propionic acid,
2-ethoxy-3-(4-{2-[3-(4-methoxyphenyl)-1-octylureido]ethoxy}phenyl)propionic acid,
2-ethoxy-3-(4-{2-[1-isobutyl-3-(4-methoxyphenyl)ureido]ethoxy}phenyl)propionic acid,
2-ethoxy-3-(4-{2-[3-(4-methoxyphenyl)-1-(3-methylbutyl)ureido]ethoxy}phenyl)propionic acid,
2-ethoxy-3-(4-{2-[3-(4-methoxyphenyl)-1-(4-methylpentyl)ureido]ethoxy}phenyl)propionic acid,
2-ethoxy-3-(4-{2-[3-(4-methoxyphenyl)-1-(2-propylpentyl)ureido]ethoxy}phenyl)propionic acid,
3-(4-{2-[1-(3,3-dimethylbutyl)-3-(4-methoxyphenyl)ureido]ethoxy}phenyl)-2-ethoxypropionic acid,
2-ethoxy-3-(4-{2-[1-(2-ethylbutyl)-3-(4-methoxyphenyl)ureido]ethoxy}phenyl)propionic acid,
3-(4-{2-[1-cyclohexylmethyl-3-(4-methoxyphenyl)ureido]ethoxy}phenyl)-2-ethoxypropionic acid,
3-(4-{2-[1-(4-cyclohexylbutyl)-3-(4-methoxyphenyl)ureido]ethoxy}phenyl)-2-ethoxypropionic acid, 3-(4-{2-[1-cyclopropylmethyl-3-(4-methoxyphenyl)ureido]
ethoxy}phenyl)-2-ethoxypropionic acid,
3-(4-{2-[1-cyclobutylmethyl-3-(4-methoxyphenyl)ureido]
ethoxy}phenyl)-2-ethoxypropionic acid,
3-(4-{2-[1-cyclopentylmethyl-3-(4-methoxyphenyl)ureido]
ethoxy}phenyl)-2-ethoxypropionic acid,
3-(4-{2-[1-(2-cyclopentylethyl)-3-(4-methoxyphenyl)ureido]ethoxy}phenyl)-2-ethoxypropionic acid,
3-(4-{2-[1-(3-cyclohexylpropyl)-3-(4-methoxyphenyl)ureido]ethoxy}phenyl)-2-ethoxypropionic acid,
2-ethoxy-3-(4-{2-[3-(4-methoxyphenyl)-1-(3-phenylpropyl)ureido]ethoxy}phenyl)propionic acid,
2-ethoxy-3-(4-{2-[3-(4-methoxyphenyl)-1-(4-phenylbutyl)ureido]ethoxy}phenyl)propionic acid,
3-(4-{2-[1-(2-butoxyethyl)-3-(4-methoxyphenyl)ureido]
ethoxy}phenyl)-2-ethoxypropionic acid,
2-ethoxy-3-(4-{2-[3-(4-methoxyphenyl)-1-(2-pentyloxyethyl)ureido]ethoxy}phenyl)propionic acid,
2-ethoxy-3-(4-{2-[3-(4-methoxyphenyl)-1-(3-propoxypropyl)ureido]ethoxy}phenyl)propionic acid,
3-(4-{2-[1-(2-butylthioethyl)-3-(4-methoxyphenyl)ureido]
ethoxy}phenyl)-2-ethoxypropionic acid,
2-ethoxy-3-(4-{2-[3-(4-methoxyphenyl)-1-(2-pentylthioethyl)ureido]ethoxy}phenyl)propionic acid,
2-ethoxy-3-(4-{2-[3-(4-methoxyphenyl)-1-(3-propylthiopropyl)ureido]ethoxy}phenyl)propionic acid,
2-ethoxy-3-(4-{2-[3-(4-methoxyphenyl)-1-(3-phenoxypropyl)ureido]ethoxy}phenyl)propionic acid,
2-ethoxy-3-(4-{2-[3-(4-methoxyphenyl)-1-(4-phenoxybutyl)ureido]ethoxy}phenyl)propionic acid,
3-(4-{2-[1-(3-benzyloxypropyl)-3-(4-methoxyphenyl)ureido]ethoxy}phenyl)-2-ethoxypropionic acid,
2-ethoxy-3-(4-{2-[3-(4-methoxyphenyl)-1-(3-phenylthiopropyl)ureido]ethoxy}phenyl)propionic acid,
2-ethoxy-3-(4-{2-[3-(4-methoxyphenyl)-1-(4-phenylthiobutyl)ureido]ethoxy}phenyl)propionic acid,
3-(4-{2-[1-(3-benzylthiopropyl)-3-(4-methoxyphenyl)ureido]ethoxy}phenyl)-2-ethoxypropionic acid,
2-ethoxy-3-(4-{2-[3-(4-methoxyphenyl)-1-(7,7,7-trifluoroheptyl)ureido]ethoxy}phenyl)propionic acid,
3-(4-{2-[1-(6,6-difluoroheptyl)-3-(4-methoxyphenyl)ureido]ethoxy}phenyl)-2-ethoxypropionic acid,
2-ethoxy-3-(4-{2-[3-(4-methoxyphenyl)-1-(6,6,6-trifluorohexyl)ureido]ethoxy}phenyl)propionic acid,
3-(4-{2-[1-(5,5-difluorohexyl)-3-(4-methoxyphenyl)ureido]
ethoxy}phenyl)-2-ethoxypropionic acid,
2-ethoxy-3-(4-{2-[1-(5,5,6,6,7,7,7-heptafluoroheptyl)-3-(4-methoxyphenyl)ureido]ethoxy}phenyl)propionic acid,
2-ethoxy-3-(4-{2-[3-(4-methoxyphenyl)-1-(2,2,3,3,4,4,5,5,6,6,7,7,7-tridecafluoroheptyl)ureido]ethoxy}phenyl)propionic acid,
2-ethoxy-3-(4-{2-[3-(4-methoxyphenyl)-1-(5,5,6,6,6-pentafluorohexyl)ureido]ethoxy}phenyl)propionic acid,
2-ethoxy-3-(4-{2-[3-(4-methoxyphenyl)-1-(2,2,3,3,4,4,5,5,6,6,6-undecafluorohexyl)ureido]ethoxy}phenyl)propionic acid,
3-[4-(2-{1-[2-(2,2-difluoropropoxy)ethyl]-3-(4-methoxyphenyl)ureido}ethoxy)phenyl]-2-ethoxypropionic acid,
2-ethoxy-3-[4-(2-{1-[2-(1,1,2,2,3,3,3-heptafluoropropoxy)ethyl]-3-(4-methoxyphenyl)ureido}ethoxy)phenyl]propionic acid,
2-ethoxy-3-[4-(2-{3-(4-methoxyphenyl)-1-[2-(4,4,4-trifluorobutoxy)ethyl]ureido}ethoxy)phenyl]propionic acid,
3-[4-(2-{1-[2-(3,3-difluorobutoxy)ethyl]-3-(4-methoxyphenyl)ureido}ethoxy)phenyl]-2-ethoxypropionic acid,
3-[4-(2-{1-[2-(2,2-difluorobutoxy)ethyl]-3-(4-methoxyphenyl)ureido}ethoxy)phenyl]-2-ethoxypropionic acid,
2-ethoxy-3-[4-(2-{3-(4-methoxyphenyl)-1-[2-(1,1,2,2,3,3,4,4,4-nonafluorobutoxy)ethyl]ureido}ethoxy)phenyl]propionic acid,
2-ethoxy-3-[4-(2-{3-(4-methoxyphenyl)-1-[3-(2,2,2-trifluoroethoxy)propyl]ureido}ethoxy)phenyl]propionic acid,
2-ethoxy-3-[4-(2-{3-(4-methoxyphenyl)-1-[3-(1,1,2,2,2-pentafluoroethoxy)propyl]ureido}ethoxy)phenyl]propionic acid,
2-ethoxy-3-[4-(2-{1-[3-(4-fluorophenoxy)propyl]-3-(4-methoxyphenyl)ureido}ethoxy)phenyl]propionic acid,
3-[4-(2-{1-[3-(3,5-dichlorophenoxy)propyl]-3-(4-methoxyphenyl)ureido}ethoxy)phenyl]-2-ethoxypropionic acid,
2-ethoxy-3-[4-(2-{1-[4-(4-fluorophenoxy)butyl]-3-(4-methoxyphenyl)ureido}ethoxy)phenyl]propionic acid,
3-[4-(2-{1-[4-(3,5-dichlorophenoxy)butyl]-3-(4-methoxyphenyl)ureido}ethoxy)phenyl]-2-ethoxypropionic acid,
2-ethoxy-3-[4-(2-{1-[2-(4-fluorobenzyloxy)ethyl]-3-(4-methoxyphenyl)ureido}ethoxy)phenyl]propionic acid,
3-[4-(2-{1-[2-(3,5-dichlorobenzyloxy)ethyl]-3-(4-methoxyphenyl)ureido}ethoxy)phenyl]-2-ethoxypropionic acid,
2-ethoxy-3-[4-(2-{1-[3-(4-fluorobenzyloxy)propyl]-3-(4-methoxyphenyl)ureido}ethoxy)phenyl]propionic acid,
3-[4-(2-{1-[3-(3,5-dichlorobenzyloxy)propyl]-3-(4-methoxyphenyl)ureido}ethoxy)phenyl]-2-ethoxypropionic acid,
2-ethoxy-3-[4-(2-{1-[4-(4-fluorobenzyloxy)butyl]-3-(4-methoxyphenyl)ureido}ethoxy)phenyl]propionic acid,
3-[4-(2-{1-[4-(3,5-dichlorobenzyloxy)butyl]-3-(4-methoxyphenyl)ureido}ethoxy)phenyl]-2-ethoxypropionic acid,
2-ethoxy-3-[4-(2-{1-[3-(4-fluorophenyl)propyl]-3-(4-methoxyphenyl)ureido}ethoxy)phenyl]propionic acid,
3-[4-(2-{1-[3-(3,5-dichlorophenyl)propyl]-3-(4-methoxyphenyl)ureido}ethoxy)phenyl]-2-ethoxypropionic acid,
2-ethoxy-3-(4-{2-[3-(4-methyl-3-nitrophenyl)-1-pentylureido]ethoxy}phenyl)propionic acid,
2-ethoxy-3-(4-{2-[1-hexyl-3-(4-methyl-3-nitrophenyl)ureido]ethoxy}phenyl)propionic acid,
2-ethoxy-3-(4-{2-[1-heptyl-3-(4-methyl-3-nitrophenyl)ureido]ethoxy}phenyl)propionic acid,
2-ethoxy-3-(4-{2-[3-(4-methyl-3-nitrophenyl)-1-octylureido]ethoxy}phenyl)propionic acid,
2-ethoxy-3-(4-{2-[1-isobutyl-3-(4-methyl-3-nitrophenyl)ureido]ethoxy}phenyl)propionic acid,
2-ethoxy-3-(4-{2-[1-(3-methylbutyl)-3-(4-methyl-3-nitrophenyl)ureido]ethoxy}phenyl)propionic acid,
2-ethoxy-3-(4-{2-[3-(4-methyl-3-nitrophenyl)-1-(4-methylpentyl)ureido]ethoxy}phenyl)propionic acid,
2-ethoxy-3-(4-{2-[3-(4-methyl-3-nitrophenyl)-1-(2-propylpentyl)ureido]ethoxy}phenyl)propionic acid,
3-(4-{2-[1-(3,3-dimethylbutyl)-3-(4-methyl-3-nitrophenyl)ureido]ethoxy}phenyl)-2-ethoxypropionic acid,
2-ethoxy-3-(4-{2-[1-(2-ethylbutyl)-3-(4-methyl-3-nitrophenyl)ureido]ethoxy}phenyl)propionic acid,
3-(4-{2-[1-cyclohexylmethyl-3-(4-methyl-3-nitrophenyl)ureido]ethoxy}phenyl)-2-ethoxypropionic acid,
3-(4-{2-[1-(4-cyclohexylbutyl)-3-(4-methyl-3-nitrophenyl)ureido]ethoxy}phenyl)-2-ethoxypropionic acid,
3-(4-{2-[1-cyclopropylmethyl-3-(4-methyl-3-nitrophenyl)ureido]ethoxy}phenyl)-2-ethoxypropionic acid,
3-(4-{2-[1-cyclobutylmethyl-3-(4-methyl-3-nitrophenyl)ureido]ethoxy}phenyl)-2-ethoxypropionic acid,
3-(4-{2-[1-cyclopentylmethyl-3-(4-methyl-3-nitrophenyl)ureido]ethoxy}phenyl)-2-ethoxypropionic acid,
3-(4-{2-[1-(2-cyclopentylethyl)-3-(4-methyl-3-nitrophenyl)ureido]ethoxy}phenyl)-2-ethoxypropionic acid,
3-(4-{2-[1-(3-cyclohexylpropyl)-3-(4-methyl-3-nitrophenyl)ureido]ethoxy}phenyl)-2-ethoxypropionic acid, 2-ethoxy-3-(4-{2-[3-(4-methyl-3-nitrophenyl)-1-(3-phenylpropyl)ureido]ethoxy}phenyl)propionic acid,
2-ethoxy-3-(4-{2-[3-(4-methyl-3-nitrophenyl)-1-(4-phenylbutyl)ureido]ethoxy}phenyl)propionic acid,
3-(4-{2-[1-(2-butoxyethyl)-3-(4-methyl-3-nitrophenyl)ureido]ethoxy}phenyl)-2-ethoxypropionic acid,
2-ethoxy-3-(4-{2-[3-(4-methyl-3-nitrophenyl)-1-(2-pentyloxyethyl)ureido]ethoxy}phenyl)propionic acid,
2-ethoxy-3-(4-{2-[3-(4-methyl-3-nitrophenyl)-1-(3-propoxypropyl)ureido]ethoxy}phenyl)propionic acid,
3-(4-{2-[1-(2-butylthioethyl)-3-(4-methyl-3-nitrophenyl)ureido]ethoxy}phenyl)-2-ethoxypropionic acid,
2-ethoxy-3-(4-{2-[3-(4-methyl-3-nitrophenyl)-1-(2-pentylthioethyl)ureido]ethoxy}phenyl)propionic acid,
2-ethoxy-3-(4-{2-[3-(4-methyl-3-nitrophenyl)-1-(3-propylthiopropyl)ureido]ethoxy}phenyl)propionic acid,
2-ethoxy-3-(4-{2-[3-(4-methyl-3-nitrophenyl)-1-(3-phenoxypropyl)ureido]ethoxy}phenyl)propionic acid,
2-ethoxy-3-(4-{2-[3-(4-methyl-3-nitrophenyl)-1-(4-phenoxybutyl)ureido]ethoxy}phenyl)propionic acid,
3-(4-{2-[1-(3-benzyloxypropyl)-3-(4-methyl-3-nitrophenyl)ureido]ethoxy}phenyl)-2-ethoxypropionic acid,
2-ethoxy-3-(4-{2-[3-(4-methyl-3-nitrophenyl)-1-(3-phenylthiopropyl)ureido]ethoxy}phenyl)propionic acid,
2-ethoxy-3-(4-{2-[3-(4-methyl-3-nitrophenyl)-1-(4-phenylthiobutyl)ureido]ethoxy}phenyl)propionic acid,
3-(4-{2-[1-(3-benzylthiopropyl)-3-(4-methyl-3-nitrophenyl)ureido]ethoxy}phenyl)-2-ethoxypropionic acid,
2-ethoxy-3-(4-{2-[3-(4-methyl-3-nitrophenyl)-1-(7,7,7-trifluoroheptyl)ureido]ethoxy}phenyl)propionic acid,
3-(4-{2-[1-(6,6-difluoroheptyl)-3-(4-methyl-3-nitrophenyl)ureido]ethoxy}phenyl)-2-ethoxypropionic acid,
2-ethoxy-3-(4-{2-[3-(4-methyl-3-nitrophenyl)-1-(6,6,6-trifluorohexyl)ureido]ethoxy}phenyl)propionic acid,
3-(4-{2-[1-(5,5-difluorohexyl)-3-(4-methyl-3-nitrophenyl)ureido]ethoxy}phenyl)-2-ethoxypropionic acid,
2-ethoxy-3-(4-{2-[1-(5,5,6,6,7,7,7-heptafluoroheptyl)-3-(4-methyl-3-nitrophenyl)ureido]ethoxy}phenyl)propionic acid,
2-ethoxy-3-(4-{2-[3-(4-methyl-3-nitrophenyl)-1-(2,2,3,3,4,4,5,5,6,6,7,7,7-tridecafluoroheptyl)ureido]ethoxy}phenyl)propionic acid,
2-ethoxy-3-(4-{2-[3-(4-methyl-3-nitrophenyl)-1-(5,5,6,6,6-pentafluorohexyl)ureido]ethoxy}phenyl)propionic acid,
2-ethoxy-3-(4-{2-[3-(4-methyl-3-nitrophenyl)-1-(2,2,3,3,4,4,5,5,6,6,6-undecafluorohexyl)ureido]ethoxy}phenyl)propionic acid,
3-[4-(2-{1-[2-(2,2-difluoropropoxy)ethyl]-3-(4-methyl-3-nitrophenyl)ureido}ethoxy)phenyl]-2-ethoxypropionic acid,
2-ethoxy-3-[4-(2-{1-[2-(1,1,2,2,3,3,3-heptafluoropropoxy)ethyl]-3-(4-methyl-3-nitrophenyl)ureido}ethoxy)phenyl]propionic acid,
2-ethoxy-3-[4-(2-{3-(4-methyl-3-nitrophenyl)-1-[2-(4,4,4-trifluorobutoxy)ethyl]ureido}ethoxy)phenyl]propionic acid,
3-[4-(2-{1-[2-(3,3-difluorobutoxy)ethyl]-3-(4-methyl-3-nitrophenyl)ureido}ethoxy)phenyl]-2-ethoxypropionic acid,
3-[4-(2-{1-[2-(2,2-difluorobutoxy)ethyl]-3-(4-methyl-3-nitrophenyl)ureido}ethoxy)phenyl]-2-ethoxypropionic acid,
2-ethoxy-3-[4-(2-{3-(4-methyl-3-nitrophenyl)-1-[2-(1,1,2,2,3,3,4,4,4-nonafluorobutoxy)ethyl]ureido}ethoxy)phenyl]propionic acid,
2-ethoxy-3-[4-(2-{3-(4-methyl-3-nitrophenyl)-1-[3-(2,2,2-trifluoroethoxy)propyl]ureido}ethoxy)phenyl]propionic acid,
2-ethoxy-3-[4-(2-{3-(4-methyl-3-nitrophenyl)-1-[3-(1,1,2,2,2-pentafluoroethoxy)propyl]ureido}ethoxy)phenyl]propionic acid,
2-ethoxy-3-[4-(2-{1-[3-(4-fluorophenoxy)propyl]-3-(4-methyl-3-nitrophenyl)ureido}ethoxy)phenyl]propionic acid,
3-[4-(2-{1-[3-(3,5-dichlorophenoxy)propyl]-3-(4-methyl-3-nitrophenyl)ureido}ethoxy)phenyl]-2-ethoxypropionic acid,
2-ethoxy-3-[4-(2-{1-[4-(4-fluorophenoxy)butyl]-3-(4-methyl-3-nitrophenyl)ureido}ethoxy)phenyl]propionic acid,
3-[4-(2-{1-[4-(3,5-dichlorophenoxy)butyl]-3-(4-methyl-3-nitrophenyl)ureido}ethoxy)phenyl]-2-ethoxypropionic acid,
2-ethoxy-3-[4-(2-{1-[2-(4-fluorobenzyloxy)ethyl]-3-(4-methyl-3-nitrophenyl)ureido}ethoxy)phenyl]propionic acid,
3-[4-(2-{1-[2-(3,5-dichlorobenzyloxy)ethyl]-3-(4-methyl-3-nitrophenyl)ureido}ethoxy)phenyl]-2-ethoxypropionic acid,
2-ethoxy-3-[4-(2-{1-[3-(4-fluorobenzyloxy)propyl]-3-(4-methyl-3-nitrophenyl)ureido}ethoxy)phenyl]propionic acid,
3-[4-(2-{1-[3-(3,5-dichlorobenzyloxy)propyl]-3-(4-methyl-3-nitrophenyl)ureido}ethoxy)phenyl]-2-ethoxypropionic acid,
2-ethoxy-3-[4-(2-{1-[4-(4-fluorobenzyloxy)butyl]-3-(4-methyl-3-nitrophenyl)ureido}ethoxy)phenyl]propionic acid,
3-[4-(2-{1-[4-(3,5-dichlorobenzyloxy)butyl]-3-(4-methyl-3-nitrophenyl)ureido}ethoxy)phenyl]-2-ethoxypropionic acid,
2-ethoxy-3-[4-(2-{1-[3-(4-fluorophenyl)propyl]-3-(4-methyl-3-nitrophenyl)ureido}ethoxy)phenyl]propionic acid,
3-[4-(2-{1-[3-(3,5-dichlorophenyl)propyl]-3-(4-methyl-3-nitrophenyl)ureido}ethoxy)phenyl]-2-ethoxypropionic acid,
2-ethoxy-3-(4-{2-[3-(2-methoxy-5-methylphenyl)-1-pentylureido]ethoxy}phenyl)propionic acid,
2-ethoxy-3-(4-{2-[1-hexyl-3-(2-methoxy-5-methylphenyl)ureido]ethoxy}phenyl)propionic acid,
2-ethoxy-3-(4-{2-[1-heptyl-3-(2-methoxy-5-methylphenyl)ureido]ethoxy}phenyl)propionic acid,
2-ethoxy-3-(4-{2-[3-(2-methoxy-5-methylphenyl)-1-octylureido]ethoxy}phenyl)propionic acid,
2-ethoxy-3-(4-{2-[1-isobutyl-3-(2-methoxy-5-methylphenyl)ureido]ethoxy}phenyl)propionic acid,
2-ethoxy-3-(4-{2-[3-(2-methoxy-5-methylphenyl)-1-(3-methylbutyl)ureido]ethoxy}phenyl)propionic acid,
2-ethoxy-3-(4-{2-[3-(2-methoxy-5-methylphenyl)-1-(4-methylpentyl)ureido]ethoxy}phenyl)propionic acid,
2-ethoxy-3-(4-{2-[3-(2-methoxy-5-methylphenyl)-1-(2-propylpentyl)ureido]ethoxy}phenyl)propionic acid,
3-(4-{2-[1-(3,3-dimethylbutyl)-3-(2-methoxy-5-methylphenyl)ureido]ethoxy}phenyl)-2-ethoxypropionic acid,
2-ethoxy-3-(4-{2-[1-(2-ethylbutyl)-3-(2-methoxy-5-methylphenyl)ureido]ethoxy}phenyl)propionic acid,
3-(4-{2-[1-cyclohexylmethyl-3-(2-methoxy-5-methylphenyl)ureido]ethoxy}phenyl)-2-ethoxypropionic acid,
3-(4-{2-[1-(4-cyclohexylbutyl)-3-(2-methoxy-5-methylphenyl)ureido]ethoxy}phenyl)-2-ethoxypropionic acid,
3-(4-{2-[1-cyclopropylmethyl-3-(2-methoxy-5-methylphenyl)ureido]ethoxy}phenyl)-2-ethoxypropionic acid,
3-(4-{2-[1-cyclobutylmethyl-3-(2-methoxy-5-methylphenyl)ureido]ethoxy}phenyl)-2-ethoxypropionic acid,
3-(4-{2-[1-cyclopentylmethyl-3-(2-methoxy-5-methylphenyl)ureido]ethoxy}phenyl)-2-ethoxypropionic acid, 3-(4-{2-[1-(2-cyclopentylethyl)-3-(2-methoxy-5-methylphenyl)ureido]ethoxy}phenyl)-2-ethoxypropionic acid,
3-(4-{2-[1-(3-cyclohexylpropyl)-3-(2-methoxy-5-methylphenyl)ureido]ethoxy}phenyl)-2-ethoxypropionic acid,
2-ethoxy-3-(4-{2-[3-(2-methoxy-5-methylphenyl)-1-(3-phenylpropyl)ureido]ethoxy}phenyl)propionic acid,
2-ethoxy-3-(4-{2-[3-(2-methoxy-5-methylphenyl)-1-(4-phenylbutyl)ureido]ethoxy}phenyl)propionic acid,
3-(4-{2-[1-(2-butoxyethyl)-3-(2-methoxy-5-methylphenyl)ureido]ethoxy}phenyl)-2-ethoxypropionic acid,
2-ethoxy-3-(4-{2-[3-(2-methoxy-5-methylphenyl)-1-(2-pentyloxyethyl)ureido]ethoxy}phenyl)propionic acid,
2-ethoxy-3-(4-{2-[3-(2-methoxy-5-methylphenyl)-1-(3-propoxypropyl)ureido]ethoxy}phenyl)propionic acid,
3-(4-{2-[1-(2-butylthioethyl)-3-(2-methoxy-5-methylphenyl)ureido]ethoxy}phenyl)-2-ethoxypropionic acid,
2-ethoxy-3-(4-{2-[3-(2-methoxy-5-methylphenyl)-1-(2-pentylthioethyl)ureido]ethoxy}phenyl)propionic acid,
2-ethoxy-3-(4-{2-[3-(2-methoxy-5-methylphenyl)-1-(3-propylthiopropyl)ureido]ethoxy}phenyl)propionic acid,
2-ethoxy-3-(4-{2-[3-(2-methoxy-5-methylphenyl)-1-(3-phenoxypropyl)ureido]ethoxy}phenyl)propionic acid,
2-ethoxy-3-(4-{2-[3-(2-methoxy-5-methylphenyl)-1-(4-phenoxybutyl)ureido]ethoxy}phenyl)propionic acid,
3-(4-{2-[1-(3-benzyloxypropyl)-3-(2-methoxy-5-methylphenyl)ureido]ethoxy}phenyl)-2-ethoxypropionic acid,
2-ethoxy-3-(4-{2-[3-(2-methoxy-5-methylphenyl)-1-(3-phenylthiopropyl)ureido]ethoxy}phenyl)propionic acid,
2-ethoxy-3-(4-{2-[3-(2-methoxy-5-methylphenyl)-1-(4-phenylthiobutyl)ureido]ethoxy}phenyl)propionic acid,
3-(4-{2-[1-(3-benzylthiopropyl)-3-(2-methoxy-5-methylphenyl)ureido]ethoxy}phenyl)-2-ethoxypropionic acid,
2-ethoxy-3-(4-{2-[3-(2-methoxy-5-methylphenyl)-1-(7,7,7-trifluoroheptyl)ureido]ethoxy}phenyl)propionic acid,
3-(4-{2-[1-(6,6-difluoroheptyl)-3-(2-methoxy-5-methylphenyl)ureido]ethoxy}phenyl)-2-ethoxypropionic acid,
2-ethoxy-3-(4-{2-[3-(2-methoxy-5-methylphenyl)-1-(6,6,6-trifluorohexyl)ureido]ethoxy}phenyl)propionic acid,
3-(4-{2-[1-(5,5-difluorohexyl)-3-(2-methoxy-5-methylphenyl)ureido]ethoxy}phenyl)-2-ethoxypropionic acid,
2-ethoxy-3-(4-{2-[1-(5,5,6,6,7,7,7-heptafluoroheptyl)-3-(2-methoxy-5-methylphenyl)ureido]ethoxy}phenyl)propionic acid,
2-ethoxy-3-(4-{2-[3-(2-methoxy-5-methylphenyl)-1-(2,2,3,3,4,4,5,5,6,6,7,7,7-tridecafluoroheptyl)ureido]ethoxy}phenyl)propionic acid,
2-ethoxy-3-(4-{2-[3-(2-methoxy-5-methylphenyl)-1-(5,5,6,6,6-pentafluorohexyl)ureido]ethoxy}phenyl)propionic acid,
2-ethoxy-3-(4-{2-[3-(2-methoxy-5-methylphenyl)-1-(2,2,3,3,4,4,5,5,6,6,6-undecafluorohexyl)ureido]ethoxy}phenyl)propionic acid,
3-[4-(2-{1-[2-(2,2-difluoropropoxy)ethyl]-3-(2-methoxy-5-methylphenyl)ureido}ethoxy)phenyl]-2-ethoxypropionic acid,
2-ethoxy-3-[4-(2-{1-[2-(1,1,2,2,3,3,3-heptafluoropropoxy)ethyl]-3-(2-methoxy-5-methylphenyl)ureido}ethoxy)phenyl]propionic acid,
2-ethoxy-3-[4-(2-{3-(2-methoxy-5-methylphenyl)-1-[2-(4,4,4-trifluorobutoxy)ethyl]ureido}ethoxy)phenyl]propionic acid,
3-[4-(2-{1-[2-(3,3-difluorobutoxy)ethyl]-3-(2-methoxy-5-methylphenyl)ureido}ethoxy)phenyl]-2-ethoxypropionic acid,
3-[4-(2-{1-[2-(2,2-difluorobutoxy)ethyl]-3-(2-methoxy-5-methylphenyl)ureido}ethoxy)phenyl]-2-ethoxypropionic acid,
2-ethoxy-3-[4-(2-{3-(2-methoxy-5-methylphenyl)-1-[2-(1,1,2,2,3,3,4,4,4-nonafluorobutoxy)ethyl]ureido}ethoxy)phenyl]propionic acid,
2-ethoxy-3-[4-(2-{3-(2-methoxy-5-methylphenyl)-1-[3-(2,2,2-trifluoroethoxy)propyl]ureido}ethoxy)phenyl]propionic acid,
2-ethoxy-3-[4-(2-{3-(2-methoxy-5-methylphenyl)-1-[3-(1,1,2,2,2-pentafluoroethoxy)propyl]ureido}ethoxy)phenyl]propionic acid,
2-ethoxy-3-[4-(2-{1-[3-(4-fluorophenoxy)propyl]-3-(2-methoxy-5-methylphenyl)ureido}ethoxy)phenyl]propionic acid,
3-[4-(2-{1-[3-(3,5-dichlorophenoxy)propyl]-3-(2-methoxy-5-methylphenyl)ureido}ethoxy)phenyl]-2-ethoxypropionic acid,
2-ethoxy-3-[4-(2-{1-[4-(4-fluorophenoxy)butyl]-3-(2-methoxy-5-methylphenyl)ureido}ethoxy)phenyl]propionic acid,
3-[4-(2-{1-[4-(3,5-dichlorophenoxy)butyl]-3-(2-methoxy-5-methylphenyl)ureido}ethoxy)phenyl]-2-ethoxypropionic acid,
2-ethoxy-3-[4-(2-{1-[2-(4-fluorobenzyloxy)ethyl]-3-(2-methoxy-5-methylphenyl)ureido}ethoxy)phenyl]propionic acid,
3-[4-(2-{1-[2-(3,5-dichlorobenzyloxy)ethyl]-3-(2-methoxy-5-methylphenyl)ureido}ethoxy)phenyl]-2-ethoxypropionic acid,
2-ethoxy-3-[4-(2-{1-[3-(4-fluorobenzyloxy)propyl]-3-(2-methoxy-5-methylphenyl)ureido}ethoxy)phenyl]propionic acid,
3-[4-(2-{1-[3-(3,5-dichlorobenzyloxy)propyl]-3-(2-methoxy-5-methylphenyl)ureido}ethoxy)phenyl]-2-ethoxypropionic acid,
2-ethoxy-3-[4-(2-{1-[4-(4-fluorobenzyloxy)butyl]-3-(2-methoxy-5-methylphenyl)ureido}ethoxy)phenyl]propionic acid,
3-[4-(2-{1-[4-(3,5-dichlorobenzyloxy)butyl]-3-(2-methoxy-5-methylphenyl)ureido}ethoxy)phenyl]-2-ethoxypropionic acid,
2-ethoxy-3-[4-(2-{1-[3-(4-fluorophenyl)propyl]-3-(2-methoxy-5-methylphenyl)ureido}ethoxy)phenyl]propionic acid,
3-[4-(2-{1-[3-(3,5-dichlorophenyl)propyl]-3-(2-methoxy-5-methylphenyl)ureido}ethoxy)phenyl]-2-ethoxypropionic acid, and
3-(4-{2-3-(2,4-dimethoxyphenyl)-1-heptylureido]ethoxy}phenyl)-2-ethoxypropionic acid.

Alternative examples include 2-ethoxy-3-(4-{2-[1-heptyl-3-(1-naphthyl)ureido]ethoxy}phenyl)propionic acid,
3-(4-{2-[3-(4-cyanophenyl)-1-heptylureido]ethoxy}phenyl)-2-ethoxypropionic acid,
3-(4-{2-[3-(3-cyanophenyl)-1-heptylureido]ethoxy}phenyl)-2-ethoxypropionic acid,
2-ethoxy-3-[4-(2-{1-heptyl-3-[3,4-(methylenedioxy)phenyl]ureido}ethoxy)phenyl]propionic acid,
3-(4-{2-[1-(2-benzyloxyethyl)-3-(2,4-difluorophenyl)ureido]ethoxy}phenyl)-2-ethoxypropionic acid,
3-(4-{2-[1-(2-benzylthioethyl)-3-(2,4-difluorophenyl)ureido]ethoxy}phenyl)-2-ethoxypropionic acid,
3-(4-{2-[3-(2,4-difluorophenyl)-1-(2-ethoxyethyl)ureido]ethoxy}phenyl)-2-ethoxypropionic acid and the like.

Specific compounds wherein X is —O— include the following compounds.

Examples of the compounds wherein $R^1$ is an unsubstituted $C_{1-12}$ alkyl group include, for example, the following compounds.

2-Ethoxy-3-{4-[2-(N-methoxycarbonyl-N-pentylamino)ethoxy]phenyl}propionic acid,
2-ethoxy-3-{4-[2-(N-hexyl-N-methoxycarbonylamino)ethoxy]phenyl}propionic acid,
2-ethoxy-3-{4-[2-(N-heptyl-N-methoxycarbonylamino)ethoxy]phenyl}propionic acid,
2-ethoxy-3-{4-[2-(N-methoxycarbonyl-N-octylamino)ethoxy]phenyl}propionic acid,
2-ethoxy-3-{4-[2-(N-isobutyl-N-methoxycarbonylamino)ethoxy]phenyl}propionic acid,
2-ethoxy-3-4-{2-[N-methoxycarbonyl-N-(3-methylbutyl)amino]ethoxy}phenyl)propionic acid,
2-ethoxy-3-(4-{2-[N-methoxycarbonyl-N-(4-methylpentyl)amino]ethoxy}phenyl)propionic acid,
2-ethoxy-3-(4-{2-[N-methoxycarbonyl-N-(2-propylpentyl)amino]ethoxy}phenyl)propionic acid,
3-(4-{2-[N-(3,3-dimethylbutyl)-N-methoxycarbonylamino]ethoxy}phenyl)-2-ethoxypropionic acid,
2-ethoxy-3-(4-{2-[N-(2-ethylbutyl)-N-methoxycarbonylamino]ethoxy}phenyl)propionic acid,
3-{4-[2-(N-cyclohexylmethyl-N-methoxycarbonylamino)ethoxy]phenyl}-2-ethoxypropionic acid,
3-(4-{2-[N-(4-cyclohexylbutyl)-N-methoxycarbonylamino]ethoxy}phenyl)-2-ethoxypropionic acid,
3-{4-[2-(N-cyclopropylmethyl-N-methoxycarbonylamino)ethoxy]phenyl}-2-ethoxypropionic acid,
3-{4-[2-(N-cyclobutylmethyl-N-methoxycarbonylamino)ethoxy]phenyl}-2-ethoxypropionic acid,
3-{4-[2-(N-cyclopentylmethyl-N-methoxycarbonylamino)ethoxy]phenyl}-2-ethoxypropionic acid,
3-(4-{2-[N-(2-cyclopentylethyl)-N-methoxycarbonylamino]ethoxy}phenyl)-2-ethoxypropionic acid,
3-(4-{2-[N-(3-cyclohexylpropyl)-N-methoxycarbonylamino]ethoxy}phenyl)-2-ethoxypropionic acid,
2-ethoxy-3-(4-{2-[N-methoxycarbonyl-N-(3-phenylpropyl)amino]ethoxy}phenyl)propionic acid,
2-ethoxy-3-(4-{2-[N-methoxycarbonyl-N-(4-phenylbutyl)amino]ethoxy}phenyl)propionic acid,
3-(4-{2-[N-(2-butoxyethyl)-N-methoxycarbonylamino]ethoxy}phenyl)-2-ethoxypropionic acid,
2-ethoxy-3-(4-{2-[N-methoxycarbonyl-N-(2-pentyloxyethyl)amino]ethoxy}phenyl)propionic acid,
2-ethoxy-3-(4-{2-[N-methoxycarbonyl-N-(3-propoxypropyl)amino]ethoxy}phenyl)propionic acid,
3-(4-{2-[N-(2-butylthioethyl)-N-methoxycarbonylamino]ethoxy}phenyl)-2-ethoxypropionic acid,
2-ethoxy-3-(4-{2-[N-methoxycarbonyl-N-(2-pentylthioethyl)amino]ethoxy}phenyl)propionic acid,
2-ethoxy-3-(4-{2-[N-methoxycarbonyl-N-(3-propylthiopropyl)amino]ethoxy}phenyl)propionic acid,
2-ethoxy-3-(4-{2-[N-methoxycarbonyl-N-(3-phenoxypropyl)amino]ethoxy}phenyl)propionic acid,
2-ethoxy-3-(4-{2-[N-methoxycarbonyl-N-(4-phenoxybutyl)amino]ethoxy}phenyl)propionic acid,
3-(4-{2-[N-(3-benzyloxypropyl)-N-methoxycarbonylamino]ethoxy}phenyl)-2-ethoxypropionic acid,
2-ethoxy-3-(4-{2-[N-methoxycarbonyl-N-(3-phenylthiopropyl)amino]ethoxy}phenyl)propionic acid,
2-ethoxy-3-(4-{2-[N-methoxycarbonyl-N-(4-phenylthiobutyl)amino]ethoxy}phenyl)propionic acid,
3-(4-{2-[N-(3-benzylthiopropyl)-N-methoxycarbonylamino]ethoxy}phenyl)-2-ethoxypropionic acid,
2-ethoxy-3-(4-{2-[N-methoxycarbonyl-N-(7,7,7-trifluoroheptyl)amino]ethoxy}phenyl)propionic acid,
3-(4-{2-[N-(6,6-difluoroheptyl)-N-methoxycarbonylamino]ethoxy}phenyl)-2-ethoxypropionic acid,
2-ethoxy-3-(4-{2-[N-methoxycarbonyl-N-(6,6,6-trifluorohexyl)amino]ethoxy}phenyl)propionic acid,
3-(4-{2-[N-(5,5-difluorohexyl)-N-methoxycarbonylamino]ethoxy}phenyl)-2-ethoxypropionic acid,
2-ethoxy-3-(4-{2-[N-(5,5,6,6,7,7,7-heptafluoroheptyl)-N-methoxycarbonylamino]ethoxy}phenyl)propionic acid,
2-ethoxy-3-(4-{2-[N-methoxycarbonyl-N-(2,2,3,3,4,4,5,5,6,6,7,7,7-tridecafluoroheptyl)amino]ethoxy}phenyl)propionic acid,
2-ethoxy-3-(4-{2-[N-methoxycarbonyl-N-(5,5,6,6,6-pentafluorohexyl)amino]ethoxy}phenyl)propionic acid,
2-ethoxy-3-(4-{2-[N-methoxycarbonyl-N-(2,2,3,3,4,4,5,5,6,6,6-undecafluorohexyl)amino]ethoxy}phenyl)propionic acid,
3-[4-(2-{N-[2-(2,2-difluoropropoxy)ethyl]-N-methoxycarbonylamino}ethoxy)phenyl]-2-ethoxypropionic acid,
2-ethoxy-3-[4-(2-{N-[2-(1,1,2,2,3,3,3-heptafluoropropoxy)ethyl]-N-methoxycarbonylamino}ethoxy)phenyl]propionic acid,
2-ethoxy-3-[4-(2-{N-methoxycarbonyl-N-[2-(4,4,4-trifluorobutoxy)ethyl]amino}ethoxy)phenyl]propionic acid,
3-[4-(2-{N-[2-(3,3-difluorobutoxy)ethyl]-N-methoxycarbonylamino}ethoxy)phenyl]-2-ethoxypropionic acid,
3-[4-(2-{N-[2-(2,2-difluorobutoxy)ethyl]-N-methoxycarbonylamino}ethoxy)phenyl]-2-ethoxypropionic acid,
2-ethoxy-3-[4-(2-{N-methoxycarbonyl-N-[2-(1,1,2,2,3,3,4,4,4-nonafluorobutoxy)ethyl]amino}ethoxy)phenyl]propionic acid,
2-ethoxy-3-[4-(2-{N-methoxycarbonyl-N-[3-(2,2,2-trifluoroethoxy)propyl]amino}ethoxy)phenyl]propionic acid,
2-ethoxy-3-[4-(2-{N-methoxycarbonyl-N-[3-(1,1,2,2,2-pentafluoroethoxy)propyl]amino}ethoxy)phenyl]propionic acid,
2-ethoxy-3-[4-(2-{N-[3-(4-fluorophenoxy)propyl]-N-methoxycarbonylamino}ethoxy)phenyl]propionic acid,
3-[4-(2-{N-[3-(3,5-dichlorophenoxy)propyl]-N-methoxycarbonylamino}ethoxy)phenyl]-2-ethoxypropionic acid,
2-ethoxy-3-[4-(2-{N-[4-(4-fluorophenoxy)butyl]-N-methoxycarbonylamino}ethoxy)phenyl]propionic acid,
3-[4-(2-{N-[4-(3,5-dichlorophenoxy)butyl]-N-methoxycarbonylamino}ethoxy)phenyl]-2-ethoxypropionic acid,
2-ethoxy-3-[4-(2-{N-[2-(4-fluorobenzyloxy)ethyl]-N-methoxycarbonylamino}ethoxy)phenyl]propionic acid,
3-[4-(2-{N-[2-(3,5-dichlorobenzyloxy)ethyl]-N-methoxycarbonylamino}ethoxy)phenyl]-2-ethoxypropionic acid,
2-ethoxy-3-[4-(2-{N-[3-(4-fluorobenzyloxy)propyl]-N-methoxycarbonylamino}ethoxy)phenyl]propionic acid,
3-[4-(2-{N-[3-(3,5-dichlorobenzyloxy)propyl]-N-methoxycarbonylamino}ethoxy)phenyl]-2-ethoxypropionic acid,
2-ethoxy-3-[4-(2-{N-[4-(4-fluorobenzyloxy)butyl]-N-methoxycarbonylamino}ethoxy)phenyl]propionic acid,
3-[4-(2-{N-[4-(3,5-dichlorobenzyloxy)butyl]-N-methoxycarbonylamino}ethoxy)phenyl]-2-ethoxypropionic acid,
2-ethoxy-3-[4-(2-{N-[3-(4-fluorophenyl)propyl]-N-methoxycarbonylamino}ethoxy)phenyl]propionic acid,
3-[4-(2-{N-[3-(3,5-dichlorophenyl)propyl]-N-methoxycarbonylamino}ethoxy)phenyl]-2-ethoxypropionic acid, 2-ethoxy-3-{4-[2-(N-ethoxycarbonyl-N-pentylamino)ethoxy]phenyl}propionic acid,
2-ethoxy-3-(4-[2-(N-ethoxycarbonyl-N-hexylamino)ethoxy]phenyl}propionic acid,
2-ethoxy-3-{4-[2-(N-ethoxycarbonyl-N-heptylamino)ethoxy]phenyl}propionic acid,
2-ethoxy-3-{4-[2-(N-ethoxycarbonyl-N-octylamino)ethoxy]phenyl}propionic acid,
2-ethoxy-3-{4-[2-(N-ethoxycarbonyl-N-isobutylamino)ethoxy]phenyl}propionic acid,
2-ethoxy-3-(4-{2-[N-ethoxycarbonyl-N-(3-methylbutyl)amino]ethoxy}phenyl)propionic acid,
2-ethoxy-3-(4-{2-[N-ethoxycarbonyl-N-(4-methylpentyl)amino]ethoxy}phenyl)propionic acid,
2-ethoxy-3-(4-{2-[N-ethoxycarbonyl-N-(2-propylpentyl)amino]ethoxy}phenyl)propionic acid,
3-(4-{2-[N-(3,3-dimethylbutyl)-N-ethoxycarbonylamino]ethoxy}phenyl)-2-ethoxypropionic acid,
2-ethoxy-3-(4-{2-[N-ethoxycarbonyl-N-(2-ethylbutyl)amino]ethoxy}phenyl)propionic acid,
3-{4-[2-(N-cyclohexylmethyl-N-ethoxycarbonylamino)ethoxy]phenyl}-2-ethoxypropionic acid,
3-(4-{2-[N-(4-cyclohexylbutyl)-N-ethoxycarbonylamino]ethoxy}phenyl)-2-ethoxypropionic acid,
3-{4-[2-(N-cyclopropylmethyl-N-ethoxycarbonylamino)ethoxy]phenyl}-2-ethoxypropionic acid,
3-{4-[2-(N-cyclobutylmethyl-N-ethoxycarbonylamino)ethoxy]phenyl}-2-ethoxypropionic acid,
3-{4-[2-(N-cyclopentylmethyl-N-ethoxycarbonylamino)ethoxy]phenyl}-2-ethoxypropionic acid,
3-(4-{2-[N-(2-cyclopentylethyl)-N-ethoxycarbonylamino]ethoxy}phenyl)-2-ethoxypropionic acid,
3-(4-{2-[N-(3-cyclohexylpropyl)-N-ethoxycarbonylamino]ethoxy}phenyl)-2-ethoxypropionic acid,
2-ethoxy-3-(4-{2-[N-ethoxycarbonyl-N-(3-phenylpropyl)amino]ethoxy}phenyl)propionic acid,
2-ethoxy-3-(4-{2-[N-ethoxycarbonyl-N-(4-phenylbutyl)amino]ethoxy}phenyl)propionic acid,
3-(4-{2-[N-(2-butoxyethyl)-N-ethoxycarbonylamino]ethoxy}phenyl)-2-ethoxypropionic acid,
2-ethoxy-3-(4-{2-[N-ethoxycarbonyl-N-(2-pentyloxyethyl)amino]ethoxy}phenyl)propionic acid,
2-ethoxy-3-(4-{2-[N-ethoxycarbonyl-N-(3-propoxypropyl)amino]ethoxy}phenyl)propionic acid,
3-(4-{2-[N-(2-butylthioethyl)-N-ethoxycarbonylamino]ethoxy}phenyl)-2-ethoxypropionic acid,
2-ethoxy-3-(4-{2-[N-ethoxycarbonyl-N-(2-pentylthioethyl)amino]ethoxy}phenyl)propionic acid,
2-ethoxy-3-(4-{2-[N-ethoxycarbonyl-N-(3-propylthiopropyl)amino]ethoxy}phenyl)propionic acid,
2-ethoxy-3-(4-{2-[N-ethoxycarbonyl-N-(3-phenoxypropyl)amino]ethoxy}phenyl)propionic acid,
2-ethoxy-3-(4-{2-[N-ethoxycarbonyl-N-(4-phenoxybutyl)amino]ethoxy}phenyl)propionic acid,
3-(4-{2-[N-(3-benzyloxypropyl)-N-ethoxycarbonylamino]ethoxy}phenyl)-2-ethoxypropionic acid,
2-ethoxy-3-(4-{2-[N-ethoxycarbonyl-N-(3-phenylthiopropyl)amino]ethoxy}phenyl)propionic acid,
2-ethoxy-3-(4-{2-[N-ethoxycarbonyl-N-(4-phenylthiobutyl)amino]ethoxy}phenyl)propionic acid,
3-(4-{2-[N-(3-benzylthiopropyl)-N-ethoxycarbonylamino]ethoxy}phenyl)-2-ethoxypropionic acid,
2-ethoxy-3-(4-{2-[N-ethoxycarbonyl-N-(7,7,7-trifluoroheptyl)amino]ethoxy}phenyl)propionic acid,
3-(4-{2-[N-(6,6-difluoroheptyl)-N-ethoxycarbonylamino]ethoxy}phenyl)-2-ethoxypropionic acid,
2-ethoxy-3-(4-{2-[N-ethoxycarbonyl-N-(6,6,6-trifluorohexyl)amino]ethoxy}phenyl)propionic acid,
3-(4-{2-[N-(5,5-difluorohexyl)-N-ethoxycarbonylamino]ethoxy}phenyl)-2-ethoxypropionic acid,
2-ethoxy-3-(4-{2-[N-ethoxycarbonyl-N-(5,5,6,6,7,7,7-heptafluoroheptyl)amino]ethoxy}phenyl)propionic acid,
2-ethoxy-3-(4-{2-[N-ethoxycarbonyl-N-(2,2,3,3,4,4,5,5,6,6,7,7,7-tridecafluoroheptyl)amino]ethoxy}phenyl)propionic acid,
2-ethoxy-3-(4-{2-[N-ethoxycarbonyl-N-(5,5,6,6,6-pentafluorohexyl)amino]ethoxy}phenyl)propionic acid,
2-ethoxy-3-(4-{2-[N-ethoxycarbonyl-N-(2,2,3,3,4,4,5,5,6,6-undecafluorohexyl)amino]ethoxy}phenyl)propionic acid,
3-[4-(2-{N-[2-(2,2-difluoropropoxy)ethyl]-N-ethoxycarbonylamino}ethoxy)phenyl]-2-ethoxypropionic acid,
2-ethoxy-3-[4-(2-{N-ethoxycarbonyl-N-[2-(1,1,2,2,3,3,3-heptafluoropropoxy)ethyl]amino}ethoxy)phenyl]propionic acid,
2-ethoxy-3-[4-(2-{N-ethoxycarbonyl-N-[2-(4,4,4-trifluorobutoxy)ethyl]amino}ethoxy)phenyl]propionic acid,
3-[4-(2-{N-[2-(3,3-difluorobutoxy)ethyl]-N-ethoxycarbonylamino}ethoxy)phenyl]-2-ethoxypropionic acid,
3-[4-(2-{N-[2-(2,2-difluorobutoxy)ethyl]-N-ethoxycarbonylamino}ethoxy)phenyl]-2-ethoxypropionic acid,
2-ethoxy-3-[4-(2-{N-ethoxycarbonyl-N-[2-(1,1,2,2,3,3,4,4,4-nonafluorobutoxy)ethyl]amino}ethoxy)phenyl]propionic acid,
2-ethoxy-3-[4-(2-{N-ethoxycarbonyl-N-[3-(2,2,2-trifluoroethoxy)propyl]amino}ethoxy)phenyl]propionic acid,
2-ethoxy-3-[4-(2-{N-ethoxycarbonyl-N-[3-(1,1,2,2,2-pentafluoroethoxy)propyl]amino}ethoxy)phenyl]propionic acid,
2-ethoxy-3-[4-(2-{N-ethoxycarbonyl-N-[3-(4-fluorophenoxy)propyl]amino}ethoxy)phenyl]propionic acid,
3-[4-(2-{N-[3-(3,5-dichlorophenoxy)propyl]-N-ethoxycarbonylamino}ethoxy)phenyl]-2-ethoxypropionic acid,
2-ethoxy-3-[4-(2-{N-ethoxycarbonyl-N-[4-(4-fluorophenoxy)butyl]amino}ethoxy)phenyl]propionic acid,
3-[4-(2-{N-[4-(3,5-dichlorophenoxy)butyl]-N-ethoxycarbonylamino}ethoxy)phenyl]-2-ethoxypropionic acid,
2-ethoxy-3-[4-(2-{N-ethoxycarbonyl-N-[2-(4-fluorobenzyloxy)ethyl]amino}ethoxy)phenyl]propionic acid,
3-[4-(2-{N-[2-(3,5-dichlorobenzyloxy)ethyl]-N-ethoxycarbonylamino}ethoxy)phenyl]-2-ethoxypropionic acid,
2-ethoxy-3-[4-(2-{N-ethoxycarbonyl-N-[3-(4-fluorobenzyloxy)propyl]amino}ethoxy)phenyl]propionic acid,
3-[4-(2-{N-[3-(3,5-dichlorobenzyloxy)propyl]-N-ethoxycarbonylamino}ethoxy)phenyl]-2-ethoxypropionic acid,
2-ethoxy-3-[4-(2-{N-ethoxycarbonyl-N-[4-(4-fluorobenzyloxy)butyl]amino}ethoxy)phenyl]propionic acid,
3-[4-(2-{N-[4-(3,5-dichlorobenzyloxy)butyl]-N-ethoxycarbonylamino}ethoxy)phenyl]-2-ethoxypropionic acid,
2-ethoxy-3-[4-(2-{N-ethoxycarbonyl-N-[3-(4-fluorophenyl)propyl]amino}ethoxy)phenyl]propionic acid,
3-[4-(2-{N-[3-(3,5-dichlorophenyl)propyl]-N-ethoxycarbonylamino}ethoxy)phenyl]-2-ethoxypropionic acid, 2-ethoxy-3-{4-[2-(N-pentyl-N-propoxycarbonylamino)ethoxy]phenyl}propionic acid,
2-ethoxy-3-{4-[2-(N-hexyl-N-propoxycarbonylamino)ethoxy]phenyl}propionic acid,
2-ethoxy-3-{4-[2-(N-heptyl-N-propoxycarbonylamino)ethoxy]phenyl}propionic acid,
2-ethoxy-3-{4-[2-(N-octyl-N-propoxycarbonylamino)ethoxy]phenyl}propionic acid,
2-ethoxy-3-{4-[2-(N-isobutyl-N-propoxycarbonylamino)ethoxy]phenyl}propionic acid,
2-ethoxy-3-(4-{2-[N-(3-methylbutyl)-N-propoxycarbonylamino]ethoxy}phenyl)propionic acid,
2-ethoxy-3-(4-{2-[N-(4-methylpentyl)-N-propoxycarbonylamino]ethoxy}phenyl)propionic acid,
2-ethoxy-3-(4-{2-[N-propoxycarbonyl-N-(2-propylpentyl)amino]ethoxy}phenyl)propionic acid,
3-(4-{2-[N-(3,3-dimethylbutyl)-N-propoxycarbonylamino]ethoxy}phenyl)-2-ethoxypropionic acid,
2-ethoxy-3-(4-{2-[N-(2-ethylbutyl)-N-propoxycarbonylamino]ethoxy}phenyl)propionic acid,
3-{4-[2-(N-cyclohexylmethyl-N-propoxycarbonylamino)ethoxy]phenyl}-2-ethoxypropionic acid,
3-(4-{2-[N-(4-cyclohexylbutyl)-N-propoxycarbonylamino]ethoxy}phenyl)-2-ethoxypropionic acid,
3-{4-[2-(N-cyclopropylmethyl-N-propoxycarbonylamino)ethoxy]phenyl}-2-ethoxypropionic acid,
3-{4-[2-(N-cyclobutylmethyl-N-propoxycarbonylamino)ethoxy]phenyl}-2-ethoxypropionic acid,
3-{4-[2-(N-cyclopentylmethyl-N-propoxycarbonylamino)ethoxy]phenyl}-2-ethoxypropionic acid,
3-(4-{2-[N-(2-cyclopentylethyl)-N-propoxycarbonylamino]ethoxy}phenyl)-2-ethoxypropionic acid,
3-(4-{2-[N-(3-cyclohexylpropyl)-N-propoxycarbonylamino]ethoxy}phenyl)-2-ethoxypropionic acid,
2-ethoxy-3-(4-{2-[N-(3-phenylpropyl)-N-propoxycarbonylamino]ethoxy}phenyl)propionic acid,
2-ethoxy-3-(4-{2-[N-(4-phenylbutyl)-N-propoxycarbonylamino]ethoxy}phenyl)propionic acid,
3-(4-{2-[N-(2-butoxyethyl)-N-propoxycarbonylamino]ethoxy}phenyl)-2-ethoxypropionic acid,
2-ethoxy-3-(4-{2-[N-(2-pentyloxyethyl)-N-propoxycarbonylamino]ethoxy}phenyl)propionic acid,
2-ethoxy-3-(4-{2-[N-propoxycarbonyl-N-(3-propoxypropyl)amino]ethoxy}phenyl)propionic acid,
3-(4-{2-[N-(2-butylthioethyl)-N-propoxycarbonylamino]ethoxy}phenyl)-2-ethoxypropionic acid,
2-ethoxy-3-(4-{2-[N-(2-pentylthioethyl)-N-propoxycarbonylamino]ethoxy}phenyl)propionic acid,
2-ethoxy-3-(4-{2-[N-propoxycarbonyl-N-(3-propylthiopropyl)amino]ethoxy}phenyl)propionic acid,
2-ethoxy-3-(4-{2-[N-(3-phenoxypropyl)-N-propoxycarbonylamino]ethoxy}phenyl)propionic acid,
2-ethoxy-3-(4-{2-[N-(4-phenoxybutyl)-N-propoxycarbonylamino]ethoxy}phenyl)propionic acid,
3-(4-{2-[N-(3-benzyloxypropyl)-N-propoxycarbonylamino]ethoxy}phenyl)-2-ethoxypropionic acid,
2-ethoxy-3-(4-{2-[N-(3-phenylthiopropyl)-N-propoxycarbonylamino]ethoxy}phenyl)propionic acid,
2-ethoxy-3-(4-{2-[N-(4-phenylthiobutyl)-N-propoxycarbonylamino] ethoxy}phenyl)propionic acid,
3-(4-{2-[N-(3-benzylthiopropyl)-N-propoxycarbonylamino]ethoxy}phenyl)-2-ethoxypropionic acid,
2-ethoxy-3-(4-{2-[N-propoxycarbonyl-N-(7,7,7-trifluoroheptyl)amino]ethoxy}phenyl)propionic acid,
3-(4-{2-[N-(6,6-difluoroheptyl)-N-propoxycarbonylamino]ethoxy}phenyl)-2-ethoxypropionic acid,
2-ethoxy-3-(4-{2-[N-propoxycarbonyl-N-(6,6,6-trifluorohexyl)amino]ethoxy}phenyl)propionic acid,
3-(4-{2-[N-(5,5-difluorohexyl)-N-propoxycarbonylamino]ethoxy}phenyl)-2-ethoxypropionic acid,
2-ethoxy-3-(4-{2-[N-(5,5,6,6,7,7,7-heptafluoroheptyl)-N-propoxycarbonylamino]ethoxy}phenyl)propionic acid,
2-ethoxy-3-(4-{2-[N-propoxycarbonyl-N-(2,2,3,3,4,4,5,5,6,6,7,7,7-tridecafluoroheptyl)amino]ethoxy}phenyl)propionic acid,
2-ethoxy-3-(4-{2-[N-(5,5,6,6,6-pentafluorohexyl)-N-propoxycarbonylamino]ethoxy}phenyl)propionic acid,
2-ethoxy-3-(4-{2-[N-propoxycarbonyl-N-(2,2,3,3,4,4,5,5,6,6,6-undecafluorohexyl)amino]ethoxy}phenyl)propionic acid,
3-[4-(2-{N-[2-(2,2-difluoropropoxy)ethyl]-N-propoxycarbonylamino}ethoxy)phenyl]-2-ethoxypropionic acid,
2-ethoxy-3-[4-(2-{N-[2-(1,1,2,2,3,3,3-heptafluoropropoxy)ethyl]-N-propoxycarbonylamino}ethoxy)phenyl]propionic acid,
2-ethoxy-3-[4-(2-{N-propoxycarbonyl-N-[2-(4,4,4-trifluorobutoxy)ethyl]amino}ethoxy)phenyl]propionic acid,
3-[4-(2-{N-[2-(3,3-difluorobutoxy)ethyl]-N-propoxycarbonylamino}ethoxy)phenyl]-2-ethoxypropionic acid,
3-[4-(2-{N-[2-(2,2-difluorobutoxy)ethyl]-N-propoxycarbonylamino}ethoxy)phenyl]-2-ethoxypropionic acid,
2-ethoxy-3-[4-(2-{N-[2-(1,1,2,2,3,3,4,4,4-nonafluorobutoxy)ethyl]-N-propoxycarbonylamino}ethoxy)phenyl]propionic acid,
2-ethoxy-3-[4-(2-{N-propoxycarbonyl-N-[3-(2,2,2-trifluoroethoxy)propyl]amino}ethoxy)phenyl]propionic acid,
2-ethoxy-3-[4-(2-{N-[3-(1,1,2,2,2-pentafluoroethoxy)propyl]-N-propoxycarbonylamino}ethoxy)phenyl]propionic acid,
2-ethoxy-3-[4-(2-{N-[3-(4-fluorophenoxy)propyl]-N-propoxycarbonylamino}ethoxy)phenyl]propionic acid,
3-[4-(2-{N-[3-(3,5-dichlorophenoxy)propyl]-N-propoxycarbonylamino}ethoxy)phenyl]-2-ethoxypropionic acid,
2-ethoxy-3-[4-(2-{N-[4-(4-fluorophenoxy)butyl]-N-propoxycarbonylamino}ethoxy)phenyl]propionic acid,
3-[4-(2-{N-[4-(3,5-dichlorophenoxy)butyl]-N-propoxycarbonylamino}ethoxy)phenyl]-2-ethoxypropionic acid,
2-ethoxy-3-[4-(2-{N-[2-(4-fluorobenzyloxy)ethyl]-N-propoxycarbonylamino}ethoxy)phenyl]propionic acid,
3-[4-(2-{N-[2-(3,5-dichlorobenzyloxy)ethyl]-N-propoxycarbonylamino}ethoxy)phenyl]-2-ethoxypropionic acid,
2-ethoxy-3-[4-(2-{N-[3-(4-fluorobenzyloxy)propyl]-N-propoxycarbonylamino}ethoxy)phenyl]propionic acid,
3-[4-(2-{N-[3-(3,5-dichlorobenzyloxy)propyl]-N-propoxycarbonylamino}ethoxy)phenyl]-2-ethoxypropionic acid,
2-ethoxy-3-[4-(2-{N-[4-(4-fluorobenzyloxy)butyl]-N-propoxycarbonylamino}ethoxy)phenyl]propionic acid,
3-[4-(2-{N-[4-(3,5-dichlorobenzyloxy)butyl]-N-propoxycarbonylamino}ethoxy)phenyl]-2-ethoxypropionic acid,
2-ethoxy-3-[4-(2-{N-[3-(4-fluorophenyl)propyl]-N-propoxycarbonylamino}ethoxy)phenyl]propionic acid,
3-[4-(2-{N-[3-(3,5-dichlorophenyl)propyl]-N-propoxycarbonylamino}ethoxy)phenyl]-2-ethoxypropionic acid, 3-{4-[2-(N-butoxycarbonyl-N-pentylamino)ethoxy]phenyl}-2-ethoxypropionic acid,
3-{4-[2-(N-butoxycarbonyl-N-hexylamino)ethoxy]phenyl}-2-ethoxypropionic acid,
3-{4-[2-(N-butoxycarbonyl-N-heptylamino)ethoxy]phenyl}-2-ethoxypropionic acid,
3-{4-[2-(N-butoxycarbonyl-N-octylamino)ethoxy]phenyl}-2-ethoxypropionic acid,
3-{4-[2-(N-butoxycarbonyl-N-isobutylamino)ethoxy]phenyl}-2-ethoxypropionic acid,
3-(4-{2-[N-butoxycarbonyl-N-(3-methylbutyl)amino]ethoxy}phenyl)-2-ethoxypropionic acid,
3-(4-{2-[N-butoxycarbonyl-N-(4-methylpentyl)amino]ethoxy}phenyl)-2-ethoxypropionic acid,
3-(4-{2-[N-butoxycarbonyl-N-(2-propylpentyl)amino]ethoxy}phenyl)-2-ethoxypropionic acid,
3-(4-{2-[N-butoxycarbonyl-N-(3,3-dimethylbutyl)amino]ethoxy}phenyl)-2-ethoxypropionic acid,
3-(4-{2-[N-butoxycarbonyl-N-(2-ethylbutyl)amino]ethoxy}phenyl)-2-ethoxypropionic acid,
3-{4-[2-(N-butoxycarbonyl-N-cyclohexylmethylamino)ethoxy]phenyl}-2-ethoxypropionic acid,
3-(4-{2-[N-butoxycarbonyl-N-(4-cyclohexylbutyl)amino]ethoxy}phenyl)-2-ethoxypropionic acid,
3-{4-[2-(N-butoxycarbonyl-N-cyclopropylmethylamino)ethoxy]phenyl}-2-ethoxypropionic acid,
3-{4-[2-(N-butoxycarbonyl-N-cyclobutylmethylamino)ethoxy]phenyl}-2-ethoxypropionic acid,
3-{4-[2-(N-butoxycarbonyl-N-cyclopentylmethylamino)ethoxy]phenyl}-2-ethoxypropionic acid,
3-(4-{2-[N-butoxycarbonyl-N-(2-cyclopentylethyl)amino]ethoxy}phenyl)-2-ethoxypropionic acid,
3-(4-{2-[N-butoxycarbonyl-N-(3-cyclohexylpropyl)amino]ethoxy}phenyl)-2-ethoxypropionic acid,
3-(4-{2-[N-butoxycarbonyl-N-(3-phenylpropyl)amino]ethoxy}phenyl)-2-ethoxypropionic acid,
3-(4-{2-[N-butoxycarbonyl-N-(4-phenylbutyl)amino]ethoxy}phenyl)-2-ethoxypropionic acid,
3-(4-{2-[N-(2-butoxyethyl)-N-butoxycarbonylamino]ethoxy}phenyl)-2-ethoxypropionic acid,
3-(4-{2-[N-butoxycarbonyl-N-(2-pentyloxyethyl)amino]ethoxy}phenyl)-2-ethoxypropionic acid,
3-(4-{2-[N-butoxycarbonyl-N-(3-propoxypropyl)amino]ethoxy}phenyl)-2-ethoxypropionic acid,
3-(4-{2-[N-butoxycarbonyl-N-(2-butylthioethyl)amino]ethoxy}phenyl)-2 -ethoxypropionic acid,
3-(4-{2-[N-butoxycarbonyl-N-(2-pentylthioethyl)amino]ethoxy}phenyl)-2-ethoxypropionic acid,
3-(4-{2-[N-butoxycarbonyl-N-(3-propylthiopropyl)amino]ethoxy}phenyl)-2-ethoxypropionic acid,
3-(4-{2-[N-butoxycarbonyl-N-(3-phenoxypropyl)amino]ethoxy}phenyl)-2-ethoxypropionic acid,
3-(4-{2-[N-butoxycarbonyl-N-(4-phenoxybutyl)amino]ethoxy}phenyl)-2-ethoxypropionic acid,
3-(4-{2-[N-(3-benzyloxypropyl)-N-butoxycarbonylamino]ethoxy}phenyl)-2-ethoxypropionic acid,
3-(4-{2-[N-butoxycarbonyl-N-(3-phenylthiopropyl)amino]ethoxy}phenyl)-2-ethoxypropionic acid,
3-(4-{2-[N-butoxycarbonyl-N-(4-phenylthiobutyl)amino]ethoxy}phenyl)-2-ethoxypropionic acid,
3-(4-{2-[N-(3-benzylthiopropyl)-N-butoxycarbonylamino]ethoxy}phenyl)-2-ethoxypropionic acid,
3-(4-{2-[N-butoxycarbonyl-N-(7,7,7-trifluoroheptyl)amino]ethoxy}phenyl)-2-ethoxypropionic acid,
3-(4-{2-[N-butoxycarbonyl-N-(6,6-difluoroheptyl)amino]ethoxy}phenyl)-2-ethoxypropionic acid,
3-(4-{2-[N-butoxycarbonyl-N-(6,6,6-trifluorohexyl)amino]ethoxy}phenyl)-2-ethoxypropionic acid,
3-(4-{2-[N-butoxycarbonyl-N-(5,5-difluorohexyl)amino]ethoxy}phenyl)-2-ethoxypropionic acid,
3-(4-{2-[N-butoxycarbonyl-N-(5,5,6,6,7,7,7-heptafluoroheptyl)amino]ethoxy}phenyl)-2-ethoxypropionic acid,
3-(4-{2-[N-butoxycarbonyl-N-(2,2,3,3,4,4,5,5,6,6,7,7,7-tridecafluoroheptyl)amino]ethoxy}phenyl)-2-ethoxypropionic acid,
3-(4-{2-[N-butoxycarbonyl-N-(5,5,6,6,6-pentafluorohexyl)amino]ethoxy}phenyl)-2-ethoxypropionic acid,
3-(4-{2-[N-butoxycarbonyl-N-(2,2,3,3,4,4,5,5,6,6,6-undecafluorohexyl)amino]ethoxy}phenyl)-2-ethoxypropionic acid,
3-[4-(2-{N-butoxycarbonyl-N-[2-(2,2-difluoropropoxy)ethyl]amino}ethoxy)phenyl]-2-ethoxypropionic acid,
3-[4-(2-{N-butoxycarbonyl-N-[2-(1,1,2,2,3,3,3-heptafluoropropoxy)ethyl]amino}ethoxy)phenyl]-2-ethoxypropionic acid,
3-[4-(2-{N-butoxycarbonyl-N-[2-(4,4,4-trifluorobutoxy)ethyl]amino}ethoxy)phenyl]-2-ethoxypropionic acid,
3-[4-(2-{N-butoxycarbonyl-N-[2-(3,3-difluorobutoxy)ethyl]amino}ethoxy)phenyl]-2-ethoxypropionic acid,
3-[4-(2-{N-butoxycarbonyl-N-[2-(2,2-difluorobutoxy)ethyl]amino}ethoxy)phenyl]-2-ethoxypropionic acid,
3-[4-(2-{N-butoxycarbonyl-N-[2-(1,1,2,2,3,3,4,4,4-nonafluorobutoxy)ethyl]amino}ethoxy)phenyl]-2-ethoxypropionic acid,
3-[4-(2-{N-butoxycarbonyl-N-[3-(2,2,2-trifluoroethoxy)propyl]amino}ethoxy)phenyl]-2-ethoxypropionic acid,
3-[4-(2-{N-butoxycarbonyl-N-[3-(1,1,2,2,2-pentafluoroethoxy)propyl]amino}ethoxy)phenyl]-2-ethoxypropionic acid,
3-[4-(2-{N-butoxycarbonyl-N-[3-(4-fluorophenoxy)propyl]amino}ethoxy)phenyl]-2-ethoxypropionic acid,
3-[4-(2-{N-butoxycarbonyl-N-[3-(3,5-dichlorophenoxy)propyl]amino}ethoxy)phenyl]-2-ethoxypropionic acid,
3-[4-(2-{N-butoxycarbonyl-N-[4-(4-fluorophenoxy)butyl]amino}ethoxy)phenyl]-2-ethoxypropionic acid,
3-[4-(2-{N-butoxycarbonyl-N-[4-(3,5-dichlorophenoxy)butyl]amino}ethoxy)phenyl]-2-ethoxypropionic acid,
3-[4-(2-{N-butoxycarbonyl-N-[2-(4-fluorobenzyloxy)ethyl]amino}ethoxy)phenyl]-2-ethoxypropionic acid,
3-[4-(2-{N-butoxycarbonyl-N-[2-(3,5-dichlorobenzyloxy)ethyl]amino}ethoxy)phenyl]-2-ethoxypropionic acid,
3-[4-(2-{N-butoxycarbonyl-N-[3-(4-fluorobenzyloxy)propyl]amino}ethoxy)phenyl]-2-ethoxypropionic acid,
3-[4-(2-{N-butoxycarbonyl-N-[3-(3,5-dichlorobenzyloxy)propyl]amino}ethoxy)phenyl]-2-ethoxypropionic acid,
3-[4-(2-{N-butoxycarbonyl-N-[4-(4-fluorobenzyloxy)butyl]amino}ethoxy)phenyl]-2 -ethoxypropionic acid,
3-[4-(2-{N-butoxycarbonyl-N-[4-(3,5-dichlorobenzyloxy)butyl]amino}ethoxy)phenyl]-2-ethoxypropionic acid,
3-[4-(2-{N-butoxycarbonyl-N-[3-(4-fluorophenyl)propyl]amino}ethoxy)phenyl]-2-ethoxypropionic acid,
3-[4-(2-{N-butoxycarbonyl-N-[3-(3,5-dichlorophenyl)propyl]amino}ethoxy)phenyl]-2-ethoxypropionic acid,
2-ethoxy-3-{4-[2-(N-isopropoxycarbonyl-N-pentylamino)ethoxy]phenyl}propionic acid,
2-ethoxy-3-{4-[2-(N-hexyl-N-isopropoxycarbonylamino)ethoxy]phenyl}propionic acid,
2-ethoxy-3-{4-[2-(N-heptyl-N-isopropoxycarbonylamino)ethoxy]phenyl}propionic acid,
2-ethoxy-3-{4-[2-(N-isopropoxycarbonyl-N-octylamino)ethoxy]phenyl}propionic acid,
2-ethoxy-3-{4-[2-(N-isobutyl-N-isopropoxycarbonylamino)ethoxy]phenyl}propionic acid, 2-ethoxy-3-(4-{2-[N-isopropoxycarbonyl-N-(3-methylbutyl)amino]ethoxy}phenyl)propionic acid,
2-ethoxy-3-(4-{2-[N-isopropoxycarbonyl-N-(4-methylpentyl)amino]ethoxy}phenyl)propionic acid,
2-ethoxy-3-(4-{2-[N-isopropoxycarbonyl-N-(2-propylpentyl)amino]ethoxy}phenyl)propionic acid,
3-(4-{2-[N-(3,3-dimethylbutyl)-N-isopropoxycarbonylamino]ethoxy}phenyl)-2-ethoxypropionic acid,
2-ethoxy-3-(4-{2-[N-(2-ethylbutyl)-N-isopropoxycarbonylamino]ethoxy}phenyl)propionic acid,
3-{4-[2-(N-cyclohexylmethyl-N-isopropoxycarbonylamino)ethoxy]phenyl}-2-ethoxypropionic acid,
3-(4-{2-[N-(4-cyclohexylbutyl)-N-isopropoxycarbonylamino]ethoxy}phenyl)-2-ethoxypropionic acid,
3-{4-[2-(N-cyclopropylmethyl-N-isopropoxycarbonylamino)ethoxy]phenyl}-2-ethoxypropionic acid,
3-{4-[2-(N-cyclobutylmethyl-N-isopropoxycarbonylamino)ethoxy]phenyl}-2-ethoxypropionic acid,
3-{4-[2-(N-cyclopentylmethyl-N-isopropoxycarbonylamino)ethoxy]phenyl}-2-ethoxypropionic acid,
3-(4-{2-[N-(2-cyclopentylethyl)-N-isopropoxycarbonylamino]ethoxy}phenyl)-2-ethoxypropionic acid,
3-(4-{2-[N-(3-cyclohexylpropyl)-N-isopropoxycarbonylamino]ethoxy}phenyl)-2-ethoxypropionic acid,
2-ethoxy-3-(4-{2-[N-isopropoxycarbonyl-N-(3-phenylpropyl)amino]ethoxy}phenyl)propionic acid,
2-ethoxy-3-(4-{2-[N-isopropoxycarbonyl-N-(4-phenylbutyl)amino]ethoxy}phenyl)propionic acid,
3-(4-{2-[N-(2-butoxyethyl)-N-isopropoxycarbonylamino]ethoxy}phenyl)-2-ethoxypropionic acid,
2-ethoxy-3-(4-{2-[N-isopropoxycarbonyl-N-(2-pentyloxyethyl)amino]ethoxy}phenyl)propionic acid,
2-ethoxy-3-(4-{2-[N-isopropoxycarbonyl-N-(3-propoxypropyl)amino]ethoxy}phenyl)propionic acid,
3-(4-{2-[N-(2-butylthioethyl)-N-isopropoxycarbonylamino]ethoxy}phenyl)-2-ethoxypropionic acid,
2-ethoxy-3-(4-{2-[N-isopropoxycarbonyl-N-(2-pentylthioethyl)amino]ethoxy}phenyl)propionic acid,
2-ethoxy-3-(4-{2-[N-isopropoxycarbonyl-N-(3-propylthiopropyl)amino]ethoxy}phenyl)propionic acid,
2-ethoxy-3-(4-{2-[N-isopropoxycarbonyl-N-(3-phenoxypropyl)amino]ethoxy}phenyl)propionic acid,
2-ethoxy-3-(4-{2-[N-isopropoxycarbonyl-N-(4-phenoxybutyl)amino]ethoxy}phenyl)propionic acid,
3-(4-{2-[N-(3-benzyloxypropyl)-N-isopropoxycarbonylamino]ethoxy}phenyl)-2-ethoxypropionic acid,
2-ethoxy-3-(4-{2-[N-isopropoxycarbonyl-N-(3-phenylthiopropyl)amino]ethoxy}phenyl)propionic acid,
2-ethoxy-3-(4-{2-[N-isopropoxycarbonyl-N-(4-phenylthiobutyl)amino]ethoxy}phenyl)propionic acid,
3-(4-{2-[N-(3-benzylthiopropyl)-N-isopropoxycarbonylamino]ethoxy}phenyl)-2-ethoxypropionic acid,
2-ethoxy-3-(4-{2-[N-isopropoxycarbonyl-N-(7,7,7-trifluoroheptyl)amino]ethoxy}phenyl)propionic acid,
3-(4-{2-[N-(6,6-difluoroheptyl)-N-isopropoxycarbonylamino]ethoxy}phenyl)-2-ethoxypropionic acid,
2-ethoxy-3-(4-{2-[N-isopropoxycarbonyl-N-(6,6,6-trifluorohexyl)amino]ethoxy}phenyl)propionic acid,
3-(4-{2-[N-(5,5-difluorohexyl)-N-isopropoxycarbonylamino]ethoxy}phenyl)-2-ethoxypropionic acid,
2-ethoxy-3-(4-{2-[N-(5,5,6,6,7,7,7-heptafluoroheptyl)-N-isopropoxycarbonylamino]ethoxy}phenyl)propionic acid,
2-ethoxy-3-(4-{2-[N-isopropoxycarbonyl-N-(2,2,3,3,4,4,5,5,6,6,7,7,7-tridecafluoroheptyl)amino]ethoxy}phenyl)propionic acid,
2-ethoxy-3-(4-{2-[N-isopropoxycarbonyl-N-(5,5,6,6,6-pentafluorohexyl)amino]ethoxy}phenyl)propionic acid,
2-ethoxy-3-(4-{2-[N-isopropoxycarbonyl-N-(2,2,3,3,4,4,5,5,6,6,6-undecafluorohexyl)amino]ethoxy}phenyl)propionic acid,
3-[4-(2-{N-[2-(2,2-difluoropropoxy)ethyl]-N-isopropoxycarbonylamino}ethoxy)phenyl]-2-ethoxypropionic acid,
2-ethoxy-3-[4-(2-{N-[2-(1,1,2,2,3,3,3-heptafluoropropoxy)ethyl]-N-isopropoxycarbonylamino}ethoxy)phenyl]propionic acid,
2-ethoxy-3-[4-(2-{N-isopropoxycarbonyl-N-[2-(4,4,4-trifluorobutoxy)ethyl]amino}ethoxy)phenyl]propionic acid,
3-[4-(2-{N-[2-(3,3-difluorobutoxy)ethyl]-N-isopropoxycarbonylamino}ethoxy)phenyl]-2-ethoxypropionic acid,
3-[4-(2-{N-[2-(2,2-difluorobutoxy)ethyl]-N-isopropoxycarbonylamino}ethoxy)phenyl]-2-ethoxypropionic acid,
2-ethoxy-3-[4-(2-{N-isopropoxycarbonyl-N-[2-(1,1,2,2,3,3,4,4,4-nonafluorobutoxy)ethyl]amino}ethoxy)phenyl]propionic acid,
2-ethoxy-3-[4-(2-{N-isopropoxycarbonyl-N-[3-(2,2,2-trifluoroethoxy)propyl]amino}ethoxy)phenyl]propionic acid,
2-ethoxy-3-[4-(2-{N-isopropoxycarbonyl-N-[3-(1,1,2,2,2-pentafluoroethoxy)propyl]amino}ethoxy)phenyl]propionic acid,
2-ethoxy-3-[4-(2-{N-[3-(4-fluorophenoxy)propyl]-N-isopropoxycarbonylamino}ethoxy)phenyl]propionic acid,
3-[4-(2-{N-[3-(3,5-dichlorophenoxy)propyl]-N-isopropoxycarbonylamino} ethoxy)phenyl]-2-ethoxypropionic acid,
2-ethoxy-3-[4-(2-{N-[4-(4-fluorophenoxy)butyl]-N-isopropoxycarbonylamino}ethoxy)phenyl]propionic acid,
3-[4-(2-{N-[4-(3,5-dichlorophenoxy)butyl]-N-isopropoxycarbonylamino}ethoxy)phenyl]-2-ethoxypropionic acid,
2-ethoxy-3-[4-(2-{N-[2-(4-fluorobenzyloxy)ethyl]-N-isopropoxycarbonylamino}ethoxy)phenyl]propionic acid,
3-[4-(2-{N-[2-(3,5-dichlorobenzyloxy)ethyl]-N-isopropoxycarbonylamino}ethoxy)phenyl]-2-ethoxypropionic acid,
2-ethoxy-3-[4-(2-{N-[3-(4-fluorobenzyloxy)propyl]-N-isopropoxycarbonylamino}ethoxy)phenyl]propionic acid,
3-[4-(2-{N-[3-(3,5-dichlorobenzyloxy)propyl]-N-isopropoxycarbonylamino}ethoxy)phenyl]-2-ethoxypropionic acid,
2-ethoxy-3-[4-(2-{N-[4-(4-fluorobenzyloxy)butyl]-N-isopropoxycarbonylamino}ethoxy)phenyl]propionic acid,
3-[4-(2-{N-[4-(3,5-dichlorobenzyloxy)butyl]-N-isopropoxycarbonylamino}ethoxy)phenyl]-2-ethoxypropionic acid,
2-ethoxy-3-[4-(2-{N-[3-(4-fluorophenyl)propyl]-N-isopropoxycarbonylamino}ethoxy)phenyl]propionic acid,
3-[4-(2-{N-[3-(3,5-dichlorophenyl)propyl]-N-isopropoxycarbonylamino}ethoxy)phenyl]-2-ethoxypropionic acid,
2-ethoxy-3-{4-[2-(N-isobutoxycarbonyl-N-pentylamino)ethoxy]phenyl}propionic acid, 2-ethoxy-3-{4-[2-(N-hexyl-N-isobutoxycarbonylamino) ethoxy]phenyl}propionic acid,
2-ethoxy-3-{4-[2-(N-heptyl-N-isobutoxycarbonylamino) ethoxy]phenyl}propionic acid,
2-ethoxy-3-{4-[2-(N-isobutoxycarbonyl-N-octylamino) ethoxy]phenyl}propionic acid,
2-ethoxy-3-{4-[2-(N-isobutyl-N-isobutoxycarbonylamino) ethoxy]phenyl}propionic acid,
2-ethoxy-3-(4-{2-[N-isobutoxycarbonyl-N-(3-methylbutyl) amino]ethoxy}phenyl)propionic acid,
2-ethoxy-3-(4-{2-[N-isobutoxycarbonyl-N-(4-methylpentyl)amino]ethoxy}phenyl)propionic acid,
2-ethoxy-3-(4-{2-[N-isobutoxycarbonyl-N-(2-propylpentyl)amino]ethoxy}phenyl)propionic acid,
3-(4-{2-[N-(3,3-dimethylbutyl)-N-isobutoxycarbonylamino]ethoxy}phenyl)-2 -ethoxypropionic acid,
2-ethoxy-3-(4-{2-[N-(2-ethylbutyl)-N-isobutoxycarbonylamino]ethoxy}phenyl)propionic acid,
3-{4-[2-(N-cyclohexylmethyl-N-isobutoxycarbonylamino) ethoxy]phenyl}-2-ethoxypropionic acid,
3-(4-{2-[N-(4-cyclohexylbutyl)-N-isobutoxycarbonylamino]ethoxy}phenyl)-2-ethoxypropionic acid,
3-{4-[2-(N-cyclopropylmethyl-N-isobutoxycarbonylamino) ethoxy]phenyl}-2-ethoxypropionic acid,
3-{4-[2-(N-cyclobutylmethyl-N-isobutoxycarbonylamino) ethoxy]phenyl}-2-ethoxypropionic acid,
3-{4-[2-(N-cyclopentylmethyl-N-isobutoxycarbonylamino) ethoxy]phenyl}-2-ethoxypropionic acid,
3-(4-{2-[N-(2-cyclopentylethyl)-N-isobutoxycarbonylamino]ethoxy}phenyl)-2-ethoxypropionic acid,
3-(4-{2-[N-(3-cyclohexylpropyl)-N-isobutoxycarbonylamino]ethoxy}phenyl)-2-ethoxypropionic acid,
2-ethoxy-3-(4-{2-[N-isobutoxycarbonyl-N-(3-phenylpropyl)amino]ethoxy}phenyl)propionic acid,
2-ethoxy-3-(4-{2-[N-isobutoxycarbonyl-N-(4-phenylbutyl) amino]ethoxy}phenyl)propionic acid,
3-(4-{2-[N-(2-butoxyethyl)-N-isobutoxycarbonylamino] ethoxy}phenyl)-2-ethoxypropionic acid,
2-ethoxy-3-(4-{2-[N-isobutoxycarbonyl-N-(2-pentyloxyethyl)amino]ethoxy}phenyl)propionic acid,
2-ethoxy-3-(4-{2-[N-isobutoxycarbonyl-N-(3-propoxypropyl)amino]ethoxy}phenyl)propionic acid,
3-(4-{2-[N-(2-butylthioethyl)-N-isobutoxycarbonylamino] ethoxy}phenyl)-2-ethoxypropionic acid,
2-ethoxy-3-(4-{2-[N-isobutoxycarbonyl-N-(2-pentylthioethyl)amino]ethoxy}phenyl)propionic acid,
2-ethoxy-3-(4-{2-[N-isobutoxycarbonyl-N-(3-propylthiopropyl)amino]ethoxy}phenyl)propionic acid,
2-ethoxy-3-(4-{2-[N-isobutoxycarbonyl-N-(3-phenoxypropyl)amino]ethoxy}phenyl)propionic acid,
2-ethoxy-3-(4-{2-[N-isobutoxycarbonyl-N-(4-phenoxybutyl)amino]ethoxy}phenyl)propionic acid,
3-(4-{2-[N-(3-benzyloxypropyl)-N-isobutoxycarbonylamino]ethoxy}phenyl)-2-ethoxypropionic acid,
2-ethoxy-3-(4-{2-[N-isobutoxycarbonyl-N-(3-phenylthiopropyl)amino]ethoxy}phenyl)propionic acid,
2-ethoxy-3-(4-{2-[N-isobutoxycarbonyl-N-(4-phenylthiobutyl)amino]ethoxy}phenyl)propionic acid,
3-(4-{2-[N-(3-benzylthiopropyl)-N-isobutoxycarbonylamino]ethoxy}phenyl)-2-ethoxypropionic acid,
2-ethoxy-3-(4-{2-[N-isobutoxycarbonyl-N-(7,7,7-trifluoroheptyl)amino]ethoxy}phenyl)propionic acid,
3-(4-{2-[N-(6,6-difluoroheptyl)-N-isobutoxycarbonylamino]ethoxy}phenyl)-2-ethoxypropionic acid,
2-ethoxy-3-(4-{2-[N-isobutoxycarbonyl-N-(6,6,6-trifluorohexyl)amino]ethoxy}phenyl)propionic acid,
3-(4-{2-[N-(5,5-difluorohexyl)-N-isobutoxycarbonylamino]ethoxy}phenyl)-2-ethoxypropionic acid,
2-ethoxy-3-(4-{2-[N-(5,5,6,6,7,7,7-heptafluoroheptyl)-N-isobutoxycarbonylamino]ethoxy}phenyl)propionic acid,
2-ethoxy-3-(4-{2-[N-isobutoxycarbonyl-N-(2,2,3,3,4,4,5,5,6,6,7,7,7-tridecafluoroheptyl)amino]ethoxy}phenyl)propionic acid,
2-ethoxy-3-(4-{2-[N-isobutoxycarbonyl-N-(5,5,6,6,6-pentafluorohexyl)amino]ethoxy}phenyl)propionic acid,
2-ethoxy-3-(4-{2-[N-isobutoxycarbonyl-N-(2,2,3,3,4,4,5,5,6,6,6-undecafluorohexyl)amino]ethoxy}phenyl)propionic acid,
3-[4-(2-{N-[2-(2,2-difluoropropoxy)ethyl]-N-isobutoxycarbonylamino}ethoxy)phenyl]-2-ethoxypropionic acid,
2-ethoxy-3-[4-(2-{N-[2-(1,1,2,2,3,3,3-heptafluoropropoxy) ethyl]-N-isobutoxycarbonylamino}ethoxy)phenyl]propionic acid,
2-ethoxy-3-[4-(2-{N-isobutoxycarbonyl-N-[2-(4,4,4 -trifluorobutoxy)ethyl]amino}ethoxy)phenyl]propionic acid,
3-[4-(2-{N-[2-(3,3-difluorobutoxy)ethyl]-N-isobutoxycarbonylamino}ethoxy)phenyl]-2-ethoxypropionic acid,
3-[4-(2-{N-[2-(2,2-difluorobutoxy)ethyl]-N-isobutoxycarbonylamino}ethoxy)phenyl]-2-ethoxypropionic acid,
2-ethoxy-3-[4-(2-{N-isobutoxycarbonyl-N-[2-(1,1,2,2,3,3,4,4,4-nonafluorobutoxy)ethyl]amino}ethoxy)phenyl]propionic acid,
2-ethoxy-3-[4-(2-{N-isobutoxycarbonyl-N-[3-(2,2,2-trifluoroethoxy)propyl]amino}ethoxy)phenyl]propionic acid,
2-ethoxy-3-[4-(2-{N-isobutoxycarbonyl-N-[3-(1,1,2,2,2-pentafluoroethoxy)propyl]amino}ethoxy)phenyl]propionic acid,
2-ethoxy-3-[4-(2-{N-[3-(4-fluorophenoxy)propyl]-N-isobutoxycarbonylamino}ethoxy)phenyl]propionic acid,
3-[4-(2-{N-[3-(3,5-dichlorophenoxy)propyl]-N-isobutoxycarbonylamino}ethoxy)phenyl]-2-ethoxypropionic acid,
2-ethoxy-3-[4-(2-{N-[4-(4-fluorophenoxy)butyl]-N-isobutoxycarbonylamino}ethoxy)phenyl]propionic acid,
3-[4-(2-{N-[4-(3,5-dichlorophenoxy)butyl]-N-isobutoxycarbonylamino}ethoxy)phenyl]-2-ethoxypropionic acid,
2-ethoxy-3-[4-(2-{N-[2-(4-fluorobenzyloxy)ethyl]-N-isobutoxycarbonylamino}ethoxy)phenyl]propionic acid,
3-[4-(2-{N-[2-(3,5-dichlorobenzyloxy)ethyl]-N-isobutoxycarbonylamino}ethoxy)phenyl]-2-ethoxypropionic acid,
2-ethoxy-3-[4-(2-{N-[3-(4-fluorobenzyloxy)propyl]-N-isobutoxycarbonylamino}ethoxy)phenyl]propionic acid,
3-[4-(2-{N-[3-(3,5-dichlorobenzyloxy)propyl]-N-isobutoxycarbonylamino}ethoxy)phenyl]-2-ethoxypropionic acid,
2-ethoxy-3-[4-(2-{N-[4-(4-fluorobenzyloxy)butyl]-N-isobutoxycarbonylamino}ethoxy)phenyl]propionic acid,
3-[4-(2-{N-[4-(3,5-dichlorobenzyloxy)butyl]-N-isobutoxycarbonylamino}ethoxy)phenyl]-2-ethoxypropionic acid,
2-ethoxy-3-[4-(2-{N-[3-(4-fluorophenyl)propyl]-N-isobutoxycarbonylamino}ethoxy)phenyl]propionic acid,
3-[4-(2-{N-[3-(3,5-dichlorophenyl)propyl]-N-isobutoxycarbonylamino}ethoxy)phenyl]-2-ethoxypropionic acid,
2-ethoxy-3-(4-{2-[N-(1-methylpropoxycarbonyl)-N-pentylamino]ethoxy}phenyl)propionic acid, 2-ethoxy-3-(4-{2-[N-hexyl-N-(1-methylpropoxycarbonyl)amino]ethoxy}phenyl)propionic acid,
2-ethoxy-3-(4-{2-[N-heptyl-N-(1-methylpropoxycarbonyl)amino]ethoxy}phenyl)propionic acid,
2-ethoxy-3-(4-{2-[N-(1-methylpropoxycarbonyl)-N-octylamino]ethoxy}phenyl)propionic acid,
2-ethoxy-3-(4-{2-[N-isobutyl-N-(1-methylpropoxycarbonyl)amino]ethoxy}phenyl)propionic acid,
2-ethoxy-3-(4-{2-[N-(1-methylpropoxycarbonyl)-N-(3-methylbutyl)amino]ethoxy}phenyl)propionic acid,
2-ethoxy-3-(4-{2-[N-(4-methylpentyl)-N-(1-methylpropoxycarbonyl)amino]ethoxy}phenyl)propionic acid,
2-ethoxy-3-(4-{2-[N-(1-methylpropoxycarbonyl)-N-(2-propylpentyl)amino]ethoxy}phenyl)propionic acid,
3-(4-{2-[N-(3,3-dimethylbutyl)-N-(1-methylpropoxycarbonyl)amino]ethoxy}phenyl)-2-ethoxypropionic acid,
2-ethoxy-3-(4-{2-[N-(2-ethylbutyl)-N-(1-methylpropoxycarbonyl)amino]ethoxy}phenyl)propionic acid,
3-(4-{2-[N-cyclohexylmethyl-N-(1-methylpropoxycarbonyl)amino]ethoxy}phenyl)-2-ethoxypropionic acid,
3-(4-{2-[N-(4-cyclohexylbutyl)-N-(1-methylpropoxycarbonyl)amino]ethoxy}phenyl)-2-ethoxypropionic acid,
3-(4-{2-[N-cyclopropylmethyl-N-(1-methylpropoxycarbonyl)amino]ethoxy}phenyl)-2-ethoxypropionic acid,
3-(4-{2-[N-cyclobutylmethyl-N-(1-methylpropoxycarbonyl)amino]ethoxy}phenyl)-2-ethoxypropionic acid,
3-(4-{2-[N-cyclopentylmethyl-N-(1-methylpropoxycarbonyl)amino]ethoxy}phenyl)-2-ethoxypropionic acid,
3-(4-{2-[N-(2-cyclopentylethyl)-N-(1-methylpropoxycarbonyl)amino]ethoxy}phenyl)-2-ethoxypropionic acid,
3-(4-{2-[N-(3-cyclohexylpropyl)-N-(1-methylpropoxycarbonyl)amino]ethoxy}phenyl)-2-ethoxypropionic acid,
2-ethoxy-3-(4-{2-[N-(1-methylpropoxycarbonyl)-N-(3-phenylpropyl)amino]ethoxy}phenyl)propionic acid,
2-ethoxy-3-(4-{2-[N-(1-methylpropoxycarbonyl)-N-(4-phenylbutyl)amino]ethoxy}phenyl)propionic acid,
3-(4-{2-[N-(2-butoxyethyl)-N-(1-methylpropoxycarbonyl)amino]ethoxy}phenyl)-2-ethoxypropionic acid,
2-ethoxy-3-(4-{2-[N-(1-methylpropoxycarbonyl)-N-(2-pentyloxyethyl)amino]ethoxy}phenyl)propionic acid,
2-ethoxy-3-(4-{2-[N-(1-methylpropoxycarbonyl)-N-(3-propoxypropyl)amino]ethoxy}phenyl)propionic acid,
3-(4-{2-[N-(2-butylthioethyl)-N-(1-methylpropoxycarbonyl)amino]ethoxy}phenyl)-2-ethoxypropionic acid,
2-ethoxy-3-(4-{2-[N-(1-methylpropoxycarbonyl)-N-(2-pentylthioethyl)amino]ethoxy}phenyl)propionic acid,
2-ethoxy-3-(4-{2-[N-(1-methylpropoxycarbonyl)-N-(3-propylthiopropyl)amino]ethoxy}phenyl)propionic acid,
2-ethoxy-3-(4-{2-[N-(1-methylpropoxycarbonyl)-N-(3-phenoxypropyl)amino]ethoxy}phenyl)propionic acid,
2-ethoxy-3-(4-{2-[N-(1-methylpropoxycarbonyl)-N-(4-phenoxybutyl)amino]ethoxy}phenyl)propionic acid,
3-(4-{2-[N-(3-benzyloxypropyl)-N-(1-methylpropoxycarbonyl)amino]ethoxy}phenyl)-2-ethoxypropionic acid,
2-ethoxy-3-(4-{2-[N-(1-methylpropoxycarbonyl)-N-(3-phenylthiopropyl)amino]ethoxy}phenyl)propionic acid,
2-ethoxy-3-(4-{2-[N-(1-methylpropoxycarbonyl)-N-(4-phenylthiobutyl)amino]ethoxy}phenyl)propionic acid,
3-(4-{2-[N-(3-benzylthiopropyl)-N-(1-methylpropoxycarbonyl)amino]ethoxy}phenyl)-2-ethoxypropionic acid,
2-ethoxy-3-(4-{2-[N-(1-methylpropoxycarbonyl)-N-(7,7,7-trifluoroheptyl)amino]ethoxy}phenyl)propionic acid,
3-(4-{2-[N-(6,6-difluoroheptyl)-N-(1-methylpropoxycarbonyl)amino]ethoxy}phenyl)-2-ethoxypropionic acid,
2-ethoxy-3-(4-{2-[N-(1-methylpropoxycarbonyl)-N-(6,6,6-trifluorohexyl)amino]ethoxy}phenyl)propionic acid,
3-(4-{2-[N-(5,5-difluorohexyl)-N-(1-methylpropoxycarbonyl)amino]ethoxy}phenyl)-2-ethoxypropionic acid,
2-ethoxy-3-(4-{2-[N-(5,5,6,6,7,7,7-heptafluoroheptyl)-N-(1-methylpropoxycarbonyl)amino]ethoxy}phenyl)propionic acid,
2-ethoxy-3-(4-{2-[N-(1-methylpropoxycarbonyl)-N-(2,2,3,3,4,4,5,5,6,6,7,7,7-tridecafluoroheptyl)amino]ethoxy}phenyl)propionic acid,
2-ethoxy-3-(4-{2-[N-(1-methylpropoxycarbonyl)-N-(5,5,6,6,6-pentafluorohexyl)amino]ethoxy}phenyl)propionic acid,
2-ethoxy-3-(4-{2-[N-(1-methylpropoxycarbonyl)-N-(2,2,3,3,4,4,5,5,6,6,6-undecafluorohexyl)amino]ethoxy}phenyl)propionic acid,
3-[4-(2-{N-[2-(2,2-difluoropropoxy)ethyl]-N-(1-methylpropoxycarbonyl)amino}ethoxy)phenyl]-2-ethoxypropionic acid,
2-ethoxy-3-[4-(2-{N-[2-(1,1,2,2,3,3,3-heptafluoropropoxy)ethyl]-N-(1-methylpropoxycarbonyl)amino}ethoxy)phenyl]propionic acid,
2-ethoxy-3-[4-(2-{N-(1-methylpropoxycarbonyl)-N-[2-(4,4,4-trifluorobutoxy)ethyl]amino}ethoxy)phenyl]propionic acid,
3-[4-(2-{N-[2-(3,3-difluorobutoxy)ethyl]-N-(1-methylpropoxycarbonyl)amino}ethoxy)phenyl]-2-ethoxypropionic acid,
3-[4-(2-{N-[2-(2,2-difluorobutoxy)ethyl]-N-(1-methylpropoxycarbonyl)amino}ethoxy)phenyl]-2-ethoxypropionic acid,
2-ethoxy-3-[4-(2-{N-(1-methylpropoxycarbonyl)-N-[2-(1,1,2,2,3,3,4,4,4-nonafluorobutoxy)ethyl]amino}ethoxy)phenyl]propionic acid,
2-ethoxy-3-[4-(2-{N-(1-methylpropoxycarbonyl)-N-[3-(2,2,2-trifluoroethoxy)propyl]amino}ethoxy)phenyl]propionic acid,
2-ethoxy-3-[4-(2-{N-(1-methylpropoxycarbonyl)-N-[3-(1,1,2,2,2-pentafluoroethoxy)propyl]amino}ethoxy)phenyl]propionic acid,
2-ethoxy-3-[4-(2-{N-[3-(4-fluorophenoxy)propyl]-N-(1-methylpropoxycarbonyl)amino}ethoxy)phenyl]propionic acid,
3-[4-(2-{N-[3-(3,5-dichlorophenoxy)propyl]-N-(1-methylpropoxycarbonyl)amino}ethoxy)phenyl]-2-ethoxypropionic acid,
2-ethoxy-3-[4-(2-{N-[4-(4-fluorophenoxy)butyl]-N-(1-methylpropoxycarbonyl)amino}ethoxy)phenyl]propionic acid,
3-[4-(2-{N-[4-(3,5-dichlorophenoxy)butyl]-N-(1-methylpropoxycarbonyl)amino}ethoxy)phenyl]-2-ethoxypropionic acid,
2-ethoxy-3-[4-(2-{N-[2-(4-fluorobenzyloxy)ethyl]-N-(1-methylpropoxycarbonyl)amino}ethoxy)phenyl]propionic acid,
3-[4-(2-{N-[2-(3,5-dichlorobenzyloxy)ethyl]-N-(1-methylpropoxycarbonyl)amino}ethoxy)phenyl]-2-ethoxypropionic acid,
2-ethoxy-3-[4-(2-{N-[3-(4-fluorobenzyloxy)propyl]-N-(1-methylpropoxycarbonyl)amino}ethoxy)phenyl]propionic acid,
3-[4-(2-{N-[3-(3,5-dichlorobenzyloxy)propyl]-N-(1-methylpropoxycarbonyl)amino}ethoxy)phenyl]-2-ethoxypropionic acid,
2-ethoxy-3-[4-(2-{N-[4-(4-fluorobenzyloxy)butyl]-N-(1-methylpropoxycarbonyl)amino}ethoxy)phenyl]propionic acid, 3-[4-(2-{N-[4-(3,5-dichlorobenzyloxy)butyl]-N-(1-methylpropoxycarbonyl)amino}ethoxy)phenyl]-2-ethoxypropionic acid,
2-ethoxy-3-[4-(2-{N-[3-(4-fluorophenyl)propyl]-N-(1-methylpropoxycarbonyl)amino}ethoxy)phenyl]propionic acid,
3-[4-(2-{N-[3-(3,5-dichlorophenyl)propyl]-N-(1-methylpropoxycarbonyl)amino}ethoxy)phenyl]-2-ethoxypropionic acid,
3-(4-{2-[N-(2,2-dimethylpropoxycarbonyl)-N-pentylamino]ethoxy}phenyl)-2-ethoxypropionic acid,
3-(4-{2-[N-(2,2-dimethylpropoxycarbonyl)-N-hexylamino]ethoxy}phenyl)-2-ethoxypropionic acid,
3-(4-{2-[N-(2,2-dimethylpropoxycarbonyl)-N-heptylamino]ethoxy}phenyl)-2-ethoxypropionic acid,
3-(4-{2-[N-(2,2-dimethylpropoxycarbonyl)-N-octylamino]ethoxy}phenyl)-2-ethoxypropionic acid,
3-(4-{2-[N-(2,2-dimethylpropoxycarbonyl)-N-isobutylamino]ethoxy}phenyl)-2-ethoxypropionic acid,
3-(4-{2-[N-(2,2-dimethylpropoxycarbonyl)-N-(3-methylbutyl)amino]ethoxy}phenyl)-2-ethoxypropionic acid,
3-(4-{2-[N-(2,2-dimethylpropoxycarbonyl)-N-(4-methylpentyl)amino]ethoxy}phenyl)-2-ethoxypropionic acid,
3-(4-{2-[N-(2,2-dimethylpropoxycarbonyl)-N-(2-propylpentyl)amino]ethoxy}phenyl)-2-ethoxypropionic acid,
3-(4-{2-[N-(3,3-dimethylbutyl)-N-(2,2-dimethylpropoxycarbonyl)amino]ethoxy}phenyl)-2-ethoxypropionic acid,
3-(4-{2-[N-(2,2-dimethylpropoxycarbonyl)-N-(2-ethylbutyl)amino]ethoxy}phenyl)-2-ethoxypropionic acid,
3-(4-{2-[N-cyclohexylmethyl-N-(2,2-dimethylpropoxycarbonyl)amino]ethoxy}phenyl)-2-ethoxypropionic acid,
3-(4-{2-[N-(4-cyclohexylbutyl)-N-(2,2-dimethylpropoxycarbonyl)amino]ethoxy}phenyl)-2-ethoxypropionic acid,
3-(4-{2-[N-cyclopropylmethyl-N-(2,2-dimethylpropoxycarbonyl)amino]ethoxy}phenyl)-2-ethoxypropionic acid,
3-(4-{2-[N-cyclobutylmethyl-N-(2,2-dimethylpropoxycarbonyl)amino]ethoxy}phenyl)-2-ethoxypropionic acid,
3-(4-{2-[N-cyclopentylmethyl-N-(2,2-dimethylpropoxycarbonyl)amino]ethoxy}phenyl)-2-ethoxypropionic acid,
3-(4-{2-[N-(2-cyclopentylethyl)-N-(2,2-dimethylpropoxycarbonyl)amino]ethoxy}phenyl)-2-ethoxypropionic acid,
3-(4-{2-[N-(3-cyclohexylpropyl)-N-(2,2-dimethylpropoxycarbonyl)amino]ethoxy}phenyl)-2-ethoxypropionic acid,
3-(4-{2-[N-(2,2-dimethylpropoxycarbonyl)-N-(3-phenylpropyl)amino]ethoxy}phenyl)-2-ethoxypropionic acid,
3-(4-{2-[N-(2,2-dimethylpropoxycarbonyl)-N-(4-phenylbutyl)amino]ethoxy}phenyl)-2-ethoxypropionic acid,
3-(4-{2-[N-(2-butoxyethyl)-N-(2,2-dimethylpropoxycarbonyl)amino]ethoxy}phenyl)-2-ethoxypropionic acid,
3-(4-{2-[N-(2,2-dimethylpropoxycarbonyl)-N-(2-pentyloxyethyl)amino]ethoxy}phenyl)-2-ethoxypropionic acid,
3-(4-{2-[N-(2,2-dimethylpropoxycarbonyl)-N-(3-propoxypropyl)amino]ethoxy}phenyl)-2-ethoxypropionic acid,
3-(4-{2-[N-(2-butylthioethyl)-N-(2,2-dimethylpropoxycarbonyl)amino]ethoxy}phenyl)- 2-ethoxypropionic acid,
3-(4-{2-[N-(2,2-dimethylpropoxycarbonyl)-N-(2-pentylthioethyl)amino]ethoxy}phenyl)-2-ethoxypropionic acid,
3-(4-{2-[N-(2,2-dimethylpropoxycarbonyl)-N-(3-propylthiopropyl)amino]ethoxy}phenyl)-2-ethoxypropionic acid,
3-(4-{2-[N-(2,2-dimethylpropoxycarbonyl)-N-(3-phenoxypropyl)amino]ethoxy}phenyl)-2-ethoxypropionic acid,
3-(4-{2-[N-(2,2-dimethylpropoxycarbonyl)-N-(4-phenoxybutyl)amino]ethoxy}phenyl)-2-ethoxypropionic acid,
3-(4-{2-[N-(3-benzyloxypropyl)-N-(2,2-dimethylpropoxycarbonyl)amino]ethoxy}phenyl)-2-ethoxypropionic acid,
3-(4-{2-[N-(2,2-dimethylpropoxycarbonyl)-N-(3-phenylthiopropyl)amino]ethoxy}phenyl)-2-ethoxypropionic acid,
3-(4-{2-[N-(2,2-dimethylpropoxycarbonyl)-N-(4-phenylthiobutyl)amino]ethoxy}phenyl)-2-ethoxypropionic acid,
3-(4-{2-[N-(3-benzylthiopropyl)-N-(2,2-dimethylpropoxycarbonyl)amino]ethoxy}phenyl)-2-ethoxypropionic acid,
3-(4-{2-[N-(2,2-dimethylpropoxycarbonyl)-N-(7,7,7-trifluoroheptyl)amino]ethoxy}phenyl)-2-ethoxypropionic acid,
3-(4-{2-[N-(6,6-difluoroheptyl)-N-(2,2-dimethylpropoxycarbonyl)amino]ethoxy}phenyl)-2-ethoxypropionic acid,
3-(4-{2-[N-(2,2-dimethylpropoxycarbonyl)-N-(6,6,6-trifluorohexyl)amino]ethoxy}phenyl)-2-ethoxypropionic acid,
3-(4-{2-[N-(5,5-difluorohexyl)-N-(2,2-dimethylpropoxycarbonyl)amino]ethoxy}phenyl)-2-ethoxypropionic acid,
3-(4-{2-[N-(2,2-dimethylpropoxycarbonyl)-N-(5,5,6,6,7,7,7-heptafluoroheptyl)amino]ethoxy}phenyl)-2-ethoxypropionic acid,
3-(4-{2-[N-(2,2-dimethylpropoxycarbonyl)-N-(2,2,3,3,4,4,5,5,6,6,7,7,7-tridecafluoroheptyl)amino]ethoxy}phenyl)-2-ethoxypropionic acid,
3-(4-{2-[N-(2,2-dimethylpropoxycarbonyl)-N-(5,5,6,6,6-pentafluorohexyl)amino]ethoxy}phenyl)-2-ethoxypropionic acid,
3-(4-{2-[N-(2,2-dimethylpropoxycarbonyl)-N-(2,2,3,3,4,4,5,5,6,6-undecafluorohexyl)amino]ethoxy}phenyl)-2-ethoxypropionic acid,
3-[4-(2-{N-[2-(2,2-difluoropropoxy)ethyl]-N-(2,2-dimethylpropoxycarbonyl)amino}ethoxy)phenyl]-2-ethoxypropionic acid,
3-[4-(2-{N-(2,2-dimethylpropoxycarbonyl)-N-[2-(1,1,2,2,3,3,3-heptafluoropropoxy)ethyl]amino}ethoxy)phenyl]-2-ethoxypropionic acid,
3-[4-(2-{N-(2,2-dimethylpropoxycarbonyl)-N-[2-(4,4,4-trifluorobutoxy)ethyl]amino}ethoxy)phenyl]-2-ethoxypropionic acid,
3-[4-(2-{N-[2-(3,3-difluorobutoxy)ethyl]-N-(2,2-dimethylpropoxycarbonyl)amino}ethoxy)phenyl]-2-ethoxypropionic acid,
3-[4-(2-{N-[2-(2,2-difluorobutoxy)ethyl]-N-(2,2-dimethylpropoxycarbonyl)amino}ethoxy)phenyl]-2-ethoxypropionic acid,
3-[4-(2-{N-(2,2-dimethylpropoxycarbonyl)-N-[2-(1,1,2,2,3,3,4,4,4-nonafluorobutoxy)ethyl]amino}ethoxy)phenyl]-2-ethoxypropionic acid,
3-[4-(2-{N-(2,2-dimethylpropoxycarbonyl)-N-[3-(2,2,2-trifluoroethoxy)propyl]amino}ethoxy)phenyl]-2-ethoxypropionic acid,
3-[4-(2-{N-(2,2-dimethylpropoxycarbonyl)-N-[3-(1,1,2,2,2-pentafluoroethoxy)propyl]amino}ethoxy)phenyl]-2-ethoxypropionic acid,
3-[4-(2-{N-(2,2-dimethylpropoxycarbonyl)-N-[3-(4-fluorophenoxy)propyl]amino}ethoxy)phenyl]-2-ethoxypropionic acid,
3-[4-(2-{N-[3-(3,5-dichlorophenoxy)propyl]-N-(2,2-dimethylpropoxycarbonyl)amino}ethoxy)phenyl]-2-ethoxypropionic acid,
3-[4-(2-{N-(2,2-dimethylpropoxycarbonyl)-N-[4-(4-fluorophenoxy)butyl]amino}ethoxy)phenyl]-2-ethoxypropionic acid,
3-[4-(2-{N-[4-(3,5-dichlorophenoxy)butyl]-N-(2,2-dimethylpropoxycarbonyl)amino}ethoxy)phenyl]-2-ethoxypropionic acid,
3-[4-(2-{N-(2,2-dimethylpropoxycarbonyl)-N-[2-(4-fluorobenzyloxy)ethyl]amino}ethoxy)phenyl]-2-ethoxypropionic acid, 3-[4-(2-{N-[2-(3,5-dichlorobenzyloxy)ethyl]-N-(2,2-dimethylpropoxycarbonyl)amino}ethoxy)phenyl]-2-ethoxypropionic acid,
3-[4-(2-{N-(2,2-dimethylpropoxycarbonyl)-N-[3-(4-fluorobenzyloxy)propyl]amino}ethoxy)phenyl]-2-ethoxypropionic acid,
3-[4-(2-{N-[3-(3,5-dichlorobenzyloxy)propyl]-N-(2,2-dimethylpropoxycarbonyl)amino}ethoxy)phenyl]-2-ethoxypropionic acid,
3-[4-(2-{N-(2,2-dimethylpropoxycarbonyl)-N-[4-(4 -fluorobenzyloxy)butyl]amino}ethoxy)phenyl]-2-ethoxypropionic acid,
3-[4-(2-{N-[4-(3,5-dichlorobenzyloxy)butyl]-N-(2,2-dimethylpropoxycarbonyl)amino}ethoxy)phenyl]-2-ethoxypropionic acid,
3-[4-(2-{N-(2,2-dimethylpropoxycarbonyl)-N-[3-(4-fluorophenyl)propyl]amino}ethoxy)phenyl]-2-ethoxypropionic acid,
3-[4-(2-{N-[3-(3,5-dichlorophenyl)propyl]-N-(2,2-dimethylpropoxycarbonyl)amino}ethoxy)phenyl]-2-ethoxypropionic acid,
3-{4-[2-(N-cyclopentyloxycarbonyl-N-pentylamino)ethoxy]phenyl}-2-ethoxypropionic acid,
3-{4-[2-(N-cyclopentyloxycarbonyl-N-hexylamino)ethoxy]phenyl}-2-ethoxypropionic acid,
3-{4-[2-(N-cyclopentyloxycarbonyl-N-heptylamino)ethoxy]phenyl}-2-ethoxypropionic acid,
3-{4-[2-(N-cyclopentyloxycarbonyl-N-octylamino)ethoxy]phenyl}-2-ethoxypropionic acid,
3-{4-[2-(N-cyclopentyloxycarbonyl-N-isobutylamino)ethoxy]phenyl}-2-ethoxypropionic acid,
3-(4-{2-[N-cyclopentyloxycarbonyl-N-(3-methylbutyl)amino]ethoxy}phenyl)-2-ethoxypropionic acid,
3-(4-{2-[N-cyclopentyloxycarbonyl-N-(4-methylpentyl)amino]ethoxy}phenyl)-2-ethoxypropionic acid,
3-(4-{2-[N-cyclopentyloxycarbonyl-N-(2-propylpentyl)amino]ethoxy}phenyl)-2-ethoxypropionic acid,
3-(4-{2-[N-cyclopentyloxycarbonyl-N-(3,3-dimethylbutyl)amino]ethoxy}phenyl)-2-ethoxypropionic acid,
3-(4-{2-[N-cyclopentyloxycarbonyl-N-(2-ethylbutyl)amino]ethoxy}phenyl)-2-ethoxypropionic acid,
3-{4-[2-(N-cyclohexylmethyl-N-cyclopentyloxycarbonylamino)ethoxy]phenyl}-2-ethoxypropionic acid,
3-(4-{2-[N-(4-cyclohexylbutyl)-N-cyclopentyloxycarbonylamino]ethoxy}phenyl)-2-ethoxypropionic acid,
3-{4-[2-(N-cyclopentyloxycarbonyl-N-cyclopropylmethylamino)ethoxy]phenyl}-2-ethoxypropionic acid,
3-{4-[2-(N-cyclobutylmethyl-N-cyclopentyloxycarbonylamino)ethoxy]phenyl}-2-ethoxypropionic acid,
3-{4-[2-(N-cyclopentyloxycarbonyl-N-cyclopentylmethylamino)ethoxy]phenyl}-2-ethoxypropionic acid,
3-(4-{2-[N-cyclopentyloxycarbonyl-N-(2-cyclopentylethyl)amino]ethoxy}phenyl)-2-ethoxypropionic acid,
3-(4-{2-[N-(3-cyclohexylpropyl)-N-cyclopentyloxycarbonylamino]ethoxy}phenyl)-2-ethoxypropionic acid,
3-(4-{2-[N-cyclopentyloxycarbonyl-N-(3-phenylpropyl)amino]ethoxy}phenyl)-2-ethoxypropionic acid,
3-(4-{2-[N-cyclopentyloxycarbonyl-N-(4-phenylbutyl)amino]ethoxy}phenyl)-2-ethoxypropionic acid,
3-(4-{2-[N-(2-butoxyethyl)-N-cyclopentyloxycarbonylamino]ethoxy}phenyl)-2-ethoxypropionic acid,
3-(4-{2-[N-cyclopentyloxycarbonyl-N-(2-pentyloxyethyl)amino]ethoxy}phenyl)-2-ethoxypropionic acid,
3-(4-{2-[N-cyclopentyloxycarbonyl-N-(3-propoxypropyl)amino]ethoxy}phenyl)-2-ethoxypropionic acid,
3-(4-{2-[N-(2-butylthioethyl)-N-cyclopentyloxycarbonylamino]ethoxy}phenyl)-2-ethoxypropionic acid,
3-(4-{2-[N-cyclopentyloxycarbonyl-N-(2-pentylthioethyl)amino]ethoxy}phenyl)-2-ethoxypropionic acid,
3-(4-{2-[N-cyclopentyloxycarbonyl-N-(3-propylthiopropyl)amino]ethoxy}phenyl)-2-ethoxypropionic acid,
3-(4-{2-[N-cyclopentyloxycarbonyl-N-(3-phenoxypropyl)amino]ethoxy}phenyl)-2-ethoxypropionic acid,
3-(4-{2-[N-cyclopentyloxycarbonyl-N-(4-phenoxybutyl)amino]ethoxy}phenyl)-2-ethoxypropionic acid,
3-(4-{2-[N-(3-benzyloxypropyl)-N-cyclopentyloxycarbonylamino]ethoxy}phenyl)-2-ethoxypropionic acid,
3-(4-{2-[N-cyclopentyloxycarbonyl-N-(3-phenylthiopropyl)amino]ethoxy}phenyl)-2-ethoxypropionic acid,
3-(4-{2-[N-cyclopentyloxycarbonyl-N-(4-phenylthiobutyl)amino]ethoxy}phenyl)-2 -ethoxypropionic acid,
3-(4-{2-[N-(3-benzylthiopropyl)-N-cyclopentyloxycarbonylamino]ethoxy}phenyl)-2-ethoxypropionic acid,
3-(4-{2-[N-cyclopentyloxycarbonyl-N-(7,7,7-trifluoroheptyl)amino]ethoxy}phenyl)-2-ethoxypropionic acid,
3-(4-{2-[N-cyclopentyloxycarbonyl-N-(6,6-difluoroheptyl)amino]ethoxy}phenyl)-2-ethoxypropionic acid,
3-(4-{2-[N-cyclopentyloxycarbonyl-N-(6,6,6-trifluorohexyl)amino]ethoxy}phenyl)-2-ethoxypropionic acid,
3-(4-{2-[N-cyclopentyloxycarbonyl-N-(5,5-difluorohexyl)amino]ethoxy}phenyl)-2-ethoxypropionic acid,
3-(4-{2-[N-cyclopentyloxycarbonyl-N-(5,5,6,6,7,7,7-heptafluoroheptyl)amino]ethoxy}phenyl)-2-ethoxypropionic acid,
3-(4-{2-[N-cyclopentyloxycarbonyl-N-(2,2,3,3,4,4,5,5,6,6,7,7,7-tridecafluoroheptyl)amino]ethoxy}phenyl)-2-ethoxypropionic acid,
3-(4-{2-[N-cyclopentyloxycarbonyl-N-(5,5,6,6,6-pentafluorohexyl)amino]ethoxy}phenyl)-2-ethoxypropionic acid,
3-(4-{2-[N-cyclopentyloxycarbonyl-N-(2,2,3,3,4,4,5,5,6,6,6-undecafluorohexyl)amino]ethoxy}phenyl)-2-ethoxypropionic acid,
3-[4-(2-{N-cyclopentyloxycarbonyl-N-[2-(2,2-difluoropropoxy)ethyl]amino}ethoxy)phenyl]-2-ethoxypropionic acid,
3-[4-(2-{N-cyclopentyloxycarbonyl-N-[2-(1,1,2,2,3,3,3-heptafluoropropoxy)ethyl]amino}ethoxy)phenyl]-2-ethoxypropionic acid,
3-[4-(2-{N-cyclopentyloxycarbonyl-N-[2-(4,4,4-trifluorobutoxy)ethyl]amino}ethoxy)phenyl]-2-ethoxypropionic acid,
3-[4-(2-{N-cyclopentyloxycarbonyl-N-[2-(3,3-difluorobutoxy)ethyl]amino}ethoxy)phenyl]-2-ethoxypropionic acid,
3-[4-(2-{N-cyclopentyloxycarbonyl-N-[2-(2,2-difluorobutoxy)ethyl]amino}ethoxy)phenyl]-2-ethoxypropionic acid,
3-[4-(2-{N-cyclopentyloxycarbonyl-N-[2-(1,1,2,2,3,3,4,4,4-nonafluorobutoxy)ethyl]amino}ethoxy)phenyl]-2-ethoxypropionic acid,
3-[4-(2-{N-cyclopentyloxycarbonyl-N-[3-(2,2,2-trifluoroethoxy)propyl]amino}ethoxy)phenyl]-2-ethoxypropionic acid,
3-[4-(2-{N-cyclopentyloxycarbonyl-N-[3-(1,1,2,2,2-pentafluoroethoxy)propyl]amino}ethoxy)phenyl]-2-ethoxypropionic acid,
3-[4-(2-{N-cyclopentyloxycarbonyl-N-[3-(4-fluorophenoxy)propyl]amino}ethoxy)phenyl]-2-ethoxypropionic acid,
3-[4-(2-{N-cyclopentyloxycarbonyl-N-[3-(3,5-dichlorophenoxy)propyl]amino}ethoxy)phenyl]-2-ethoxypropionic acid, 3-[4-(2-{N-cyclopentyloxycarbonyl-N-[4-(4-fluorophenoxy)butyl]amino}ethoxy)phenyl]-2-ethoxypropionic acid,
3-[4-(2-{N-cyclopentyloxycarbonyl-N-[4-(3,5-dichlorophenoxy)butyl]amino}ethoxy)phenyl]-2-ethoxypropionic acid,
3-[4-(2-{N-cyclopentyloxycarbonyl-N-[2-(4-fluorobenzyloxy)ethyl]amino}ethoxy)phenyl]-2-ethoxypropionic acid,
3-[4-(2-{N-cyclopentyloxycarbonyl-N-[2-(3,5-dichlorobenzyloxy)ethyl]amino}ethoxy)phenyl]-2-ethoxypropionic acid,
3-[4-(2-{N-cyclopentyloxycarbonyl-N-[3-(4-fluorobenzyloxy)propyl]amino}ethoxy)phenyl]-2-ethoxypropionic acid,
3-[4-(2-{N-cyclopentyloxycarbonyl-N-[3-(3,5-dichlorobenzyloxy)propyl]amino}ethoxy)phenyl]-2-ethoxypropionic acid,
3-[4-(2-{N-cyclopentyloxycarbonyl-N-[4-(4-fluorobenzyloxy)butyl]amino}ethoxy)phenyl]-2-ethoxypropionic acid,
3-[4-(2-{N-cyclopentyloxycarbonyl-N-[4-(3,5-dichlorobenzyloxy)butyl]amino}ethoxy)phenyl]-2-ethoxypropionic acid,
3-[4-(2-{N-cyclopentyloxycarbonyl-N-[3-(4-fluorophenyl)propyl]amino}ethoxy)phenyl]-2-ethoxypropionic acid,
3-[4-(2-{N-cyclopentyloxycarbonyl-N-[3-(3,5-dichlorophenyl)propyl]amino}ethoxy)phenyl]-2-ethoxypropionic acid,
3-{4-[2-(N-cyclohexyloxycarbonyl-N-pentylamino)ethoxy]phenyl}-2-ethoxypropionic acid,
3-{4-[2-(N-cyclohexyloxycarbonyl-N-hexylamino)ethoxy]phenyl}-2-ethoxypropionic acid,
3-{4-[2-(N-cyclohexyloxycarbonyl-N-heptylamino)ethoxy]phenyl}-2-ethoxypropionic acid,
3-{4-[2-(N-cyclohexyloxycarbonyl-N-octylamino)ethoxy]phenyl}-2-ethoxypropionic acid,
3-{4-[2-(N-cyclohexyloxycarbonyl-N-isobutylamino)ethoxy]phenyl}-2-ethoxypropionic acid,
3-(4-{2-[N-cyclohexyloxycarbonyl-N-(3-methylbutyl)amino]ethoxy}phenyl)-2-ethoxypropionic acid,
3-(4-{2-[N-cyclohexyloxycarbonyl-N-(4-methylpentyl)amino]ethoxy}phenyl)-2-ethoxypropionic acid,
3-(4-{2-[N-cyclohexyloxycarbonyl-N-(2-propylpentyl)amino]ethoxy}phenyl)-2-ethoxypropionic acid,
3-(4-{2-[N-cyclohexyloxycarbonyl-N-(3,3-dimethylbutyl)amino]ethoxy}phenyl)-2-ethoxypropionic acid,
3-(4-{2-[N-cyclohexyloxycarbonyl-N-(2-ethylbutyl)amino]ethoxy}phenyl)-2-ethoxypropionic acid,
3-{4-[2-(N-cyclohexyloxycarbonyl-N-cyclohexylmethylamino)ethoxy]phenyl}-2-ethoxypropionic acid,
3-(4-{2-[N-cyclohexyloxycarbonyl-N-(4-cyclohexylbutyl)amino]ethoxy}phenyl)-2-ethoxypropionic acid,
3-{4-[2-(N-cyclohexyloxycarbonyl-N-cyclopropylmethylamino)ethoxy]phenyl}-2-ethoxypropionic acid,
3-{4-[2-(N-cyclobutylmethyl-N-cyclohexyloxycarbonylamino)ethoxy]phenyl}-2-ethoxypropionic acid,
3-{4-[2-(N-cyclohexyloxycarbonyl-N-cyclopentylmethylamino)ethoxy]phenyl}-2-ethoxypropionic acid,
3-(4-{2-[N-cyclohexyloxycarbonyl-N-(2-cyclopentylethyl)amino]ethoxy}phenyl)-2-ethoxypropionic acid,
3-(4-{2-[N-cyclohexyloxycarbonyl-N-(3-cyclohexylpropyl)amino]ethoxy}phenyl)-2-ethoxypropionic acid,
3-(4-{2-[N-cyclohexyloxycarbonyl-N-(3-phenylpropyl)amino]ethoxy}phenyl)-2-ethoxypropionic acid,
3-(4-{2-[N-cyclohexyloxycarbonyl-N-(4-phenylbutyl)amino]ethoxy}phenyl)-2-ethoxypropionic acid,
3-(4-{2-[N-(2-butoxyethyl)-N-cyclohexyloxycarbonylamino]ethoxy}phenyl)-2-ethoxypropionic acid,
3-(4-{2-[N-cyclohexyloxycarbonyl-N-(2-pentyloxyethyl)amino]ethoxy}phenyl)-2 -ethoxypropionic acid,
3-(4-{2-[N-cyclohexyloxycarbonyl-N-(3-propoxypropyl)amino]ethoxy}phenyl)-2-ethoxypropionic acid,
3-(4-{2-[N-(2-butylthioethyl)-N-cyclohexyloxycarbonylamino]ethoxy}phenyl)-2-ethoxypropionic acid,
3-(4-{2-[N-cyclohexyloxycarbonyl-N-(2-pentylthioethyl)amino]ethoxy}phenyl)-2-ethoxypropionic acid,
3-(4-{2-[N-cyclohexyloxycarbonyl-N-(3-propylthiopropyl)amino]ethoxy}phenyl)-2-ethoxypropionic acid,
3-(4-{2-[N-cyclohexyloxycarbonyl-N-(3-phenoxypropyl)amino]ethoxy}phenyl)-2-ethoxypropionic acid,
3-(4-{2-[N-cyclohexyloxycarbonyl-N-(4-phenoxybutyl)amino]ethoxy}phenyl)-2-ethoxypropionic acid,
3-(4-{2-[N-(3-benzyloxypropyl)-N-cyclohexyloxycarbonylamino]ethoxy}phenyl)-2-ethoxypropionic acid,
3-(4-{2-[N-cyclohexyloxycarbonyl-N-(3-phenylthiopropyl)amino]ethoxy}phenyl)-2-ethoxypropionic acid,
3-(4-{2-[N-cyclohexyloxycarbonyl-N-(4-phenylthiobutyl)amino]ethoxy}phenyl)-2-ethoxypropionic acid,
3-(4-{2-[N-(3-benzylthiopropyl)-N-cyclohexyloxycarbonylamino]ethoxy}phenyl)-2-ethoxypropionic acid,
3-(4-{2-[N-cyclohexyloxycarbonyl-N-(7,7,7-trifluoroheptyl)amino]ethoxy}phenyl)-2-ethoxypropionic acid,
3-(4-{2-[N-cyclohexyloxycarbonyl-N-(6,6-difluoroheptyl)amino]ethoxy}phenyl)-2-ethoxypropionic acid,
3-(4-{2-[N-cyclohexyloxycarbonyl-N-(6,6,6-trifluorohexyl)amino]ethoxy}phenyl)-2-ethoxypropionic acid,
3-(4-{2-[N-cyclohexyloxycarbonyl-N-(5,5-difluorohexyl)amino]ethoxy}phenyl)-2-ethoxypropionic acid,
3-(4-{2-[N-cyclohexyloxycarbonyl-N-(5,5,6,6,7,7,7-heptafluoroheptyl)amino]ethoxy}phenyl)-2-ethoxypropionic acid,
3-(4-{2-[N-cyclohexyloxycarbonyl-N-(2,2,3,3,4,4,5,5,6,6,7,7,7-tridecafluoroheptyl)amino]ethoxy}phenyl)-2-ethoxypropionic acid,
3-(4-{2-[N-cyclohexyloxycarbonyl-N-(5,5,6,6,6-pentafluorohexyl)amino]ethoxy}phenyl)-2-ethoxypropionic acid,
3-(4-{2-[N-cyclohexyloxycarbonyl-N-(2,2,3,3,4,4,5,5,6,6,6-undecafluorohexyl)amino]ethoxy}phenyl)-2-ethoxypropionic acid,
3-[4-(2-{N-cyclohexyloxycarbonyl-N-[2-(2,2-difluoropropoxy)ethyl]amino}ethoxy)phenyl]-2-ethoxypropionic acid,
3-[4-(2-{N-cyclohexyloxycarbonyl-N-[2-(1,1,2,2,3,3,3-heptafluoropropoxy)ethyl]amino}ethoxy)phenyl]-2-ethoxypropionic acid,
3-[4-(2-{N-cyclohexyloxycarbonyl-N-[2-(4,4,4-trifluorobutoxy)ethyl]amino}ethoxy)phenyl]-2-ethoxypropionic acid,
3-[4-(2-{N-cyclohexyloxycarbonyl-N-[2-(3,3-difluorobutoxy)ethyl]amino}ethoxy)phenyl]-2-ethoxypropionic acid,
3-[4-(2-{N-cyclohexyloxycarbonyl-N-[2-(2,2-difluorobutoxy)ethyl]amino}ethoxy)phenyl]-2-ethoxypropionic acid,
3-[4-(2-{N-cyclohexyloxycarbonyl-N-[2-(1,1,2,2,3,3,4,4,4-nonafluorobutoxy)ethyl]amino}ethoxy)phenyl]-2-ethoxypropionic acid,
3-[4-(2-{N-cyclohexyloxycarbonyl-N-[3-(2,2,2-trifluoroethoxy)propyl]amino}ethoxy)phenyl]-2-ethoxypropionic acid,
3-[4-(2-{N-cyclohexyloxycarbonyl-N-[3-(1,1,2,2,2-pentafluoroethoxy)propyl]amino}ethoxy)phenyl]-2-ethoxypropionic acid, 3-[4-(2-{N-cyclohexyloxycarbonyl-N-[3-(4-fluorophenoxy)propyl]amino}ethoxy)phenyl]-2-ethoxypropionic acid,
3-[4-(2-{N-cyclohexyloxycarbonyl-N-[3-(3,5-dichlorophenoxy)propyl]amino}ethoxy)phenyl]-2-ethoxypropionic acid,
3-[4-(2-{N-cyclohexyloxycarbonyl-N-[4-(4-fluorophenoxy)butyl]amino}ethoxy)phenyl]-2-ethoxypropionic acid,
3-[4-(2-{N-cyclohexyloxycarbonyl-N-[4-(3,5-dichlorophenoxy)butyl]amino}ethoxy)phenyl]-2-ethoxypropionic acid,
3-[4-(2-{N-cyclohexyloxycarbonyl-N-[2-(4-fluorobenzyloxy)ethyl]amino}ethoxy)phenyl]-2-ethoxypropionic acid,
3-[4-(2-{N-cyclohexyloxycarbonyl-N-[2-(3,5-dichlorobenzyloxy)ethyl]amino}ethoxy)phenyl]-2-ethoxypropionic acid,
3-[4-(2-{N-cyclohexyloxycarbonyl-N-[3-(4 -fluorobenzyloxy)propyl]amino}ethoxy)phenyl]-2-ethoxypropionic acid,
3-[4-(2-{N-cyclohexyloxycarbonyl-N-[3-(3,5-dichlorobenzyloxy)propyl]amino}ethoxy)phenyl]-2-ethoxypropionic acid,
3-[4-(2-{N-cyclohexyloxycarbonyl-N-[4-(4-fluorobenzyloxy)butyl]amino}ethoxy)phenyl]-2-ethoxypropionic acid,
3-[4-(2-{N-cyclohexyloxycarbonyl-N-[4-(3,5-dichlorobenzyloxy)butyl]amino}ethoxy)phenyl]-2-ethoxypropionic acid,
3-[4-(2-{N-cyclohexyloxycarbonyl-N-[3-(4-fluorophenyl)propyl]amino}ethoxy)phenyl]-2-ethoxypropionic acid, and
3-[4-(2-{N-cyclohexyloxycarbonyl-N-[3-(3,5-dichlorophenyl)propyl]amino}ethoxy)phenyl]-2-ethoxypropionic acid.

Examples of the compounds wherein $R^1$ is a substituted $C_{1-12}$ alkyl group include, for example, the following compounds.

2-Ethoxy-3-(4-{2-[N-pentyl-N-(2,2,2-trifluoroethoxycarbonyl)amino]ethoxy}phenyl)propionic acid,
2-ethoxy-3-(4-{2-[N-hexyl-N-(2,2,2-trifluoroethoxycarbonyl)amino]ethoxy}phenyl)propionic acid,
2-ethoxy-3-(4-{2-[N-heptyl-N-(2,2,2-trifluoroethoxycarbonyl)amino]ethoxy}phenyl)propionic acid,
2-ethoxy-3-(4-{2-[N-octyl-N-(2,2,2-trifluoroethoxycarbonyl)amino]ethoxy}phenyl)propionic acid,
2-ethoxy-3-(4-{2-[N-isobutyl-N-(2,2,2-trifluoroethoxycarbonyl)amino]ethoxy}phenyl)propionic acid,
2-ethoxy-3-(4-{2-[N-(3-methylbutyl)-N-(2,2,2-trifluoroethoxycarbonyl)amino]ethoxy}phenyl)propionic acid,
2-ethoxy-3-(4-{2-[N-(4-methylpentyl)-N-(2,2,2-trifluoroethoxycarbonyl)amino]ethoxy}phenyl)propionic acid,
2-ethoxy-3-(4-{2-[N-(2-propylpentyl)-N-(2,2,2-trifluoroethoxycarbonyl)amino]ethoxy}phenyl)propionic acid,
3-(4-{2-[N-(3,3-dimethylbutyl)-N-(2,2,2-trifluoroethoxycarbonyl)amino]ethoxy}phenyl)-2-ethoxypropionic acid,
2-ethoxy-3-(4-{2-[N-(2-ethylbutyl)-N-(2,2,2-trifluoroethoxycarbonyl)amino]ethoxy}phenyl)propionic acid,
3-(4-{2-[N-cyclohexylmethyl-N-(2,2,2-trifluoroethoxycarbonyl)amino]ethoxy}phenyl)-2-ethoxypropionic acid,
3-(4-{2-[N-(4-cyclohexylbutyl)-N-(2,2,2-trifluoroethoxycarbonyl)amino]ethoxy}phenyl)-2-ethoxypropionic acid,
3-(4-{2-[N-cyclopropylmethyl-N-(2,2,2-trifluoroethoxycarbonyl)amino]ethoxy}phenyl)-2-ethoxypropionic acid,
3-(4-{2-[N-cyclobutylmethyl-N-(2,2,2-trifluoroethoxycarbonyl)amino]ethoxy}phenyl)-2-ethoxypropionic acid,
3-(4-{2-[N-cyclopentylmethyl-N-(2,2,2-trifluoroethoxycarbonyl)amino]ethoxy}phenyl)-2-ethoxypropionic acid,
3-(4-{2-[N-(2-cyclopentylethyl)-N-(2,2,2-trifluoroethoxycarbonyl)amino]ethoxy}phenyl)-2-ethoxypropionic acid,
3-(4-{2-[N-(3-cyclohexylpropyl)-N-(2,2,2-trifluoroethoxycarbonyl)amino]ethoxy}phenyl)-2-ethoxypropionic acid,
2-ethoxy-3-(4-{2-[N-(3-phenylpropyl)-N-(2,2,2-trifluoroethoxycarbonyl)amino]ethoxy}phenyl)propionic acid,
2-ethoxy-3-(4-{2-[N-(4-phenylbutyl)-N-(2,2,2-trifluoroethoxycarbonyl)amino]ethoxy}phenyl)propionic acid,
3-(4-{2-[N-(2-butoxyethyl)-N-(2,2,2-trifluoroethoxycarbonyl)amino]ethoxy}phenyl)-2-ethoxypropionic acid,
2-ethoxy-3-(4-{2-[N-(2-pentyloxyethyl)-N-(2,2,2-trifluoroethoxycarbonyl)amino]ethoxy}phenyl)propionic acid,
2-ethoxy-3-(4-{2-[N-(3-propoxypropyl)-N-(2,2,2-trifluoroethoxycarbonyl)amino]ethoxy}phenyl)propionic acid,
3-(4-{2-[N-(2-butylthioethyl)-N-(2,2,2-trifluoroethoxycarbonyl)amino]ethoxy}phenyl)-2-ethoxypropionic acid,
2-ethoxy-3-(4-{2-[N-(2-pentylthioethyl)-N-(2,2,2-trifluoroethoxycarbonyl)amino]ethoxy}phenyl)propionic acid,
2-ethoxy-3-(4-{2-[N-(3-propylthiopropyl)-N-(2,2,2-trifluoroethoxycarbonyl)amino]ethoxy}phenyl)propionic acid,
2-ethoxy-3-(4-{2-[N-(3-phenoxypropyl)-N-(2,2,2-trifluoroethoxycarbonyl)amino]ethoxy}phenyl)propionic acid,
2-ethoxy-3-(4-{2-[N-(4-phenoxybutyl)-N-(2,2,2 -trifluoroethoxycarbonyl)amino]ethoxy}phenyl)propionic acid,
3-(4-{2-[N-(3-benzyloxypropyl)-N-(2,2,2-trifluoroethoxycarbonyl)amino]ethoxy}phenyl)-2-ethoxypropionic acid,
2-ethoxy-3-(4-{2-[N-(3-phenylthiopropyl)-N-(2,2,2-trifluoroethoxycarbonyl)amino]ethoxy}phenyl)propionic acid,
2-ethoxy-3-(4-{2-[N-(4-phenylthiobutyl)-N-(2,2,2-trifluoroethoxycarbonyl)amino]ethoxy}phenyl)propionic acid,
3-(4-{2-[N-(3-benzylthiopropyl)-N-(2,2,2-trifluoroethoxycarbonyl)amino]ethoxy}phenyl)-2-ethoxypropionic acid,
2-ethoxy-3-(4-{2-[N-(2,2,2-trifluoroethoxycarbonyl)-N-(7,7,7-trifluoroheptyl)amino]ethoxy}phenyl)propionic acid,
2-ethoxy-3-(4-{2-[N-(2,2,2-trifluoroethoxycarbonyl)-N-(6,6-difluoroheptyl)amino]ethoxy}phenyl)propionic acid,
2-ethoxy-3-(4-{2-[N-(2,2,2-trifluoroethoxycarbonyl)-N-(6,6,6-trifluorohexyl)amino]ethoxy}phenyl)propionic acid,
3-(4-{2-[N-(5,5-difluorohexyl)-N-(2,2,2-trifluoroethoxycarbonyl)amino]ethoxy}phenyl)-2-ethoxypropionic acid,
2-ethoxy-3-(4-{2-[N-(5,5,6,6,7,7,7-heptafluoroheptyl)-N-(2,2,2-trifluoroethoxycarbonyl)amino]ethoxy}phenyl)propionic acid,
2-ethoxy-3-(4-{2-[N-(2,2,3,3,4,4,5,5,6,6,7,7,7-tridecafluoroheptyl)-N-(2,2,2-trifluoroethoxycarbonyl)amino]ethoxy}phenyl)propionic acid,
2-ethoxy-3-(4-{2-[N-(5,5,6,6,6-pentafluorohexyl)-N-(2,2,2-trifluoroethoxycarbonyl)amino]ethoxy}phenyl)propionic acid,
2-ethoxy-3-(4-{2-[N-(2,2,2-trifluoroethoxycarbonyl)-N-(2,2,3,3,4,4,5,5,6,6,6-undecafluorohexyl)amino]ethoxy}phenyl)propionic acid,
3-[4-(2-{N-[2-(2,2-difluoropropoxy)ethyl]-N-(2,2,2-trifluoroethoxycarbonyl)amino}ethoxy)phenyl]-2-ethoxypropionic acid,
2-ethoxy-3-[4-(2-{N-[2-(1,1,2,2,3,3,3-heptafluoropropoxy)ethyl]-N-(2,2,2-trifluoroethoxycarbonyl)amino}ethoxy)phenyl]propionic acid,
2-ethoxy-3-[4-(2-{N-[2-(4,4,4-trifluorobutoxy)ethyl]-N-(2,2,2-trifluoroethoxycarbonyl)amino}ethoxy)phenyl]propionic acid,
3-[4-(2-{N-[2-(3,3-difluorobutoxy)ethyl]-N-(2,2,2-trifluoroethoxycarbonyl)amino}ethoxy)phenyl]-2-ethoxypropionic acid, 3-[4-(2-{N-[2-(2,2-difluorobutoxy)ethyl]-N-(2,2,2-trifluoroethoxycarbonyl)amino}ethoxy)phenyl]-2-ethoxypropionic acid,
2-ethoxy-3-[4-(2-{N-[2-(1,1,2,2,3,3,4,4,4-nonafluorobutoxy)ethyl]-N-(2,2,2-trifluoroethoxycarbonyl) amino}ethoxy)phenyl]propionic acid,
2-ethoxy-3-[4-(2-{N-[3-(2,2,2-trifluoroethoxy)propyl]-N-(2,2,2-trifluoroethoxycarbonyl)amino}ethoxy)phenyl] propionic acid,
2-ethoxy-3-[4-(2-{N-[3-(1,1,2,2,2-pentafluoroethoxy)propyl]-N-(2,2,2-trifluoroethoxycarbonyl)amino}ethoxy) phenyl]propionic acid,
2-ethoxy-3-[4-(2-{N-[3-(4-fluorophenoxy)propyl]-N-(2,2,2-trifluoroethoxycarbonyl)amino}ethoxy)phenyl]propionic acid,
3-[4-(2-{N-[3-(3,5-dichlorophenoxy)propyl]-N-(2,2,2-trifluoroethoxycarbonyl)amino}ethoxy)phenyl]-2-ethoxypropionic acid,
2-ethoxy-3-[4-(2-{N-[4-(4-fluorophenoxy)butyl]-N-(2,2,2-trifluoroethoxycarbonyl)amino}ethoxy)phenyl]propionic acid,
3-[4-(2-{N-[4-(3,5-dichlorophenoxy)butyl]-N-(2,2,2-trifluoroethoxycarbonyl)amino}ethoxy)phenyl]-2-ethoxypropionic acid,
2-ethoxy-3-[4-(2-{N-[2-(4-fluorobenzyloxy)ethyl]-N-(2,2,2-trifluoroethoxycarbonyl)amino}ethoxy)phenyl]propionic acid,
3-[4-(2-{N-[2-(3,5-dichlorobenzyloxy)ethyl]-N-(2,2,2-trifluoroethoxycarbonyl)amino}ethoxy)phenyl]-2-ethoxypropionic acid,
2-ethoxy-3-[4-(2-{N-[3-(4-fluorobenzyloxy)propyl]-N-(2,2,2-trifluoroethoxycarbonyl)amino}ethoxy)phenyl]propionic acid,
3-[4-(2-{N-[3-(3,5-dichlorobenzyloxy)propyl]-N-(2,2,2-trifluoroethoxycarbonyl)amino}ethoxy)phenyl]-2-ethoxypropionic acid,
2-ethoxy-3-[4-(2-{N-[4-(4-fluorobenzyloxy)butyl]-N-(2,2,2-trifluoroethoxycarbonyl)amino}ethoxy)phenyl]propionic acid,
3-[4-(2-{N-[4-(3,5-dichlorobenzyloxy)butyl]-N-(2,2,2-trifluoroethoxycarbonyl)amino}ethoxy)phenyl]-2-ethoxypropionic acid,
2-ethoxy-3-[4-(2-{N-[3-(4-fluorophenyl)propyl]-N-(2,2,2-trifluoroethoxycarbonyl)amino}ethoxy)phenyl]propionic acid,
3-[4-(2-{N-[3-(3,5-dichlorophenyl)propyl]-N-(2,2,2-trifluoroethoxycarbonyl)amino}ethoxy)phenyl]-2-ethoxypropionic acid,
2-ethoxy-3-(4-{2-[N-(2-methoxyethoxycarbonyl)-N-pentylamino] ethoxy}phenyl)propionic acid,
2-ethoxy-3-(4-{2-[N-hexyl-N-(2-methoxyethoxycarbonyl) amino]ethoxy}phenyl)propionic acid,
2-ethoxy-3-(4-{2-[N-heptyl-N-(2-methoxyethoxycarbonyl) amino]ethoxy}phenyl)propionic acid,
2-ethoxy-3-(4-{2-[N-(2-methoxyethoxycarbonyl)-N-octylamino]ethoxy}phenyl)propionic acid,
2-ethoxy-3-(4-{2-[N-isobutyl-N-(2-methoxyethoxycarbonyl)amino]ethoxy}phenyl)propionic acid,
2-ethoxy-3-(4-{2-[N-(3-methylbutyl)-N-(2-methoxyethoxycarbonyl)amino]ethoxy}phenyl)propionic acid,
2-ethoxy-3-(4-{2-[N-(2-methoxyethoxycarbonyl)-N-(4-methylpentyl)amino]ethoxy}phenyl)propionic acid,
2-ethoxy-3-(4-{2-[N-(2-methoxyethoxycarbonyl)-N-(2-propylpentyl)amino]ethoxy}phenyl)propionic acid,
3-(4-{2-[N-(3,3-dimethylbutyl)-N-(2-methoxyethoxycarbonyl)amino]ethoxy}phenyl)-2-ethoxypropionic acid,
2-ethoxy-3-(4-{2-[N-(2-ethylbutyl)-N-(2-methoxyethoxycarbonyl)amino]ethoxy}phenyl)propionic acid,
3-(4-{2-[N-cyclohexylmethyl-N-(2-methoxyethoxycarbonyl)amino]ethoxy}phenyl)-2-ethoxypropionic acid,
3-(4-{2-[N-(4-cyclohexylbutyl)-N-(2-methoxyethoxycarbonyl)amino]ethoxy}phenyl)-2-ethoxypropionic acid,
3-(4-{2-[N-cyclopropylmethyl-N-(2-methoxyethoxycarbonyl)amino]ethoxy}phenyl)-2-ethoxypropionic acid,
3-(4-{2-[N-cyclobutylmethyl-N-(2-methoxyethoxycarbonyl)amino]ethoxy}phenyl)-2-ethoxypropionic acid,
3-(4-{2-[N-cyclopentylmethyl-N-(2-methoxyethoxycarbonyl)amino]ethoxy}phenyl)-2-ethoxypropionic acid,
3-(4-{2-[N-(2-cyclopentylethyl)-N-(2-methoxyethoxycarbonyl)amino]ethoxy}phenyl)-2-ethoxypropionic acid,
3-(4-{2-[N-(3-cyclohexylpropyl)-N-(2-methoxyethoxycarbonyl)amino]ethoxy}phenyl)-2-ethoxypropionic acid,
2-ethoxy-3-(4-{2-[N-(2-methoxyethoxycarbonyl)-N-(3-phenylpropyl)amino]ethoxy}phenyl)propionic acid,
2-ethoxy-3-(4-{2-[N-(2-methoxyethoxycarbonyl)-N-(4-phenylbutyl)amino]ethoxy}phenyl)propionic acid,
3-(4-{2-[N-(2-butoxyethyl)-N-(2-methoxyethoxycarbonyl) amino]ethoxy}phenyl)-2-ethoxypropionic acid,
2-ethoxy-3-(4-{2-[N-(2-methoxyethoxycarbonyl)-N-(2-pentyloxyethyl)amino]ethoxy}phenyl)propionic acid,
2-ethoxy-3-(4-{2-[N-(2-methoxyethoxycarbonyl)-N-(3-propoxypropyl)amino]ethoxy}phenyl)propionic acid,
3-(4-{2-[N-(2-butylthioethyl)-N-(2-methoxyethoxycarbonyl)amino]ethoxy}phenyl)-2-ethoxypropionic acid,
2-ethoxy-3-(4-{2-[N-(2-methoxyethoxycarbonyl)-N-(2-pentylthioethyl)amino]ethoxy}phenyl)propionic acid,
2-ethoxy-3-(4-{2-[N-(2-methoxyethoxycarbonyl)-N-(3-propylthiopropyl)amino]ethoxy}phenyl)propionic acid,
2-ethoxy-3-(4-{2-[N-(2-methoxyethoxycarbonyl)-N-(3-phenoxypropyl)amino]ethoxy}phenyl)propionic acid,
2-ethoxy-3-(4-{2-[N-(2-methoxyethoxycarbonyl)-N-(4-phenoxybutyl)amino]ethoxy}phenyl)propionic acid,
3-(4-{2-[N-(3-benzyloxypropyl)-N-(2-methoxyethoxycarbonyl)amino]ethoxy}phenyl)-2-ethoxypropionic acid,
2-ethoxy-3-(4-{2-[N-(2-methoxyethoxycarbonyl)-N-(3-phenylthiopropyl)amino]ethoxy}phenyl)propionic acid,
2-ethoxy-3-(4-{2-[N-(2-methoxyethoxycarbonyl)-N-(4-phenylthiobutyl)amino]ethoxy}phenyl)propionic acid,
3-(4-{2-[N-(3-benzylthiopropyl)-N-(2-methoxyethoxycarbonyl)amino]ethoxy}phenyl)-2-ethoxypropionic acid,
2-ethoxy-3-(4-{2-[N-(2-methoxyethoxycarbonyl)-N-(7,7,7-trifluoroheptyl)amino]ethoxy}phenyl)propionic acid,
3-(4-{2-[N-(6,6-difluoroheptyl)-N-(2-methoxyethoxycarbonyl)amino]ethoxy}phenyl)-2-ethoxypropionic acid,
2-ethoxy-3-(4-{2-[N-(2-methoxyethoxycarbonyl)-N-(6,6,6-trifluorohexyl)amino]ethoxy}phenyl)propionic acid,
3-(4-{2-[N-(5,5-difluorohexyl)-N-(2-methoxyethoxycarbonyl)amino]ethoxy}phenyl)-2-ethoxypropionic acid,
2-ethoxy-3-(4-{2-[N-(5,5,6,6,7,7,7-heptafluoroheptyl)-N-(2-methoxyethoxycarbonyl)amino]ethoxy}phenyl)propionic acid,
2-ethoxy-3-(4-{2-[N-(2-methoxyethoxycarbonyl)-N-(2,2,3,3,4,4,5,5,6,6,7,7,7-tridecafluoroheptyl)amino]ethoxy}phenyl)propionic acid,
2-ethoxy-3-(4-{2-[N-(2-methoxyethoxycarbonyl)-N-(5,5,6,6,6-pentafluorohexyl)amino]ethoxy}phenyl)propionic acid,
2-ethoxy-3-(4-{2-[N-(2-methoxyethoxycarbonyl)-N-(2,2,3,3,4,4,5,5,6,6,6-undecafluorohexyl)amino]ethoxy}phenyl) propionic acid,
3-[4-(2-{N-[2-(2,2-difluoropropoxy)ethyl]-N-(2-methoxyethoxycarbonyl)amino}ethoxy)phenyl]-2-ethoxypropionic acid, 2-ethoxy-3-[4-(2-{N-[2-(1,1,2,2,3,3,3-heptafluoropropoxy)ethyl]-N-(2-methoxyethoxycarbonyl)amino}ethoxy)phenyl]propionic acid,
2-ethoxy-3-[4-(2-{N-(2-methoxyethoxycarbonyl)-N-[2-(4,4,4-trifluorobutoxy)ethyl]amino}ethoxy)phenyl]propionic acid,
3-[4-(2-{N-[2-(3,3-difluorobutoxy)ethyl]-N-(2-methoxyethoxycarbonyl)amino}ethoxy)phenyl]-2-ethoxypropionic acid,
3-[4-(2-{N-[2-(2,2-difluorobutoxy)ethyl]-N-(2-methoxyethoxycarbonyl)amino}ethoxy)phenyl]-2-ethoxypropionic acid,
2-ethoxy-3-[4-(2-{N-(2-methoxyethoxycarbonyl)-N-[2-(1,1,2,2,3,3,4,4,4-nonafluorobutoxy)ethyl]amino}ethoxy)phenyl]propionic acid,
2-ethoxy-3-[4-(2-{N-(2-methoxyethoxycarbonyl)-N-[3-(2,2,2-trifluoroethoxy)propyl]amino}ethoxy)phenyl]propionic acid,
2-ethoxy-3-[4-(2-{N-(2-methoxyethoxycarbonyl)-N-[3-(1,1,2,2,2-pentafluoroethoxy)propyl]amino}ethoxy)phenyl]propionic acid,
2-ethoxy-3-[4-(2-{N-[3-(4-fluorophenoxy)propyl]-N-(2-methoxyethoxycarbonyl)amino}ethoxy)phenyl]propionic acid,
3-[4-(2-{N-[3-(3,5-dichlorophenoxy)propyl]-N-(2-methoxyethoxycarbonyl)amino}ethoxy)phenyl]-2-ethoxypropionic acid,
2-ethoxy-3-[4-(2-{N-[4-(4-fluorophenoxy)butyl]-N-(2-methoxyethoxycarbonyl)amino}ethoxy)phenyl]propionic acid,
3-[4-(2-{N-[4-(3,5-dichlorophenoxy)butyl]-N-(2-methoxyethoxycarbonyl)amino}ethoxy)phenyl]-2-ethoxypropionic acid,
2-ethoxy-3-[4-(2-{N-[2-(4-fluorobenzyloxy)ethyl]-N-(2-methoxyethoxycarbonyl)amino}ethoxy)phenyl]propionic acid,
3-[4-(2-{N-[2-(3,5-dichlorobenzyloxy)ethyl]-N-(2-methoxyethoxycarbonyl)amino}ethoxy)phenyl]-2-ethoxypropionic acid,
2-ethoxy-3-[4-(2-{N-[3-(4-fluorobenzyloxy)propyl]-N-(2-methoxyethoxycarbonyl)amino}ethoxy)phenyl]propionic acid,
3-[4-(2-{N-[3-(3,5-dichlorobenzyloxy)propyl]-N-(2-methoxyethoxycarbonyl)amino}ethoxy)phenyl]-2-ethoxypropionic acid,
2-ethoxy-3-[4-(2-{N-[4-(4-fluorobenzyloxy)butyl]-N-(2-methoxyethoxycarbonyl)amino}ethoxy)phenyl]propionic acid,
3-[4-(2-{N-[4-(3,5-dichlorobenzyloxy)butyl]-N-(2-methoxyethoxycarbonyl)amino}ethoxy)phenyl]-2-ethoxypropionic acid,
2-ethoxy-3-[4-(2-{N-[3-(4-fluorophenyl)propyl]-N-(2-methoxyethoxycarbonyl)amino}ethoxy)phenyl]propionic acid,
3-[4-(2-{N-[3-(3,5-dichlorophenyl)propyl]-N-(2-methoxyethoxycarbonyl)amino}ethoxy)phenyl]-2-ethoxypropionic acid,
3-{4-[2-(N-benzyloxycarbonyl-N-pentylamino)ethoxy]phenyl}-2-ethoxypropionic acid,
3-{4-[2-(N-benzyloxycarbonyl-N-hexylamino)ethoxy]phenyl}-2-ethoxypropionic acid,
3-{4-[2-(N-benzyloxycarbonyl-N-heptylamino)ethoxy]phenyl}-2-ethoxypropionic acid,
3-{4-[2-(N-benzyloxycarbonyl-N-octylamino)ethoxy]phenyl}-2-ethoxypropionic acid,
3-{4-[2-(N-benzyloxycarbonyl-N-isobutylamino)ethoxy]phenyl}-2-ethoxypropionic acid,
3-(4-{2-[N-benzyloxycarbonyl-N-(3-methylbutyl)amino]ethoxy}phenyl)-2-ethoxypropionic acid,
3-(4-{2-[N-benzyloxycarbonyl-N-(4-methylpentyl)amino]ethoxy}phenyl)-2-ethoxypropionic acid,
3-(4-{2-[N-benzyloxycarbonyl-N-(2-propylpentyl)amino]ethoxy}phenyl)-2-ethoxypropionic acid,
3-(4-{2-[N-benzyloxycarbonyl-N-(3,3-dimethylbutyl)amino]ethoxy}phenyl)-2-ethoxypropionic acid,
3-(4-{2-[N-benzyloxycarbonyl-N-(2-ethylbutyl)amino]ethoxy}phenyl)-2-ethoxypropionic acid,
3-{4-[2-(N-benzyloxycarbonyl-N-cyclohexylmethylamino)ethoxy]phenyl}-2-ethoxypropionic acid,
3-(4-{2-[N-benzyloxycarbonyl-N-(4-cyclohexylbutyl)amino]ethoxy}phenyl)-2-ethoxypropionic acid,
3-{4-[2-(N-benzyloxycarbonyl-N-cyclopropylmethylamino)ethoxy]phenyl}-2-ethoxypropionic acid,
3-{4-[2-(N-benzyloxycarbonyl-N-cyclobutylmethylamino)ethoxy]phenyl}-2-ethoxypropionic acid,
3-{4-[2-(N-benzyloxycarbonyl-N-cyclopentylmethylamino)ethoxy]phenyl}-2-ethoxypropionic acid,
3-(4-{2-[N-benzyloxycarbonyl-N-(2-cyclopentylethyl)amino]ethoxy}phenyl)-2-ethoxypropionic acid,
3-(4-{2-[N-benzyloxycarbonyl-N-(3-cyclohexylpropyl)amino]ethoxy}phenyl)-2-ethoxypropionic acid,
3-(4-{2-[N-benzyloxycarbonyl-N-(3-phenylpropyl)amino]ethoxy}phenyl)-2-ethoxypropionic acid,
3-(4-{2-[N-benzyloxycarbonyl-N-(4-phenylbutyl)amino]ethoxy}phenyl)-2-ethoxypropionic acid,
3-(4-{2-[N-benzyloxycarbonyl-N-(2-butoxyethyl)amino]ethoxy}phenyl)-2-ethoxypropionic acid,
3-(4-{2-[N-benzyloxycarbonyl-N-(2-pentyloxyethyl)amino]ethoxy}phenyl)-2-ethoxypropionic acid,
3-(4-{2-[N-benzyloxycarbonyl-N-(3-propoxypropyl)amino]ethoxy}phenyl)-2-ethoxypropionic acid,
3-(4-{2-[N-benzyloxycarbonyl-N-(2-butylthioethyl)amino]ethoxy}phenyl)-2-ethoxypropionic acid,
3-(4-{2-[N-benzyloxycarbonyl-N-(2-pentylthioethyl)amino]ethoxy}phenyl)-2-ethoxypropionic acid,
3-(4-{2-[N-benzyloxycarbonyl-N-(3-propylthiopropyl)amino]ethoxy}phenyl)-2-ethoxypropionic acid,
3-(4-{2-[N-benzyloxycarbonyl-N-(3-phenoxypropyl)amino]ethoxy}phenyl)-2-ethoxypropionic acid,
3-(4-{2-[N-benzyloxycarbonyl-N-(4-phenoxybutyl)amino]ethoxy}phenyl)-2 -ethoxypropionic acid,
3-(4-{2-[N-benzyloxycarbonyl-N-(3-benzyloxypropyl)amino]ethoxy}phenyl)-2-ethoxypropionic acid,
3-(4-{2-[N-benzyloxycarbonyl-N-(3-phenylthiopropyl)amino]ethoxy}phenyl)-2-ethoxypropionic acid,
3-(4-{2-[N-benzyloxycarbonyl-N-(4-phenylthiobutyl)amino]ethoxy}phenyl)-2-ethoxypropionic acid,
3-(4-{2-[N-benzyloxycarbonyl-N-(3-benzylthiopropyl)amino]ethoxy}phenyl)-2-ethoxypropionic acid,
3-(4-{2-[N-benzyloxycarbonyl-N-(7,7,7-trifluoroheptyl)amino]ethoxy}phenyl)-2-ethoxypropionic acid,
3-(4-{2-[N-benzyloxycarbonyl-N-(6,6-difluoroheptyl)amino]ethoxy}phenyl)-2-ethoxypropionic acid,
3-(4-{2-[N-benzyloxycarbonyl-N-(6,6,6-trifluorohexyl)amino]ethoxy}phenyl)-2-ethoxypropionic acid,
3-(4-{2-[N-benzyloxycarbonyl-N-(5,5-difluorohexyl)amino]ethoxy}phenyl)-2-ethoxypropionic acid,
3-(4-{2-[N-benzyloxycarbonyl-N-(5,5,6,6,7,7,7-heptafluoroheptyl)amino]ethoxy}phenyl)-2-ethoxypropionic acid,
3-(4-{2-[N-benzyloxycarbonyl-N-(2,2,3,3,4,4,5,5,6,6,7,7,7-tridecafluoroheptyl)amino]ethoxy}phenyl)-2-ethoxypropionic acid,
3-(4-{2-[N-benzyloxycarbonyl-N-(5,5,6,6,6-pentafluorohexyl)amino]ethoxy}phenyl)-2-ethoxypropionic acid, 3-(4-{2-[N-benzyloxycarbonyl-N-(2,2,3,3,4,4,5,5,6,6,6-undecafluorohexyl)amino]ethoxy}phenyl)-2-ethoxypropionic acid,
3-[4-(2-{N-benzyloxycarbonyl-N-[2-(2,2-difluoropropoxy)ethyl]amino}ethoxy)phenyl]-2-ethoxypropionic acid,
3-[4-(2-{N-benzyloxycarbonyl-N-[2-(1,1,2,2,3,3,3-heptafluoropropoxy)ethyl]amino}ethoxy)phenyl]-2-ethoxypropionic acid,
3-[4-(2-{N-benzyloxycarbonyl-N-[2-(4,4,4-trifluorobutoxy)ethyl]amino}ethoxy)phenyl]-2-ethoxypropionic acid,
3-[4-(2-{N-benzyloxycarbonyl-N-[2-(3,3-difluorobutoxy)ethyl]amino}ethoxy)phenyl]-2-ethoxypropionic acid,
3-[4-(2-{N-benzyloxycarbonyl-N-[2-(2,2-difluorobutoxy)ethyl]amino}ethoxy)phenyl]-2-ethoxypropionic acid,
3-[4-(2-{N-benzyloxycarbonyl-N-[2-(1,1,2,2,3,3,4,4,4-nonafluorobutoxy)ethyl]amino}ethoxy)phenyl]-2-ethoxypropionic acid,
3-[4-(2-{N-benzyloxycarbonyl-N-[3-(2,2,2-trifluoroethoxy)propyl]amino}ethoxy)phenyl]-2-ethoxypropionic acid,
3-[4-(2-{N-benzyloxycarbonyl-N-[3-(1,1,2,2,2-pentafluoroethoxy)propyl]amino}ethoxy)phenyl]-2-ethoxypropionic acid,
3-[4-(2-{N-benzyloxycarbonyl-N-[3-(4-fluorophenoxy)propyl]amino}ethoxy)phenyl]-2-ethoxypropionic acid,
3-[4-(2-{N-benzyloxycarbonyl-N-[3-(3,5-dichlorophenoxy)propyl]amino}ethoxy)phenyl]-2-ethoxypropionic acid,
3-[4-(2-{N-benzyloxycarbonyl-N-[4-(4-fluorophenoxy)butyl]amino}ethoxy)phenyl]-2-ethoxypropionic acid,
3-[4-(2-{N-benzyloxycarbonyl-N-[4-(3,5-dichlorophenoxy)butyl]amino}ethoxy)phenyl]-2-ethoxypropionic acid,
3-[4-(2-{N-benzyloxycarbonyl-N-[2-(4-fluorobenzyloxy)ethyl]amino}ethoxy)phenyl]-2-ethoxypropionic acid,
3-[4-(2-{N-benzyloxycarbonyl-N-[2-(3,5-dichlorobenzyloxy)ethyl]amino}ethoxy)phenyl]-2-ethoxypropionic acid,
3-[4-(2-{N-benzyloxycarbonyl-N-[3-(4-fluorobenzyloxy)propyl]amino}ethoxy)phenyl]-2-ethoxypropionic acid,
3-[4-(2-{N-benzyloxycarbonyl-N-[3-(3,5-dichlorobenzyloxy)propyl]amino}ethoxy)phenyl]-2-ethoxypropionic acid,
3-[4-(2-{N-benzyloxycarbonyl-N-[4-(4-fluorobenzyloxy)butyl]amino}ethoxy)phenyl]-2-ethoxypropionic acid,
3-[4-(2-{N-benzyloxycarbonyl-N-[4-(3,5-dichlorobenzyloxy)butyl]amino}ethoxy)phenyl]-2-ethoxypropionic acid,
3-[4-(2-{N-benzyloxycarbonyl-N-[3-(4-fluorophenyl)propyl]amino}ethoxy)phenyl]-2-ethoxypropionic acid,
3-[4-(2-{N-benzyloxycarbonyl-N-[3-(3,5-dichlorophenyl)propyl]amino}ethoxy)phenyl]-2-ethoxypropionic acid,
2-ethoxy-3-{4-[2-(N-pentyl-N-phenethyloxycarbonylamino)ethoxy]phenyl}propionic acid,
2-ethoxy-3-{4-[2-(N-hexyl-N-phenethyloxycarbonylamino)ethoxy]phenyl}propionic acid,
2-ethoxy-3-{4-[2-(N-heptyl-N-phenethyloxycarbonylamino)ethoxy]phenyl}propionic acid,
2-ethoxy-3-{4-[2-(N-octyl-N-phenethyloxycarbonylamino)ethoxy]phenyl}propionic acid,
2-ethoxy-3-{4-[2-(N-isobutyl-N-phenethyloxycarbonylamino)ethoxy]phenyl}propionic acid,
2-ethoxy-3-(4-{2-[N-(3-methylbutyl)-N-phenethyloxycarbonylamino]ethoxy}phenyl)propionic acid,
2-ethoxy-3-(4-{2-[N-(4-methylpentyl)-N-phenethyloxycarbonylamino]ethoxy}phenyl)propionic acid,
2-ethoxy-3-(4-{2-[N-phenethyloxycarbonyl-N-(2-propylpentyl)amino]ethoxy}phenyl)propionic acid,
3-(4-{2-[N-(3,3-dimethylbutyl)-N-phenethyloxycarbonylamino]ethoxy}phenyl)-2-ethoxypropionic acid,
2-ethoxy-3-(4-{2-[N-(2-ethylbutyl)-N-phenethyloxycarbonylamino]ethoxy}phenyl)propionic acid,
3-{4-[2-(N-cyclohexylmethyl-N-phenethyloxycarbonylamino)ethoxy]phenyl}-2-ethoxypropionic acid,
3-(4-{2-[N-(4-cyclohexylbutyl)-N-phenethyloxycarbonylamino]ethoxy}phenyl)-2-ethoxypropionic acid,
3-{4-[2-(N-cyclopropylmethyl-N-phenethyloxycarbonylamino)ethoxy]phenyl}-2-ethoxypropionic acid,
3-{4-[2-(N-cyclobutylmethyl-N-phenethyloxycarbonylamino)ethoxy]phenyl}-2-ethoxypropionic acid,
3-{4-[2-(N-cyclopentylmethyl-N-phenethyloxycarbonylamino)ethoxy]phenyl}-2-ethoxypropionic acid,
3-(4-{2-[N-(2-cyclopentylethyl)-N-phenethyloxycarbonylamino]ethoxy}phenyl)-2-ethoxypropionic acid,
3-(4-{2-[N-(3-cyclohexylpropyl)-N-phenethyloxycarbonylamino]ethoxy}phenyl)-2-ethoxypropionic acid,
2-ethoxy-3-(4-{2-[N-phenethyloxycarbonyl-N-(3-phenylpropyl)amino]ethoxy}phenyl)propionic acid,
2-ethoxy-3-(4-{2-[N-phenethyloxycarbonyl-N-(4-phenylbutyl)amino]ethoxy}phenyl)propionic acid,
2-ethoxy-3-(4-{2-[N-phenethyloxycarbonyl-N-(2-butoxyethyl)amino]ethoxy}phenyl)propionic acid,
2-ethoxy-3-(4-{2-[N-(2-pentyloxyethyl)-N-phenethyloxycarbonylamino]ethoxy}phenyl)propionic acid,
2-ethoxy-3-(4-{2-[N-phenethyloxycarbonyl-N-(3-propoxypropyl)amino]ethoxy}phenyl)propionic acid,
3-(4-{2-[N-(2-butylthioethyl)-N-phenethyloxycarbonylamino]ethoxy}phenyl)-2-ethoxypropionic acid,
2-ethoxy-3-(4-{2-[N-(2-pentylthioethyl)-N-phenethyloxycarbonylamino]ethoxy}phenyl)propionic acid,
2-ethoxy-3-(4-{2-[N-phenethyloxycarbonyl-N-(3-propylthiopropyl)amino]ethoxy}phenyl)propionic acid,
2-ethoxy-3-(4-{2-[N-phenethyloxycarbonyl-N-(3-phenoxypropyl)amino]ethoxy}phenyl)propionic acid,
2-ethoxy-3-(4-{2-[N-phenethyloxycarbonyl-N-(4-phenoxybutyl)amino]ethoxy}phenyl)propionic acid,
3-(4-{2-[N-(3-benzyloxypropyl)-N-phenethyloxycarbonylamino]ethoxy}phenyl)-2-ethoxypropionic acid,
2-ethoxy-3-(4-{2-[N-phenethyloxycarbonyl-N-(3-phenylthiopropyl)amino]ethoxy}phenyl)propionic acid,
2-ethoxy-3-(4-{2-[N-phenethyloxycarbonyl-N-(4-phenylthiobutyl)amino]ethoxy}phenyl)propionic acid,
2-ethoxy-3-(4-{2-[N-phenethyloxycarbonyl-N-(3-benzylthiopropyl)amino]ethoxy}phenyl)propionic acid,
2-ethoxy-3-(4-{2-[N-phenethyloxycarbonyl-N-(7,7,7-trifluoroheptyl)amino]ethoxy}phenyl)propionic acid,
3-(4-{2-[N-(6,6-difluoroheptyl)-N-phenethyloxycarbonylamino]ethoxy}phenyl)-2-ethoxypropionic acid,
2-ethoxy-3-(4-{2-[N-phenethyloxycarbonyl-N-(6,6,6-trifluorohexyl)amino]ethoxy}phenyl)propionic acid,
3-(4-{2-[N-(5,5-difluorohexyl)-N-phenethyloxycarbonylamino]ethoxy}phenyl)-2-ethoxypropionic acid,
2-ethoxy-3-(4-{2-[N-(5,5,6,6,7,7,7-heptafluoroheptyl)-N-phenethyloxycarbonylamino]ethoxy}phenyl)propionic acid,
2-ethoxy-3-(4-{2-[N-phenethyloxycarbonyl-N-(2,2,3,3,4,4,5,5,6,6,7,7,7-tridecafluoroheptyl)amino]ethoxy}phenyl)propionic acid,
2-ethoxy-3-(4-{2-[N-(5,5,6,6,6-pentafluorohexyl)-N-phenethyloxycarbonylamino]ethoxy}phenyl)propionic acid,
2-ethoxy-3-(4-{2-[N-phenethyloxycarbonyl-N-(2,2,3,3,4,4,5,5,6,6,6-undecafluorohexyl)amino]ethoxy}phenyl)propionic acid, 3-[4-(2-{N-[2-(2,2-difluoropropoxy)ethyl]-N-phenethyloxycarbonylamino}ethoxy)phenyl]-2-ethoxypropionic acid, 2-ethoxy-3-[4-(2-{N-[2-(1,1,2,2,3,3,3-heptafluoropropoxy)ethyl]-N-phenethyloxycarbonylamino}ethoxy)phenyl] propionic acid, 2-ethoxy-3-[4-(2-{N-phenethyloxycarbonyl-N-[2-(4,4,4-trifluorobutoxy)ethyl]amino}ethoxy)phenyl]propionic acid, 3-[4-(2-{N-[2-(3,3-difluorobutoxy)ethyl]-N-phenethyloxycarbonylamino}ethoxy)phenyl]-2-ethoxypropionic acid, 3-[4-(2-{N-[2-(2,2-difluorobutoxy)ethyl]-N-phenethyloxycarbonylamino}ethoxy)phenyl]-2-ethoxypropionic acid, 2-ethoxy-3-[4-(2-{N-[2-(1,1,2,2,3,3,4,4,4-nonafluorobutoxy)ethyl]-N-phenethyloxycarbonylamino}ethoxy)phenyl]propionic acid, 2-ethoxy-3-[4-(2-{N-phenethyloxycarbonyl-N-[3-(2,2,2-trifluoroethoxy)propyl]amino}ethoxy)phenyl]propionic acid, 2-ethoxy-3-[4-(2-{N-[3-(1,1,2,2,2-pentafluoroethoxy)propyl]-N-phenethyloxycarbonylamino}ethoxy)phenyl]propionic acid, 2-ethoxy-3-[4-(2-{N-[3-(4-fluorophenoxy)propyl]-N-phenethyloxycarbonylamino}ethoxy)phenyl]propionic acid, 3-[4-(2-{N-[3-(3,5-dichlorophenoxy)propyl]-N-phenethyloxycarbonylamino}ethoxy)phenyl]-2-ethoxypropionic acid, 2-ethoxy-3-[4-(2-{N-[4-(4-fluorophenoxy)butyl]-N-phenethyloxycarbonylamino}ethoxy)phenyl]propionic acid, 3-[4-(2-{N-[4-(3,5-dichlorophenoxy)butyl]-N-phenethyloxycarbonylamino}ethoxy)phenyl]-2-ethoxypropionic acid, 2-ethoxy-3-[4-(2-{N-[2-(4-fluorobenzyloxy)ethyl]-N-phenethyloxycarbonylamino}ethoxy)phenyl]propionic acid, 3-[4-(2-{N-[2-(3,5-dichlorobenzyloxy)ethyl]-N-phenethyloxycarbonylamino}ethoxy)phenyl]-2-ethoxypropionic acid, 2-ethoxy-3-[4-(2-{N-[3-(4-fluorobenzyloxy)propyl]-N-phenethyloxycarbonylamino}ethoxy)phenyl]propionic acid, 3-[4-(2-{N-[3-(3,5-dichlorobenzyloxy)propyl]-N-phenethyloxycarbonylamino}ethoxy)phenyl]-2-ethoxypropionic acid, 2-ethoxy-3-[4-(2-{N-[4-(4-fluorobenzyloxy)butyl]-N-phenethyloxycarbonylamino}ethoxy)phenyl]propionic acid, 3-[4-(2-{N-[4-(3,5-dichlorobenzyloxy)butyl]-N-phenethyloxycarbonylamino}ethoxy)phenyl]-2-ethoxypropionic acid, 2-ethoxy-3-[4-(2-{N-[3-(4-fluorophenyl)propyl]-N-phenethyloxycarbonylamino}ethoxy)phenyl]propionic acid, 3-[4-(2-{N-[3-(3,5-dichlorophenyl)propyl]-N-phenethyloxycarbonylamino}ethoxy)phenyl]-2-ethoxypropionic acid, 3-(4-{2-[N-(2,4-difluorobenzyloxycarbonyl)-N-pentylamino]ethoxy}phenyl)-2-ethoxypropionic acid, 3-(4-{2-[N-(2,4-difluorobenzyloxycarbonyl)-N-hexylamino]ethoxy}phenyl)-2-ethoxypropionic acid, 3-(4-{2-[N-(2,4-difluorobenzyloxycarbonyl)-N-heptylamino]ethoxy}phenyl)-2-ethoxypropionic acid, 3-(4-{2-[N-(2,4-difluorobenzyloxycarbonyl)-N-octylamino]ethoxy}phenyl)-2-ethoxypropionic acid, 3-(4-{2-[N-(2,4-difluorobenzyloxycarbonyl)-N-isobutylamino]ethoxy}phenyl)-2-ethoxypropionic acid, 3-(4-{2-[N-(2,4-difluorobenzyloxycarbonyl)-N-(3-methylbutyl)amino]ethoxy}phenyl)-2-ethoxypropionic acid, 3-(4-{2-[N-(2,4-difluorobenzyloxycarbonyl)-N-(4-methylpentyl)amino]ethoxy}phenyl)-2-ethoxypropionic acid, 3-(4-{2-[N-(2,4-difluorobenzyloxycarbonyl)-N-(2-propylpentyl)amino]ethoxy}phenyl)-2-ethoxypropionic acid, 3-(4-{2-[N-(3,3-dimethylbutyl)-N-(2,4-difluorobenzyloxycarbonyl)amino]ethoxy}phenyl)-2-ethoxypropionic acid, 3-(4-{2-[N-(2,4-difluorobenzyloxycarbonyl)-N-(2-ethylbutyl)amino]ethoxy}phenyl)-2-ethoxypropionic acid, 3-(4-{2-[N-cyclohexylmethyl-N-(2,4-difluorobenzyloxycarbonyl)amino]ethoxy}phenyl)-2-ethoxypropionic acid, 3-(4-{2-[N-(4-cyclohexylbutyl)-N-(2,4-difluorobenzyloxycarbonyl)amino]ethoxy}phenyl)-2-ethoxypropionic acid, 3-(4-{2-[N-cyclopropylmethyl-N-(2,4-difluorobenzyloxycarbonyl)amino]ethoxy}phenyl)-2-ethoxypropionic acid, 3-(4-{2-[N-cyclobutylmethyl-N-(2,4-difluorobenzyloxycarbonyl)amino]ethoxy}phenyl)-2-ethoxypropionic acid, 3-(4-{2-[N-cyclopentylmethyl-N-(2,4-difluorobenzyloxycarbonyl)amino]ethoxy}phenyl)-2-ethoxypropionic acid, 3-(4-{2-[N-(2-cyclopentylethyl)-N-(2,4-difluorobenzyloxycarbonyl)amino]ethoxy}phenyl)-2-ethoxypropionic acid, 3-(4-{2-[N-(3-cyclohexylpropyl)-N-(2,4-difluorobenzyloxycarbonyl)amino]ethoxy}phenyl)-2-ethoxypropionic acid, 3-(4-{2-[N-(2,4-difluorobenzyloxycarbonyl)-N-(3-phenylpropyl)amino]ethoxy}phenyl)-2-ethoxypropionic acid, 3-(4-{2-[N-(2,4-difluorobenzyloxycarbonyl)-N-(4-phenylbutyl)amino]ethoxy}phenyl)-2-ethoxypropionic acid, 3-(4-{2-[N-(2-butoxyethyl)-N-(2,4-difluorobenzyloxycarbonyl)amino]ethoxy}phenyl)-2-ethoxypropionic acid, 3-(4-{2-[N-(2,4-difluorobenzyloxycarbonyl)-N-(2-pentyloxyethyl)amino]ethoxy}phenyl)-2-ethoxypropionic acid, 3-(4-{2-[N-(2,4-difluorobenzyloxycarbonyl)-N-(3-propoxypropyl)amino]ethoxy}phenyl)-2-ethoxypropionic acid, 3-(4-{2-[N-(2-butylthioethyl)-N-(2,4-difluorobenzyloxycarbonyl)amino]ethoxy}phenyl)-2-ethoxypropionic acid, 3-(4-{2-[N-(2,4-difluorobenzyloxycarbonyl)-N-(2-pentylthioethyl)amino]ethoxy}phenyl)-2-ethoxypropionic acid, 3-(4-{2-[N-(2,4-difluorobenzyloxycarbonyl)-N-(3-propylthiopropyl)amino]ethoxy}phenyl)-2-ethoxypropionic acid, 3-(4-{2-[N-(2,4-difluorobenzyloxycarbonyl)-N-(3-phenoxypropyl)amino]ethoxy}phenyl)-2-ethoxypropionic acid, 3-(4-{2-[N-(2,4-difluorobenzyloxycarbonyl)-N-(4-phenoxybutyl)amino]ethoxy}phenyl)-2-ethoxypropionic acid, 3-(4-{2-[N-(2,4-difluorobenzyloxycarbonyl)-N-(3-benzyloxypropyl)amino]ethoxy}phenyl)-2-ethoxypropionic acid, 3-(4-{2-[N-(2,4-difluorobenzyloxycarbonyl)-N-(3-phenylthiopropyl)amino]ethoxy}phenyl)-2-ethoxypropionic acid, 3-(4-{2-[N-(2,4-difluorobenzyloxycarbonyl)-N-(4-phenylthiobutyl)amino]ethoxy}phenyl)-2-ethoxypropionic acid, 3-(4-{2-[N-(2,4-difluorobenzyloxycarbonyl)-N-(3-benzylthiopropyl)amino]ethoxy}phenyl)-2-ethoxypropionic acid, 3-(4-{2-[N-(2,4-difluorobenzyloxycarbonyl)-N-(7,7,7-trifluoroheptyl)amino]ethoxy}phenyl)-2-ethoxypropionic acid, 3-(4-{2-[N-(6,6-difluoroheptyl)-N-(2,4-difluorobenzyloxy-
carbonyl)amino]ethoxy}phenyl)-2-ethoxypropionic acid,
3-(4-{2-[N-(2,4-difluorobenzyloxycarbonyl)-N-(6,6,6-trif-
luorohexyl)amino]ethoxy}phenyl)-2-ethoxypropionic
acid,
3-(4-{2-[N-(5,5-difluorohexyl)-N-(2,4-difluorobenzyloxy-
carbonyl)amino]ethoxy}phenyl)-2-ethoxypropionic acid,
3-(4-{2-[N-(2,4-difluorobenzyloxycarbonyl)-N-(5,5,6,6,7,
7,7-heptafluoroheptyl)amino]ethoxy}phenyl)-2-ethox-
ypropionic acid,
3-(4-{2-[N-(2,4-difluorobenzyloxycarbonyl)-N-(2,2,3,3,4,
4,5,5,6,6,7,7,7-tridecafluoroheptyl)amino]
ethoxy}phenyl)-2-ethoxypropionic acid,
3-(4-{2-[N-(2,4-difluorobenzyloxycarbonyl)-N-(5,5,6,6,6-
pentafluorohexyl)amino]ethoxy}phenyl)-2-ethoxypropi-
onic acid,
3-(4-{2-[N-(2,4-difluorobenzyloxycarbonyl)-N-(2,2,3,3,4,
4,5,5,6,6,6-undecafluorohexyl)amino]ethoxy}phenyl)-2-
ethoxypropionic acid,
3-[4-(2-{N-[2-(2,2-difluoropropoxy)ethyl]-N-(2,4-difluo-
robenzyloxycarbonyl)amino}ethoxy)phenyl]-2-ethox-
ypropionic acid,
3-[4-(2-{N-(2,4-difluorobenzyloxycarbonyl)-N-[2-(1,1,2,2,
3,3,3-heptafluoropropoxy)ethyl]amino}ethoxy)phenyl]-
2-ethoxypropionic acid,
3-[4-(2-{N-(2,4-difluorobenzyloxycarbonyl)-N-[2-(4,4,4
-trifluorobutoxy)ethyl]amino}ethoxy)phenyl]-2-ethox-
ypropionic acid,
3-[4-(2-{N-[2-(3,3-difluorobutoxy)ethyl]-N-(2,4-difluo-
robenzyloxycarbonyl)amino}ethoxy)phenyl]-2-ethox-
ypropionic acid,
3-[4-(2-{N-[2-(2,2-difluorobutoxy)ethyl]-N-(2,4-difluo-
robenzyloxycarbonyl)amino}ethoxy)phenyl]-2-ethox-
ypropionic acid,
3-[4-(2-{N-(2,4-difluorobenzyloxycarbonyl)-N-[2-(1,1,2,2,
3,3,4,4,4-nonafluorobutoxy)ethyl]amino}ethoxy)phe-
nyl]-2-ethoxypropionic acid,
3-[4-(2-{N-(2,4-difluorobenzyloxycarbonyl)-N-[3-(2,2,2-
trifluoroethoxy)propyl]amino}ethoxy)phenyl]-2-ethox-
ypropionic acid,
3-[4-(2-{N-(2,4-difluorobenzyloxycarbonyl)-N-[3-(1,1,2,2,
2-pentafluoroethoxy)propyl]amino}ethoxy)phenyl]-2-
ethoxypropionic acid,
3-[4-(2-{N-(2,4-difluorobenzyloxycarbonyl)-N-[3-(4-fluo-
rophenoxy)propyl]amino}ethoxy)phenyl]-2-ethoxypropi-
onic acid,
3-[4-(2-{N-[3-(3,5-dichlorophenoxy)propyl]-N-(2,4-difluo-
robenzyloxycarbonyl)amino}ethoxy)phenyl]-2-ethox-
ypropionic acid,
3-[4-(2-{N-(2,4-difluorobenzyloxycarbonyl)-N-[4-(4-fluo-
rophenoxy)butyl]amino}ethoxy)phenyl]-2-ethoxypropi-
onic acid,
3-[4-(2-{N-[4-(3,5-dichlorophenoxy)butyl]-N-(2,4-difluo-
robenzyloxycarbonyl)amino}ethoxy)phenyl]-2-ethox-
ypropionic acid,
3-[4-(2-{N-(2,4-difluorobenzyloxycarbonyl)-N-[2-(4-fluo-
robenzyloxy)ethyl]amino}ethoxy)phenyl]-2-ethoxypro-
pionic acid,
3-[4-(2-{N-[2-(3,5-dichlorobenzyloxy)ethyl]-N-(2,4-difluo-
robenzyloxycarbonyl)amino}ethoxy)phenyl]-2-ethox-
ypropionic acid,
3-[4-(2-{N-(2,4-difluorobenzyloxycarbonyl)-N-[3-(4-fluo-
robenzyloxy)propyl]amino}ethoxy)phenyl]-2-ethoxypro-
pionic acid,
3-[4-(2-{N-[3-(3,5-dichlorobenzyloxy)propyl]-N-(2,4-dif-
luorobenzyloxycarbonyl)amino}ethoxy)phenyl]-2-ethox-
ypropionic acid,
3-[4-(2-{N-(2,4-difluorobenzyloxycarbonyl)-N-[4-(4-fluo-
robenzyloxy)butyl]amino}ethoxy)phenyl]-2-ethoxypro-
pionic acid,
3-[4-(2-{N-[4-(3,5-dichlorobenzyloxy)butyl]-N-(2,4-dif-
luorobenzyloxycarbonyl)amino}ethoxy)phenyl]-2-ethox-
ypropionic acid,
3-[4-(2-{N-(2,4-difluorobenzyloxycarbonyl)-N-[3-(4-fluo-
rophenyl)propyl]amino}ethoxy)phenyl]-2-ethoxypropi-
onic acid,
3-[4-(2-{N-[3-(3,5-dichlorophenyl)propyl]-N-(2,4-difluo-
robenzyloxycarbonyl)amino}ethoxy)phenyl]-2-ethox-
ypropionic acid,
2-ethoxy-3-(4-{2-[N-(4-fluorobenzyloxycarbonyl)-N-pen-
tylamino]ethoxy}phenyl)propionic acid,
2-ethoxy-3-(4-{2-[N-(4-fluorobenzyloxycarbonyl)-N-hexy-
lamino]ethoxy}phenyl)propionic acid,
2-ethoxy-3-(4-{2-[N-(4-fluorobenzyloxycarbonyl)-N-hep-
tylamino]ethoxy}phenyl)propionic acid,
2-ethoxy-3-(4-{2-[N-(4-fluorobenzyloxycarbonyl)-N-octy-
lamino]ethoxy}phenyl)propionic acid,
2-ethoxy-3-(4-{2-[N-(4-fluorobenzyloxycarbonyl)-N-
isobutylamino]ethoxy}phenyl)propionic acid,
2-ethoxy-3-(4-{2-[N-(4-fluorobenzyloxycarbonyl)-N-(3-
methylbutyl)amino]ethoxy}phenyl)propionic acid,
2-ethoxy-3-(4-{2-[N-(4-fluorobenzyloxycarbonyl)-N-(4-
methylpentyl)amino]ethoxy}phenyl)propionic acid,
2-ethoxy-3-(4-{2-[N-(4-fluorobenzyloxycarbonyl)-N-(2-
propylpentyl)amino]ethoxy}phenyl)propionic acid,
3-(4-{2-[N-(3,3-dimethylbutyl)-N-(4-fluorobenzyloxycar-
bonyl)amino]ethoxy}phenyl)-2-ethoxypropionic acid,
2-ethoxy-3-(4-{2-[N-(2-ethylbutyl)-N-(4-fluorobenzyloxy-
carbonyl)amino]ethoxy}phenyl)propionic acid,
3-(4-{2-[N-cyclohexylmethyl-N-(4-fluorobenzyloxycarbo-
nyl)amino]ethoxy}phenyl)-2-ethoxypropionic acid,
3-(4-{2-[N-(4-cyclohexylbutyl)-N-(4-fluorobenzyloxycar-
bonyl)amino]ethoxy}phenyl)-2-ethoxypropionic acid,
3-(4-{2-[N-cyclopropylmethyl-N-(4-fluorobenzyloxycarbo-
nyl)amino]ethoxy}phenyl)-2-ethoxypropionic acid,
3-(4-{2-[N-cyclobutylmethyl-N-(4-fluorobenzyloxycarbo-
nyl)amino]ethoxy}phenyl)-2-ethoxypropionic acid,
3-(4-{2-[N-cyclopentylmethyl-N-(4-fluorobenzyloxycarbo-
nyl)amino]ethoxy}phenyl)-2-ethoxypropionic acid,
3-(4-{2-[N-(2-cyclopentylethyl)-N-(4-fluorobenzyloxycar-
bonyl)amino]ethoxy}phenyl)-2 -ethoxypropionic acid,
3-(4-{2-[N-(3-cyclohexylpropyl)-N-(4-fluorobenzyloxycar-
bonyl)amino]ethoxy}phenyl)-2-ethoxypropionic acid,
2-ethoxy-3-(4-{2-[N-(4-fluorobenzyloxycarbonyl)-N-(3-
phenylpropyl)amino]ethoxy}phenyl)propionic acid,
2-ethoxy-3-(4-{2-[N-(4-fluorobenzyloxycarbonyl)-N-(4-
phenylbutyl)amino]ethoxy}phenyl)propionic acid,
3-(4-{2-[N-(2-butoxyethyl)-N-(4-fluorobenzyloxycarbonyl)
amino]ethoxy}phenyl)-2-ethoxypropionic acid,
2-ethoxy-3-(4-{2-[N-(4-fluorobenzyloxycarbonyl)-N-(2-
pentyloxyethyl)amino]ethoxy}phenyl)propionic acid,
2-ethoxy-3-(4-{2-[N-(4-fluorobenzyloxycarbonyl)-N-(3-
propoxypropyl)amino]ethoxy}phenyl)propionic acid,
3-(4-{2-[N-(2-butylthioethyl)-N-(4-fluorobenzyloxycarbo-
nyl)amino]ethoxy}phenyl)-2-ethoxypropionic acid,
2-ethoxy-3-(4-{2-[N-(4-fluorobenzyloxycarbonyl)-N-(2-
pentylthioethyl)amino]ethoxy}phenyl)propionic acid,
2-ethoxy-3-(4-{2-[N-(4-fluorobenzyloxycarbonyl)-N-(3-
propylthiopropyl)amino]ethoxy}phenyl)propionic acid,
2-ethoxy-3-(4-{2-[N-(4-fluorobenzyloxycarbonyl)-N-(3-
phenoxypropyl)amino]ethoxy}phenyl)propionic acid,
2-ethoxy-3-(4-{2-[N-(4-fluorobenzyloxycarbonyl)-N-(4-
phenoxybutyl)amino]ethoxy}phenyl)propionic acid, 3-(4-{2-[N-(3-benzyloxypropyl)-N-(4-fluorobenzyloxycarbonyl)amino]ethoxy}phenyl)-2-ethoxypropionic acid,
2-ethoxy-3-(4-{2-[N-(4-fluorobenzyloxycarbonyl)-N-(3-phenylthiopropyl)amino]ethoxy}phenyl)propionic acid,
2-ethoxy-3-(4-{2-[N-(4-fluorobenzyloxycarbonyl)-N-(4-phenylthiobutyl)amino]ethoxy}phenyl)propionic acid,
3-(4-{2-[N-(3-benzylthiopropyl)-N-(4-fluorobenzyloxycarbonyl)amino]ethoxy}phenyl)-2-ethoxypropionic acid,
2-ethoxy-3-(4-{2-[N-(4-fluorobenzyloxycarbonyl)-N-(7,7,7-trifluoroheptyl)amino]ethoxy}phenyl)propionic acid,
3-(4-{2-[N-(6,6-difluoroheptyl)-N-(4-fluorobenzyloxycarbonyl)amino]ethoxy}phenyl)-2-ethoxypropionic acid,
2-ethoxy-3-(4-{2-[N-(4-fluorobenzyloxycarbonyl)-N-(6,6,6-trifluorohexyl)amino]ethoxy}phenyl)propionic acid,
3-(4-{2-[N-(5,5-difluorohexyl)-N-(4-fluorobenzyloxycarbonyl)amino}ethoxy}phenyl)-2-ethoxypropionic acid,
2-ethoxy-3-(4-{2-[N-(4-fluorobenzyloxycarbonyl)-N-(5,5,6,6,7,7,7-heptafluoroheptyl)amino]ethoxy}phenyl)propionic acid,
2-ethoxy-3-(4-{2-[N-(4-fluorobenzyloxycarbonyl)-N-(2,2,3,3,4,4,5,5,6,6,7,7,7-tridecafluoroheptyl)amino]ethoxy}phenyl)propionic acid,
2-ethoxy-3-(4-{2-[N-(4-fluorobenzyloxycarbonyl)-N-(5,5,6,6,6-pentafluorohexyl)amino]ethoxy}phenyl)propionic acid,
2-ethoxy-3-(4-{2-[N-(4-fluorobenzyloxycarbonyl)-N-(2,2,3,3,4,4,5,5,6,6-undecafluorohexyl)amino]ethoxy}phenyl)propionic acid,
3-[4-(2-{N-[2-(2,2-difluoropropoxy)ethyl]-N-(4-fluorobenzyloxycarbonyl)amino}ethoxy)phenyl]-2-ethoxypropionic acid,
2-ethoxy-3-[4-(2-{N-(4-fluorobenzyloxycarbonyl)-N-[2-(1,1,2,2,3,3,3-heptafluoropropoxy)ethyl]amino}ethoxy)phenyl]propionic acid,
2-ethoxy-3-[4-(2-{N-(4-fluorobenzyloxycarbonyl)-N-[2-(4,4,4-trifluorobutoxy)ethyl]amino}ethoxy)phenyl]propionic acid,
3-[4-(2-{N-[2-(3,3-difluorobutoxy)ethyl]-N-(4-fluorobenzyloxycarbonyl)amino}ethoxy)phenyl]-2-ethoxypropionic acid,
3-[4-(2-{N-[2-(2,2-difluorobutoxy)ethyl]-N-(4-fluorobenzyloxycarbonyl)amino}ethoxy)phenyl]-2-ethoxypropionic acid,
2-ethoxy-3-[4-(2-{N-(4-fluorobenzyloxycarbonyl)-N-[2-(1,1,2,2,3,3,4,4,4-nonafluorobutoxy)ethyl]amino }ethoxy)phenyl]propionic acid,
2-ethoxy-3-[4-(2-{N-(4-fluorobenzyloxycarbonyl)-N-[3-(2,2,2-trifluoroethoxy)propyl]amino}ethoxy)phenyl]propionic acid,
2-ethoxy-3-[4-(2-{N-(4-fluorobenzyloxycarbonyl)-N-[3-(1,1,2,2,2-pentafluoroethoxy)propyl]amino}ethoxy)phenyl] propionic acid,
2-ethoxy-3-[4-(2-{N-(4-fluorobenzyloxycarbonyl)-N-[3-(4-fluorophenoxy)propyl]amino]ethoxy)phenyl]propionic acid,
3-[4-(2-{N-[3-(3,5-dichlorophenoxy)propyl]-N-(4-fluorobenzyloxycarbonyl)amino}ethoxy)phenyl]-2-ethoxypropionic acid,
2-ethoxy-3-[4-(2-{N-(4-fluorobenzyloxycarbonyl)-N-[4-(4-fluorophenoxy)butyl]amino}ethoxy)phenyl]propionic acid,
3-[4-(2-{N-[4-(3,5-dichlorophenoxy)butyl]-N-(4-fluorobenzyloxycarbonyl)amino}ethoxy)phenyl]-2-ethoxypropionic acid,
2-ethoxy-3-[4-(2-{N-(4-fluorobenzyloxycarbonyl)-N-[2-(4-fluorobenzyloxy)ethyl]amino}ethoxy)phenyl]propionic acid,
3-[4-(2-(N-[2-(3,5-dichlorobenzyloxy)ethyl]-N-(4-fluorobenzyloxycarbonyl)amino}ethoxy)phenyl]-2-ethoxypropionic acid,
2-ethoxy-3-[4-(2-{N-(4-fluorobenzyloxycarbonyl)-N-[3-(4-fluorobenzyloxy)propyl]amino}ethoxy)phenyl]propionic acid,
3-[4-(2-{N-[3-(3,5-dichlorobenzyloxy)propyl]-N-(4-fluorobenzyloxycarbonyl)amino}ethoxy)phenyl]-2-ethoxypropionic acid,
2-ethoxy-3-[4-(2-{N-(4-fluorobenzyloxycarbonyl)-N-[4-(4-fluorobenzyloxy)butyl]amino}ethoxy)phenyl]propionic acid,
3-[4-(2-{N-[4-(3,5-dichlorobenzyloxy)butyl]-N-(4-fluorobenzyloxycarbonyl)amino}ethoxy)phenyl]-2-ethoxypropionic acid,
2-ethoxy-3-[4-(2-{N-(4-fluorobenzyloxycarbonyl)-N-[3-(4-fluorophenyl)propyl]amino}ethoxy)phenyl]propionic acid, and
3-[4-(2-{N-[3-(3,5-dichlorophenyl)propyl]-N-(4-fluorobenzyloxycarbonyl)amino}ethoxy)phenyl]-2-ethoxypropionic acid.

Examples of the compounds wherein $R^1$ is indan-5-yl group include, for example, the following compounds.
2-Ethoxy-3-{4-[2-(N-indan-5-yloxycarbonyl-N-pentylamino)ethoxy]phenyl}propionic acid,
2-ethoxy-3-(4-[2-(N-hexyl-N-indan-5-yloxycarbonylamino)ethoxy]phenyl}propionic acid,
2-ethoxy-3-{4-[2-(N-heptyl-N-indan-5-yloxycarbonylamino)ethoxy]phenyl}propionic acid,
2-ethoxy-3-{4-[2-(N-indan-5-yloxycarbonyl-N-octylamino)ethoxy]phenyl}propionic acid,
2-ethoxy-3-{4-[2-(N-indan-5-yloxycarbonyl-N-isobutylamino)ethoxy]phenyl}propionic acid,
2-ethoxy-3-(4-{2-[N-indan-5-yloxycarbonyl-N-(3-methylbutyl)amino]ethoxy}phenyl)propionic acid,
2-ethoxy-3-(4-{2-[N-indan-5-yloxycarbonyl-N-(4-methylpentyl)amino]ethoxy}phenyl)propionic acid,
2-ethoxy-3-(4-{2-[N-indan-5-yloxycarbonyl-N-(2-propylpentyl)amino]ethoxy}phenyl)propionic acid,
3-(4-{2-[N-(3,3-dimethylbutyl)-N-indan-5-yloxycarbonylamino]ethoxy}phenyl)-2-ethoxypropionic acid,
2-ethoxy-3-(4-{2-[N-(2-ethylbutyl)-N-indan-5-yloxycarbonylamino]ethoxy}phenyl)propionic acid,
3-(4-[2-(N-cyclohexylmethyl-N-indan-5-yloxycarbonylamino)ethoxy]phenyl}-2-ethoxypropionic acid,
3-(4-{2-[N-(4-cyclohexylbutyl)-N-indan-5-yloxycarbonylamino]ethoxy}phenyl)-2-ethoxypropionic acid,
3-(4-[2-(N-cyclopropylmethyl-N-indan-5-yloxycarbonylamino)ethoxy]phenyl}-2-ethoxypropionic acid,
3-{4-[2-(N-cyclobutylmethyl-N-indan-5-yloxycarbonylamino)ethoxy]phenyl}-2-ethoxypropionic acid,
3-{4-[2-(N-cyclopentylmethyl-N-indan-5-yloxycarbonylamino)ethoxy]phenyl}-2-ethoxypropionic acid,
3-(4-{2-[N-(2-cyclopentylethyl)-N-indan-5-yloxycarbonylamino]ethoxy}phenyl)-2-ethoxypropionic acid,
3-(4-{2-[N-(3-cyclohexylpropyl)-N-indan-5-yloxycarbonylamino]ethoxy}phenyl)-2-ethoxypropionic acid,
2-ethoxy-3-(4-{2-[N-indan-5-yloxycarbonyl-N-(3-phenylpropyl)amino]ethoxy}phenyl)propionic acid,
2-ethoxy-3-(4-{2-[N-indan-5-yloxycarbonyl-N-(4-phenylbutyl)amino]ethoxy}phenyl)propionic acid,
3-(4-{2-[N-(2-butoxyethyl)-N-indan-5-yloxycarbonylamino]ethoxy}phenyl)-2-ethoxypropionic acid,
2-ethoxy-3-(4-{2-[N-indan-5-yloxycarbonyl-N-(2-pentyloxyethyl)amino]ethoxy}phenyl)propionic acid,
2-ethoxy-3-(4-{2-[N-indan-5-yloxycarbonyl-N-(3-propoxypropyl)amino]ethoxy}phenyl)propionic acid, 3-(4-{2-[N-(2-butylthioethyl)-N-indan-5-yloxycarbonylamino]ethoxy}phenyl)-2-ethoxypropionic acid,
2-ethoxy-3-(4-{2-[N-indan-5-yloxycarbonyl-N-(2-pentylthioethyl)amino]ethoxy}phenyl)propionic acid,
2-ethoxy-3-(4-{2-[N-indan-5-yloxycarbonyl-N-(3-propylthiopropyl)amino]ethoxy}phenyl)propionic acid,
2-ethoxy-3-(4-{2-[N-indan-5-yloxycarbonyl-N-(3-phenoxypropyl)amino]ethoxy}phenyl)propionic acid,
2-ethoxy-3-(4-{2-[N-indan-5-yloxycarbonyl-N-(4-phenoxybutyl)amino]ethoxy}phenyl)propionic acid,
3-(4-{2-[N-(3-benzyloxypropyl)-N-indan-5-yloxycarbonylamino]ethoxy}phenyl)-2-ethoxypropionic acid,
2-ethoxy-3-(4-{2-[N-indan-5-yloxycarbonyl-N-(3-phenylthiopropyl)amino]ethoxy}phenyl)propionic acid,
2-ethoxy-3-(4-{2-[N-indan-5-yloxycarbonyl-N-(4-phenylthiobutyl)amino]ethoxy}phenyl)propionic acid,
3-(4-{2-[N-(3-benzylthiopropyl)-N-indan-5-yloxycarbonylamino]ethoxy}phenyl)-2-ethoxypropionic acid,
2-ethoxy-3-(4-{2-[N-indan-5-yloxycarbonyl-N-(7,7,7-trifluoroheptyl)amino]ethoxy}phenyl)propionic acid,
3-(4-{2-[N-(6,6-difluoroheptyl)-N-indan-5-yloxycarbonylamino]ethoxy}phenyl)-2-ethoxypropionic acid,
2-ethoxy-3-(4-{2-[N-indan-5-yloxycarbonyl-N-(6,6,6-trifluorohexyl)amino]ethoxy}phenyl)propionic acid,
3-(4-{2-[N-(5,5-difluorohexyl)-N-indan-5-yloxycarbonylamino]ethoxy}phenyl)-2-ethoxypropionic acid,
2-ethoxy-3-(4-{2-[N-(5,5,6,6,7,7,7-heptafluoroheptyl)-N-indan-5-yloxycarbonylamino]ethoxy}phenyl)propionic acid,
2-ethoxy-3-(4-{2-[N-indan-5-yloxycarbonyl-N-(2,2,3,3,4,4,5,5,6,6,7,7,7-tridecafluoroheptyl)amino]ethoxy}phenyl)propionic acid,
2-ethoxy-3-(4-{2-[N-indan-5-yloxycarbonyl-N-(5,5,6,6,6-pentafluorohexyl)amino]ethoxy}phenyl)propionic acid,
2-ethoxy-3-(4-{2-[N-indan-5-yloxycarbonyl-N-(2,2,3,3,4,4,5,5,6,6,6-undecafluorohexyl)amino]ethoxy}phenyl)propionic acid,
3-[4-(2-{N-[2-(2,2-difluoropropoxy)ethyl]-N-indan-5-yloxycarbonylamino}ethoxy)phenyl]-2-ethoxypropionic acid,
2-ethoxy-3-[4-(2-{N-[2-(1,1,2,2,3,3,3-heptafluoropropoxy)ethyl]-N-indan-5-yloxycarbonylamino}ethoxy)phenyl]propionic acid,
2-ethoxy-3-[4-(2-{N-indan-5-yloxycarbonyl-N-[2-(4,4,4-trifluorobutoxy)ethyl]amino}ethoxy)phenyl]propionic acid,
3-[4-(2-{N-[2-(3,3-difluorobutoxy)ethyl]-N-indan-5-yloxycarbonylamino}ethoxy)phenyl]-2-ethoxypropionic acid,
3-[4-(2-{N-[2-(2,2-difluorobutoxy)ethyl]-N-indan-5-yloxycarbonylamino}ethoxy)phenyl]-2-ethoxypropionic acid,
2-ethoxy-3-[4-(2-{N-indan-5-yloxycarbonyl-N-[2-(1,1,2,2,3,3,4,4,4-nonafluorobutoxy)ethyl]amino}ethoxy)phenyl]propionic acid,
2-ethoxy-3-[4-(2-{N-indan-5-yloxycarbonyl-N-[3-(2,2,2-trifluoroethoxy)propyl]amino}ethoxy)phenyl]propionic acid,
2-ethoxy-3-[4-(2-{N-indan-5-yloxycarbonyl-N-[3-(1,1,2,2,2-pentafluoroethoxy)propyl]amino}ethoxy)phenyl]propionic acid,
2-ethoxy-3-[4-(2-{N-[3-(4-fluorophenoxy)propyl]-N-indan-5-yloxycarbonylamino}ethoxy)phenyl]propionic acid,
3-[4-(2-{N-[3-(3,5-dichlorophenoxy)propyl]-N-indan-5-yloxycarbonylamino}ethoxy)phenyl]-2-ethoxypropionic acid,
2-ethoxy-3-[4-(2-{N-[4-(4-fluorophenoxy)butyl]-N-indan-5-yloxycarbonylamino}ethoxy)phenyl]propionic acid,
3-[4-(2-{N-[4-(3,5-dichlorophenoxy)butyl]-N-indan-5-yloxycarbonylamino}ethoxy)phenyl]-2-ethoxypropionic acid,
2-ethoxy-3-[4-(2-{N-[2-(4-fluorobenzyloxy)ethyl]-N-indan-5-yloxycarbonylamino}ethoxy)phenyl]propionic acid,
3-[4-(2-{N-[2-(3,5-dichlorobenzyloxy)ethyl]-N-indan-5-yloxycarbonylamino}ethoxy)phenyl]-2-ethoxypropionic acid,
2-ethoxy-3-[4-(2-{N-[3-(4-fluorobenzyloxy)propyl]-N-indan-5-yloxycarbonylamino}ethoxy)phenyl]propionic acid,
3-[4-(2-{N-[3-(3,5-dichlorobenzyloxy)propyl]-N-indan-5-yloxycarbonylamino}ethoxy)phenyl]-2-ethoxypropionic acid,
2-ethoxy-3-[4-(2-{N-[4-(4-fluorobenzyloxy)butyl]-N-indan-5-yloxycarbonylamino}ethoxy)phenyl]propionic acid,
3-[4-(2-{N-[4-(3,5-dichlorobenzyloxy)butyl]-N-indan-5-yloxycarbonylamino}ethoxy)phenyl]-2-ethoxypropionic acid,
2-ethoxy-3-[4-(2-{N-[3-(4-fluorophenyl)propyl]-N-indan-5-yloxycarbonylamino}ethoxy)phenyl]propionic acid, and
3-[4-(2-{N-[3-(3,5-dichlorophenyl)propyl]-N-indan-5-yloxycarbonylamino}ethoxy)phenyl]-2-ethoxypropionic acid.

Examples of the compounds wherein $R^1$ is a group represented by the formula (1-1) also include, for example, the following compounds.

2-Ethoxy-3-{4-[2-(N-pentyl-N-phenoxycarbonylamino)ethoxy]phenyl}propionic acid,
2-ethoxy-3-{4-[2-(N-hexyl-N-phenoxycarbonylamino)ethoxy]phenyl}propionic acid,
2-ethoxy-3-{4-[2-(N-heptyl-N-phenoxycarbonylamino)ethoxy]phenyl}propionic acid,
2-ethoxy-3-{4-[2-(N-octyl-N-phenoxycarbonylamino)ethoxy]phenyl}propionic acid,
2-ethoxy-3-{4-[2-(N-isobutyl-N-phenoxycarbonylamino)ethoxy]phenyl}propionic acid,
2-ethoxy-3-(4-{2-[N-(3-methylbutyl)-N-phenoxycarbonylamino]ethoxy}phenyl)propionic acid,
2-ethoxy-3-(4-{2-[N-(4-methylpentyl)-N-phenoxycarbonylamino]ethoxy}phenyl)propionic acid,
2-ethoxy-3-(4-{2-[N-phenoxycarbonyl-N-(2-propylpentyl)amino]ethoxy}phenyl)propionic acid,
3-(4-{2-[N-(3,3-dimethylbutyl)-N-phenoxycarbonylamino]ethoxy}phenyl)-2-ethoxypropionic acid,
2-ethoxy-3-(4-{2-[N-(2-ethylbutyl)-N-phenoxycarbonylamino]ethoxy}phenyl)propionic acid,
3-(4-[2-(N-cyclohexylmethyl-N-phenoxycarbonylamino)ethoxy]phenyl}-2-ethoxypropionic acid,
3-(4-{2-[N-(4-cyclohexylbutyl)-N-phenoxycarbonylamino]ethoxy}phenyl)-2-ethoxypropionic acid,
3-{4-[2-(N-cyclopropylmethyl-N-phenoxycarbonylamino)ethoxy]phenyl}-2-ethoxypropionic acid,
3-{4-[2-(N-cyclobutylmethyl-N-phenoxycarbonylamino)ethoxy]phenyl}-2-ethoxypropionic acid,
3-{4-[2-(N-cyclopentylmethyl-N-phenoxycarbonylamino)ethoxy]phenyl}-2-ethoxypropionic acid,
3-(4-{2-[N-(2-cyclopentylethyl)-N-phenoxycarbonylamino]ethoxy}phenyl)-2-ethoxypropionic acid,
3-(4-{2-[N-(3-cyclohexylpropyl)-N-phenoxycarbonylamino]ethoxy}phenyl)-2-ethoxypropionic acid, 2-ethoxy-3-(4-{2-[N-phenoxycarbonyl-N-(3-phenylpropyl)amino]ethoxy}phenyl)propionic acid,
2-ethoxy-3-(4-{2-[N-phenoxycarbonyl-N-(4-phenylbutyl)amino]ethoxy}phenyl)propionic acid,
3-(4-{2-[N-(2-butoxyethyl)-N-phenoxycarbonylamino]ethoxy}phenyl)-2-ethoxypropionic acid,
2-ethoxy-3-(4-{2-[N-(2-pentyloxyethyl)-N-phenoxycarbonylamino]ethoxy}phenyl)propionic acid,
2-ethoxy-3-(4-{2-[N-phenoxycarbonyl-N-(3-propoxypropyl)amino]ethoxy}phenyl)propionic acid,
3-(4-{2-[N-(2-butylthioethyl)-N-phenoxycarbonylamino]ethoxy}phenyl)-2-ethoxypropionic acid,
2-ethoxy-3-(4-{2-[N-(2-pentylthioethyl)-N-phenoxycarbonylamino]ethoxy}phenyl)propionic acid,
2-ethoxy-3-(4-{2-[N-phenoxycarbonyl-N-(3-propylthiopropyl)amino]ethoxy}phenyl)propionic acid,
2-ethoxy-3-(4-{2-[N-(3-phenoxypropyl)-N-phenoxycarbonylamino]ethoxy}phenyl)propionic acid,
2-ethoxy-3-(4-{2-[N-(4-phenoxybutyl)-N-phenoxycarbonylamino]ethoxy}phenyl)propionic acid,
3-(4-{2-[N-(3-benzyloxypropyl)-N-phenoxycarbonylamino]ethoxy}phenyl)-2-ethoxypropionic acid,
2-ethoxy-3-(4-{2-[N-phenoxycarbonyl-N-(3-phenylthiopropyl)amino]ethoxy}phenyl)propionic acid,
2-ethoxy-3-(4-{2-[N-phenoxycarbonyl-N-(4-phenylthiobutyl)amino]ethoxy}phenyl)propionic acid,
3-(4-{2-[N-(3-benzylthiopropyl)-N-phenoxycarbonylamino]ethoxy}phenyl)-2 -ethoxypropionic acid,
2-ethoxy-3-(4-{2-[N-phenoxycarbonyl-N-(7,7,7-trifluoroheptyl)amino]ethoxy}phenyl)propionic acid,
3-(4-{2-[N-(6,6-difluoroheptyl)-N-phenoxycarbonylamino]ethoxy}phenyl)-2-ethoxypropionic acid,
2-ethoxy-3-(4-{2-[N-phenoxycarbonyl-N-(6,6,6-trifluorohexyl)amino]ethoxy}phenyl)propionic acid,
3-(4-{2-[N-(5,5-difluorohexyl)-N-phenoxycarbonylamino]ethoxy}phenyl)-2-ethoxypropionic acid,
2-ethoxy-3-(4-{2-[N-(5,5,6,6,7,7,7-heptafluoroheptyl)-N-phenoxycarbonylamino]ethoxy}phenyl)propionic acid,
2-ethoxy-3-(4-{2-[N-phenoxycarbonyl-N-(2,2,3,3,4,4,5,5,6,6,7,7,7-tridecafluoroheptyl)amino]ethoxy}phenyl)propionic acid,
2-ethoxy-3-(4-{2-[N-(5,5,6,6,6-pentafluorohexyl)-N-phenoxycarbonylamino]ethoxy}phenyl)propionic acid,
2-ethoxy-3-(4-{2-[N-phenoxycarbonyl-N-(2,2,3,3,4,4,5,5,6,6,6-undecafluorohexyl)amino]ethoxy}phenyl)propionic acid,
3-[4-(2-{N-[2-(2,2-difluoropropoxy)ethyl]-N-phenoxycarbonylamino}ethoxy)phenyl]-2-ethoxypropionic acid,
2-ethoxy-3-[4-(2-{N-[2-(1,1,2,2,3,3,3-heptafluoropropoxy)ethyl]-N-phenoxycarbonylamino}ethoxy)phenyl]propionic acid,
2-ethoxy-3-[4-(2-{N-phenoxycarbonyl-N-[2-(4,4,4-trifluorobutoxy)ethyl]amino}ethoxy)phenyl]propionic acid,
3-[4-(2-{N-[2-(3,3-difluorobutoxy)ethyl]-N-phenoxycarbonylamino}ethoxy)phenyl]-2-ethoxypropionic acid,
3-[4-(2-{N-[2-(2,2-difluorobutoxy)ethyl]-N-phenoxycarbonylamino}ethoxy)phenyl]-2-ethoxypropionic acid,
2-ethoxy-3-[4-(2-{N-[2-(1,1,2,2,3,3,4,4,4-nonafluorobutoxy)ethyl]-N-phenoxycarbonylamino}ethoxy)phenyl]propionic acid,
2-ethoxy-3-[4-(2-{N-phenoxycarbonyl-N-[3-(2,2,2-trifluoroethoxy)propyl]amino}ethoxy)phenyl]propionic acid,
2-ethoxy-3-[4-(2-{N-[3-(1,1,2,2,2-pentafluoroethoxy)propyl]-N-phenoxycarbonylamino}ethoxy)phenyl]propionic acid,
2-ethoxy-3-[4-(2-{N-[3-(4-fluorophenoxy)propyl]-N-phenoxycarbonylamino}ethoxy)phenyl]propionic acid,
3-[4-(2-{N-[3-(3,5-dichlorophenoxy)propyl]-N-phenoxycarbonylamino}ethoxy)phenyl]-2-ethoxypropionic acid,
2-ethoxy-3-[4-(2-{N-[4-(4-fluorophenoxy)butyl]-N-phenoxycarbonylamino}ethoxy)phenyl]propionic acid,
3-[4-(2-{N-[4-(3,5-dichlorophenoxy)butyl]-N-phenoxycarbonylamino}ethoxy)phenyl]-2-ethoxypropionic acid,
2-ethoxy-3-[4-(2-{N-[2-(4-fluorobenzyloxy)ethyl]-N-phenoxycarbonylamino}ethoxy)phenyl]propionic acid,
3-[4-(2-{N-[2-(3,5-dichlorobenzyloxy)ethyl]-N-phenoxycarbonylamino}ethoxy)phenyl]-2-ethoxypropionic acid,
2-ethoxy-3-[4-(2-{N-[3-(4-fluorobenzyloxy)propyl]-N-phenoxycarbonylamino}ethoxy)phenyl]propionic acid,
3-[4-(2-{N-[3-(3,5-dichlorobenzyloxy)propyl]-N-phenoxycarbonylamino}ethoxy)phenyl]-2-ethoxypropionic acid,
2-ethoxy-3-[4-(2-{N-[4-(4-fluorobenzyloxy)butyl]-N-phenoxycarbonylamino}ethoxy)phenyl]propionic acid,
3-[4-(2-{N-[4-(3,5-dichlorobenzyloxy)butyl]-N-phenoxycarbonylamino}ethoxy)phenyl]-2-ethoxypropionic acid,
2-ethoxy-3-[4-(2-{N-[3-(4-fluorophenyl)propyl]-N-phenoxycarbonylamino}ethoxy)phenyl]propionic acid,
3-[4-(2-{N-[3-(3,5-dichlorophenyl)propyl]-N-phenoxycarbonylamino}ethoxy)phenyl]-2-ethoxypropionic acid,
3-(4-{2-[N-(2,4-difluorophenoxycarbonyl)-N-pentylamino]ethoxy}phenyl)-2-ethoxypropionic acid,
3-(4-{2-[N-(2,4-difluorophenoxycarbonyl)-N-hexylamino]ethoxy}phenyl)-2-ethoxypropionic acid,
3-(4-{2-[N-(2,4-difluorophenoxycarbonyl)-N-heptylamino]ethoxy}phenyl)-2-ethoxypropionic acid,
3-(4-{2-[N-(2,4-difluorophenoxycarbonyl)-N-octylamino]ethoxy}phenyl)-2-ethoxypropionic acid,
3-(4-{2-[N-(2,4-difluorophenoxycarbonyl)-N-isobutylamino]ethoxy}phenyl)-2 -ethoxypropionic acid,
3-(4-{2-[N-(2,4-difluorophenoxycarbonyl)-N-(3-methylbutyl)amino]ethoxy}phenyl)-2-ethoxypropionic acid,
3-(4-{2-[N-(2,4-difluorophenoxycarbonyl)-N-(4-methylpentyl)amino]ethoxy}phenyl)-2-ethoxypropionic acid,
3-(4-{2-[N-(2,4-difluorophenoxycarbonyl)-N-(2-propylpentyl)amino]ethoxy}phenyl)-2-ethoxypropionic acid,
3-(4-{2-[N-(2,4-difluorophenoxycarbonyl)-N-(3,3-dimethylbutyl)amino]ethoxy}phenyl)-2-ethoxypropionic acid,
3-(4-{2-[N-(2,4-difluorophenoxycarbonyl)-N-(2-ethylbutyl)amino]ethoxy}phenyl)-2-ethoxypropionic acid,
3-(4-{2-[N-cyclohexylmethyl-N-(2,4-difluorophenoxycarbonyl)amino]ethoxy}phenyl)-2-ethoxypropionic acid,
3-(4-{2-[N-(4-cyclohexylbutyl)-N-(2,4-difluorophenoxycarbonyl)amino]ethoxy}phenyl)-2-ethoxypropionic acid,
3-(4-{2-[N-cyclopropylmethyl-N-(2,4-difluorophenoxycarbonyl)amino]ethoxy}phenyl)-2-ethoxypropionic acid,
3-(4-{2-[N-cyclobutylmethyl-N-(2,4-difluorophenoxycarbonyl)amino]ethoxy}phenyl)-2-ethoxypropionic acid,
3-(4-{2-[N-cyclopentylmethyl-N-(2,4-difluorophenoxycarbonyl)amino]ethoxy}phenyl)-2-ethoxypropionic acid,
3-(4-{2-[N-(2-cyclopentylethyl)-N-(2,4-difluorophenoxycarbonyl)amino]ethoxy}phenyl)-2-ethoxypropionic acid,
3-(4-{2-[N-(3-cyclohexylpropyl)-N-(2,4-difluorophenoxycarbonyl)amino]ethoxy}phenyl)-2-ethoxypropionic acid, 3-(4-{2-[N-(2,4-difluorophenoxycarbonyl)-N-(3-phenyl-propyl)amino]ethoxy}phenyl)-2-ethoxypropionic acid,
3-(4-{2-[N-(2,4-difluorophenoxycarbonyl)-N-(4-phenylbu-tyl)amino]ethoxy}phenyl)-2-ethoxypropionic acid,
3-(4-{2-[N-(2-butoxyethyl)-N-(2,4-difluorophenoxycarbo-nyl)amino]ethoxy}phenyl)-2-ethoxypropionic acid,
3-(4-{2-[N-(2,4-difluorophenoxycarbonyl)-N-(2-pentyloxy-ethyl)amino]ethoxy}phenyl)-2-ethoxypropionic acid,
3-(4-{2-[N-(2,4-difluorophenoxycarbonyl)-N-(3-pro-poxypropyl)amino]ethoxy}phenyl)-2-ethoxypropionic acid,
3-(4-{2-[N-(2-butylthioethyl)-N-(2,4-difluorophenoxycar-bonyl)amino]ethoxy}phenyl)-2-ethoxypropionic acid,
3-(4-{2-[N-(2,4-difluorophenoxycarbonyl)-N-(2-pentylth-ioethyl)amino]ethoxy}phenyl)-2-ethoxypropionic acid,
3-(4-{2-[N-(2,4-difluorophenoxycarbonyl)-N-(3-propylthi-opropyl)amino]ethoxy}phenyl)-2-ethoxypropionic acid,
3-(4-{2-[N-(2,4-difluorophenoxycarbonyl)-N-(3-phenox-ypropyl)amino]ethoxy}phenyl)-2-ethoxypropionic acid,
3-(4-{2-[N-(2,4-difluorophenoxycarbonyl)-N-(4-phenoxy-butyl)amino]ethoxy}phenyl)-2-ethoxypropionic acid,
3-(4-{2-[N-(3-benzyloxypropyl)-N-(2,4-difluorophenoxy-carbonyl)amino]ethoxy}phenyl)-2-ethoxypropionic acid,
3-(4-{2-[N-(2,4-difluorophenoxycarbonyl)-N-(3-phenylthi-opropyl)amino]ethoxy}phenyl)-2-ethoxypropionic acid,
3-(4-{2-[N-(2,4-difluorophenoxycarbonyl)-N-(4-phenylth-iobutyl)amino]ethoxy}phenyl)-2-ethoxypropionic acid,
3-(4-{2-[N-(3-benzylthiopropyl)-N-(2,4-difluorophenoxy-carbonyl)amino]ethoxy}phenyl)-2-ethoxypropionic acid,
3-(4-{2-[N-(2,4-difluorophenoxycarbonyl)-N-(7,7,7-trifluo-roheptyl)amino]ethoxy}phenyl)-2-ethoxypropionic acid,
3-(4-{2-[N-(6,6-difluoroheptyl)-N-(2,4-difluorophenoxy-carbonyl)amino]ethoxy}phenyl)-2-ethoxypropionic acid,
3-(4-{2-[N-(2,4-difluorophenoxycarbonyl)-N-(6,6,6-trifluo-rohexyl)amino]ethoxy}phenyl)-2-ethoxypropionic acid,
3-(4-{2-[N-(5,5-difluorohexyl)-N-(2,4-difluorophenoxycar-bonyl)amino]ethoxy}phenyl)-2-ethoxypropionic acid,
3-(4-{2-[N-(2,4-difluorophenoxycarbonyl)-N-(5,5,6,6,7,7,7-heptafluoroheptyl)amino]ethoxy}phenyl)-2-ethoxypro-pionic acid,
3-(4-{2-[N-(2,4-difluorophenoxycarbonyl)-N-(2,2,3,3,4,4,5,5,6,6,7,7,7-tridecafluoroheptyl)amino]ethoxy}phenyl)-2-ethoxypropionic acid,
3-(4-{2-[N-(2,4-difluorophenoxycarbonyl)-N-(5,5,6,6,6-pentafluorohexyl)amino]ethoxy}phenyl)-2-ethoxypropi-onic acid,
3-(4-{2-[N-(2,4-difluorophenoxycarbonyl)-N-(2,2,3,3,4,4,5,5,6,6,6-undecafluorohexyl)amino]ethoxy}phenyl)-2-ethoxypropionic acid,
3-[4-(2-{N-(2,4-difluorophenoxycarbonyl)-N-[2-(2,2-dif-luoropropoxy)ethyl]amino}ethoxy)phenyl]-2-ethoxypro-pionic acid,
3-[4-(2-{N-(2,4-difluorophenoxycarbonyl)-N-[2-(1,1,2,2,3,3,3-heptafluoropropoxy)ethyl]amino}ethoxy)phenyl]-2-ethoxypropionic acid,
3-[4-(2-{N-(2,4-difluorophenoxycarbonyl)-N-[2-(4,4,4-trif-luorobutoxy)ethyl]amino}ethoxy)phenyl]-2-ethoxypropi-onic acid,
3-[4-(2-{N-[2-(3,3-difluorobutoxy)ethyl]-N-(2,4-difluo-rophenoxycarbonyl)amino}ethoxy)phenyl]-2-ethoxypro-pionic acid,
3-[4-(2-{N-[2-(2,2-difluorobutoxy)ethyl]-N-(2,4--difluo-rophenoxycarbonyl)amino}ethoxy)phenyl]-2-ethoxypro-pionic acid,
3-[4-(2-{N-(2,4-difluorophenoxycarbonyl)-N-[2-(1,1,2,2,3,3,4,4,4-nonafluorobutoxy)ethyl]amino}ethoxy)phenyl]-2-ethoxypropionic acid, 3-[4-(2-{N-(2,4-difluorophenoxycarbonyl)-N-[3-(2,2,2-trif-luoroethoxy)propyl]amino}ethoxy)phenyl]-2-ethoxypro-pionic acid,
3-[4-(2-{N-(2,4-difluorophenoxycarbonyl)-N-[3-(1,1,2,2,2-pentafluoroethoxy)propyl]amino}ethoxy)phenyl]-2-ethoxypropionic acid,
3-[4-(2-{N-(2,4-difluorophenoxycarbonyl)-N-[3-(4-fluo-rophenoxy)propyl]amino}ethoxy)phenyl]-2-ethoxypropi-onic acid,
3-[4-(2-{N-[3-(3,5-dichlorophenoxy)propyl]-N-(2,4-difluo-rophenoxycarbonyl)amino}ethoxy)phenyl]-2-ethoxypro-pionic acid,
3-[4-(2-{N-(2,4-difluorophenoxycarbonyl)-N-[4-(4-fluo-rophenoxy)butyl]amino}ethoxy)phenyl]-2-ethoxypropi-onic acid,
3-[4-(2-{N-[4-(3,5-dichlorophenoxy)butyl]-N-(2,4-difluo-rophenoxycarbonyl)amino}ethoxy)phenyl]-2-ethoxypro-pionic acid,
3-[4-(2-{N-(2,4-difluorophenoxycarbonyl)-N-[2-(4-fluo-robenzyloxy)ethyl]amino}ethoxy)phenyl]-2-ethoxypro-pionic acid,
3-[4-(2-{N-[2-(3,5-dichlorobenzyloxy)ethyl]-N-(2,4-difluo-rophenoxycarbonyl)amino}ethoxy)phenyl]-2-ethoxypro-pionic acid,
3-[4-(2-{N-(2,4-difluorophenoxycarbonyl)-N-[3-(4-fluo-robenzyloxy)propyl]amino}ethoxy)phenyl]-2-ethoxypro-pionic acid,
3-[4-(2-{N-[3-(3,5-dichlorobenzyloxy)propyl]-N-(2,4-dif-luorophenoxycarbonyl)amino}ethoxy)phenyl]-2-ethox-ypropionic acid,
3-[4-(2-{N-(2,4-difluorophenoxycarbonyl)-N-[4-(4-fluo-robenzyloxy)butyl]amino}ethoxy)phenyl]-2-ethoxypro-pionic acid,
3-[4-(2-{N-[4-(3,5-dichlorobenzyloxy)butyl]-N-(2,4-dif-luorophenoxycarbonyl)amino}ethoxy)phenyl]-2-ethox-ypropionic acid,
3-[4-(2-{N-(2,4-difluorophenoxycarbonyl)-N-[3-(4-fluo-rophenyl)propyl]amino}ethoxy)phenyl]-2-ethoxypropi-onic acid,
3-[4-(2-{N-[3-(3,5-dichlorophenyl)propyl]-N-(2,4-difluo-rophenoxycarbonyl)amino}ethoxy)phenyl]-2-ethoxypro-pionic acid,
3-(4-{2-[N-(3,4-difluorophenoxycarbonyl)-N-pentylamino]ethoxy}phenyl)-2-ethoxypropionic acid,
3-(4-{2-[N-(3,4-difluorophenoxycarbonyl)-N-hexylamino]ethoxy}phenyl)-2-ethoxypropionic acid,
3-(4-{2-[N-(3,4-difluorophenoxycarbonyl)-N-heptylamino]ethoxy}phenyl)-2-ethoxypropionic acid,
3-(4-{2-[N-(3,4-difluorophenoxycarbonyl)-N-octylamino]ethoxy}phenyl)-2-ethoxypropionic acid,
3-(4-{2-[N-(3,4-difluorophenoxycarbonyl)-N-isobuty-lamino]ethoxy}phenyl)-2-ethoxypropionic acid,
3-(4-{2-[N-(3,4-difluorophenoxycarbonyl)-N-(3-methylbu-tyl)amino]ethoxy}phenyl)-2-ethoxypropionic acid,
3-(4-{2-[N-(3,4-difluorophenoxycarbonyl)-N-(4-methyl-pentyl)amino]ethoxy}phenyl)-2-ethoxypropionic acid,
3-(4-{2-[N-(3,4-difluorophenoxycarbonyl)-N-(2-propyl-pentyl)amino]ethoxy}phenyl)-2-ethoxypropionic acid,
3-(4-{2-[N-(3,4-difluorophenoxycarbonyl)-N-(3,3-dimeth-ylbutyl)amino]ethoxy}phenyl)-2-ethoxypropionic acid,
3-(4-{2-[N-(3,4-difluorophenoxycarbonyl)-N-(2-ethylbu-tyl)amino]ethoxy}phenyl)-2-ethoxypropionic acid,
3-(4-{2-[N-cyclohexylmethyl-N-(3,4-difluorophenoxycar-bonyl)amino]ethoxy}phenyl)-2-ethoxypropionic acid,
3-(4-{2-[N-(4-cyclohexylbutyl)-N-(3,4-difluorophenoxy-carbonyl)amino]ethoxy}phenyl)- 2-ethoxypropionic acid, 3-(4-{2-[N-cyclopropylmethyl-N-(3,4-difluorophenoxycarbonyl)amino]ethoxy}phenyl)-2-ethoxypropionic acid,
3-(4-{2-[N-cyclobutylmethyl-N-(3,4-difluorophenoxycarbonyl)amino]ethoxy}phenyl)-2-ethoxypropionic acid,
3-(4-{2-[N-cyclopentylmethyl-N-(3,4-difluorophenoxycarbonyl)amino]ethoxy}phenyl)-2-ethoxypropionic acid,
3-(4-{2-[N-(2-cyclopentylethyl)-N-(3,4-difluorophenoxycarbonyl)amino]ethoxy}phenyl)-2-ethoxypropionic acid,
3-(4-{2-[N-(3-cyclohexylpropyl)-N-(3,4-difluorophenoxycarbonyl)amino]ethoxy}phenyl)-2-ethoxypropionic acid,
3-(4-{2-[N-(3,4-difluorophenoxycarbonyl)-N-(3-phenylpropyl)amino]ethoxy}phenyl)-2-ethoxypropionic acid,
3-(4-{2-[N-(3,4-difluorophenoxycarbonyl)-N-(4-phenylbutyl)amino]ethoxy}phenyl)-2-ethoxypropionic acid,
3-(4-{2-[N-(2-butoxyethyl)-N-(3,4-difluorophenoxycarbonyl)amino]ethoxy}phenyl)-2-ethoxypropionic acid,
3-(4-{2-[N-(3,4-difluorophenoxycarbonyl)-N-(2-pentyloxyethyl)amino]ethoxy}phenyl)-2-ethoxypropionic acid,
3-(4-{2-[N-(3,4-difluorophenoxycarbonyl)-N-(3-propoxypropyl)amino]ethoxy}phenyl)-2-ethoxypropionic acid,
3-(4-{2-[N-(2-butylthioethyl)-N-(3,4-difluorophenoxycarbonyl)amino]ethoxy}phenyl)-2-ethoxypropionic acid,
3-(4-{2-[N-(3,4-difluorophenoxycarbonyl)-N-(2-pentylthioethyl)amino]ethoxy}phenyl)-2-ethoxypropionic acid,
3-(4-{2-[N-(3,4-difluorophenoxycarbonyl)-N-(3-propylthiopropyl)amino]ethoxy}phenyl)-2-ethoxypropionic acid,
3-(4-{2-[N-(3,4-difluorophenoxycarbonyl)-N-(3-phenoxypropyl)amino]ethoxy}phenyl)-2-ethoxypropionic acid,
3-(4-{2-[N-(3,4-difluorophenoxycarbonyl)-N-(4-phenoxybutyl)amino]ethoxy}phenyl)-2-ethoxypropionic acid,
3-(4-{2-[N-(3-benzyloxypropyl)-N-(3,4-difluorophenoxycarbonyl)amino]ethoxy}phenyl)-2-ethoxypropionic acid,
3-(4-{2-[N-(3,4-difluorophenoxycarbonyl)-N-(3-phenylthiopropyl)amino]ethoxy}phenyl)-2-ethoxypropionic acid,
3-(4-{2-[N-(3,4-difluorophenoxycarbonyl)-N-(4-phenylthiobutyl)amino]ethoxy}phenyl)-2-ethoxypropionic acid,
3-(4-{2-[N-(3-benzylthiopropyl)-N-(3,4-difluorophenoxycarbonyl)amino]ethoxy}phenyl)-2-ethoxypropionic acid,
3-(4-{2-[N-(3,4-difluorophenoxycarbonyl)-N-(7,7,7-trifluoroheptyl)amino]ethoxy}phenyl)-2-ethoxypropionic acid,
3-(4-{2-[N-(6,6-difluoroheptyl)-N-(3,4-difluorophenoxycarbonyl)amino]ethoxy}phenyl)-2-ethoxypropionic acid,
3-(4-{2-[N-(3,4-difluorophenoxycarbonyl)-N-(6,6,6-trifluorohexyl)amino]ethoxy}phenyl)-2-ethoxypropionic acid,
3-(4-{2-[N-(5,5-difluorohexyl)-N-(3,4-difluorophenoxycarbonyl)amino]ethoxy}phenyl)-2-ethoxypropionic acid,
3-(4-{2-[N-(3,4-difluorophenoxycarbonyl)-N-(5,5,6,6,7,7,7-heptafluoroheptyl)amino]ethoxy}phenyl)-2-ethoxypropionic acid,
3-(4-{2-[N-(3,4-difluorophenoxycarbonyl)-N-(2,2,3,3,4,4,5,5,6,6,7,7,7-tridecafluoroheptyl)amino]ethoxy}phenyl)-2-ethoxypropionic acid,
3-(4-{2-[N-(3,4-difluorophenoxycarbonyl)-N-(5,5,6,6,6-pentafluorohexyl)amino]ethoxy}phenyl)-2-ethoxypropionic acid,
3-(4-{2-[N-(3,4-difluorophenoxycarbonyl)-N-(2,2,3,3,4,4,5,5,6,6,6-undecafluorohexyl)amino]ethoxy}phenyl)-2-ethoxypropionic acid,
3-[4-(2-{N-(3,4-difluorophenoxycarbonyl)-N-[2-(2,2-difluoropropoxy)ethyl]amino}ethoxy)phenyl]-2-ethoxypropionic acid,
3-[4-(2-{N-(3,4-difluorophenoxycarbonyl)-N-[2-(1,1,2,2,3,3,3-heptafluoropropoxy)ethyl]amino}ethoxy)phenyl]-2-ethoxypropionic acid,
3-[4-(2-{N-(3,4-difluorophenoxycarbonyl)-N-[2-(4,4,4-trifluorobutoxy)ethyl]amino}ethoxy)phenyl]-2-ethoxypropionic acid,
3-[4-(2-{N-[2-(3,3-difluorobutoxy)ethyl]-N-(3,4-difluorophenoxycarbonyl)amino}ethoxy)phenyl]-2-ethoxypropionic acid,
3-[4-(2-{N-[2-(2,2-difluorobutoxy)ethyl]-N-(3,4-difluorophenoxycarbonyl)amino}ethoxy)phenyl]-2-ethoxypropionic acid,
3-[4-(2-{N-(3,4-difluorophenoxycarbonyl)-N-[2-(1,1,2,2,3,3,4,4,4-nonafluorobutoxy)ethyl]amino}ethoxy)phenyl]-2-ethoxypropionic acid,
3-[4-(2-{N-(3,4-difluorophenoxycarbonyl)-N-[3-(2,2,2-trifluoroethoxy)propyl]amino}ethoxy)phenyl]-2-ethoxypropionic acid,
3-[4-(2-{N-(3,4-difluorophenoxycarbonyl)-N-[3-(1,1,2,2,2-pentafluoroethoxy)propyl]amino}ethoxy)phenyl]-2-ethoxypropionic acid,
3-[4-(2-{N-(3,4-difluorophenoxycarbonyl)-N-[3-(4-fluorophenoxy)propyl]amino}ethoxy)phenyl]-2-ethoxypropionic acid,
3-[4-(2-{N-[3-(3,5-dichlorophenoxy)propyl]-N-(3,4-difluorophenoxycarbonyl)amino}ethoxy)phenyl]-2-ethoxypropionic acid,
3-[4-(2-{N-(3,4-difluorophenoxycarbonyl)-N-[4-(4-fluorophenoxy)butyl]amino}ethoxy)phenyl]-2-ethoxypropionic acid,
3-[4-(2-{N-[4-(3,5-dichlorophenoxy)butyl]-N-(3,4-difluorophenoxycarbonyl)amino}ethoxy)phenyl]-2-ethoxypropionic acid,
3-[4-(2-{N-(3,4-difluorophenoxycarbonyl)-N-[2-(4-fluorobenzyloxy)ethyl]amino}ethoxy)phenyl]-2-ethoxypropionic acid,
3-[4-(2-{N-[2-(3,5-dichlorobenzyloxy)ethyl]-N-(3,4-difluorophenoxycarbonyl)amino}ethoxy)phenyl]-2-ethoxypropionic acid,
3-[4-(2-{N-(3,4-difluorophenoxycarbonyl)-N-[3-(4-fluorobenzyloxy)propyl]amino}ethoxy)phenyl]-2-ethoxypropionic acid,
3-[4-(2-{N-[3-(3,5-dichlorobenzyloxy)propyl]-N-(3,4-difluorophenoxycarbonyl)amino}ethoxy)phenyl]-2-ethoxypropionic acid,
3-[4-(2-{N-(3,4-difluorophenoxycarbonyl)-N-[4-(4-fluorobenzyloxy)butyl]amino}ethoxy)phenyl]-2-ethoxypropionic acid,
3-[4-(2-{N-[4-(3,5-dichlorobenzyloxy)butyl]-N-(3,4-difluorophenoxycarbonyl)amino}ethoxy)phenyl]-2-ethoxypropionic acid,
3-[4-(2-{N-(3,4-difluorophenoxycarbonyl)-N-[3-(4-fluorophenyl)propyl]amino}ethoxy)phenyl]-2-ethoxypropionic acid,
3-[4-(2-{N-[3-(3,5-dichlorophenyl)propyl]-N-(3,4-difluorophenoxycarbonyl)amino}ethoxy)phenyl]-2-ethoxypropionic acid,
2-ethoxy-3-(4-{2-[N-(2-fluorophenoxycarbonyl)-N-pentylamino]ethoxy}phenyl)propionic acid,
2-ethoxy-3-(4-{2-[N-(2-fluorophenoxycarbonyl)-N-hexylamino]ethoxy}phenyl)propionic acid,
2-ethoxy-3-(4-{2-[N-(2-fluorophenoxycarbonyl)-N-heptylamino]ethoxy}phenyl)propionic acid,
2-ethoxy-3-(4-{2-[N-(2-fluorophenoxycarbonyl)-N-octylamino]ethoxy}phenyl)propionic acid,
2-ethoxy-3-(4-{2-[N-(2-fluorophenoxycarbonyl)-N-isobutylamino]ethoxy}phenyl)propionic acid,
2-ethoxy-3-(4-{2-[N-(2-fluorophenoxycarbonyl)-N-(3-methylbutyl)amino]ethoxy}phenyl)propionic acid, 2-ethoxy-3-(4-{2-[N-(2-fluorophenoxycarbonyl)-N-(4-methylpentyl)amino]ethoxy}phenyl)propionic acid,
2-ethoxy-3-(4-{2-[N-(2-fluorophenoxycarbonyl)-N-(2-propylpentyl)amino]ethoxy}phenyl)propionic acid,
3-(4-{2-[N-(3,3-dimethylbutyl)-N-(2-fluorophenoxycarbonyl)amino]ethoxy}phenyl)-2-ethoxypropionic acid,
2-ethoxy-3-(4-{2-[N-(2-ethylbutyl)-N-(2-fluorophenoxycarbonyl)amino]ethoxy}phenyl)propionic acid,
3-(4-{2-[N-cyclohexylmethyl-N-(2-fluorophenoxycarbonyl)amino]ethoxy}phenyl)-2-ethoxypropionic acid,
3-(4-{2-[N-(4-cyclohexylbutyl)-N-(2-fluorophenoxycarbonyl)amino]ethoxy}phenyl)-2-ethoxypropionic acid,
3-(4-{2-[N-cyclopropylmethyl-N-(2-fluorophenoxycarbonyl)amino]ethoxy}phenyl)-2-ethoxypropionic acid,
3-(4-{2-[N-cyclobutylmethyl-N-(2-fluorophenoxycarbonyl)amino]ethoxy}phenyl)-2-ethoxypropionic acid,
3-(4-{2-[N-cyclopentylmethyl-N-(2-fluorophenoxycarbonyl)amino]ethoxy}phenyl)-2-ethoxypropionic acid,
3-(4-{2-[N-(2-cyclopentylethyl)-N-(2-fluorophenoxycarbonyl)amino]ethoxy}phenyl)-2-ethoxypropionic acid,
3-(4-{2-[N-(3-cyclohexylpropyl)-N-(2-fluorophenoxycarbonyl)amino]ethoxy}phenyl)-2-ethoxypropionic acid,
2-ethoxy-3-(4-{2-[N-(2-fluorophenoxycarbonyl)-N-(3-phenylpropyl)amino]ethoxy}phenyl)propionic acid,
2-ethoxy-3-(4-{2-[N-(2-fluorophenoxycarbonyl)-N-(4-phenylbutyl)amino]ethoxy}phenyl)propionic acid,
3-(4-{2-[N-(2-butoxyethyl)-N-(2-fluorophenoxycarbonyl)amino]ethoxy}phenyl)-2-ethoxypropionic acid,
2-ethoxy-3-(4-{2-[N-(2-fluorophenoxycarbonyl)-N-(2-pentyloxyethyl)amino]ethoxy}phenyl)propionic acid,
2-ethoxy-3-(4-{2-[N-(2-fluorophenoxycarbonyl)-N-(3-propoxypropyl)amino]ethoxy}phenyl)propionic acid,
3-(4-{2-[N-(2-butylthioethyl)-N-(2-fluorophenoxycarbonyl)amino]ethoxy}phenyl)-2-ethoxypropionic acid,
2-ethoxy-3-(4-{2-[N-(2-fluorophenoxycarbonyl)-N-(2-pentylthioethyl)amino]ethoxy}phenyl)propionic acid,
2-ethoxy-3-(4-{2-[N-(2-fluorophenoxycarbonyl)-N-(3-propylthiopropyl)amino]ethoxy}phenyl)propionic acid,
2-ethoxy-3-(4-{2-[N-(2-fluorophenoxycarbonyl)-N-(3-phenoxypropyl)amino]ethoxy}phenyl)propionic acid,
2-ethoxy-3-(4-{2-[N-(2-fluorophenoxycarbonyl)-N-(4-phenoxybutyl)amino]ethoxy}phenyl)propionic acid,
3-(4-{2-[N-(3-benzyloxypropyl)-N-(2-fluorophenoxycarbonyl)amino]ethoxy}phenyl)-2-ethoxypropionic acid,
2-ethoxy-3-(4-{2-[N-(2-fluorophenoxycarbonyl)-N-(3-phenylthiopropyl)amino]ethoxy}phenyl)propionic acid,
2-ethoxy-3-(4-{2-[N-(2-fluorophenoxycarbonyl)-N-(4-phenylthiobutyl)amino]ethoxy}phenyl)propionic acid,
3-(4-{2-[N-(3-benzylthiopropyl)-N-(2-fluorophenoxycarbonyl)amino]ethoxy}phenyl)-2-ethoxypropionic acid,
2-ethoxy-3-(4-{2-[N-(2-fluorophenoxycarbonyl)-N-(7,7,7-trifluoroheptyl)amino]ethoxy}phenyl)propionic acid,
3-(4-{2-[N-(6,6-difluoroheptyl)-N-(2-fluorophenoxycarbonyl)amino]ethoxy}phenyl)-2-ethoxypropionic acid,
2-ethoxy-3-(4-{2-[N-(2-fluorophenoxycarbonyl)-N-(6,6,6-trifluorohexyl)amino]ethoxy}phenyl)propionic acid,
3-(4-{2-[N-(5,5-difluorohexyl)-N-(2-fluorophenoxycarbonyl)amino]ethoxy}phenyl)-2-ethoxypropionic acid,
2-ethoxy-3-(4-{2-[N-(2-fluorophenoxycarbonyl)-N-(5,5,6,6,7,7,7-heptafluoroheptyl)amino]ethoxy}phenyl)propionic acid,
2-ethoxy-3-(4-{2-[N-(2-fluorophenoxycarbonyl)-N-(2,2,3,3,4,4,5,5,6,6,7,7,7-tridecafluoroheptyl)amino]ethoxy}phenyl)propionic acid,
2-ethoxy-3-(4-{2-[N-(2-fluorophenoxycarbonyl)-N-(5,5,6,6,6-pentafluorohexyl)amino]ethoxy}phenyl)propionic acid,
2-ethoxy-3-(4-{2-[N-(2-fluorophenoxycarbonyl)-N-(2,2,3,3,4,4,5,5,6,6,6-undecafluorohexyl)amino]ethoxy}phenyl)propionic acid,
3-[4-(2-{N-[2-(2,2-difluoropropoxy)ethyl]-N-(2-fluorophenoxycarbonyl)amino}ethoxy)phenyl]-2-ethoxypropionic acid,
2-ethoxy-3-[4-(2-{N-(2-fluorophenoxycarbonyl)-N-[2-(1,1,2,2,3,3,3-heptafluoropropoxy)ethyl]amino}ethoxy)phenyl]propionic acid,
2-ethoxy-3-[4-(2-{N-(2-fluorophenoxycarbonyl)-N-[2-(4,4,4-trifluorobutoxy)ethyl]amino}ethoxy)phenyl]propionic acid,
3-[4-(2-{N-[2-(3,3-difluorobutoxy)ethyl]-N-(2-fluorophenoxycarbonyl)amino}ethoxy)phenyl]-2-ethoxypropionic acid,
3-[4-(2-{N-[2-(2,2-difluorobutoxy)ethyl]-N-(2-fluorophenoxycarbonyl)amino}ethoxy)phenyl]-2-ethoxypropionic acid,
2-ethoxy-3-[4-(2-{N-(2-fluorophenoxycarbonyl)-N-[2-(1,1,2,2,3,3,4,4,4-nonafluorobutoxy)ethyl]amino}ethoxy)phenyl]propionic acid,
2-ethoxy-3-[4-(2-{N-(2-fluorophenoxycarbonyl)-N-[3-(2,2,2-trifluoroethoxy)propyl]amino}ethoxy)phenyl]propionic acid,
2-ethoxy-3-[4-(2-{N-(2-fluorophenoxycarbonyl)-N-[3-(1,1,2,2,2-pentafluoroethoxy)propyl]amino}ethoxy)phenyl]propionic acid,
2-ethoxy-3-[4-(2-{N-[3-(4-fluorophenoxy)propyl]-N-(2-fluorophenoxycarbonyl)amino}ethoxy)phenyl]propionic acid,
3-[4-(2-{N-[3-(3,5-dichlorophenoxy)propyl]-N-(2-fluorophenoxycarbonyl)amino}ethoxy)phenyl]-2-ethoxypropionic acid,
2-ethoxy-3-[4-(2-{N-[4-(4-fluorophenoxy)butyl]-N-(2-fluorophenoxycarbonyl)amino}ethoxy)phenyl]propionic acid,
3-[4-(2-{N-[4-(3,5-dichlorophenoxy)butyl]-N-(2-fluorophenoxycarbonyl)amino}ethoxy)phenyl]-2-ethoxypropionic acid,
2-ethoxy-3-[4-(2-{N-[2-(4-fluorobenzyloxy)ethyl]-N-(2-fluorophenoxycarbonyl)amino}ethoxy)phenyl]propionic acid,
3-[4-(2-{N-[2-(3,5-dichlorobenzyloxy)ethyl]-N-(2-fluorophenoxycarbonyl)amino}ethoxy)phenyl]-2-ethoxypropionic acid,
2-ethoxy-3-[4-(2-{N-[3-(4-fluorobenzyloxy)propyl]-N-(2-fluorophenoxycarbonyl)amino}ethoxy)phenyl]propionic acid,
3-[4-(2-{N-[3-(3,5-dichlorobenzyloxy)propyl]-N-(2-fluorophenoxycarbonyl)amino}ethoxy)phenyl]-2-ethoxypropionic acid,
2-ethoxy-3-[4-(2-{N-[4-(4-fluorobenzyloxy)butyl]-N-(2-fluorophenoxycarbonyl)amino}ethoxy)phenyl]propionic acid,
3-[4-(2-{N-[4-(3,5-dichlorobenzyloxy)butyl]-N-(2-fluorophenoxycarbonyl)amino}ethoxy)phenyl]-2-ethoxypropionic acid,
2-ethoxy-3-[4-(2-{N-(2-fluorophenoxycarbonyl)-N-[3-(4-fluorophenyl)propyl]amino}ethoxy)phenyl]propionic acid,
3-[4-(2-{N-[3-(3,5-dichlorophenyl)propyl]-N-(2-fluorophenoxycarbonyl)amino}ethoxy)phenyl]-2-ethoxypropionic acid,
2-ethoxy-3-(4-{2-[N-(3-fluorophenoxycarbonyl)-N-pentylamino]ethoxy}phenyl)propionic acid,
2-ethoxy-3-(4-{2-[N-(3-fluorophenoxycarbonyl)-N-hexylamino]ethoxy}phenyl)propionic acid, 2-ethoxy-3-(4-{2-[N-(3-fluorophenoxycarbonyl)-N-heptylamino]ethoxy}phenyl)propionic acid,
2-ethoxy-3-(4-{2-[N-(3-fluorophenoxycarbonyl)-N-octylamino]ethoxy}phenyl)propionic acid,
2-ethoxy-3-(4-{2-[N-(3-fluorophenoxycarbonyl)-N-isobutylamino]ethoxy}phenyl)propionic acid,
2-ethoxy-3-(4-{2-[N-(3-fluorophenoxycarbonyl)-N-(3-methylbutyl)amino]ethoxy}phenyl)propionic acid,
2-ethoxy-3-(4-{2-[N-(3-fluorophenoxycarbonyl)-N-(4-methylpentyl)amino]ethoxy}phenyl)propionic acid,
2-ethoxy-3-(4-{2-[N-(3-fluorophenoxycarbonyl)-N-(2-propylpentyl)amino]ethoxy}phenyl)propionic acid,
3-(4-{2-[N-(3,3-dimethylbutyl)-N-(3-fluorophenoxycarbonyl)amino]ethoxy}phenyl)-2-ethoxypropionic acid,
2-ethoxy-3-(4-{2-[N-(2-ethylbutyl)-N-(3-fluorophenoxycarbonyl)amino]ethoxy}phenyl)propionic acid,
3-(4-{2-[N-cyclohexylmethyl-N-(3-fluorophenoxycarbonyl)amino]ethoxy}phenyl)-2-ethoxypropionic acid,
3-(4-{2-[N-(4-cyclohexylbutyl)-N-(3-fluorophenoxycarbonyl)amino]ethoxy}phenyl)-2-ethoxypropionic acid,
3-(4-{2-[N-cyclopropylmethyl-N-(3-fluorophenoxycarbonyl)amino]ethoxy}phenyl)-2-ethoxypropionic acid,
3-(4-{2-[N-cyclobutylmethyl-N-(3-fluorophenoxycarbonyl)amino]ethoxy}phenyl)-2-ethoxypropionic acid,
3-(4-{2-[N-cyclopentylmethyl-N-(3-fluorophenoxycarbonyl)amino]ethoxy}phenyl)-2-ethoxypropionic acid,
3-(4-{2-[N-(2-cyclopentylethyl)-N-(3-fluorophenoxycarbonyl)amino]ethoxy}phenyl)-2-ethoxypropionic acid,
3-(4-{2-[N-(3-cyclohexylpropyl)-N-(3-fluorophenoxycarbonyl)amino]ethoxy}phenyl)-2-ethoxypropionic acid,
2-ethoxy-3-(4-{2-[N-(3-fluorophenoxycarbonyl)-N-(3-phenylpropyl)amino]ethoxy}phenyl)propionic acid,
2-ethoxy-3-(4-{2-[N-(3-fluorophenoxycarbonyl)-N-(4-phenylbutyl)amino]ethoxy}phenyl)propionic acid,
3-(4-{2-[N-(2-butoxyethyl)-N-(3-fluorophenoxycarbonyl)amino]ethoxy}phenyl)-2-ethoxypropionic acid,
2-ethoxy-3-(4-{2-[N-(3-fluorophenoxycarbonyl)-N-(2-pentyloxyethyl)amino]ethoxy}phenyl)propionic acid,
2-ethoxy-3-(4-{2-[N-(3-fluorophenoxycarbonyl)-N-(3-propoxypropyl)amino]ethoxy}phenyl)propionic acid,
3-(4-{2-[N-(2-butylthioethyl)-N-(3-fluorophenoxycarbonyl)amino]ethoxy}phenyl)-2-ethoxypropionic acid,
2-ethoxy-3-(4-{2-[N-(3-fluorophenoxycarbonyl)-N-(2-pentylthioethyl)amino]ethoxy}phenyl)propionic acid,
2-ethoxy-3-(4-{2-[N-(3-fluorophenoxycarbonyl)-N-(3-propylthiopropyl)amino]ethoxy}phenyl)propionic acid,
2-ethoxy-3-(4-{2-[N-(3-fluorophenoxycarbonyl)-N-(3-phenoxypropyl)amino]ethoxy}phenyl)propionic acid,
2-ethoxy-3-(4-{2-[N-(3-fluorophenoxycarbonyl)-N-(4-phenoxybutyl)amino]ethoxy}phenyl)propionic acid,
3-(4-{2-[N-(3-benzyloxypropyl)-N-(3-fluorophenoxycarbonyl)amino]ethoxy}phenyl)-2-ethoxypropionic acid,
2-ethoxy-3-(4-{2-[N-(3-fluorophenoxycarbonyl)-N-(3-phenylthiopropyl)amino]ethoxy}phenyl)propionic acid,
2-ethoxy-3-(4-{2-[N-(3-fluorophenoxycarbonyl)-N-(4-phenylthiobutyl)amino]ethoxy}phenyl)propionic acid,
3-(4-{2-[N-(3-benzylthiopropyl)-N-(3-fluorophenoxycarbonyl)amino]ethoxy}phenyl)-2-ethoxypropionic acid,
2-ethoxy-3-(4-{2-[N-(3-fluorophenoxycarbonyl)-N-(7,7,7-trifluoroheptyl)amino]ethoxy}phenyl)propionic acid,
3-(4-{2-[N-(6,6-difluoroheptyl)-N-(3-fluorophenoxycarbonyl)amino]ethoxy}phenyl)-2-ethoxypropionic acid,
2-ethoxy-3-(4-{2-[N-(3-fluorophenoxycarbonyl)-N-(6,6,6-trifluorohexyl)amino]ethoxy}phenyl)propionic acid,
3-(4-{2-[N-(5,5-difluorohexyl)-N-(3-fluorophenoxycarbonyl)amino]ethoxy}phenyl)-2-ethoxypropionic acid,
2-ethoxy-3-(4-{2-[N-(3-fluorophenoxycarbonyl)-N-(5,5,6,6,7,7,7-heptafluoroheptyl)amino]ethoxy}phenyl)propionic acid,
2-ethoxy-3-(4-{2-[N-(3-fluorophenoxycarbonyl)-N-(2,2,3,3,4,4,5,5,6,6,7,7,7-tridecafluoroheptyl)amino]ethoxy}phenyl)propionic acid,
2-ethoxy-3-(4-{2-[N-(3-fluorophenoxycarbonyl)-N-(5,5,6,6,6-pentafluorohexyl)amino]ethoxy}phenyl)propionic acid,
2-ethoxy-3-(4-{2-[N-(3-fluorophenoxycarbonyl)-N-(2,2,3,3,4,4,5,5,6,6,6-undecafluorohexyl)amino]ethoxy}phenyl)propionic acid,
3-[4-(2-{N-[2-(2,2-difluoropropoxy)ethyl]-N-(3-fluorophenoxycarbonyl)amino}ethoxy)phenyl]-2-ethoxypropionic acid,
2-ethoxy-3-[4-(2-{N-(3-fluorophenoxycarbonyl)-N-[2-(1,1,2,2,3,3,3-heptafluoropropoxy)ethyl]amino}ethoxy)phenyl]propionic acid,
2-ethoxy-3-[4-(2-{N-(3-fluorophenoxycarbonyl)-N-[2-(4,4,4-trifluorobutoxy)ethyl]amino}ethoxy)phenyl]propionic acid,
3-[4-(2-{N-[2-(3,3-difluorobutoxy)ethyl]-N-(3-fluorophenoxycarbonyl)amino}ethoxy)phenyl]-2-ethoxypropionic acid,
3-[4-(2-{N-[2-(2,2-difluorobutoxy)ethyl]-N-(3-fluorophenoxycarbonyl)amino}ethoxy)phenyl]-2-ethoxypropionic acid,
2-ethoxy-3-[4-(2-{N-(3-fluorophenoxycarbonyl)-N-[2-(1,1,2,2,3,3,4,4,4-nonafluorobutoxy)ethyl]amino}ethoxy)phenyl]propionic acid,
2-ethoxy-3-[4-(2-{N-(3-fluorophenoxycarbonyl)-N-[3-(2,2,2-trifluoroethoxy)propyl]amino}ethoxy)phenyl]propionic acid,
2-ethoxy-3-[4-(2-{N-(3-fluorophenoxycarbonyl)-N-[3-(1,1,2,2,2-pentafluoroethoxy)propyl]amino}ethoxy)phenyl]propionic acid,
2-ethoxy-3-[4-(2-{N-[3-(4-fluorophenoxy)propyl]-N-(3-fluorophenoxycarbonyl)amino}ethoxy)phenyl]propionic acid,
3-[4-(2-{N-[3-(3,5-dichlorophenoxy)propyl]-N-(3-fluorophenoxycarbonyl)amino}ethoxy)phenyl]-2-ethoxypropionic acid,
2-ethoxy-3-[4-(2-{N-[4-(4-fluorophenoxy)butyl]-N-(3-fluorophenoxycarbonyl)amino}ethoxy)phenyl]propionic acid,
3-[4-(2-{N-[4-(3,5-dichlorophenoxy)butyl]-N-(3-fluorophenoxycarbonyl)amino}ethoxy)phenyl]-2-ethoxypropionic acid,
2-ethoxy-3-[4-(2-{N-[2-(4-fluorobenzyloxy)ethyl]-N-(3-fluorophenoxycarbonyl)amino}ethoxy)phenyl]propionic acid,
3-[4-(2-{N-[2-(3,5-dichlorobenzyloxy)ethyl]-N-(3-fluorophenoxycarbonyl)amino}ethoxy)phenyl]-2-ethoxypropionic acid,
2-ethoxy-3-[4-(2-{N-[3-(4-fluorobenzyloxy)propyl]-N-(3-fluorophenoxycarbonyl)amino}ethoxy)phenyl]propionic acid,
3-[4-(2-{N-[3-(3,5-dichlorobenzyloxy)propyl]-N-(3-fluorophenoxycarbonyl)amino}ethoxy)phenyl]-2-ethoxypropionic acid,
2-ethoxy-3-[4-(2-{N-[4-(4-fluorobenzyloxy)butyl]-N-(3-fluorophenoxycarbonyl)amino}ethoxy)phenyl]propionic acid,
3-[4-(2-{N-[4-(3,5-dichlorobenzyloxy)butyl]-N-(3-fluorophenoxycarbonyl)amino}ethoxy)phenyl]-2-ethoxypropionic acid, 2-ethoxy-3-[4-(2-{N-(3-fluorophenoxycarbonyl)-N-[3-(4-fluorophenyl)propyl]amino}ethoxy)phenyl]propionic acid,
3-[4-(2-{N-[3-(3,5-dichlorophenyl)propyl]-N-(3-fluorophenoxycarbonyl)amino}ethoxy)phenyl]-2-ethoxypropionic acid,
2-ethoxy-3-(4-{2-[N-(4-fluorophenoxycarbonyl)-N-pentylamino]ethoxy}phenyl)propionic acid,
2-ethoxy-3-(4-{2-[N-(4-fluorophenoxycarbonyl)-N-hexylamino]ethoxy}phenyl)propionic acid,
2-ethoxy-3-(4-{2-[N-(4-fluorophenoxycarbonyl)-N-heptylamino]ethoxy}phenyl)propionic acid,
2-ethoxy-3-(4-{2-[N-(4-fluorophenoxycarbonyl)-N-octylamino]ethoxy}phenyl)propionic acid,
2-ethoxy-3-(4-{2-[N-(4-fluorophenoxycarbonyl)-N-isobutylamino]ethoxy}phenyl)propionic acid,
2-ethoxy-3-(4-{2-[N-(4-fluorophenoxycarbonyl)-N-(3-methylbutyl)amino]ethoxy}phenyl)propionic acid,
2-ethoxy-3-(4-{2-[N-(4-fluorophenoxycarbonyl)-N-(4-methylpentyl)amino]ethoxy}phenyl)propionic acid,
2-ethoxy-3-(4-{2-[N-(4-fluorophenoxycarbonyl)-N-(2-propylpentyl)amino]ethoxy}phenyl)propionic acid,
3-(4-{2-[N-(3,3-dimethylbutyl)-N-(4-fluorophenoxycarbonyl)amino]ethoxy}phenyl)-2-ethoxypropionic acid,
2-ethoxy-3-(4-{2-[N-(2-ethylbutyl)-N-(4-fluorophenoxycarbonyl)amino]ethoxy}phenyl)propionic acid,
3-(4-{2-[N-cyclohexylmethyl-N-(4-fluorophenoxycarbonyl)amino]ethoxy}phenyl)-2-ethoxypropionic acid,
3-(4-{2-[N-(4-cyclohexylbutyl)-N-(4-fluorophenoxycarbonyl)amino]ethoxy}phenyl)-2-ethoxypropionic acid,
3-(4-{2-[N-cyclopropylmethyl-N-(4-fluorophenoxycarbonyl)amino]ethoxy}phenyl)-2-ethoxypropionic acid,
3-(4-{2-[N-cyclobutylmethyl-N-(4-fluorophenoxycarbonyl)amino]ethoxy}phenyl)-2-ethoxypropionic acid,
3-(4-{2-[N-cyclopentylmethyl-N-(4-fluorophenoxycarbonyl)amino]ethoxy}phenyl)-2-ethoxypropionic acid,
3-(4-{2-[N-(2-cyclopentylethyl)-N-(4-fluorophenoxycarbonyl)amino]ethoxy}phenyl)-2-ethoxypropionic acid,
3-(4-{2-[N-(3-cyclohexylpropyl)-N-(4-fluorophenoxycarbonyl)amino]ethoxy}phenyl)-2-ethoxypropionic acid,
2-ethoxy-3-(4-{2-[N-(4-fluorophenoxycarbonyl)-N-(3-phenylpropyl)amino]ethoxy}phenyl)propionic acid,
2-ethoxy-3-(4-{2-[N-(4-fluorophenoxycarbonyl)-N-(4-phenylbutyl)amino]ethoxy}phenyl)propionic acid,
3-(4-{2-[N-(2-butoxyethyl)-N-(4-fluorophenoxycarbonyl)amino]ethoxy}phenyl)-2-ethoxypropionic acid,
2-ethoxy-3-(4-{2-[N-(4-fluorophenoxycarbonyl)-N-(2-pentyloxyethyl)amino]ethoxy}phenyl)propionic acid,
2-ethoxy-3-(4-{2-[N-(4-fluorophenoxycarbonyl)-N-(3-propoxypropyl)amino]ethoxy}phenyl)propionic acid,
3-(4-{2-[N-(2-butylthioethyl)-N-(4-fluorophenoxycarbonyl)amino]ethoxy}phenyl)-2-ethoxypropionic acid,
2-ethoxy-3-(4-{2-[N-(4-fluorophenoxycarbonyl)-N-(2-pentylthioethyl)amino]ethoxy}phenyl)propionic acid,
2-ethoxy-3-(4-{2-[N-(4-fluorophenoxycarbonyl)-N-(3-propylthiopropyl)amino]ethoxy}phenyl)propionic acid,
2-ethoxy-3-(4-{2-[N-(4-fluorophenoxycarbonyl)-N-(3-phenoxypropyl)amino]ethoxyphenyl)propionic acid,
2-ethoxy-3-(4-{2-[N-(4-fluorophenoxycarbonyl)-N-(4-phenoxybutyl)amino]ethoxy}phenyl)propionic acid,
3-(4-{2-[N-(3-benzyloxypropyl)-N-(4-fluorophenoxycarbonyl)amino]ethoxy}phenyl)-2-ethoxypropionic acid,
2-ethoxy-3-(4-{2-[N-(4-fluorophenoxycarbonyl)-N-(3-phenylthiopropyl)amino]ethoxy}phenyl)propionic acid,
2-ethoxy-3-(4-{2-[N-(4-fluorophenoxy carbonyl)-N-(4-phenylthiobutyl)amino]ethoxy}phenyl)propionic acid,
3-(4-{2-[N-(3-benzylthiopropyl)-N-(4-fluorophenoxycarbonyl)amino]ethoxy}phenyl)-2-ethoxypropionic acid,
2-ethoxy-3-(4-{2-[N-(4-fluorophenoxycarbonyl)-N-(7,7,7-trifluoroheptyl)amino]ethoxy}phenyl)propionic acid,
3-(4-{2-[N-(6,6-difluoroheptyl)-N-(4-fluorophenoxycarbonyl)amino]ethoxy}phenyl)-2-ethoxypropionic acid,
2-ethoxy-3-(4-{2-[N-(4-fluorophenoxycarbonyl)-N-(6,6,6-trifluorohexyl)amino]ethoxy}phenyl)propionic acid,
3-(4-{2-[N-(5,5-difluorohexyl)-N-(4-fluorophenoxycarbonyl)amino]ethoxy}phenyl)-2-ethoxypropionic acid,
2-ethoxy-3-(4-{2-[N-(4-fluorophenoxycarbonyl)-N-(5,5,6,6,7,7,7-heptafluoroheptyl)amino]ethoxy}phenyl)propionic acid,
2-ethoxy-3-(4-{2-[N-(4-fluorophenoxycarbonyl)-N-(2,2,3,3,4,4,5,5,6,6,7,7,7-tridecafluoroheptyl)amino]ethoxy}phenyl)propionic acid,
2-ethoxy-3-(4-{2-[N-(4-fluorophenoxycarbonyl)-N-(5,5,6,6,6-pentafluorohexyl)amino]ethoxy)phenyl)propionic acid,
2-ethoxy-3-(4-{2-[N-(4-fluorophenoxycarbonyl)-N-(2,2,3,3,4,4,5,5,6,6,6-undecafluorohexyl)amino]ethoxy}phenyl)propionic acid,
3-[4-(2-{N-[2-(2,2-difluoropropoxy)ethyl]-N-(4-fluorophenoxycarbonyl)amino}ethoxy)phenyl]-2-ethoxypropionic acid,
2-ethoxy-3-[4-(2-(N-(4-fluorophenoxycarbonyl)-N-[2-(1,1,2,2,3,3,3-heptafluoropropoxy)ethyl]amino}ethoxy)phenyl]propionic acid,
2-ethoxy-3-[4-(2-{N-(4-fluorophenoxycarbonyl)-N-[2-(4,4,4-trifluorobutoxy)ethyl]amino}ethoxy)phenyl]propionic acid,
3-[4-(2-{N-[2-(3,3-difluorobutoxy)ethyl]-N-(4-fluorophenoxycarbonyl)amino}ethoxy)phenyl]-2-ethoxypropionic acid,
3-[4-(2-{N-[2-(2,2-difluorobutoxy)ethyl]-N-(4-fluorophenoxycarbonyl)amino}ethoxy)phenyl]-2-ethoxypropionic acid,
2-ethoxy-3-[4-(2-{N-(4-fluorophenoxycarbonyl)-N-[2-(1,1,2,2,3,3,4,4,4-nonafluorobutoxy)ethyl]amino}ethoxy)phenyl]propionic acid,
2-ethoxy-3-[4-(2-{N-(4-fluorophenoxycarbonyl)-N-[3-(2,2,2-trifluoroethoxy)propyl]amino}ethoxy)phenyl]propionic acid,
2-ethoxy-3-[4-(2-{N-(4-fluorophenoxycarbonyl)-N-[3-(1,1,2,2,2-pentafluoroethoxy)propyl]amino}ethoxy)phenyl] propionic acid,
2-ethoxy-3-[4-(2-{N-[3-(4-fluorophenoxy)propyl]-N-(4-fluorophenoxycarbonyl)amino}ethoxy)phenyl]propionic acid,
3-[4-(2-{N-[3-(3,5-dichlorophenoxy)propyl]-N-(4-fluorophenoxycarbonyl)amino}ethoxy)phenyl]-2-ethoxypropionic acid,
2-ethoxy-3-[4-(2-{N-[4-(4-fluorophenoxy)butyl]-N-(4-fluorophenoxycarbonyl)amino}ethoxy)phenyl]propionic acid,
3-[4-(2-{N-[4-(3,5-dichlorophenoxy)butyl]-N-(4-fluorophenoxycarbonyl)amino}ethoxy)phenyl]-2-ethoxypropionic acid,
2-ethoxy-3-[4-(2-{N-[2-(4-fluorobenzyloxy)ethyl]-N-(4-fluorophenoxycarbonyl)amino}ethoxy)phenyl]propionic acid,
3-[4-(2-{N-[2-(3,5-dichlorobenzyloxy)ethyl]-N-(4-fluorophenoxycarbonyl)amino}ethoxy)phenyl]-2-ethoxypropionic acid,
2-ethoxy-3-[4-(2-{N-[3-(4-fluorobenzyloxy)propyl]-N-(4-fluorophenoxycarbonyl)amino}ethoxy)phenyl]propionic acid, 3-[4-(2-{N-[3-(3,5-dichlorobenzyloxy)propyl]-N-(4-fluorophenoxycarbonyl)amino}ethoxy)phenyl]-2-ethoxypropionic acid,
2-ethoxy-3-[4-(2-{N-[4-(4-fluorobenzyloxy)butyl]-N-(4-fluorophenoxycarbonyl)amino}ethoxy)phenyl]propionic acid,
3-[4-(2-{N-[4-(3,5-dichlorobenzyloxy)butyl]-N-(4-fluorophenoxycarbonyl)amino}ethoxy)phenyl]-2-ethoxypropionic acid,
2-ethoxy-3-[4-(2-{N-(4-fluorophenoxycarbonyl)-N-[3-(4-fluorophenyl)propyl]amino}ethoxy)phenyl]propionic acid,
3-[4-(2-{N-[3-(3,5-dichlorophenyl)propyl]-N-(4-fluorophenoxycarbonyl)amino}ethoxy)phenyl]-2-ethoxypropionic acid,
3-(4-{2-[N-(4-bromophenoxycarbonyl)-N-pentylamino]ethoxy}phenyl)-2-ethoxypropionic acid,
3-(4-{2-[N-(4-bromophenoxycarbonyl)-N-hexylamino]ethoxy}phenyl)-2-ethoxypropionic acid,
3-(4-{2-[N-(4-bromophenoxycarbonyl)-N-heptylamino]ethoxy}phenyl)-2-ethoxypropionic acid,
3-(4-{2-[N-(4-bromophenoxycarbonyl)-N-octylamino]ethoxy}phenyl)-2-ethoxypropionic acid,
3-(4-{2-[N-(4-bromophenoxycarbonyl)-N-isobutylamino]ethoxy}phenyl)-2-ethoxypropionic acid,
3-(4-{2-[N-(4-bromophenoxycarbonyl)-N-(3-methylbutyl)amino]ethoxy}phenyl)-2-ethoxypropionic acid,
3-(4-{2-[N-(4-bromophenoxycarbonyl)-N-(4-methylpentyl)amino]ethoxy}phenyl)-2-ethoxypropionic acid,
3-(4-{2-[N-(4-bromophenoxycarbonyl)-N-(2-propylpentyl)amino]ethoxy}phenyl)-2-ethoxypropionic acid,
3-(4-{2-[N-(4-bromophenoxycarbonyl)-N-(3,3-dimethylbutyl)amino]ethoxy}phenyl)-2-ethoxypropionic acid,
3-(4-{2-[N-(4-bromophenoxycarbonyl)-N-(2-ethylbutyl)amino]ethoxy}phenyl)-2-ethoxypropionic acid,
3-(4-{2-[N-(4-bromophenoxycarbonyl)-N-cyclohexylmethylamino]ethoxy}phenyl)-2-ethoxypropionic acid,
3-(4-{2-[N-(4-bromophenoxycarbonyl)-N-(4-cyclohexylbutyl)amino]ethoxy}phenyl)-2-ethoxypropionic acid,
3-(4-{2-[N-(4-bromophenoxycarbonyl)-N-cyclopropylmethylamino]ethoxy}phenyl)-2-ethoxypropionic acid,
3-(4-{2-[N-(4-bromophenoxycarbonyl)-N-cyclobutylmethylamino]ethoxy}phenyl)-2-ethoxypropionic acid,
3-(4-{2-[N-(4-bromophenoxycarbonyl)-N-cyclopentylmethylamino]ethoxy}phenyl)-2-ethoxypropionic acid,
3-(4-{2-[N-(4-bromophenoxycarbonyl)-N-(2-cyclopentylethyl)amino]ethoxy}phenyl)-2-ethoxypropionic acid,
3-(4-{2-[N-(4-bromophenoxycarbonyl)-N-(3-cyclohexylpropyl)amino]ethoxy}phenyl)-2-ethoxypropionic acid,
3-(4-{2-[N-(4-bromophenoxycarbonyl)-N-(3-phenylpropyl)amino]ethoxy}phenyl)-2-ethoxypropionic acid,
3-(4-{2-[N-(4-bromophenoxycarbonyl)-N-(4-phenylbutyl)amino]ethoxy}phenyl)-2-ethoxypropionic acid,
3-(4-{2-[N-(4-bromophenoxycarbonyl)-N-(2-butoxyethyl)amino]ethoxy}phenyl)-2-ethoxypropionic acid,
3-(4-{2-[N-(4-bromophenoxycarbonyl)-N-(2-pentyloxyethyl)amino]ethoxy}phenyl)-2-ethoxypropionic acid,
3-(4-{2-[N-(4-bromophenoxycarbonyl)-N-(3-propoxypropyl)amino]ethoxy}phenyl)-2-ethoxypropionic acid,
3-(4-{2-[N-(4-bromophenoxycarbonyl)-N-(2-butylthioethyl)amino]ethoxy}phenyl)-2-ethoxypropionic acid,
3-(4-{2-[N-(4-bromophenoxycarbonyl)-N-(2-pentylthioethyl)amino]ethoxy}phenyl)-2-ethoxypropionic acid,
3-(4-{2-[N-(4-bromophenoxycarbonyl)-N-(3-propylthiopropyl)amino]ethoxy}phenyl)-2-ethoxypropionic acid,
3-(4-{2-[N-(4-bromophenoxycarbonyl)-N-(3-phenoxypropyl)amino]ethoxy}phenyl)-2-ethoxypropionic acid,
3-(4-{2-[N-(4-bromophenoxycarbonyl)-N-(4-phenoxybutyl)amino]ethoxy}phenyl)-2-ethoxypropionic acid,
3-(4-{2-[N-(3-benzyloxypropyl)-N-(4-bromophenoxycarbonyl)amino]ethoxy}phenyl)-2-ethoxypropionic acid,
3-(4-{2-[N-(4-bromophenoxycarbonyl)-N-(3-phenylopropyl)amino]ethoxy}phenyl)-2-ethoxypropionic acid,
3-(4-{2-[N-(4-bromophenoxycarbonyl)-N-(4-phenylthiobutyl)amino]ethoxy}phenyl)-2-ethoxypropionic acid,
3-(4-{2-[N-(3-benzylthiopropyl)-N-(4-bromophenoxycarbonyl)amino]ethoxy}phenyl)-2-ethoxypropionic acid,
3-(4-{2-[N-(4-bromophenoxycarbonyl)-N-(7,7,7-trifluoroheptyl)amino]ethoxy}phenyl)-2-ethoxypropionic acid,
3-(4-{2-[N-(4-bromophenoxycarbonyl)-N-(6,6-difluoroheptyl)amino]ethoxy}phenyl)-2-ethoxypropionic acid,
3-(4-{2-[N-(4-bromophenoxycarbonyl)-N-(6,6,6-trifluorohexyl)amino]ethoxy}phenyl)-2-ethoxypropionic acid,
3-(4-{2-[N-(4-bromophenoxycarbonyl)-N-(5,5-difluorohexyl)amino]ethoxy}phenyl)-2-ethoxypropionic acid,
3-(4-{2-[N-(4-bromophenoxycarbonyl)-N-(5,5,6,6,7,7,7-heptafluoroheptyl)amino]ethoxy}phenyl)-2-ethoxypropionic acid,
3-(4-{2-[N-(4-bromophenoxycarbonyl)-N-(2,2,3,3,4,4,5,5,6,6,7,7,7-tridecafluoroheptyl)amino]ethoxy}phenyl)-2-ethoxypropionic acid,
3-(4-{2-[N-(4-bromophenoxycarbonyl)-N-(5,5,6,6,6-pentafluorohexyl)amino]ethoxy}phenyl)-2-ethoxypropionic acid,
3-(4-{2-[N-(4-bromophenoxycarbonyl)-N-(2,2,3,3,4,4,5,5,6,6,6-undecafluorohexyl)amino]ethoxy}phenyl)-2-ethoxypropionic acid,
3-[4-(2-{N-(4-bromophenoxycarbonyl)-N-[2-(2,2-difluoropropoxy)ethyl]amino}ethoxy)phenyl]-2-ethoxypropionic acid,
3-[4-(2-{N-(4-bromophenoxycarbonyl)-N-[2-(1,1,2,2,3,3,3-heptafluoropropoxy)ethyl]amino}ethoxy)phenyl]-2-ethoxypropionic acid,
3-[4-(2-{N-(4-bromophenoxycarbonyl)-N-[2-(4,4,4-trifluorobutoxy)ethyl]amino}ethoxy)phenyl]-2-ethoxypropionic acid,
3-[4-(2-{N-(4-bromophenoxycarbonyl)-N-[2-(3,3-difluorobutoxy)ethyl]amino}ethoxy)phenyl]-2-ethoxypropionic acid,
3-[4-(2-{N-(4-bromophenoxycarbonyl)-N-[2-(2,2-difluorobutoxy)ethyl]amino}ethoxy)phenyl]-2-ethoxypropionic acid,
3-[4-(2-{N-(4-bromophenoxycarbonyl)-N-[2-(1,1,2,2,3,3,4,4,4-nonafluorobutoxy)ethyl]amino}ethoxy)phenyl]-2-ethoxypropionic acid,
3-[4-(2-{N-(4-bromophenoxycarbonyl)-N-[3-(2,2,2-trifluoroethoxy)propyl]amino}ethoxy)phenyl]-2-ethoxypropionic acid,
3-[4-(2-{N-(4-bromophenoxycarbonyl)-N-[3-(1,1,2,2,2-pentafluoroethoxy)propyl]amino}ethoxy)phenyl]-2-ethoxypropionic acid,
3-[4-(2-{N-(4-bromophenoxycarbonyl)-N-[3-(4-fluorophenoxy)propyl]amino}ethoxy)phenyl]-2-ethoxypropionic acid,
3-[4-(2-{N-(4-bromophenoxycarbonyl)-N-[3-(3,5-dichlorophenoxy)propyl]amino}ethoxy)phenyl]-2-ethoxypropionic acid,
3-[4-(2-{N-(4-bromophenoxycarbonyl)-N-[4-(4-fluorophenoxy)butyl]amino}ethoxy)phenyl]-2-ethoxypropionic acid,
3-[4-(2-{N-(4-bromophenoxycarbonyl)-N-[4-(3,5-dichlorophenoxy)butyl]amino}ethoxy)phenyl]-2-ethoxypropionic acid, 3-[4-(2-{N-(4-bromophenoxycarbonyl)-N-[2-(4-fluorobenzyloxy)ethyl]amino}ethoxy)phenyl]-2-ethoxypropionic acid,
3-[4-(2-{N-(4-bromophenoxycarbonyl)-N-[2-(3,5-dichlorobenzyloxy)ethyl]amino}ethoxy)phenyl]-2-ethoxypropionic acid,
3-[4-(2-{N-(4-bromophenoxycarbonyl)-N-[3-(4-fluorobenzyloxy)propyl]amino}ethoxy)phenyl]-2-ethoxypropionic acid,
3-[4-(2-{N-(4-bromophenoxycarbonyl)-N-[3-(3,5-dichlorobenzyloxy)propyl]amino}ethoxy)phenyl]-2-ethoxypropionic acid,
3-[4-(2-(N-(4-bromophenoxycarbonyl)-N-[4-(4-fluorobenzyloxy)butyl]amino}ethoxy)phenyl]-2-ethoxypropionic acid,
3-[4-(2-{N-(4-bromophenoxycarbonyl)-N-[4-(3,5-dichlorobenzyloxy)butyl]amino}ethoxy)phenyl]-2-ethoxypropionic acid,
3-[4-(2-{N-(4-bromophenoxycarbonyl)-N-[3-(4-fluorophenyl)propyl]amino}ethoxy)phenyl]-2-ethoxypropionic acid,
3-[4-(2-{N-(4-bromophenoxycarbonyl)-N-[3-(3,5-dichlorophenyl)propyl]amino}ethoxy)phenyl]-2-ethoxypropionic acid,
3-(4-{2-[N-(2-chlorophenoxy carbonyl)-N-pentylamino]ethoxy}phenyl)-2-ethoxypropionic acid,
3-(4-{2-[N-(2-chlorophenoxycarbonyl)-N-hexylamino]ethoxy}phenyl)-2-ethoxypropionic acid,
3-(4-{2-[N-(2-chlorophenoxycarbonyl)-N-heptylamino]ethoxy}phenyl)-2-ethoxypropionic acid,
3-(4-{2-[N-(2-chlorophenoxycarbonyl)-N-octylamino]ethoxy}phenyl)-2-ethoxypropionic acid,
3-(4-{2-[N-(2-chlorophenoxycarbonyl)-N-isobutylamino]ethoxy}phenyl)-2-ethoxypropionic acid,
3-(4-{2-[N-(2-chlorophenoxycarbonyl)-N-(3-methylbutyl)amino]ethoxy}phenyl)-2-ethoxypropionic acid,
3-(4-{2-[N-(2-chlorophenoxycarbonyl)-N-(4-methylpentyl)amino]ethoxy}phenyl)-2-ethoxypropionic acid,
3-(4-{2-[N-(2-chlorophenoxycarbonyl)-N-(2-propylpentyl)amino]ethoxy}phenyl)-2-ethoxypropionic acid,
3-(4-{2-[N-(2-chlorophenoxycarbonyl)-N-(3,3-dimethylbutyl)amino]ethoxy}phenyl)-2-ethoxypropionic acid,
3-(4-{2-[N-(2-chlorophenoxycarbonyl)-N-(2-ethylbutyl)amino]ethoxy}phenyl)-2-ethoxypropionic acid,
3-(4-{2-[N-(2-chlorophenoxycarbonyl)-N-cyclohexylmethylamino]ethoxy}phenyl)-2-ethoxypropionic acid,
3-(4-{2-[N-(2-chlorophenoxycarbonyl)-N-(4-cyclohexylbutyl)amino]ethoxy}phenyl)-2-ethoxypropionic acid,
3-(4-{2-[N-(2-chlorophenoxycarbonyl)-N-cyclopropylmethylamino]ethoxy}phenyl)-2-ethoxypropionic acid,
3-(4-{2-[N-(2-chlorophenoxycarbonyl)-N-cyclobutylmethylamino]ethoxy}phenyl)-2 -ethoxypropionic acid,
3-(4-{2-[N-(2-chlorophenoxycarbonyl)-N-cyclopentylmethylamino]ethoxy}phenyl)-2-ethoxypropionic acid,
3-(4-{2-[N-(2-chlorophenoxycarbonyl)-N-(2-cyclopentylethyl)amino]ethoxy}phenyl)-2-ethoxypropionic acid,
3-(4-{2-[N-(2-chlorophenoxycarbonyl)-N-(3-cyclohexylpropyl)amino]ethoxy}phenyl)-2-ethoxypropionic acid,
3-(4-{2-[N-(2-chlorophenoxycarbonyl)-N-(3-phenylpropyl)amino]ethoxy}phenyl)-2-ethoxypropionic acid,
3-(4-{2-[N-(2-chlorophenoxycarbonyl)-N-(4-phenylbutyl)amino]ethoxy}phenyl)-2-ethoxypropionic acid,
3-(4-{2-[N-(2-butoxyethyl)-N-(2-chlorophenoxycarbonyl)amino]ethoxy}phenyl)-2-ethoxypropionic acid,
3-(4-{2-[N-(2-chlorophenoxycarbonyl)-N-(2-pentyloxyethyl)amino]ethoxy}phenyl)-2-ethoxypropionic acid,
3-(4-{2-[N-(2-chlorophenoxycarbonyl)-N-(3-propoxypropyl)amino]ethoxy}phenyl)-2-ethoxypropionic acid,
3-(4-{2-[N-(2-butylthioethyl)-N-(2-chlorophenoxycarbonyl)amino]ethoxy}phenyl)-2-ethoxypropionic acid,
3-(4-{2-[N-(2-chlorophenoxycarbonyl)-N-(2-pentylthioethyl)amino]ethoxy}phenyl)-2-ethoxypropionic acid,
3-(4-{2-[N-(2-chlorophenoxycarbonyl)-N-(3-propylthiopropyl)amino]ethoxy}phenyl)-2-ethoxypropionic acid,
3-(4-{2-[N-(2-chlorophenoxycarbonyl)-N-(3-phenoxypropyl)amino]ethoxy}phenyl)-2-ethoxypropionic acid,
3-(4-{2-[N-(2-chlorophenoxycarbonyl)-N-(4-phenoxybutyl)amino]ethoxy}phenyl)-2-ethoxypropionic acid,
3-(4-{2-[N-(3-benzyloxypropyl)-N-(2-chlorophenoxycarbonyl)amino]ethoxy}phenyl)-2-ethoxypropionic acid,
3-(4-{2-[N-(2-chlorophenoxycarbonyl)-N-(3-phenylthiopropyl)amino]ethoxy}phenyl)-2-ethoxypropionic acid,
3-(4-{2-[N-(2-chlorophenoxycarbonyl)-N-(4-phenylthiobutyl)amino]ethoxy}phenyl)-2-ethoxypropionic acid,
3-(4-{2-[N-(3-benzylthiopropyl)-N-(2-chlorophenoxycarbonyl)amino]ethoxy}phenyl)-2-ethoxypropionic acid,
3-(4-{2-[N-(2-chlorophenoxycarbonyl)-N-(7,7,7-trifluoroheptyl)amino]ethoxy}phenyl)-2-ethoxypropionic acid,
3-(4-{2-[N-(2-chlorophenoxycarbonyl)-N-(6,6-difluoroheptyl)amino]ethoxy}phenyl)-2-ethoxypropionic acid,
3-(4-{2-[N-(2-chlorophenoxycarbonyl)-N-(6,6,6-trifluorohexyl)amino]ethoxy}phenyl)-2-ethoxypropionic acid,
3-(4-{2-[N-(2-chlorophenoxycarbonyl)-N-(5,5-difluorohexyl)amino]ethoxy}phenyl)-2-ethoxypropionic acid,
3-(4-{2-[N-(2-chlorophenoxycarbonyl)-N-(5,5,6,6,7,7,7-heptafluoroheptyl)amino]ethoxy}phenyl)-2-ethoxypropionic acid,
3-(4-{2-[N-(2-chlorophenoxycarbonyl)-N-(2,2,3,3,4,4,5,5,6,6,7,7,7-tridecafluoroheptyl)amino]ethoxy}phenyl)-2-ethoxypropionic acid,
3-(4-{2-[N-(2-chlorophenoxycarbonyl)-N-(5,5,6,6,6-pentafluorohexyl)amino]ethoxy}phenyl)-2-ethoxypropionic acid,
3-(4-{2-[N-(2-chlorophenoxycarbonyl)-N-(2,2,3,3,4,4,5,5,6,6,6-undecafluorohexyl)amino]ethoxy}phenyl)-2-ethoxypropionic acid,
3-[4-(2-{N-(2-chlorophenoxycarbonyl)-N-[2-(2,2-difluoropropoxy)ethyl]amino}ethoxy)phenyl]-2-ethoxypropionic acid,
3-[4-(2-{N-(2-chlorophenoxycarbonyl)-N-[2-(1,1,2,2,3,3,3-heptafluoropropoxy)ethyl]amino}ethoxy)phenyl]-2-ethoxypropionic acid,
3-[4-(2-{N-(2-chlorophenoxycarbonyl)-N-[2-(4,4,4-trifluorobutoxy)ethyl]amino}ethoxy)phenyl]-2-ethoxypropionic acid,
3-[4-(2-{N-(2-chlorophenoxycarbonyl)-N-[2-(3,3-difluorobutoxy)ethyl]amino}ethoxy)phenyl]-2-ethoxypropionic acid,
3-[4-(2-{N-(2-chlorophenoxycarbonyl)-N-[2-(2,2-difluorobutoxy)ethyl]amino}ethoxy)phenyl]-2-ethoxypropionic acid,
3-[4-(2-{N-(2-chlorophenoxycarbonyl)-N-[2-(1,1,2,2,3,3,4,4,4-nonafluorobutoxy)ethyl]amino}ethoxy)phenyl]-2-ethoxypropionic acid,
3-[4-(2-{N-(2-chlorophenoxycarbonyl)-N-[3-(2,2,2-trifluoroethoxy)propyl]amino}ethoxy)phenyl]-2-ethoxypropionic acid,
3-[4-(2-{N-(2-chlorophenoxycarbonyl)-N-[3-(1,1,2,2,2-pentafluoroethoxy)propyl]amino}ethoxy)phenyl]-2-ethoxypropionic acid,
3-[4-(2-{N-(2-chlorophenoxycarbonyl)-N-[3-(4-fluorophenoxy)propyl]amino}ethoxy)phenyl]-2-ethoxypropionic acid, 3-[4-(2-{N-(2-chlorophenoxycarbonyl)-N-[3-(3,5-dichlorophenoxy)propyl]amino}ethoxy)phenyl]-2-ethoxypropionic acid,
3-[4-(2-{N-(2-chlorophenoxycarbonyl)-N-[4-(4-fluorophenoxy)butyl]amino}ethoxy)phenyl]-2-ethoxypropionic acid,
3-[4-(2-{N-(2-chlorophenoxycarbonyl)-N-[4-(3,5-dichlorophenoxy)butyl]amino}ethoxy)phenyl]-2-ethoxypropionic acid,
3-[4-(2-{N-(2-chlorophenoxycarbonyl)-N-[2-(4-fluorobenzyloxy)ethyl]amino}ethoxy)phenyl]-2-ethoxypropionic acid,
3-[4-(2-{N-(2-chlorophenoxycarbonyl)-N-[2-(3,5-dichlorobenzyloxy)ethyl]amino}ethoxy)phenyl]-2-ethoxypropionic acid,
3-[4-(2-{N-(2-chlorophenoxycarbonyl)-N-[3-(4-fluorobenzyloxy)propyl]amino}ethoxy)phenyl]-2-ethoxypropionic acid,
3-[4-(2-{N-(2-chlorophenoxycarbonyl)-N-[3-(3,5-dichlorobenzyloxy)propyl]amino}ethoxy)phenyl]-2-ethoxypropionic acid,
3-[4-(2-{N-(2-chlorophenoxycarbonyl)-N-[4-(4-fluorobenzyloxy)butyl]amino}ethoxy)phenyl]-2-ethoxypropionic acid,
3-[4-(2-{N-(2-chlorophenoxycarbonyl)-N-[4-(3,5-dichlorobenzyloxy)butyl]amino}ethoxy)phenyl]-2-ethoxypropionic acid,
3-[4-(2-{N-(2-chlorophenoxycarbonyl)-N-[3-(4-fluorophenyl)propyl]amino}ethoxy)phenyl]-2-ethoxypropionic acid,
3-[4-(2-{N-(2-chlorophenoxycarbonyl)-N-[3-(3,5-dichlorophenyl)propyl]amino}ethoxy)phenyl]-2-ethoxypropionic acid,
3-(4-{2-[N-(4-chlorophenoxycarbonyl)-N-pentylamino]ethoxy}phenyl)-2-ethoxypropionic acid,
3-(4-{2-[N-(4-chlorophenoxycarbonyl)-N-hexylamino]ethoxy}phenyl)-2-ethoxypropionic acid,
3-(4-{2-[N-(4-chlorophenoxycarbonyl)-N-heptylamino]ethoxy}phenyl)-2-ethoxypropionic acid,
3-(4-{2-[N-(4-chlorophenoxycarbonyl)-N-octylamino]ethoxy}phenyl)-2-ethoxypropionic acid,
3-(4-{2-[N-(4-chlorophenoxycarbonyl)-N-isobutylamino]ethoxy}phenyl)-2-ethoxypropionic acid,
3-(4-{2-[N-(4-chlorophenoxycarbonyl)-N-(3-methylbutyl)amino]ethoxy}phenyl)-2-ethoxypropionic acid,
3-(4-{2-[N-(4-chlorophenoxycarbonyl)-N-(4-methylpentyl)amino]ethoxy}phenyl)-2-ethoxypropionic acid,
3-(4-{2-[N-(4-chlorophenoxycarbonyl)-N-(2-propylpentyl)amino]ethoxy}phenyl)-2-ethoxypropionic acid,
3-(4-{2-[N-(4-chlorophenoxycarbonyl)-N-(3,3-dimethylbutyl)amino]ethoxy}phenyl)-2-ethoxypropionic acid,
3-(4-{2-[N-(4-chlorophenoxycarbonyl)-N-(2-ethylbutyl)amino]ethoxy}phenyl)-2-ethoxypropionic acid,
3-(4-{2-[N-(4-chlorophenoxycarbonyl)-N-cyclohexylmethylamino]ethoxy}phenyl)-2-ethoxypropionic acid,
3-(4-{2-[N-(4-chlorophenoxycarbonyl)-N-(4-cyclohexylbutyl)amino]ethoxy}phenyl)-2-ethoxypropionic acid,
3-(4-{2-[N-(4-chlorophenoxycarbonyl)-N-cyclopropylmethylamino]ethoxy}phenyl)-2-ethoxypropionic acid,
3-(4-{2-[N-(4-chlorophenoxycarbonyl)-N-cyclobutylmethylamino]ethoxy}phenyl)-2-ethoxypropionic acid,
3-(4-{2-[N-(4-chlorophenoxycarbonyl)-N-cyclopentylmethylamino]ethoxy}phenyl)-2-ethoxypropionic acid,
3-(4-{2-[N-(4-chlorophenoxycarbonyl)-N-(2-cyclopentylethyl)amino]ethoxy}phenyl)-2-ethoxypropionic acid,
3-(4-{2-[N-(4-chlorophenoxycarbonyl)-N-(3-cyclohexylpropyl)amino]ethoxy}phenyl)-2-ethoxypropionic acid,
3-(4-{2-[N-(4-chlorophenoxycarbonyl)-N-(3-phenylpropyl)amino]ethoxy}phenyl)-2-ethoxypropionic acid,
3-(4-{2-[N-(4-chlorophenoxycarbonyl)-N-(4-phenylbutyl)amino]ethoxy}phenyl)-2-ethoxypropionic acid,
3-(4-{2-[N-(2-butoxyethyl)-N-(4-chlorophenoxycarbonyl)amino]ethoxy}phenyl)-2-ethoxypropionic acid,
3-(4-{2-[N-(4-chlorophenoxycarbonyl)-N-(2-pentyloxyethyl)amino]ethoxy}phenyl)-2 -ethoxypropionic acid,
3-(4-{2-[N-(4-chlorophenoxycarbonyl)-N-(3-propoxypropyl)amino]ethoxy}phenyl)-2-ethoxypropionic acid,
3-(4-{2-[N-(2-butylthioethyl)-N-(4-chlorophenoxycarbonyl)amino]ethoxy}phenyl)-2-ethoxypropionic acid,
3-(4-{2-[N-(4-chlorophenoxycarbonyl)-N-(2-pentylthioethyl)amino]ethoxy}phenyl)-2-ethoxypropionic acid,
3-(4-{2-[N-(4-chlorophenoxycarbonyl)-N-(3-propylthiopropyl)amino]ethoxy}phenyl)-2-ethoxypropionic acid,
3-(4-{2-[N-(4-chlorophenoxycarbonyl)-N-(3-phenoxypropyl)amino]ethoxy}phenyl)-2-ethoxypropionic acid,
3-(4-{2-[N-(4-chlorophenoxycarbonyl)-N-(4-phenoxybutyl)amino]ethoxy}phenyl)-2-ethoxypropionic acid,
3-(4-{2-[N-(3-benzyloxypropyl)-N-(4-chlorophenoxycarbonyl)amino]ethoxy}phenyl)-2-ethoxypropionic acid,
3-(4-{2-[N-(4-chlorophenoxycarbonyl)-N-(3-phenylthiopropyl)amino]ethoxy}phenyl)-2-ethoxypropionic acid,
3-(4-{2-[N-(4-chlorophenoxycarbonyl)-N-(4-phenylthiobutyl)amino]ethoxy}phenyl)-2-ethoxypropionic acid,
3-(4-{2-[N-(3-benzylthiopropyl)-N-(4-chlorophenoxycarbonyl)amino]ethoxy}phenyl)-2-ethoxypropionic acid,
3-(4-{2-[N-(4-chlorophenoxycarbonyl)-N-(7,7,7-trifluoroheptyl)amino]ethoxy}phenyl)-2-ethoxypropionic acid,
3-(4-{2-[N-(4-chlorophenoxycarbonyl)-N-(6,6-difluoroheptyl)amino]ethoxy}phenyl)-2-ethoxypropionic acid,
3-(4-{2-[N-(4-chlorophenoxycarbonyl)-N-(6,6,6-trifluorohexyl)amino]ethoxy}phenyl)-2-ethoxypropionic acid,
3-(4-{2-[N-(4-chlorophenoxycarbonyl)-N-(5,5-difluorohexyl)amino]ethoxy}phenyl)-2-ethoxypropionic acid,
3-(4-{2-[N-(4-chlorophenoxycarbonyl)-N-(5,5,6,6,7,7,7-heptafluoroheptyl)amino]ethoxy}phenyl)-2-ethoxypropionic acid,
3-(4-{2-[N-(4-chlorophenoxycarbonyl)-N-(2,2,3,3,4,4,5,5,6,6,7,7,7-tridecafluoroheptyl)amino]ethoxy}phenyl)-2-ethoxypropionic acid,
3-(4-{2-[N-(4-chlorophenoxycarbonyl)-N-(5,5,6,6,6-pentafluorohexyl)amino]ethoxy}phenyl)-2-ethoxypropionic acid,
3-(4-{2-[N-(4-chlorophenoxycarbonyl)-N-(2,2,3,3,4,4,5,5,6,6,6-undecafluorohexyl)amino]ethoxy}phenyl)-2-ethoxypropionic acid,
3-[4-(2-{N-(4-chlorophenoxycarbonyl)-N-[2-(2,2-difluoropropoxy)ethyl]amino}ethoxy)phenyl]-2-ethoxypropionic acid,
3-[4-(2-{N-(4-chlorophenoxycarbonyl)-N-[2-(1,1,2,2,3,3,3-heptafluoropropoxy)ethyl]amino}ethoxy)phenyl]-2-ethoxypropionic acid,
3-[4-(2-{N-(4-chlorophenoxycarbonyl)-N-[2-(4,4,4-trifluorobutoxy)ethyl]amino}ethoxy)phenyl]-2-ethoxypropionic acid,
3-[4-(2-{N-(4-chlorophenoxycarbonyl)-N-[2-(3,3-difluorobutoxy)ethyl]amino}ethoxy)phenyl]-2-ethoxypropionic acid,
3-[4-(2-{N-(4-chlorophenoxycarbonyl)-N-[2-(2,2-difluorobutoxy)ethyl]amino}ethoxy)phenyl]-2-ethoxypropionic acid,
3-[4-(2-{N-(4-chlorophenoxycarbonyl)-N-[2-(1,1,2,2,3,3,4,4,4-nonafluorobutoxy)ethyl]amino}ethoxy)phenyl]-2-ethoxypropionic acid, 3-[4-(2-{N-(4-chlorophenoxycarbonyl)-N-[3-(2,2,2-trifluoroethoxy)propyl]amino}ethoxy)phenyl]-2-ethoxypropionic acid,
3-[4-(2-{N-(4-chlorophenoxycarbonyl)-N-[3-(1,1,2,2,2-pentafluoroethoxy)propyl]amino}ethoxy)phenyl]-2-ethoxypropionic acid,
3-[4-(2-{N-(4-chlorophenoxycarbonyl)-N-[3-(4-fluorophenoxy)propyl]amino}ethoxy)phenyl]-2-ethoxypropionic acid,
3-[4-(2-{N-(4-chlorophenoxycarbonyl)-N-[3-(3,5-dichlorophenoxy)propyl]amino}ethoxy)phenyl]-2-ethoxypropionic acid,
3-[4-(2-{N-(4-chlorophenoxycarbonyl)-N-[4-(4-fluorophenoxy)butyl]amino}ethoxy)phenyl]-2-ethoxypropionic acid,
3-[4-(2-{N-(4-chlorophenoxycarbonyl)-N-[4-(3,5-dichlorophenoxy)butyl]amino}ethoxy)phenyl]-2-ethoxypropionic acid,
3-[4-(2-{N-(4-chlorophenoxycarbonyl)-N-[2-(4-fluorobenzyloxy)ethyl]amino}ethoxy)phenyl]-2-ethoxypropionic acid,
3-[4-(2-{N-(4-chlorophenoxycarbonyl)-N-[2-(3,5-dichlorobenzyloxy)ethyl]amino}ethoxy)phenyl]-2-ethoxypropionic acid,
3-[4-(2-{N-(4-chlorophenoxycarbonyl)-N-[3-(4-fluorobenzyloxy)propyl]amino}ethoxy)phenyl]-2-ethoxypropionic acid,
3-[4-(2-{N-(4-chlorophenoxycarbonyl)-N-[3-(3,5-dichlorobenzyloxy)propyl]amino}ethoxy)phenyl]-2-ethoxypropionic acid,
3-[4-(2-{N-(4-chlorophenoxycarbonyl)-N-[4-(4-fluorobenzyloxy)butyl]amino}ethoxy)phenyl]-2-ethoxypropionic acid,
3-[4-(2-{N-(4-chlorophenoxycarbonyl)-N-[4-(3,5-dichlorobenzyloxy)butyl]amino}ethoxy)phenyl]-2-ethoxypropionic acid,
3-[4-(2-{N-(4-chlorophenoxycarbonyl)-N-[3-(4-fluorophenyl)propyl]amino}ethoxy)phenyl]-2-ethoxypropionic acid,
3-[4-(2-{N-(4-chlorophenoxycarbonyl)-N-[3-(3,5-dichlorophenyl)propyl]amino}ethoxy)phenyl]-2-ethoxypropionic acid,
3-(4-{2-[N-(2,4-dichlorophenoxycarbonyl)-N-pentylamino]ethoxy}phenyl)-2-ethoxypropionic acid,
3-(4-{2-[N-(2,4-dichlorophenoxycarbonyl)-N-hexylamino]ethoxy}phenyl)-2-ethoxypropionic acid,
3-(4-{2-[N-(2,4-dichlorophenoxycarbonyl)-N-heptylamino]ethoxy}phenyl)-2-ethoxypropionic acid,
3-(4-{2-[N-(2,4-dichlorophenoxycarbonyl)-N-octylamino]ethoxy}phenyl)-2-ethoxypropionic acid,
3-(4-{2-[N-(2,4-dichlorophenoxycarbonyl)-N-isobutylamino]ethoxy}phenyl)-2-ethoxypropionic acid,
3-(4-{2-[N-(2,4-dichlorophenoxycarbonyl)-N-(3-methylbutyl)amino]ethoxy}phenyl)-2-ethoxypropionic acid,
3-(4-{2-[N-(2,4-dichlorophenoxycarbonyl)-N-(4-methylpentyl)amino]ethoxy}phenyl)-2-ethoxypropionic acid,
3-(4-{2-[N-(2,4-dichlorophenoxycarbonyl)-N-(2-propylpentyl)amino]ethoxy}phenyl)-2-ethoxypropionic acid,
3-(4-{2-[N-(2,4-dichlorophenoxycarbonyl)-N-(3,3-dimethylbutyl)amino]ethoxy}phenyl)-2-ethoxypropionic acid,
3-(4-{2-[N-(2,4-dichlorophenoxycarbonyl)-N-(2-ethylbutyl)amino]ethoxy}phenyl)-2-ethoxypropionic acid,
3-(4-{2-[N-cyclohexylmethyl-N-(2,4-dichlorophenoxycarbonyl)amino]ethoxy}phenyl)-2-ethoxypropionic acid,
3-(4-{2-[N-(4-cyclohexylbutyl)-N-(2,4-dichlorophenoxycarbonyl)amino]ethoxy}phenyl)-2-ethoxypropionic acid,
3-(4-{2-[N-cyclopropylmethyl-N-(2,4-dichlorophenoxycarbonyl)amino]ethoxy}phenyl)-2-ethoxypropionic acid,
3-(4-{2-[N-cyclobutylmethyl-N-(2,4-dichlorophenoxycarbonyl)amino]ethoxy}phenyl)-2-ethoxypropionic acid,
3-(4-{2-[N-cyclopentylmethyl-N-(2,4-dichlorophenoxycarbonyl)amino]ethoxy}phenyl)-2-ethoxypropionic acid,
3-(4-{2-[N-(2-cyclopentylethyl)-N-(2,4-dichlorophenoxycarbonyl)amino]ethoxy}phenyl)-2-ethoxypropionic acid,
3-(4-{2-[N-(3-cyclohexylpropyl)-N-(2,4-dichlorophenoxycarbonyl)amino]ethoxy}phenyl)-2-ethoxypropionic acid,
3-(4-{2-[N-(2,4-dichlorophenoxycarbonyl)-N-(3-phenylpropyl)amino]ethoxy}phenyl)-2-ethoxypropionic acid,
3-(4-{2-[N-(2,4-dichlorophenoxycarbonyl)-N-(4-phenylbutyl)amino]ethoxy}phenyl)-2-ethoxypropionic acid,
3-(4-{2-[N-(2-butoxyethyl)-N-(2,4-dichlorophenoxycarbonyl)amino]ethoxy}phenyl)-2-ethoxypropionic acid,
3-(4-{2-[N-(2,4-dichlorophenoxycarbonyl)-N-(2-pentyloxyethyl)amino]ethoxy}phenyl)-2-ethoxypropionic acid,
3-(4-{2-[N-(2,4-dichlorophenoxycarbonyl)-N-(3-propoxypropyl)amino]ethoxy}phenyl)-2-ethoxypropionic acid,
3-(4-{2-[N-(2-butylthioethyl)-N-(2,4-dichlorophenoxycarbonyl)amino]ethoxy}phenyl)-2-ethoxypropionic acid,
3-(4-{2-[N-(2,4-dichlorophenoxycarbonyl)-N-(2-pentylthioethyl)amino]ethoxy}phenyl)-2-ethoxypropionic acid,
3-(4-{2-[N-(2,4-dichlorophenoxycarbonyl)-N-(3-propylthiopropyl)amino]ethoxy}phenyl)-2-ethoxypropionic acid,
3-(4-{2-[N-(2,4-dichlorophenoxycarbonyl)-N-(3-phenoxypropyl)amino]ethoxy}phenyl)-2-ethoxypropionic acid,
3-(4-{2-[N-(2,4-dichlorophenoxycarbonyl)-N-(4-phenoxybutyl)amino]ethoxy}phenyl)-2-ethoxypropionic acid,
3-(4-{2-[N-(3-benzyloxypropyl)-N-(2,4-dichlorophenoxycarbonyl)amino]ethoxy}phenyl)- 2-ethoxypropionic acid,
3-(4-{2-[N-(2,4-dichlorophenoxycarbonyl)-N-(3-phenylthiopropyl)amino]ethoxy}phenyl)-2-ethoxypropionic acid,
3-(4-{2-[N-(2,4-dichlorophenoxycarbonyl)-N-(4-phenylthiobutyl)amino]ethoxy}phenyl)-2-ethoxypropionic acid,
3-(4-{2-[N-(3-benzylthiopropyl)-N-(2,4-dichlorophenoxycarbonyl)amino]ethoxy}phenyl)-2-ethoxypropionic acid,
3-(4-{2-[N-(2,4-dichlorophenoxycarbonyl)-N-(7,7,7-trifluoroheptyl)amino]ethoxy}phenyl)-2-ethoxypropionic acid,
3-(4-{2-[N-(2,4-dichlorophenoxycarbonyl)-N-(6,6-difluoroheptyl)amino]ethoxy}phenyl)-2-ethoxypropionic acid,
3-(4-{2-[N-(2,4-dichlorophenoxycarbonyl)-N-(6,6,6-trifluorohexyl)amino]ethoxy}phenyl)-2-ethoxypropionic acid,
3-(4-{2-[N-(2,4-dichlorophenoxycarbonyl)-N-(5,5-difluorohexyl)amino]ethoxy}phenyl)-2-ethoxypropionic acid,
3-(4-{2-[N-(2,4-dichlorophenoxycarbonyl)-N-(5,5,6,6,7,7,7-heptafluoroheptyl)amino]ethoxy}phenyl)-2-ethoxypropionic acid,
3-(4-{2-[N-(2,4-dichlorophenoxycarbonyl)-N-(2,2,3,3,4,4,5,5,6,6,7,7,7-tridecafluoroheptyl)amino]ethoxy}phenyl)-2-ethoxypropionic acid,
3-(4-{2-[N-(2,4-dichlorophenoxycarbonyl)-N-(5,5,6,6,6-pentafluorohexyl)amino]ethoxy}phenyl)-2-ethoxypropionic acid,
3-(4-{2-[N-(2,4-dichlorophenoxycarbonyl)-N-(2,2,3,3,4,4,5,5,6,6-undecafluorohexyl)amino]ethoxy}phenyl)-2-ethoxypropionic acid,
3-[4-(2-{N-(2,4-dichlorophenoxycarbonyl)-N-[2-(2,2-difluoropropoxy)ethyl]amino}ethoxy)phenyl]-2-ethoxypropionic acid, 3-[4-(2-{N-(2,4-dichlorophenoxycarbonyl)-N-[2-(1,1,2,2,3,3,3-heptafluoropropoxy)ethyl]amino}ethoxy)phenyl]-2-ethoxypropionic acid,
3-[4-(2-{N-(2,4-dichlorophenoxycarbonyl)-N-[2-(4,4,4-trifluorobutoxy)ethyl]amino}ethoxy)phenyl]-2-ethoxypropionic acid,
3-[4-(2-{N-(2,4-dichlorophenoxycarbonyl)-N-[2-(3,3-difluorobutoxy)ethyl]amino}ethoxy)phenyl]-2-ethoxypropionic acid,
3-[4-(2-{N-(2,4-dichlorophenoxycarbonyl)-N-[2-(2,2-difluorobutoxy)ethyl]amino}ethoxy)phenyl]-2-ethoxypropionic acid,
3-[4-(2-{N-(2,4-dichlorophenoxycarbonyl)-N-[2-(1,1,2,2,3,3,4,4,4-nonafluorobutoxy)ethyl]amino}ethoxy)phenyl]-2-ethoxypropionic acid,
3-[4-(2-{N-(2,4-dichlorophenoxycarbonyl)-N-[3-(2,2,2-trifluoroethoxy)propyl]amino}ethoxy)phenyl]-2-ethoxypropionic acid,
3-[4-(2-{N-(2,4-dichlorophenoxycarbonyl)-N-[3-(1,1,2,2,2-pentafluoroethoxy)propyl]amino}ethoxy)phenyl]-2-ethoxypropionic acid,
3-[4-(2-{N-(2,4-dichlorophenoxycarbonyl)-N-[3-(4-fluorophenoxy)propyl]amino}ethoxy)phenyl]-2-ethoxypropionic acid,
3-[4-(2-{N-[3-(3,5-dichlorophenoxy)propyl]-N-(2,4-dichlorophenoxycarbonyl)amino}ethoxy)phenyl]-2-ethoxypropionic acid,
3-[4-(2-{N-(2,4-dichlorophenoxycarbonyl)-N-[4-(4-fluorophenoxy)butyl]amino}ethoxy)phenyl]-2-ethoxypropionic acid,
3-[4-(2-{N-[4-(3,5-dichlorophenoxy)butyl]-N-(2,4-dichlorophenoxycarbonyl)amino}ethoxy)phenyl]-2-ethoxypropionic acid,
3-[4-(2-{N-(2,4-dichlorophenoxycarbonyl)-N-[2-(4-fluorobenzyloxy)ethyl]amino}ethoxy)phenyl]-2-ethoxypropionic acid,
3-[4-(2-{N-[2-(3,5-dichlorobenzyloxy)ethyl]-N-(2,4-dichlorophenoxycarbonyl)amino}ethoxy)phenyl]-2-ethoxypropionic acid,
3-[4-(2-{N-(2,4-dichlorophenoxycarbonyl)-N-[3-(4-fluorobenzyloxy)propyl]amino}ethoxy)phenyl]-2-ethoxypropionic acid,
3-[4-(2-{N-[3-(3,5-dichlorobenzyloxy)propyl]-N-(2,4-dichlorophenoxycarbonyl)amino}ethoxy)phenyl]-2-ethoxypropionic acid,
3-[4-(2-{N-(2,4-dichlorophenoxycarbonyl)-N-[4-(4-fluorobenzyloxy)butyl]amino}ethoxy)phenyl]-2-ethoxypropionic acid,
3-[4-(2-{N-[4-(3,5-dichlorobenzyloxy)butyl]-N-(2,4-dichlorophenoxycarbonyl)amino}ethoxy)phenyl]-2-ethoxypropionic acid,
3-[4-(2-{N-(2,4-dichlorophenoxycarbonyl)-N-[3-(4-fluorophenyl)propyl]amino}ethoxy)phenyl]-2-ethoxypropionic acid,
3-[4-(2-{N-(2,4-dichlorophenoxycarbonyl)-N-[3-(3,5-dichlorophenyl)propyl]amino}ethoxy)phenyl]-2-ethoxypropionic acid,
2-ethoxy-3-(4-{2-[N-(4-isopropylphenoxycarbonyl)-N-pentylamino]ethoxy}phenyl)propionic acid,
2-ethoxy-3-(4-{2-[N-hexyl-N-(4-isopropylphenoxycarbonyl)amino]ethoxy}phenyl)propionic acid,
2-ethoxy-3-(4-{2-[N-heptyl-N-(4-isopropylphenoxycarbonyl)amino]ethoxy}phenyl)propionic acid,
2-ethoxy-3-(4-{2-[N-(4-isopropylphenoxycarbonyl)-N-octylamino]ethoxy}phenyl)propionic acid,
2-ethoxy-3-(4-{2-[N-isobutyl-N-(4-isopropylphenoxycarbonyl)amino]ethoxy}phenyl)propionic acid,
2-ethoxy-3-(4-{2-[N-(4-isopropylphenoxycarbonyl)-N-(3-methylbutyl)amino]ethoxy}phenyl)propionic acid,
2-ethoxy-3-(4-{2-[N-(4-isopropylphenoxycarbonyl)-N-(4-methylpentyl)amino]ethoxy}phenyl)propionic acid,
2-ethoxy-3-(4-{2-[N-(4-isopropylphenoxycarbonyl)-N-(2-propylpentyl)amino]ethoxy}phenyl)propionic acid,
3-(4-{2-[N-(3,3-dimethylbutyl)-N-(4-isopropylphenoxycarbonyl)amino]ethoxy}phenyl)-2-ethoxypropionic acid,
2-ethoxy-3-(4-{2-[N-(2-ethylbutyl)-N-(4-isopropylphenoxycarbonyl)amino]ethoxy}phenyl)propionic acid,
3-(4-{2-[N-cyclohexylmethyl-N-(4-isopropylphenoxycarbonyl)amino]ethoxy}phenyl)-2-ethoxypropionic acid,
3-(4-{2-[N-(4-cyclohexylbutyl)-N-(4-isopropylphenoxycarbonyl)amino]ethoxy}phenyl)-2-ethoxypropionic acid,
3-(4-{2-[N-cyclopropylmethyl-N-(4-isopropylphenoxycarbonyl)amino]ethoxy}phenyl)-2-ethoxypropionic acid,
3-(4-{2-[N-cyclobutylmethyl-N-(4-isopropylphenoxycarbonyl)amino]ethoxy}phenyl)-2-ethoxypropionic acid,
3-(4-{2-[N-cyclopentylmethyl-N-(4-isopropylphenoxycarbonyl)amino]ethoxy}phenyl)-2-ethoxypropionic acid,
3-(4-{2-[N-(2-cyclopentylethyl)-N-(4-isopropylphenoxycarbonyl)amino]ethoxy}phenyl)-2-ethoxypropionic acid,
3-(4-{2-[N-(3-cyclohexylpropyl)-N-(4-isopropylphenoxycarbonyl)amino]ethoxy}phenyl)-2-ethoxypropionic acid,
2-ethoxy-3-(4-{2-[N-(4-isopropylphenoxycarbonyl)-N-(3-phenylpropyl)amino]ethoxy}phenyl)propionic acid,
2-ethoxy-3-(4-{2-[N-(4-isopropylphenoxycarbonyl)-N-(4-phenylbutyl)amino]ethoxy}phenyl)propionic acid,
3-(4-{2-[N-(2-butoxyethyl)-N-(4-isopropylphenoxycarbonyl)amino]ethoxy}phenyl)-2-ethoxypropionic acid,
2-ethoxy-3-(4-{2-[N-(4-isopropylphenoxycarbonyl)-N-(2-pentyloxyethyl)amino]ethoxy}phenyl)propionic acid,
2-ethoxy-3-(4-{2-[N-(4-isopropylphenoxycarbonyl)-N-(3-propoxypropyl)amino]ethoxy}phenyl)propionic acid,
3-(4-{2-[N-(2-butylthioethyl)-N-(4-isopropylphenoxycarbonyl)amino]ethoxy}phenyl)-2-ethoxypropionic acid,
2-ethoxy-3-(4-{2-[N-(4-isopropylphenoxycarbonyl)-N-(2-pentylthioethyl)amino]ethoxy}phenyl)propionic acid,
2-ethoxy-3-(4-{2-[N-(4-isopropylphenoxycarbonyl)-N-(3-propylthiopropyl)amino]ethoxy}phenyl)propionic acid,
2-ethoxy-3-(4-{2-[N-(4-isopropylphenoxycarbonyl)-N-(3-phenoxypropyl)amino]ethoxy}phenyl)propionic acid,
2-ethoxy-3-(4-{2-[N-(4-isopropylphenoxycarbonyl)-N-(4-phenoxybutyl)amino]ethoxy}phenyl)propionic acid,
3-(4-{2-[N-(3-benzyloxypropyl)-N-(4-isopropylphenoxycarbonyl)amino]ethoxy}phenyl)-2-ethoxypropionic acid,
2-ethoxy-3-(4-{2-[N-(4-isopropylphenoxycarbonyl)-N-(3-phenylthiopropyl)amino]ethoxy}phenyl)propionic acid,
2-ethoxy-3-(4-{2-[N-(4-isopropylphenoxycarbonyl)-N-(4-phenylthiobutyl)amino]ethoxy}phenyl)propionic acid,
3-(4-{2-[N-(3-benzylthiopropyl)-N-(4-isopropylphenoxycarbonyl)amino]ethoxy}phenyl)-2-ethoxypropionic acid,
2-ethoxy-3-(4-{2-[N-(4-isopropylphenoxycarbonyl)-N-(7,7,7-trifluoroheptyl)amino]ethoxy}phenyl)propionic acid,
3-(4-{2-[N-(6,6-difluoroheptyl)-N-(4-isopropylphenoxycarbonyl)amino]ethoxy}phenyl)-2-ethoxypropionic acid,
2-ethoxy-3-(4-{2-[N-(4-isopropylphenoxycarbonyl)-N-(6,6,6-trifluorohexyl)amino]ethoxy}phenyl)propionic acid,
3-(4-{2-[N-(5,5-difluorohexyl)-N-(4-isopropylphenoxycarbonyl)amino]ethoxy}phenyl)-2-ethoxypropionic acid,
2-ethoxy-3-(4-{2-[N-(5,5,6,6,7,7,7-heptafluoroheptyl)-N-(4-isopropylphenoxycarbonyl)amino]ethoxy}phenyl)propionic acid,
2-ethoxy-3-(4-{2-[N-(4-isopropylphenoxycarbonyl)-N-(2,2,3,3,4,4,5,5,6,6,7,7,7-tridecafluoroheptyl)amino]ethoxy}phenyl)propionic acid, 2-ethoxy-3-(4-{2-[N-(4-isopropylphenoxycarbonyl)-N-(5,5,6,6,6-pentafluorohexyl)amino]ethoxy}phenyl)propionic acid,
2-ethoxy-3-(4-{2-[N-(4-isopropylphenoxycarbonyl)-N-(2,2,3,3,4,4,5,5,6,6,6-undecafluorohexyl)amino]ethoxy}phenyl)propionic acid,
3-[4-(2-{N-[2-(2,2-difluoropropoxy)ethyl]-N-(4-isopropylphenoxycarbonyl)amino}ethoxy)phenyl]-2-ethoxypropionic acid,
2-ethoxy-3-[4-(2-{N-[2-(1,1,2,2,3,3,3-heptafluoropropoxy)ethyl]-N-(4-isopropylphenoxycarbonyl)amino}ethoxy)phenyl]propionic acid,
2-ethoxy-3-[4-(2-{N-(4-isopropylphenoxycarbonyl)-N-[2-(4,4,4-trifluorobutoxy)ethyl]amino}ethoxy)phenyl]propionic acid,
3-[4-(2-{N-[2-(3,3-difluorobutoxy)ethyl]-N-(4-isopropylphenoxycarbonyl)amino}ethoxy)phenyl]-2-ethoxypropionic acid,
3-[4-(2-{N-[2-(2,2-difluorobutoxy)ethyl]-N-(4-isopropylphenoxycarbonyl)amino}ethoxy)phenyl]-2-ethoxypropionic acid,
2-ethoxy-3-[4-(2-{N-(4-isopropylphenoxycarbonyl)-N-[2-(1,1,2,2,3,3,4,4,4-nonafluorobutoxy)ethyl]amino}ethoxy)phenyl]propionic acid,
2-ethoxy-3-[4-(2-{N-(4-isopropylphenoxycarbonyl)-N-[3-(2,2,2-trifluoroethoxy)propyl]amino}ethoxy)phenyl]propionic acid,
2-ethoxy-3-[4-(2-{N-(4-isopropylphenoxycarbonyl)-N-[3-(1,1,2,2,2-pentafluoroethoxy)propyl]amino}ethoxy)phenyl]propionic acid,
2-ethoxy-3-[4-(2-{N-[3-(4-fluorophenoxy)propyl]-N-(4-isopropylphenoxycarbonyl)amino}ethoxy)phenyl]propionic acid,
3-[4-(2-{N-[3-(3,5-dichlorophenoxy)propyl]-N-(4-isopropylphenoxycarbonyl)amino}ethoxy)phenyl]-2-ethoxypropionic acid,
2-ethoxy-3-[4-(2-{N-[4-(4-fluorophenoxy)butyl]-N-(4-isopropylphenoxycarbonyl)amino}ethoxy)phenyl]propionic acid,
3-[4-(2-{N-[4-(3,5-dichlorophenoxy)butyl]-N-(4-isopropylphenoxycarbonyl)amino}ethoxy)phenyl]-2-ethoxypropionic acid,
2-ethoxy-3-[4-(2-{N-[2-(4-fluorobenzyloxy)ethyl]-N-(4-isopropylphenoxycarbonyl)amino}ethoxy)phenyl]propionic acid,
3-[4-(2-{N-[2-(3,5-dichlorobenzyloxy)ethyl]-N-(4-isopropylphenoxycarbonyl)amino}ethoxy)phenyl]-2-ethoxypropionic acid,
2-ethoxy-3-[4-(2-{N-[3-(4-fluorobenzyloxy)propyl]-N-(4-isopropylphenoxycarbonyl)amino}ethoxy)phenyl]propionic acid,
3-[4-(2-{N-[3-(3,5-dichlorobenzyloxy)propyl]-N-(4-isopropylphenoxycarbonyl)amino}ethoxy)phenyl]-2-ethoxypropionic acid,
2-ethoxy-3-[4-(2-{N-[4-(4-fluorobenzyloxy)butyl]-N-(4-isopropylphenoxycarbonyl)amino}ethoxy)phenyl]propionic acid,
3-[4-(2-{N-[4-(3,5-dichlorobenzyloxy)butyl]-N-(4-isopropylphenoxycarbonyl)amino}ethoxy)phenyl]-2-ethoxypropionic acid,
2-ethoxy-3-[4-(2-{N-[3-(4-fluorophenyl)propyl]-N-(4-isopropylphenoxycarbonyl)amino}ethoxy)phenyl]propionic acid,
3-[4-(2-{N-[3-(3,5-dichlorophenyl)propyl]-N-(4-isopropylphenoxycarbonyl)amino}ethoxy)phenyl]-2-ethoxypropionic acid,
2-ethoxy-3-(4-{2-[N-pentyl-N-(4-phenoxyphenoxycarbonyl)amino]ethoxy}phenyl)propionic acid,
2-ethoxy-3-(4-{2-[N-hexyl-N-(4-phenoxyphenoxycarbonyl)amino]ethoxy}phenyl)propionic acid,
2-ethoxy-3-(4-{2-[N-heptyl-N-(4-phenoxyphenoxycarbonyl)amino]ethoxy}phenyl)propionic acid,
2-ethoxy-3-(4-{2-[N-octyl-N-(4-phenoxyphenoxycarbonyl)amino]ethoxy}phenyl)propionic acid,
2-ethoxy-3-(4-{2-[N-isobutyl-N-(4-phenoxyphenoxycarbonyl)amino]ethoxy}phenyl)propionic acid,
2-ethoxy-3-(4-{2-[N-(3-methylbutyl)-N-(4-phenoxyphenoxycarbonyl)amino]ethoxy}phenyl)propionic acid,
2-ethoxy-3-(4-{2-[N-(4-methylpentyl)-N-(4-phenoxyphenoxycarbonyl)amino]ethoxy}phenyl)propionic acid,
2-ethoxy-3-(4-{2-[N-(4-phenoxyphenoxycarbonyl)-N-(2-propylpentyl)amino]ethoxy}phenyl)propionic acid,
3-(4-{2-[N-(3,3-dimethylbutyl)-N-(4-phenoxyphenoxycarbonyl)amino]ethoxy}phenyl)-2-ethoxypropionic acid,
2-ethoxy-3-(4-{2-[N-(2-ethylbutyl)-N-(4-phenoxyphenoxycarbonyl)amino]ethoxy}phenyl)propionic acid,
3-(4-{2-[N-cyclohexylmethyl-N-(4-phenoxyphenoxycarbonyl)amino]ethoxy}phenyl)-2-ethoxypropionic acid,
3-(4-{2-[N-(4-cyclohexylbutyl)-N-(4-phenoxyphenoxycarbonyl)amino]ethoxy}phenyl)-2-ethoxypropionic acid,
3-(4-{2-[N-cyclopropylmethyl-N-(4-phenoxyphenoxycarbonyl)amino]ethoxy}phenyl)-2-ethoxypropionic acid,
3-(4-{2-[N-cyclobutylmethyl-N-(4-phenoxyphenoxycarbonyl)amino]ethoxy}phenyl)-2-ethoxypropionic acid,
3-(4-{2-[N-cyclopentylmethyl-N-(4-phenoxyphenoxycarbonyl)amino]ethoxy}phenyl)-2-ethoxypropionic acid,
3-(4-{2-[N-(2-cyclopentylethyl)-N-(4-phenoxyphenoxycarbonyl)amino]ethoxy}phenyl)-2-ethoxypropionic acid,
3-(4-{2-[N-(3-cyclohexylpropyl)-N-(4-phenoxyphenoxycarbonyl)amino]ethoxy}phenyl)-2-ethoxypropionic acid,
2-ethoxy-3-(4-{2-[N-(4-phenoxyphenoxycarbonyl)-N-(3-phenylpropyl)amino]ethoxy}phenyl)propionic acid,
2-ethoxy-3-(4-{2-[N-(4-phenoxyphenoxycarbonyl)-N-(4-phenylbutyl)amino]ethoxy}phenyl)propionic acid,
3-(4-{2-[N-(2-butoxyethyl)-N-(4-phenoxyphenoxycarbonyl)amino]ethoxy}phenyl)-2-ethoxypropionic acid,
2-ethoxy-3-(4-{2-[N-(2-pentyloxyethyl)-N-(4-phenoxyphenoxycarbonyl)amino]ethoxy}phenyl)propionic acid,
2-ethoxy-3-(4-{2-[N-(4-phenoxyphenoxycarbonyl)-N-(3-propoxypropyl)amino]ethoxy}phenyl)propionic acid,
3-(4-{2-[N-(2-butylthioethyl)-N-(4-phenoxyphenoxycarbonyl)amino]ethoxy}phenyl)-2-ethoxypropionic acid,
2-ethoxy-3-(4-{2-[N-(2-pentylthioethyl)-N-(4-phenoxyphenoxycarbonyl)amino]ethoxy}phenyl)propionic acid,
2-ethoxy-3-(4-{2-[N-(4-phenoxyphenoxycarbonyl)-N-(3-propylthiopropyl)amino]ethoxy}phenyl)propionic acid,
2-ethoxy-3-(4-{2-[N-(4-phenoxyphenoxycarbonyl)-N-(3-phenoxypropyl)amino]ethoxy}phenyl)propionic acid,
2-ethoxy-3-(4-{2-[N-(4-phenoxybutyl)-N-(4-phenoxyphenoxycarbonyl)amino]ethoxy}phenyl)propionic acid,
3-(4-{2-[N-(3-benzyloxypropyl)-N-(4-phenoxyphenoxycarbonyl)amino]ethoxy}phenyl)-2-ethoxypropionic acid,
2-ethoxy-3-(4-{2-[N-(4-phenoxyphenoxycarbonyl)-N-(3-phenylthiopropyl)amino]ethoxy}phenyl)propionic acid,
2-ethoxy-3-(4-{2-[N-(4-phenoxyphenoxycarbonyl)-N-(4-phenylthiobutyl)amino]ethoxy}phenyl)propionic acid,
3-(4-{2-[N-(3-benzylthiopropyl)-N-(4-phenoxyphenoxycarbonyl)amino]ethoxy}phenyl)-2-ethoxypropionic acid,
2-ethoxy-3-(4-{2-[N-(4-phenoxyphenoxycarbonyl)-N-(7,7,7-trifluoroheptyl)amino]ethoxy}phenyl)propionic acid,
3-(4-{2-[N-(6,6-difluoroheptyl)-N-(4-phenoxyphenoxycarbonyl)amino]ethoxy}phenyl)-2-ethoxypropionic acid, 2-ethoxy-3-(4-{2-[N-(4-phenoxyphenoxycarbonyl)-N-(6,6,6-trifluorohexyl)amino]ethoxy}phenyl)propionic acid,
3-(4-{2-[N-(5,5-difluorohexyl)-N-(4-phenoxyphenoxycarbonyl)amino]ethoxy}phenyl)-2-ethoxypropionic acid,
2-ethoxy-3-(4-{2-[N-(5,5,6,6,7,7,7-heptafluoroheptyl)-N-(4-phenoxyphenoxycarbonyl)amino]ethoxy}phenyl)propionic acid,
2-ethoxy-3-(4-{2-[N-(4-phenoxyphenoxycarbonyl)-N-(2,2,3,3,4,4,5,5,6,6,7,7,7-tridecafluoroheptyl)amino]ethoxy}phenyl)propionic acid,
2-ethoxy-3-(4-{2-[N-(5,5,6,6,6-pentafluorohexyl)-N-(4-phenoxyphenoxycarbonyl)amino]ethoxy}phenyl)propionic acid,
2-ethoxy-3-(4-{2-[N-(4-phenoxyphenoxycarbonyl)-N-(2,2,3,3,4,4,5,5,6,6,6-undecafluorohexyl)amino]ethoxy}phenyl)propionic acid,
3-[4-(2-{N-[2-(2,2-difluoropropoxy)ethyl]-N-(4-phenoxyphenoxycarbonyl)amino}ethoxy)phenyl]-2-ethoxypropionic acid,
2-ethoxy-3-[4-(2-{N-[2-(1,1,2,2,3,3,3-heptafluoropropoxy)ethyl]-N-(4-phenoxyphenoxycarbonyl)amino}ethoxy)phenyl]propionic acid,
2-ethoxy-3-[4-(2-{N-(4-phenoxyphenoxycarbonyl)-N-[2-(4,4,4-trifluorobutoxy)ethyl]amino}ethoxy)phenyl]propionic acid,
3-[4-(2-{N-[2-(3,3-difluorobutoxy)ethyl]-N-(4-phenoxyphenoxycarbonyl)amino}ethoxy)phenyl]-2-ethoxypropionic acid,
3-[4-(2-{N-[2-(2,2-difluorobutoxy)ethyl]-N-(4-phenoxyphenoxycarbonyl)amino}ethoxy)phenyl]-2-ethoxypropionic acid,
2-ethoxy-3-[4-(2-{N-[2-(1,1,2,2,3,3,4,4,4-nonafluorobutoxy)ethyl]-N-(4-phenoxyphenoxycarbonyl)amino}ethoxy)phenyl]propionic acid,
2-ethoxy-3-[4-(2-{N-(4-phenoxyphenoxycarbonyl)-N-[3-(2,2,2-trifluoroethoxy)propyl]amino}ethoxy)phenyl]propionic acid,
2-ethoxy-3-[4-(2-{N-[3-(1,1,2,2,2-pentafluoroethoxy)propyl]-N-(4-phenoxyphenoxycarbonyl)amino}ethoxy)phenyl]propionic acid,
2-ethoxy-3-[4-(2-{N-[3-(4-fluorophenoxy)propyl]-N-(4-phenoxyphenoxycarbonyl)amino}ethoxy)phenyl]propionic acid,
3-[4-(2-{N-[3-(3,5-dichlorophenoxy)propyl]-N-(4-phenoxyphenoxycarbonyl)amino}ethoxy)phenyl]-2-ethoxypropionic acid,
2-ethoxy-3-[4-(2-{N-[4-(4-fluorophenoxy)butyl]-N-(4-phenoxyphenoxycarbonyl)amino}ethoxy)phenyl]propionic acid,
3-[4-(2-{N-[4-(3,5-dichlorophenoxy)butyl]-N-(4-phenoxyphenoxycarbonyl)amino}ethoxy)phenyl]-2-ethoxypropionic acid,
2-ethoxy-3-[4-(2-{N-[2-(4-fluorobenzyloxy)ethyl]-N-(4-phenoxyphenoxycarbonyl)amino}ethoxy)phenyl]propionic acid,
3-[4-(2-{N-[2-(3,5-dichlorobenzyloxy)ethyl]-N-(4-phenoxyphenoxycarbonyl)amino}ethoxy)phenyl]-2-ethoxypropionic acid,
2-ethoxy-3-[4-(2-{N-[3-(4-fluorobenzyloxy)propyl]-N-(4-phenoxyphenoxycarbonyl)amino}ethoxy)phenyl]propionic acid,
3-[4-(2-{N-[3-(3,5-dichlorobenzyloxy)propyl]-N-(4-phenoxyphenoxycarbonyl)amino}ethoxy)phenyl]-2-ethoxypropionic acid,
2-ethoxy-3-[4-(2-{N-[4-(4-fluorobenzyloxy)butyl]-N-(4-phenoxyphenoxycarbonyl)amino}ethoxy)phenyl]propionic acid,
3-[4-(2-{N-[4-(3,5-dichlorobenzyloxy)butyl]-N-(4-phenoxyphenoxycarbonyl)amino}ethoxy)phenyl]-2-ethoxypropionic acid,
2-ethoxy-3-[4-(2-{N-[3-(4-fluorophenyl)propyl]-N-(4-phenoxyphenoxycarbonyl)amino}ethoxy)phenyl]propionic acid,
3-[4-(2-{N-[3-(3,5-dichlorophenyl)propyl]-N-(4-phenoxyphenoxycarbonyl)amino}ethoxy)phenyl]-2-ethoxypropionic acid,
2-ethoxy-3-(4-{2-[N-(2-methylphenoxycarbonyl)-N-pentylamino]ethoxy}phenyl)propionic acid,
2-ethoxy-3-(4-{2-[N-hexyl-N-(2-methylphenoxycarbonyl)amino]ethoxy}phenyl)propionic acid,
2-ethoxy-3-(4-{2-[N-heptyl-N-(2-methylphenoxycarbonyl)amino]ethoxy}phenyl)propionic acid,
2-ethoxy-3-(4-{2-[N-(2-methylphenoxycarbonyl)-N-octylamino]ethoxy}phenyl)propionic acid,
2-ethoxy-3-(4-{2-[N-isobutyl-N-(2-methylphenoxycarbonyl)amino]ethoxy}phenyl)propionic acid,
2-ethoxy-3-(4-{2-[N-(3-methylbutyl)-N-(2-methylphenoxycarbonyl)amino]ethoxy}phenyl)propionic acid,
2-ethoxy-3-(4-{2-[N-(4-methylpentyl)-N-(2-methylphenoxycarbonyl)amino]ethoxy}phenyl)propionic acid,
2-ethoxy-3-(4-{2-[N-(2-methylphenoxycarbonyl)-N-(2-propylpentyl)amino]ethoxy}phenyl)propionic acid,
3-(4-{2-[N-(3,3-dimethylbutyl)-N-(2-methylphenoxycarbonyl)amino]ethoxy}phenyl)-2-ethoxypropionic acid,
2-ethoxy-3-(4-{2-[N-(2-ethylbutyl)-N-(2-methylphenoxycarbonyl)amino]ethoxyphenyl)propionic acid,
3-(4-{2-[N-cyclohexylmethyl-N-(2-methylphenoxycarbonyl)amino]ethoxy}phenyl)-2-ethoxypropionic acid,
3-(4-{2-[N-(4-cyclohexylbutyl)-N-(2-methylphenoxycarbonyl)amino]ethoxy}phenyl)-2-ethoxypropionic acid,
3-(4-{2-[N-cyclopropylmethyl-N-(2-methylphenoxycarbonyl)amino]ethoxy}phenyl)-2-ethoxypropionic acid,
3-(4-{2-[N-cyclobutylmethyl-N-(2-methylphenoxycarbonyl)amino]ethoxy}phenyl)-2-ethoxypropionic acid,
3-(4-{2-[N-cyclopentylmethyl-N-(2-methylphenoxycarbonyl)amino]ethoxy}phenyl)-2-ethoxypropionic acid,
3-(4-{2-[N-(2-cyclopentylethyl)-N-(2-methylphenoxycarbonyl)amino]ethoxy}phenyl)-2-ethoxypropionic acid,
3-(4-{2-[N-(3-cyclohexylpropyl)-N-(2-methylphenoxycarbonyl)amino]ethoxy}phenyl)-2-ethoxypropionic acid,
2-ethoxy-3-(4-{2-[N-(2-methylphenoxycarbonyl)-N-(3-phenylpropyl)amino]ethoxy}phenyl)propionic acid,
2-ethoxy-3-(4-{2-[N-(2-methylphenoxycarbonyl)-N-(4-phenylbutyl)amino]ethoxy}phenyl)propionic acid,
3-(4-{2-[N-(2-butoxyethyl)-N-(2-methylphenoxycarbonyl)amino]ethoxy}phenyl)-2-ethoxypropionic acid,
2-ethoxy-3-(4-{2-[N-(2-methylphenoxycarbonyl)-N-(2-pentyloxyethyl)amino]ethoxy}phenyl)propionic acid,
2-ethoxy-3-(4-{2-[N-(2-methylphenoxycarbonyl)-N-(3-propoxypropyl)amino]ethoxy}phenyl)propionic acid,
3-(4-{2-[N-(2-butylthioethyl)-N-(2-methylphenoxycarbonyl)amino]ethoxy}phenyl)-2-ethoxypropionic acid,
2-ethoxy-3-(4-{2-[N-(2-methylphenoxycarbonyl)-N-(2-pentylthioethyl)amino]ethoxy}phenyl)propionic acid,
2-ethoxy-3-(4-{2-[N-(2-methylphenoxycarbonyl)-N-(3-propylthiopropyl)amino]ethoxy}phenyl)propionic acid,
2-ethoxy-3-(4-{2-[N-(2-methylphenoxycarbonyl)-N-(3-phenoxypropyl)amino]ethoxy}phenyl)propionic acid,
2-ethoxy-3-(4-{2-[N-(2-methylphenoxycarbonyl)-N-(4-phenoxybutyl)amino]ethoxy}phenyl)propionic acid,
3-(4-{2-[N-(3-benzyloxypropyl)-N-(2-methylphenoxycarbonyl)amino]ethoxy}phenyl)-2-ethoxypropionic acid,
2-ethoxy-3-(4-{2-[N-(2-methylphenoxycarbonyl)-N-(3-phenylthiopropyl)amino]ethoxy}phenyl)propionic acid, 2-ethoxy-3-(4-{2-[N-(2-methylphenoxycarbonyl)-N-(4-phenylthiobutyl)amino]ethoxy}phenyl)propionic acid,
3-(4-{2-[N-(3-benzylthiopropyl)-N-(2-methylphenoxycarbonyl)amino]ethoxy}phenyl)-2-ethoxypropionic acid,
2-ethoxy-3-(4-{2-[N-(2-methylphenoxycarbonyl)-N-(7,7,7-trifluoroheptyl)amino]ethoxy}phenyl)propionic acid,
3-(4-{2-[N-(6,6-difluoroheptyl)-N-(2-methylphenoxycarbonyl)amino]ethoxy}phenyl)-2-ethoxypropionic acid,
2-ethoxy-3-(4-{2-[N-(2-methylphenoxycarbonyl)-N-(6,6,6-trifluorohexyl)amino]ethoxy}phenyl)propionic acid,
3-(4-{2-[N-(5,5-difluorohexyl)-N-(2-methylphenoxycarbonyl)amino]ethoxy}phenyl)-2-ethoxypropionic acid,
2-ethoxy-3-(4-{2-[N-(5,5,6,6,7,7,7-heptafluoroheptyl)-N-(2-methylphenoxycarbonyl)amino]ethoxy}phenyl)propionic acid,
2-ethoxy-3-(4-{2-[N-(2-methylphenoxycarbonyl)-N-(2,2,3,3,4,4,5,5,6,6,7,7,7-tridecafluoroheptyl)amino]ethoxy}phenyl)propionic acid,
2-ethoxy-3-(4-{2-[N-(2-methylphenoxycarbonyl)-N-(5,5,6,6,6-pentafluorohexyl)amino]ethoxy}phenyl)propionic acid,
2-ethoxy-3-(4-{2-[N-(2-methylphenoxycarbonyl)-N-(2,2,3,3,4,4,5,5,6,6,6-undecafluorohexyl)amino]ethoxy}phenyl)propionic acid,
3-[4-(2-{N-[2-(2,2-difluoropropoxy)ethyl]-N-(2-methylphenoxycarbonyl)amino}ethoxy)phenyl]-2-ethoxypropionic acid,
2-ethoxy-3-[4-(2-{N-[2-(1,1,2,2,3,3,3-heptafluoropropoxy)ethyl]-N-(2-methylphenoxycarbonyl)amino)ethoxy)phenyl]propionic acid,
2-ethoxy-3-[4-(2-{N-(2-methylphenoxycarbonyl)-N-[2-(4,4,4-trifluorobutoxy)ethyl]amino}ethoxy)phenyl]propionic acid,
3-[4-(2-{N-[2-(3,3-difluorobutoxy)ethyl]-N-(2-methylphenoxycarbonyl)amino}ethoxy)phenyl]-2-ethoxypropionic acid,
3-[4-(2-{N-[2-(2,2-difluorobutoxy)ethyl]-N-(2-methylphenoxycarbonyl)amino}ethoxy)phenyl]-2-ethoxypropionic acid,
2-ethoxy-3-[4-(2-{N-(2-methylphenoxycarbonyl)-N-[2-(1,1,2,2,3,3,4,4,4-nonafluorobutoxy)ethyl]amino}ethoxy)phenyl]propionic acid,
2-ethoxy-3-[4-(2-{N-(2-methylphenoxycarbonyl)-N-[3-(2,2,2-trifluoroethoxy)propyl]amino}ethoxy)phenyl]propionic acid,
2-ethoxy-3-[4-(2-{N-(2-methylphenoxycarbonyl)-N-[3-(1,1,2,2,2-pentafluoroethoxy)propyl]amino}ethoxy)phenyl]propionic acid,
2-ethoxy-3-[4-(2-{N-[3-(4-fluorophenoxy)propyl]-N-(2-methylphenoxycarbonyl)amino}ethoxy)phenyl]propionic acid,
3-[4-(2-{N-[3-(3,5-dichlorophenoxy)propyl]-N-(2-methylphenoxycarbonyl)amino}ethoxy)phenyl]-2-ethoxypropionic acid,
2-ethoxy-3-[4-(2-{N-[4-(4-fluorophenoxy)butyl]-N-(2-methylphenoxycarbonyl)amino}ethoxy)phenyl]propionic acid,
3-[4-(2-{N-[4-(3,5-dichlorophenoxy)butyl]-N-(2-methylphenoxycarbonyl)amino}ethoxy)phenyl]-2-ethoxypropionic acid,
2-ethoxy-3-[4-(2-{N-[2-(4-fluorobenzyloxy)ethyl]-N-(2-methylphenoxycarbonyl)amino}ethoxy)phenyl]propionic acid,
3-[4-(2-{N-[2-(3,5-dichlorobenzyloxy)ethyl]-N-(2-methylphenoxycarbonyl)amino}ethoxy)phenyl]-2-ethoxypropionic acid,
2-ethoxy-3-[4-(2-{N-[3-(4-fluorobenzyloxy)propyl]-N-(2-methylphenoxycarbonyl)amino}ethoxy)phenyl]propionic acid,
3-[4-(2-{N-[3-(3,5-dichlorobenzyloxy)propyl]-N-(2-methylphenoxycarbonyl)amino}ethoxy)phenyl]-2-ethoxypropionic acid,
2-ethoxy-3-[4-(2-{N-[4-(4-fluorobenzyloxy)butyl]-N-(2-methylphenoxycarbonyl)amino}ethoxy)phenyl]propionic acid,
3-[4-(2-{N-[4-(3,5-dichlorobenzyloxy)butyl]-N-(2-methylphenoxycarbonyl)amino}ethoxy)phenyl]-2-ethoxypropionic acid,
2-ethoxy-3-[4-(2-{N-[3-(4-fluorophenyl)propyl]-N-(2-methylphenoxycarbonyl)amino}ethoxy)phenyl]propionic acid,
3-[4-(2-(N-[3-(3,5-dichlorophenyl)propyl]-N-(2-methylphenoxycarbonyl)amino}ethoxy)phenyl]-2-ethoxypropionic acid,
2-ethoxy-3-(4-{2-[N-(3-methylphenoxycarbonyl)-N-pentylamino]ethoxy}phenyl)propionic acid,
2-ethoxy-3-(4-{2-[N-hexyl-N-(3-methylphenoxycarbonyl)amino]ethoxy}phenyl)propionic acid,
2-ethoxy-3-(4-{2-[N-heptyl-N-(3-methylphenoxycarbonyl)amino]ethoxy}phenyl)propionic acid,
2-ethoxy-3-(4-{2-[N-(3-methylphenoxycarbonyl)-N-octylamino]ethoxy}phenyl)propionic acid,
2-ethoxy-3-(4-{2-[N-isobutyl-N-(3-methylphenoxycarbonyl)amino]ethoxy}phenyl)propionic acid,
2-ethoxy-3-(4-{2-[N-(3-methylbutyl)-N-(3-methylphenoxycarbonyl)amino]ethoxy}phenyl)propionic acid,
2-ethoxy-3-(4-{2-[N-(4-methylpentyl)-N-(3-methylphenoxycarbonyl)amino]ethoxy}phenyl)propionic acid,
2-ethoxy-3-(4-{2-[N-(3-methylphenoxycarbonyl)-N-(2-propylpentyl)amino]ethoxy}phenyl)propionic acid,
3-(4-{2-[N-(3,3-dimethylbutyl)-N-(3-methylphenoxycarbonyl)amino]ethoxy}phenyl)-2-ethoxypropionic acid,
2-ethoxy-3-(4-{2-[N-(2-ethylbutyl)-N-(3-methylphenoxycarbonyl)amino]ethoxy}phenyl)propionic acid,
3-(4-{2-[N-cyclohexylmethyl-N-(3-methylphenoxycarbonyl)amino]ethoxy}phenyl)-2-ethoxypropionic acid,
3-(4-{2-[N-(4-cyclohexylbutyl)-N-(3-methylphenoxycarbonyl)amino]ethoxy}phenyl)-2-ethoxypropionic acid,
3-(4-{2-[N-cyclopropylmethyl-N-(3-methylphenoxycarbonyl)amino]ethoxy}phenyl)-2-ethoxypropionic acid,
3-(4-{2-[N-cyclobutylmethyl-N-(3-methylphenoxycarbonyl)amino]ethoxy}phenyl)-2-ethoxypropionic acid,
3-(4-{2-[N-cyclopentylmethyl-N-(3-methylphenoxycarbonyl)amino]ethoxy}phenyl)-2-ethoxypropionic acid,
3-(4-{2-[N-(2-cyclopentylethyl)-N-(3-methylphenoxycarbonyl)amino]ethoxy}phenyl)-2-ethoxypropionic acid,
3-(4-{2-[N-(3-cyclohexylpropyl)-N-(3-methylphenoxycarbonyl)amino]ethoxy}phenyl)-2-ethoxypropionic acid,
2-ethoxy-3-(4-{2-[N-(3-methylphenoxycarbonyl)-N-(3-phenylpropyl)amino]ethoxy}phenyl)propionic acid,
2-ethoxy-3-(4-{2-[N-(3-methylphenoxycarbonyl)-N-(4-phenylbutyl)amino]ethoxy}phenyl)propionic acid,
3-(4-{2-[N-(2-butoxyethyl)-N-(3-methylphenoxycarbonyl)amino]ethoxy}phenyl)-2-ethoxypropionic acid,
2-ethoxy-3-(4-{2-[N-(3-methylphenoxycarbonyl)-N-(2-pentyloxyethyl)amino]ethoxy}phenyl)propionic acid,
2-ethoxy-3-(4-{2-[N-(3-methylphenoxycarbonyl)-N-(3-propoxypropyl)amino]ethoxy}phenyl)propionic acid,
3-(4-{2-[N-(2-butylthioethyl)-N-(3-methylphenoxycarbonyl)amino]ethoxy}phenyl)-2-ethoxypropionic acid,
2-ethoxy-3-(4-{2-[N-(3-methylphenoxycarbonyl)-N-(2-pentylthioethyl)amino]ethoxy}phenyl)propionic acid, 2-ethoxy-3-(4-{2-[N-(3-methylphenoxycarbonyl)-N-(3-propylthiopropyl)amino]ethoxy}phenyl)propionic acid,
2-ethoxy-3-(4-{2-[N-(3-methylphenoxycarbonyl)-N-(3-phenoxypropyl)amino]ethoxy}phenyl)propionic acid,
2-ethoxy-3-(4-{2-[N-(3-methylphenoxycarbonyl)-N-(4-phenoxybutyl)amino]ethoxy}phenyl)propionic acid,
3-(4-{2-[N-(3-benzyloxypropyl)-N-(3-methylphenoxycarbonyl)amino]ethoxy}phenyl)-2-ethoxypropionic acid,
2-ethoxy-3-(4-{2-[N-(3-methylphenoxycarbonyl)-N-(3-phenylthiopropyl)amino]ethoxy}phenyl)propionic acid,
2-ethoxy-3-(4-{2-[N-(3-methylphenoxycarbonyl)-N-(4-phenylthiobutyl)amino]ethoxy}phenyl)propionic acid,
3-(4-{2-[N-(3-benzylthiopropyl)-N-(3-methylphenoxycarbonyl)amino]ethoxy}phenyl)-2-ethoxypropionic acid,
2-ethoxy-3-(4-{2-[N-(3-methylphenoxycarbonyl)-N-(7,7,7-trifluoroheptyl)amino]ethoxy}phenyl)propionic acid,
3-(4-{2-[N-(6,6-difluoroheptyl)-N-(3-methylphenoxycarbonyl)amino]ethoxy}phenyl)-2-ethoxypropionic acid,
2-ethoxy-3-(4-{2-[N-(3-methylphenoxycarbonyl)-N-(6,6,6-trifluorohexyl)amino]ethoxy}phenyl)propionic acid,
3-(4-{2-[N-(5,5-difluorohexyl)-N-(3-methylphenoxycarbonyl)amino]ethoxy}phenyl)-2-ethoxypropionic acid,
2-ethoxy-3-(4-{2-[N-(5,5,6,6,7,7,7-heptafluoroheptyl)-N-(3-methylphenoxycarbonyl)amino]ethoxy}phenyl)propionic acid,
2-ethoxy-3-(4-{2-[N-(3-methylphenoxycarbonyl)-N-(2,2,3,3,4,4,5,5,6,6,7,7,7-tridecafluoroheptyl)amino]ethoxy}phenyl)propionic acid,
2-ethoxy-3-(4-{2-[N-(3-methylphenoxycarbonyl)-N-(5,5,6,6,6-pentafluorohexyl)amino]ethoxy}phenyl)propionic acid,
2-ethoxy-3-(4-{2-[N-(3-methylphenoxycarbonyl)-N-(2,2,3,3,4,4,5,5,6,6,6-undecafluorohexyl)amino]ethoxy}phenyl)propionic acid,
3-[4-(2-{N-[2-(2,2-difluoropropoxy)ethyl]-N-(3-methylphenoxycarbonyl)amino}ethoxy)phenyl]-2-ethoxypropionic acid,
2-ethoxy-3-[4-(2-{N-[2-(1,1,2,2,3,3,3-heptafluoropropoxy)ethyl]-N-(3-methylphenoxycarbonyl)amino}ethoxy)phenyl]propionic acid,
2-ethoxy-3-[4-(2-{N-(3-methylphenoxycarbonyl)-N-[2-(4,4,4-trifluorobutoxy)ethyl]amino}ethoxy)phenyl]propionic acid,
3-[4-(2-{N-[2-(3,3-difluorobutoxy)ethyl]-N-(3-methylphenoxycarbonyl)amino}ethoxy)phenyl]-2-ethoxypropionic acid,
3-[4-(2-{N-[2-(2,2-difluorobutoxy)ethyl]-N-(3-methylphenoxycarbonyl)amino}ethoxy)phenyl]-2-ethoxypropionic acid,
2-ethoxy-3-[4-(2-{N-(3-methylphenoxycarbonyl)-N-[2-(1,1,2,2,3,3,4,4,4-nonafluorobutoxy)ethyl]amino}ethoxy)phenyl]propionic acid,
2-ethoxy-3-[4-(2-{N-(3-methylphenoxycarbonyl)-N-[3-(2,2,2-trifluoroethoxy)propyl]amino}ethoxy)phenyl]propionic acid,
2-ethoxy-3-[4-(2-{N-(3-methylphenoxycarbonyl)-N-[3-(1,1,2,2,2-pentafluoroethoxy)propyl]amino}ethoxy)phenyl]propionic acid,
2-ethoxy-3-[4-(2-{N-[3-(4-fluorophenoxy)propyl]-N-(3-methylphenoxycarbonyl)amino}ethoxy)phenyl]propionic acid,
3-[4-(2-{N-[3-(3,5-dichlorophenoxy)propyl]-N-(3-methylphenoxycarbonyl)amino}ethoxy)phenyl]-2-ethoxypropionic acid,
2-ethoxy-3-[4-(2-{N-[4-(4-fluorophenoxy)butyl]-N-(3-methylphenoxycarbonyl)amino}ethoxy)phenyl]propionic acid,
3-[4-(2-{N-[4-(3,5-dichlorophenoxy)butyl]-N-(3-methylphenoxycarbonyl)amino}ethoxy)phenyl]-2-ethoxypropionic acid,
2-ethoxy-3-[4-(2-{N-[2-(4-fluorobenzyloxy)ethyl]-N-(3-methylphenoxycarbonyl)amino}ethoxy)phenyl]propionic acid,
3-[4-(2-{N-[2-(3,5-dichlorobenzyloxy)ethyl]-N-(3-methylphenoxycarbonyl)amino}ethoxy)phenyl]-2-ethoxypropionic acid,
2-ethoxy-3-[4-(2-{N-[3-(4-fluorobenzyloxy)propyl]-N-(3-methylphenoxycarbonyl)amino}ethoxy)phenyl]propionic acid,
3-[4-(2-{N-[3-(3,5-dichlorobenzyloxy)propyl]-N-(3-methylphenoxycarbonyl)amino}ethoxy)phenyl]-2-ethoxypropionic acid,
2-ethoxy-3-[4-(2-{N-[4-(4-fluorobenzyloxy)butyl]-N-(3-methylphenoxycarbonyl)amino}ethoxy)phenyl]propionic acid,
3-[4-(2-{N-[4-(3,5-dichlorobenzyloxy)butyl]-N-(3-methylphenoxycarbonyl)amino}ethoxy)phenyl]-2-ethoxypropionic acid,
2-ethoxy-3-[4-(2-{N-[3-(4-fluorophenyl)propyl]-N-(3-methylphenoxycarbonyl)amino}ethoxy)phenyl]propionic acid,
3-[4-(2-{N-[3-(3,5-dichlorophenyl)propyl]-N-(3-methylphenoxycarbonyl)amino}ethoxy)phenyl]-2-ethoxypropionic acid,
2-ethoxy-3-(4-{2-[N-(4-methylphenoxycarbonyl)-N-pentylamino]ethoxy}phenyl)propionic acid,
2-ethoxy-3-(4-{2-[N-hexyl-N-(4-methylphenoxycarbonyl)amino]ethoxy}phenyl)propionic acid,
2-ethoxy-3-(4-{2-[N-heptyl-N-(4-methylphenoxycarbonyl)amino]ethoxy}phenyl)propionic acid,
2-ethoxy-3-(4-{2-[N-(4-methylphenoxycarbonyl)-N-octylamino]ethoxy}phenyl)propionic acid,
2-ethoxy-3-(4-{2-[N-isobutyl-N-(4-methylphenoxycarbonyl)amino]ethoxy}phenyl)propionic acid,
2-ethoxy-3-(4-{2-[N-(3-methylbutyl)-N-(4-methylphenoxycarbonyl)amino]ethoxy}phenyl)propionic acid,
2-ethoxy-3-(4-{2-[N-(4-methylpentyl)-N-(4-methylphenoxycarbonyl)amino]ethoxy}phenyl)propionic acid,
2-ethoxy-3-(4-{2-[N-(4-methylphenoxycarbonyl)-N-(2-propylpentyl)amino]ethoxy}phenyl)propionic acid,
3-(4-{2-[N-(3,3-dimethylbutyl)-N-(4-methylphenoxycarbonyl)amino]ethoxy}phenyl)-2-ethoxypropionic acid,
2-ethoxy-3-(4-{2-[N-(2-ethylbutyl)-N-(4-methylphenoxycarbonyl)amino]ethoxy}phenyl)propionic acid,
3-(4-{2-[N-cyclohexylmethyl-N-(4-methylphenoxycarbonyl)amino]ethoxy}phenyl)-2-ethoxypropionic acid,
3-(4-{2-[N-(4-cyclohexylbutyl)-N-(4-methylphenoxycarbonyl)amino]ethoxy}phenyl)-2-ethoxypropionic acid,
3-(4-{2-[N-cyclopropylmethyl-N-(4-methylphenoxycarbonyl)amino]ethoxy}phenyl)-2-ethoxypropionic acid,
3-(4-{2-[N-cyclobutylmethyl-N-(4-methylphenoxycarbonyl)amino]ethoxy}phenyl)-2-ethoxypropionic acid,
3-(4-{2-[N-cyclopentylmethyl-N-(4-methylphenoxycarbonyl)amino]ethoxy}phenyl)-2-ethoxypropionic acid,
3-(4-{2-[N-(2-cyclopentylethyl)-N-(4-methylphenoxycarbonyl)amino]ethoxy}phenyl)-2-ethoxypropionic acid,
3-(4-{2-[N-(3-cyclohexylpropyl)-N-(4-methylphenoxycarbonyl)amino]ethoxy}phenyl)-2-ethoxypropionic acid,
2-ethoxy-3-(4-{2-[N-(4-methylphenoxycarbonyl)-N-(3-phenylpropyl)amino]ethoxy}phenyl)propionic acid,
2-ethoxy-3-(4-{2-[N-(4-methylphenoxycarbonyl)-N-(4-phenylbutyl)amino]ethoxy}phenyl)propionic acid,
3-(4-{2-[N-(2-butoxyethyl)-N-(4-methylphenoxycarbonyl)amino]ethoxy}phenyl)-2-ethoxypropionic acid, 2-ethoxy-3-(4-{2-[N-(4-methylphenoxycarbonyl)-N-(2-pentyloxyethyl)amino]ethoxy}phenyl)propionic acid,
2-ethoxy-3-(4-{2-[N-(4-methylphenoxycarbonyl)-N-(3-propoxypropyl)amino]ethoxy}phenyl)propionic acid,
3-(4-{2-[N-(2-butylthioethyl)-N-(4-methylphenoxycarbonyl)amino]ethoxy}phenyl)-2-ethoxypropionic acid,
2-ethoxy-3-(4-{2-[N-(4-methylphenoxycarbonyl)-N-(2-pentylthioethyl)amino]ethoxy}phenyl)propionic acid,
2-ethoxy-3-(4-{2-[N-(4-methylphenoxycarbonyl)-N-(3-propylthiopropyl)amino]ethoxy}phenyl)propionic acid,
2-ethoxy-3-(4-{2-[N-(4-methylphenoxycarbonyl)-N-(3-phenoxypropyl)amino]ethoxy}phenyl)propionic acid,
2-ethoxy-3-(4-{2-[N-(4-methylphenoxycarbonyl)-N-(4-phenoxybutyl)amino]ethoxy}phenyl)propionic acid,
3-(4-{2-[N-(3-benzyloxypropyl)-N-(4-methylphenoxycarbonyl)amino]ethoxy}phenyl)-2-ethoxypropionic acid,
2-ethoxy-3-(4-{2-[N-(4-methylphenoxycarbonyl)-N-(3-phenylthiopropyl)amino]ethoxy}phenyl)propionic acid,
2-ethoxy-3-(4-{2-[N-(4-methylphenoxycarbonyl)-N-(4-phenylthiobutyl)amino]ethoxy}phenyl)propionic acid,
3-(4-{2-[N-(3-benzylthiopropyl)-N-(4-methylphenoxycarbonyl)amino]ethoxy}phenyl)-2-ethoxypropionic acid,
2-ethoxy-3-(4-{2-[N-(4-methylphenoxycarbonyl)-N-(7,7,7-trifluoroheptyl)amino]ethoxy}phenyl)propionic acid,
3-(4-{2-[N-(6,6-difluoroheptyl)-N-(4-methylphenoxycarbonyl)amino]ethoxy}phenyl)-2-ethoxypropionic acid,
2-ethoxy-3-(4-{2-[N-(4-methylphenoxycarbonyl)-N-(6,6,6-trifluorohexyl)amino]ethoxy}phenyl)propionic acid,
3-(4-{2-[N-(5,5-difluorohexyl)-N-(4-methylphenoxycarbonyl)amino]ethoxy}phenyl)-2-ethoxypropionic acid,
2-ethoxy-3-(4-{2-[N-(5,5,6,6,7,7,7-heptafluoroheptyl)-N-(4-methylphenoxycarbonyl)amino]ethoxy}phenyl)propionic acid,
2-ethoxy-3-(4-{2-[N-(4-methylphenoxycarbonyl)-N-(2,2,3,3,4,4,5,5,6,6,7,7,7-tridecafluoroheptyl)amino]ethoxy}phenyl)propionic acid,
2-ethoxy-3-(4-{2-[N-(4-methylphenoxycarbonyl)-N-(5,5,6,6,6-pentafluorohexyl)amino]ethoxy}phenyl)propionic acid,
2-ethoxy-3-(4-{2-[N-(4-methylphenoxycarbonyl)-N-(2,2,3,3,4,4,5,5,6,6,6-undecafluorohexyl)amino]ethoxy}phenyl)propionic acid,
3-[4-(2-{N-[2-(2,2-difluoropropoxy)ethyl]-N-(4-methylphenoxycarbonyl)amino}ethoxy)phenyl]-2-ethoxypropionic acid,
2-ethoxy-3-[4-(2-{N-[2-(1,1,2,2,3,3,3-heptafluoropropoxy)ethyl]-N-(4-methylphenoxycarbonyl)amino}ethoxy)phenyl]propionic acid,
2-ethoxy-3-[4-(2-{N-(4-methylphenoxycarbonyl)-N-[2-(4,4,4-trifluorobutoxy)ethyl]amino}ethoxy)phenyl]propionic acid,
3-[4-(2-{N-[2-(3,3-difluorobutoxy)ethyl]-N-(4-methylphenoxycarbonyl)amino}ethoxy)phenyl]-2-ethoxypropionic acid,
3-[4-(2-{N-[2-(2,2-difluorobutoxy)ethyl]-N-(4-methylphenoxycarbonyl)amino}ethoxy)phenyl]-2-ethoxypropionic acid,
2-ethoxy-3-[4-(2-{N-(4-methylphenoxycarbonyl)-N-[2-(1,1,2,2,3,3,4,4,4-nonafluorobutoxy)ethyl]amino}ethoxy)phenyl]propionic acid,
2-ethoxy-3-[4-(2-{N-(4-methylphenoxycarbonyl)-N-[3-(2,2,2-trifluoroethoxy)propyl]amino}ethoxy)phenyl]propionic acid,
2-ethoxy-3-[4-(2-{N-(4-methylphenoxycarbonyl)-N-[3-(1,1,2,2,2-pentafluoroethoxy)propyl]amino}ethoxy)phenyl]propionic acid,
2-ethoxy-3-[4-(2-{N-[3-(4-fluorophenoxy)propyl]-N-(4-methylphenoxycarbonyl)amino}ethoxy)phenyl]propionic acid,
3-[4-(2-{N-[3-(3,5-dichlorophenoxy)propyl]-N-(4-methylphenoxycarbonyl)amino}ethoxy)phenyl]-2-ethoxypropionic acid,
2-ethoxy-3-[4-(2-{N-[4-(4-fluorophenoxy)butyl]-N-(4-methylphenoxycarbonyl)amino}ethoxy)phenyl]propionic acid,
3-[4-(2-{N-[4-(3,5-dichlorophenoxy)butyl]-N-(4-methylphenoxycarbonyl)amino}ethoxy)phenyl]-2-ethoxypropionic acid,
2-ethoxy-3-[4-(2-{N-[2-(4-fluorobenzyloxy)ethyl]-N-(4-methylphenoxycarbonyl)amino}ethoxy)phenyl]propionic acid,
3-[4-(2-{N-[2-(3,5-dichlorobenzyloxy)ethyl]-N-(4-methylphenoxycarbonyl)amino}ethoxy)phenyl]-2-ethoxypropionic acid,
2-ethoxy-3-[4-(2-{N-[3-(4-fluorobenzyloxy)propyl]-N-(4-methylphenoxycarbonyl)amino}ethoxy)phenyl]propionic acid,
3-[4-(2-{N-[3-(3,5-dichlorobenzyloxy)propyl]-N-(4-methylphenoxycarbonyl)amino}ethoxy)phenyl]-2-ethoxypropionic acid,
2-ethoxy-3-[4-(2-{N-[4-(4-fluorobenzyloxy)butyl]-N-(4-methylphenoxycarbonyl)amino}ethoxy)phenyl]propionic acid,
3-[4-(2-{N-[4-(3,5-dichlorobenzyloxy)butyl]-N-(4-methylphenoxycarbonyl)amino}ethoxy)phenyl]-2-ethoxypropionic acid,
2-ethoxy-3-[4-(2-{N-[3-(4-fluorophenyl)propyl]-N-(4-methylphenoxycarbonyl)amino}ethoxy)phenyl]propionic acid,
3-[4-(2-{N-[3-(3,5-dichlorophenyl)propyl]-N-(4-methylphenoxycarbonyl)amino}ethoxy)phenyl]-2-ethoxypropionic acid,
2-ethoxy-3-(4-{2-[N-pentyl-N-(2,4,5-trimethylphenoxycarbonyl)amino]ethoxy}phenyl)propionic acid,
2-ethoxy-3-(4-{2-[N-hexyl-N-(2,4,5-trimethylphenoxycarbonyl)amino]ethoxy}phenyl)propionic acid,
2-ethoxy-3-(4-{2-[N-heptyl-N-(2,4,5-trimethylphenoxycarbonyl)amino]ethoxy}phenyl)propionic acid,
2-ethoxy-3-(4-{2-[N-octyl-N-(2,4,5-trimethylphenoxycarbonyl)amino]ethoxy}phenyl)propionic acid,
2-ethoxy-3-(4-{2-[N-isobutyl-N-(2,4,5-trimethylphenoxycarbonyl)amino]ethoxy}phenyl)propionic acid,
2-ethoxy-3-(4-{2-[N-(3-methylbutyl)-N-(2,4,5-trimethylphenoxycarbonyl)amino]ethoxy}phenyl)propionic acid,
2-ethoxy-3-(4-{2-[N-(4-methylpentyl)-N-(2,4,5-trimethylphenoxycarbonyl)amino]ethoxy}phenyl)propionic acid,
2-ethoxy-3-(4-{2-[N-(2-propylpentyl)-N-(2,4,5-trimethylphenoxycarbonyl)amino]ethoxy}phenyl)propionic acid,
3-(4-{2-[N-(3,3-dimethylbutyl)-N-(2,4,5-trimethylphenoxycarbonyl)amino]ethoxy}phenyl)-2-ethoxypropionic acid,
2-ethoxy-3-(4-{2-[N-(2-ethylbutyl)-N-(2,4,5-trimethylphenoxycarbonyl)amino]ethoxy}phenyl)propionic acid,
3-(4-{2-[N-cyclohexylmethyl-N-(2,4,5-trimethylphenoxycarbonyl)amino]ethoxy}phenyl)-2-ethoxypropionic acid,
3-(4-{2-[N-(4-cyclohexylbutyl)-N-(2,4,5-trimethylphenoxycarbonyl)amino]ethoxy}phenyl)-2-ethoxypropionic acid,
3-(4-{2-[N-cyclopropylmethyl-N-(2,4,5-trimethylphenoxycarbonyl)amino]ethoxy}phenyl)-2-ethoxypropionic acid, 3-(4-{2-[N-cyclobutylmethyl-N-(2,4,5-trimethylphenoxycarbonyl)amino]ethoxy}phenyl)-2-ethoxypropionic acid,
3-(4-{2-[N-cyclopentylmethyl-N-(2,4,5-trimethylphenoxycarbonyl)amino]ethoxy}phenyl)-2-ethoxypropionic acid,
3-(4-{2-[N-(2-cyclopentylethyl)-N-(2,4,5-trimethylphenoxycarbonyl)amino]ethoxy}phenyl)-2-ethoxypropionic acid,
3-(4-{2-[N-(3-cyclohexylpropyl)-N-(2,4,5-trimethylphenoxycarbonyl)amino]ethoxy}phenyl)-2-ethoxypropionic acid,
2-ethoxy-3-(4-{2-[N-(3-phenylpropyl)-N-(2,4,5-trimethylphenoxycarbonyl)amino]ethoxy}phenyl)propionic acid,
2-ethoxy-3-(4-{2-[N-(4-phenylbutyl)-N-(2,4,5-trimethylphenoxycarbonyl)amino]ethoxy}phenyl)propionic acid,
3-(4-{2-[N-(2-butoxyethyl)-N-(2,4,5-trimethylphenoxycarbonyl)amino]ethoxy}phenyl)-2-ethoxypropionic acid,
2-ethoxy-3-(4-{2-[N-(2-pentyloxyethyl)-N-(2,4,5-trimethylphenoxycarbonyl)amino]ethoxy}phenyl)propionic acid,
2-ethoxy-3-(4-{2-[N-(3-propoxypropyl)-N-(2,4,5-trimethylphenoxycarbonyl)amino]ethoxy}phenyl)propionic acid,
3-(4-{2-[N-(2-butylthioethyl)-N-(2,4,5-trimethylphenoxycarbonyl)amino]ethoxy}phenyl)-2-ethoxypropionic acid,
2-ethoxy-3-(4-{2-[N-(2-pentylthioethyl)-N-(2,4,5-trimethylphenoxycarbonyl)amino]ethoxy}phenyl)propionic acid,
2-ethoxy-3-(4-{2-[N-(3-propylthiopropyl)-N-(2,4,5-trimethylphenoxycarbonyl)amino]ethoxy}phenyl)propionic acid,
2-ethoxy-3-(4-{2-[N-(3-phenoxypropyl)-N-(2,4,5-trimethylphenoxycarbonyl)amino]ethoxy}phenyl)propionic acid,
2-ethoxy-3-(4-{2-[N-(4-phenoxybutyl)-N-(2,4,5-trimethylphenoxycarbonyl)amino]ethoxy}phenyl)propionic acid,
3-(4-{2-[N-(3-benzyloxypropyl)-N-(2,4,5-trimethylphenoxycarbonyl)amino]ethoxy}phenyl)-2-ethoxypropionic acid,
2-ethoxy-3-(4-{2-[N-(3-phenylthiopropyl)-N-(2,4,5-trimethylphenoxycarbonyl)amino]ethoxy}phenyl)propionic acid,
2-ethoxy-3-(4-{2-[N-(4-phenylthiobutyl)-N-(2,4,5-trimethylphenoxycarbonyl)amino]ethoxy}phenyl)propionic acid,
3-(4-{2-[N-(3-benzylthiopropyl)-N-(2,4,5-trimethylphenoxycarbonyl)amino]ethoxy}phenyl)-2-ethoxypropionic acid,
2-ethoxy-3-(4-{2-[N-(7,7,7-trifluoroheptyl)-N-(2,4,5-trimethylphenoxycarbonyl)amino]ethoxy}phenyl)propionic acid,
3-(4-{2-[N-(6,6-difluoroheptyl)-N-(2,4,5-trimethylphenoxycarbonyl)amino]ethoxy}phenyl)-2-ethoxypropionic acid,
2-ethoxy-3-(4-{2-[N-(6,6,6-trifluorohexyl)-N-(2,4,5-trimethylphenoxycarbonyl)amino]ethoxy}phenyl)propionic acid,
3-(4-{2-[N-(5,5-difluorohexyl)-N-(2,4,5-trimethylphenoxycarbonyl)amino]ethoxy}phenyl)-2-ethoxypropionic acid,
2-ethoxy-3-(4-{2-[N-(5,5,6,6,7,7,7-heptafluoroheptyl)-N-(2,4,5-trimethylphenoxycarbonyl)amino]ethoxy}phenyl)propionic acid,
2-ethoxy-3-(4-{2-[N-(2,2,3,3,4,4,5,5,6,6,7,7,7-tridecafluoroheptyl)-N-(2,4,5 -trimethylphenoxycarbonyl)amino]ethoxy}phenyl)propionic acid,
2-ethoxy-3-(4-{2-[N-(5,5,6,6,6-pentafluorohexyl)-N-(2,4,5-trimethylphenoxycarbonyl)amino]ethoxy}phenyl)propionic acid,
2-ethoxy-3-(4-{2-[N-(2,4,5-trimethylphenoxycarbonyl)-N-(2,2,3,3,4,4,5,5,6,6,6-undecafluorohexyl)amino]ethoxy}phenyl)propionic acid,
3-[4-(2-{N-[2-(2,2-difluoropropoxy)ethyl]-N-(2,4,5-trimethylphenoxycarbonyl)amino}ethoxy)phenyl]-2-ethoxypropionic acid,
2-ethoxy-3-[4-(2-{N-[2-(1,1,2,2,3,3,3-heptafluoropropoxy)ethyl]-N-(2,4,5-trimethylphenoxycarbonyl)amino}ethoxy)phenyl]propionic acid,
2-ethoxy-3-[4-(2-{N-[2-(4,4,4-trifluorobutoxy)ethyl]-N-(2,4,5-trimethylphenoxycarbonyl)amino}ethoxy)phenyl]propionic acid,
3-[4-(2-{N-[2-(3,3-difluorobutoxy)ethyl]-N-(2,4,5-trimethylphenoxycarbonyl)amino}ethoxy)phenyl]-2-ethoxypropionic acid,
3-[4-(2-{N-[2-(2,2-difluorobutoxy)ethyl]-N-(2,4,5-trimethylphenoxycarbonyl)amino}ethoxy)phenyl]-2-ethoxypropionic acid,
2-ethoxy-3-[4-(2-{N-[2-(1,1,2,2,3,3,4,4,4-nonafluorobutoxy)ethyl]-N-(2,4,5-trimethylphenoxycarbonyl)amino}ethoxy)phenyl]propionic acid,
2-ethoxy-3-[4-(2-{N-[3-(2,2,2-trifluoroethoxy)propyl]-N-(2,4,5-trimethylphenoxycarbonyl)amino}ethoxy)phenyl]propionic acid,
2-ethoxy-3-[4-(2-{N-[3-(1,1,2,2,2-pentafluoroethoxy)propyl]-N-(2,4,5-trimethylphenoxycarbonyl)amino}ethoxy)phenyl]propionic acid,
2-ethoxy-3-[4-(2-{N-[3-(4-fluorophenoxy)propyl]-N-(2,4,5-trimethylphenoxycarbonyl)amino}ethoxy)phenyl]propionic acid,
3-[4-(2-{N-[3-(3,5-dichlorophenoxy)propyl]-N-(2,4,5-trimethylphenoxycarbonyl)amino}ethoxy)phenyl]-2-ethoxypropionic acid,
2-ethoxy-3-[4-(2-{N-[4-(4-fluorophenoxy)butyl]-N-(2,4,5-trimethylphenoxycarbonyl)amino}ethoxy)phenyl]propionic acid,
3-[4-(2-{N-[4-(3,5-dichlorophenoxy)butyl]-N-(2,4,5-trimethylphenoxycarbonyl)amino}ethoxy)phenyl]-2-ethoxypropionic acid,
2-ethoxy-3-[4-(2-{N-[2-(4-fluorobenzyloxy)ethyl]-N-(2,4,5-trimethylphenoxycarbonyl)amino}ethoxy)phenyl]propionic acid,
3-[4-(2-{N-[2-(3,5-dichlorobenzyloxy)ethyl]-N-(2,4,5-trimethylphenoxycarbonyl)amino}ethoxy)phenyl]-2-ethoxypropionic acid,
2-ethoxy-3-[4-(2-{N-[3-(4-fluorobenzyloxy)propyl]-N-(2,4,5-trimethylphenoxycarbonyl)amino}ethoxy)phenyl]propionic acid,
3-[4-(2-{N-[3-(3,5-dichlorobenzyloxy)propyl]-N-(2,4,5-trimethylphenoxycarbonyl)amino}ethoxy)phenyl]-2-ethoxypropionic acid,
2-ethoxy-3-[4-(2-{N-[4-(4-fluorobenzyloxy)butyl]-N-(2,4,5-trimethylphenoxycarbonyl)amino}ethoxy)phenyl]propionic acid,
3-[4-(2-{N-[4-(3,5-dichlorobenzyloxy)butyl]-N-(2,4,5-trimethylphenoxycarbonyl)amino}ethoxy)phenyl]-2-ethoxypropionic acid,
2-ethoxy-3-[4-(2-(N-[3-(4-fluorophenyl)propyl]-N-(2,4,5-trimethylphenoxycarbonyl)amino}ethoxy)phenyl]propionic acid,
3-[4-(2-{N-[3-(3,5-dichlorophenyl)propyl]-N-(2,4,5-trimethylphenoxycarbonyl)amino}ethoxy)phenyl]-2-ethoxypropionic acid, 2-ethoxy-3-(4-{2-[N-pentyl-N-(2,4,6-trimethylphenoxycarbonyl)amino]ethoxy}phenyl)propionic acid,
2-ethoxy-3-(4-{2-[N-hexyl-N-(2,4,6-trimethylphenoxycarbonyl)amino]ethoxy)phenyl)propionic acid,
2-ethoxy-3-(4-{2-[N-heptyl-N-(2,4,6-trimethylphenoxycarbonyl)amino]ethoxy}phenyl)propionic acid,
2-ethoxy-3-(4-{2-[N-octyl-N-(2,4,6-trimethylphenoxycarbonyl)amino]ethoxy}phenyl)propionic acid,
2-ethoxy-3-(4-{2-[N-isobutyl-N-(2,4,6-trimethylphenoxycarbonyl)amino]ethoxy}phenyl)propionic acid,
2-ethoxy-3-(4-{2-[N-(3-methylbutyl)-N-(2,4,6-trimethylphenoxycarbonyl)amino]ethoxy}phenyl)propionic acid,
2-ethoxy-3-(4-{2-[N-(4-methylpentyl)-N-(2,4,6-trimethylphenoxycarbonyl)amino]ethoxy}phenyl)propionic acid,
2-ethoxy-3-(4-{2-[N-(2-propylpentyl)-N-(2,4,6-trimethylphenoxycarbonyl)amino]ethoxy}phenyl)propionic acid,
3-(4-{2-[N-(3,3-dimethylbutyl)-N-(2,4,6-trimethylphenoxycarbonyl)amino]ethoxy}phenyl)-2-ethoxypropionic acid,
2-ethoxy-3-(4-{2-[N-(2-ethylbutyl)-N-(2,4,6-trimethylphenoxycarbonyl)amino]ethoxy}phenyl)propionic acid,
3-(4-{2-[N-cyclohexylmethyl-N-(2,4,6 -trimethylphenoxycarbonyl)amino ethoxy}phenyl)-2-ethoxypropionic acid,
3-(4-{2-[N-(4-cyclohexylbutyl)-N-(2,4,6-trimethylphenoxycarbonyl)amino]ethoxy}phenyl)-2-ethoxypropionic acid,
3-(4-{2-[N-cyclopropylmethyl-N-(2,4,6-trimethylphenoxycarbonyl)amino]ethoxy}phenyl)-2-ethoxypropionic acid,
3-(4-{2-[N-cyclobutylmethyl-N-(2,4,6-trimethylphenoxycarbonyl)amino]ethoxy}phenyl)-2-ethoxypropionic acid,
3-(4-{2-[N-cyclopentylmethyl-N-(2,4,6-trimethylphenoxycarbonyl)amino]ethoxy}phenyl)-2-ethoxypropionic acid,
3-(4-{2-[N-(2-cyclopentylethyl)-N-(2,4,6-trimethylphenoxycarbonyl)amino]ethoxy}phenyl)-2-ethoxypropionic acid,
3-(4-{2-[N-(3-cyclohexylpropyl)-N-(2,4,6-trimethylphenoxycarbonyl)amino]ethoxy}phenyl)-2-ethoxypropionic acid,
2-ethoxy-3-(4-{2-[N-(3-phenylpropyl)-N-(2,4,6-trimethylphenoxycarbonyl)amino]ethoxy}phenyl)propionic acid,
2-ethoxy-3-(4-{2-[N-(4-phenylbutyl)-N-(2,4,6-trimethylphenoxycarbonyl)amino]ethoxy}phenyl)propionic acid,
3-(4-{2-[N-(2-butoxyethyl)-N-(2,4,6-trimethylphenoxycarbonyl)amino]ethoxy}phenyl)-2-ethoxypropionic acid,
2-ethoxy-3-(4-{2-[N-(2-pentyloxyethyl)-N-(2,4,6-trimethylphenoxycarbonyl)amino]ethoxy}phenyl)propionic acid,
2-ethoxy-3-(4-{2-[N-(3-propoxypropyl)-N-(2,4,6-trimethylphenoxycarbonyl)amino]ethoxy}phenyl)propionic acid,
3-(4-{2-[N-(2-butylthioethyl)-N-(2,4,6-trimethylphenoxycarbonyl)amino]ethoxy}phenyl)-2-ethoxypropionic acid,
2-ethoxy-3-(4-{2-[N-(2-pentylthioethyl)-N-(2,4,6-trimethylphenoxycarbonyl)amino]ethoxy}phenyl)propionic acid,
2-ethoxy-3-(4-{2-[N-(3-propylthiopropyl)-N-(2,4,6-trimethylphenoxycarbonyl)amino]ethoxy}phenyl)propionic acid,
2-ethoxy-3-(4-{2-[N-(3-phenoxypropyl)-N-(2,4,6-trimethylphenoxycarbonyl)amino]ethoxy}phenyl)propionic acid,
2-ethoxy-3-(4-{2-[N-(4-phenoxybutyl)-N-(2,4,6-trimethylphenoxycarbonyl)amino]ethoxy}phenyl)propionic acid,
3-(4-{2-[N-(3-benzyloxypropyl)-N-(2,4,6-trimethylphenoxycarbonyl)amino]ethoxy}phenyl)-2-ethoxypropionic acid,
2-ethoxy-3-(4-{2-[N-(3-phenylthiopropyl)-N-(2,4,6-trimethylphenoxycarbonyl)amino]ethoxy}phenyl)propionic acid,
2-ethoxy-3-(4-{2-[N-(4-phenylthiobutyl)-N-(2,4,6-trimethylphenoxycarbonyl)amino]ethoxy}phenyl)propionic acid,
3-(4-{2-[N-(3-benzylthiopropyl)-N-(2,4,6-trimethylphenoxycarbonyl)amino]ethoxy}phenyl)-2-ethoxypropionic acid,
2-ethoxy-3-(4-{2-[N-(7,7,7-trifluoroheptyl)-N-(2,4,6-trimethylphenoxycarbonyl)amino]ethoxy}phenyl)propionic acid,
3-(4-{2-[N-(6,6-difluoroheptyl)-N-(2,4,6-trimethylphenoxycarbonyl)amino]ethoxy}phenyl)-2-ethoxypropionic acid,
2-ethoxy-3-(4-{2-[N-(6,6,6-trifluorohexyl)-N-(2,4,6-trimethylphenoxycarbonyl)amino]ethoxy}phenyl)propionic acid,
3-(4-{2-[N-(5,5-difluorohexyl)-N-(2,4,6-trimethylphenoxycarbonyl)amino]ethoxy}phenyl)-2-ethoxypropionic acid,
2-ethoxy-3-(4-{2-[N-(5,5,6,6,7,7,7-heptafluoroheptyl)-N-(2,4,6-trimethylphenoxycarbonyl)amino]ethoxy}phenyl)propionic acid,
2-ethoxy-3-(4-{2-[N-(2,2,3,3,4,4,5,5,6,6,7,7,7-tridecafluoroheptyl)-N-(2,4,6-trimethylphenoxycarbonyl)amino]ethoxy}phenyl)propionic acid,
2-ethoxy-3-(4-{2-[N-(5,5,6,6,6-pentafluorohexyl)-N-(2,4,6-trimethylphenoxycarbonyl)amino]ethoxy}phenyl)propionic acid,
2-ethoxy-3-(4-{2-[N-(2,4,6-trimethylphenoxycarbonyl)-N-(2,2,3,3,4,4,5,5,6,6,6-undecafluorohexyl)amino]ethoxy}phenyl)propionic acid,
3-[4-(2-{N-[2-(2,2-difluoropropoxy)ethyl]-N-(2,4,6-trimethylphenoxycarbonyl)amino}ethoxy)phenyl]-2-ethoxypropionic acid,
2-ethoxy-3-[4-(2-{N-[2-(1,1,2,2,3,3,3-heptafluoropropoxy)ethyl]-N-(2,4,6-trimethylphenoxycarbonyl)amino}ethoxy)phenyl]propionic acid,
2-ethoxy-3-[4-(2-{N-[2-(4,4,4-trifluorobutoxy)ethyl]-N-(2,4,6-trimethylphenoxycarbonyl)amino}ethoxy)phenyl]propionic acid,
3-[4-(2-{N-[2-(3,3-difluorobutoxy)ethyl]-N-(2,4,6-trimethylphenoxycarbonyl)amino}ethoxy)phenyl]-2-ethoxypropionic acid,
3-[4-(2-{N-[2-(2,2-difluorobutoxy)ethyl]-N-(2,4,6 -trimethylphenoxycarbonyl)amino}ethoxy)phenyl]-2-ethoxypropionic acid,
2-ethoxy-3-[4-(2-{N-[2-(1,1,2,2,3,3,4,4,4-nonafluorobutoxy)ethyl]-N-(2,4,6-trimethylphenoxycarbonyl)amino}ethoxy)phenyl]propionic acid,
2-ethoxy-3-[4-(2-{N-[3-(2,2,2-trifluoroethoxy)propyl]-N-(2,4,6-trimethylphenoxycarbonyl)amino}ethoxy)phenyl]propionic acid,
2-ethoxy-3-[4-(2-{N-[3-(1,1,2,2,2-pentafluoroethoxy)propyl]-N-(2,4,6-trimethylphenoxycarbonyl)amino}ethoxy)phenyl]propionic acid,
2-ethoxy-3-[4-(2-{N-[3-(4-fluorophenoxy)propyl]-N-(2,4,6-trimethylphenoxycarbonyl)amino}ethoxy)phenyl]propionic acid, 3-[4-(2-{N-[3-(3,5-dichlorophenoxy)propyl]-N-(2,4,6-trimethylphenoxycarbonyl)amino}ethoxy)phenyl]-2-ethoxypropionic acid,
2-ethoxy-3-[4-(2-{N-[4-(4-fluorophenoxy)butyl]-N-(2,4,6-trimethylphenoxycarbonyl)amino}ethoxy)phenyl]propionic acid,
3-[4-(2-{N-[4-(3,5-dichlorophenoxy)butyl]-N-(2,4,6-trimethylphenoxycarbonyl)amino}ethoxy)phenyl]-2-ethoxypropionic acid,
2-ethoxy-3-[4-(2-{N-[2-(4-fluorobenzyloxy)ethyl]-N-(2,4,6-trimethylphenoxycarbonyl)amino}ethoxy)phenyl]propionic acid,
3-[4-(2-{N-[2-(3,5-dichlorobenzyloxy)ethyl]-N-(2,4,6-trimethylphenoxycarbonyl)amino}ethoxy)phenyl]-2-ethoxypropionic acid,
2-ethoxy-3-[4-(2-{N-[3-(4-fluorobenzyloxy)propyl]-N-(2,4,6-trimethylphenoxycarbonyl)amino}ethoxy)phenyl]propionic acid,
3-[4-(2-{N-[3-(3,5-dichlorobenzyloxy)propyl]-N-(2,4,6-trimethylphenoxycarbonyl)amino}ethoxy)phenyl]-2-ethoxypropionic acid,
2-ethoxy-3-[4-(2-{N-[4-(4-fluorobenzyloxy)butyl]-N-(2,4,6-trimethylphenoxycarbonyl)amino}ethoxy)phenyl]propionic acid,
3-[4-(2-{N-[4-(3,5-dichlorobenzyloxy)butyl]-N-(2,4,6-trimethylphenoxycarbonyl)amino}ethoxy)phenyl]-2-ethoxypropionic acid,
2-ethoxy-3-[4-(2-{N-[3-(4-fluorophenyl)propyl]-N-(2,4,6-trimethylphenoxycarbonyl)amino}ethoxy)phenyl]propionic acid,
3-[4-(2-{N-[3-(3,5-dichlorophenyl)propyl]-N-(2,4,6-trimethylphenoxycarbonyl)amino}ethoxy)phenyl]-2-ethoxypropionic acid,
2-ethoxy-3-(4-{2-[N-pentyl-N-(2-trifluoromethylphenoxycarbonyl)amino]ethoxy}phenyl)propionic acid,
2-ethoxy-3-(4-{2-[N-hexyl-N-(2-trifluoromethylphenoxycarbonyl)amino]ethoxy}phenyl)propionic acid,
2-ethoxy-3-(4-{2-[N-heptyl-N-(2-trifluoromethylphenoxycarbonyl)amino]ethoxy}phenyl)propionic acid,
2-ethoxy-3-(4-{2-[N-octyl-N-(2-trifluoromethylphenoxycarbonyl)amino]ethoxy}phenyl)propionic acid,
2-ethoxy-3-(4-{2-[N-isobutyl-N-(2-trifluoromethylphenoxycarbonyl)amino]ethoxy}phenyl)propionic acid,
2-ethoxy-3-(4-{2-[N-(3-methylbutyl)-N-(2-trifluoromethylphenoxycarbonyl)amino]ethoxy}phenyl)propionic acid,
2-ethoxy-3-(4-{2-[N-(4-methylpentyl)-N-(2-trifluoromethylphenoxycarbonyl)amino]ethoxy}phenyl)propionic acid,
2-ethoxy-3-(4-{2-[N-(2-propylpentyl)-N-(2-trifluoromethylphenoxycarbonyl)amino]ethoxy}phenyl)propionic acid,
3-(4-{2-[N-(3,3-dimethylbutyl)-N-(2-trifluoromethylphenoxycarbonyl)amino]ethoxy}phenyl)-2-ethoxypropionic acid,
2-ethoxy-3-(4-{2-[N-(2-ethylbutyl)-N-(2-trifluoromethylphenoxycarbonyl)amino]ethoxy}phenyl)propionic acid,
3-(4-{2-[N-cyclohexylmethyl-N-(2-trifluoromethylphenoxycarbonyl)amino]ethoxy}phenyl)-2-ethoxypropionic acid,
3-(4-{2-[N-(4-cyclohexylbutyl)-N-(2-trifluoromethylphenoxycarbonyl)amino]ethoxy}phenyl)-2-ethoxypropionic acid,
3-(4-{2-[N-cyclopropylmethyl-N-(2-trifluoromethylphenoxycarbonyl)amino]ethoxy}phenyl)-2-ethoxypropionic acid,
3-(4-{2-[N-cyclobutylmethyl-N-(2-trifluoromethylphenoxycarbonyl)amino]ethoxy}phenyl)-2-ethoxypropionic acid,
3-(4-{2-[N-cyclopentylmethyl-N-(2-trifluoromethylphenoxycarbonyl)amino]ethoxy}phenyl)-2-ethoxypropionic acid,
3-(4-{2-[N-(2-cyclopentylethyl)-N-(2-trifluoromethylphenoxycarbonyl)amino]ethoxy}phenyl)-2-ethoxypropionic acid,
3-(4-{2-[N-(3-cyclohexylpropyl)-N-(2-trifluoromethylphenoxycarbonyl)amino]ethoxy}phenyl)-2-ethoxypropionic acid,
2-ethoxy-3-(4-{2-[N-(3-phenylpropyl)-N-(2-trifluoromethylphenoxycarbonyl)amino]ethoxy}phenyl)propionic acid,
2-ethoxy-3-(4-{2-[N-(4-phenylbutyl)-N-(2-trifluoromethylphenoxycarbonyl)amino]ethoxy}phenyl)propionic acid,
3-(4-{2-[N-(2-butoxyethyl)-N-(2-trifluoromethylphenoxycarbonyl)amino]ethoxy}phenyl)-2-ethoxypropionic acid,
2-ethoxy-3-(4-{2-[N-(2-pentyloxyethyl)-N-(2-trifluoromethylphenoxycarbonyl)amino]ethoxy}phenyl)propionic acid,
2-ethoxy-3-(4-{2-[N-(3-propoxypropyl)-N-(2-trifluoromethylphenoxycarbonyl)amino]ethoxy}phenyl)propionic acid,
3-(4-{2-[N-(2-butylthioethyl)-N-(2-trifluoromethylphenoxycarbonyl)amino]ethoxy}phenyl)-2-ethoxypropionic acid,
2-ethoxy-3-(4-{2-[N-(2-pentylthioethyl)-N-(2-trifluoromethylphenoxycarbonyl)amino]ethoxy}phenyl)propionic acid,
2-ethoxy-3-(4-{2-[N-(3-propylthiopropyl)-N-(2-trifluoromethylphenoxycarbonyl)amino]ethoxy}phenyl)propionic acid,
2-ethoxy-3-(4-{2-[N-(3-phenoxypropyl)-N-(2-trifluoromethylphenoxycarbonyl)amino]ethoxy}phenyl)propionic acid,
2-ethoxy-3-(4-{2-[N-(4-phenoxybutyl)-N-(2-trifluoromethylphenoxycarbonyl)amino]ethoxy}phenyl)propionic acid,
3-(4-{2-[N-(3-benzyloxypropyl)-N-(2-trifluoromethylphenoxycarbonyl)amino]ethoxy}phenyl)-2-ethoxypropionic acid,
2-ethoxy-3-(4-{2-[N-(3-phenylthiopropyl)-N-(2-trifluoromethylphenoxycarbonyl)amino]ethoxy}phenyl)propionic acid,
2-ethoxy-3-(4-{2-[N-(4-phenylthiobutyl)-N-(2-trifluoromethylphenoxycarbonyl)amino]ethoxy}phenyl)propionic acid,
3-(4-{2-[N-(3-benzylthiopropyl)-N-(2-trifluoromethylphenoxycarbonyl)amino]ethoxy}phenyl)-2-ethoxypropionic acid,
2-ethoxy-3-(4-{2-[N-(7,7,7-trifluoroheptyl)-N-(2-trifluoromethylphenoxycarbonyl)amino]ethoxy}phenyl)propionic acid,
3-(4-{2-[N-(6,6-difluoroheptyl)-N-(2-trifluoromethylphenoxycarbonyl)amino]ethoxy}phenyl)-2-ethoxypropionic acid,
2-ethoxy-3-(4-{2-[N-(6,6,6-trifluorohexyl)-N-(2-trifluoromethylphenoxycarbonyl)amino]ethoxy}phenyl)propionic acid,
3-(4-{2-[N-(5,5-difluorohexyl)-N-(2-trifluoromethylphenoxycarbonyl)amino]ethoxy}phenyl)-2-ethoxypropionic acid, 2-ethoxy-3-(4-{2-[N-(5,5,6,6,7,7,7-heptafluoroheptyl)-N-(2-trifluoromethylphenoxycarbonyl)amino]ethoxy}phenyl)propionic acid, 2-ethoxy-3-(4-{2-[N-(2,2,3,3,4,4,5,5,6,6,7,7,7-tridecafluoroheptyl)-N-(2-trifluoromethylphenoxycarbonyl)amino]ethoxy}phenyl)propionic acid, 2-ethoxy-3-(4-{2-[N-(5,5,6,6,6-pentafluorohexyl)-N-(2-trifluoromethylphenoxycarbonyl)amino]ethoxy}phenyl)propionic acid, 2-ethoxy-3-(4-{2-[N-(2-trifluoromethylphenoxycarbonyl)-N-(2,2,3,3,4,4,5,5,6,6,6-undecafluorohexyl)amino]ethoxy}phenyl)propionic acid, 3-[4-(2-{N-[2-(2,2-difluoropropoxy)ethyl]-N-(2-trifluoromethylphenoxycarbonyl)amino}ethoxy)phenyl]-2-ethoxypropionic acid, 2-ethoxy-3-[4-(2-{N-[2-(1,1,2,2,3,3,3-heptafluoropropoxy)ethyl]-N-(2-trifluoromethylphenoxycarbonyl)amino}ethoxy)phenyl]propionic acid, 2-ethoxy-3-[4-(2-{N-[2-(4,4,4-trifluorobutoxy)ethyl]-N-(2-trifluoromethylphenoxycarbonyl)amino}ethoxy)phenyl]propionic acid, 3-[4-(2-{N-[2-(3,3-difluorobutoxy)ethyl]-N-(2-trifluoromethylphenoxycarbonyl)amino}ethoxy)phenyl]-2-ethoxypropionic acid, 3-[4-(2-{N-[2-(2,2-difluorobutoxy)ethyl]-N-(2-trifluoromethylphenoxycarbonyl)amino}ethoxy)phenyl]-2-ethoxypropionic acid, 2-ethoxy-3-[4-(2-{N-[2-(1,1,2,2,3,3,4,4,4-nonafluorobutoxy)ethyl]-N-(2-trifluoromethylphenoxycarbonyl)amino}ethoxy)phenyl]propionic acid, 2-ethoxy-3-[4-(2-(N-[3-(2,2,2-trifluoroethoxy)propyl]-N-(2-trifluoromethylphenoxycarbonyl)amino}ethoxy)phenyl]propionic acid, 2-ethoxy-3-[4-(2-{N-[3-(1,1,2,2,2-pentafluoroethoxy)propyl]-N-(2-trifluoromethylphenoxycarbonyl)amino}ethoxy)phenyl]propionic acid, 2-ethoxy-3-[4-(2-{N-[3-(4-fluorophenoxy)propyl]-N-(2-trifluoromethylphenoxycarbonyl)amino}ethoxy)phenyl]propionic acid, 3-[4-(2-(N-[3-(3,5-dichlorophenoxy)propyl]-N-(2-trifluoromethylphenoxycarbonyl)amino}ethoxy)phenyl]-2-ethoxypropionic acid, 2-ethoxy-3-[4-(2-{N-[4-(4-fluorophenoxy)butyl]-N-(2-trifluoromethylphenoxycarbonyl)amino}ethoxy)phenyl]propionic acid, 3-[4-(2-{N-[4-(3,5-dichlorophenoxy)butyl]-N-(2 -trifluoromethylphenoxycarbonyl)amino}ethoxy)phenyl]-2-ethoxypropionic acid, 2-ethoxy-3-[4-(2-{N-[2-(4-fluorobenzyloxy)ethyl]-N-(2-trifluoromethylphenoxycarbonyl)amino}ethoxy)phenyl]propionic acid, 3-[4-(2-{N-[2-(3,5-dichlorobenzyloxy)ethyl]-N-(2-trifluoromethylphenoxycarbonyl)amino}ethoxy)phenyl]-2-ethoxypropionic acid, 2-ethoxy-3-[4-(2-{N-[3-(4-fluorobenzyloxy)propyl]-N-(2-trifluoromethylphenoxycarbonyl)amino}ethoxy)phenyl]propionic acid, 3-[4-(2-{N-[3-(3,5-dichlorobenzyloxy)propyl]-N-(2-trifluoromethylphenoxycarbonyl)amino}ethoxy)phenyl]-2-ethoxypropionic acid, 2-ethoxy-3-[4-(2-{N-[4-(4-fluorobenzyloxy)butyl]-N-(2-trifluoromethylphenoxycarbonyl)amino}ethoxy)phenyl]propionic acid, 3-[4-(2-{N-[4-(3,5-dichlorobenzyloxy)butyl]-N-(2-trifluoromethylphenoxycarbonyl)amino}ethoxy)phenyl]-2-ethoxypropionic acid, 2-ethoxy-3-[4-(2-{N-[3-(4-fluorophenyl)propyl]-N-(2-trifluoromethylphenoxycarbonyl)amino}ethoxy)phenyl]propionic acid, 3-[4-(2-{N-[3-(3,5-dichlorophenyl)propyl]-N-(2-trifluoromethylphenoxycarbonyl)amino}ethoxy)phenyl]-2-ethoxypropionic acid, 2-ethoxy-3-(4-{2-[N-pentyl-N-(3-trifluoromethylphenoxycarbonyl)amino]ethoxy}phenyl)propionic acid, 2-ethoxy-3-(4-{2-[N-hexyl-N-(3-trifluoromethylphenoxycarbonyl)amino]ethoxy}phenyl)propionic acid, 2-ethoxy-3-(4-{2-[N-heptyl-N-(3-trifluoromethylphenoxycarbonyl)amino]ethoxy}phenyl)propionic acid, 2-ethoxy-3-(4-{2-[N-octyl-N-(3-trifluoromethylphenoxycarbonyl)amino]ethoxy}phenyl)propionic acid, 2-ethoxy-3-(4-{2-[N-isobutyl-N-(3-trifluoromethylphenoxycarbonyl)amino]ethoxy}phenyl)propionic acid, 2-ethoxy-3-(4-{2-[N-(3-methylbutyl)-N-(3-trifluoromethylphenoxycarbonyl)amino]ethoxy}phenyl)propionic acid, 2-ethoxy-3-(4-{2-[N-(4-methylpentyl)-N-(3-trifluoromethylphenoxycarbonyl)amino]ethoxy}phenyl)propionic acid, 2-ethoxy-3-(4-{2-[N-(2-propylpentyl)-N-(3-trifluoromethylphenoxycarbonyl)amino]ethoxy}phenyl)propionic acid, -(4-{2-[N-(3,3-dimethylbutyl)-N-(3-trifluoromethylphenoxycarbonyl)amino]ethoxy}phenyl)-2-ethoxypropionic acid, 2-ethoxy-3-(4-{2-[N-(2-ethylbutyl)-N-(3-trifluoromethylphenoxycarbonyl)amino]ethoxy}phenyl)propionic acid, 3-(4-{2-[N-cyclohexylmethyl-N-(3-trifluoromethylphenoxycarbonyl)amino]ethoxy}phenyl)-2-ethoxypropionic acid, 3-(4-{2-[N-(4-cyclohexylbutyl)-N-(3-trifluoromethylphenoxycarbonyl)amino]ethoxy}phenyl)-2-ethoxypropionic acid, 3-(4-{2-[N-cyclopropylmethyl-N-(3-trifluoromethylphenoxycarbonyl)amino]ethoxy}phenyl)-2-ethoxypropionic acid, 3-(4-{2-[N-cyclobutylmethyl-N-(3-trifluoromethylphenoxycarbonyl)amino]ethoxy}phenyl)-2-ethoxypropionic acid, 3-(4-{2-[N-cyclopentylmethyl-N-(3-trifluoromethylphenoxycarbonyl)amino]ethoxy}phenyl)-2-ethoxypropionic acid, 3-(4-{2-[N-(2-cyclopentylethyl)-N-(3-trifluoromethylphenoxycarbonyl)amino]ethoxy}phenyl)-2-ethoxypropionic acid, 3-(4-{2-[N-(3-cyclohexylpropyl)-N-(3-trifluoromethylphenoxycarbonyl)amino]ethoxy}phenyl)-2-ethoxypropionic acid, 2-ethoxy-3-(4-{2-[N-(3-phenylpropyl)-N-(3-trifluoromethylphenoxycarbonyl)amino]ethoxy}phenyl)propionic acid, 2-ethoxy-3-(4-{2-[N-(4-phenylbutyl)-N-(3-trifluoromethylphenoxycarbonyl)amino]ethoxy}phenyl)propionic acid, 3-(4-{2-[N-(2-butoxyethyl)-N-(3-trifluoromethylphenoxycarbonyl)amino]ethoxy}phenyl)-2-ethoxypropionic acid, 2-ethoxy-3-(4-{2-[N-(2-pentyloxyethyl)-N-(3-trifluoromethylphenoxycarbonyl)amino]ethoxy}phenyl)propionic acid, 2-ethoxy-3-(4-{2-[N-(3-propoxypropyl)-N-(3-trifluoromethylphenoxycarbonyl)amino]ethoxy}phenyl)propionic acid, 3-(4-{2-[N-(2-butylthioethyl)-N-(3-trifluoromethylphenoxycarbonyl)amino]ethoxy}phenyl)-2-ethoxypropionic acid,
2-ethoxy-3-(4-{2-[N-(2-pentylthioethyl)-N-(3-trifluoromethylphenoxycarbonyl)amino]ethoxy}phenyl)propionic acid,
2-ethoxy-3-(4-{2-[N-(3-propylthiopropyl)-N-(3-trifluoromethylphenoxycarbonyl)amino]ethoxy}phenyl)propionic acid,
2-ethoxy-3-(4-{2-[N-(3-phenoxypropyl)-N-(3-trifluoromethylphenoxycarbonyl)amino]ethoxy}phenyl)propionic acid,
2-ethoxy-3-(4-{2-[N-(4-phenoxybutyl)-N-(3-trifluoromethylphenoxycarbonyl)amino]ethoxy}phenyl)propionic acid,
3-(4-{2-[N-(3-benzyloxypropyl)-N-(3-trifluoromethylphenoxycarbonyl)amino]ethoxy}phenyl)-2-ethoxypropionic acid,
2-ethoxy-3-(4-{2-[N-(3-phenylthiopropyl)-N-(3-trifluoromethylphenoxycarbonyl)amino]ethoxy}phenyl)propionic acid,
2-ethoxy-3-(4-{2-[N-(4-phenylthiobutyl)-N-(3-trifluoromethylphenoxycarbonyl)amino]ethoxy}phenyl)propionic acid,
3-(4-{2-[N-(3-benzylthiopropyl)-N-(3-trifluoromethylphenoxycarbonyl)amino]ethoxy}phenyl)-2-ethoxypropionic acid,
2-ethoxy-3-(4-{2-[N-(7,7,7-trifluoroheptyl)-N-(3-trifluoromethylphenoxycarbonyl)amino]ethoxy}phenyl)propionic acid,
3-(4-{2-[N-(6,6-difluoroheptyl)-N-(3-trifluoromethylphenoxycarbonyl)amino]ethoxy}phenyl)-2-ethoxypropionic acid,
2-ethoxy-3-(4-{2-[N-(6,6,6-trifluorohexyl)-N-(3-trifluoromethylphenoxycarbonyl)amino]ethoxy}phenyl)propionic acid,
3-(4-{2-[N-(5,5-difluorohexyl)-N-(3-trifluoromethylphenoxycarbonyl)amino]ethoxy}phenyl)-2-ethoxypropionic acid,
2-ethoxy-3-(4-{2-[N-(5,5,6,6,7,7,7-heptafluoroheptyl)-N-(3-trifluoromethylphenoxycarbonyl)amino]ethoxy}phenyl)propionic acid,
2-ethoxy-3-(4-{2-[N-(2,2,3,3,4,4,5,5,6,6,7,7,7-tridecafluoroheptyl)-N-(3-trifluoromethylphenoxycarbonyl)amino]ethoxy}phenyl)propionic acid,
2-ethoxy-3-(4-{2-[N-(5,5,6,6,6-pentafluorohexyl)-N-(3-trifluoromethylphenoxycarbonyl)amino]ethoxy}phenyl)propionic acid,
2-ethoxy-3-(4-{2-[N-(3-trifluoromethylphenoxycarbonyl)-N-(2,2,3,3,4,4,5,5,6,6,6-undecafluorohexyl)amino]ethoxy}phenyl)propionic acid,
3-[4-(2-{N-[2-(2,2-difluoropropoxy)ethyl]-N-(3-trifluoromethylphenoxycarbonyl)amino}ethoxy)phenyl]-2-ethoxypropionic acid,
2-ethoxy-3-[4-(2-{N-[2-(1,1,2,2,3,3,3-heptafluoropropoxy)ethyl]-N-(3-trifluoromethylphenoxycarbonyl)amino}ethoxy)phenyl]propionic acid,
2-ethoxy-3-[4-(2-{N-[2-(4,4,4-trifluorobutoxy)ethyl]-N-(3-trifluoromethylphenoxycarbonyl)amino}ethoxy)phenyl]propionic acid,
3-[4-(2-{N-[2-(3,3-difluorobutoxy)ethyl]-N-(3-trifluoromethylphenoxycarbonyl)amino}ethoxy)phenyl]-2-ethoxypropionic acid,
3-[4-(2-{N-[2-(2,2-difluorobutoxy)ethyl]-N-(3-trifluoromethylphenoxycarbonyl)amino}ethoxy)phenyl]-2-ethoxypropionic acid,
2-ethoxy-3-[4-(2-{N-[2-(1,1,2,2,3,3,4,4,4-nonafluorobutoxy)ethyl]-N-(3-trifluoromethylphenoxycarbonyl)amino}ethoxy)phenyl]propionic acid,
2-ethoxy-3-[4-(2-{N-[3-(2,2,2-trifluoroethoxy)propyl]-N-(3-trifluoromethylphenoxycarbonyl)amino}ethoxy)phenyl]propionic acid,
2-ethoxy-3-[4-(2-{N-[3-(1,1,2,2,2-pentafluoroethoxy)propyl]-N-(3-trifluoromethylphenoxycarbonyl)amino}ethoxy)phenyl]propionic acid,
2-ethoxy-3-[4-(2-{N-[3-(4-fluorophenoxy)propyl]-N-(3-trifluoromethylphenoxycarbonyl)amino}ethoxy)phenyl]propionic acid,
3-[4-(2-{N-[3-(3,5-dichlorophenoxy)propyl]-N-(3-trifluoromethylphenoxycarbonyl)amino}ethoxy)phenyl]-2-ethoxypropionic acid,
2-ethoxy-3-[4-(2-{N-[4-(4-fluorophenoxy)butyl]-N-(3-trifluoromethylphenoxycarbonyl)amino}ethoxy)phenyl]propionic acid,
3-[4-(2-{N-[4-(3,5-dichlorophenoxy)butyl]-N-(3-trifluoromethylphenoxycarbonyl)amino}ethoxy)phenyl]-2-ethoxypropionic acid,
2-ethoxy-3-[4-(2-{N-[2-(4-fluorobenzyloxy)ethyl]-N-(3-trifluoromethylphenoxycarbonyl)amino}ethoxy)phenyl]propionic acid,
3-[4-(2-{N-[2-(3,5-dichlorobenzyloxy)ethyl]-N-(3-trifluoromethylphenoxycarbonyl)amino}ethoxy)phenyl]-2-ethoxypropionic acid,
2-ethoxy-3-[4-(2-{N-[3-(4-fluorobenzyloxy)propyl]-N-(3-trifluoromethylphenoxycarbonyl)amino}ethoxy)phenyl]propionic acid,
3-[4-(2-{N-[3-(3,5-dichlorobenzyloxy)propyl]-N-(3-trifluoromethylphenoxycarbonyl)amino}ethoxy)phenyl]-2-ethoxypropionic acid,
2-ethoxy-3-[4-(2-{N-[4-(4-fluorobenzyloxy)butyl]-N-(3-trifluoromethylphenoxycarbonyl)amino}ethoxy)phenyl]propionic acid,
3-[4-(2-{N-[4-(3,5-dichlorobenzyloxy)butyl]-N-(3-trifluoromethylphenoxycarbonyl)amino}ethoxy)phenyl]-2-ethoxypropionic acid,
2-ethoxy-3-[4-(2-{N-[3-(4-fluorophenyl)propyl]-N-(3-trifluoromethylphenoxycarbonyl)amino}ethoxy)phenyl]propionic acid,
3-[4-(2-{N-[3-(3,5-dichlorophenyl)propyl]-N-(3-trifluoromethylphenoxycarbonyl)amino}ethoxy)phenyl]-2-ethoxypropionic acid,
2-ethoxy-3-(4-{2-[N-pentyl-N-(4-trifluoromethylphenoxycarbonyl)amino]ethoxy}phenyl)propionic acid,
2-ethoxy-3-(4-{2-[N-hexyl-N-(4-trifluoromethylphenoxycarbonyl)amino]ethoxy}phenyl)propionic acid,
2-ethoxy-3-(4-{2-[N-heptyl-N-(4-trifluoromethylphenoxycarbonyl)amino]ethoxy}phenyl)propionic acid,
2-ethoxy-3-(4-{2-[N-octyl-N-(4-trifluoromethylphenoxycarbonyl)amino]ethoxy}phenyl)propionic acid,
2-ethoxy-3-(4-{2-[N-isobutyl-N-(4-trifluoromethylphenoxycarbonyl)amino]ethoxy}phenyl)propionic acid,
2-ethoxy-3-(4-{2-[N-(3-methylbutyl)-N-(4-trifluoromethylphenoxycarbonyl)amino]ethoxy}phenyl)propionic acid,
2-ethoxy-3-(4-{2-[N-(4-methylpentyl)-N-(4-trifluoromethylphenoxycarbonyl)amino]ethoxy}phenyl)propionic acid,
2-ethoxy-3-(4-{2-[N-(2-propylpentyl)-N-(4-trifluoromethylphenoxycarbonyl)amino]ethoxy}phenyl)propionic acid,
3-(4-{2-[N-(3,3-dimethylbutyl)-N-(4-trifluoromethylphenoxycarbonyl)amino]ethoxy}phenyl)-2-ethoxypropionic acid, 2-ethoxy-3-(4-{2-[N-(2-ethylbutyl)-N-(4-trifluoromethylphenoxycarbonyl)amino]ethoxy}phenyl)propionic acid,
3-(4-{2-[N-cyclohexylmethyl-N-(4-trifluoromethylphenoxycarbonyl)amino]ethoxy}phenyl)-2-ethoxypropionic acid,
3-(4-{2-[N-(4-cyclohexylbutyl)-N-(4-trifluoromethylphenoxycarbonyl)amino]ethoxy}phenyl)-2-ethoxypropionic acid,
3-(4-{2-[N-cyclopropylmethyl-N-(4-trifluoromethylphenoxycarbonyl)amino]ethoxy}phenyl)-2-ethoxypropionic acid,
3-(4-{2-[N-cyclobutylmethyl-N-(4-trifluoromethylphenoxycarbonyl)amino]ethoxy}phenyl)-2-ethoxypropionic acid,
3-(4-{2-[N-cyclopentylmethyl-N-(4-trifluoromethylphenoxycarbonyl)amino]ethoxy}phenyl)-2-ethoxypropionic acid,
3-(4-{2-[N-(2-cyclopentylethyl)-N-(4-trifluoromethylphenoxycarbonyl)amino]ethoxy}phenyl)-2-ethoxypropionic acid,
3-(4-{2-[N-(3-cyclohexylpropyl)-N-(4-trifluoromethylphenoxycarbonyl)amino]ethoxy}phenyl)-2-ethoxypropionic acid,
2-ethoxy-3-(4-{2-[N-(3-phenylpropyl)-N-(4-trifluoromethylphenoxycarbonyl)amino]ethoxy}phenyl)propionic acid,
2-ethoxy-3-(4-{2-[N-(4-phenylbutyl)-N-(4-trifluoromethylphenoxycarbonyl)amino]ethoxy}phenyl)propionic acid,
3-(4-{2-[N-(2-butoxyethyl)-N-(4-trifluoromethylphenoxycarbonyl)amino]ethoxy}phenyl)-2-ethoxypropionic acid,
2-ethoxy-3-(4-{2-[N-(2-pentyloxyethyl)-N-(4-trifluoromethylphenoxycarbonyl)amino]ethoxy}phenyl)propionic acid,
2-ethoxy-3-(4-{2-[N-(3-propoxypropyl)-N-(4-trifluoromethylphenoxycarbonyl)amino]ethoxy}phenyl)propionic acid,
3-(4-{2-[N-(2-butylthioethyl)-N-(4-trifluoromethylphenoxycarbonyl)amino]ethoxy}phenyl)-2-ethoxypropionic acid,
2-ethoxy-3-(4-{2-[N-(2-pentylthioethyl)-N-(4-trifluoromethylphenoxycarbonyl)amino]ethoxy}phenyl)propionic acid,
2-ethoxy-3-(4-{2-[N-(3-propylthiopropyl)-N-(4-trifluoromethylphenoxycarbonyl)amino]ethoxy}phenyl)propionic acid,
2-ethoxy-3-(4-{2-[N-(3-phenoxypropyl)-N-(4-trifluoromethylphenoxycarbonyl)amino]ethoxy}phenyl)propionic acid,
2-ethoxy-3-(4-{2-[N-(4-phenoxybutyl)-N-(4-trifluoromethylphenoxycarbonyl)amino]ethoxy}phenyl)propionic acid,
3-(4-{2-[N-(3-benzyloxypropyl)-N-(4-trifluoromethylphenoxycarbonyl)amino]ethoxy}phenyl)-2-ethoxypropionic acid,
2-ethoxy-3-(4-{2-[N-(3-phenylthiopropyl)-N-(4-trifluoromethylphenoxycarbonyl)amino]ethoxy}phenyl)propionic acid,
2-ethoxy-3-(4-{2-[N-(4-phenylthiobutyl)-N-(4-trifluoromethylphenoxycarbonyl)amino]ethoxy}phenyl)propionic acid,
3-(4-{2-[N-(3-benzylthiopropyl)-N-(4-trifluoromethylphenoxycarbonyl)amino]ethoxy}phenyl)-2-ethoxypropionic acid,
2-ethoxy-3-(4-{2-[N-(7,7,7-trifluoroheptyl)-N-(4-trifluoromethylphenoxycarbonyl)amino]ethoxy}phenyl)propionic acid,
3-(4-{2-[N-(6,6-difluoroheptyl)-N-(4-trifluoromethylphenoxycarbonyl)amino]ethoxy}phenyl)-2-ethoxypropionic acid,
2-ethoxy-3-(4-{2-[N-(6,6,6-trifluorohexyl)-N-(4-trifluoromethylphenoxycarbonyl)amino]ethoxy}phenyl)propionic acid,
3-(4-{2-[N-(5,5-difluorohexyl)-N-(4-trifluoromethylphenoxycarbonyl)amino]ethoxy}phenyl)-2-ethoxypropionic acid,
2-ethoxy-3-(4-{2-[N-(5,5,6,6,7,7,7-heptafluoroheptyl)-N-(4-trifluoromethylphenoxycarbonyl)amino]ethoxy}phenyl)propionic acid,
2-ethoxy-3-(4-{2-[N-(2,2,3,3,4,4,5,5,6,6,7,7,7-tridecafluoroheptyl)-N-(4-trifluoromethylphenoxycarbonyl)amino]ethoxy}phenyl)propionic acid,
2-ethoxy-3-(4-{2-[N-(5,5,6,6,6-pentafluorohexyl)-N-(4-trifluoromethylphenoxycarbonyl)amino]ethoxy}phenyl)propionic acid,
2-ethoxy-3-(4-{2-[N-(4-trifluoromethylphenoxycarbonyl)-N-(2,2,3,3,4,4,5,5,6,6,6-undecafluorohexyl)amino]ethoxy}phenyl)propionic acid,
3-[4-(2-{N-[2-(2,2-difluoropropoxy)ethyl]-N-(4-trifluoromethylphenoxycarbonyl)amino}ethoxy)phenyl]-2-ethoxypropionic acid,
2-ethoxy-3-[4-(2-{N-[2-(1,1,2,2,3,3,3-heptafluoropropoxy)ethyl]-N-(4-trifluoromethylphenoxycarbonyl)amino}ethoxy)phenyl]propionic acid,
2-ethoxy-3-[4-(2-{N-[2-(4,4,4-trifluorobutoxy)ethyl]-N-(4-trifluoromethylphenoxycarbonyl)amino}ethoxy)phenyl]propionic acid,
3-[4-(2-{N-[2-(3,3-difluorobutoxy)ethyl]-N-(4-trifluoromethylphenoxycarbonyl)amino}ethoxy)phenyl]-2-ethoxypropionic acid,
3-[4-(2-{N-[2-(2,2-difluorobutoxy)ethyl]-N-(4-trifluoromethylphenoxycarbonyl)amino}ethoxy)phenyl]-2-ethoxypropionic acid,
2-ethoxy-3-[4-(2-{N-[2-(1,1,2,2,3,3,4,4,4-nonafluorobutoxy)ethyl]-N-(4-trifluoromethylphenoxycarbonyl)amino}ethoxy)phenyl]propionic acid,
2-ethoxy-3-[4-(2-{N-[3-(2,2,2-trifluoroethoxy)propyl]-N-(4-trifluoromethylphenoxycarbonyl)amino}ethoxy)phenyl]propionic acid,
2-ethoxy-3-[4-(2-{N-[3-(1,1,2,2,2-pentafluoroethoxy)propyl]-N-(4-trifluoromethylphenoxycarbonyl)amino}ethoxy)phenyl]propionic acid,
2-ethoxy-3-[4-(2-{N-[3-(4-fluorophenoxy)propyl]-N-(4-trifluoromethylphenoxycarbonyl)amino}ethoxy)phenyl]propionic acid,
3-[4-(2-{N-[3-(3,5-dichlorophenoxy)propyl]-N-(4-trifluoromethylphenoxycarbonyl)amino}ethoxy)phenyl]-2-ethoxypropionic acid,
2-ethoxy-3-[4-(2-{N-[4-(4-fluorophenoxy)butyl]-N-(4-trifluoromethylphenoxycarbonyl)amino}ethoxy)phenyl]propionic acid,
3-[4-(2-{N-[4-(3,5-dichlorophenoxy)butyl]-N-(4-trifluoromethylphenoxycarbonyl)amino}ethoxy)phenyl]-2-ethoxypropionic acid,
2-ethoxy-3-[4-(2-{N-[2-(4-fluorobenzyloxy)ethyl]-N-(4-trifluoromethylphenoxycarbonyl)amino}ethoxy)phenyl]propionic acid,
3-[4-(2-{N-[2-(3,5-dichlorobenzyloxy)ethyl]-N-(4-trifluoromethylphenoxycarbonyl)amino}ethoxy)phenyl]-2-ethoxypropionic acid, 2-ethoxy-3-[4-(2-{N-[3-(4-fluorobenzyloxy)propyl]-N-(4-trifluoromethylphenoxycarbonyl)amino}ethoxy)phenyl]propionic acid,
3-[4-(2-{N-[3-(3,5-dichlorobenzyloxy)propyl]-N-(4-trifluoromethylphenoxycarbonyl)amino}ethoxy)phenyl]-2-ethoxypropionic acid,
2-ethoxy-3-[4-(2-{N-[4-(4-fluorobenzyloxy)butyl]-N-(4-trifluoromethylphenoxycarbonyl)amino}ethoxy)phenyl]propionic acid,
3-[4-(2-{N-[4-(3,5-dichlorobenzyloxy)butyl]-N-(4-trifluoromethylphenoxycarbonyl)amino}ethoxy)phenyl]-2-ethoxypropionic acid,
2-ethoxy-3-[4-(2-{N-[3-(4-fluorophenyl)propyl]-N-(4-trifluoromethylphenoxycarbonyl)amino}ethoxy)phenyl]propionic acid,
3-[4-(2-{N-[3-(3,5-dichlorophenyl)propyl]-N-(4-trifluoromethylphenoxycarbonyl)amino}ethoxy)phenyl]-2-ethoxypropionic acid,
2-ethoxy-3-(4-{2-[N-pentyl-N-(2-trifluoromethoxyphenoxycarbonyl)amino]ethoxy}phenyl)propionic acid,
2-ethoxy-3-(4-{2-[N-hexyl-N-(2-trifluoromethoxyphenoxycarbonyl)amino]ethoxy}phenyl)propionic acid,
2-ethoxy-3-(4-{2-[N-heptyl-N-(2-trifluoromethoxyphenoxycarbonyl)amino]ethoxy}phenyl)propionic acid,
2-ethoxy-3-(4-{2-[N-octyl-N-(2-trifluoromethoxyphenoxycarbonyl)amino]ethoxy}phenyl)propionic acid,
2-ethoxy-3-(4-{2-[N-isobutyl-N-(2-trifluoromethoxyphenoxycarbonyl)amino]ethoxy}phenyl)propionic acid,
2-ethoxy-3-(4-{2-[N-(3-methylbutyl)-N-(2-trifluoromethoxyphenoxycarbonyl)amino]ethoxy}phenyl)propionic acid,
2-ethoxy-3-(4-{2-[N-(4-methylpentyl)-N-(2-trifluoromethoxyphenoxycarbonyl)amino]ethoxy}phenyl)propionic acid,
2-ethoxy-3-(4-{2-[N-(2-propylpentyl)-N-(2-trifluoromethoxyphenoxycarbonyl)amino]ethoxy}phenyl)propionic acid,
3-(4-{2-[N-(3,3-dimethylbutyl)-N-(2-trifluoromethoxyphenoxycarbonyl)amino]ethoxy}phenyl)-2-ethoxypropionic acid,
2-ethoxy-3-(4-{2-[N-(2-ethylbutyl)-N-(2-trifluoromethoxyphenoxycarbonyl)amino]ethoxy}phenyl)propionic acid,
3-(4-{2-[N-cyclohexylmethyl-N-(2-trifluoromethoxyphenoxycarbonyl)amino]ethoxy}phenyl)-2-ethoxypropionic acid,
3-(4-{2-[N-(4-cyclohexylbutyl)-N-(2-trifluoromethoxyphenoxycarbonyl)amino]ethoxy}phenyl)-2-ethoxypropionic acid,
3-(4-{2-[N-cyclopropylmethyl-N-(2-trifluoromethoxyphenoxycarbonyl)amino]ethoxy}phenyl)-2-ethoxypropionic acid,
3-(4-{2-[N-cyclobutylmethyl-N-(2-trifluoromethoxyphenoxycarbonyl)amino]ethoxy}phenyl)-2-ethoxypropionic acid,
3-(4-{2-[N-cyclopentylmethyl-N-(2-trifluoromethoxyphenoxycarbonyl)amino]ethoxy}phenyl)-2-ethoxypropionic acid,
3-(4-{2-[N-(2-cyclopentylethyl)-N-(2-trifluoromethoxyphenoxycarbonyl)amino]ethoxy}phenyl)-2-ethoxypropionic acid,
3-(4-{2-[N-(3-cyclohexylpropyl)-N-(2-trifluoromethoxyphenoxycarbonyl)amino]ethoxy}phenyl)-2-ethoxypropionic acid,
2-ethoxy-3-(4-{2-[N-(3-phenylpropyl)-N-(2-trifluoromethoxyphenoxycarbonyl)amino]ethoxy}phenyl)propionic acid,
2-ethoxy-3-(4-{2-[N-(4-phenylbutyl)-N-(2-trifluoromethoxyphenoxycarbonyl)amino]ethoxy}phenyl)propionic acid,
3-(4-{2-[N-(2-butoxyethyl)-N-(2-trifluoromethoxyphenoxycarbonyl)amino]ethoxy}phenyl)-2-ethoxypropionic acid,
2-ethoxy-3-(4-{2-[N-(2-pentyloxyethyl)-N-(2-trifluoromethoxyphenoxycarbonyl)amino]ethoxy}phenyl)propionic acid,
2-ethoxy-3-(4-{2-[N-(3-propoxypropyl)-N-(2-trifluoromethoxyphenoxycarbonyl)amino]ethoxy}phenyl)propionic acid,
3-(4-{2-[N-(2-butylthioethyl)-N-(2-trifluoromethoxyphenoxycarbonyl)amino]ethoxy}phenyl)-2-ethoxypropionic acid,
2-ethoxy-3-(4-{2-[N-(2-pentylthioethyl)-N-(2-trifluoromethoxyphenoxycarbonyl)amino]ethoxy}phenyl)propionic acid,
2-ethoxy-3-(4-{2-[N-(3-propylthiopropyl)-N-(2-trifluoromethoxyphenoxycarbonyl)amino]ethoxy}phenyl)propionic acid,
2-ethoxy-3-(4-{2-[N-(3-phenoxypropyl)-N-(2-trifluoromethoxyphenoxycarbonyl)amino]ethoxy}phenyl)propionic acid,
2-ethoxy-3-(4-{2-[N-(4-phenoxybutyl)-N-(2-trifluoromethoxyphenoxycarbonyl)amino]ethoxy}phenyl)propionic acid,
3-(4-{2-[N-(3-benzyloxypropyl)-N-(2-trifluoromethoxyphenoxycarbonyl)amino]ethoxy}phenyl)-2-ethoxypropionic acid,
2-ethoxy-3-(4-{2-[N-(3-phenylthiopropyl)-N-(2-trifluoromethoxyphenoxycarbonyl)amino]ethoxy}phenyl)propionic acid,
2-ethoxy-3-(4-{2-[N-(4-phenylthiobutyl)-N-(2-trifluoromethoxyphenoxycarbonyl)amino]ethoxy}phenyl)propionic acid,
3-(4-{2-[N-(3-benzylthiopropyl)-N-(2-trifluoromethoxyphenoxycarbonyl)amino]ethoxy}phenyl)-2-ethoxypropionic acid,
2-ethoxy-3-(4-{2-[N-(7,7,7-trifluoroheptyl)-N-(2-trifluoromethoxyphenoxycarbonyl)amino]ethoxy}phenyl)propionic acid,
3-(4-{2-[N-(6,6-difluoroheptyl)-N-(2-trifluoromethoxyphenoxycarbonyl)amino]ethoxy}phenyl)-2-ethoxypropionic acid,
2-ethoxy-3-(4-{2-[N-(6,6,6-trifluorohexyl)-N-(2-trifluoromethoxyphenoxycarbonyl)amino]ethoxy}phenyl)propionic acid,
3-(4-{2-[N-(5,5-difluorohexyl)-N-(2-trifluoromethoxyphenoxycarbonyl)amino]ethoxy}phenyl)-2-ethoxypropionic acid,
2-ethoxy-3-(4-{2-[N-(5,5,6,6,7,7,7-heptafluoroheptyl)-N-(2-trifluoromethoxyphenoxycarbonyl)amino]ethoxy}phenyl)propionic acid,
2-ethoxy-3-(4-{2-[N-(2,2,3,3,4,4,5,5,6,6,7,7,7-tridecafluoroheptyl)-N-(2-trifluoromethoxyphenoxycarbonyl)amino]ethoxy}phenyl)propionic acid,
2-ethoxy-3-(4-{2-[N-(5,5,6,6,6-pentafluorohexyl)-N-(2-trifluoromethoxyphenoxycarbonyl)amino]ethoxy}phenyl)propionic acid,
2-ethoxy-3-(4-{2-[N-(2-trifluoromethoxyphenoxycarbonyl)-N-(2,2,3,3,4,4,5,5,6,6,6-undecafluorohexyl)amino]ethoxy}phenyl)propionic acid,
3-[4-(2-{N-[2-(2,2-difluoropropoxy)ethyl]-N-(2-trifluoromethoxyphenoxycarbonyl)amino}ethoxy)phenyl]-2-ethoxypropionic acid, 2-ethoxy-3-[4-(2-{N-[2-(1,1,2,2,3,3,3-heptafluoropropoxy)ethyl]-N-(2-trifluoromethoxyphenoxycarbonyl)amino}ethoxy)phenyl]propionic acid,
2-ethoxy-3-[4-(2-{N-[2-(4,4,4-trifluorobutoxy)ethyl]-N-(2-trifluoromethoxyphenoxycarbonyl)amino}ethoxy)phenyl]propionic acid,
3-[4-(2-{N-[2-(3,3-difluorobutoxy)ethyl]-N-(2-trifluoromethoxyphenoxycarbonyl)amino}ethoxy)phenyl]-2-ethoxypropionic acid,
3-[4-(2-{N-[2-(2,2-difluorobutoxy)ethyl]-N-(2-trifluoromethoxyphenoxycarbonyl)amino}ethoxy)phenyl]-2-ethoxypropionic acid,
2-ethoxy-3-[4-(2-{N-[2-(1,1,2,2,3,3,4,4,4-nonafluorobutoxy)ethyl]-N-(2-trifluoromethoxyphenoxycarbonyl)amino}ethoxy)phenyl]propionic acid,
2-ethoxy-3-[4-(2-{N-[3-(2,2,2-trifluoroethoxy)propyl]-N-(2-trifluoromethoxyphenoxycarbonyl)amino}ethoxy)phenyl]propionic acid,
2-ethoxy-3-[4-(2-{N-[3-(1,1,2,2,2-pentafluoroethoxy)propyl]-N-(2-trifluoromethoxyphenoxycarbonyl)amino}ethoxy)phenyl]propionic acid,
2-ethoxy-3-[4-(2-{N-[3-(4-fluorophenoxy)propyl]-N-(2-trifluoromethoxyphenoxycarbonyl)amino}ethoxy)phenyl]propionic acid,
3-[4-(2-{N-[3-(3,5-dichlorophenoxy)propyl]-N-(2-trifluoromethoxyphenoxycarbonyl)amino}ethoxy)phenyl]-2-ethoxypropionic acid,
2-ethoxy-3-[4-(2-{N-[4-(4-fluorophenoxy)butyl]-N-(2-trifluoromethoxyphenoxycarbonyl)amino}ethoxy)phenyl]propionic acid,
3-[4-(2-{N-[4-(3,5-dichlorophenoxy)butyl]-N-(2-trifluoromethoxyphenoxycarbonyl)amino}ethoxy)phenyl]-2-ethoxypropionic acid,
2-ethoxy-3-[4-(2-{N-[2-(4-fluorobenzyloxy)ethyl]-N-(2-trifluoromethoxyphenoxycarbonyl)amino}ethoxy)phenyl]propionic acid,
3-[4-(2-{N-[2-(3,5-dichlorobenzyloxy)ethyl]-N-(2-trifluoromethoxyphenoxycarbonyl)amino}ethoxy)phenyl]-2-ethoxypropionic acid,
2-ethoxy-3-[4-(2-{N-[3-(4-fluorobenzyloxy)propyl]-N-(2-trifluoromethoxyphenoxycarbonyl)amino}ethoxy)phenyl]propionic acid,
3-[4-(2-{N-[3-(3,5-dichlorobenzyloxy)propyl]-N-(2-trifluoromethoxyphenoxycarbonyl)amino}ethoxy)phenyl]-2-ethoxypropionic acid,
2-ethoxy-3-[4-(2-{N-[4-(4-fluorobenzyloxy)butyl]-N-(2-trifluoromethoxyphenoxycarbonyl)amino}ethoxy)phenyl]propionic acid,
3-[4-(2-{N-[4-(3,5-dichlorobenzyloxy)butyl]-N-(2-trifluoromethoxyphenoxycarbonyl)amino}ethoxy)phenyl]-2-ethoxypropionic acid,
2-ethoxy-3-[4-(2-{N-[3-(4-fluorophenyl)propyl]-N-(2-trifluoromethoxyphenoxycarbonyl)amino}ethoxy)phenyl]propionic acid,
3-[4-(2-{N-[3-(3,5-dichlorophenyl)propyl]-N-(2-trifluoromethoxyphenoxycarbonyl)amino}ethoxy)phenyl]-2-ethoxypropionic acid,
2-ethoxy-3-(4-{2-[N-pentyl-N-(4-trifluoromethoxyphenoxycarbonyl)amino]ethoxy}phenyl)propionic acid,
2-ethoxy-3-(4-{2-[N-hexyl-N-(4-trifluoromethoxyphenoxycarbonyl)amino]ethoxy}phenyl)propionic acid,
2-ethoxy-3-(4-{2-[N-heptyl-N-(4-trifluoromethoxyphenoxycarbonyl)amino]ethoxy}phenyl)propionic acid,
2-ethoxy-3-(4-{2-[N-octyl-N-(4-trifluoromethoxyphenoxycarbonyl)amino]ethoxy}phenyl)propionic acid,
2-ethoxy-3-(4-{2-[N-isobutyl-N-(4-trifluoromethoxyphenoxycarbonyl)amino]ethoxy}phenyl)propionic acid,
2-ethoxy-3-(4-{2-[N-(3-methylbutyl)-N-(4-trifluoromethoxyphenoxycarbonyl)amino]ethoxy}phenyl)propionic acid,
2-ethoxy-3-(4-{2-[N-(4-methylpentyl)-N-(4-trifluoromethoxyphenoxycarbonyl)amino]ethoxy}phenyl)propionic acid,
2-ethoxy-3-(4-{2-[N-(2-propylpentyl)-N-(4-trifluoromethoxyphenoxycarbonyl)amino]ethoxy}phenyl)propionic acid,
3-(4-{2-[N-(3,3-dimethylbutyl)-N-(4-trifluoromethoxyphenoxycarbonyl)amino]ethoxy}phenyl)-2-ethoxypropionic acid,
2-ethoxy-3-(4-{2-[N-(2-ethylbutyl)-N-(4-trifluoromethoxyphenoxycarbonyl)amino]ethoxy}phenyl)propionic acid,
3-(4-{2-[N-cyclohexylmethyl-N-(4-trifluoromethoxyphenoxycarbonyl)amino]ethoxy}phenyl)-2-ethoxypropionic acid,
3-(4-{2-[N-(4-cyclohexylbutyl)-N-(4-trifluoromethoxyphenoxycarbonyl)amino]ethoxy}phenyl)-2-ethoxypropionic acid,
3-(4-{2-[N-cyclopropylmethyl-N-(4-trifluoromethoxyphenoxycarbonyl)amino]ethoxy}phenyl)-2-ethoxypropionic acid,
3-(4-{2-[N-cyclobutylmethyl-N-(4-trifluoromethoxyphenoxycarbonyl)amino]ethoxy}phenyl)-2-ethoxypropionic acid,
3-(4-{2-[N-cyclopentylmethyl-N-(4-trifluoromethoxyphenoxycarbonyl)amino]ethoxy}phenyl)-2-ethoxypropionic acid,
3-(4-{2-[N-(2-cyclopentylethyl)-N-(4-trifluoromethoxyphenoxycarbonyl)amino]ethoxy}phenyl)-2-ethoxypropionic acid,
3-(4-{2-[N-(3-cyclohexylpropyl)-N-(4-trifluoromethoxyphenoxycarbonyl)amino]ethoxy}phenyl)-2-ethoxypropionic acid,
2-ethoxy-3-(4-{2-[N-(3-phenylpropyl)-N-(4-trifluoromethoxyphenoxycarbonyl)amino]ethoxy}phenyl)propionic acid,
2-ethoxy-3-(4-{2-[N-(4-phenylbutyl)-N-(4-trifluoromethoxyphenoxycarbonyl)amino]ethoxy}phenyl)propionic acid,
3-(4-{2-[N-(2-butoxyethyl)-N-(4-trifluoromethoxyphenoxycarbonyl)amino]ethoxy}phenyl)-2-ethoxypropionic acid,
2-ethoxy-3-(4-{2-[N-(2-pentyloxyethyl)-N-(4-trifluoromethoxyphenoxycarbonyl)amino]ethoxy}phenyl)propionic acid,
2-ethoxy-3-(4-{2-[N-(3-propoxypropyl)-N-(4-trifluoromethoxyphenoxycarbonyl)amino]ethoxy}phenyl)propionic acid,
3-(4-{2-[N-(2-butylthioethyl)-N-(4-trifluoromethoxyphenoxycarbonyl)amino]ethoxy}phenyl)-2-ethoxypropionic acid,
2-ethoxy-3-(4-{2-[N-(2-pentylthioethyl)-N-(4-trifluoromethoxyphenoxycarbonyl)amino]ethoxy}phenyl)propionic acid,
2-ethoxy-3-(4-{2-[N-(3-propylthiopropyl)-N-(4-trifluoromethoxyphenoxycarbonyl)amino]ethoxy}phenyl)propionic acid,
2-ethoxy-3-(4-{2-[N-(3-phenoxypropyl)-N-(4-trifluoromethoxyphenoxycarbonyl)amino]ethoxy}phenyl)propionic acid,
2-ethoxy-3-(4-{2-[N-(4-phenoxybutyl)-N-(4-trifluoromethoxyphenoxycarbonyl)amino]ethoxy}phenyl)propionic acid, 3-(4-{2-[N-(3-benzyloxypropyl)-N-(4-trifluoromethoxyphenoxycarbonyl)amino]ethoxy}phenyl)-2-ethoxypropionic acid,
2-ethoxy-3-(4-{2-[N-(3-phenylthiopropyl)-N-(4-trifluoromethoxyphenoxycarbonyl)amino]ethoxy}phenyl)propionic acid,
2-ethoxy-3-(4-{2-[N-(4-phenylthiobutyl)-N-(4-trifluoromethoxyphenoxycarbonyl)amino]ethoxy}phenyl)propionic acid,
3-(4-{2-[N-(3-benzylthiopropyl)-N-(4-trifluoromethoxyphenoxycarbonyl)amino]ethoxy}phenyl)-2-ethoxypropionic acid,
2-ethoxy-3-(4-{2-[N-(7,7,7-trifluoroheptyl)-N-(4-trifluoromethoxyphenoxycarbonyl)amino]ethoxy}phenyl)propionic acid,
3-(4-{2-[N-(6,6-difluoroheptyl)-N-(4-trifluoromethoxyphenoxycarbonyl)amino]ethoxy}phenyl)-2-ethoxypropionic acid,
2-ethoxy-3-(4-{2-[N-(6,6,6-trifluorohexyl)-N-(4-trifluoromethoxyphenoxycarbonyl)amino]ethoxy}phenyl)propionic acid,
3-(4-{2-[N-(5,5-difluorohexyl)-N-(4-trifluoromethoxyphenoxycarbonyl)amino]ethoxy}phenyl)-2-ethoxypropionic acid,
2-ethoxy-3-(4-{2-[N-(5,5,6,6,7,7,7-heptafluoroheptyl)-N-(4-trifluoromethoxyphenoxycarbonyl)amino]ethoxy}phenyl)propionic acid,
2-ethoxy-3-(4-{2-[N-(2,2,3,3,4,4,5,5,6,6,7,7,7-tridecafluoroheptyl)-N-(4-trifluoromethoxyphenoxycarbonyl)amino]ethoxy}phenyl)propionic acid,
2-ethoxy-3-(4-{2-[N-(5,5,6,6,6-pentafluorohexyl)-N-(4-trifluoromethoxyphenoxycarbonyl)amino]ethoxy}phenyl)propionic acid,
2-ethoxy-3-(4-{2-[N-(4-trifluoromethoxyphenoxycarbonyl)-N-(2,2,3,3,4,4,5,5,6,6,6-undecafluorohexyl)amino]ethoxy}phenyl)propionic acid,
3-[4-(2-{N-[2-(2,2-difluoropropoxy)ethyl]-N-(4-trifluoromethoxyphenoxycarbonyl)amino}ethoxy)phenyl]-2-ethoxypropionic acid,
2-ethoxy-3-[4-(2-{N-[2-(1,1,2,2,3,3,3-heptafluoropropoxy)ethyl]-N-(4-trifluoromethoxyphenoxycarbonyl)amino}ethoxy)phenyl]propionic acid,
2-ethoxy-3-[4-(2-{N-[2-(4,4,4-trifluorobutoxy)ethyl]-N-(4-trifluoromethoxyphenoxycarbonyl)amino}ethoxy)phenyl]propionic acid,
3-[4-(2-{N-[2-(3,3-difluorobutoxy)ethyl]-N-(4-trifluoromethoxyphenoxycarbonyl)amino}ethoxy)phenyl]-2-ethoxypropionic acid,
3-[4-(2-{N-[2-(2,2-difluorobutoxy)ethyl]-N-(4-trifluoromethoxyphenoxycarbonyl)amino}ethoxy)phenyl]-2-ethoxypropionic acid,
2-ethoxy-3-[4-(2-{N-[2-(1,1,2,2,3,3,4,4,4-nonafluorobutoxy)ethyl]-N-(4-trifluoromethoxyphenoxycarbonyl)amino}ethoxy)phenyl]propionic acid,
2-ethoxy-3-[4-(2-{N-[3-(2,2,2-trifluoroethoxy)propyl]-N-(4-trifluoromethoxyphenoxycarbonyl)amino}ethoxy)phenyl]propionic acid,
2-ethoxy-3-[4-(2-{N-[3-(1,1,2,2,2-pentafluoroethoxy)propyl]-N-(4-trifluoromethoxyphenoxycarbonyl)amino}ethoxy)phenyl]propionic acid,
2-ethoxy-3-[4-(2-{N-[3-(4-fluorophenoxy)propyl]-N-(4-trifluoromethoxyphenoxycarbonyl)amino}ethoxy)phenyl]propionic acid,
3-[4-(2-{N-[3-(3,5-dichlorophenoxy)propyl]-N-(4-trifluoromethoxyphenoxycarbonyl)amino}ethoxy)phenyl]-2-ethoxypropionic acid,
2-ethoxy-3-[4-(2-{N-[4-(4-fluorophenoxy)butyl]-N-(4-trifluoromethoxyphenoxycarbonyl)amino}ethoxy)phenyl]propionic acid,
3-[4-(2-{N-[4-(3,5-dichlorophenoxy)butyl]-N-(4-trifluoromethoxyphenoxycarbonyl)amino}ethoxy)phenyl]-2-ethoxypropionic acid,
2-ethoxy-3-[4-(2-{N-[2-(4-fluorobenzyloxy)ethyl]-N-(4-trifluoromethoxyphenoxycarbonyl)amino}ethoxy)phenyl]propionic acid,
3-[4-(2-{N-[2-(3,5-dichlorobenzyloxy)ethyl]-N-(4-trifluoromethoxyphenoxycarbonyl)amino}ethoxy)phenyl]-2-ethoxypropionic acid,
2-ethoxy-3-[4-(2-{N-[3-(4-fluorobenzyloxy)propyl]-N-(4-trifluoromethoxyphenoxycarbonyl)amino}ethoxy)phenyl]propionic acid,
3-[4-(2-{N-[3-(3,5-dichlorobenzyloxy)propyl]-N-(4-trifluoromethoxyphenoxycarbonyl)amino}ethoxy)phenyl]-2-ethoxypropionic acid,
2-ethoxy-3-[4-(2-{N-[4-(4-fluorobenzyloxy)butyl]-N-(4-trifluoromethoxyphenoxycarbonyl)amino}ethoxy)phenyl]propionic acid,
3-[4-(2-{N-[4-(3,5-dichlorobenzyloxy)butyl]-N-(4-trifluoromethoxyphenoxycarbonyl)amino}ethoxy)phenyl]-2-ethoxypropionic acid,
2-ethoxy-3-[4-(2-{N-[3-(4-fluorophenyl)propyl]-N-(4-trifluoromethoxyphenoxycarbonyl)amino}ethoxy)phenyl]propionic acid,
3-[4-(2-{N-[3-(3,5-dichlorophenyl)propyl]-N-(4-trifluoromethoxyphenoxycarbonyl)amino}ethoxy)phenyl]-2-ethoxypropionic acid,
2-ethoxy-3-(4-{2-[N-(2-methoxyphenoxycarbonyl)-N-pentylamino]ethoxy}phenyl)propionic acid,
2-ethoxy-3-(4-{2-[N-hexyl-N-(2-methoxyphenoxycarbonyl)amino]ethoxy}phenyl)propionic acid,
2-ethoxy-3-(4-{2-[N-heptyl-N-(2-methoxyphenoxycarbonyl)amino]ethoxy}phenyl)propionic acid,
2-ethoxy-3-(4-{2-[N-(2-methoxyphenoxycarbonyl)-N-octylamino]ethoxy}phenyl)propionic acid,
2-ethoxy-3-(4-{2-[N-isobutyl-N-(2-methoxyphenoxycarbonyl)amino]ethoxy}phenyl)propionic acid,
2-ethoxy-3-(4-{2-[N-(3-methylbutyl)-N-(2-methoxyphenoxycarbonyl)amino]ethoxy}phenyl)propionic acid,
2-ethoxy-3-(4-{2-[N-(4-methylpentyl)-N-(2-methoxyphenoxycarbonyl)amino]ethoxy}phenyl)propionic acid,
2-ethoxy-3-(4-{2-[N-(2-methoxyphenoxycarbonyl)-N-(2-propylpentyl)amino]ethoxy}phenyl)propionic acid,
3-(4-{2-[N-(3,3-dimethylbutyl)-N-(2-methoxyphenoxycarbonyl)amino]ethoxy}phenyl)-2-ethoxypropionic acid,
2-ethoxy-3-(4-{2-[N-(2-ethylbutyl)-N-(2-methoxyphenoxycarbonyl)amino]ethoxy}phenyl)propionic acid,
3-(4-{2-[N-cyclohexylmethyl-N-(2-methoxyphenoxycarbonyl)amino]ethoxy}phenyl)-2-ethoxypropionic acid,
3-(4-{2-[N-(4-cyclohexylbutyl)-N-(2-methoxyphenoxycarbonyl)amino]ethoxy}phenyl)-2-ethoxypropionic acid,
3-(4-{2-[N-cyclopropylmethyl-N-(2-methoxyphenoxycarbonyl)amino]ethoxy}phenyl)-2-ethoxypropionic acid,
3-(4-{2-[N-cyclobutylmethyl-N-(2-methoxyphenoxycarbonyl)amino]ethoxy}phenyl)-2-ethoxypropionic acid,
3-(4-{2-[N-cyclopentylmethyl-N-(2-methoxyphenoxycarbonyl)amino]ethoxy}phenyl)-2-ethoxypropionic acid,
3-(4-{2-[N-(2-cyclopentylethyl)-N-(2-methoxyphenoxycarbonyl)amino]ethoxy}phenyl)-2-ethoxypropionic acid,
3-(4-{2-[N-(3-cyclohexylpropyl)-N-(2-methoxyphenoxycarbonyl)amino]ethoxy}phenyl)-2-ethoxypropionic acid,
2-ethoxy-3-(4-{2-[N-(2-methoxyphenoxycarbonyl)-N-(3-phenylpropyl)amino]ethoxy}phenyl)propionic acid, 2-ethoxy-3-(4-{2-[N-(2-methoxyphenoxycarbonyl)-N-(4-phenylbutyl)amino]ethoxy}phenyl)propionic acid,
3-(4-{2-[N-(2-butoxyethyl)-N-(2-methoxyphenoxycarbonyl)amino]ethoxy}phenyl)-2-ethoxypropionic acid,
2-ethoxy-3-(4-{2-[N-(2-methoxyphenoxycarbonyl)-N-(2-pentyloxyethyl)amino]ethoxy}phenyl)propionic acid,
2-ethoxy-3-(4-{2-[N-(2-methoxyphenoxycarbonyl)-N-(3-propoxypropyl)amino]ethoxy}phenyl)propionic acid,
3-(4-{2-[N-(2-butylthioethyl)-N-(2-methoxyphenoxycarbonyl)amino]ethoxy}phenyl)-2-ethoxypropionic acid,
2-ethoxy-3-(4-{2-[N-(2-methoxyphenoxycarbonyl)-N-(2-pentylthioethyl)amino]ethoxy}phenyl)propionic acid,
2-ethoxy-3-(4-{2-[N-(2-methoxyphenoxycarbonyl)-N-(3-propylthiopropyl)amino]ethoxy}phenyl)propionic acid,
2-ethoxy-3-(4-{2-[N-(2-methoxyphenoxycarbonyl)-N-(3-phenoxypropyl)amino]ethoxy}phenyl)propionic acid,
2-ethoxy-3-(4-{2-[N-(2-methoxyphenoxycarbonyl)-N-(4-phenoxybutyl)amino]ethoxy}phenyl)propionic acid,
3-(4-{2-[N-(3-benzyloxypropyl)-N-(2-methoxyphenoxycarbonyl)amino]ethoxy}phenyl)-2-ethoxypropionic acid,
2-ethoxy-3-(4-{2-[N-(2-methoxyphenoxycarbonyl)-N-(3-phenylthiopropyl)amino]ethoxy}phenyl)propionic acid,
2-ethoxy-3-(4-{2-[N-(2-methoxyphenoxycarbonyl)-N-(4-phenylthiobutyl)amino]ethoxy}phenyl)propionic acid,
3-(4-{2-[N-(3-benzylthiopropyl)-N-(2-methoxyphenoxycarbonyl)amino]ethoxy}phenyl)-2-ethoxypropionic acid,
2-ethoxy-3-(4-{2-[N-(2-methoxyphenoxycarbonyl)-N-(7,7,7-trifluoroheptyl)amino]ethoxy}phenyl)propionic acid,
3-(4-{2-[N-(6,6-difluoroheptyl)-N-(2-methoxyphenoxycarbonyl)amino]ethoxy}phenyl)-2-ethoxypropionic acid,
2-ethoxy-3-(4-{2-[N-(2-methoxyphenoxycarbonyl)-N-(6,6,6-trifluorohexyl)amino]ethoxy}phenyl)propionic acid,
3-(4-{2-[N-(5,5-difluorohexyl)-N-(2-methoxyphenoxycarbonyl)amino]ethoxy}phenyl)-2-ethoxypropionic acid,
2-ethoxy-3-(4-{2-[N-(5,5,6,6,7,7,7-heptafluoroheptyl)-N-(2-methoxyphenoxycarbonyl)amino]ethoxy}phenyl)propionic acid,
2-ethoxy-3-(4-{2-[N-(2-methoxyphenoxycarbonyl)-N-(2,2,3,3,4,4,5,5,6,6,7,7,7-tridecafluoroheptyl)amino]ethoxy}phenyl)propionic acid,
2-ethoxy-3-(4-{2-[N-(2-methoxyphenoxycarbonyl)-N-(5,5,6,6,6-pentafluorohexyl)amino]ethoxy}phenyl)propionic acid,
2-ethoxy-3-(4-{2-[N-(2-methoxyphenoxycarbonyl)-N-(2,2,3,3,4,4,5,5,6,6,6-undecafluorohexyl)amino]ethoxy}phenyl)propionic acid,
3-[4-(2-{N-[2-(2,2-difluoropropoxy)ethyl]-N-(2-methoxyphenoxycarbonyl)amino}ethoxy)phenyl]-2-ethoxypropionic acid,
2-ethoxy-3-[4-(2-{N-[2-(1,1,2,2,3,3,3-heptafluoropropoxy)ethyl]-N-(2-methoxyphenoxycarbonyl)amino}ethoxy)phenyl]propionic acid,
2-ethoxy-3-[4-(2-{N-(2-methoxyphenoxycarbonyl)-N-[2-(4,4,4-trifluorobutoxy)ethyl]amino}ethoxy)phenyl]propionic acid,
3-[4-(2-{N-[2-(3,3-difluorobutoxy)ethyl]-N-(2-methoxyphenoxycarbonyl)amino}ethoxy)phenyl]-2-ethoxypropionic acid,
3-[4-(2-{N-[2-(2,2-difluorobutoxy)ethyl]-N-(2-methoxyphenoxycarbonyl)amino}ethoxy)phenyl]-2-ethoxypropionic acid,
2-ethoxy-3-[4-(2-{N-(2-methoxyphenoxycarbonyl)-N-[2-(1,1,2,2,3,3,4,4,4-nonafluorobutoxy)ethyl]amino}ethoxy)phenyl]propionic acid,
2-ethoxy-3-[4-(2-{N-(2-methoxyphenoxycarbonyl)-N-[3-(2,2,2-trifluoroethoxy)propyl]amino}ethoxy)phenyl]propionic acid,
2-ethoxy-3-[4-(2-{N-(2-methoxyphenoxycarbonyl)-N-[3-(1,1,2,2,2-pentafluoroethoxy)propyl]amino}ethoxy)phenyl]propionic acid,
2-ethoxy-3-[4-(2-{N-[3-(4-fluorophenoxy)propyl]-N-(2-methoxyphenoxycarbonyl)amino}ethoxy)phenyl]propionic acid,
3-[4-(2-{N-[3-(3,5-dichlorophenoxy)propyl]-N-(2-methoxyphenoxycarbonyl)amino}ethoxy)phenyl]-2-ethoxypropionic acid,
2-ethoxy-3-[4-(2-{N-[4-(4-fluorophenoxy)butyl]-N-(2-methoxyphenoxycarbonyl)amino}ethoxy)phenyl]propionic acid,
3-[4-(2-{N-[4-(3,5-dichlorophenoxy)butyl]-N-(2-methoxyphenoxycarbonyl)amino}ethoxy)phenyl]-2-ethoxypropionic acid,
2-ethoxy-3-[4-(2-{N-[2-(4-fluorobenzyloxy)ethyl]-N-(2-methoxyphenoxycarbonyl)amino}ethoxy)phenyl]propionic acid,
3-[4-(2-{N-[2-(3,5-dichlorobenzyloxy)ethyl]-N-(2-methoxyphenoxycarbonyl)amino}ethoxy)phenyl]-2-ethoxypropionic acid,
2-ethoxy-3-[4-(2-{N-[3-(4-fluorobenzyloxy)propyl]-N-(2-methoxyphenoxycarbonyl)amino}ethoxy)phenyl]propionic acid,
3-[4-(2-{N-[3-(3,5-dichlorobenzyloxy)propyl]-N-(2-methoxyphenoxycarbonyl)amino}ethoxy)phenyl]-2-ethoxypropionic acid,
2-ethoxy-3-[4-(2-{N-[4-(4-fluorobenzyloxy)butyl]-N-(2-methoxyphenoxycarbonyl)amino}ethoxy)phenyl]propionic acid,
3-[4-(2-{N-[4-(3,5-dichlorobenzyloxy)butyl]-N-(2-methoxyphenoxycarbonyl)amino}ethoxy)phenyl]-2-ethoxypropionic acid,
2-ethoxy-3-[4-(2-{N-[3-(4-fluorophenyl)propyl]-N-(2-methoxyphenoxycarbonyl)amino}ethoxy)phenyl]propionic acid,
3-[4-(2-{N-[3-(3,5-dichlorophenyl)propyl]-N-(2-methoxyphenoxycarbonyl)amino}ethoxy)phenyl]-2-ethoxypropionic acid,
2-ethoxy-3-(4-{2-[N-(3-methoxyphenoxycarbonyl)-N-pentylamino]ethoxy}phenyl)propionic acid,
2-ethoxy-3-(4-{2-[N-hexyl-N-(3-methoxyphenoxycarbonyl)amino]ethoxy}phenyl)propionic acid,
2-ethoxy-3-(4-{2-[N-heptyl-N-(3-methoxyphenoxycarbonyl)amino]ethoxy}phenyl)propionic acid,
2-ethoxy-3-(4-{2-[N-(3-methoxyphenoxycarbonyl)-N-octylamino]ethoxy}phenyl)propionic acid,
2-ethoxy-3-(4-{2-[N-isobutyl-N-(3-methoxyphenoxycarbonyl)amino]ethoxy}phenyl)propionic acid,
2-ethoxy-3-(4-{2-[N-(3-methylbutyl)-N-(3-methoxyphenoxycarbonyl)amino]ethoxy}phenyl)propionic acid,
2-ethoxy-3-(4-{2-[N-(4-methylpentyl)-N-(3-methoxyphenoxycarbonyl)amino]ethoxy}phenyl)propionic acid,
2-ethoxy-3-(4-{2-[N-(3-methoxyphenoxycarbonyl)-N-(2-propylpentyl)amino]ethoxy}phenyl)propionic acid,
3-(4-{2-[N-(3,3-dimethylbutyl)-N-(3-methoxyphenoxycarbonyl)amino]ethoxy}phenyl)-2-ethoxypropionic acid,
2-ethoxy-3-(4-{2-[N-(2-ethylbutyl)-N-(3-methoxyphenoxycarbonyl)amino]ethoxy}phenyl)propionic acid,
3-(4-{2-[N-cyclohexylmethyl-N-(3-methoxyphenoxycarbonyl)amino]ethoxy}phenyl)-2-ethoxypropionic acid,
3-(4-{2-[N-(4-cyclohexylbutyl)-N-(3-methoxyphenoxycarbonyl)amino]ethoxy}phenyl)-2-ethoxypropionic acid,
3-(4-{2-[N-cyclopropylmethyl-N-(3-methoxyphenoxycarbonyl)amino]ethoxy}phenyl)-2-ethoxypropionic acid,
3-(4-{2-[N-cyclobutylmethyl-N-(3-methoxyphenoxycarbonyl)amino]ethoxy}phenyl)-2-ethoxypropionic acid, 3-(4-{2-[N-cyclopentylmethyl-N-(3-methoxyphenoxycarbonyl)amino]ethoxy}phenyl)-2-ethoxypropionic acid,
3-(4-{2-[N-(2-cyclopentylethyl)-N-(3-methoxyphenoxycarbonyl)amino]ethoxy}phenyl)-2-ethoxypropionic acid,
3-(4-{2-[N-(3-cyclohexylpropyl)-N-(3-methoxyphenoxycarbonyl)amino]ethoxy}phenyl)-2-ethoxypropionic acid,
2-ethoxy-3-(4-{2-[N-(3-methoxyphenoxycarbonyl)-N-(3-phenylpropyl)amino]ethoxy}phenyl)propionic acid,
2-ethoxy-3-(4-{2-[N-(3-methoxyphenoxycarbonyl)-N-(4-phenylbutyl)amino]ethoxy}phenyl)propionic acid,
3-(4-{2-[N-(2-butoxyethyl)-N-(3-methoxyphenoxycarbonyl)amino]ethoxy}phenyl)-2-ethoxypropionic acid,
2-ethoxy-3-(4-{2-[N-(3-methoxyphenoxycarbonyl)-N-(2-pentyloxyethyl)amino]ethoxy}phenyl)propionic acid,
2-ethoxy-3-(4-{2-[N-(3-methoxyphenoxycarbonyl)-N-(3-propoxypropyl)amino]ethoxy}phenyl)propionic acid,
3-(4-{2-[N-(2-butylthioethyl)-N-(3-methoxyphenoxycarbonyl)amino]ethoxy}phenyl)-2-ethoxypropionic acid,
2-ethoxy-3-(4-{2-[N-(3-methoxyphenoxycarbonyl)-N-(2-pentylthioethyl)amino]ethoxy}phenyl)propionic acid,
2-ethoxy-3-(4-{2-[N-(3-methoxyphenoxycarbonyl)-N-(3-propylthiopropyl)amino]ethoxy}phenyl)propionic acid,
2-ethoxy-3-(4-{2-[N-(3-methoxyphenoxycarbonyl)-N-(3-phenoxypropyl)amino]ethoxy}phenyl)propionic acid,
2-ethoxy-3-(4-{2-[N-(3-methoxyphenoxycarbonyl)-N-(4-phenoxybutyl)amino]ethoxy}phenyl)propionic acid,
3-(4-{2-[N-(3-benzyloxypropyl)-N-(3-methoxyphenoxycarbonyl)amino]ethoxy}phenyl)-2-ethoxypropionic acid,
2-ethoxy-3-(4-{2-[N-(3-methoxyphenoxycarbonyl)-N-(3-phenylthiopropyl)amino]ethoxy}phenyl)propionic acid,
2-ethoxy-3-(4-{2-[N-(3-methoxyphenoxycarbonyl)-N-(4-phenylthiobutyl)amino]ethoxy}phenyl)propionic acid,
3-(4-{2-[N-(3-benzylthiopropyl)-N-(3-methoxyphenoxycarbonyl)amino]ethoxy}phenyl)-2-ethoxypropionic acid,
2-ethoxy-3-(4-{2-[N-(3-methoxyphenoxycarbonyl)-N-(7,7,7-trifluoroheptyl)amino]ethoxy}phenyl)propionic acid,
3-(4-{2-[N-(6,6-difluoroheptyl)-N-(3-methoxyphenoxycarbonyl)amino]ethoxy}phenyl)-2-ethoxypropionic acid,
2-ethoxy-3-(4-{2-[N-(3-methoxyphenoxycarbonyl)-N-(6,6,6-trifluorohexyl)amino]ethoxy}phenyl)propionic acid,
3-(4-{2-[N-(5,5-difluorohexyl)-N-(3-methoxyphenoxycarbonyl)amino]ethoxy}phenyl)-2-ethoxypropionic acid,
2-ethoxy-3-(4-{2-[N-(5,5,6,6,7,7,7-heptafluoroheptyl)-N-(3-methoxyphenoxycarbonyl)amino]ethoxy}phenyl)propionic acid,
2-ethoxy-3-(4-{2-[N-(3-methoxyphenoxycarbonyl)-N-(2,2,3,3,4,4,5,5,6,6,7,7,7-tridecafluoroheptyl)amino]ethoxy}phenyl)propionic acid,
2-ethoxy-3-(4-{2-[N-(3-methoxyphenoxycarbonyl)-N-(5,5,6,6,6-pentafluorohexyl)amino]ethoxy}phenyl)propionic acid,
2-ethoxy-3-(4-{2-[N-(3-methoxyphenoxycarbonyl)-N-(2,2,3,3,4,4,5,5,6,6-undecafluorohexyl)amino]ethoxy}phenyl)propionic acid,
3-[4-(2-{N-[2-(2,2-difluoropropoxy)ethyl]-N-(3-methoxyphenoxycarbonyl)amino}ethoxy)phenyl]-2-ethoxypropionic acid,
2-ethoxy-3-[4-(2-{N-[2-(1,1,2,2,3,3,3-heptafluoropropoxy)ethyl]-N-(3-methoxyphenoxycarbonyl)amino}ethoxy)phenyl]propionic acid,
2-ethoxy-3-[4-(2-{N-(3-methoxyphenoxycarbonyl)-N-[2-(4,4,4-trifluorobutoxy)ethyl]amino}ethoxy)phenyl]propionic acid,
3-[4-(2-{N-[2-(3,3-difluorobutoxy)ethyl]-N-(3-methoxyphenoxycarbonyl)amino}ethoxy)phenyl]-2-ethoxypropionic acid,
3-[4-(2-{N-[2-(2,2-difluorobutoxy)ethyl]-N-(3-methoxyphenoxycarbonyl)amino}ethoxy)phenyl]-2-ethoxypropionic acid,
2-ethoxy-3-[4-(2-{N-(3-methoxyphenoxycarbonyl)-N-[2-(1,1,2,2,3,3,4,4,4-nonafluorobutoxy)ethyl]amino}ethoxy)phenyl]propionic acid,
2-ethoxy-3-[4-(2-{N-(3-methoxyphenoxycarbonyl)-N-[3-(2,2,2-trifluoroethoxy)propyl]amino}ethoxy)phenyl]propionic acid,
2-ethoxy-3-[4-(2-{N-(3-methoxyphenoxycarbonyl)-N-[3-(1,1,2,2,2-pentafluoroethoxy)propyl]amino}ethoxy)phenyl]propionic acid,
2-ethoxy-3-[4-(2-{N-[3-(4-fluorophenoxy)propyl]-N-(3-methoxyphenoxycarbonyl)amino}ethoxy)phenyl]propionic acid,
3-[4-(2-{N-[3-(3,5-dichlorophenoxy)propyl]-N-(3-methoxyphenoxycarbonyl)amino}ethoxy)phenyl]-2-ethoxypropionic acid,
2-ethoxy-3-[4-(2-{N-[4-(4-fluorophenoxy)butyl]-N-(3-methoxyphenoxycarbonyl)amino}ethoxy)phenyl]propionic acid,
3-[4-(2-{N-[4-(3,5-dichlorophenoxy)butyl]-N-(3-methoxyphenoxycarbonyl)amino}ethoxy)phenyl]-2-ethoxypropionic acid,
2-ethoxy-3-[4-(2-{N-[2-(4-fluorobenzyloxy)ethyl]-N-(3-methoxyphenoxycarbonyl)amino}ethoxy)phenyl]propionic acid,
3-[4-(2-{N-[2-(3,5-dichlorobenzyloxy)ethyl]-N-(3-methoxyphenoxycarbonyl)amino}ethoxy)phenyl]-2-ethoxypropionic acid,
2-ethoxy-3-[4-(2-{N-[3-(4-fluorobenzyloxy)propyl]-N-(3-methoxyphenoxycarbonyl)amino}ethoxy)phenyl]propionic acid,
3-[4-(2-{N-[3-(3,5-dichlorobenzyloxy)propyl]-N-(3-methoxyphenoxycarbonyl)amino}ethoxy)phenyl]-2-ethoxypropionic acid,
2-ethoxy-3-[4-(2-{N-[4-(4-fluorobenzyloxy)butyl]-N-(3-methoxyphenoxycarbonyl)amino}ethoxy)phenyl]propionic acid,
3-[4-(2-{N-[4-(3,5-dichlorobenzyloxy)butyl]-N-(3-methoxyphenoxycarbonyl)amino}ethoxy)phenyl]-2-ethoxypropionic acid,
2-ethoxy-3-[4-(2-{N-[3-(4-fluorophenyl)propyl]-N-(3-methoxyphenoxycarbonyl)amino}ethoxy)phenyl]propionic acid,
3-[4-(2-{N-[3-(3,5-dichlorophenyl)propyl]-N-(3-methoxyphenoxycarbonyl)amino}ethoxy)phenyl]-2-ethoxypropionic acid,
2-ethoxy-3-(4-{2-[N-(4-methoxyphenoxycarbonyl)-N-pentylamino] ethoxy}phenyl)propionic acid,
2-ethoxy-3-(4-{2-[N-hexyl-N-(4-methoxyphenoxycarbonyl)amino]ethoxy}phenyl)propionic acid,
2-ethoxy-3-(4-{2-[N-heptyl-N-(4-methoxyphenoxycarbonyl)amino]ethoxy}phenyl)propionic acid,
2-ethoxy-3-(4-{2-[N-(4-methoxyphenoxycarbonyl)-N-octylamino]ethoxy}phenyl)propionic acid,
2-ethoxy-3-(4-{2-[N-isobutyl-N-(4-methoxyphenoxycarbonyl)amino]ethoxy}phenyl)propionic acid,
2-ethoxy-3-(4-{2-[N-(4-methoxyphenoxycarbonyl)-N-(3-methylbutyl)amino]ethoxy}phenyl)propionic acid,
2-ethoxy-3-(4-{2-[N-(4-methoxyphenoxycarbonyl)-N-(4-methylpentyl)amino]ethoxy}phenyl)propionic acid,
2-ethoxy-3-(4-{2-[N-(4-methoxyphenoxycarbonyl)-N-(2-propylpentyl)amino]ethoxy}phenyl)propionic acid,
3-(4-{2-[N-(3,3-dimethylbutyl)-N-(4-methoxyphenoxycarbonyl)amino]ethoxy}phenyl)-2-ethoxypropionic acid, 2-ethoxy-3-(4-{2-[N-(2-ethylbutyl)-N-(4-methoxyphenoxycarbonyl)amino]ethoxy}phenyl)propionic acid,
3-(4-{2-[N-cyclohexylmethyl-N-(4-methoxyphenoxycarbonyl)amino]ethoxy}phenyl)-2-ethoxypropionic acid,
3-(4-{2-[N-(4-cyclohexylbutyl)-N-(4-methoxyphenoxycarbonyl)amino]ethoxy}phenyl)-2-ethoxypropionic acid,
3-(4-{2-[N-cyclopropylmethyl-N-(4-methoxyphenoxycarbonyl)amino]ethoxy}phenyl)-2-ethoxypropionic acid,
3-(4-{2-[N-cyclobutylmethyl-N-(4-methoxyphenoxycarbonyl)amino]ethoxy}phenyl)-2-ethoxypropionic acid,
3-(4-{2-[N-cyclopentylmethyl-N-(4-methoxyphenoxycarbonyl)amino]ethoxy}phenyl)-2-ethoxypropionic acid,
3-(4-{2-[N-(2-cyclopentylethyl)-N-(4-methoxyphenoxycarbonyl)amino]ethoxy}phenyl)-2-ethoxypropionic acid,
3-(4-{2-[N-(3-cyclohexylpropyl)-N-(4-methoxyphenoxycarbonyl)amino]ethoxy}phenyl)-2-ethoxypropionic acid,
2-ethoxy-3-(4-{2-[N-(4-methoxyphenoxycarbonyl)-N-(3-phenylpropyl)amino]ethoxy}phenyl)propionic acid,
2-ethoxy-3-(4-{2-[N-(4-methoxyphenoxycarbonyl)-N-(4-phenylbutyl)amino]ethoxy}phenyl)propionic acid,
3-(4-{2-[N-(2-butoxyethyl)-N-(4-methoxyphenoxycarbonyl)amino]ethoxy}phenyl)-2-ethoxypropionic acid,
2-ethoxy-3-(4-{2-[N-(4-methoxyphenoxycarbonyl)-N-(2-pentyloxyethyl)amino]ethoxy}phenyl)propionic acid,
2-ethoxy-3-(4-{2-[N-(4-methoxyphenoxycarbonyl)-N-(3-propoxypropyl)amino]ethoxy}phenyl)propionic acid,
3-(4-{2-[N-(2-butylthioethyl)-N-(4-methoxyphenoxycarbonyl)amino]ethoxy}phenyl)-2-ethoxypropionic acid,
2-ethoxy-3-(4-{2-[N-(4-methoxyphenoxycarbonyl)-N-(2-pentylthioethyl)amino]ethoxy}phenyl)propionic acid,
2-ethoxy-3-(4-{2-[N-(4-methoxyphenoxycarbonyl)-N-(3-propylthiopropyl)amino]ethoxy}phenyl)propionic acid,
2-ethoxy-3-(4-{2-[N-(4-methoxyphenoxycarbonyl)-N-(3-phenoxypropyl)amino]ethoxy}phenyl)propionic acid,
2-ethoxy-3-(4-{2-[N-(4-methoxyphenoxycarbonyl)-N-(4-phenoxybutyl)amino]ethoxy}phenyl)propionic acid,
3-(4-{2-[N-(3-benzyloxypropyl)-N-(4-methoxyphenoxycarbonyl)amino]ethoxy}phenyl)-2-ethoxypropionic acid,
2-ethoxy-3-(4-{2-[N-(4-methoxyphenoxycarbonyl)-N-(3-phenylthiopropyl)amino]ethoxy}phenyl)propionic acid,
2-ethoxy-3-(4-{2-[N-(4-methoxyphenoxycarbonyl)-N-(4-phenylthiobutyl)amino]ethoxy}phenyl)propionic acid,
3-(4-{2-[N-(3-benzylthiopropyl)-N-(4-methoxyphenoxycarbonyl)amino]ethoxy}phenyl)-2-ethoxypropionic acid,
2-ethoxy-3-(4-{2-[N-(4-methoxyphenoxycarbonyl)-N-(7,7,7-trifluoroheptyl)amino]ethoxy}phenyl)propionic acid,
3-(4-{2-[N-(6,6-difluoroheptyl)-N-(4-methoxyphenoxycarbonyl)amino]ethoxy}phenyl)-2-ethoxypropionic acid,
2-ethoxy-3-(4-{2-[N-(4-methoxyphenoxycarbonyl)-N-(6,6,6-trifluorohexyl)amino]ethoxy}phenyl)propionic acid,
3-(4-{2-[N-(5,5-difluorohexyl)-N-(4-methoxyphenoxycarbonyl)amino]ethoxy}phenyl)-2-ethoxypropionic acid,
2-ethoxy-3-(4-{2-[N-(5,5,6,6,7,7,7-heptafluoroheptyl)-N-(4-methoxyphenoxycarbonyl)amino]ethoxy}phenyl)propionic acid,
2-ethoxy-3-(4-{2-[N-(4-methoxyphenoxycarbonyl)-N-(2,2,3,3,4,4,5,5,6,6,7,7,7-tridecafluoroheptyl)amino]ethoxy}phenyl)propionic acid,
2-ethoxy-3-(4-{2-[N-(4-methoxyphenoxycarbonyl)-N-(5,5,6,6,6-pentafluorohexyl)amino]ethoxy}phenyl)propionic acid,
2-ethoxy-3-(4-{2-[N-(4-methoxyphenoxycarbonyl)-N-(2,2,3,3,4,4,5,5,6,6,6-undecafluorohexyl)amino]ethoxy}phenyl)propionic acid,
3-[4-(2-{N-[2-(2,2-difluoropropoxy)ethyl]-N-(4-methoxyphenoxycarbonyl)amino}ethoxy)phenyl]-2-ethoxypropionic acid,
2-ethoxy-3-[4-(2-{N-[2-(1,1,2,2,3,3,3-heptafluoropropoxy)ethyl]-N-(4-methoxyphenoxycarbonyl)amino}ethoxy)phenyl]propionic acid,
2-ethoxy-3-[4-(2-{N-(4-methoxyphenoxycarbonyl)-N-[2-(4,4,4-trifluorobutoxy)ethyl]amino}ethoxy)phenyl]propionic acid,
3-[4-(2-{N-[2-(3,3-difluorobutoxy)ethyl]-N-(4-methoxyphenoxycarbonyl)amino}ethoxy)phenyl]-2-ethoxypropionic acid,
3-[4-(2-{N-[2-(2,2-difluorobutoxy)ethyl]-N-(4-methoxyphenoxycarbonyl)amino}ethoxy)phenyl]-2-ethoxypropionic acid,
2-ethoxy-3-[4-(2-{N-(4-methoxyphenoxycarbonyl)-N-[2-(1,1,2,2,3,3,4,4,4-nonafluorobutoxy)ethyl]amino}ethoxy)phenyl]propionic acid,
2-ethoxy-3-[4-(2-{N-(4-methoxyphenoxycarbonyl)-N-[3-(2,2,2-trifluoroethoxy)propyl]amino}ethoxy)phenyl]propionic acid,
2-ethoxy-3-[4-(2-{N-(4-methoxyphenoxycarbonyl)-N-[3-(1,1,2,2,2-pentafluoroethoxy)propyl]amino}ethoxy)phenyl]propionic acid,
2-ethoxy-3-[4-(2-{N-[3-(4-fluorophenoxy)propyl]-N-(4-methoxyphenoxycarbonyl)amino}ethoxy)phenyl]propionic acid,
3-[4-(2-{N-[3-(3,5-dichlorophenoxy)propyl]-N-(4-methoxyphenoxycarbonyl)amino}ethoxy)phenyl]-2-ethoxypropionic acid,
2-ethoxy-3-[4-(2-{N-[4-(4-fluorophenoxy)butyl]-N-(4-methoxyphenoxycarbonyl)amino}ethoxy)phenyl]propionic acid,
3-[4-(2-{N-[4-(3,5-dichlorophenoxy)butyl]-N-(4-methoxyphenoxycarbonyl)amino}ethoxy)phenyl]-2-ethoxypropionic acid,
2-ethoxy-3-[4-(2-{N-[2-(4-fluorobenzyloxy)ethyl]-N-(4-methoxyphenoxycarbonyl)amino}ethoxy)phenyl]propionic acid,
3-[4-(2-{N-[2-(3,5-dichlorobenzyloxy)ethyl]-N-(4-methoxyphenoxycarbonyl)amino}ethoxy)phenyl]-2-ethoxypropionic acid,
2-ethoxy-3-[4-(2-{N-[3-(4-fluorobenzyloxy)propyl]-N-(4-methoxyphenoxycarbonyl)amino}ethoxy)phenyl]propionic acid,
3-[4-(2-{N-[3-(3,5-dichlorobenzyloxy)propyl]-N-(4-methoxyphenoxycarbonyl)amino}ethoxy)phenyl]-2-ethoxypropionic acid,
2-ethoxy-3-[4-(2-{N-[4-(4-fluorobenzyloxy)butyl]-N-(4-methoxyphenoxycarbonyl)amino}ethoxy)phenyl]propionic acid,
3-[4-(2-{N-[4-(3,5-dichlorobenzyloxy)butyl]-N-(4-methoxyphenoxycarbonyl)amino}ethoxy)phenyl]-2-ethoxypropionic acid,
2-ethoxy-3-[4-(2-{N-[3-(4-fluorophenyl)propyl]-N-(4-methoxyphenoxycarbonyl)amino}ethoxy)phenyl]propionic acid,
3-[4-(2-{N-[3-(3,5-dichlorophenyl)propyl]-N-(4-methoxyphenoxycarbonyl)amino}ethoxy)phenyl]-2-ethoxypropionic acid,
2-ethoxy-3-(4-{2-[N-(4-methyl-3-nitrophenoxycarbonyl)-N-pentylamino]ethoxy}phenyl)propionic acid,
2-ethoxy-3-(4-{2-[N-hexyl-N-(4-methyl-3-nitrophenoxycarbonyl)amino]ethoxy}phenyl)propionic acid,
2-ethoxy-3-(4-{2-[N-heptyl-N-(4-methyl-3-nitrophenoxycarbonyl)amino]ethoxy}phenyl)propionic acid,
2-ethoxy-3-(4-{2-[N-(4-methyl-3-nitrophenoxycarbonyl)-N-octylamino]ethoxy}phenyl)propionic acid,
2-ethoxy-3-(4-{2-[N-isobutyl-N-(4-methyl-3-nitrophenoxycarbonyl)amino]ethoxy}phenyl)propionic acid, 2-ethoxy-3-(4-{2-[N-(3-methylbutyl)-N-(4-methyl-3-nitrophenoxycarbonyl)amino]ethoxy}phenyl)propionic acid,
2-ethoxy-3-(4-{2-[N-(4-methyl-3-nitrophenoxycarbonyl)-N-(4-methylpentyl)amino]ethoxy}phenyl)propionic acid,
2-ethoxy-3-(4-{2-[N-(4-methyl-3-nitrophenoxycarbonyl)-N-(2-propylpentyl)amino]ethoxy}phenyl)propionic acid,
3-(4-{2-[N-(3,3-dimethylbutyl)-N-(4-methyl-3-nitrophenoxycarbonyl)amino]ethoxy}phenyl)-2-ethoxypropionic acid,
2-ethoxy-3-(4-{2-[N-(2-ethylbutyl)-N-(4-methyl-3-nitrophenoxycarbonyl)amino]ethoxy}phenyl)propionic acid,
3-(4-{2-[N-cyclohexylmethyl-N-(4-methyl-3-nitrophenoxycarbonyl)amino]ethoxy}phenyl)-2-ethoxypropionic acid,
3-(4-{2-[N-(4-cyclohexylbutyl)-N-(4-methyl-3-nitrophenoxycarbonyl)amino]ethoxy}phenyl)-2-ethoxypropionic acid,
3-(4-{2-[N-cyclopropylmethyl-N-(4-methyl-3-nitrophenoxycarbonyl)amino]ethoxy}phenyl)-2-ethoxypropionic acid,
3-(4-{2-[N-cyclobutylmethyl-N-(4-methyl-3-nitrophenoxycarbonyl)amino]ethoxy}phenyl)-2-ethoxypropionic acid,
3-(4-{2-[N-cyclopentylmethyl-N-(4-methyl-3-nitrophenoxycarbonyl)amino]ethoxy}phenyl)-2-ethoxypropionic acid,
3-(4-{2-[N-(2-cyclopentylethyl)-N-(4-methyl-3-nitrophenoxycarbonyl)amino]ethoxy}phenyl)-2-ethoxypropionic acid,
3-(4-{2-[N-(3-cyclohexylpropyl)-N-(4-methyl-3-nitrophenoxycarbonyl)amino]ethoxy}phenyl)-2-ethoxypropionic acid,
2-ethoxy-3-(4-{2-[N-(4-methyl-3-nitrophenoxycarbonyl)-N-(3-phenylpropyl)amino]ethoxy}phenyl)propionic acid,
2-ethoxy-3-(4-{2-[N-(4-methyl-3-nitrophenoxycarbonyl)-N-(4-phenylbutyl)amino]ethoxy}phenyl)propionic acid,
3-(4-{2-[N-(2-butoxyethyl)-N-(4-methyl-3-nitrophenoxycarbonyl)amino]ethoxy}phenyl)-2-ethoxypropionic acid,
2-ethoxy-3-(4-{2-[N-(4-methyl-3-nitrophenoxycarbonyl)-N-(2-pentyloxyethyl)amino]ethoxy}phenyl)propionic acid,
2-ethoxy-3-(4-{2-[N-(4-methyl-3-nitrophenoxycarbonyl)-N-(3-propoxypropyl)amino]ethoxy}phenyl)propionic acid,
3-(4-{2-[N-(2-butylthioethyl)-N-(4-methyl-3-nitrophenoxycarbonyl)amino]ethoxy}phenyl)-2-ethoxypropionic acid,
2-ethoxy-3-(4-{2-[N-(4-methyl-3-nitrophenoxycarbonyl)-N-(2-pentylthioethyl)amino]ethoxy}phenyl)propionic acid,
2-ethoxy-3-(4-{2-[N-(4-methyl-3-nitrophenoxycarbonyl)-N-(3-propylthiopropyl)amino]ethoxy}phenyl)propionic acid,
2-ethoxy-3-(4-{2-[N-(4-methyl-3-nitrophenoxycarbonyl)-N-(3-phenoxypropyl)amino]ethoxy}phenyl)propionic acid,
2-ethoxy-3-(4-{2-[N-(4-methyl-3-nitrophenoxycarbonyl)-N-(4-phenoxybutyl)amino]ethoxy}phenyl)propionic acid,
3-(4-{2-[N-(3-benzyloxypropyl)-N-(4-methyl-3-nitrophenoxycarbonyl)amino]ethoxy}phenyl)-2-ethoxypropionic acid,
2-ethoxy-3-(4-{2-[N-(4-methyl-3-nitrophenoxycarbonyl)-N-(3-phenylthiopropyl)amino]ethoxy}phenyl)propionic acid,
2-ethoxy-3-(4-{2-[N-(4-methyl-3-nitrophenoxycarbonyl)-N-(4-phenylthiobutyl)amino]ethoxy}phenyl)propionic acid,
3-(4-{2-[N-(3-benzylthiopropyl)-N-(4-methyl-3-nitrophenoxycarbonyl)amino]ethoxy}phenyl)-2-ethoxypropionic acid,
2-ethoxy-3-(4-{2-[N-(4-methyl-3-nitrophenoxycarbonyl)-N-(7,7,7-trifluoroheptyl)amino]ethoxy}phenyl)propionic acid,
3-(4-{2-[N-(6,6-difluoroheptyl)-N-(4-methyl-3-nitrophenoxycarbonyl)amino]ethoxy}phenyl)-2-ethoxypropionic acid,
2-ethoxy-3-(4-{2-[N-(4-methyl-3-nitrophenoxycarbonyl)-N-(6,6,6-trifluorohexyl)amino]ethoxy}phenyl)propionic acid,
3-(4-{2-[N-(5,5-difluorohexyl)-N-(4-methyl-3-nitrophenoxycarbonyl)amino]ethoxy}phenyl)-2-ethoxypropionic acid,
2-ethoxy-3-(4-{2-[N-(5,5,6,6,7,7,7-heptafluoroheptyl)-N-(4-methyl-3-nitrophenoxycarbonyl)amino]ethoxy}phenyl)propionic acid,
2-ethoxy-3-(4-{2-[N-(4-methyl-3-nitrophenoxycarbonyl)-N-(2,2,3,3,4,4,5,5,6,6,7,7,7-tridecafluoroheptyl)amino]ethoxy}phenyl)propionic acid,
2-ethoxy-3-(4-{2-[N-(4-methyl-3-nitrophenoxycarbonyl)-N-(5,5,6,6,6-pentafluorohexyl)amino]ethoxy}phenyl)propionic acid,
2-ethoxy-3-(4-{2-[N-(4-methyl-3-nitrophenoxycarbonyl)-N-(2,2,3,3,4,4,5,5,6,6,6-undecafluorohexyl)amino]ethoxy}phenyl)propionic acid,
3-[4-(2-{N-[2-(2,2-difluoropropoxy)ethyl]-N-(4-methyl-3-nitrophenoxycarbonyl)amino}ethoxy)phenyl]-2-ethoxypropionic acid,
2-ethoxy-3-[4-(2-{N-[2-(1,1,2,2,3,3,3-heptafluoropropoxy)ethyl]-N-(4-methyl-3-nitrophenoxycarbonyl)amino}ethoxy)phenyl]propionic acid,
2-ethoxy-3-[4-(2-{N-(4-methyl-3-nitrophenoxycarbonyl)-N-[2-(4,4,4-trifluorobutoxy)ethyl]amino}ethoxy)phenyl]propionic acid,
3-[4-(2-{N-[2-(3,3-difluorobutoxy)ethyl]-N-(4-methyl-3-nitrophenoxycarbonyl)amino}ethoxy)phenyl]-2-ethoxypropionic acid,
3-[4-(2-{N-[2-(2,2-difluorobutoxy)ethyl]-N-(4-methyl-3-nitrophenoxycarbonyl)amino}ethoxy)phenyl]-2-ethoxypropionic acid,
2-ethoxy-3-[4-(2-{N-(4-methyl-3-nitrophenoxycarbonyl)-N-[2-(1,1,2,2,3,3,4,4,4-nonafluorobutoxy)ethyl]amino}ethoxy)phenyl]propionic acid,
2-ethoxy-3-[4-(2-{N-(4-methyl-3-nitrophenoxycarbonyl)-N-[3-(2,2,2-trifluoroethoxy)propyl]amino}ethoxy)phenyl]propionic acid,
2-ethoxy-3-[4-(2-{N-(4-methyl-3-nitrophenoxycarbonyl)-N-[3-(1,1,2,2,2-pentafluoroethoxy)propyl]amino}ethoxy)phenyl]propionic acid,
2-ethoxy-3-[4-(2-{N-[3-(4-fluorophenoxy)propyl]-N-(4-methyl-3-nitrophenoxycarbonyl)amino}ethoxy)phenyl]propionic acid,
3-[4-(2-{N-[3-(3,5-dichlorophenoxy)propyl]-N-(4-methyl-3-nitrophenoxycarbonyl)amino}ethoxy)phenyl]-2-ethoxypropionic acid,
2-ethoxy-3-[4-(2-{N-[4-(4-fluorophenoxy)butyl]-N-(4-methyl-3-nitrophenoxycarbonyl)amino}ethoxy)phenyl]propionic acid,
3-[4-(2-{N-[4-(3,5-dichlorophenoxy)butyl]-N-(4-methyl-3-nitrophenoxycarbonyl)amino}ethoxy)phenyl]-2-ethoxypropionic acid,
2-ethoxy-3-[4-(2-{N-[2-(4-fluorobenzyloxy)ethyl]-N-(4-methyl-3-nitrophenoxycarbonyl)amino}ethoxy)phenyl]propionic acid, 3-[4-(2-{N-[2-(3,5-dichlorobenzyloxy)ethyl]-N-(4-methyl-3-nitrophenoxycarbonyl)amino}ethoxy)phenyl]-2-ethoxypropionic acid, 2-ethoxy-3-[4-(2-{N-[3-(4-fluorobenzyloxy)propyl]-N-(4-methyl-3-nitrophenoxycarbonyl)amino}ethoxy)phenyl]propionic acid, 3-[4-(2-{N-[3-(3,5-dichlorobenzyloxy)propyl]-N-(4-methyl-3-nitrophenoxycarbonyl)amino}ethoxy)phenyl]-2-ethoxypropionic acid, 2-ethoxy-3-[4-(2-{N-[4-(4-fluorobenzyloxy)butyl]-N-(4-methyl-3-nitrophenoxycarbonyl)amino}ethoxy)phenyl]propionic acid, 3-[4-(2-{N-[4-(3,5-dichlorobenzyloxy)butyl]-N-(4-methyl-3-nitrophenoxycarbonyl)amino}ethoxy)phenyl]-2-ethoxypropionic acid, 2-ethoxy-3-[4-(2-{N-[3-(4-fluorophenyl)propyl]-N-(4-methyl-3-nitrophenoxycarbonyl)amino}ethoxy)phenyl]propionic acid, 3-[4-(2-{N-[3-(3,5-dichlorophenyl)propyl]-N-(4-methyl-3-nitrophenoxycarbonyl)amino}ethoxy)phenyl]-2-ethoxypropionic acid, 2-ethoxy-3-(4-{2-[N-(2-methoxy-5-methylphenoxycarbonyl)-N-pentylamino]ethoxy}phenyl)propionic acid, 2-ethoxy-3-(4-{2-[N-hexyl-N-(2-methoxy-5-methylphenoxycarbonyl)amino]ethoxy}phenyl)propionic acid, 2-ethoxy-3-(4-{2-[N-heptyl-N-(2-methoxy-5-methylphenoxycarbonyl)amino]ethoxy}phenyl)propionic acid, 2-ethoxy-3-(4-{2-[N-(2-methoxy-5-methylphenoxycarbonyl)-N-octylamino]ethoxy}phenyl)propionic acid, 2-ethoxy-3-(4-{2-[N-isobutyl-N-(2-methoxy-5-methylphenoxycarbonyl)amino]ethoxy}phenyl)propionic acid, 2-ethoxy-3-(4-{2-[N-(2-methoxy-5-methylphenoxycarbonyl)-N-(3-methylbutyl)amino]ethoxy}phenyl)propionic acid, 2-ethoxy-3-(4-{2-[N-(2-methoxy-5-methylphenoxycarbonyl)-N-(4-methylpentyl)amino]ethoxy}phenyl)propionic acid, 2-ethoxy-3-(4-{2-[N-(2-methoxy-5-methylphenoxycarbonyl)-N-(2-propylpentyl)amino]ethoxy}phenyl)propionic acid, 3-(4-{2-[N-(3,3-dimethylbutyl)-N-(2-methoxy-5-methylphenoxycarbonyl)amino]ethoxy}phenyl)-2-ethoxypropionic acid, 2-ethoxy-3-(4-{2-[N-(2-ethylbutyl)-N-(2-methoxy-5-methylphenoxycarbonyl)amino]ethoxy}phenyl)propionic acid, 3-(4-{2-[N-cyclohexylmethyl-N-(2-methoxy-5-methylphenoxycarbonyl)amino]ethoxy}phenyl)-2-ethoxypropionic acid, 3-(4-{2-[N-(4-cyclohexylbutyl)-N-(2-methoxy-5-methylphenoxycarbonyl)amino]ethoxy}phenyl)-2-ethoxypropionic acid, 3-(4-{2-[N-cyclopropylmethyl-N-(2-methoxy-5-methylphenoxycarbonyl)amino]ethoxy}phenyl)-2-ethoxypropionic acid, 3-(4-{2-[N-cyclobutylmethyl-N-(2-methoxy-5-methylphenoxycarbonyl)amino]ethoxy}phenyl)-2-ethoxypropionic acid, 3-(4-{2-[N-cyclopentylmethyl-N-(2-methoxy-5-methylphenoxycarbonyl)amino]ethoxy}phenyl)-2-ethoxypropionic acid, 3-(4-{2-[N-(2-cyclopentylethyl)-N-(2-methoxy-5-methylphenoxycarbonyl)amino]ethoxy}phenyl)-2-ethoxypropionic acid, 3-(4-{2-[N-(3-cyclohexylpropyl)-N-(2-methoxy-5-methylphenoxycarbonyl)amino]ethoxy}phenyl)-2-ethoxypropionic acid, 2-ethoxy-3-(4-{2-[N-(2-methoxy-5-methylphenoxycarbonyl)-N-(3-phenylpropyl)amino]ethoxy}phenyl)propionic acid, 2-ethoxy-3-(4-{2-[N-(2-methoxy-5-methylphenoxycarbonyl)-N-(4-phenylbutyl)amino]ethoxy}phenyl)propionic acid, 3-(4-{2-[N-(2-butoxyethyl)-N-(2-methoxy-5-methylphenoxycarbonyl)amino]ethoxy}phenyl)-2-ethoxypropionic acid, 2-ethoxy-3-(4-{2-[N-(2-methoxy-5-methylphenoxycarbonyl)-N-(2-pentyloxyethyl)amino]ethoxy}phenyl)propionic acid, 2-ethoxy-3-(4-{2-[N-(2-methoxy-5-methylphenoxycarbonyl)-N-(3-propoxypropyl)amino]ethoxy}phenyl)propionic acid, 3-(4-{2-[N-(2-butylthioethyl)-N-(2-methoxy-5-methylphenoxycarbonyl)amino]ethoxy}phenyl)-2-ethoxypropionic acid, 2-ethoxy-3-(4-{2-[N-(2-methoxy-5-methylphenoxycarbonyl)-N-(2-pentylthioethyl)amino]ethoxy}phenyl)propionic acid, 2-ethoxy-3-(4-{2-[N-(2-methoxy-5-methylphenoxycarbonyl)-N-(3-propylthiopropyl)amino]ethoxy}phenyl)propionic acid, 2-ethoxy-3-(4-{2-[N-(2-methoxy-5-methylphenoxycarbonyl)-N-(3-phenoxypropyl)amino]ethoxy}phenyl)propionic acid, 2-ethoxy-3-(4-{2-[N-(2-methoxy-5-methylphenoxycarbonyl)-N-(4-phenoxybutyl)amino]ethoxy}phenyl)propionic acid, 3-(4-{2-[N-(3-benzyloxypropyl)-N-(2-methoxy-5-methylphenoxycarbonyl)amino]ethoxy}phenyl)-2-ethoxypropionic acid, 2-ethoxy-3-(4-{2-[N-(2-methoxy-5-methylphenoxycarbonyl)-N-(3-phenylthiopropyl)amino]ethoxy}phenyl)propionic acid, 2-ethoxy-3-(4-{2-[N-(2-methoxy-5-methylphenoxycarbonyl)-N-(4-phenylthiobutyl)amino]ethoxy}phenyl)propionic acid, 3-(4-{2-[N-(3-benzylthiopropyl)-N-(2-methoxy-5-methylphenoxycarbonyl)amino]ethoxy}phenyl)-2-ethoxypropionic acid, 2-ethoxy-3-(4-{2-[N-(2-methoxy-5-methylphenoxycarbonyl)-N-(7,7,7-trifluoroheptyl)amino]ethoxy}phenyl)propionic acid, 3-(4-{2-[N-(6,6-difluoroheptyl)-N-(2-methoxy-5-methylphenoxycarbonyl)amino]ethoxy}phenyl)-2-ethoxypropionic acid, 2-ethoxy-3-(4-{2-[N-(2-methoxy-5-methylphenoxycarbonyl)-N-(6,6,6-trifluorohexyl)amino]ethoxy}phenyl)propionic acid, 3-(4-{2-[N-(5,5-difluorohexyl)-N-(2-methoxy-5-methylphenoxycarbonyl)amino]ethoxy}phenyl)-2-ethoxypropionic acid, 2-ethoxy-3-(4-{2-[N-(5,5,6,6,7,7,7-heptafluoroheptyl)-N-(2-methoxy-5-methylphenoxycarbonyl)amino]ethoxy}phenyl)propionic acid, 2-ethoxy-3-(4-{2-[N-(2-methoxy-5-methylphenoxycarbonyl)-N-(2,2,3,3,4,4,5,5,6,6,7,7,7-tridecafluoroheptyl)amino]ethoxy}phenyl)propionic acid, 2-ethoxy-3-(4-{2-[N-(2-methoxy-5-methylphenoxycarbonyl)-N-(5,5,6,6,6-pentafluorohexyl)amino]ethoxy}phenyl)propionic acid, 2-ethoxy-3-(4-{2-[N-(2-methoxy-5-methylphenoxycarbonyl)-N-(2,2,3,3,4,4,5,5,6,6-undecafluorohexyl)amino]ethoxy}phenyl)propionic acid, 3-[4-(2-{N-[2-(2,2-difluoropropoxy)ethyl]-N-(2-methoxy-5-methylphenoxycarbonyl)amino}ethoxy)phenyl]-2-ethoxypropionic acid,
2-ethoxy-3-[4-(2-{N-[2-(1,1,2,2,3,3,3-heptafluoropropoxy)ethyl]-N-(2-methoxy-5-methylphenoxycarbonyl)amino}ethoxy)phenyl]propionic acid,
2-ethoxy-3-[4-(2-{N-(2-methoxy-5-methylphenoxycarbonyl)-N-[2-(4,4,4-trifluorobutoxy)ethyl]amino}ethoxy)phenyl]propionic acid,
3-[4-(2-{N-[2-(3,3-difluorobutoxy)ethyl]-N-(2-methoxy-5-methylphenoxycarbonyl)amino}ethoxy)phenyl]-2-ethoxypropionic acid,
3-[4-(2-{N-[2-(2,2-difluorobutoxy)ethyl]-N-(2-methoxy-5-methylphenoxycarbonyl)amino}ethoxy)phenyl]-2-ethoxypropionic acid,
2-ethoxy-3-[4-(2-{N-(2-methoxy-5-methylphenoxycarbonyl)-N-[2-(1,1,2,2,3,3,4,4,4-nonafluorobutoxy)ethyl]amino}ethoxy)phenyl]propionic acid,
2-ethoxy-3-[4-(2-{N-(2-methoxy-5-methylphenoxycarbonyl)-N-[3-(2,2,2-trifluoroethoxy)propyl]amino}ethoxy)phenyl]propionic acid,
2-ethoxy-3-[4-(2-{N-(2-methoxy-5-methylphenoxycarbonyl)-N-[3-(1,1,2,2,2-pentafluoroethoxy)propyl]amino}ethoxy)phenyl]propionic acid,
2-ethoxy-3-[4-(2-{N-[3-(4-fluorophenoxy)propyl]-N-(2-methoxy-5 -methylphenoxycarbonyl)amino}ethoxy)phenyl]propionic acid,
3-[4-(2-{N-[3-(3,5-dichlorophenoxy)propyl]-N-(2-methoxy-5-methylphenoxycarbonyl)amino}ethoxy)phenyl]-2-ethoxypropionic acid,
2-ethoxy-3-[4-(2-{N-[4-(4-fluorophenoxy)butyl]-N-(2-methoxy-5-methylphenoxycarbonyl)amino}ethoxy)phenyl]propionic acid,
3-[4-(2-{N-[4-(3,5-dichlorophenoxy)butyl]-N-(2-methoxy-5-methylphenoxycarbonyl)amino}ethoxy)phenyl]-2-ethoxypropionic acid,
2-ethoxy-3-[4-(2-{N-[2-(4-fluorobenzyloxy)ethyl]-N-(2-methoxy-5-methylphenoxycarbonyl)amino}ethoxy)phenyl]propionic acid,
3-[4-(2-{N-[2-(3,5-dichlorobenzyloxy)ethyl]-N-(2-methoxy-5-methylphenoxycarbonyl)amino}ethoxy)phenyl]-2-ethoxypropionic acid,
2-ethoxy-3-[4-(2-{N-[3-(4-fluorobenzyloxy)propyl]-N-(2-methoxy-5-methylphenoxycarbonyl)amino}ethoxy)phenyl]propionic acid,
3-[4-(2-{N-[3-(3,5-dichlorobenzyloxy)propyl]-N-(2-methoxy-5-methylphenoxycarbonyl)amino}ethoxy)phenyl]-2-ethoxypropionic acid,
2-ethoxy-3-[4-(2-{N-[4-(4-fluorobenzyloxy)butyl]-N-(2-methoxy-5-methylphenoxycarbonyl)amino}ethoxy)phenyl]propionic acid,
3-[4-(2-{N-[4-(3,5-dichlorobenzyloxy)butyl]-N-(2-methoxy-5-methylphenoxycarbonyl)amino}ethoxy)phenyl]-2-ethoxypropionic acid,
2-ethoxy-3-[4-(2-{N-[3-(4-fluorophenyl)propyl]-N-(2-methoxy-5-methylphenoxycarbonyl)amino}ethoxy)phenyl]propionic acid, and
3-[4-(2-{N-[3-(3,5-dichlorophenyl)propyl]-N-(2-methoxy-5-methylphenoxycarbonyl)amino}ethoxy)phenyl]-2-ethoxypropionic acid.

Examples further include 3-{4-[2-(N-allyloxycarbonyl-N-heptylamino)ethoxy]phenyl}-2-ethoxypropionic acid,
2-ethoxy-3-(4-{2-[N-heptyl-N-(4-nitrobenzyloxycarbonyl)amino]ethoxy}phenyl)propionic acid,
2-ethoxy-3-(4-{2-[N-heptyl-N-(2-methoxyethoxycarbonyl)amino]ethoxy}phenyl)propionic acid,
2-ethoxy-3-{4-[2-(N-heptyl-N-propargyloxycarbonylamino)ethoxy]phenyl}propionic acid,
2-ethoxy-3-(4-{2-[N-heptyl-N-(2-naphthyloxycarbonyl)amino]ethoxy}phenyl)propionic acid,
3-(4-{2-[N-(3-butenyloxycarbonyl)-N-heptylamino]ethoxy}phenyl)-2-ethoxypropionic acid,
3-{4-[2-(N-butoxycarbonyl-N-heptylamino)ethoxy]phenyl}-2-ethoxypropionic acid and the like.

Further, examples of the compounds wherein $R^4$ is isopropyl group include, for example, the following compounds.

3-(4-[2-(N-Heptyl-N-methoxycarbonylamino)ethoxy]phenyl}-2-isopropoxypropionic acid,
3-(4-{2-[N-(2-butoxyethyl)-N-methoxycarbonylamino]ethoxy}phenyl)-2-isopropoxypropionic acid,
3-(4-[2-(N-ethoxycarbonyl-N-heptylamino)ethoxy]phenyl}-2-isopropoxypropionic acid,
3-(4-{2-[N-(2-butoxyethyl)-N-ethoxycarbonylamino]ethoxy}phenyl)-2-isopropoxypropionic acid,
3-{4-[2-(N-heptyl-N-propoxycarbonylamino)ethoxy]phenyl}-2-isopropoxypropionic acid,
3-(4-{2-[N-(2-butoxyethyl)-N-propoxycarbonylamino]ethoxy}phenyl)-2-isopropoxypropionic acid,
3-{4-[2-(N-butoxycarbonyl-N-heptylamino)ethoxy]phenyl}-2-isopropoxypropionic acid,
3-(4-{2-[N-butoxycarbonyl-N-(2-butoxyethyl)amino]ethoxy}phenyl)-2-isopropoxypropionic acid,
3-{4-[2-(N-heptyl-N-isopropoxycarbonylamino)ethoxy]phenyl}-2-isopropoxypropionic acid,
3-(4-{2-[N-(2-butoxyethyl)-N-isopropoxycarbonylamino]ethoxy}phenyl)-2-isopropoxypropionic acid,
3-(4-[2-(N-heptyl-N-isobutoxycarbonylamino)ethoxy]phenyl}-2-isopropoxypropionic acid,
3-(4-{2-[N-(2-butoxyethyl)-N-isobutoxycarbonylamino]ethoxy}phenyl)-2-isopropoxypropionic acid,
3-{4-[2-(N-sec-butoxycarbonyl-N-heptylamino)ethoxy]phenyl}-2-isopropoxypropionic acid,
3-(4-{2-[N-sec-butoxycarbonyl-N-(2-butoxyethyl)amino]ethoxy}phenyl)-2-isopropoxypropionic acid,
3-{4-[2-(N-tert-butoxycarbonyl-N-heptylamino)ethoxy]phenyl}-2-isopropoxypropionic acid,
3-(4-{2-[N-tert-butoxycarbonyl-N-(2-butoxyethyl)amino]ethoxy}phenyl)-2-isopropoxypropionic acid,
3-(4-{2-[N-heptyl-N-(2,2,2-trifluoroethoxycarbonyl)amino]ethoxy}phenyl)-2-isopropoxypropionic acid,
3-(4-{2-[N-(2-butoxyethyl)-N-(2,2,2-trifluoroethoxycarbonyl)amino]ethoxy}phenyl)-2-isopropoxypropionic acid,
3-{4-[3-(N-heptyl-N-methoxycarbonylamino)propoxy]phenyl}-2-isopropoxypropionic acid,
3-(4-{3-[N-(2-butoxyethyl)-N-methoxycarbonylamino]propoxy}phenyl)-2-isopropoxypropionic acid,
3-{4-[3-(N-ethoxycarbonyl-N-heptylamino)propoxy]phenyl}-2-isopropoxypropionic acid,
3-(4-{3-[N-(2-butoxyethyl)-N-ethoxycarbonylamino]propoxy}phenyl)-2-isopropoxypropionic acid,
3-{4-[3-(N-heptyl-N-propoxycarbonylamino)propoxy]phenyl}-2-isopropoxypropionic acid,
3-(4-{3-[N-(2-butoxyethyl)-N-propoxycarbonylamino]propoxy}phenyl)-2-isopropoxypropionic acid,
3-{4-[3-(N-butoxycarbonyl-N-heptylamino)propoxy]phenyl}-2-isopropoxypropionic acid,
3-(4-{3-[N-butoxycarbonyl-N-(2-butoxyethyl)amino]propoxy}phenyl)-2-isopropoxypropionic acid,
3-{4-[3-(N-heptyl-N-isopropoxycarbonylamino)propoxy]phenyl}-2-isopropoxypropionic acid,
3-(4-{3-[N-(2-butoxyethyl)-N-isopropoxycarbonylamino]propoxy}phenyl)-2-isopropoxypropionic acid, 3-{4-[3-(N-heptyl-N-isobutoxycarbonylamino)propoxy]phenyl}-2-isopropoxypropionic acid,
3-(4-{3-[N-(2-butoxyethyl)-N-isobutoxycarbonylamino]propoxy}phenyl)-2-isopropoxypropionic acid,
3-{4-[3-(N-sec-butoxycarbonyl-N-heptylamino)propoxy]phenyl}-2-isopropoxypropionic acid,
3-(4-{3-[N-sec-butoxycarbonyl-N-(2-butoxyethyl)amino]propoxy}phenyl)-2-isopropoxypropionic acid,
3-{4-[3-(N-tert-butoxycarbonyl-N-heptylamino)propoxy]phenyl}-2-isopropoxypropionic acid,
3-(4-{3-[N-tert-butoxycarbonyl-N-(2-butoxyethyl)amino]propoxy}phenyl)-2-isopropoxypropionic acid,
3-(4-{3-[N-heptyl-N-(2,2,2-trifluoroethoxycarbonyl)amino]propoxy}phenyl)-2-isopropoxypropionic acid, and
3-(4-{3-[N-(2-butoxyethyl)-N-(2,2,2-trifluoroethoxycarbonyl)amino]propoxy}phenyl)-2-isopropoxypropionic acid.

Further, examples of the compounds wherein n is 3 include, for example, the following compounds.
2-Ethoxy-3-{4-[3-(N-heptyl-N-methoxycarbonylamino)propoxy]phenyl}propionic acid,
3-(4-{3-[N-(2-butoxyethyl)-N-methoxycarbonylamino]propoxy}phenyl)-2-ethoxypropionic acid,
2-ethoxy-3-{4-[3-(N-ethoxycarbonyl-N-heptylamino)propoxy]phenyl}propionic acid,
3-(4-{3-[N-(2-butoxyethyl)-N-ethoxycarbonylamino]propoxy}phenyl)-2-ethoxypropionic acid,
2-ethoxy-3-{4-[3-(N-heptyl-N-propoxycarbonylamino)propoxy]phenyl}propionic acid,
3-(4-{3-[N-(2-butoxyethyl)-N-propoxycarbonylamino]propoxy}phenyl)-2-ethoxypropionic acid,
3-{4-[3-(N-butoxycarbonyl-N-heptylamino)propoxy]phenyl}-2-ethoxypropionic acid,
3-(4-{3-[N-butoxycarbonyl-N-(2-butoxyethyl)amino]propoxy}phenyl)-2-ethoxypropionic acid,
2-ethoxy-3-{4-[3-(N-heptyl-N-isopropoxycarbonylamino)propoxy]phenyl}propionic acid,
3-(4-{3-[N-(2-butoxyethyl)-N-isopropoxycarbonylamino]propoxy}phenyl)-2-ethoxypropionic acid,
2-ethoxy-3-{4-[3-(N-heptyl-N-isobutoxycarbonylamino)propoxy]phenyl}propionic acid,
3-(4-{3-[N-(2-butoxyethyl)-N-isobutoxycarbonylamino]propoxy}phenyl)-2-ethoxypropionic acid,
3-{4-[3-(N-sec-butoxycarbonyl-N-heptylamino)propoxy]phenyl}-2-ethoxypropionic acid,
3-(4-{3-[N-sec-butoxycarbonyl-N-(2-butoxyethyl)amino]propoxy}phenyl)-2-ethoxypropionic acid,
3-{4-[3-(N-tert-butoxycarbonyl-N-heptylamino)propoxy]phenyl}-2-ethoxypropionic acid,
3-(4-{3-[N-tert-butoxycarbonyl-N-(2-butoxyethyl)amino]propoxy}phenyl)-2-ethoxypropionic acid,
2-ethoxy-3-(4-{3-[N-heptyl-N-(2,2,2-trifluoroethoxycarbonyl)amino]propoxy}phenyl)propionic acid, and
3-(4-{3-[N-(2-butoxyethyl)-N-(2,2,2-trifluoroethoxycarbonyl)amino]propoxy}phenyl)-2-ethoxypropionic acid.

Examples also include salts of the aforementioned compounds.

The compounds of the formula (1) according to the present invention can be produced, for example, by the following methods for preparation.

(Methods for Preparation)
That is, a compound represented by the following formula (3):

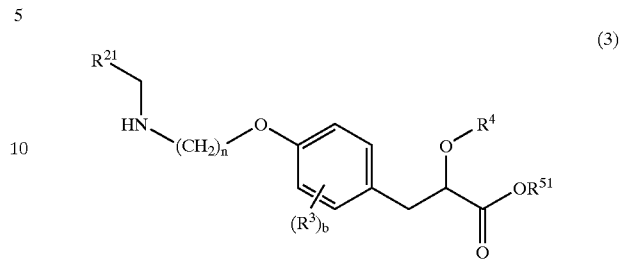

wherein $R^{21}$ represents a $C_{1-11}$ alkyl group which may be substituted with a substituent selected from the group consisting of a lower alkoxyl group, an aryloxy group, an aralkyloxy group, a lower alkylthio group, an arylthio group, an aralkylthio group, and phenyl group wherein $R^{21}$ may be further substituted with one or more halogen atoms, $(R^3)_b$ represents "b" substituents ("b" is an integer from 0 to 4) selected from the group consisting of a halogen atom, a lower alkyl group, and a lower alkoxyl group, which may be identical or different, $R^4$ represents a lower alkyl group, $R^{51}$ represents a protective group of the carboxyl group, and "n" represents an integer from 2 to 4, can be reacted with a compound represented by the following formula (4):

$$R^1—Y \qquad (4)$$

wherein $R^1$ represents a $C_{1-12}$ alkyl group which may be substituted with one or more substituents selected from the group consisting of a halogen atom, a lower alkoxyl group, and a phenyl group which may be substituted with one or more halogen atoms or a group represented by the aforementioned formula (1-1) wherein $(R^6)_a$ represents "a" substituents ("a" is an integer from 0 to 5) selected from the group consisting of a halogen atom, a lower alkyl group, a lower alkoxyl group, a lower alkylthio group, nitro group, a lower alkoxycarbonyl group, cyano group, trifluoromethyl group, trifluoromethoxy group, and a phenyloxy group, which may be the same or different, or a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, and Y represents —NCO or —OCOW wherein W represents a leaving group, to prepare a compound represented by the following formula (2):

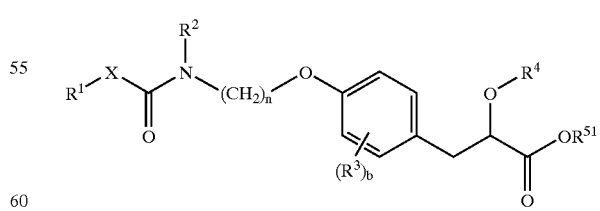

wherein $R^1$, $(R^3)_b$, $R^4$, $R^{51}$, and n have the same meanings as those defined above, and $R^2$ represents a $C_{2-12}$ alkyl group which may be substituted with any of a lower alkoxyl group, an aryloxy group, an aralkyloxy group, a lower alkylthio group, an arylthio group, an aralkylthio group, and a phenyl group, wherein $R^2$ may be further substituted with one or more halogen atoms provided that the methylene group in $R^2$ bonding to the nitrogen atom is not substituted with a halogen atom, and X represents —NH— or —O—, and the protective group $R^{51}$ in the formula (2) can be deprotected as required for conversion into $R^5$ mentioned below to prepare a compound represented by the formula (1) mentioned above, wherein $R^1$, $R^2$, $(R^3)_b$, $R^4$, n and *1 have the same meanings as those defined above, and $R^5$ represents hydrogen atom or a lower alkyl group.

Among the compounds represented by the formula (1), the compounds wherein $R^5$ in the formula represents hydrogen atom can be obtained by deprotecting a compound represented by the formula (2) as described above. Further, the compounds wherein $R^5$ is a lower alkyl group correspond to the compounds represented by the aforementioned formula (2) wherein $R^{51}$ is a lower alkyl group, and thus deprotection is not required for the preparation thereof.

The aforementioned protective group of the carboxyl group represented by $R^{51}$ may be an ordinary protective group for carboxyl group, and it may be a lower alkyl group. That is, in the present invention, other protective groups for carboxyl group may also be selected as $R^{51}$ besides a lower alkyl group. These other protective groups for carboxyl group are not particularly limited so long as they can protect carboxyl group and then be deprotected, and examples include, for example, phenyl group, trityl group, benzyl group, 2-tetrahydropyranyl group, 2-tetrahydrofuranyl group, triethylsilyl group, dimethylphenylsilyl group, tert-butyldimethylsilyl group, allyl group and the like. Examples of the lower alkyl group include methyl group, ethyl group, propyl group, isopropyl group, butyl group, isobutyl group, tert-butyl group and the like. The deprotection reaction may be performed by a known method, for example, a method described in Protective Groups in Organic Synthesis, published by John Wiley and Sons (1999) or the like. For example, a method utilizing an acid, base, UV ray, tetrabutylammonium fluoride, palladium acetate or the like, a method based on reduction and the like are used. In particular, when the deprotection is performed by using an acid or base, for example, hydrochloric acid, sulfuric acid, acetic acid, hydrobromic acid and the like are mentioned as the acid. Examples of the base include alkaline metal carbonates such as potassium carbonate and sodium carbonate, alkaline metal alkoxides such as sodium methoxide, alkaline metal hydroxides such as potassium hydroxide, sodium hydroxide and lithium hydroxide and the like. The amount of the acid or base is, for example, an equal amount or an excessive amount with respect to the compound represented by the formula (2), preferably 1 to 100 equivalences as the amount of acid or 1 to 10 equivalences as the amount of base. As a solvent, a polar solvent or mixed solvent of a polar solvent and water can be used. Examples of the polar solvent include alcohols such as ethanol and methanol, ethers such as dioxane, tetrahydrofuran and diethyl ether, dimethyl sulfoxide, acetone and the like, and preferred are mixed solvents of a polar solvent such as ethanol, methanol, dioxane and acetone and water and the like. The reaction temperature may be usually, for example, from -20° C. to 150° C., preferably from -10° C. to 100° C. Although the reaction time is not particularly limited, it is usually, for example, from 0.2 to 200 hours. Further, when a base is used, the reaction time is usually, for example, from 1 to 12 hours, and when an acid is used, it is usually, for example, from 1 to 100 hours.

The compounds represented by the aforementioned general formula (2) can be prepared by reacting a compound represented by the formula (3) with a compound represented by the formula (4). $R^{21}$ in the formula (3) represents a $C_{1-11}$ alkyl group which may be substituted with any of a lower alkoxyl group, an aryloxy group, an aralkyloxy group, a lower alkylthio group, an arylthio group, and an aralkylthio group, wherein $R^{21}$ may be further substituted with one or more halogen atoms, and the $C_{1-11}$ alkyl group may contain a branched or cyclic structure. $R^{21}$ together with the adjacent methylene have the same meaning as that of $R^2$ in the formula (2). Therefore, preferred examples of the $C_{1-11}$ alkyl group which may be substituted with any of the substituents as $R^{21}$ include a group of a straight or branched saturated hydrocarbon having 1 to 11 carbon atoms, which may further contain a cyclic structure, and such a group substituted with any of the substituents. Specific examples include, for example, methyl group, ethyl group, propyl group, butyl group, pentyl group, hexyl group, heptyl group, octyl group, nonyl group, decyl group, undecyl group, isopropyl group, 2-methylpropyl group, 3-methylbutyl group, 3-pentyl group, 2-methyl-2-butyl group, 4-heptyl group, cyclopropyl group, cyclobutyl group, cyclopentyl group, cyclohexyl group, cyclopentylmethyl group, 2-cyclohexylethyl group and 3-cyclohexylpropyl group are preferred. Among these, preferred are methyl group, ethyl group, propyl group, butyl group, pentyl group, hexyl group, heptyl group, octyl group, 2-methylpropyl group, 3-methylbutyl group, 2-methyl-2-butyl group, cyclopentylmethyl group, 2-cyclohexylethyl group, and 3-cyclohexylpropyl group, and more preferred examples include methyl group, ethyl group, propyl group, pentyl group, hexyl group, heptyl group, 3-methylbutyl group, 2-methyl-2-butyl group, and 3-cyclohexylpropyl group. This $C_{1-11}$ alkyl group may be substituted with any of the aforementioned substituents. The type and number of the substituents are the same as those mentioned in the explanation of the substituents of $R^2$. Where the $C_{1-11}$ alkyl group is substituted with such substituents, and where the positions of the carbon atoms of the $C_{1-11}$ alkyl group are defined 1-, 2-, . . . n-position from the terminal carbon atom on the side of bonding to the nitrogen atom (the n-position mentioned above is the position of the carbon atom most distal from the bonding, and therefore it means 2-position for ethyl group, or 3-position for propyl group), the substitution position is preferably between 1-position and n-position, particularly preferably n-position or (n−1)-position.

$R^{21}$ may further be substituted with one or more halogen atoms. Examples of the halogen atom include fluorine, chlorine, bromine, and iodine. Fluorine, chlorine, and bromine are preferred, and fluorine and chlorine are more preferred. The number of the halogen atoms is not particularly limited so long as the number is substitutable. The number is, for example, usually 1 to 15, preferably 1 to 10, more preferably 1 to 5. Substitution positions of the halogen atoms may be any positions in the alkyl moiety of $R^2$, or any positions in the moieties of substituents. Further, the substitution positions may include the both types.

Y in the compound represented by the formula (4) represents —NCO or —OCOW, and W represents a leaving group. Examples of W include fluorine, chlorine, bromine, p-nitrophenyl group, phenyl group and the like. Among them, chlorine and p-nitrophenyl group are preferred, and chlorine is particularly preferred. Preferred examples of the compounds represented by the formula (4) include phenyl isocyanate, 2,4-difluorophenyl isocyanate, isopropyl isocyanate, 5-indanyl isocyanate, phenyl chloroformate, 4-fluorophenyl chloroformate, isopropyl chloroformate, benzyl chloroformate (all available from Aldrich), 2-naphthyl chloroformate (available from Tokyo Kasei Kogyo) and the like.

Further, among the compounds represented by the formula (4), a compound wherein Y is —OCOCl is obtained by reacting an alcoholic compound $R^1$—OH($R^1$ has the same meaning as that defined above) with a chloroformylating agent. Examples of the chloroformylating agent include, for example, phosgene, triphosgene and the like. The amount of the chloroformylating agent is, for example, an equivalent amount to an excessive amount based on the alcoholic compound, and the amount is, for example, from 1 to 10 equivalences, preferably from 1 to 5 equivalences. As the solvent, an inactive solvent can be used. Examples of the inactive solvent include, for example, dichloromethane, chloroform, carbon tetrachloride, benzene, toluene, xylene, diethyl ether, tetrahydrofuran, dioxane, dimethoxyethane, ethyl acetate, butyl acetate and the like. Preferred are dichloromethane, diethyl ether and tetrahydrofuran. It is also preferable to use a mixture of two or more kinds of these solvents. The reaction temperature is usually, for example, from −20° C. to 100° C., preferably from −10° C. to 50° C. Although the reaction time is not particularly limited, the reaction time is, for example, from 0.2 to 24 hours, preferably from 1 to 5 hours. The reaction may be performed in the presence of a base. The base may be an inorganic or organic base, and examples include, for example, sodium hydroxide, potassium hydroxide, potassium carbonate, sodium carbonate, sodium methoxide, trimethylamine, triethylamine, diisopropylethylamine, N-methylmorpholine, pyridine and the like. The amount of the base is from an equivalent amount to an excessive amount, preferably from 1 to 100 equivalences, more preferably from 1 to 10 equivalences, on the basis of the alcoholic compound.

When a compound represented by the formula (4) and a compound represented by the formula (3) are reacted, the compound represented by the formula (4) is preferably used in from an equivalent amount to an excessive amount, for example, from 1 to 10 equivalences, preferably from 1 to 2 equivalences, on the basis of the compound represented by the formula (3). As the solvent, an inactive solvent can be used. Examples of the inactive solvent include, for example, dichloromethane, chloroform, carbon tetrachloride, benzene, toluene, xylene, diethyl ether, tetrahydrofuran, dioxane, dimethoxyethane, ethyl acetate, butyl acetate and the like. Preferred are dichloromethane, diethyl ether and tetrahydrofuran. It is also preferable to use a mixture of two or more kinds of these solvents. The reaction temperature is usually, for example, from −20° C. to 100° C., preferably from −10° C. to 50° C. Although the reaction time is not particularly limited, it is, for example, from 0.2 to 24 hours, preferably from 1 to 5 hours. The reaction may be performed in the presence of an acid or base. The acid may be an inorganic or organic acid, and examples include, for example, hydrochloric acid, sulfuric acid, hydrobromic acid, formic acid, acetic acid and the like. The base may be an inorganic or organic base, and examples include, for example, sodium hydroxide, potassium hydroxide, potassium carbonate, sodium carbonate, sodium methoxide, trimethylamine, triethylamine, diisopropylethylamine, N-methylmorpholine, pyridine and the like. The amount of the acid or base is preferably from an equivalent amount to an excessive amount, more preferably from 1 to 100 equivalences, particularly preferably from 1 to 10 equivalences, with respect to the compound represented by the formula (3).

The compound represented by the aforementioned formula (3) can be obtained by reducing a compound represented by the following formula (5):

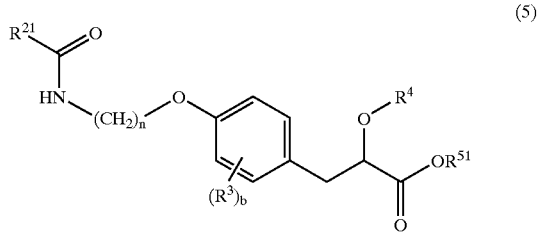

wherein $R^{21}$, $(R^3)_b$, $R^4$, $R^{51}$, and n have the same meanings as those defined above. Examples of the reducing agent used in the reaction include, for example, borane complexes such as borane/tetrahydrofuran, borane/dimethyl sulfide, borane/pyridine, borane/trimethylamine and borane/triphenylphosphine, diborane, sodium borohydride, lithium aluminum hydride and the like. The amount of the reducing agent is usually from an equivalent amount to an excessive amount, preferably from 1 to 100 equivalences, more preferably from 1 to 10 equivalences. Further, Lewis acid such as $SnCl_4$ can also be added, if needed. As the solvent, an inactive solvent can be used. Examples of the inactive solvent include, for example, dichloromethane, chloroform, carbon tetrachloride, benzene, toluene, xylene, diethyl ether, tetrahydrofuran, dioxane, dimethoxyethane and the like. Preferred are dichloromethane, diethyl ether and tetrahydrofuran. It is also preferable to use a mixture of two or more kinds of these solvents. The reaction temperature is usually from −20° C. to 100° C., preferably from −10° C. to 50° C. The reaction time is, for example, from 0.2 to 24 hours, preferably from 1 to 12 hours.

The compound represented by the aforementioned formula (5) can be obtained by condensing a compound represented by the following formula (6):

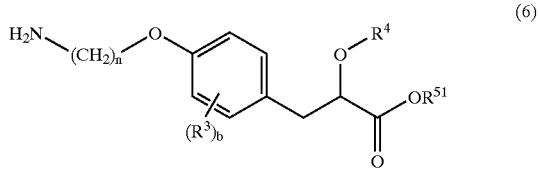

wherein $R^3$, $R^4$, $R^{51}$, and n have the same meanings as those defined above, and a compound represented by the following formula (7):

wherein $R^{21}$ has the same meaning as that defined above, and Z represents a leaving group or a substituent acquiring leaving ability upon activation. Examples of the leaving group as Z include a halogen atom, an acyloxy group, an alkoxycarbonyloxy group and the like, and a preferred example includes a halogen atom. Examples of the halogen atom include chlorine, bromine, iodine and fluorine. Examples of the acyloxy group include, for example, pivaloyloxy group, acetyloxy group and the like. Examples of the alkoxycarbonyloxy group include, for example, isobutyloxycarbonyloxy group. Examples of the substituent acquiring leaving ability upon activation include, for example, hydroxyl group. The amount of the compound represented by the formula (7) on the basis of the compound represented by the formula (6) is from an equivalent amount to an excessive amount, for example, from 1 to 10 equivalences, preferably from 1 to 3 equivalences. As the solvent used in the reaction, an inactive solvent can be used. Examples of the inactive solvent include, for example, dichloromethane, chloroform, carbon tetrachloride, benzene, toluene, xylene, diethyl ether, tetrahydrofuran, dioxane, dimethoxyethane, ethyl acetate, butyl acetate, pyridine and the like. Preferred are dichloromethane, diethyl ether and tetrahydrofuran. It is also preferable to use a mixture of two or more kinds of these solvents. The reaction temperature is usually, for example, from −20° C. to 100° C., preferably from −10° C. to 50° C. The reaction may be performed in the presence of a base. The base may be an inorganic or organic base, and examples include, for example, sodium hydroxide, potassium hydroxide, potassium carbonate, sodium carbonate, sodium methoxide, trimethylamine, triethylamine, diisopropylethylamine, N-methylmorpholine, pyridine and the like. The amount of the base is, for example, an equivalent amount to an excessive amount, preferably from 1 to 100 equivalences, more preferably from 1 to 10 equivalences, with respect to the compound represented by the formula (6). The reaction time of the condensation reaction is, for example, from 0.2 to 24 hours, preferably from 1 to 5 hours, for a compound of the formula (7) wherein Z is a leaving group. For a compound of the formula (7) wherein Z is a substituent acquiring leaving ability upon activation, the condensation reaction can be performed by adding a condensing agent. As the condensing agent, 3-(3-dimethylaminopropyl)-1-ethylcarbodiimide, 3-(3-dimethylaminopropyl)-1-ethylcarbodiimide hydrochloride, N,N'-dicyclohexylcarbodiimide, N,N'-diisopropylcarbodiimide and the like can be used. The reaction time is, for example, from 0.2 to 24 hours, preferably from 1 to 12 hours. Preferred examples of the compound represented by the formula (7) include heptanoyl chloride, hexanoyl chloride, octanoyl chloride, heptanoic acid, hexanoic acid, octanoic acid (all available from Aldrich), n-butoxyacetic acid (available from Tokyo Kasei Kogyo) and the like.

The compound represented by the aforementioned formula (6) can be obtained by subjecting a compound represented by the following formula (8):

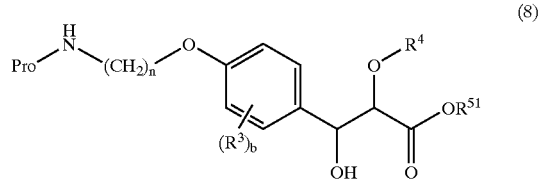

wherein Pro represents a protective group of the amino group, and $(R^3)_b$, $R^4$, $R^{51}$, and n have the same meanings as those defined above, to a deoxidation reaction and deprotection. When the deprotection reaction simultaneously advances under the condition of the deoxidation reaction, the deprotection step becomes unnecessary. The protective groups of the amino group are not particularly limited so long as they are ordinarily used. Examples of readily used protective groups include a carbamate type protective group, an amide type protective group, an imide type protective group and the like. Examples of the carbamate type protective group include, for example, t-butoxycarbonyl group, benzyloxycarbonyl group and the like. The deoxidation reaction can be performed by a reduction reaction using a metal hydride, catalytic hydrogenation reaction or the like. For example, where a metal hydride is used in the reduction reaction, for example, a hydrosilane can be used as the metal hydride. Examples of the hydrosilane include triethylsilane, trichlorosilane, dimethylphenylsilane and the like. The amount of the metal hydride is from an equivalent amount to an excessive amount, usually preferably, for example, from 1 to 100 equivalences, more preferably from 1 to 10 equivalences. As the solvent used in the reaction, an inactive solvent or an acidic solvent can be used. Examples of the inactive solvent include, for example, dichloromethane, chloroform, carbon tetrachloride, benzene, toluene, xylene, diethyl ether, tetrahydrofuran, dioxane, dimethoxyethane, ethyl acetate, butyl acetate, pyridine and the like. Preferred are dichloromethane, diethyl ether and tetrahydrofuran. Examples of the acidic solvent include trifluoroacetic acid, acetic acid and the like. It is also preferable to use a mixture of two or more kinds of these solvents. The reaction temperature is, for example, usually from −20° C. to 100° C., preferably from −10° C. to 50° C. The reaction time is, for example, usually from 0.5 to 24 hours, preferably from 2 to 10 hours. The reaction may be performed in the presence of an acid catalyst. Examples of the acid catalyst include, for example, Lewis acids such as sulfuric acid, hydrochloric acid, acetic acid, trifluoroacetic acid and boron trifluoride/ethyl ether complex, and preferred are trifluoroacetic acid and boron trifluoride/ethyl ether complex. Acetic acid, trifluoroacetic acid and the like can also serve as the acidic solvent mentioned above. When the deoxidation reaction is performed under an acidic condition, the acidic condition-sensitive protective group of the amino group, Pro, is usually simultaneously removed. Examples of the acidic condition-sensitive protective group of amino group include, for example, t-butoxycarbonyl group and the like. Where a catalytic hydrogenation reaction is employed for the reduction reaction, the reaction can be performed with the coexistence of a metal catalyst in a hydrogen atmosphere or in the presence of a hydrogen source such as formic acid. Examples of the metal catalyst include transition metal catalysts such as palladium/carbon, palladium black, platinum oxide, Raney nickel, Wilkinson's catalyst and the like. The amount of the metal catalyst is usually, for example, from about 0.001 to 10 equivalences on the basis of the compound represented by the formula (8). As the solvent used in the reaction, an inactive solvent can be used. Examples of the inactive solvent include, for example, dichloromethane, chloroform, carbon tetrachloride, benzene, toluene, xylene, diethyl ether, tetrahydrofuran, dioxane, dimethoxyethane, N,N-dimethylformamide, methanol, ethanol, isopropanol and the like. Preferred are methanol and tetrahydrofuran. It is also preferable to use a mixture of two or more kinds of these solvents. The reaction temperature is, for example, usually from −20° C. to 100° C., preferably from −10° C. to 50° C. The reaction time is, for example, usually from 0.5 to 24 hours, preferably from 2 to 10 hours. The deprotection reaction may advance simultaneously with the deoxidation reaction by the catalytic hydrogenation reaction. Examples of such a protective group, Pro, include, for example, benzyloxycarbonyl group. When the deprotection reaction is separately performed after the deoxidation reaction, the deprotection reaction may be performed by a known method, for example, a method described in Protective Groups in Organic Synthesis, published by John Wiley and Sons (1999) or the like. For example, a method utilizing an acid, base, UV ray, tetrabutylammonium fluoride, palladium acetate or the like, a method based on reduction and the like are used.

The compounds represented by the aforementioned formula (8) can be obtained by reacting a compound represented by the following formula (9):

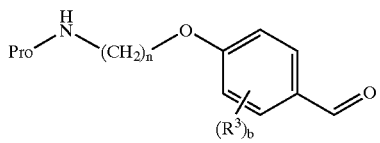

(9)

wherein Pro, n and $(R^3)_b$ have the same meanings as those defined above, with a compound represented by the following formula (10):

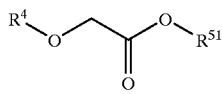

(10)

wherein $R^4$ and $R^{51}$ have the same meanings as those defined above. The amount of the compound represented by the formula (10) is, for example, an equivalent amount to an excessive amount, for example, from 1 to 10 equivalences, preferably from 1 to 3 equivalences, on the basis of the compound represented by the formula (9). As the solvent used in the reaction, an inactive solvent can be used. Examples of the inactive solvent include, for example, dichloromethane, chloroform, carbon tetrachloride, benzene, toluene, xylene, diethyl ether, tetrahydrofuran, dioxane, dimethoxyethane, ethyl acetate, butyl acetate, pyridine and the like. Preferred are dichloromethane, diethyl ether and tetrahydrofuran. It is also preferable to use a mixture of two or more kinds of these solvents. The reaction temperature is, for example, usually from −100° C. to 100° C., preferably from −80° C. to 50° C. The reaction can be performed by first allowing a base, silylating agent or boron compound to react with a compound represented by the formula (10) to form an enolate and then allowing a compound of the formula (9) to react on the enolate. The base used in the above process is not particularly limited, and examples include metal amides and the like. Examples of the metal amide include, for example, lithium diisopropylamide and the like. Examples of the silylating agent include, for example, trimethylsilyl chloride, trimethylsilyl trifluoromethanesulfonate and the like. Examples of the boron compound include, for example, dibutylboron trifluoromethanesulfonate and the like. The reaction time is, for example, usually from 0.5 to 24 hours, preferably from 2 to 10 hours. Preferred examples of the compound represented by the formula (10) include ethoxyacetic acid ethyl ester, methoxyacetic acid ethyl ester (both available from Aldrich), isopropoxyacetic acid isopropyl ester (which can be prepared by the method described in U.S. Pat. No. 1,759,331, 1928) and the like.

The compound represented by the aforementioned formula (9) can be obtained by reacting a compound represented by the following formula (11):

(11)

wherein Pro and n have the same meanings as those defined above, and L represents a leaving group, with a compound represented by the following formula (12):

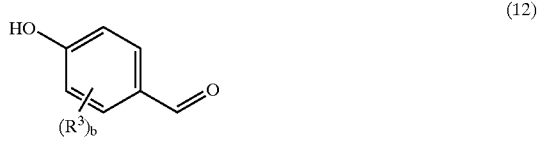

(12)

wherein $(R^3)_b$ has the same meaning as that defined above. The amount of the compound represented by the formula (12) is, for example, from 0.1 to 10 equivalences, preferably from 0.5 to 2 equivalences, on the basis of the compound represented by the formula (11). As the solvent used in the reaction, an inactive solvent can be used. Examples of the inactive solvent include, for example, dichloromethane, chloroform, carbon tetrachloride, benzene, toluene, xylene, diethyl ether, tetrahydrofuran, dioxane, dimethoxyethane, ethyl acetate, butyl acetate, pyridine, N,N-dimethylformamide, dimethyl sulfoxide and the like. Preferred are N,N-dimethylformamide, dimethyl sulfoxide and tetrahydrofuran. It is also preferable to use a mixture of two or more kinds of these solvents. The reaction temperature is usually from −10° C. to 150° C., preferably from 0° C. to 100° C. The reaction can be performed by, for example, first allowing a base to react with the compound represented by the formula (12) and then reacting the product with a compound represented by the formula (11). Alternatively, a base and a compound represented by the formula (11) may be allowed to simultaneously react on the compound represented by the formula (12). Examples of the base include, for example, sodium hydride, sodium carbonate, potassium carbonate, triethylamine and the like. The reaction time is from 0.1 to 50 hours, usually from 0.5 to 5 hours. Preferred examples of the compound represented by the formula (12) include 4-hydroxybenzaldehyde, 2-chloro-4-hydroxybenzaldehyde, vanillin, 4-hydroxy-3-methylbenzaldehyde (all available from Aldrich) and the like. L in the formula (11) is not particularly limited so long as the group can become a substituent which undergoes nucleophilic substitution by the compound represented by the formula (12) and is thereby eliminated. Preferred examples include methanesulfonyloxy group, p-toluenesulfonyloxy group, Cl, Br, I, and the like. More preferred is methanesulfonyloxy group. The compound represented by the aforementioned formula (11) can be obtained from a compound represented by the following formula (13):

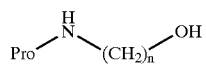
(13)

wherein Pro and n have the same meanings as those defined above. Among the compounds represented by the formula (11), the compounds wherein L is a sulfonate such as methanesulfonyloxy group and p-toluenesulfonyloxy group can be obtained by reacting a compound represented by the aforementioned formula (13) with a sulfonyl chloride such as methanesulfonyl chloride or p-toluenesulfonyl chloride. The reaction can be performed in an inactive solvent. Examples of the inactive solvent include, for example, pyridine, dichloromethane, and tetrahydrofuran, and a particularly preferred example is pyridine. The reaction can be performed in the presence of a base, if necessary. Examples of the base include triethylamine, diisopropylethylamine, N-methylmorpholine, potassium carbonate, sodium carbonate, sodium hydrogencarbonate and the like. Further, among the compounds represented by the aforementioned formula (11), the compounds wherein L is a halogen atom such as Cl, Br, and I can be obtained by reacting a compound represented by the aforementioned formula (13) with a halogen source compound. Examples of the halogen source compound include, for example, $CCl_4$, $CBr_4$, lithium chloride, lithium bromide and the like. The reaction can be performed in an inactive solvent, and examples of the inactive solvent include N,N-dimethylformamide, tetrahydrofuran, dimethyl sulfoxide, dioxane, diethyl ether and the like. The reaction can be performed in the presence of a phosphorus compound such as triphenylphosphine, and if necessary, an azo compound such as azodicarboxylic acid diethyl ester in a solvent such as N,N-dimethylformamide and tetrahydrofuran. Preferred examples of the compound represented by the formula (13) include N-(t-butoxycarbonyl)-2-aminoethanol, N-(t-butoxycarbonyl)-3-aminopropanol (all available from Tokyo Kasei Kogyo) and the like.

The compounds represented by the formula (1), prepared according to the methods for preparation exemplified above, contain an asymmetric carbon to which —O—$R^4$ binds as described above. Further, they may contain one or more other asymmetric carbons depending on type of substituent. For example, when the compounds represented by the formula (1) contain only one asymmetric carbon to which —O—$R^4$ bonds, pure enantiomers can be separated by chromatography utilizing an optically active column in any of synthetic steps of the compounds represented by the formula (1), (2), (3), (5), or (6), or they can be reacted with other optically active compounds to derive them into diastereomers or form salts with the optically active compounds, and then pure stereoisomers can be separated by silica gel chromatography or fractional crystallization to finally separate optical antipodes of the compounds represented by the formula (1).

Salts of the compounds represented by the formula (1) also fall within the scope of the present invention. The salts are carboxylates, for example, and pharmaceutically acceptable salts are preferred. Examples of the carboxylates include, for example, salts with alkali metals such as sodium salts and potassium salts, salts with alkaline earth metals such as magnesium salts and calcium salts, amine addition salts such as triethylamine salts, triethylamine salts, pyridine salts, procaine salts, picoline salts, dicyclohexylamine salts, N,N'-dibenzylethylenediamine salts, N-methylglucamine salts, diethanolamine salts, triethanolamine salts, tris(hydroxymethyl)aminomethane salts and phenethylbenzylamine salts, amino acid addition salts such as arginine salts, lysine salts, ornithine salts, serine salts, glycine salts, aspartic acid salts, and glutamic acid salts. Further, hydrates or solvates of the compounds represented by the formula (1) or salts thereof are also fall within the scope of the present invention. These substances can exist in any crystal form, and all the substances fall within the scope of the present invention irrespective of the crystal form.

No toxicity has been observed in the compounds of the present invention and pharmaceutically acceptable salts thereof, and since they have, for example, hypoglycemic action, triglyceride reducing action, and total cholesterol reducing action, they are useful as active ingredients of medicaments. The medicament of the present invention can be used as, for example, a hypoglycemic agent, and/or triglyceride reducing agent, and/or total cholesterol reducing agent.

The hypoglycemic agent of the present invention can reduce blood glucose, and the agent can be used for, for example, prophylactic treatment and/or therapeutic treatment of a disease resulting from hyperglycemia. Examples of the disease resulting from hyperglycemia include, for example, diabetes mellitus and diabetic complications. Specific examples of diabetic complications include, for example, diabetic retinopathy, diabetic nephropathy, diabetic neuropathy and the like.

The triglyceride reducing agent of the present invention can reduce triglyceride in blood, and the agent can be used for, for example, prophylactic treatment and/or therapeutic treatment of a disease resulting from triglyceride existing in blood at a high concentration. Examples of the disease resulting from triglyceride existing in blood at a high concentration include, for example, hypertriglyceridemia.

The total cholesterol reducing agent of the present invention can reduce total cholesterol in blood, and it can be used as, for example, an agent for prophylactic treatment and/or therapeutic treatment of a disease originating in total cholesterol existing in blood at a high concentration. The medicament of the present invention can also reduce non-HDL cholesterol (represented by a value obtained by subtracting a high density lipoprotein (HDL) cholesterol level from the total cholesterol level, this includes a low density lipoprotein (LDL) cholesterol level and very low density lipoprotein (VLDL) cholesterol level), and thus it is also useful as an LDL cholesterol reducing agent and/or a VLDL cholesterol reducing agent. Examples of the disease originating in total cholesterol existing in blood at a high concentration include, for example, hypercholesterolemia.

Further, examples of diseases resulting from two or more conjugated causes among those mentioned above include, for example, Syndrome X, arteriosclerosis and the like. Examples of diseases included in arteriosclerosis or originating in arteriosclerosis include, for example, cerebral infarction, myocardial infarction, heart failure, obstructive arteriosclerosis, cerebrovascular dementia and the like (Brain 21, 3, 85–88, 2000), and the medicament of the present invention can be used as an agent for prophylactic treatment or therapeutic treatment of these diseases.

Preferred examples of the medicament of the present invention include medicaments for prophylactic treatment and/or therapeutic treatment of a disease selected from the group consisting of diabetes mellitus, diabetic complications, hyperlipemia, Syndrome X and arteriosclerosis. Further, a particularly preferred example includes a medicament for prophylactic treatment and/or therapeutic treatment of diabetes mellitus and/or hyperlipemia. Furthermore, it is also preferable to use the medicament for prophylactic treatment and/or therapeutic treatment of hypertriglyceridemia or hypercholesterolemia among hyperlipemia.

The medicament of the present invention is also useful as a medicament for prophylactic treatment and/or therapeutic treatment of obesity, fatty liver, hypo-HLD-cholesterolemia, hypertension, hyperphagia, inflammation, irritable bowel syndrome, osteoporosis, Alzheimer's disease, cancer or the like.

As the medicament of the present invention, a substance selected from the group consisting of the compounds represented by the above-mentioned formula (1) and pharmaceutically acceptable salts thereof, and hydrates thereof and solvate thereof can be used. Although the aforementioned substance per se, which is an active ingredient, may be administered as the medicament of the present invention, it is generally preferable to add a pharmaceutically acceptable carrier to the aforementioned substance, which is an active ingredient, to prepare a pharmaceutical composition and administer the composition. Examples of the pharmaceutically acceptable carrier include excipients, lubricants, additives and the like. The route of administration of the medicament of the present invention is not particularly limited, and the medicament can be orally or parenterally administered. Examples of preparations suitable for oral administration include, for example, tablets, powders, granules, capsules, sugar-coated pills, solutions, syrups and the like. Examples of preparations suitable for parenteral administration include, for example, injections for intramuscular administration, subcutaneous administration, intraperitoneal administration, or intravenous administration, drip infusions, inhalants, transdermal preparations and the like. The medicament of the present invention can be preferably orally administered. Doses of the medicament of the present invention may vary depending on the age, body weight, and degree of symptoms of a patient, and the medicament may be generally administered at a dose of from 0.01 to 2000 mg per day for an adult once or several times a day. As for administration period, the medicament may usually be administered every day for several weeks to several months. However, both of the daily dose and the administration period may be increased or decreased depending on symptoms of a patient.

The medicament of the present invention can be used in combination with agents including antidiabetic agents, agents for therapeutic treatment of diabetic complications, antilipemic agents, hypotensors, antiobestic agents, diuretics, chemotherapeutic agents, agents for immune therapy and the like (hereafter referred to as "combinable agents"). The combinable agents may be either low molecular weight compounds or proteins, polypeptides, or antibodies, which are polymers, vaccines or the like. Administration times of the medicament of the present invention and the combinable agent are not limited, and they may be administered to a patient simultaneously or with a certain interval. The doses of the combinable agents can be suitably chosen based on clinically used doses. The formulating ratio of the medicament of the present invention and the combinable agent can be suitably chosen depending on the subject of administration, administration route, objective disease, pathological condition, a type of combination and the like. For example, when the subject of administration is a human, the dose of combinable agent can be chosen from the range of from 0.01 to 100 weight parts relative to 1 weight part of the medicament of the present invention (weight of active ingredient).

Examples of the antidiabetic agents include insulin preparations (e.g., animal insulin preparations extracted from pancreas of bovine or porcine; human insulin preparations synthesized by genetic engineering using E. coli, yeast or the like; insulin zinc; protamine/insulin zinc; fragments or derivatives of insulin (e.g., INS-1 and the like) and the like), insulin resistance improving agents (e.g., pioglitazone hydrochloride, rosiglitazone or maleate thereof, GI-262570, JTT-501, MCC-555 (Journal Medicinal Chemistry, 43, 527–550, 2000), YM-440 (Metabolism, 49, 411–417, 2000), KRP-297 (Bioorganic Medicinal Chemistry Letters, 9, 533–538, 1999), CS-011, FK-614, NNC 61-0029 ((−)DRF 2725 (compound (6)), Journal Medicinal Chemistry, 44, 2675–2678, 2001), AZ-242 (Structure, 9, 699–706, 2001), BMS-298585, TAK-559 (Chem. Pharm. Bull., 51, 138–151, 2003), EML-4156 and the like), α-glucosidase inhibitors (e.g., voglibose, acarbose, miglitol, emiglitate and the like), biguanide agents (e.g., fenformin, metformin, buformin and the like), insulin secretion promoters [sulfonylureas (e.g., tolbutamide, glibenclamide, gliclazide, chlorpropamide, tolazamide, acetohexamide, glyclopyramide, glimepiride, glipizide, glybuzole and the like), repaglinide, nateglinide, mitiglinide and calcium salt hydrates thereof, GLP-1 and the like], dipeptidyl peptidase IV inhibitors (e.g., NVP-DPP-278, PT-100 and the like), β3 agonists (e.g., CL-316243, SR-58611-A, UL-TG-307, SB-226552, AJ-9677, BMS-196085, AZ-40140 and the like), amylin agonists (e.g., pramlintide and the like), phosphotyrosine phosphatase inhibitors (e.g., vanadic acid and the like), glyconeogenesis inhibitors (e.g., glycogen phosphorylase inhibitors, glucose-6-phosphatase inhibitors, glucagon antagonists and the like), SGLT (sodium-glucose cotransporter) inhibitors (e.g., T-1095, KGT-1251 and the like) and the like.

Examples of the agents for therapeutic treatment of diabetic complications include aldose reductase inhibitors (e.g., tolrestat, epalrestat, zenarestat, zopolrestat, minalrestat, fidarestat (SNK-860), CT-112 and the like), neurotrophic factors (e.g., NGF, NT-3, BDNF and the like), neurotrophic factor production and secretion promoters, PKC inhibitors (e.g., LY-333531 and the like), AGE inhibitors (e.g., ALT946, pimagedine, pyridoxamine, N-phenacylthiazolium bromide (ALT766), EXO-226 and the like), oxygen radical scavengers (e.g., thioctic acid and the like), and cerebral vasodilators (e.g., tiapride, mexiletine and the like).

Examples of the antilipemic agents include statin compounds, which are cholesterol synthesis inhibitors (e.g., cerivastatin, pravastatin, simvastatin, lovastatin, atorvastatin, fluvastatin, itavastatin, Crestor, and salts thereof (e.g., sodium salt and the like) and the like), squalene synthetase inhibitor (e.g., TAK-475 and the like), ileum bile acid inhibitors (e.g., SD-5613 and the like), fibrate compounds, which have triglyceride reducing action (e.g., bezafibrate, clofibrate, simfibrate, clinofibrate, fenofibrate and the like) and the like.

Examples of the hypotensors include angiotensin converting enzyme inhibitors (e.g., captopril, enalapril, delapril and the like), angiotensin II antagonists (e.g., candesartan cilexetil, losartan, eprosartan, valsartan, telmisartan, irbesartan, tasosartan and the like), calcium antagonists (e.g., manidipine, nifedipine, nicardipine, amlodipine, efonidipine and the like), clonidine and the like.

Examples of the antiobestic agents include central antiobestic agents (e.g., dexfenfluramine, fenfluramine, phentermine, sibutramine, amfepramone, dexamphetamine, mazindol, phenylpropanolamine, clobenzorex and the like), pancreatic lipase inhibitors (e.g., orlistat and the like), β3 agonists (e.g., CL-316243, SR-58611-A, UL-TG-307, SB-226552, AJ-9677, BMS-196085, AZ-40140 and the like), peptidic anorectics (e.g., leptin, CNTF (ciliary neurotrophic factor) and the like), cholecystokinin agonists (e.g., lintitript, FPL-15849 and the like) and the like.

Examples of the diuretics include xanthine derivatives (e.g., theobromine sodium salicylate, theobromine calcium salicylate and the like), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide and the like), antialdosterone preparations (e.g., spironolactone, triamterene and the like), carbonate dehydrase inhibitors (e.g., acetazolamide and the like), chlorobenzenesulfonamide preparations (e.g., chlortalidone, mefruside, indapamide and the like), azosemide, isosorbide, ethacrynic acid, piretamide, bumetamide, furosemide and the like.

Examples of the chemotherapeutic agents include alkylating agents (e.g., cyclophosphamide, ifosphamide and the like), antimetabolites (e.g., methotrexate, 5-fluorouracil, 5-fluorouracil derivatives (furtulon, neofurtulon and the like) and the like), carcinostatic antibiotics (e.g., mitomycin, adriamycin and the like), plant-derived anticancer agents (e.g., vincristine, vindesine, Taxol and the like), cisplatin, carboplatin, etoposide and the like.

Examples of the agents for immunotherapy include microbial or bacterial ingredients (e.g., muramyldipeptide derivatives, Picibanil, and the like), polysaccharides having immunity enhancing activity (e.g., lentinan, sizofiran, Krestin and the like), cytokines obtained by genetic engineering techniques (e.g., interferons, interleukins (IL-1, IL-2, IL-12 and the like) and the like), colony stimulating factors (e.g., granulocyte colony stimulating factor, erythropoietin and the like) and the like.

Examples of the combinable agent further include agents for which cachexia improvement action is recognized in animal models or clinical cases, i.e., cyclooxygenase inhibitors (e.g., indomethacin and the like) [Cancer Research, vol. 49, pp. 5935–5939, 1989], progesterone derivatives (e.g., megesterol acetate) [Journal of Clinical Oncology, vol. 12, pp. 213–225, 1994], glucosteroids (e.g., dexamethasone and the like), metoclopramide agents, tetrahydrocannabinol agents (references for these are the same as the above), fat metabolism improving agents (e.g., eicosapentaenoic acid and the like) [British Journal of Cancer, vol. 68, pp. 314–318, 1993], growth hormones, IGF-1, TNF-α, LIF, IL-6, and antibody directed to oncostatin M, which are factors inducing cachexia, and the like.

Examples of the combinable agent further include neurogenesis promoting agents (e.g., Y-128, VX-853, Prosaptide and the like), antidepressants (e.g., desipramine, amitriptyline, imipramine and the like), antiepileptic agents (e.g., lamotrigine and the like), antiarrhythmic agents (e.g., mexiletine and the like), acetylcholine receptor ligands (e.g., ABT-594 and the like), endoserine receptor antagonists (e.g., ABT-627 and the like), monoamine uptake inhibitors (e.g., tramadol and the like), narcotic analgetics (e.g., morphine and the like), GABA receptor agonists (e.g., gabapentin and the like), a 2 receptor agonists (e.g., clonidine and the like), local analgetics (e.g., capsaicin and the like), antianxiety agents (e.g., benzodiazepine and the like), phosphodiesterase inhibitors (e.g., sildenafil (citrate) and the like) dopaminergic drugs (e.g., apomorphine and the like), remedies for osteoporosis (e.g., alfacalcidol, calcitriol, elcatonin, salmon calcitonin, estriol, ipriflavone, pamidronate disodium, sodium alendronate hydrate, incadronate disodium and the like), anti-dementia agents (e.g., tacrin, donepezil, rivastigmine, galantamine and the like), urinary incontinence and frequent urination treatment agents (e.g., flavoxate hydrochloride, oxybutynin hydrochloride, propiverine hydrochloride and the like), and the like.

The combinable agents are preferably insulin preparations, insulin resistance improving agents, α-glucosidase inhibitors, biguanide agents, insulin secretion promoters (preferably sulfonylurea agents), aldose reductase inhibitors, statin compounds, fibrate compounds and the like.

Usefulness of the medicament of the present invention can be confirmed based on antidiabetic and/or antilipemic effect and/or change of serum level by using mammals including human (e.g., mouse, rat, hamster, dog, ape and the like) or cells of mammals including human (established cancer cell line, primary cells, live cells and the like), and further higher usefulness of the medicament of the present invention as a medicament can be further confirmed by examining low toxicity concerning the antidiabetic and/or hypolipidemic effect.

Examples of examinations for confirming antidiabetic and/or antilipemic effect in an animal including human includes, for example, examinations of plasma glucose level reducing action, glucose tolerance improving action, plasma triglyceride level reducing action, intrahepatic triglyceride level reducing action, intramuscular triglyceride level reducing action, intramuscular glucose uptake action, insulin level reducing action, hepatic glyceride secretion reducing action, LDL level reducing action, HDL level increasing action, total cholesterol level reducing action, blood pressure decrease, irritable bowel syndrome model, arterial ligature hypercardia model, pancreas protecting action (insulin content), extracted blood vessel relaxation action and the like.

Examples of examinations for confirming antidiabetic and/or antilipemic effect using cells of organisms including human includes, for example, examinations of induction of cell differentiation, intracellular triglyceride accumulating action, cholesterol extracting action, fibrinogen reducing action, measurement of PAI-1 and the like.

Examples of index for confirming low degree of toxicity concerning antidiabetic and/or antilipemic effect in organisms including human includes, for example, low degrees of decrease of erythrocyte count, decrease of hemoglobin level, decrease of hematocrit, increase of body weight, expression of cardiac hypertrophy and the like.

The usefulness in human or an animal can also be confirmed based on change of serum level, enzyme induction, enzyme inhibition and the like.

EXAMPLES

The present invention will be further specifically explained with reference to the following examples. However, the scope of present invention is not limited to these examples. For thin layer chromatography (TLC), Precoated silicagel 60 F254 (Merck) was used, and spots were detected by UV irradiation (254 nm).

As the filler of silica gel column, Wako gel C-300 (Wako Pure Chemical Industries) was used. Among operations in the examples, "concentration" means evaporation of a solvent or an excessive regent under reduced pressure by using an evaporator (Tokyo Rikakikai).

For LC-MS HPLC, Develosil C30-UG-5, 4.6×50 mm (Nomura Chemical) was used as a column, and as a solvent, a linear gradient was used, in which a mixing ratio of Solvent A consisting of 0.1% aqueous acetic acid solution and Solvent B consisting of 0.1% acetic acid solution in acetonitrile was changed from 95% of Solvent A+5% of Solvent B at the start of development (0 minute) to 2% of Solvent A+98% of Solvent B (4 minutes after the start of development), and after 4 minutes, the ratio of 2% of Solvent A+98% of Solvent B was maintained. The flow rate was 2 ml/min.

Example 1

Synthesis of 3-(4-{2-[3-(2,4-difluorophenyl)-1-heptylureido]ethoxy}phenyl)-2-ethoxypropionic acid ethyl ester Step a: Synthesis of [2-(4-formylphenoxy)ethyl]carbamic acid t-butyl ester A solution of t-butyl N-(2-hydroxyethyl)carbamate (2.1 g, Aldrich) in pyridine (20 ml) was added dropwise with methanesulfonyl chloride (1.2 ml) and stirred at room temperature for 1 hour. The reaction mixture was diluted with methylene chloride and washed successively with water, aqueous sodium hydrogencarbonate, and saturated brine, dried over magnesium sulfate, and then concentrated to obtain a mesylate derivative. Separately, a solution of p-hydroxybenzaldehyde (1.59 g, Tokyo Kasei Kogyo) in dimethylformamide (DMF, 20 ml) was added with sodium hydride (572 mg, 60% dispersion in oil, Wako Pure Chemical Industries) under ice cooling and stirred for 10 minutes at room temperature. Then, this reaction mixture was added with a solution of the aforementioned mesylate derivative in DMF (20 ml) and stirred at 80° C. for 16 hours. The reaction mixture was cooled to room temperature, then concentrated, dissolved in ethyl acetate, washed successively with water and saturated brine, dried over magnesium sulfate and concentrated. The resulting residue was applied on a silica gel column and eluted with hexane/ethyl acetate (2:1) to obtain the title compound (2.8 g).

$^1$H-NMR (CDCl$_3$) δ ppm (300 MHz): 9.88 (s, 1H), 7.84 (d, 2H, J=8.8 Hz), 7.00 (d, 2H, J=8.8 Hz), 4.99 (brs, 1H), 4.11 (m, 2H), 3.57 (m, 2H), 1.46 (s, 9H)

Step b: Synthesis of 3-[4-(2-tert-butoxycarbonylaminoethoxy)phenyl]-2-ethoxy-3-hydroxypropionic acid ethyl ester A solution of ethyl ethoxyacetate (0.27 ml, Aldrich) in tetrahydrofuran (THF, 2 ml) was cooled to −78° C. under an argon atmosphere. The solution was added dropwise with an LDA solution (1.1 ml, 2.0 M solution, Aldrich) and further stirred for 30 minutes. The reaction mixture was added dropwise with the solution of the compound obtained in Step a (265 mg) in THF (2 ml) and further stirred for 20 minutes. The reaction mixture was poured into ice water and extracted with methylene chloride. The organic layer was washed successively with water and 0.1 N hydrochloric acid, dried over magnesium sulfate and concentrated. The resulting residue was applied on a silica gel column and eluted with hexane/ethyl acetate (3:2) to obtain the title compound (426 mg).

$^1$H-NMR (CDCl$_3$) δ ppm (300 MHz): 7.29 (d, 2H, J=8.6 Hz), 6.85 (d, 2H, J=8.6 Hz), 4.8–4.9 (m, 2H), 3.9–4.2 (m, 5H), 3.3–3.7 (m, 4H), 2.9–3.0 (m, 1H), 1.45 (s, 9H), 1.1–1.3 (m, 6H)

Step c: Synthesis of 3-[4-(2-aminoethoxy)phenyl]-2-ethoxypropionic acid ethyl ester The compound obtained in Step b (53.7 mg) was dissolved in trifluoroacetic acid (2 ml), added with triethylsilane (0.4 ml, Aldrich) and stirred at room temperature for 2.5 days. The reaction mixture was diluted with ethyl acetate, washed successively with saturated aqueous sodium hydrogencarbonate and saturated brine, dried over magnesium sulfate and concentrated. The resulting residue was applied on a silica gel column and eluted with chloroform/methanol (10:1) to obtain the title compound (28.1 mg).

$^1$H-NMR (CDCl$_3$) δ ppm (300 MHz): 7.15 (d, 2H, J=8.6 Hz), 6.82 (d, 2H, J=8.6 Hz), 4.16 (2H, q, J=7.1 Hz), 3.9–4.1 (m, 3H), 3.5–3.6 (m, 1H), 3.3–3.4 (m, 1H), 3.08 (brs, 2H), 2.95 (d, 2H, J=6.4 Hz), 1.1–1.3 (m, 6H)

Step d: 2-Ethoxy-3-[4-(2-heptanoylaminoethoxy)phenyl]propionic acid ethyl ester

The compound obtained in Step c (55 mg) was dissolved in methylene chloride (2 ml), added with triethylamine (56 μl and added with n-heptanoyl chloride (39 μl, produced by Tokyo Kasei Kogyo). The reaction mixture was stirred at room temperature for 30 minutes, diluted with methylene chloride, washed with saturated aqueous sodium hydrogencarbonate, dried over magnesium sulfate and concentrated. The resulting residue was applied on a silica gel column and eluted with hexane/ethyl acetate (3:2) to obtain the title compound (47.3 mg).

$^1$H-NMR (CDCl$_3$) δ ppm (300 MHz): 7.16 (d, 2H, J=8.6 Hz), 6.81 (d, 2H, J=8.6 Hz), 5.93 (brd, 1H), 4.1–4.2 (m, 2H), 3.9–4.0 (m, 3H), 3.6–3.7 (m, 3H), 3.3–3.4 (m, 1H), 2.9–3.0 (m, 2H), 2.2 (m, 2H), 1.6 (m, 2H), 1.1–1.3 (m, 12H), 0.8–0.9 (m, 3H)

Step e: 2-Ethoxy-3-[4-(2-heptylaminoethoxy)phenyl]propionic acid ethyl ester

A solution of the compound obtained in Step d (46 mg) in THF (2 ml) was added with borane/dimethyl sulfide complex (55 μl, Tokyo Kasei Kogyo). The reaction mixture was stirred at room temperature for 24 hours, added with butanol (2 ml) and stirred for 2 hours. The reaction mixture was concentrated, and the resulting residue was applied on a silica gel column and eluted with chloroform/methanol (100:5, then 100:10) to obtain the title compound (31.7 mg).

$^1$H-NMR (CDCl$_3$) δ ppm (300 MHz): 7.14 (d, 2H, J=8.3 Hz), 6.82 (d, 2H, J=8.3 Hz), 3.9–4.2 (m, 5H), 3.5–3.7 (m, 1H), 3.3–3.4 (m, 1H), 2.9–3.1 (m, 4H), 2.6–2.7 (m, 2H), 1.5 (m, 2H), 1.1–1.3 (m, 14H), 0.8–0.9 (m, 3H)

Step f: 3-(4-{2-[3-(2,4-Difluorophenyl)-1-heptylureido]ethoxy}phenyl)-2-ethoxypropionic acid ethyl ester A solution of the compound obtained in Step e (30.9 mg) in methylene chloride (2 ml) was added with 2,4-difluorophenyl isocyanate (14 μl, Aldrich) and stirred for 16 hours. The reaction mixture was concentrated, and the resulting residue was applied on a silica gel column and eluted with hexane/ethyl acetate (4:1) to obtain the title compound (41.6 mg).

$^1$H-NMR (CDCl$_3$) δ ppm (300 MHz): 8.0 (m, 1H), 7.53 (brs, 1H), 7.17 (d, 2H, J=8.6 Hz), 6.8–6.9 (m, 4H), 4.1–4.2 (m, 4H), 3.9–4.0 (m, 1H), 3.6–3.8 (m, 3H), 3.3–3.4 (m, 3H), 2.9–3.0 (m, 2H), 1.1–1.3 (m, 16H), 0.9 (m, 3H)

Example 2

Synthesis of 3-(4-{2-[3-(2,4-difluorophenyl)-1-heptylureido]ethoxy}phenyl)-2-ethoxypropionic acid A solution of the compound obtained in Example 1, Step f (40 mg) in ethanol (2 ml) was added with 1 N aqueous sodium hydroxide (0.1 ml) and stirred at room temperature for 2 hours and then at 50° C. for 1 hour. The reaction mixture was added with 1 N hydrochloric acid (0.1 ml) and concentrated, and the resulting residue was applied on a silica gel column and eluted with methylene chloride/ethanol (10:1, containing 1% acetic acid) to obtain the title compound (35.6 mg).

$^1$H-NMR (CDCl$_3$) δ ppm (300 MHz): 8.0 (m, 11H), 7.51 (brs, 1H), 7.18 (d, 2H, J=8.6 Hz), 6.8–6.9 (m, 3H), 4.0–4.2 (m, 3H), 3.3–3.8 (m, 6H), 2.9–3.1 (m, 2H), 1.1–1.3 (m, 13H), 0.9 (m, 3H)

Example 3

Synthesis of 3-(4-{2-[3-(2,4-dimethoxyphenyl)-1-heptylureido]ethoxy}phenyl)-2-ethoxypropionic acid A solution of the compound obtained in Example 1, Step e (57.3 mg) in methylene chloride (4 ml) was added with 2,4-dimethoxyphenyl isocyanate (54 μl, Aldrich) and stirred for 1 hour. The reaction mixture was added with a polyamine resin (100 mg, prepared by the method described in J. Am. Chem. Soc., 119, 4874–4881, 1997), further stirred for 1 hour and filtered, and the filtrate was concentrated. The resulting residue was dissolved in ethanol (2 ml), added with 1 N aqueous sodium hydroxide (0.2 ml) and stirred at 50° C. for 2 hours. The reaction mixture was cooled to room temperature, added with 1 N hydrochloric acid (0.2 ml) and concentrated. The resulting residue was dissolved in methylene chloride and washed with 1 N hydrochloric acid. The solution was dried and concentrated, and the resulting residue was applied on a silica gel column and eluted with hexane/acetone (2:1, containing 0.1% acetic acid) to obtain the title compound (59 mg).

$^1$H-NMR (CDCl$_3$) δ ppm (300 MHz): 7.9–8.0 (m, 1H), 7.29 (brs, 1H), 7.15 (d, 2H, J=8.6 Hz), 6.85 (d, 2H, J=8.6 Hz), 6.4–6.5 (m, 2H), 4.0–4.2 (m, 3H), 3.79 (s, 3H), 3.78 (s, 3H), 3.4–3.7 (m, 6H), 2.9–3.1 (m, 2H), 1.1–1.3 (m, 13H), 0.9 (m, 3H)

Example 4

Synthesis of 3-(4-{2-[3-(2,4-difluorophenyl)-1-pentylureido]ethoxy}phenyl)-2-ethoxypropionic acid A solution of the compound obtained in Example 1, Step c (42 mg) in methylene chloride (2 ml) was added with pyridine (32 μl) and valeryl chloride (21.4 μl, Tokyo Kasei Kogyo) and stirred at room temperature for 4 hours. The reaction mixture was added with tetrafluorophthalic anhydride (22 mg) and further stirred for 2 hours. The reaction mixture was added with a polyamine resin (100 mg, prepared by the same method as described in Example 3), stirred for 1.5 hours and filtered, and the filtrate was concentrated. The resulting residue was dissolved in THF (1 ml), added with ethyl acetate (200 μl) and borane/dimethyl sulfide complex (36 μl, Tokyo Kasei Kogyo) and stirred at room temperature for 20 hours. The reaction mixture was added with ethanol (0.2 ml) and stirred at room temperature for 1 hour and at 50° C. for 1 hour. The reaction mixture was concentrated, and the resulting residue was dissolved in methylene chloride, washed with 1 N aqueous sodium hydroxide, dried and concentrated. Because a TLC analysis verified that the reaction was incomplete, a THF solution of the residue was prepared again and subjected to the reduction reaction and the post-treatments again. By using the resulting compound, the title compound (5.6 mg) was obtained in the same manner as that of Example 3 except that 2,4-difluorophenyl isocyanate (Aldrich) was used instead of the 2,4-dimethoxyphenyl isocyanate.

LC-MS: HPLC retention time: 5.53 minutes, m/z 479 (M+1)

Example 5

Synthesis of 3-(4-{2-[1-cyclohexylmethyl-3-(2,4-difluorophenyl)ureido]ethoxy}phenyl)-2-ethoxypropionic acid The title compound was obtained in the same manner as that of Example 4 except that cyclohexanecarbonyl chloride (Aldrich) was used instead of the valeryl chloride.

LC-MS: HPLC retention time: 5.85 minutes, m/z 505 (M+1)

Example 6

Synthesis of 3-(4-{2-[3-(2,4-difluorophenyl)-1-(3-phenylpropyl)ureido]ethoxy}phenyl)-2-ethoxypropionic acid The title compound was obtained in the same manner as that of Example 4 except that hydrocinnamoyl chloride (Aldrich) was used instead of the valeryl chloride.

LC-MS: HPLC retention time: 5.69 minutes, m/z 527 (M+1)

Example 7

Synthesis of 3-{4-[2-(3-cyclohexyl-1-heptylureido)ethoxy]phenyl}-2-ethoxypropionic acid The title compound was obtained in the same manner as that of Example 3 except that cyclohexyl isocyanate (Aldrich) was used instead of the 2,4-dimethoxyphenyl isocyanate.

LC-MS: HPLC retention time: 6.02 minutes, m/z 477 (M+1)

Example 8

Synthesis of 3-(4-{2-[3-(4-bromophenyl)-1-heptylureido]ethoxy}phenyl)-2-ethoxypropionic acid The title compound was obtained in the same manner as that of Example 3 except that 4-bromophenyl isocyanate (Aldrich) was used instead of the 2,4-dimethoxyphenyl isocyanate.

LC-MS: HPLC retention time: 6.31 minutes, m/z 549 (M+1)

Example 9

Synthesis of 2-ethoxy-3-(4-{2-[1-heptyl-3-(4-nitrophenyl)ureido]ethoxy}phenyl)propionic acid The title compound was obtained in the same manner as that of Example 3 except that 4-nitrophenyl isocyanate (Aldrich) was used instead of the 2,4-dimethoxyphenyl isocyanate.

LC-MS: HPLC retention time: 6.18 minutes, m/z 516 (M+1)

Example 10

Synthesis of 2-ethoxy-3-(4-{2-[1-heptyl-3-(4-isopropylphenyl)ureido]ethoxy}phenyl)propionic acid The title compound was obtained in the same manner as that of Example 3 except that 4-isopropylphenyl isocyanate (Aldrich) was used instead of the 2,4-dimethoxyphenyl isocyanate.

LC-MS: HPLC retention time: 6.39 minutes, m/z 513 (M+1)

Example 11

Synthesis of 2-ethoxy-3-(4-{2-[1-heptyl-3-(4-phenoxyphenyl)ureido]ethoxy}phenyl)propionic acid The title compound was obtained in the same manner as that of Example 3 except that 4-phenoxyphenyl isocyanate (Aldrich) was used instead of the 2,4-dimethoxyphenyl isocyanate.

LC-MS: HPLC retention time: 6.40 minutes, m/z 563 (M+1)

Example 12

Synthesis of 2-ethoxy-3-(4-{2-[1-heptyl-3-(1-naphthyl)ureido]ethoxy}phenyl)propionic acid The title compound was obtained in the same manner as that of Example 3 except that 4-bromophenyl isocyanate (Aldrich) was used instead of the 2,4-dimethoxyphenyl isocyanate.

LC-MS: HPLC retention time: 6.13 minutes, m/z 521 (M+1)

Example 13

Synthesis of 2-ethoxy-3-(4-{2-[1-heptyl-3-(2,4,6-trimethylphenyl)ureido]ethoxy}phenyl)propionic acid The title compound was obtained in the same manner as that of Example 3 except that 2,4,6-trimethylphenyl isocyanate (Aldrich) was used instead of the 2,4-dimethoxyphenyl isocyanate.

LC-MS: HPLC retention time: 6.11 minutes, m/z 513 (M+1)

Example 14

Synthesis of 2-ethoxy-3-(4-{2-[1-heptyl-3-(2-phenylethyl)ureido]ethoxy}phenyl)propionic acid The title compound was obtained in the same manner as that of Example 3 except that phenethyl isocyanate (Aldrich) was used instead of the 2,4-dimethoxyphenyl isocyanate.

LC-MS: HPLC retention time: 5.92 minutes, m/z 499 (M+1)

Example 15

Synthesis of 2-ethoxy-3-(4-{2-[3-(4-fluorophenyl)-1-heptylureido]ethoxy}phenyl)propionic acid The title compound was obtained in the same manner as that of Example 3 except that 4-fluorophenyl isocyanate (Aldrich) was used instead of the 2,4-dimethoxyphenyl isocyanate.

LC-MS: HPLC retention time: 5.96 minutes, m/z 489 (M+1)

Example 16

Synthesis of 2-ethoxy-3-{4-[2-(1-heptyl-3-phenylureido)ethoxy]phenyl}propionic acid The title compound was obtained in the same manner as that of Example 3 except that the phenyl isocyanate (Aldrich) was used instead of the 2,4-dimethoxyphenyl isocyanate.

LC-MS: HPLC retention time: 5.88 minutes, m/z 471 (M+1)

Example 17

Synthesis of 3-(4-{2-[3-(2,4-dichlorophenyl)-1-heptylureido]ethoxy}phenyl)-2-ethoxypropionic acid The title compound was obtained in the same manner as that of Example 3 except that 2,4-dichlorophenyl isocyanate (Aldrich) was used instead of the 2,4-dimethoxyphenyl isocyanate.

LC-MS: HPLC retention time: 6.61 minutes, m/z 539 (M+1)

Example 18

Synthesis of 2-ethoxy-3-(4-{2-[1-heptyl-3-(2-trifluoromethylphenyl)ureido]ethoxy}phenyl)propionic acid The title compound was obtained in the same manner as that of Example 3 except that 2-trifluoromethylphenyl isocyanate (Aldrich) was used instead of the 2,4-dimethoxyphenyl isocyanate.

LC-MS: HPLC retention time: 6.06 minutes, m/z 539 (M+1)

Example 19

Synthesis of 3-{4-[2-(3-benzyl-1-heptylureido)ethoxy]phenyl}-2-ethoxypropionic acid The title compound was obtained in the same manner as that of Example 3 except that benzyl isocyanate (Aldrich) was used instead of the 2,4-dimethoxyphenyl isocyanate.

LC-MS: HPLC retention time: 5.67 minutes, m/z 485 (M+1)

Example 20

Synthesis of 3-(4-{2-[3-(4-cyanophenyl)-1-heptylureido]ethoxy}phenyl)-2-ethoxypropionic acid The title compound was obtained in the same manner as that of Example 3 except that 4-cyanophenyl isocyanate (Aldrich) was used instead of the 2,4-dimethoxyphenyl isocyanate.

LC-MS: HPLC retention time: 5.82 minutes, m/z 496 (M+1)

Example 21

Synthesis of 3-{4-[2-(3-cyclopentyl-1-heptylureido)ethoxy]phenyl}-2-ethoxypropionic acid The title compound was obtained in the same manner as that of Example 3 except that cyclopentyl isocyanate (Aldrich) was used instead of the 2,4-dimethoxyphenyl isocyanate.

LC-MS: HPLC retention time: 5.73 minutes, m/z 463 (M+1)

Example 22

Synthesis of 2-ethoxy-3-(4-{2-[1-heptyl-3-(2-methoxyphenyl)ureido]ethoxy}phenyl)propionic acid The title compound was obtained in the same manner as that of Example 3 except that 2-methoxyphenyl isocyanate (Aldrich) was used instead of the 2,4-dimethoxyphenyl isocyanate.

LC-MS: HPLC retention time: 6.04 minutes, m/z 501 (M+1)

Example 23

Synthesis of 2-ethoxy-3-(4-{2-[1-heptyl-3-(3-methoxyphenyl)ureido]ethoxy}phenyl)propionic acid The title compound was obtained in the same manner as that of Example 3 except that 3-methoxyphenyl isocyanate (Aldrich) was used instead of the 2,4-dimethoxyphenyl isocyanate.

LC-MS: HPLC retention time: 5.82 minutes, m/z 501 (M+1)

Example 24

Synthesis of 2-ethoxy-3-(4-{2-[1-heptyl-3-(4-methyl-3-nitrophenyl)ureido]ethoxy}phenyl)propionic acid The title compound was obtained in the same manner as that of Example 3 except that 4-methyl-3-nitrophenyl isocyanate (Aldrich) was used instead of the 2,4-dimethoxyphenyl isocyanate.

LC-MS: HPLC retention time: 6.08 minutes, m/z 530 (M+1)

Example 25

Synthesis of 3-(4-{2-[3-(3-cyanophenyl)-1-heptylureido]ethoxy}phenyl)-2-ethoxypropionic acid The title compound was obtained in the same manner as that of Example 3 except that 3-cyanophenyl isocyanate (Aldrich) was used instead of the 2,4-dimethoxyphenyl isocyanate.

LC-MS: HPLC retention time: 5.83 minutes, m/z 496 (M+1)

Example 26

Synthesis of 2-ethoxy-3-(4-{2-[1-heptyl-3-(2-methoxy-5-methyl)ureido]ethoxy}phenyl)propionic acid The title compound was obtained in the same manner as that of Example 3 except that 2-methoxy-5-methyl isocyanate (Aldrich) was used instead of the 2,4-dimethoxyphenyl isocyanate.

LC-MS: HPLC retention time: 6.25 minutes, m/z 515 (M+1)

Example 27

Synthesis of 2-ethoxy-3-(4-{2-[1-heptyl-3-(4-trifluoromethylphenyl)ureido]ethoxy}phenyl)propionic acid The title compound was obtained in the same manner as that of Example 3 except that 4-trifluoromethylphenyl isocyanate (Aldrich) was used instead of the 2,4-dimethoxyphenyl isocyanate.

LC-MS: HPLC retention time: 6.11 minutes, m/z 539 (M+1)

Example 28

Synthesis of 3-(4-{2-[3-(3,4-difluorophenyl)-1-heptylureido]ethoxy}phenyl)-2-ethoxypropionic acid The title compound was obtained in the same manner as that of Example 3 except that 3,4-difluorophenyl isocyanate (Aldrich) was used instead of the 2,4-dimethoxyphenyl isocyanate.

LC-MS: HPLC retention time: 5.92 minutes, m/z 507 (M+1)

Example 29

Synthesis of 2-ethoxy-3-(4-{2-[1-heptyl-3-(4-trifluoromethoxyphenyl)ureido]ethoxy}phenyl)propionic acid The title compound was obtained in the same manner as that of Example 3 except that 4-trifluoromethoxyphenyl isocyanate (Aldrich) was used instead of the 2,4-dimethoxyphenyl isocyanate.

LC-MS: HPLC retention time: 6.12 minutes, m/z 555 (M+1)

Example 30

Synthesis of 2-ethoxy-3-(4-{2-[1-heptyl-3-(2-trifluoromethoxyphenyl)ureido]ethoxy}phenyl)propionic acid The title compound was obtained in the same manner as that of Example 3 except that 2-trifluoromethoxyphenyl isocyanate (Aldrich) was used instead of the 2,4-dimethoxyphenyl isocyanate.

LC-MS: HPLC retention time: 6.13 minutes, m/z 555 (M+1)

Example 31

Synthesis of 2-ethoxy-3-{4-[2-(1-heptyl-3-indan-5-ylureido)ethoxy]phenyl}propionic acid The title compound was obtained in the same manner as that of Example 3 except that 5-indanyl isocyanate (Aldrich) was used instead of the 2,4-dimethoxyphenyl isocyanate.

LC-MS: HPLC retention time: 6.14 minutes, m/z 511 (M+1)

Example 32

Synthesis of 2-ethoxy-3-[4-(2-{1-heptyl-3-[3,4-(methylenedioxy)phenyl]ureido}ethoxy)phenyl]propionic acid The title compound was obtained in the same manner as that of Example 3 except that 3,4-(methylenedioxy)phenyl isocyanate (Aldrich) was used instead of the 2,4-dimethoxyphenyl isocyanate.

LC-MS: HPLC retention time: 5.67 minutes, m/z 515 (M+1)

Example 33

Synthesis of 2-ethoxy-3-(4-{2-[1-heptyl-3-(2-methylphenyl)ureido]ethoxy}phenyl)propionic acid The title compound was obtained in the same manner as that of Example 3 except that 2-methylphenyl isocyanate (Aldrich) was used instead of the 2,4-dimethoxyphenyl isocyanate.

LC-MS: HPLC retention time: 5.8 minutes, m/z 485 (M+1)

Example 34

Synthesis of 2-ethoxy-3-(4-{2-[1-heptyl-3-(3-methylphenyl)ureido]ethoxy}phenyl)propionic acid The title compound was obtained in the same manner as that of Example 3 except that 3-methylphenyl isocyanate (Aldrich) was used instead of the 2,4-dimethoxyphenyl isocyanate.

LC-MS: HPLC retention time: 5.91 minutes, m/z 485 (M+1)

Example 35

Synthesis of 2-ethoxy-3-(4-{2-[1-heptyl-3-(4-methylphenyl)ureido]ethoxy}phenyl)propionic acid The title compound was obtained in the same manner as that of Example 3 except that 4-methylphenyl isocyanate (Aldrich) was used instead of the 2,4-dimethoxyphenyl isocyanate.

LC-MS: HPLC retention time: 5.9 minutes, m/z 485 (M+1)

Example 36

Synthesis of 2-ethoxy-3-(4-{2-[1-heptyl-3-(2,4,5-trimethylphenyl)ureido]ethoxy}phenyl)propionic acid The title compound was obtained in the same manner as that of Example 3 except that 2,4,5-trimethylphenyl isocyanate (Aldrich) was used instead of the 2,4 -dimethoxyphenyl isocyanate.

LC-MS: HPLC retention time: 6.09 minutes, m/z 513 (M+1)

Example 37

Synthesis of 2-ethoxy-3-{4-[2-(1-heptyl-3-isopropylureido)ethoxy]phenyl}propionic acid The title compound was obtained in the same manner as that of Example 3 except that the isopropyl isocyanate (Aldrich) was used instead of the 2,4-dimethoxyphenyl isocyanate.

LC-MS: HPLC retention time: 5.43 minutes, m/z 437 (M+1)

Example 38

Synthesis of 3-(4-{2-[3-(2,4-difluorophenyl)-1-hexylureido]ethoxy}phenyl)-2-ethoxypropionic acid The title compound was obtained in the same manner as that of Example 4 except that caproyl chloride (Aldrich) was used instead of the valeryl chloride.

LC-MS: HPLC retention time: 5.71 minutes, m/z 493 (M+1)

Example 39

Synthesis of 3-(4-{2-[3-(2,4-difluorophenyl)-1-octylureido]ethoxy}phenyl)-2-ethoxypropionic acid The title compound was obtained in the same manner as that of Example 4 except that octanoyl chloride (Aldrich) was used instead of the valeryl chloride.

LC-MS: HPLC retention time: 6.12 minutes, m/z 521 (M+1)

Example 40

Synthesis of 3-(4-{2-[3-(2,4-difluorophenyl)-1-(2-phenylethyl)ureido]ethoxy}phenyl)-2-ethoxypropionic acid The title compound was obtained in the same manner as that of Example 4 except that phenylacetyl chloride (Aldrich) was used instead of the valeryl chloride.

LC-MS: HPLC retention time: 5.45 minutes, m/z 513 (M+1)

Example 41

Synthesis of 3-(4-{2-[3-(2,4-difluorophenyl)-1-(2-phenoxyethyl)ureido]ethoxy}phenyl)-2-ethoxypropionic acid The title compound was obtained in the same manner as that of Example 4 except that phenoxyacetyl chloride (Aldrich) was used instead of the valeryl chloride.

LC-MS: HPLC retention time: 5.47 minutes, m/z 529 (M+1)

Example 42

Synthesis of 3-(4-{2-[3-(2,4-difluorophenyl)-1-(2-phenylthioethyl)ureido]ethoxy}phenyl)-2-ethoxypropionic acid The title compound was obtained in the same manner as that of Example 4 except that phenylthioacetyl chloride (Aldrich) was used instead of the valeryl chloride.

LC-MS: HPLC retention time: 5.58 minutes, m/z 545 (M+1)

Example 43

Synthesis of 3-(4-{2-[1-(2-benzyloxyethyl)-3-(2,4-difluorophenyl)ureido]ethoxy}phenyl)-2-ethoxypropionic acid The title compound was obtained in the same manner as that of Example 4 except that benzyloxyacetyl chloride (Aldrich) was used instead of the valeryl chloride.

LC-MS: HPLC retention time: 5.54 minutes, m/z 543 (M+1)

Example 44

Synthesis of 3-(4-{2-[3-(2,4-difluorophenyl)-1-(4-methylpentyl)ureido]ethoxy}phenyl)-2-ethoxypropionic acid The title compound was obtained in the same manner as that of Example 4 except that g-methylvaleryl chloride (produced by P & B) was used instead of the valeryl chloride.

LC-MS: HPLC retention time: 5.68 minutes, m/z 493 (M+1)

Example 45

Synthesis of 3-(4-{2-[1-(2-cyclopentylethyl)-3-(2,4-difluorophenyl)ureido]ethoxy}phenyl)-2-ethoxypropionic acid The title compound was obtained in the same manner as that of Example 4 except that cyclopentylacetyl chloride (Aldrich) was used instead of the valeryl chloride.

LC-MS: HPLC retention time: 5.78 minutes, m/z 505 (M+1)

Example 46

Synthesis of 3-(4-{2-[3-(2,4-difluorophenyl)-1-(4-propylpentyl)ureido]ethoxy}phenyl)-2-ethoxypropionic acid The title compound was obtained in the same manner as that of Example 4 except that 2,2-di-n-propylacetyl chloride (produced by Lancaster) was used instead of the valeryl chloride.

LC-MS: HPLC retention time: 6.02 minutes, m/z 521 (M+1)

Example 47

Synthesis of 3-(4-{2-[1-(2-benzylthioethyl)-3-(2,4-difluorophenyl)ureido]ethoxy}phenyl)-2-ethoxypropionic acid The title compound was obtained in the same manner as that of Example 4 except that benzylthioacetic acid (Aldrich) and P-EDC (prepared by the method described in J. Am. Chem. Soc. 1997, 119, 4874–4881) were used instead of the valeryl chloride.

LC-MS: HPLC retention time: 5.52 minutes, m/z 559 (M+1)

Example 48

Synthesis of 3-(4-{2-[3-(2,4-difluorophenyl)-1-(2-ethoxyethyl)ureido]ethoxy}phenyl)-2-ethoxypropionic acid The title compound was obtained in the same manner as that of Example 4 except that ethoxyacetic acid (Aldrich) and P-EDC were used instead of the valeryl chloride.

LC-MS: HPLC retention time: 5.26 minutes, m/z 481 (M+1)

Example 49

Synthesis of 3-(4-{2-[1-(2-butoxyethyl)-3-(2,4-difluorophenyl)ureido]ethoxy}phenyl)-2-ethoxypropionic acid The title compound was obtained in the same manner as that of Example 4 except that butoxyacetic acid (produced by Tokyo Kasei Kogyo) and P-EDC were used instead of the valeryl chloride.

LC-MS: HPLC retention time: 5.63 minutes, m/z 509 (M+1)

Example 50

Synthesis of 3-(4-{2-[3-(2,4-difluorophenyl)-1-(3-phenoxypropyl)ureido]ethoxy}phenyl)-2-ethoxypropionic acid The title compound was obtained in the same manner as that of Example 4 except that 2-phenoxypropionic acid (Aldrich) and P-EDC were used instead of the valeryl chloride.

LC-MS: HPLC retention time: 5.54 minutes, m/z 543 (M+1)

Example 51

Synthesis of 3-(4-{2-[1-(4-cyclohexylbutyl)-3-(2,4-difluorophenyl)ureido]ethoxy}phenyl)-2-ethoxypropionic acid The title compound was obtained in the same manner as that of Example 4 except that 4-cyclohexyl butyrate (Aldrich) and P-EDC were used instead of the valeryl chloride.

LC-MS: HPLC retention time: 6.44 minutes, m/z 547 (M+1)

Example 52

Synthesis of 2-ethoxy-3-(4-{2-[3-(2-fluorophenyl)-1-heptylureido]ethoxy}phenyl)propionic acid The title compound was obtained in the same manner as that of Example 3 except that 2-fluorophenyl isocyanate (Aldrich) was used instead of the 2,4-dimethoxyphenyl isocyanate.

LC-MS: HPLC retention time: 5.94 minutes, m/z 489 (M+1)

Example 53

Synthesis of 2-ethoxy-3-(4-{2-[1-heptyl-3-(3-trifluoromethylphenyl)ureido]ethoxy}phenyl)propionic acid The title compound was obtained in the same manner as that of Example 3 except that 3-trifluoromethylphenyl isocyanate (Aldrich) was used instead of the 2,4-dimethoxyphenyl isocyanate.

LC-MS: HPLC retention time: 6.17 minutes, m/z 539 (M+1)

Example 54

Synthesis of 2-ethoxy-3-{4-[2-(N-heptyl-N-phenyloxycarbonylamino)ethoxy]phenyl}propionic acid The title compound was obtained in the same manner as that of Example 3 except that phenyl chloroformate (produced by Tokyo Kasei Kogyo) was used instead of the 2,4-dimethoxyphenyl isocyanate.

LC-MS: HPLC retention time: 6.17 minutes, m/z 472 (M+1)

Example 55

Synthesis of 3-(4-{2-[N-(4-chlorophenoxycarbonyl)-N-heptylamino]ethoxy}phenyl)-2-ethoxypropionic acid The title compound was obtained in the same manner as that of Example 3 except that 4-chlorophenyl chloroformate (Aldrich) was used instead of the 2,4-dimethoxyphenyl isocyanate.

LC-MS: HPLC retention time: 5.9 minutes, m/z 506 (M+1)

Example 56

Synthesis of 2-ethoxy-3-{4-[2-(N-heptyl-N-methoxycarbonylamino)ethoxy]phenyl}propionic acid The title compound was obtained in the same manner as that of Example 3 except that methoxychloroformate (Aldrich) was used instead of the 2,4-dimethoxyphenyl isocyanate.

LC-MS: HPLC retention time: 4.99 minutes, m/z 410 (M+1)

Example 57

Synthesis of 3-{4-[2-(N-benzyloxycarbonyl-N-heptylamino)ethoxy]phenyl}-2-ethoxypropionic acid The title compound was obtained in the same manner as that of Example 3 except that benzyl chloroformate (Aldrich) was used instead of the 2,4-dimethoxyphenyl isocyanate.

LC-MS: HPLC retention time: 5.67 minutes, m/z 486 (M+1)

Example 58

Synthesis of 3-{4-[2-(N-allyloxycarbonyl-N-heptylamino)ethoxy]phenyl}-2-ethoxypropionic acid The title compound was obtained in the same manner as that of Example 3 except that allyl chloroformate (Aldrich) was used instead of the 2,4-dimethoxyphenyl isocyanate.

LC-MS: HPLC retention time: 5.34 minutes, m/z 436 (M+1)

Example 59

Synthesis of 2-ethoxy-3-{4-[2-(N-heptyl-N-propoxycarbonylamino)ethoxy]phenyl}propionic acid The title compound was obtained in the same manner as that of Example 3 except that propyl chloroformate (Aldrich) was used instead of the 2,4-dimethoxyphenyl isocyanate.

LC-MS: HPLC retention time: 5.5 minutes, m/z 438 (M+1)

Example 60

Synthesis of 2-ethoxy-3-(4-{2-[N-heptyl-N-(4-nitrobenzyloxycarbonyl)amino]ethoxy}phenyl)propionic acid The title compound was obtained in the same manner as that of Example 3 except that 4-nitrobenzyl chloroformate (Aldrich) was used instead of the 2,4-dimethoxyphenyl isocyanate.

LC-MS: HPLC retention time: 5.63 minutes, m/z 531 (M+1)

Example 61

Synthesis of 2-ethoxy-3-(4-{2-[N-heptyl-N-(4-methylphenoxycarbonyl)amino]ethoxy}phenyl)propionic acid The title compound was obtained in the same manner as that of Example 3 except that 4-methylphenyl chloroformate (Aldrich) was used instead of the 2,4-dimethoxyphenyl isocyanate.

LC-MS: HPLC retention time: 5.83 minutes, m/z 486 (M+1)

Example 62

Synthesis of 3-(4-{2-[N-(4-bromophenoxycarbonyl)-N-heptylamino]ethoxy}phenyl)-2-ethoxypropionic acid The title compound was obtained in the same manner as that of Example 3 except that 4-bromophenyl chloroformate (Aldrich) was used instead of the 2,4-dimethoxyphenyl isocyanate.

LC-MS: HPLC retention time: 5.98 minutes, m/z 552 (M+1)

Example 63

Synthesis of 2-ethoxy-3-(4-{2-[N-(4-fluorophenoxycarbonyl)-N-heptylamino]ethoxy}phenyl)propionic acid The title compound was obtained in the same manner as that of Example 3 except that 4-fluorophenyl chloroformate (Aldrich) was used instead of the 2,4-dimethoxyphenyl isocyanate.

LC-MS: HPLC retention time: 5.61 minutes, m/z 490 (M+1)

Example 64

Synthesis of 2-ethoxy-3-(4-{2-[N-heptyl-N-(4-methoxyphenoxycarbonyl)amino]ethoxy}phenyl)propionic acid The title compound was obtained in the same manner as that of Example 3 except that 4-methoxyphenyl chloroformate (Aldrich) was used instead of the 2,4-dimethoxyphenyl isocyanate.

LC-MS: HPLC retention time: 5.57 minutes, m/z 502 (M+1)

Example 65

Synthesis of 2-ethoxy-3-(4-{2-[N-heptyl-N-(2-methoxyethoxycarbonyl)amino]ethoxy}phenyl)propionic acid The title compound was obtained in the same manner as that of Example 3 except that 2-methoxyethyl chloroformate (Aldrich) was used instead of the 2,4-dimethoxyphenyl isocyanate.

LC-MS: HPLC retention time: 4.95 minutes, m/z 454 (M+1)

Example 66

Synthesis of 2-ethoxy-3-{4-[2-(N-heptyl-N-isopropyloxycarbonylamino)ethoxy]phenyl}propionic acid The title compound was obtained in the same manner as that of Example 3 except that isopropyl chloroformate (Aldrich) was used instead of the 2,4-dimethoxyphenyl isocyanate.

LC-MS: HPLC retention time: 5.5 minutes, m/z 438 (M+1)

Example 67

Synthesis of 2-ethoxy-3-(4-{2-[N-heptyl-N-(2-propynyloxycarbonyl)amino]ethoxy}phenyl)propionic acid The title compound was obtained in the same manner as that of Example 3 except that propargyl chloroformate (Aldrich) was used instead of the 2,4-dimethoxyphenyl isocyanate.

LC-MS: HPLC retention time: 5.08 minutes, m/z 434 (M+1)

Example 68

Synthesis of 3-(4-{2-[N-(2-chlorophenoxycarbonyl)-N-heptylamino]ethoxy}phenyl)-2-ethoxypropionic acid The title compound was obtained in the same manner as that of Example 3 except that 2-chlorophenyl chloroformate (Aldrich) was used instead of the 2,4-dimethoxyphenyl isocyanate.

LC-MS: HPLC retention time: 5.84 minutes, m/z 506 (M+1)

Example 69

Synthesis of 2-ethoxy-3-(4-{2-[N-heptyl-N-(3-trifluoromethylphenoxycarbonyl)amino]ethoxy}phenyl)propionic acid The title compound was obtained in the same manner as that of Example 3 except that 3-trifluoromethylphenyl chloroformate (Aldrich) was used instead of the 2,4-dimethoxyphenyl isocyanate.

LC-MS: HPLC retention time: 5.98 minutes, m/z 540 (M+1)

Example 70

Synthesis of 2-ethoxy-3-(4-{2-[N-heptyl-N-(2-naphthyloxycarbonyl)amino]ethoxy}phenyl)propionic acid The title compound was obtained in the same manner as that of Example 3 except that 2-naphthyl chloroformate (Aldrich) was used instead of the 2,4-dimethoxyphenyl isocyanate.

LC-MS: HPLC retention time: 6.1 minutes, m/z 522 (M+1)

Example 71

Synthesis of 2-ethoxy-3-{4-[2-(N-heptyl-N-isobutyloxycarbonylamino)ethoxy]phenyl}propionic acid The title compound was obtained in the same manner as that of Example 3 except that isobutyl chloroformate (Aldrich) was used instead of the 2,4-dimethoxyphenyl isocyanate.

LC-MS: HPLC retention time: 5.75 minutes, m/z 452 (M+1)

Example 72

Synthesis of 3-(4-{2-[N-(2,2-dimethylpropoxycarbonyl)-N-heptylamino]ethoxy}phenyl)-2-ethoxypropionic acid The title compound was obtained in the same manner as that of Example 3 except that 2,2-dimethylpropyl chloroformate (Aldrich) was used instead of the 2,4-dimethoxyphenyl isocyanate.

LC-MS: HPLC retention time: 5.93 minutes, m/z 466 (M+1)

Example 73

Synthesis of 3-(4-{2-[N-(3-butenyloxycarbonyl)-N-heptylamino]ethoxy}phenyl)-2-ethoxypropionic acid The title compound was obtained in the same manner as that of Example 3 except that 3-butenyl chloroformate (Aldrich) was used instead of the 2,4-dimethoxyphenyl isocyanate.

LC-MS: HPLC retention time: 5.54 minutes, m/z 450 (M+1)

Example 74

Example of optical resolution of 3-(4-{2-[3-(2,4-difluorophenyl)-1-heptylureido]ethoxy}phenyl)-2-ethoxypropionic acid ethyl ester When the title compound was eluted under the HPLC conditions described below, a peak at elution time of 13.78 minutes and a peak at elution time of 19.66 minute were separated.

HPLC conditions: CHIRALCEL OJ (produced by Daicel Chemical Industries) was used as the column, and a mixed solvent of hexane: isopropanol=85:15 was used as the solvent. The flow rate was 1 ml/min.

Example 75

Synthesis of 2-ethoxy-3-{4-[2-(N-ethoxycarbonyl-N-heptylamino)ethoxy]phenyl}propionic acid The title compound was obtained in the same manner as that of Example 1 except that the reaction was performed by using ethyl chloroformate (Tokyo Kasei Kogyo) instead of the 2,4-difluorophenyl isocyanate, and the obtained compound was hydrolyzed in the same manner as that of Example 2.

$^1$H-NMR (CDCl$_3$) δ ppm (300 MHz): 7.15 (d, 2H, J=8.5 Hz), 6.81 (d, 2H, J=8.5 Hz), 4.0–4.2 (m, 5H), 3.3–3.6 (m, 6H), 2.9–3.1 (m, 2H), 1.5 (brs, 2H), 1.1–1.3 (m, 16H), 0.9 (m, 3H)

Example 76

Synthesis of 3-{4-[2-(N-tert-butoxycarbonyl-N-heptylamino)ethoxy]phenyl}-2-ethoxypropionic acid The title compound was obtained in the same manner as that of Example 1 except that the reaction was performed by using di-tert-butyl dicarbonate (Tokyo Kasei Kogyo) instead of the 2,4-difluorophenyl isocyanate, and the obtained compound was hydrolyzed in the same manner as that of Example 2.

$^1$H-NMR (CDCl$_3$) δ ppm (300 MHz): 7.12 (d, 2H, J=8.5 Hz), 6.81 (d, 2H, J=8.5 Hz), 4.0–4.1 (m, 3H), 3.3–3.6 (m, 6H), 2.9–3.1 (m, 2H), 1.5 (brs, 2H), 1.46 (s, 9H), 1.1–1.3 (m, 13H), 0.9 (m, 3H)

Example 77

Synthesis of 2-ethoxy-3-{4-[2-(N-isobutyl-N-methoxycarbonylamino)ethoxy]phenyl}propionic acid The title compound was obtained in the same manner as that of Example 4 except that the reaction was performed by using isovaleroyl chloride (Tokyo Kasei Kogyo) instead of the valeryl chloride, and methyl chloroformate (Tokyo Kasei Kogyo) was used instead of the 2,4-difluorophenyl isocyanate.

LC-MS: HPLC retention time: 4.95 minutes, m/z 382 (M+1)

Example 78

Synthesis of 2-ethoxy-3-{4-[2-(N-isobutyl-N-isopropoxycarbonylamino)ethoxy]phenyl}propionic acid The title compound was obtained in the same manner as that of Example 77 except that the reaction was performed by using isopropyl chloroformate instead of the methyl chloroformate.

LC-MS: HPLC retention time: 5.38 minutes, m/z 410 (M+1)

Example 79

Synthesis of 2-ethoxy-3-(4-{2-[N-methoxycarbonyl-N-(3-phenylpropyl)amino]ethoxy}phenyl)propionic acid The title compound was obtained in the same manner as that of Example 77 except that the reaction was performed by using hydrocinnamoyl chloride (Aldrich) instead of the isovaleroyl chloride.

LC-MS: HPLC retention time: 5.01 minutes, m/z 430 (M+1)

Example 80

Synthesis of 2-ethoxy-3-(4-{2-[N-isopropoxycarbonyl-N-(3-phenylpropyl)amino]ethoxy}phenyl)propionic acid The title compound was obtained in the same manner as that of Example 79 except that the reaction was performed by using isopropyl chloroformate instead of the methyl chloroformate.

LC-MS: HPLC retention time: 5.37 minutes, m/z 458 (M+1)

Example 81

Synthesis of 2-ethoxy-3-{4-[2-(N-hexyl-N-methoxycarbonylamino)ethoxy]phenyl)propionic acid The title compound was obtained in the same manner as that of Example 77 except that the reaction was performed by using n-hexanoyl chloride (Tokyo Kasei Kogyo) instead of the isovaleroyl chloride.

Example 82

Synthesis of 2-ethoxy-3-{4-[2-(N-hexyl-N-isopropoxycarbonylamino)ethoxy]phenyl}propionic acid The title compound was obtained in the same manner as that of Example 81 except that the reaction was performed by using isopropyl chloroformate instead of the methyl chloroformate.

LC-MS: HPLC retention time: 5.60 minutes, m/z 424 (M+1)

Example 83

Synthesis of 2-ethoxy-3-{4-[2-(N-methoxycarbonyl-N-octylamino)ethoxy] phenyl}propionic acid The title compound was obtained in the same manner as that of Example 77 except that the reaction was performed by using n-octanoyl chloride (Aldrich) instead of the isovaleroyl chloride.

LC-MS: HPLC retention time: 5.71 minutes, m/z 424 (M+1)

Example 84

Synthesis of 2-ethoxy-3-(4-{2-[N-methoxycarbonyl-N-(2-phenoxyethyl)amino]ethoxy}phenyl)propionic acid The title compound was obtained in the same manner as that of Example 77 except that the reaction was performed by using phenoxyacetyl chloride (Aldrich) instead of the isovaleroyl chloride.

LC-MS: HPLC retention time: 4.81 minutes, m/z 432 (M+1)

Example 85

Synthesis of 2-ethoxy-3-(4-{2-[N-isopropoxycarbonyl-N-(2-phenylthioethyl)amino]ethoxy}phenyl)propionic acid The title compound was obtained in the same manner as that of Example 77 except that the reaction was performed by using phenylthioacetyl chloride (Aldrich) is used instead of the isovaleroyl chloride, and isopropyl chloroformate instead of the methyl chloroformate.

LC-MS: HPLC retention time: 5.33 minutes, m/z 476 (M+1)

Example 86

Synthesis of 2-ethoxy-3-(4-{2-[N-methoxycarbonyl-N-(4-methylpentyl)amino]ethoxy}phenyl)propionic acid The title compound was obtained in the same manner as that of Example 77 except that the reaction was performed by using g-methylvaleroyl chloride (Pfaltz and Bauer) instead of the isovaleroyl chloride.

LC-MS: HPLC retention time: 5.13 minutes, m/z 396 (M+1)

Example 87

Synthesis of 2-ethoxy-3-(4-{2-[N-isopropoxycarbonyl-N-(4-methylpentyl)amino]ethoxy}phenyl)propionic acid The title compound was obtained in the same manner as that of Example 86 except that the reaction was performed by using isopropyl chloroformate instead of the methyl chloroformate.

LC-MS: HPLC retention time: 5.51 minutes, m/z 424 (M+1)

Example 88

Synthesis of 3-(4-{2-[N-(2-cyclopentylethyl)-N-methoxycarbonylamino]ethoxy}phenyl)-2-ethoxypropionic acid The title compound was obtained in the same manner as that of Example 77 except that the reaction was performed by using the cyclopentylacetyl chloride instead of the isovaleroyl chloride.

LC-MS: HPLC retention time: 5.25 minutes, m/z 408 (M+1)

Example 89

Synthesis of 3-(4-{2-[N-(2-butoxyethyl)-N-methoxycarbonylamino]ethoxy}phenyl)-2-ethoxypropionic acid The title compound was obtained in the same manner as that of Example 77 except that the reaction was performed by using n-butoxyacetic acid (Tokyo Kasei Kogyo) and P-EDC instead of the isovaleroyl chloride.

LC-MS: HPLC retention time: 4.83 minutes, m/z 412 (M+1)

Example 90

Synthesis of 2-ethoxy-3-{4-[3-(N-heptyl-N-methoxycarbonylamino)propoxy]phenyl}propionic acid The title compound was obtained in the same manner as that of Example 1 except that the reaction was performed by using tert-butyl N-(3-hydroxypropyl)carbamate (Aldrich) instead of the tert-butyl N-(2-hydroxyethyl)carbamate and methyl chloroformate (Tokyo Kasei Kogyo) instead of the 2,4-difluorophenyl isocyanate, and the obtained compound was hydrolyzed in the same manner as that of Example 2.

$^1$H-NMR (CDCl$_3$) δ ppm (300 MHz): 7.15 (d, 2H, J=8.3 Hz), 6.81 (d, 2H, J=8.5 Hz), 4.04, (dd, 1H, J=7.2, 3.9 Hz), 3.1–4.0 (m, 1H), 3.08 (dd, 1H, J=14.0, 4.0 Hz), 2.94 (dd, 1H, J=14.2, 7.7 Hz), 1.9–2.1 (m, 2H), 1.4–1.6 (m, 2H), 1.1–1.4 (m, 8H), 1.17 (t, 3H, J=7.0 Hz), 0.88 (t, 3H, J=7.0 Hz)

Example 91

Synthesis of 2-ethoxy-3-{4-[3-(N-hexyl-N-methoxycarbonylamino)propoxy]phenyl}propionic acid The title compound was obtained in the same manner as that of Example 90 except that the reaction was performed by using n-hexanoyl chloride instead of the n-heptanoyl chloride.

$^1$H-NMR (CDCl$_3$) δ ppm (300 MHz): 7.14 (d, 2H, J=8.6 Hz), 6.81 (d, 2H, J=8.6 Hz), 4.05 (dd, 1H, J=4.2, 1.1 Hz), 3.9–4.0 (m, 2H), 3.1–3.6 (m, 9H), 3.09 (dd, 1H, J=14.3, 4.2 Hz), 2.94 (dd, 1H, J=14.1, 7.5 Hz), 1.9–2.1 (m, 2H), 1.4–1.6 (m, 2H), 1.1–1.4 (m, 4H), 1.18 (t, 3H, J=7.1 Hz), 0.88 (t, 3H, J=6.8 Hz)

Example 92

Synthesis of 2-ethoxy-3-(4-{2-[N-isopropoxycarbonyl-N-(2-phenoxyethyl)amino]ethoxy}phenyl)propionic acid The title compound was obtained in the same manner as that of Example 84 except that the reaction was performed by using isopropyl chloroformate instead of the methyl chloroformate.

LC-MS: HPLC retention time: 5.16 minutes, m/z 460 (M+1)

Example 93

Synthesis of 2-ethoxy-3-(4-{2-[N-methoxycarbonyl-N-(2-phenylthioethyl)amino]ethoxy}phenyl)propionic acid The title compound was obtained in the same manner as that of Example 77 except that the reaction was performed by using phenylthioacetyl chloride (Aldrich) instead of the isovaleroyl chloride.

LC-MS: HPLC retention time: 5.01 minutes, m/z 448 (M+1)

Example 94

Synthesis of 3-(4-{2-[N-(2-cyclopentylethyl)-N-isopropoxycarbonylamino]ethoxy}phenyl)-2-ethoxypropionic acid The title compound was obtained in the same manner as that of Example 88 except that the reaction was performed by using isopropyl chloroformate instead of the methyl chloroformate.

LC-MS: HPLC retention time: 5.66 minutes, m/z 436 (M+1)

Example 95

Synthesis of 3-(4-{2-[N-(4-cyclohexylbutyl)-N-methoxycarbonylamino]ethoxy}phenyl)-2-ethoxypropionic acid The title compound was obtained in the same manner as that of Example 77 except that the reaction was performed by using 4-cyclohexylbutanoyl chloride instead of the isovaleroyl chloride.

LC-MS: HPLC retention time: 5.99 minutes, m/z 450 (M+1)

Example 96

Synthesis of 2-ethoxy-3-(4-{2-[N-heptyl-N-(2,2,2-trifluoroethoxycarbonyl)amino]ethoxy}phenyl)propionic acid ethyl ester A solution of the compound obtained in Example 1, Step e (75.9 mg) in methylene chloride (2 ml) was added with triphosgene (89 mg, Tokyo Kasei Kogyo) and triethylamine (140 μl) and stirred for 2 hours under ice cooling. The reaction mixture was added with 2,2,2-trifluoroethanol (47 μl, Tokyo Kasei Kogyo) and stirred for three days. The reaction mixture was diluted with methylene chloride, washed with 1 N HCl and saturated aqueous sodium hydrogencarbonate in this order, dried over magnesium sulfate and concentrated. The obtained residue was applied to a silica gel column and eluted with hexane/ethyl acetate (5:1) to obtain the title compound (48.5 mg).

$^1$H-NMR (CDCl$_3$) δ ppm (300 MHz): 7.16 (m, 2H), 6.79 (m, 2H), 4.1–4.2 (n, 4H), 3.96 (t, 1H, J=6.5 Hz), 3.4–3.8 (m, 8H), 2.64 (m, 2H), 1.65 (m, 2H), 1.65 (m, 2H), 1.1–1.3 (m, 16H), 0.9 (m, 3H)

Example 97

Synthesis of 2-ethoxy-3-{2-chloro-4-[2-(N-heptyl-N-methoxycarbonylamino)ethoxy]phenyl}propionic acid The title compound was obtained in the same manner as that of Example 1 except that the reaction was performed by using 2-chloro-4-hydroxybenzaldehyde (Aldrich) instead of the p-hydroxybenzaldehyde, and methyl chloroformate instead of the 2,4-difluorophenyl isocyanate, and the obtained compound was hydrolyzed in the same manner as that of Example 2.

LC-MS: HPLC retention time: 5.63 minutes, m/z 444 (M+1)

Example 98

Synthesis of 2-ethoxy-3-{4-[2-(N-heptyl-N-methoxycarbonylamino)ethoxy]-3-methoxyphenyl}propionic acid The title compound was obtained in the same manner as that of Example 97 except that the reaction was performed by using 4-hydroxy-3-methoxybenzaldehyde (Tokyo Kasei Kogyo) instead of the 2-chloro-4-hydroxybenzaldehyde.

LC-MS: HPLC retention time: 5.23 minutes, m/z 440 (M+1)

Example 99

Synthesis of 3-{4-[2-(N-heptyl-N-methoxycarbonylamino)ethoxy]phenyl}-2-methoxypropionic acid The title compound was obtained in the same manner as that of Example 1 except that the reaction was performed by using ethyl methoxyacetate (AVOCADO) instead of the ethyl ethoxyacetate, and methyl chloroformate instead of the 2,4-difluorophenyl isocyanate, and the obtained compound was hydrolyzed in the same manner as that of Example 2.

$^1$H-NMR (CDCl$_3$) δ ppm (300 MHz): 7.15 (d, 2H, J=8.3 Hz), 6.81 (d, 2H, J=7.5 Hz), 3.9–4.2 (m, 3H), 3.69 (s, 3H), 3.4–3.6 (m, 2H), 3.40 (s, 3H), 3.2–3.4 (m, 2H), 3.09 (dd, 1H, J=14.5, 4.2 Hz), 2.96 (dd, 1H, J=14.2, 7.4), 1.5–1.7 (m, 2H), 1.1–1.4 (m, 8H), 0.8–1.0 (m, 3H)

Example 100

Synthesis of 3-(4-{3-[N-(2-butoxyethyl)-N-methoxycarbonylamino]propoxy}phenyl)-2-ethoxypropionic acid The title compound was obtained in the same manner as that of Example 90 except that the reaction was performed by using n-butoxyacetic acid (Tokyo Kasei Kogyo) and 3-(3-dimethylaminopropyl)-1-ethylcarbodiimide hydrochloride instead of the n-heptanoyl chloride.

$^1$H-NMR (CDCl$_3$) δ ppm (300 MHz): 7.15 (d, 2H, J=8.5 Hz), 6.81 (d, 2H, J=8.6 Hz), 4.03 (dd, 1H, J=7.5, 4.2 Hz), 3.9–4.0 (m, 2H), 3.2–3.7 (m, 13H), 3.07 (dd, 1H, J=14.1, 4.4 Hz), 2.94 (dd, 1H, J=14.2, 7.7 Hz), 1.9–2.1 (m, 2H), 1.4–1.6 (m, 2H), 1.2–1.4 (m, 2H), 1.17 (t, 3H, 6.9 Hz), 0.91 (t, 3H, J=7.4 Hz)

Example 101

Synthesis of 2-ethoxy-3{4-[4-(N-heptyl-N-methoxycarbonylamino)butoxy]phenyl}propionic acid The title compound was obtained in the same manner as that of Example 1 except that the reaction was performed by using 4-(BOC-amino)-1-butanol (Aldrich) instead of the t-butyl N-(2-hydroxyethyl)carbamate and methyl chloroformate (Tokyo Kasei Kogyo) instead of the 2,4-difluorophenyl isocyanate, and the obtained compound was hydrolyzed in the same manner as that of Example 2.

$^1$H-NMR (CDCl$_3$) δ ppm (300 MHz): 7.15 (d, 2H, J=8.3 Hz), 6.81 (d, 2H, J=8.6 Hz), 4.03 (dd, 1H, J=7.7, 4.4 Hz), 2.6–3.9 (m, 6H), 3.68 (s, 3H), 3.06 (dd, 1H, J=14.2, 4.2 Hz), 2.94 (dd, 1H, J=14.2, 7.5 Hz), 0.6–1.8 (m, 20H)

Example 102

Synthesis of 3-(4-{2-[1-(2-butoxyethyl)-3-cyclohexylureido]ethoxy}phenyl)-2-ethoxypropionic acid Step a: Synthesis of 2-ethoxy-3-{4-[2-(2-butoxyethylamino)ethoxy]phenyl}propionic acid ethyl ester The title compound was obtained in the same manner as that up to Example 1, Step e except that the reaction was performed by using n-butoxyacetic acid (Tokyo Kasei Kogyo) and 3-(3-dimethylaminopropyl)-1-ethylcarbodiimide hydrochloride instead of the n-heptanoyl chloride.

Step b: Synthesis of 3-(4-{2-[1-(2-butoxyethyl)-3-cyclohexylureido]ethoxy}phenyl)-2-ethoxypropionic acid The title compound was obtained in the same manner as that of Example 3 except that the reaction was performed by using the compound obtained in Step a described above instead of the compound obtained in Example 1, Step e, and cyclohexyl isocyanate instead of the 2,4-dimethoxyphenyl isocyanate.

LC-MS: HPLC retention time: 5.47 minutes, m/z 479 (M+1).

Example 103

Synthesis of 3-(4-{2-[1-(2-butoxyethyl)-3-(2-methoxy-5-methylphenyl)ureido]ethoxy}phenyl)-2-ethoxypropionic acid The title compound was obtained in the same manner as that of Example 102 except that the reaction was performed by using 2-methoxy-5-methylphenyl isocyanate (Aldrich) instead of the cyclohexyl isocyanate.

LC-MS: HPLC retention time: 5.61 minutes, m/z 517 (M+1)

Example 104

Synthesis of 3-(4-{2-[1-(2-butoxyethyl)-3-(2-trifluoromethylphenyl)ureido]ethoxy}phenyl)-2-ethoxypropionic acid The title compound was obtained in the same manner as that of Example 102 except that the reaction was performed by using 2-trifluoromethylphenyl isocyanate (Aldrich) instead of the cyclohexyl isocyanate.

LC-MS: HPLC retention time: 5.59 minutes, m/z 541 (M+1)

Example 105

Synthesis of 3-(4-{2-[1-(2-butoxyethyl)-3-(2-methoxyphenyl)ureido]ethoxy}phenyl)-2-ethoxypropionic acid The title compound was obtained in the same manner as that of Example 102 except that the reaction was performed by using 2-methoxyphenyl isocyanate (Aldrich) instead of the cyclohexyl isocyanate.

LC-MS: HPLC retention time: 5.40 minutes, m/z 503 (M+1)

Example 106

Synthesis of 3-(4-{2-[1-(2-butoxyethyl)-3-(4-isopropylphenyl)ureido]ethoxy}phenyl)-2-ethoxypropionic acid The title compound was obtained in the same manner as that of Example 102 except that the reaction was performed by using 4-isopropylphenyl isocyanate (Aldrich) instead of the cyclohexyl isocyanate.

LC-MS: HPLC retention time: 5.87 minutes, m/z 515 (M+1)

Example 107

Synthesis of 3-(4-{2-[1-(2-butoxyethyl)-3-indan-5-ylureido]ethoxy}phenyl)-2-ethoxypropionic acid The title compound was obtained in the same manner as that of Example 102 except that the reaction was performed by using 5-indanyl isocyanate (Aldrich) instead of the cyclohexyl isocyanate.

LC-MS: HPLC retention time: 5.80 minutes, m/z 513 (M+1)

Example 108

Synthesis of 3-(4-{2-[1-(2-butoxyethyl)-3-(4-trifluoromethoxyphenyl)ureido]ethoxy}phenyl)-2-ethoxypropionic acid The title compound was obtained in the same manner as that of Example 102 except that the reaction was performed by using 4-trifluoromethoxyphenyl isocyanate (Aldrich) instead of the cyclohexyl isocyanate.

LC-MS: HPLC retention time: 5.74 minutes, m/z 557 (M+1)

Example 109

Synthesis of 3-(4-{2-[1-(2-butoxyethyl)-3-(4-trifluoromethylphenyl)ureido]ethoxy}phenyl)-2-ethoxypropionic acid The title compound was obtained in the same manner as that of Example 102 except that the reaction was performed by using 4-trifluoromethylphenyl isocyanate (Aldrich) instead of the cyclohexyl isocyanate.

LC-MS: HPLC retention time: 5.73 minutes, m/z 541 (M+1)

Example 110

Synthesis of 3-(4-{2-[1-(2-butoxyethyl)-3-(4-methylphenyl)ureido]ethoxy}phenyl)-2-ethoxypropionic acid The title compound was obtained in the same manner as that of Example 102 except that the reaction was performed by using 4-methylphenyl isocyanate (Aldrich) instead of the cyclohexyl isocyanate.

LC-MS: HPLC retention time: 5.53 minutes, m/z 487 (M+1)

Example 111

Synthesis of 3-(4-{2-[1-(2-butoxyethyl)-3-(2-trifluoromethoxyphenyl)ureido]ethoxy}phenyl)-2-ethoxypropionic acid The title compound was obtained in the same manner as that of Example 102 except that the reaction was performed by using 2-trifluoromethoxyphenyl isocyanate (Aldrich) instead of the cyclohexyl isocyanate.

LC-MS: HPLC retention time: 5.73 minutes, m/z 557 (M+1)

Example 112

Synthesis of 3-(4-{2-[1-(2-butoxyethyl)-3-naphthalen-1-ylureido]ethoxy}phenyl)-2-ethoxypropionic acid The title compound was obtained in the same manner as that of Example 102 except that the reaction was performed by using 1-naphthyl isocyanate (Aldrich) instead of cyclohexyl isocyanate.

LC-MS: HPLC retention time: 5.64 minutes, m/z 523 (M+1)

Example 113

Synthesis of 3-(4-{2-[1-(2-butoxyethyl)-3-(4-cyanophenyl)ureido]ethoxy}phenyl)-2-ethoxypropionic acid The title compound was obtained in the same manner as that of Example 102 except that the reaction was performed by using 3-cyanophenyl isocyanate (Aldrich) instead of the cyclohexyl isocyanate.

LC-MS: HPLC retention time: 5.32 minutes, m/z 498 (M+1)

Example 114

Synthesis of 3-(4-{2-[N-benzyloxycarbonyl-N-(2-butoxyethyl)amino]ethoxy}phenyl)-2-ethoxypropionic acid The title compound was obtained in the same manner as that of Example 102 except that the reaction was performed by using benzyl chloroformate (Aldrich) instead of the cyclohexyl isocyanate.

LC-MS: HPLC retention time: 5.54 minutes, m/z 488 (M+1)

Example 115

Synthesis of 3-(4-{2-[N-(2-butoxyethyl)-N-propoxycarbonylamino]ethoxy}phenyl)-2-ethoxypropionic acid The title compound was obtained in the same manner as that of Example 102 except that the reaction was performed by using propyl chloroformate (Aldrich) instead of the cyclohexyl isocyanate.

LC-MS: HPLC retention time: 5.40 minutes, m/z 440 (M+1)

Example 116

Synthesis of 3-(4-{2-[N-(2-butoxyethyl)-N-ethoxycarbonylamino]ethoxy}phenyl)-2-ethoxypropionic acid The title compound was obtained in the same manner as that of Example 102 except that the reaction was performed by using ethyl chloroformate (Tokyo Kasei Kogyo) instead of the cyclohexyl isocyanate.

LC-MS: HPLC retention time: 5.19 minutes, m/z 426 (M+1)

Example 117

Synthesis of 3-(4-{2-[N-(2-butoxyethyl)-N-(4-fluorophenyloxycarbonyl)amino]ethoxy}phenyl)-2-ethoxypropionic acid The title compound was obtained in the same manner as that of Example 102 except that the reaction was performed by using 4-fluorophenyl chloroformate (Aldrich) instead of the cyclohexyl isocyanate.

LC-MS: HPLC retention time: 5.52 minutes, m/z 492 (M+1)

Example 118

Synthesis of 3-{4-[2-(N-heptyl-N-methoxycarbonylamino)ethoxy]phenyl}-2-isopropoxypropionic acid The title compound was obtained in the same manner as that of Example 99 except that the reaction was performed by using isopropoxyacetic acid isopropyl ester (prepared by the method described in U.S. Pat. No. 1,759,331, 1928 using isopropanol and chloroacetic acid ester derivative as starting materials) instead of the ethyl methoxyacetate.

$^1$H-NMR (CDCl$_3$) δ ppm (300 MHz): 7.15 (d, 2H, J=8.5 Hz), 6.81 (d, 2H, J=8.3 Hz), 4.0–4.1 (m, 3H), 3.70 (s, 3H), 3.2–3.7 (m, 5H), 3.07 (dd, 1H, J=14.2, 3.9 Hz), 2.89 (dd, 1H, J=14.0, 7.7 Hz), 1.4–1.6 (m, 2H), 1.2–1.4 (m, 8H), 1.16 (d, 3H, J=6.1 Hz), 1.02 (d, 3H, 6.1 Hz), 0.88 (dd, 3H, J=7.0, 6.4 Hz)

Example 119

Synthesis of 3-(4-{2-[N-(2-butoxyethyl)-N-isopropoxycarbonylamino]ethoxy}phenyl)-2-ethoxypropionic acid The title compound was obtained in the same manner as that of Example 100 except that the reaction was performed by using isopropyl chloroformate instead of the methyl chloroformate.

$^1$H-NMR (CDCl$_3$) δ ppm (300 MHz): 7.14 (d, 2H, J=8.5 Hz), 6.81 (d, 2H, J=8.5 Hz), 4.8–5.0 (m, 1H), 4.04 (dd, 1H, J=7.5, 3.3 Hz), 3.1–4.1 (m, 12H), 3.05 (dd, 1H, J=14.0, 4.1 Hz), 2.94 (dd, 1H, J=14.2, 7.7 Hz), 1.8–2.1 (m, 2H), 1.0–1.6 (m, 16H), 0.91 (dd, 3H, J=7.4, 7.2 Hz)

Example 120

Synthesis of 3-{4-[2-(N-heptyl-N-methoxycarbonylamino)ethoxy]phenyl}-2-propoxypropionic acid The title compound was obtained in the same manner as that of Example 99 except that the reaction was performed by using propoxyacetic acid propyl ester (prepared in the same manner as that of Example 118) instead of the ethyl methoxyacetate.

LC-MS: HPLC retention time: 5.22 minutes, m/z 424 (M+1)

Example 121

Synthesis of 2-butoxy-3-{4-[2-(N-heptyl-N-methoxycarbonylamino)ethoxy]phenyl}propionic acid The title compound was obtained in the same manner as that of Example 99 except that the reaction was performed by using n-butoxyacetic acid butyl ester (prepared in the same manner as that of Example 118) instead of the ethyl methoxy acetate.

LC-MS: HPLC retention time: 5.50 minutes, m/z 438 (M+1)

Example 122

Synthesis of 3-(4-{2-[N-(2-butoxyethyl)-N-isopropoxycarbonylamino]ethoxy}phenyl)-2-ethoxypropionic acid The title compound was obtained in the same manner as that of Example 102 except that the reaction was performed by using isopropyl chloroformate (Tokyo Kasei Kogyo) instead of the cyclohexyl isocyanate.

LC-MS: HPLC retention time: 5.10 minutes, m/z 440 (M+1)

Example 123

Synthesis of 3-(4-{2-[N-(2-butoxyethyl)-N-isobutoxycarbonylamino]ethoxy}phenyl)-2-ethoxypropionic acid The title compound was obtained in the same manner as that of Example 102 except that the reaction was performed by using isobutyl chloroformate (Aldrich) instead of the cyclohexyl isocyanate.

$^1$H-NMR (CDCl$_3$) δ ppm (300 MHz): 7.14 (d, 2H, J=8.6 Hz), 6.8–6.9 (m, 2H), 4.0–4.2 (m, 4H), 3.87 (d, 2H, J=6.4 Hz), 3.3–3.7 (m, 9H), 3.08 (dd, 1H, J=14.2, 4.0 Hz), 2.94 (dd, 1H, J=14.2, 7.4 Hz), 1.8–2.0 (m, 1H), 1.2–1.6 (m, 4H), 1.18 (t, 3H, J=7.0 Hz), 0.8–1.0 (m, 6H)

Example 124

Synthesis of 3-{4-[2-(N-ethoxycarbonyl-N-heptylamino)ethoxy]phenyl}-2-isopropoxypropionic acid The title compound was obtained in the same manner as that of Example 118 except that the reaction was performed by using ethyl chloroformate (Tokyo Kasei Kogyo) instead of the methyl chloroformate.

$^1$H-NMR (CDCl$_3$) δ ppm (300 MHz): 7.14 (d, 2H, J=8.5 Hz), 6.81 (d, 2H, J=8.6 Hz), 4.0–4.2 (m, 5H), 3.4–3.7 (m, 3H), 3.32 (dd, 2H, J=7.2, 6.9 Hz), 3.06 (dd, 1H, J=13.8, 3.5 Hz), 2.88 (dd, 1H, J=13.8, 8.1), 1.4–1.6 (m, 2H), 1.2–1.3 (m, 11H), 1.16 (d, 3H, J=6.1 Hz), 1.02 (d, 3H, 5.9 Hz), 0.88 (dd, 3H, J=7.0, 6.2 Hz)

Example 125

Synthesis of 3-{4-[2-(N-heptyl-N-isopropoxycarbonylamino)ethoxy]phenyl}-2-isopropoxypropionic acid The title compound was obtained in the same manner as that of Example 118 except that the reaction was performed by using isopropyl chloroformate (Tokyo Kasei Kogyo) instead of the methyl chloroformate.

$^1$H-NMR (CDCl$_3$) δ ppm (300 MHz): 7.14 (d, 2H, J=8.5 Hz), 6.82 (d, 2H, J=8.5 Hz), 4.8–5.0 (m, 1H), 4.0–4.2 (m, 3H), 3.4–3.6 (m, 3H), 3.2–3.4 (m, 2H), 3.07 (dd, 1H, J=14.0, 3.7 Hz), 2.89 (dd, 1H, J=14.1, 8.1 Hz), 1.2–1.4 (m, 14H), 1.16 (d, 3H, J=6.1 Hz), 1.03 (d, 3H, 6.1 Hz), 0.88 (dd, 3H, J=6.8, 5.9 Hz)

Example 126

Synthesis of 3-{4-[2-(N-heptyl-N-propoxycarbonylamino)ethoxy] phenyl}-2-isopropoxypropionic acid The title compound was obtained in the same manner as that of Example 118 except that the reaction was performed by using propyl chloroformate (Tokyo Kasei Kogyo) instead of the methyl chloroformate.

$^1$H-NMR (CDCl$_3$) δ ppm (300 MHz): 7.15 (d, 2H, J=8.5 Hz), 6.81 (d, 2H, J=7.9 Hz), 4.0–4.1 (m, 5H), 3.4–3.6 (m, 3H), 3.2–3.4 (m, 2H), 3.06 (dd, 1H, J=14.0, 3.9 Hz), 2.89 (dd, 1H, J=14.0, 8.1 Hz), 1.5–1.7 (m, 4H), 1.2–1.5 (m, 8H), 1.16 (d, 3H, J=6.2 Hz), 1.01 (d, 3H, 6.1 Hz), 0.8–1.1 (m, 6H)

Example 127

Synthesis of 3-{4-[2-(N-heptyl-N-isobutoxycarbonylamino)ethoxy]phenyl}-2-isopropoxypropionic acid The title compound was obtained in the same manner as that of Example 118 except that the reaction was performed by using isobutyl chloroformate (Tokyo Kasei Kogyo) instead of the methyl chloroformate.

$^1$H-NMR (CDCl$_3$) δ ppm (300 MHz): 7.14 (d, 2H, J=8.6 Hz), 6.81 (d, 2H, J=7.4 Hz), 4.0–4.2 (m, 3H), 3.86 (d, 2H, J=6.4 Hz), 3.4–3.7 (m, 3H), 3.2–3.4 (m, 2H), 3.07 (dd, 1H, J=14.2, 3.9 Hz), 2.88 (dd, 1H, J=14.0, 8.1 Hz), 1.8–2.0 (m, 1H), 1.5–1.6 (m, 2H), 1.2–1.3 (m, 4H), 1.16 (d, 3H, J=6.1 Hz), 1.02 (d, 3H, J=6.1 Hz), 0.8–1.0 (m, 9H)

Example 128

Synthesis of 3-(4-{2-[N-(2-butoxyethyl)-N-methoxycarbonylamino]ethoxy}phenyl)-2-isopropoxypropionic acid The title compound was obtained in the same manner as that of Example 118 except that the reaction was performed by using n-butoxyacetic acid (Tokyo Kasei Kogyo) and 3-(3-dimethylaminopropyl)-1-ethylcarbodiimide hydrochloride instead of the heptanoyl chloride.

$^1$H-NMR (CDCl$_3$) δ ppm (300 MHz): 7.14 (d, 2H, J=8.6 Hz), 6.81 (d, 2H, J=6.3 Hz), 4.0–4.2 (m, 3H), 3.70 (s, 3H), 3.06 (dd, 1H, J=13.8, 3.7 Hz), 2.88 (dd, 1H, J=13.8, 7.9 Hz), 1.5–1.7 (m, 2H), 1.3–1.5 (m, 2H), 1.16 (d, 3H, J=6.1 Hz), 1.02 (d, 3H, 5.9 Hz), 0.91 (t, 3H, J=7.2 Hz)

Example 129

Synthesis of 3-(4-{2-[N-(2-butoxyethyl)-N-ethoxycarbonylamino]ethoxy}phenyl)-2-isopropoxypropionic acid The title compound was obtained in the same manner as that of Example 128 except that the reaction was performed by using ethyl chloroformate (Tokyo Kasei Kogyo) instead of the methyl chloroformate.

$^1$H-NMR (CDCl$_3$) δ ppm (300 MHz): 7.14 (d, 2H, J=8.5 Hz), 6.81 (d, 2H, J=8.1 Hz), 4.0–4.2 (m, 5H), 3.4–3.7 (m, 7H), 3.42 (t, 2H, J=6.5 Hz), 3.06 (dd, 1H, J=14.0, 4.0 Hz), 2.88 (dd, 1H, J=14.1, 8.1 Hz), 1.5–1.6 (m, 2H), 1.3–1.5 (m, 2H), 1.26 (t, 3H, J=7.1 Hz), 1.16 (d, 3H, J=6.1 Hz), 1.02 (d, 3H, J=6.1 Hz), 0.91 (t, 3H, J=7.2 Hz)

Example 130

Synthesis of 3-(4-{2-[N-(2-butoxyethyl)-N-isopropoxycarbonylamino]ethoxy}phenyl)-2-isopropoxypropionic acid The title compound was obtained in the same manner as that of Example 128 except that the reaction was performed by using isopropyl chloroformate (Tokyo Kasei Kogyo) instead of the methyl chloroformate.

$^1$H-NMR (CDCl$_3$) δ ppm (300 MHz): 7.15 (d, 2H, J=8.5 Hz), 6.82 (d, 2H, J=8.1 Hz), 4.8–5.0 (m, 1H), 4.0–4.1 (m, 3H), 3.4–3.7 (m, 7H), 3.42 (t, 2H, J=6.6 Hz), 3.05 (dd, 1H, J=14.1, 4.0 Hz), 2.88 (dd, 1H, J=14.0, 8.3 Hz), 1.5–1.6 (m, 2H), 1.3–1.5 (m, 2H), 1.25 (d, 6H, J=6.2 Hz), 1.16 (d, 3H, J=6.1 Hz), 1.01 (d, 3H, J=6.1 Hz), 0.90 (t, 3H, J=7.2 Hz)

Example 131

Synthesis of 3-(4-{2-[N-(2-butoxyethyl)-N-propoxycarbonylamino]ethoxy}phenyl)-2-isopropoxypropionic acid The title compound was obtained in the same manner as that of Example 128 except that the reaction was performed by using propyl chloroformate (Tokyo Kasei Kogyo) instead of the methyl chloroformate.

$^1$H-NMR (CDCl$_3$) δ ppm (300 MHz): 7.14 (d, 2H, J=8.5 Hz), 6.81 (d, 2H, J=5.7 Hz), 4.0–4.1 (m, 5H), 3.2–3.8 (m, 9H), 3.05 (dd, 1H, J=14.0, 3.9 Hz), 2.88 (dd, 1H, J=13.8, 8.1 Hz), 1.1–1.7 (m, 6H), 1.16 (d, 3H, J=6.1 Hz), 0.7–1.1 (m, 9H)

Example 132

Synthesis of 3-(4-{2-[N-(2-butoxyethyl)-N-isobutoxycarbonylamino]ethoxy}phenyl)-2-isopropoxypropionic acid The title compound was obtained in the same manner as that of Example 128 except that the reaction was performed by using isobutyl chloroformate (Tokyo Kasei Kogyo) instead of the methyl chloroformate.

$^1$H-NMR (CDCl$_3$) δ ppm (300 MHz): 7.15 (d, 2H, J=8.6 Hz), 6.7–6.9 (m, 2H), 4.0–4.2 (m, 3H), 3.8–3.9 (m, 2H), 3.70 (t, 2H, J=5.7 Hz), 3.4–3.6 (m, 5H), 3.42 (t, 2H, J=6.5 Hz), 3.05 (dd, 1H, J=14.0, 3.9 Hz), 2.88 (dd, 1H, J=14.0, 8.3 Hz), 1.8–2.0 (m, 1H), 1.0–1.6 (m, 4H), 1.23 (d, 3H, J=6.3 Hz), 1.16 (d, 3H, J=6.1 Hz), 0.8–1.2 (m, 9H)

Example 133

Synthesis of 3-(4-{2-[N-(2-butoxyethyl)-N-isopropoxycarbonylamino]ethoxy}phenyl)-2-isopropoxypropionic acid The title compound was obtained in the same manner as that of Example 130 except that the reaction was performed by using t-butyl N-(3-hydroxypropyl)carbamate (Aldrich) instead of the t-butyl N-(2-hydroxyethyl)carbamate.

$^1$H-NMR (CDCl$_3$) δ ppm (300 MHz): 7.14 (d, 2H, J=8.5 Hz), 6.81 (d, 2H, J=8.6 Hz), 4.8–5.0 (m, 1H), 4.08 (dd, 1H, J=8.1, 4.0), 3.8–4.0 (m, 2H), 3.3–3.6 (m, 9H), 3.06 (dd, 1H, J=14.2, 3.9 Hz), 2.88 (dd, 1H, J=14.1, 8.1 Hz), 1.9–2.1 (m, 2H), 1.1–1.6 (m, 10H), 1.16 (d, 3H, J=6.1 Hz), 1.02 (d, 3H, J=6.1 Hz), 0.91 (t, 3H, J=7.4 Hz)

Example 134

Synthesis of 3-(4-{2-[N-(2-butoxyethyl)-N-isobutoxycarbonylamino]ethoxy}phenyl)-2-isopropoxypropionic acid The title compound was obtained in the same manner as that of Example 133 except that the reaction was performed by using isobutyl chloroformate (Tokyo Kasei Kogyo) instead of the isopropyl chloroformate.

$^1$H-NMR (CDCl$_3$) δ ppm (300 MHz): 7.14 (d, 2H, J=8.6 Hz), 6.80 (d, 2H, J=8.3 Hz), 4.09 (dd, 1H, J=7.9, 4.0 Hz), 3.9–4.0 (br, 2H), 3.85 (d, 2H, J=6.4 Hz), 3.3–3.6 (m, 9H), 3.07 (dd, 1H, J=14.0, 3.7 Hz), 2.88 (dd, 1H, J=14.0, 7.7 Hz), 1.8–2.1 (br, 3H), 1.2–1.6 (m, 4H), 1.16 (d, 3H, J=6.3 Hz), 1.03 (d, 3H, J=6.1 Hz), 0.8–1.0 (m, 9H).

Test Example 1

Test for Measuring Hypoglycemic Action and Triglyceride-Decreasing Action in db/db Mice Each of test compounds was administered once a day for 2 weeks to db/db mice genetically presenting pathological conditions of obesity, hyperglycemia, and hyperlipidemia. Blood was collected from the mice immediately before the start of administration of a test sample or a vehicle on the first day. Plasma glucose levels and triglyceride levels were measured, and the mice were divided into groups so that average glucose levels and triglyceride levels gave no significant value among the groups. All the test samples were suspended in a 0.5% methylcellulose (MC) solution and orally administered. For a vehicle-administered control group, a 0.5% MC solution was orally administered. Blood samples were collected from the mice on the 15th day, and plasma glucose levels and triglyceride levels were measured. A hypoglycemic rate and triglyceride-reducing rate were calculated by using the following equations.

The results are shown in Table 1.

Hypoglycemic rate = [(Blood glucose level of vehicle group on 15th day) – (Blood glucose level of each group on 15th day)]/(Blood glucose level of vehicle group on 15th day) × 100

Triglyceride reducing rate = [(Triglyceride level of vehicle group on 15th day) – (Triglyceride level of each group on 15th day)]/(Triglyceride level of vehicle group on 15th day) × 100

TABLE 1

| Compound of Example | Dose (mg/kg) | Hypoglycemic rate (%) | Triglyceride reducing rate (%) |
|---|---|---|---|
| Example 2 | 10 | 34 | 53 |
| Example 56 | 1 | 26 | 49 |
| Example 57 | 3 | 35 | 46 |
| Example 59 | 3 | 18 | 21 |
| Example 66 | 1 | 32 | 57 |
| Example 67 | 1 | 17 | 26 |
| Example 71 | 1 | 28 | 40 |
| Example 73 | 3 | 30 | 43 |
| Example 75 | 3 | 38 | 32 |
| Example 92 | 3 | 4 | 12 |
| Example 96 | 3 | 38 | 31 |
| Example 115 | 3 | 11 | 18 |
| Example 118 | 1 | 42 | 51 |
| Example 120 | 1 | 39 | 48 |
| Example 122 | 3 | 14 | 21 |
| Example 123 | 3 | 8 | 32 |
| Example 125 | 1 | 42 | 64 |
| Example 130 | 1 | 41 | 40 |
| Example 132 | 1 | 7 | 14 |

From these results, it was found that the compounds of the present invention markedly decreased the blood glucose level and triglyceride level in db/db mice, and thus it was strongly suggested that the compounds of the present invention were useful as agents for diabetes mellitus and/or hyperlipidemia.

Test Example 2

Test for Measuring Total Plasma Cholesterol Reducing Action and Non-HDL Cholesterol (VLDL Cholesterol+LDL Cholesterol) Reducing Action in Hamster A test compound (10 mg/kg) was administered once a day for one week to hamsters fed with high cholesterol diet (CE-2 (Clea Japan)+1% cholesterol+10% coconut oil) for five days. The plasma cholesterol level and the plasma HDL cholesterol level were measured immediately before the start of the administration of the test sample or vehicle on the 1st day, and the hamsters were divided into groups so that the groups gave no significant value of initial levels of the both measurements. Each of the test samples was dissolved in a 0.5% methylcellulose (MC) solution and orally administered. A 0.5% methylcellulose (MC) solution was orally administered to the hamsters as a vehicle control group. A blood sample was collected on the 8th day, and the plasma cholesterol level and the plasma HDL cholesterol level were measured. The total cholesterol reducing rate was obtained by using the following equation.

Total cholesterol reducing rate (%) = [(Total cholesterol level of vehicle group on 8th day) − (Total cholesterol level of each group on 8th day)]/(Total cholesterol level of vehicle group on 8th day) × 100

Further, non-HDL cholesterol level (LDL cholesterol level+VLDL cholesterol level) was calculated as (Total cholesterol level−HDL cholesterol level), and the reducing rate thereof was calculated by using the following equation.

Non-HDL cholesterol reducing rate(%) = [(Non-HDL cholesterol level of vehicle group on 8th day) − (Non-HDL cholesterol level of each group on 8th day)]/(Non-HDL cholesterol level of vehicle group on 8th day) × 100

The results are shown in Table 2.

TABLE 2

| Compound of Example | Total cholesterol reducing rate (%) | Non-HDL cholesterol reducing rate (%) |
|---|---|---|
| Example 2 | 30 | 29 |
| Example 56 | 39 | 40 |
| Example 57 | 41 | 43 |
| Example 59 | 37 | 35 |
| Example 66 | 40 | 42 |
| Example 67 | 34 | 32 |
| Example 71 | 12 | 10 |
| Example 73 | 45 | 45 |
| Example 75 | 48 | 46 |
| Example 92 | 8 | 10 |
| Example 96 | 24 | 23 |
| Example 115 | 17 | 17 |
| Example 118 | 45 | 50 |
| Example 120 | 28 | 25 |
| Example 122 | 10 | 9 |
| Example 123 | 25 | 25 |
| Example 125 | 45 | 48 |
| Example 130 | 22 | 22 |
| Example 132 | 18 | 20 |

From these results, it was found that the compounds of the present invention markedly reduced total cholesterol and non-HDL cholesterol in hamsters, and thus it was strongly suggested that the compounds of the present invention were useful as antilipemic agents.

Test Example 3

Measurement of Liver Triglyceride Contents in Zucker Rats

To Zucker rats, a vehicle (0.5% MC), a compound of the present invention or fenofibrate (Sigma) was administered once a day for 2 weeks. The livers were isolated on the next day of the final administration, and amounts of triglyceride in the livers were determined. Triglyceride was extracted by adding 5 ml of a mixture of hexane and isopropanol (2:1, V/V) to 100 mg of liver, homogenizing the liver using Polytron homogenizer, then sufficiently stirring and centrifuging the homogenate at 2000 g for 10 minutes at room temperature. The amount of triglyceride in the solution layer was measured.

The results are shown in Table 3.

TABLE 3

| Compound of Example | Dose | Triglyceride reducing rate (%) |
|---|---|---|
| Fenofibrate | 100 mg/kg | 22 |
| Example 2 | 10 mg/kg | 19 |
| Example 56 | 1 mg/kg | 42 |
| Example 57 | 1 mg/kg | 41 |
| Example 59 | 1 mg/kg | 40 |
| Example 66 | 1 mg/kg | 44 |
| Example 67 | 1 mg/kg | 47 |
| Example 71 | 1 mg/kg | 28 |
| Example 73 | 1 mg/kg | 34 |
| Example 75 | 1 mg/kg | 32 |
| Example 92 | 1 mg/kg | 2 |
| Example 96 | 1 mg/kg | 39 |
| Example 115 | 1 mg/kg | 42 |
| Example 118 | 1 mg/kg | 47 |
| Example 120 | 1 mg/kg | 28 |
| Example 122 | 1 mg/kg | 2 |
| Example 123 | 1 mg/kg | 35 |
| Example 125 | 1 mg/kg | 36 |
| Example 130 | 1 mg/kg | 32 |
| Example 132 | 1 mg/kg | 39 |

The compound administered group used in this experiment showed reduction of the amounts of triglyceride in livers.

Fenofibrate used in this experiment is known as a PPARα agonist (J. Natl. Cancer Inst., 90, 1702–1709, 1998), and is known to decrease triglyceride in livers of rats (Biochimie, 80, 943–948, 1998). Since the compounds of the present invention also decreased triglyceride in liver like fenofibrate, it was suggested that the compounds of the present invention had the PPARα activity.

Test Example 4

Test for Uptake of Glucose By Adipocytes and Test for Triglyceride Accumulation in Adipocytes According to the method of Mukherjee et al. (Mol. Endocrinol, 14, 1425–1433, 2000), a glucose uptake experiment was performed by using cultured cells. 3T3-L1 precursor adipocytes were cultured for 4 to 5 days in the presence of a test compound, and then stimulated with 100 nM insulin, and then the amount of [$^3$H]-2-deoxy-glucose (2DG) uptake by the cells was measured. The results are shown in Table 4. The amount of glucose uptake provided after the treatment with 100 nM of each compound was measured, and represented as a relative value based on the amount of glucose uptake provided after the treatment with 10 μM rosiglitazone, which was taken as 100%.

Further, 3T3-L1 precursor adipocytes were cultured for 4 to 5 days in the presence of a test compound, and then the amount of triglyceride in the cells was measured according to the method of Shibata T et al. (Eur. J. Pharmacol., 364 (2–3), 211–219, 1999). The results are shown in Table 4. The amount of accumulated triglyceride provided after the treatment with 100 nM of each compound was measured, and represented as a relative value based on the amount of accumulated triglyceride provided after the treatment with 10 μM rosiglitazone, which was taken as 100%.

TABLE 4

| Compound of Example | Amount of glucose uptake (%) | Amount of accumulated triglyceride (%) |
|---|---|---|
| Example 2 | 95 | 90 |
| Example 56 | 90 | 85 |
| Example 57 | 80 | 75 |
| Example 59 | 88 | 77 |
| Example 66 | 95 | 80 |
| Example 67 | 91 | 92 |
| Example 71 | 83 | 85 |
| Example 73 | 99 | 96 |
| Example 75 | 98 | 98 |
| Example 92 | 90 | 92 |
| Example 96 | 85 | 80 |
| Example 115 | 98 | 95 |
| Example 118 | 60 | 55 |
| Example 120 | 90 | 88 |
| Example 122 | 92 | 90 |
| Example 123 | 99 | 96 |
| Example 125 | 97 | 98 |
| Example 130 | 92 | 90 |
| Example 132 | 96 | 97 |

As a result, promotion of differentiation of 3T3-L1 precursor adipocytes into adipocytes and promotion of glucose uptake and triglyceride accumulation by insulin were provided by the compounds used in this experiment.

Rosiglitazone used in this experiment is known as a PPARγ agonist (Biochem. Biophys. Res. Commun., 229 (3), 752–7, 1996), and is reported to promote differentiation of 3T3-L1 precursor adipocytes into adipocytes and promote glucose uptake and triglyceride accumulation by insulin by the PPARγ action (Endocrine Reviews 20 (5), 649–88, 1999). Since the compounds of the present invention also promoted differentiation of 3T3-L1 precursor adipocytes into adipocytes and promoted glucose uptake and accumulation of triglyceride by insulin like rosiglitazone, it was suggested that the compounds of the present invention also had the PPARγ activity.

Test Example 5

Acute Toxicity Test in Normal Mice

Each of test compounds (Examples 2, 56, 57, 59, 66, 67, 70, 71, 73, 75, 92, 96, 115, 118, 120, 122, 123, 125, 130, 132) was orally administered to normal mice. All the test samples were suspended in a 0.5% methylcellulose (MC) solution and then orally administered at a dose of 100 mg/kg. Mortality rate [=(Number of death in each group)/(Number of mice used in each group)×100] was calculated.

As a result, all the test compounds used gave mortality rate of 0%, and it was shown that the compounds of the present invention were safe compounds almost free from toxicity.

Test Example 6 Other Test Methods (1) Expression of PPARα and PPARγ Target Genes in db/db Mice In Vivo From the results of Test Examples 3, and 4, it was suggested that the compounds of the present invention had the PPARα action and PPARγ action. The fact that a test compound acts on a PPARα receptor and PPARγ receptor in animals can be verified by observing changes in expression of PPARα and PPARγ target genes in tissues dissected from animals administered with the test compound. Examples of the method that meet the purpose include Northern blotting, RT-PCR and the like.

For example, in order to amplify a target gene by using RT-PCR among the aforementioned techniques, liver or epididymal adipose tissue are dissected from mice used in Test Example 1 and homogenized in TRIzol reagent (GIBCO BRL, Cat. 15596-018), and purified RNA is obtained by using RNeasy Mini Kit (QIAGEN, Cat. 74104) as an RNA extraction kit. By using the purified RNA and variety of primers which are DNA fragments containing the gene sequences of RNA and PPAR target genes, reverse transcription and amplification of DNA for 15 to 30 cycles are performed by RT-PCR using One Step RT-PCR kit (QIAGEN, Cat. 210210). Then, the products can be separated by agarose gel electrophoresis, and density of a band corresponding to a target gene can be quantified to determine an increase or decrease of transcripts factor of the target gene. As described in the report of Mei-Hui Hsu et al. (J. Biol. Chem., 276 (30), 27950–27958, 2001), ACS (Acyl-CoA synthase), ACO (Acyl-CoA oxidase), L-FABP (Liver fatty acid binding protein), ApoCIII (Apolipoprotein CIII) genes and the like are available as the target genes of PPARα. As the target genes of PPARγ, aP2 (Lipid-binding adipocyte $P_2$), LPL (Lipoprotein lipase) genes and the like are available as described in the report of James M. Way et al. (Endocrinology, 142 (3), 1269–1277, 2001). Each of the genes was amplified in the aforementioned reports by using primers for each of human-type gene and rat-type gene. For this test, it is most preferable to use primers of a mouse-type gene sequence. Besides the aforementioned methods, the real-time PCR method using TaqMan probe (the method of Dilip D. Patel et al.; Journal of Lipid Research, 42, 328–337, 2001) can also be used for the RT-PCR method. By performing the aforementioned test, PPARα agonist activity and PPARγ agonist activity of the compounds of the present invention can be verified in tissues of db/db mice.

(2) Test for PPAR Receptor Transcription Activity

From the results of Test Examples 3, and 4, it was suggested that the compounds of the present invention were agonists acting on PPARα and PPARγ receptors. This action can also be verified by measuring enhancement of transcription activity by PPARα or PPARγ receptor with treatment by the compounds, as in the method of Braj B. Lohray et al. (J. Med. Chem, 44, 2675–2678, 2001). That is, as a GAL4-PPAR fusion plasmid, a fusion plasmid is prepared by using a vector pFA-CMV plasmid (Stratagene, Cat. 219036), for which a region for the 1–147 amino acids of GAL4 is ligated to a DNA fragment of 499th to 1410th nucleotides of human PPARα (GenBank™ accession number: S74349, coding for the 167th amino acid to the C-terminus amino acid) or to 577th to 1520th nucleotides of human PPARγ (GenBank™ accession number: U79012, coding for the 193rd amino acid to the C-terminus amino acid). As a reporter plasmid, pFR-Luc plasmid (Stratagene, Cat. 219050) is used which has five copies of DNA binding region of GAL4 and a luciferase gene downstream from the TATA box. HEK293 cells are seeded at $1\times10^4$ cells/well in 96-well plates and cultured for 12 hour in DMEM medium containing 5% fetal bovine serum from which free fatty acids are removed, and then the cells are cotransfected with the GAL4-PPAR plasmid and pFR-Luc plasmid by using FuGENE6 (Roche, Cat. 1815075). Twenty four hours after the cotransfection, a compound of the present invention is added, and the culture is continued for 24 hours. Then, after the medium is removed, the cells are added with PicaGene LT2.0 (Toyo Ink Mfg.) and shaken for 30 minutes, and the luciferase activity is measured by using Luminous CT-9000D (Dia-Iatron) detector. By observing an increase of the luciferase activity on the basis of the addition of the compound of the present invention during the culture, it can be verified that the compound of the present invention acts on PPARα and PPARγ.

Industrial Applicability

The compounds of the present invention have superior hypoglycemic action, hypolipidemic action and total cholesterol reducing action and have high safety, and thus the compounds are useful as active ingredients of medicaments for prophylactic and/or therapeutic treatments of diseases including diabetes mellitus, hyperlipidemia and the like.

What is claimed is:

1. A compound represented by the following formula (1) or a salt thereof:

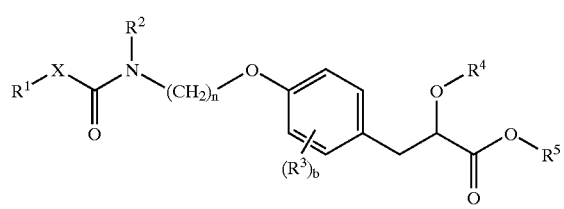

(1)

wherein $R^1$ represents a $C_{1-12}$ alkyl group which may be substituted with one or more substituents selected from the group consisting of a halogen atom, a lower alkoxyl group, and a phenyl group which may be substituted with one or more halogen atoms or a group represented by the following formula (1-1):

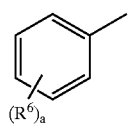

(1-1)

wherein a is an integer from 0 to 5 and $R^6$ represents at least one substituent selected from the group consisting of a halogen atom, a lower alkyl group, a lower alkoxyl group, a lower alkylthio group, nitro group, a lower alkoxycarbonyl group, cyano group, trifluoromethyl group, trifluoromethoxy group, or a phenyloxy group, which may be the same or different, or represents a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, $R^2$ represents a $C_{2-12}$ alkyl group which may be substituted with one or more substituents selected from the group consisting of a lower alkoxyl group, an aryloxy group, an aralkyloxy group, a lower alkylthio group, an arylthio group, an aralkylthio group, and a phenyl group, wherein $R^2$ may be further substituted with one or more halogen atoms provided that $R^2$, except for the methylene group in $R^2$ that binds to the nitrogen atom, may be substituted with one or more halogen atoms, b is an integer from 0 to 4 and $R^3$ is at least one substituent selected from the group consisting of a halogen atom, a lower alkyl group, or a lower alkoxyl group, which may be the same or different, $R^4$ represents a lower alkyl group, $R^5$ represents hydrogen atom or a lower alkyl group, n is an integer from 2 to 4, and X represents —NH— or —O—.

2. The compound according to claim 1 or the salt thereof, wherein $R^1$ represents a $C_{1-12}$ alkyl group which may be substituted with one or more substituents selected from the group consisting of a halogen atom, a lower alkoxyl group, and a phenyl group which may be substituted with one or more halogen atoms.

3. The compound according to claim 1 or the salt thereof, wherein $R^2$ represents a $C_{2-12}$ alkyl group which may be substituted with one or more substituents selected from the group consisting of a lower alkoxyl group and a lower alkylthio group.

4. The compound according to claim 1 or the salt thereof, wherein b is 0.

5. The compound according to claim 1 or the salt thereof, wherein $R^4$ represents methyl group, ethyl group or isopropyl group.

6. The compound according to claim 1 or the salt thereof, wherein $R^5$ represents hydrogen atom or ethyl group.

7. The compound according to claim 1 or the salt thereof, wherein n is 2 or 3.

8. The compound according to claim 1 or the salt thereof, wherein X represents —O—.

9. The compound according to claim 1 or 2 or the salt thereof, wherein $R^2$ represents a $C_{2-12}$ alkyl group which may be substituted with one or more substituents selected from the group consisting of a lower alkoxyl group, an aryloxy group, an aralkyloxy group, and a phenyl group, wherein $R^2$ may be further substituted with one or more halogen atoms provided that $R^2$, except for the methylene group in $R^2$ that binds to the nitrogen atom, may be substituted with one or more halogen atoms, b is 0, $R^4$ represents ethyl group, $R^5$ represents hydrogen atom or ethyl group, n represents 2, and X represents —O—.

10. The compound according to claim 1 or the salt thereof, wherein $R^1$ represents a group represented by the formula (1-1) wherein a is an integer from 0 to 5, $R^6$ represents fluorine, $R^2$ represents an alkyl group selected from the group consisting of normal pentyl group, normal hexyl group, normal heptyl group, and normal octyl group, b is 0, $R^4$ represents ethyl group, $R^5$ represents hydrogen atom or ethyl group, n is 2, and X represents —NH—.

11. The compound according to claim 1 or the salt thereof, wherein $R^1$ represents a substituent selected from the group consisting of methyl group, ethyl group, benzyl group, allyl group, propyl group, p-tolyl group, 4-bromophenyl group, 4-fluorophenyl group, 2-methoxyethyl group, isopropyl group, 2-propynyl group, 2-naphthyl group, isobutyl group, 2,2-dimethylpropyl group, and 3-butenyl group, $R^2$ represents heptyl group, b is 0, $R^4$ represents ethyl group, $R^5$ represents hydrogen atom or ethyl group, n is 2, and X represents —O—.

12. A compound or a salt thereof, which is selected from the group consisting of (R)-3-(4-{2-[3-(2,4-difluorophenyl)-1-heptylureido]ethoxy}phenyl)-2-ethoxypropionic acid, (R)-3-(4-{2-[3-(2,4-difluorophenyl)-1-heptylureido] ethoxy}phenyl)-2-ethoxypropionic acid ethyl ester, (S)-3-(4-{2-[3-(2,4-difluorophenyl)-1-heptylureido] ethoxy}phenyl)-2-ethoxypropionic acid, (S)-3-(4-{2-[3-(2, 4-difluorophenyl)-1-heptylureido]ethoxy}phenyl)-2-ethoxypropionic acid ethyl ester, 3-(4-{2-[3-(2,4-difluorophenyl)-1-heptylureido]ethoxy}phenyl)-2- ethoxypropionic acid and 3-(4-{2-[3-(2,4-difluorophenyl)-1-heptylureido]ethoxy}phenyl)-2-ethoxypropionic acid ethyl ester.

13. A compound or a salt thereof, which is selected from the group consisting of 2-ethoxy-3-(4-{2-[heptyl(isopropyloxycarbonyl)amino]ethoxy}phenyl)propionic acid, 2-ethoxy-3-(4-{2-[heptyl(isopropyloxycarbonyl)amino]ethoxy}phenyl)propionic acid ethyl ester, (R)-2-ethoxy-3-(4-{2-[heptyl(isopropyloxycarbonyl)amino]ethoxy}phenyl)propionic acid, (R)-2-ethoxy-3-(4-{2-[heptyl(isopropyloxycarbonyl)amino]ethoxy}phenyl)propionic acid ethyl ester, (S)-2-ethoxy-3-(4-{2-[heptyl(isopropyloxycarbonyl)amino]ethoxy}phenyl)propionic acid and (S)-2-ethoxy-3-(4-{2-[heptyl(isopropyloxycarbonyl)amino]ethoxy}phenyl)propionic acid ethyl ester.

14. A compound or a salt thereof, which is selected from the group consisting of 3-(4-{2-[benzyloxycarbonyl(heptyl)amino]ethoxy}phenyl)-2-ethoxypropionic acid, 3-(4-{2-[benzyloxycarbonyl(heptyl)amino]ethoxy}phenyl)-2-ethoxypropionic acid ethyl ester, (R)-3-(4-{2-[benzyloxycarbonyl(heptyl)amino]ethoxy}phenyl)-2-ethoxypropionic acid, (R)-3-(4-{2-[benzyloxycarbonyl(heptyl)amino]ethoxy}phenyl)-2-ethoxypropionic acid ethyl ester, (S)-3-(4-{2-[benzyloxycarbonyl(heptyl)amino]ethoxy}phenyl)-2-ethoxypropionic acid and (S)-3-(4-{2-[benzyloxycarbonyl(heptyl)amino]ethoxy}phenyl)-2-ethoxypropionic acid ethyl ester.

15. A compound or a salt thereof, which is selected from the group consisting of (R)-2-ethoxy-3-{4-[2-(N-heptyl-N-methoxycarbonylamino)ethoxy]phenyl}propionic acid, (R)-2-ethoxy-3-{4-[2-(N-heptyl-N-methoxycarbonylamino)ethoxy]phenyl}propionic acid ethyl ester, (S)-2-ethoxy-3-{4-[2-(N-heptyl-N-methoxycarbonylamino)ethoxy]phenyl}propionic acid, (S)-2-ethoxy-3-{4-[2-(N-heptyl-N-methoxycarbonylamino)ethoxy]phenyl}propionic acid ethyl ester, 2-ethoxy-3-{4-[2-(N-heptyl-N-methoxycarbonylamino)ethoxy]phenyl}propionic acid and 2-ethoxy-3-{4-[2-(N-heptyl-N-methoxycarbonylamino)ethoxy]phenyl}propionic acid ethyl ester.

16. A pharmaceutical composition comprising the compound according to claim 1 or a pharmaceutically acceptable salt thereof as an active ingredient.

17. The pharmaceutical composition according to claim 16, which is a hypoglycemic agent and/or triglyceride reducing agent and/or total cholesterol reducing agent.

18. The pharmaceutical composition according to claim 16, which is used for prophylactic and/or therapeutic treatment of diabetes mellitus and/or hyperlipidemia.

19. A method for preparing the compound represented by the formula (1) or the salt thereof according to claim 1, which comprises the step of reacting a compound represented by the following formula (3):

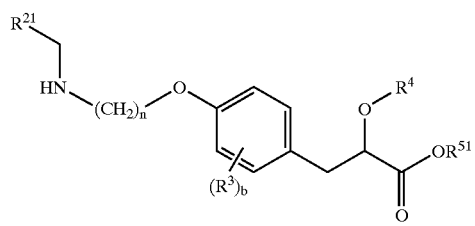

(3)

wherein $R^{21}$ represents a $C_{1-11}$ alkyl group which may be substituted with one or more substituents selected from the group consisting of a lower alkoxyl group, an aryloxy group, an aralkyloxy group, a lower alkylthio group, an arylthio group, an aralkylthio group, and a phenyl group, wherein $R^{21}$ may be further substituted with one or more halogen atoms, b is an integer from 0 to 4, $R^3$ is at least one substituent selected from the group consisting of a halogen atom, a lower alkyl group, or a lower alkoxyl group, which may be the same or different, $R^4$ represents a lower alkyl group, $R^{51}$ represents a protective group of the carboxyl group, and n is an integer from 2 to 4, with a compound represented by the following formula (4):

$$R^1—Y \qquad (4)$$

wherein $R^1$ represents a $C_{1-12}$ alkyl group which may be substituted with one or more substituents selected from the group consisting of a halogen atom, a lower alkoxyl group, and a phenyl group which may be substituted with one or more halogen atoms, or represents a group represented by the following formula (1-1):

(1-1)

wherein a is an integer from 0 to 5, $R^6$ is at least one substituent selected from the group consisting of a halogen atom, a lower alkyl group, a lower alkoxyl group, a lower alkylthio group, nitro group, a lower alkoxycarbonyl group, cyano group, trifluoromethyl group, trifluoromethoxy group, or a phenyloxy group, which may be the same or different, or represents a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, and Y represents —NCO or —OCOW where W represents a leaving group, to prepare a compound represented by the following formula (2):

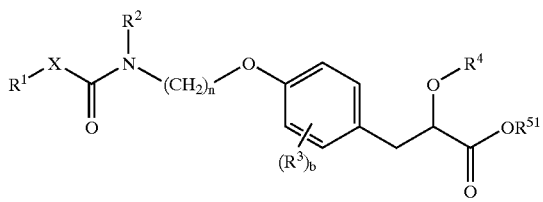

(2)

wherein $R^1$, $R^3$, b, $R^4$, $R^{51}$, and n are the same as those defined above, and $R^2$ represents a $C_{2-12}$ alkyl group which may be substituted with one or more substituents selected from the group consisting of a lower alkoxyl group, an aryloxy group, an aralkyloxy group, a lower alkylthio group, an arylthio group, an aralkylthio group, and a phenyl group, wherein $R^2$ may be further substituted with one or more halogen atoms provided that $R^2$, except for the methylene group in $R^2$ that binds to the nitrogen atom, may be substituted with one or more halogen atoms, and removing the protective group $R^{51}$, if necessary.

20. The method according to claim 19, wherein the protective group $R^{51}$ is at least one selected from the group consisting of lower alkyl group, phenyl group, trityl group, benzyl group, 2-tetrahydropyranyl group, 2-tetrahydrofuranyl group, triethylsilyl group, dimethylphenylsilyl group, tert-butyldimethylsilyl group, or allyl group.

21. The pharmaceutical composition according to claim 16, which is a hypoglycemic agent and/or triglyceride reducing agent.

22. The method according to claim 19, wherein $R^{51}$ is a lower alkyl group and Y represents —NCO or —OCOCl.

23. A method of treating a disease comprising administering an effective amount of the pharmaceutical composition according to claim 16 to a mammal, wherein said disease is characterized by being responsive to a hypoglycemic agent, a triglyceride reducing agent or a total cholesterol reducing agent.

24. A method of treating a disease comprising administering an effective amount of the pharmaceutical composition according to claim 16 to a mammal, wherein said disease is diabetes mellitus or hyperlipidemia.

25. A compound represented by the following formula (1) or a salt thereof:

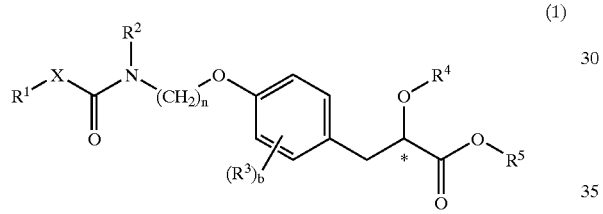

(1)

wherein
$R^1$ represents a $C_{1-12}$ alkyl group which may be substituted with one or more substituents selected from the group consisting of a halogen atom, a lower alkoxyl group, and a phenyl group which may be substituted with one or more halogen atoms or a group represented by the following formula (1-1):

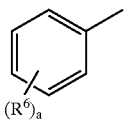

(1-1)

wherein a is an integer from 0 to 5 and $R^6$ represents a substituent selected from the group consisting of a halogen atom, a lower alkyl group, a lower alkoxyl group, a lower alkylthio group, nitro group, a lower alkoxycarbonyl group, cyano group, trifluoromethyl group, trifluoromethoxy group, and a phenyloxy group, which may be the same or different, or represents a substituent selected from the group consisting of 1-naphthyl group, 2-naphthyl group, 5-indanyl group, 5,6,7,8-tetrahydronaphthalen-2-yl group, allyl group, 3-butenyl group, and 2-propynyl group, $R^2$ represents a $C_{2-12}$ alkyl group which may be substituted with a substituent selected from the group consisting of a lower alkoxyl group, an aryloxy group, an aralkyloxy group, a lower alkylthio group, an arylthio group, an aralkylthio group, and a phenyl group, wherein $R^2$ may be further substituted with one or more halogen atoms, b is an integer from 0 to 4 and $R^3$ is a substituent selected from the group consisting of a halogen atom, a lower alkyl group, and a lower alkoxyl group, which may be the same or different, $R^4$ represents a lower alkyl group, $R^5$ represents hydrogen atom or a lower alkyl group, n represents an integer from 2 to 4, X represents —NH— or —O—, and

* represents an asymmetric carbon.

* * * * *